(12) United States Patent
Boyd-Kirkup et al.

(10) Patent No.: US 10,633,456 B1
(45) Date of Patent: Apr. 28, 2020

(54) VISTA ANTIGEN-BINDING MOLECULES

(71) Applicant: Hummingbird Bioscience Holdings Pte. Ltd., Singapore (SG)

(72) Inventors: Jerome Douglas Boyd-Kirkup, Singapore (SG); Piers Ingram, Singapore (SG); Dipti Thakkar, Singapore (SG); Zhihao Wu, Singapore (SG); Konrad Paszkiewicz, Singapore (SG); Vicente Sancenon, Singapore (SG); Siyu Guan, Singapore (SG)

(73) Assignee: Hummingbird Bioscience Holdings Pte. Ltd., Singapore (KR)

( * ) Notice: Subject to any disclaimer, the term of this patent is extended or adjusted under 35 U.S.C. 154(b) by 0 days.

(21) Appl. No.: 16/596,739

(22) Filed: Oct. 8, 2019

Related U.S. Application Data

(63) Continuation of application No. PCT/EP2019/058036, filed on Mar. 29, 2019.

(51) Int. Cl.
*C07K 16/00* (2006.01)
*C07K 16/46* (2006.01)

(52) U.S. Cl.
CPC .......... *C07K 16/464* (2013.01); *C07K 16/468* (2013.01); *C07K 2317/522* (2013.01); *C07K 2317/524* (2013.01); *C07K 2317/526* (2013.01); *C07K 2317/565* (2013.01); *C07K 2317/567* (2013.01); *C07K 2317/72* (2013.01)

(58) Field of Classification Search
CPC .................................................. C07K 16/464
See application file for complete search history.

(56) References Cited

U.S. PATENT DOCUMENTS

| | | |
|---|---|---|
| 9,381,244 B2 | 7/2016 | Noelle |
| 2012/0100140 A1 | 4/2012 | Reyes et al. |
| 2013/0177557 A1 | 7/2013 | Noelle et al. |
| 2016/0159927 A1 | 6/2016 | Molloy et al. |
| 2016/0369005 A1 | 12/2016 | Lippincott et al. |
| 2017/0051061 A1 | 2/2017 | Snyder et al. |
| 2017/0119877 A1 | 5/2017 | Green et al. |
| 2017/0184604 A1 | 6/2017 | Lee et al. |
| 2017/0233479 A1 | 8/2017 | Snyder et al. |
| 2019/0300610 A1 | 10/2019 | Boyd-Kirkup et al. |

FOREIGN PATENT DOCUMENTS

| | | |
|---|---|---|
| WO | WO 2014/039983 A1 | 3/2014 |
| WO | WO 2014/190356 A2 | 11/2014 |
| WO | WO 2014/197849 A2 | 12/2014 |
| WO | WO 2015/097536 A2 | 7/2015 |
| WO | WO 2015/187359 A1 | 12/2015 |
| WO | WO 2015/191881 A2 | 12/2015 |
| WO | WO 2016/081746 A2 | 5/2016 |
| WO | WO 2016/090347 A1 | 6/2016 |
| WO | WO 2016/094837 A2 | 6/2016 |
| WO | WO 2017/023749 A1 | 2/2017 |
| WO | WO 2017/137830 A1 | 8/2017 |
| WO | WO 2017/165683 A1 | 9/2017 |
| WO | WO 2017/181139 A2 | 10/2017 |
| WO | WO 2018/027042 A1 | 2/2018 |
| WO | WO 2018/132476 A1 | 7/2018 |
| WO | WO 2018/169993 A1 | 9/2018 |

OTHER PUBLICATIONS

International Search Report and Written Opinion for Application No. PCT/EP2018/058258, dated Sep. 11, 2018.
International Search Report and Written Opinion for Application No. PCT/EP2019/058036, dated May 31, 2019.
Boyd-Kirkup et al., Integrative immune profiling of syngeneic tumor models provides predictive immune signatures for treatment response with HMBD002, a novel anti-VISTA neutralizing antibody. Cancer Research. Jul. 2018;78(13):supplement. Abstract 1729. 2 pages.
Boyd-Kirkup et al., HMBD-002-V4: A novel anti-VISTA antibody that uniquely binds murine and human VISTA and potently inhibits tumor growth by remodeling the immunosuppressive tumor microenvironment. J. ImmunoTherapy of Cancer. 2018;6(Suppl. 1):115. Abstract P477.
Boyd-Kirkup et al., HMBD-002-V4: A novel anti-VISTA antibody that uniquely binds murine and human VISTA and potently inhibits tumor growth by remodeling the immunosuppressive tumor microenvironment. Presented at 2018 SITC Annual Meeting. Poster. 1 page.
Green et al., Selective Involvement of the Checkpoint Regulator VISTA in Suppression of B-Cell, but Not T-Cell, Responsiveness by Monocytic Myeloid-Derived Suppressor Cells from Mice Infected with an Immunodeficiency-Causing Retrovirus. J Virol. Sep. 2015;89(18):9693-8. doi:10.1128/JVI.00888-15. Epub Jul. 8, 2015.
Ingram et al., HMBD002, a novel neutralizing antibody targeting a specific epitope on the co-inhibitory immune checkpoint receptor VIS TA, displays potent anti-tumor effects in pre-clinical models. Cancer Research. Jul. 2017;77(13):supplement. Abstract 587.
Ingram et al., HMBD002, a novel neutralizing antibody targeting a specific epitope on the co-inhibitory immune checkpoint receptor VIS TA, displays potent anti-tumor effects in pre-clinical models. Presented at AACR Annual meeting Apr. 2, 2017. Poster. 1 page.
Jensen et al., Anti-VISTA antibody enhances the anti-tumor immune response in mice with mammary tumors Eur J Immunol. 2016;46(suppl 1):109. Abstract 2208.
Kondo et al., Differential contribution of three immune checkpoint (VISTA, CTLA-4, PD-1) pathways to antitumor responses against squamous cell carcinoma. Oral Oncol. Jun. 2016;57:54-60. doi: 10.1016/j.oraloncology.2016.04.005. Epub May 3, 2016.
Le Mercier et al., VISTA Regulates the Development of Protective Antitumor Immunity. Cancer Res. Apr. 1, 2014;74(7):1933-44. doi: 10.1158/0008-5472.CAN-13-1506.

(Continued)

*Primary Examiner* — Sheela J. Huff
(74) *Attorney, Agent, or Firm* — Wolf, Greenfield & Sacks, P.C.

(57) ABSTRACT

VISTA antigen-binding molecules are disclosed. Also disclosed are nucleic acids and expression vectors encoding, compositions comprising, and methods using, the VISTA antigen-binding molecules.

25 Claims, 92 Drawing Sheets

Specification includes a Sequence Listing.

(56) References Cited

OTHER PUBLICATIONS

Lo et al., Effector-attenuating Substitutions That Maintain Antibody Stability and Reduce Toxicity in Mice. J Biol Chem. Mar. 3, 2017;292(9):3900-3908. doi: 10.1074/jbc.M116.767749. Epub Jan. 11, 2017.

Nowak et al., Immunoregulatory functions of VISTA. Immunol Rev. Mar. 2017;276(1):66-79. doi: 10.1111/imr.12525.

Pilones et al., Anti-VISTA Antibody increases tumor-specific T cells and prolongs survival of metastatic carcinoma-bearing mice treated with radiation therapy, Cytoxan, and PD-1 Blockade. Int J Radiation Oncol. 2017;99(2S). Abstract 277. S128.

Wang et al., VISTA, a novel mouse Ig superfamily ligand that negatively regulates T cell responses. J Exp Med. Mar. 14, 2011;208(3):577-92. doi: 10.1084/jem.20100619. Epub Mar. 7, 2011.

U.S. Appl. No. 16/180,949, filed Nov. 5, 2018, Boyd-Kirkup et al.

PCT/EP2018/058258, dated Sep. 11, 2018, International Search Report and Written Opinion.

PCT/EP2019/058036, dated May 31, 2019, International Search Report and Written Opinion.

Blando et al., Comparison of immune infiltrates in melanoma and pancreatic cancer highlights VISTA as a potential target in pancreatic cancer. Proc Natl Acad Sci U.S. A. Jan. 29, 2019;116(5):1692-1697. doi: 10.1073/pnas.1811067116. Epub Jan. 11, 2019.

Broughton et al., Defining the Signature of VISTA on Myeloid Cell Chemokine Responsiveness. Front Immunol. 2019; 10: 2641. EPub Nov. 19, 2019. doi: 10.3389/fimmu.2019.02641.

Eltanbouly et al., VISTA: a novel immunotherapy target for normalizing innate and adaptive immunity. Semin Immunol. Apr. 2019;42:101308. doi: 10.1016/j.smim.2019.101308.

Eltanbouly et al., VISTA is a checkpoint regulator for naïve T cell quiescence and peripheral tolerance. Science. Jan. 17, 2020;367(6475). pii: eaay0524. doi: 10.1126/science.aay0524. 16 pages.

Johnston et al., VISTA is an acidic pH-selective ligand for PSGL-1. Nature. Oct. 2019;574(7779):565-570. doi: 10.1038/s41586-019-1674-5. Epub Oct. 23, 2019.

Mehta et al., Structure and Functional Binding Epitope of V-domain Ig Suppressor of T Cell Activation. Cell Rep. Sep. 3, 2019;28(10):2509-2516.e5. doi: 10.1016/j.celrep.2019.07.073.

Mulati et al., VISTA expressed in tumour cells regulates T cell function. Br J Cancer. Jan. 2019;120(1):115-127. doi: 10.1038/s41416-018-0313-5. Epub Nov. 9, 2018.

Wang et al., VSIG-3 as a ligand of VISTA inhibits human T-cell function. Immunology. Jan. 2019;156(1):74-85. doi: 10.1111/imm.13001. Epub Oct. 10, 2018.

| V4 Conc. (nM) | Response | KD (M) | KD Error | kon(1/Ms) | kon Error | kdis(1/s) | kdis Error | RMax | RMax Error | kobs(1/s) | Req | Req/Rmax(%) | Full X^2 | Full R^2 |
|---|---|---|---|---|---|---|---|---|---|---|---|---|---|---|
| 666.5 | 0.4104 | 1.13E-07 | 5.65E-09 | 3.95E+04 | 1.58E+03 | 4.45E-03 | 1.34E-04 | 0.4719 | 0.0083 | 3.08E-02 | 0.4036 | 85.5 | 0.0099 | 0.9948 |
| 333.3 | 0.2261 | 1.13E-07 | 5.65E-09 | 3.95E+04 | 1.58E+03 | 4.45E-03 | 1.34E-04 | 0.3459 | 0.0097 | 1.76E-02 | 0.2584 | 74.7 | 0.0099 | 0.9948 |
| 166.6 | 0.1064 | 1.13E-07 | 5.65E-09 | 3.95E+04 | 1.58E+03 | 4.45E-03 | 1.34E-04 | 0.2573 | 0.0101 | 1.10E-02 | 0.1534 | 59.6 | 0.0099 | 0.9948 |
| 83.3 | 0.0514 | 1.13E-07 | 5.65E-09 | 3.95E+04 | 1.58E+03 | 4.45E-03 | 1.34E-04 | 0.207 | 0.0116 | 7.74E-03 | 0.0879 | 42.5 | 0.0099 | 0.9948 |
| 41.7 | 0.0275 | 1.13E-07 | 5.65E-09 | 3.95E+04 | 1.58E+03 | 4.45E-03 | 1.34E-04 | 0.1952 | 0.0172 | 6.10E-03 | 0.0527 | 27 | 0.0099 | 0.9948 |

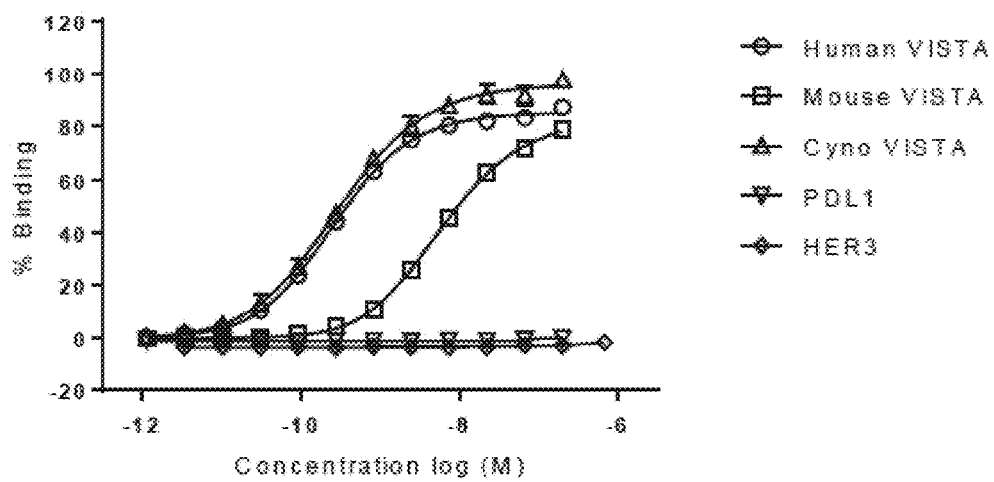
Figure 4A
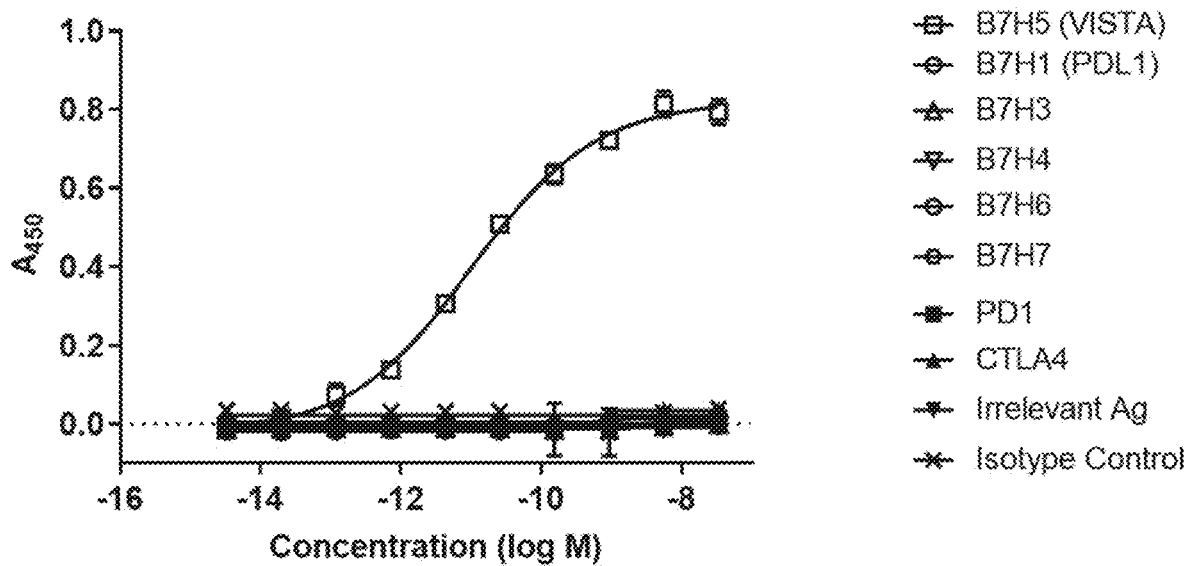
Figure 4B mFcγRIV $k_{on}$ = ND    $K_D$ = ND    $k_{dis}$ = ND mFcγRIII $k_{on} = 2.7e^5 M^{-1} s^{-1}$    $K_D = 455$ nM    $k_{dis} = 12.5e^{-2} s^{-1}$ mFcγRIIb $k_{on} = 0.90e^5 \, M^{-1} \, s^{-1}$   $K_D = 1300 \, nM$   $k_{dis} = 11.7e^{-2} \, s^{-1}$ mFcRn $k_{on} = 1.7e^5 \, M^{-1} \, s^{-1}$   $K_D = 93.9 \, nM$   $k_{dis} = 1.6e^{-2} \, s^{-1}$ mFcγRIV $k_{on} = 0.92e^5 \, M^{-1} \, s^{-1}$    $K_D = 372 \, nM$    $k_{dis} = 3.4e^{-2} \, s^{-1}$ mFcγRIII $k_{on} = 0.67e^5 \, M^{-1} \, s^{-1}$    $K_D = 977 \, nM$    $k_{dis} = 6.6e^{-2} \, s^{-1}$ mFcγRIIb $k_{on} = 0.55e^5 \, M^{-1} \, s^{-1}$   $K_D = 2190 \, nM$   $k_{dis} = 12.0e^{-2} \, s^{-1}$ mFcRn $k_{on} = 2.2e^5 \, M^{-1} \, s^{-1}$   $K_D = 49.6 \, nM$   $k_{dis} = 1.1e^{-2} \, s^{-1}$ mFcγRIIb $k_{on}$ = ND   $K_D$ = ND   $k_{dis}$ = ND mFcRn $k_{on} = 2.7e^5\,M^{-1}\,s^{-1}$   $K_D = 35.8\,nM$   $k_{dis} = 0.97e^{-2}\,s^{-1}$

Calculated $k_{on}$ (M$^{-1}$ s$^{-1}$)

| Receptor | 4M2-C12 mIgG2a $k_a$ (M-s) | 4M2-C12 mIgG1 $k_a$ (M-s) | 4M2-C12 mIgG2a LALA-PG $k_a$ (M-s) | 4M2-C12 mIgG2a bio $k_a$ (M-s) |
|---|---|---|---|---|
| | 1 | 2 | | |
| mFcRn | $1.9e^5$ | $2.2e^5$ | $1.7e^5$ | $2.7e^5$ | $1.8e^5$ |
| mFcgRIV | $0.96e^5$ | $0.92e^5$ | ND | ND | ND |
| mFcgRIII | $0.55e^5$ | $0.67e^5$ | $2.7e^5$ | ND | ND |
| mFcgRIIb | $0.51e^5$ | $0.55e^5$ | $0.90e^5$ | ND | ND |

ND = Not Determined due to low binding affinity

Figure 29A

Calculated $k_{dis}$ (s$^{-1}$)

| Receptor | 4M2-C12 mIgG2a $k_d$ (s) | 4M2-C12 mIgG1 $k_d$ (s) | 4M2-C12 mIgG2a LALA-PG $k_d$ (s) | 4M2-C12 mIgG2a bio $k_d$ (s) |
|---|---|---|---|---|
| | 1 | 2 | | |
| mFcRn | $0.59e^{-2}$ | $1.1e^{-2}$ | $1.6e^{-2}$ | $0.97e^{-2}$ | $0.75e^{-2}$ |
| mFcgRIV | $2.5e^{-2}$ | $3.4e^{-2}$ | ND | ND | $34.8e^{-2}$ |
| mFcgRIII | $4.4e^{-2}$ | $6.6e^{-2}$ | $12.5e^{-2}$ | ND | ND |
| mFcgRIIb | $4.5e^{-2}$ | $12.0e^{-2}$ | $11.7e^{-2}$ | ND | ND |

ND = Not Determined due to low binding affinity

Figure 29B

Calculated $K_D$ (nM)

| Receptor | Function | Binding | mIgG | hIgG | hIgG1 ($K_D$ nM) | hIgG2 ($K_D$ nM) | hIgG3 ($K_D$ nM) | hIgG4 ($K_D$ nM) |
|---|---|---|---|---|---|---|---|---|
| mFcRn | Recycling (Increased affinity → Increased half life) | Medium | mIgG1: 1157<br>mIgG2a: 490<br>mIgG2b: 545<br>mIgG3: 140 | hIgG1: 72<br>hIgG2: 63<br>hIgG3: 230<br>hIgG4: 116 | 31.5 | 49.5 | 93.9 | 35.8 | 42.5 |
| mFcgRIV CD16-2 | Cell activation | High | mIgG1: ND<br>mIgG2a: 34.5<br>mIgG2b: 59<br>mIgG3: ND | hIgG1: 280<br>hIgG2: 0<br>hIgG3: 170<br>hIgG4: 26000 | 258 | 372 | ND | ND | ND |
| mFcgRIII CD16 | Cell activation | Low | mIgG1: 3200<br>mIgG2a: 1460<br>mIgG2b: 1555<br>mIgG3: ND | hIgG1: 9300<br>hIgG2: 9700<br>hIgG3: 1300<br>hIgG4: 21000 | 794 | 977 | 455 | ND | ND |
| mFcgRIIb CD32 | Cell inhibition | Low | mIgG1: 301<br>mIgG2a: 2390<br>mIgG2b: 448<br>mIgG3: ND | hIgG1: 1100<br>hIgG2: 7900<br>hIgG3: 700<br>hIgG4: 11000 | 876 | 2190 | 1300 | ND | ND |

ND = $K_D$ Not Determined due to low binding affinity

Figure 29C

| Antibody | mouse VISTA | | | human VISTA | | |
|---|---|---|---|---|---|---|
| | $K_D$ (nM) | $K_{on}$ ($M^{-1}s^{-1}$) | $K_{off}$ ($s^{-1}$) | $K_D$ (nM) | $K_{on}$ ($M^{-1}s^{-1}$) | $K_{off}$ ($s^{-1}$) |
| V4_C1 | 60.7 | 2.43E+05 | 14.7E-03 | <0.001 | 3.43E+05 | <1.0E-07 |
| V4_C9 | 3.81 | 3.11E+05 | 1.18E-03 | <0.001 | 3.33E+05 | <1.0E-07 |
| V4_C24 | <0.001 | 4.01E+05 | <1.0E-07 | <0.001 | 3.84E+05 | <1.0E-07 |
| V4_C26 | <0.001 | 4.03E+05 | <1.0E-07 | <0.001 | 4.04E+05 | <1.0E-07 |
| V4_C27 | <0.001 | 4.26E+05 | <1.0E-07 | <0.001 | 4.65E+05 | <1.0E-07 |
| V4_C28 | 0.17 | 4.75E+05 | 0.082E-03 | <0.001 | 5.07E+05 | <1.0E-07 |
| V4_C30 | 0.005 | 5.05E+05 | 0.0028E-03 | <0.001 | 5.93E+05 | <1.0E-07 |
| V4_C31 | <0.001 | 5.70E+05 | <1.0E-07 | <0.001 | 6.23E+05 | <1.0E-07 |

Figure 45D

| Antibody | mouse VISTA | | |
|---|---|---|---|
| | $K_D$ (nM) | $k_{on}$ (M⁻¹s⁻¹) | $k_{off}$ (s⁻¹) |
| V4_C1 | 66.7 | 3.30E+05 | 22.0E-03 |
| V4_C9 | 4.26 | 1.57E+05 | 0.67E-03 |
| VSTB112 | NS | NS | NS |
| V4_C24 | <0.001 | 4.62E+05 | <1.0E-07 |
| V4_C26 | 0.183 | 4.13E+05 | 0.076E-03 |
| V4_C27 | 0.137 | 3.98E+05 | 0.055E-03 |
| V4_C28 | 0.489 | 5.20E+05 | 0.25E-03 |
| V4_C30 | <0.001 | 5.33E+05 | <1.0E-07 |
| V4_C31 | <0.001 | 3.44E+05 | <1.0E-07 |

Figure 46B

| Antibody | human VSTA | | | mouse VSTA | | |
|---|---|---|---|---|---|---|
| | $K_D$ (nM) | $K_{on}$ ($M^{-1}s^{-1}$) | $K_{off}$ ($s^{-1}$) | $K_D$ (nM) | $K_{on}$ ($M^{-1}s^{-1}$) | $K_{off}$ ($s^{-1}$) |
| V4_C1 | <0.001 | 3.91E+05 | <1.0E-07 | 58.5 | 2.77E+05 | 16.2E-03 |
| V4_C9 | 0.125 | 4.50E+05 | 0.056E-03 | 2.88 | 3.61E+05 | 1.04E-03 |
| VSTB112 | <0.001 | 1.79E+05 | <1.0E-07 | NA | NA | NA |
| V4_C24 | <0.001 | 3.73E+05 | <1.0E-07 | 0.202 | 3.78E+05 | 0.076E-03 |
| V4_C26 | 0.241 | 4.07E+05 | 0.098E-03 | 0.530 | 3.82E+05 | 0.20E-03 |
| V4_C27 | 0.119 | 5.11E+05 | 0.061E-03 | 0.395 | 3.92E+05 | 0.16E-03 |

Figure 47C

| | V4pr | V4_C1 | V4_C9 | V4_C24 | V4_C26 | V4_C27 | V4_C28 | V4_C30 | V4_C31 | Atz | VSTB112 | hIgG |
|---|---|---|---|---|---|---|---|---|---|---|---|---|
| hVISTA | 0.036 | 0.0024 | 0.031 | 0.010 | 0.0034 | <0.0007 | 0.0015 | <0.0007 | 0.0032 | 102 | 0.042 | 152 |
| mVISTA | 0.43 | 3.1 | 0.11 | 0.017 | 0.0089 | 0.0023 | 0.0045 | 0.0013 | 0.0030 | 97 | >200 | 77 |

| | V4 C1 | V4 C9 | V4 C24 | V4 C26 | V4 C27 | V4 C28 | V4 C30 | V4 C31 | VST112 | Isotype |
|---|---|---|---|---|---|---|---|---|---|---|
| hVISTA | 0.042 | 0.030 | 0.032 | 0.038 | 0.037 | 0.053 | 0.088 | 0.020 | 0.054 | > 200 |
| mVISTA | 1.60 | 0.044 | 0.042 | 0.058 | 0.047 | 0.064 | 0.123 | 0.028 | > 200 | > 200 |

| | V4c24 | V4c26 | V4c27 | V4c1 | V4c9 | V4c10114 | Hu IgGVHH |
|---|---|---|---|---|---|---|---|
| hVISTA | 0.073 | 0.064 | 0.047 | 0.065 | 0.107 | 0.072 | 98.5 |
| mVISTA | 0.116 | 0.086 | 0.073 | 2.44 | 0.180 | >200 | >200 |
Figure 51C
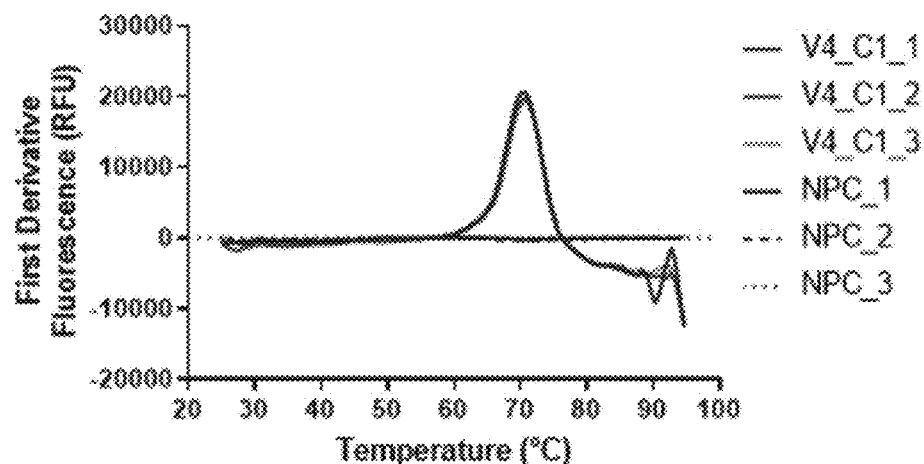
Figure 52A
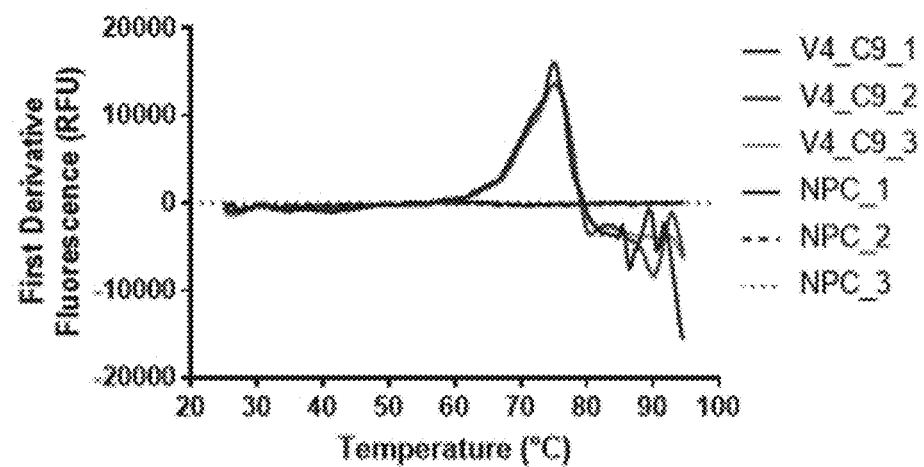
Figure 52B

| Antibody | Tm | | |
|---|---|---|---|
| | Fc | Fab | |
| | Tm1 [°C] | Tm2 [°C] | Shoulder |
| V4p | 67.5 | | Shoulder at 63 |
| V4_C1 | 70.5 | | |
| V4_C9 | 75.1 | | Shoulder at 72C |
| V4_C24 | 72.3 | | |
| V4_C26 | 72.9 | | |
| V4_C27 | 70.3 | 75.6 | |
| V4_C28 | 70.5 | 76.3 | |
| V4_C30 | 70.2 | 77.5 | |
| V4_C31 | | 74.5 | Shoulder at 71.5C |
| VSTB112 | 69.9 | 82.3 | |

| Antibody | % Identity (human) | | Potentially immunogenic peptides | |
|---|---|---|---|---|
| | HC | LC | HC | LC |
| V4 | 69.7 | 63.2 | 2 | 3 |
| V4_C1 | 86.9 | 85.3 | 6 | 3 |
| V4_C9 | 86.9 | 86.3 | 4 | 3 |
| V4_C24 | 85.9 | 85.3 | 2 | 3 |
| V4_C26 | 85.9 | 85.3 | 2 | 2 |
| V4_C27 | 85.9 | 85.3 | 2 | 3 |
| V4_C28 | 85.9 | 85.3 | 2 | 3 |
| V4_C30 | 85.9 | 84.2 | 2 | 3 |
| V4_C31 | 85.9 | 83.2 | 2 | 2 |

| EC$_{50}$ (M) | human VISTA | mouse VISTA | Rat VISTA | Cyno VISTA |
|---|---|---|---|---|
| V4 | 3.19E-11 | 3.87E-10 | 1.25E-09 | 4.72E-11 |
| V4C24 | 2.68E-11 | 3.04E-11 | 2.01E-10 | 3.85E-11 |
| V4C26 | 2.41E-11 | 3.25E-11 | 1.60E-10 | 3.56E-11 |
| V4C27 | 2.95E-11 | 3.74E-11 | 1.96E-10 | 3.24E-11 |
| V4C28 | 3.46E-11 | 3.65E-11 | 2.17E-10 | 3.67E-11 |
| V4C30 | 3.18E-11 | 3.26E-11 | 2.06E-10 | 2.72E-11 |
| V4C31 | 4.08E-11 | 4.00E-11 | 2.24E-10 | 3.21E-11 |
| Isotype | > 3.3e-008 | > 3.3e-008 | > 3.3e-008 | > 3.3e-008 |

Normal spleen
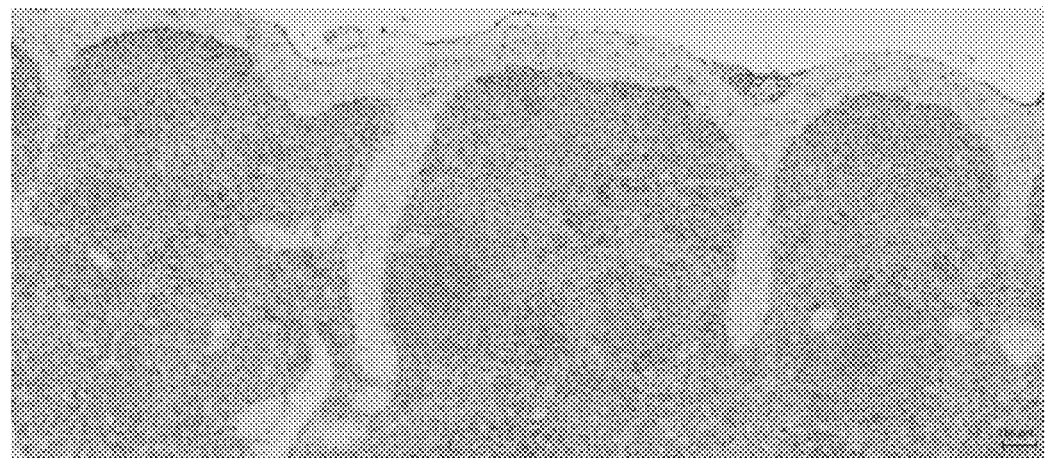
4x
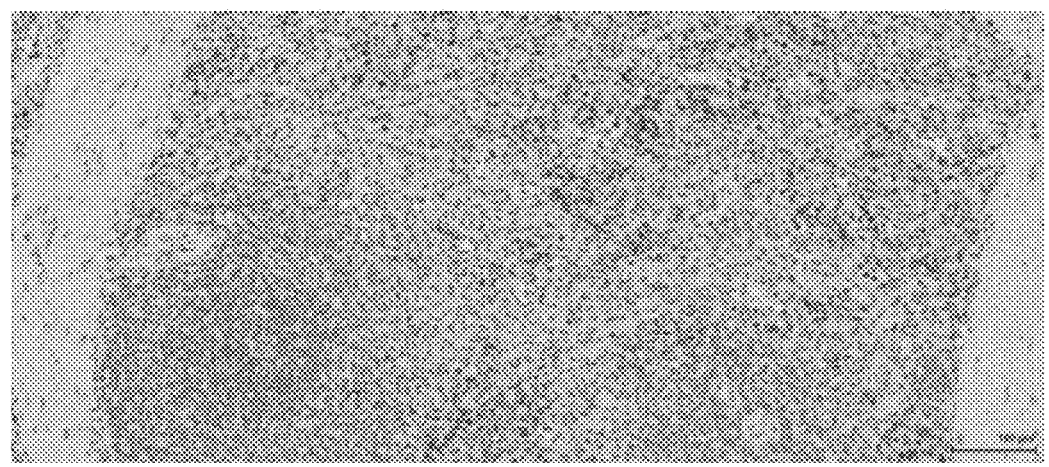
10x
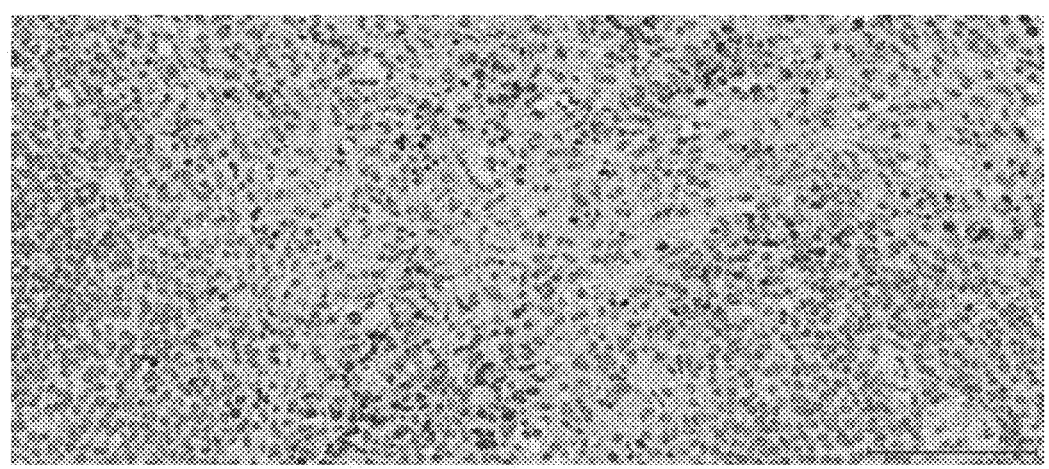
20x
Figure 59A

Normal ovary
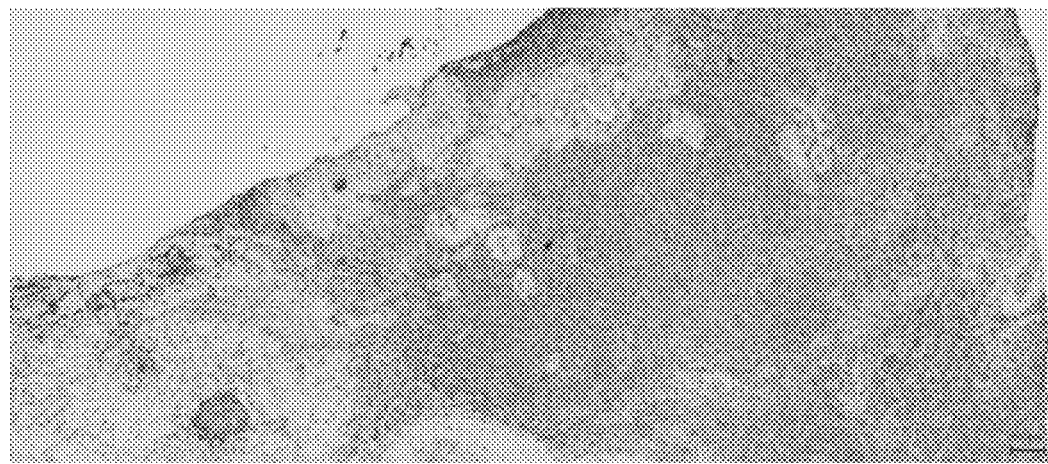
4x
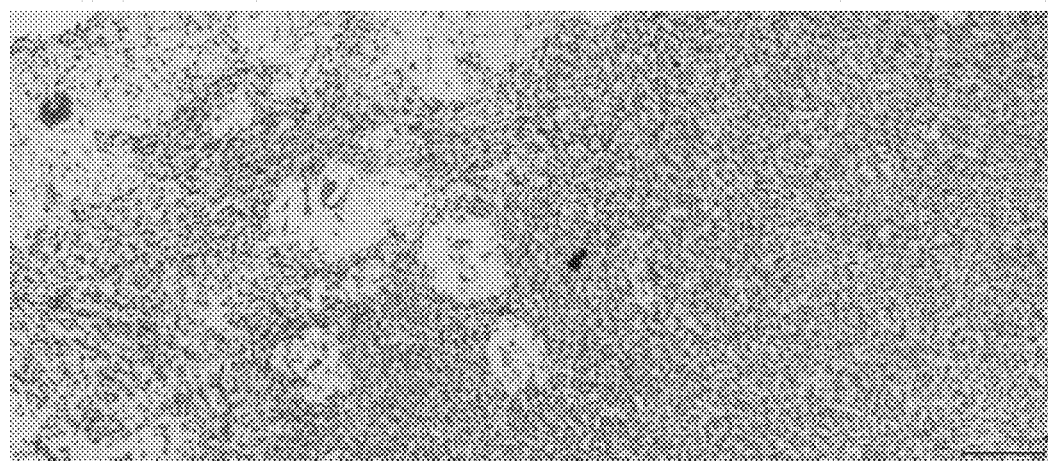
10x
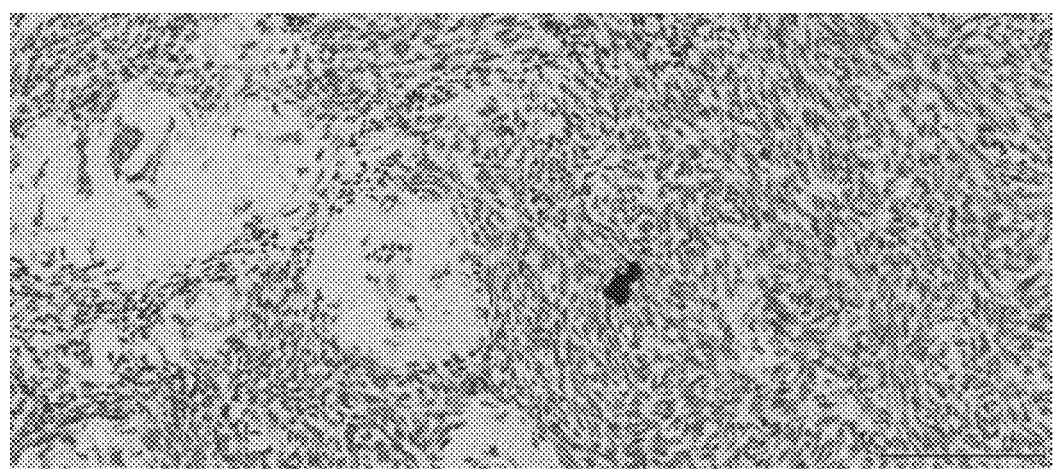
20x
Figure 59B

| Treatment Arm | Dose | Red Blood Cell | | | | | | |
|---|---|---|---|---|---|---|---|---|
| | | RBC Count (10^9/L) | Hemoglobin (g/dl) | Hematocrit (%) | Anemia Parameters | | | Platelet count (10^9/L) |
| | | | | | MCV (fml) | MCH (pg) | MCHC (g/dl) | |
| Vehicle | 0 | 10.73 | 16.3 | 45.67 | 43 | 15.2 | 35.7 | 774 |
| VdP | 50 mg/kg | 11.02 | 17.2 | 47.64 | 43 | 15.6 | 36 | 720 |

Figure 64A

| Treatment Arm | Dose | White Blood Cell | | | |
|---|---|---|---|---|---|
| | | WBC Count (10^9/L) | Lymphocyte Count (10^9/L) | Monocyte Count (10^9/L) | Neutrophil Count (10^9/L) |
| Vehicle | 0 | 5.57 | 3.4 | 0.05 | 1.7 |
| VdP | 50 mg/kg | 5.98 | 4.22 | 0.05 | 1.71 |

Figure 64B

| Treatment Arm | Dose | Biochemistry | | | |
|---|---|---|---|---|---|
| | | Liver (U/L) | | Kidney (mg/dL) | |
| | | ALT | ALP | CREA | BUN |
| Vehicle | 0 | 29 | 102 | 17 | 0.2 |
| VdP | 50 mg/kg | 23 | 50 | 19 | 0.2 |

Figure 64C

| Treatment Arm | Time (hr) | Red Blood Cell | | | | | | |
|---|---|---|---|---|---|---|---|---|
| | | | | Anemia Parameters | | | | |
| | | RBC Count (10^9/L) | Hemoglobin (g/dl) | Hematocrit (%) | MCV (fml) | MCH (pg) | MCHC (g/dl) | Platelet count (10^9/L) |
| Vehicle | 0 | 7.94 | 14.97 | 45.50 | 57.33 | 18.87 | 32.87 | 223.3 |
| | 6 | 8.58 | 16.15 | 48.57 | 56.50 | 18.90 | 17.80 | 886.5 |
| | 24 | 8.25 | 15.70 | 46.55 | 56.33 | 19.03 | 33.73 | 427.0 |
| | 96 | 7.97 | 13.37 | 45.39 | 56.67 | 16.80 | 29.50 | 229.0 |
| | 168 | 8.27 | 15.87 | 46.96 | 57.00 | 19.20 | 33.80 | 244.7 |
| Vehicle | 0 | 7.65 | 14.30 | 43.82 | 57.33 | 18.60 | 41.73 | 172.3 |
| | 6 | 8.03 | 14.77 | 45.04 | 56.33 | 18.50 | 32.90 | 99.00 |
| | 24 | 8.14 | 14.73 | 45.84 | 56.33 | 18.17 | 32.23 | 305.7 |
| | 96 | 7.97 | 13.93 | 45.02 | 56.33 | 17.50 | 30.97 | 269.3 |
| | 168 | 8.15 | 15.50 | 45.53 | 55.67 | 19.03 | 34.03 | 151.1 |
| Vehicle | 0 | 7.94 | 14.23 | 46.23 | 58.00 | 17.83 | 30.63 | 247.0 |
| | 6 | 10.51 | 20.40 | 61.26 | 58.33 | 19.40 | 33.30 | 427.3 |
| | 24 | 8.04 | 14.90 | 45.31 | 56.00 | 18.50 | 32.83 | 293.3 |
| | 96 | 6.77 | 12.23 | 38.43 | 57.00 | 18.07 | 31.70 | 183.7 |
| | 168 | 7.69 | 13.73 | 43.65 | 57.00 | 17.97 | 31.53 | 303.0 |

Figure 65A

| Treatment Group | Time (hr) | WBC Count (10^9/L) | Lymphocyte Count (10^9/L) | Monocyte Count (10^9/L) | Neutrophil Count (10^9/L) |
|---|---|---|---|---|---|
| Vehicle | 0 | 14.86 | 12.53 | 0.40 | 1.93 |
| | 6 | 10.88 | 8.63 | 0.21 | 2.03 |
| | 24 | 9.85 | 8.15 | 0.20 | 1.50 |
| | 96 | 11.68 | 8.94 | 0.59 | 2.15 |
| | 168 | 15.82 | 12.28 | 1.22 | 2.32 |
| V1 TAG | 0 | 9.02 | 7.52 | 0.55 | 0.94 |
| | 6 | 8.79 | 5.84 | 0.35 | 2.60 |
| | 24 | 10.38 | 8.66 | 0.16 | 1.57 |
| | 96 | 10.89 | 8.91 | 0.35 | 1.63 |
| | 168 | 19.90 | 17.23 | 0.82 | 1.73 |
| V3 TAG | 0 | 8.42 | 7.38 | 0.08 | 0.96 |
| | 6 | 18.20 | 10.76 | 0.62 | 6.82 |
| | 24 | 7.44 | 5.73 | 0.48 | 1.23 |
| | 96 | 7.32 | 5.56 | 0.15 | 1.61 |
| | 168 | 10.05 | 8.44 | 0.34 | 1.28 |

Figure 65B

| Condition | Time (h) | Liver (U/L) | | Kidney (mg/dL) | | Pancreas | | Electrolytes | | | |
|---|---|---|---|---|---|---|---|---|---|---|---|
| | | ALT | ALP | CREA | BUN | GLU (mg/dL) | AMY (U/L) | NA (meq/L) | K (meq/L) | P (mg/dL) | CA (mg/dL) |
| Vehicle | 0 | 52.33 | 246.0 | 0.33 | 21.33 | 173.7 | 549.3 | 137.3 | 7.90 | 8.47 | 11.33 |
| | 6 | 28.67 | 210.7 | 0.37 | 10.33 | 195.7 | 517.7 | 134.0 | 6.00 | 8.20 | 10.87 |
| | 24 | 36.67 | 258.0 | 0.40 | 15.33 | 182.0 | 564.3 | 137.7 | 6.73 | 7.77 | 11.27 |
| | 96 | 32.33 | 218.3 | 0.10 | 12.67 | 176.3 | 532.0 | 134.0 | 5.50 | 8.07 | 10.93 |
| | 168 | 40.33 | 283.0 | 0.27 | 13.00 | 190.0 | 623.3 | 135.7 | 6.37 | 7.30 | 11.13 |
| Vehicle | 0 | 31.00 | 259.0 | 0.27 | 11.67 | 175.3 | 619.0 | 137.3 | 7.23 | 8.33 | 11.33 |
| | 6 | 35.67 | 261.7 | 0.33 | 12.00 | 140.3 | 590.0 | 139.3 | 8.43 | 9.97 | 11.63 |
| | 24 | 33.67 | 257.3 | 0.20 | 12.33 | 154.0 | 639.0 | 136.3 | 7.57 | 8.10 | 11.30 |
| | 96 | 35.67 | 235.7 | 0.23 | 11.50 | 181.7 | 648.0 | 135.7 | 6.67 | 8.33 | 11.20 |
| | 168 | 38.67 | 269.7 | 0.23 | 13.33 | 179.7 | 657.0 | 136.7 | 7.00 | 8.20 | 11.33 |
| Vehicle | 0 | 38.33 | 277.0 | 0.30 | 11.67 | 171.3 | 622.3 | 135.3 | 7.23 | 8.43 | 11.23 |
| | 6 | 57.00 | 217.0 | 0.20 | 10.00 | 138.7 | 469.0 | 144.3 | 44.03 | 8.20 | 11.15 |
| | 24 | 34.67 | 275.0 | 0.33 | 12.33 | 158.3 | 633.0 | 134.7 | 6.70 | 8.07 | 11.10 |
| | 96 | 36.00 | 196.3 | 0.23 | 11.67 | 172.0 | 585.7 | 138.0 | 8.90 | 9.23 | 11.53 |
| | 168 | 36.00 | 229.3 | 0.30 | 14.00 | 179.0 | 644.7 | 136.3 | 6.90 | 7.67 | 11.23 |

Figure 65C

VISTA ANTIGEN-BINDING MOLECULES

RELATED APPLICATIONS

This application is a continuation of International Patent Application No. PCT/EP2019/058036, filed Mar. 29, 2019, the contents and elements of which are herein incorporated by reference for all purposes.

FIELD OF THE INVENTION

The present invention relates to the fields of molecular biology, more specifically antibody technology. The present invention also relates to methods of medical treatment and prophylaxis.

BACKGROUND TO THE INVENTION

Myeloid Derived Suppressor Cell (MDSC)-mediated suppression of immune response has been identified in multiple solid tumors and lymphomas. MDSCs are elevated in advanced colorectal cancer (Toor et al, Front Immunol. 2016; 7:560). MDSCs are also observed in breast cancer, and the percentage of MDSCs in the peripheral blood is increased in patients with later stage breast cancer (Markowitz et al, Breast Cancer Res Treat. 2013 July; 140(1):13-21). MDSC abundance is also correlated with poor prognosis in solid tumors (Charoentong et al, Cell Rep. 2017 Jan. 3; 18(1):248-262).

MDSCs exert suppression over T cells through multiple mechanisms, including the production of reactive oxygen species, nitric oxide, and arginase. These ultimately lead to suppression of DC, NK and T cell activity and increased tumor burden (Umansky et al., Vaccines (Basel) (2016) 4(4):36). MDSCs also contribute to the tumor development and metastasis through the production of soluble factors such as matrix metalloproteinases, VEGF, bFGF, TGF-β and S100A8/A9 which promote neovascularisation, invasion, proliferation and metastasis.

Targeting V-type immunoglobulin domain-containing suppressor of T-cell activation (VISTA), an immune checkpoint molecule expressed primarily on MDSCs, is an attractive therapeutic strategy for removing MDSC-mediated suppression of effector immune cell function.

WO 2017/137830 A1 discloses anti-VISTA antibody VSTB174, which is disclosed at e.g. paragraph [00221] to comprise the variable regions of anti-VISTA antibody VSTB112. Paragraph [00362] discloses that VSTB123 comprises the variable regions of VSTB174. Example 25 of WO 2017/137830 A1 at paragraph [0417] and FIG. 42A disclose that mIgG2a antibody VSTB123 was able to inhibit tumor growth in a MB49 tumor model. Paragraph [0418] and FIG. 42A disclose that by contrast VSTB124—which is the same antibody provided in IgG2a LALA format; see paragraph [0408]—did not inhibit tumor growth. Based on these results Example 25 concludes at paragraph [0419] that efficacy with anti-VISTA antibody treatment might require active Fc. Accordingly, the proposed mechanism of action for the anti-VISTA antibody represented schematically at FIG. 47 (see the legend to FIG. 47 at paragraph [0053]) involves Fc-mediated engagement of FcγRIII expressed by NK cells.

Hamster monoclonal anti-VISTA antibody mAb13F3 is disclosed in Le Mercier et al. Cancer Res. (2014) 74(7): 1933-44 to inhibit tumor growth in B16OVA and B16-BL6 melanoma models. Page 1942, paragraph spanning left and right columns teaches that immunogenicity and the FcR binding activity of the VISTA mAb might be critical limiting factors for achieving optimal target neutralization and therapeutic efficacy.

SUMMARY OF THE INVENTION

In a first aspect the present invention provides an antigen-binding molecule, optionally isolated, which is capable of binding to VISTA and inhibiting VISTA-mediated signalling, independently of Fc-mediated function.

Also provided is an antigen-binding molecule, optionally isolated, which is capable of binding to VISTA and inhibiting VISTA-mediated signalling, wherein the antigen-binding molecule is not able to induce an Fc-mediated antibody effector function.

In some embodiments the antigen-binding molecule is not able to induce antibody-dependent cellular cytotoxicity (ADCC) and/or is not able to induce antibody-dependent cell-mediated phagocytosis (ADCP) and/or is not able to induce complement-dependent cytotoxicity (CDC).

Also provided is an antigen-binding molecule, optionally isolated, which is capable of binding to VISTA and inhibiting VISTA-mediated signalling, wherein the antigen-binding molecule does not bind to an Fcγ receptor and/or wherein the antigen-binding molecule does not bind to C1q.

In some embodiments the antigen-binding molecule is capable of binding to VISTA in the Ig-like V-type domain.

In some embodiments the antigen-binding molecule is capable of binding to a polypeptide comprising or consisting of the amino acid sequence of SEQ ID NO:6.

In some embodiments the antigen-binding molecule is capable of binding to a polypeptide comprising or consisting of the amino acid sequence of SEQ ID NO:31.

In some embodiments the antigen-binding molecule does not compete with IGN175A for binding to VISTA (e.g. as determined by epitope binning analysis, e.g. as described in Example 8).

In some embodiments the antigen-binding molecule is not capable of binding to a peptide consisting of the amino acid sequence of SEQ ID NO:275.

In some embodiments the antigen-binding molecule comprises:
  (i) a heavy chain variable (VH) region incorporating the following CDRs:
    HC-CDR1 having the amino acid sequence of SEQ ID NO:305
    HC-CDR2 having the amino acid sequence of SEQ ID NO:306
    HC-CDR3 having the amino acid sequence of SEQ ID NO:307; and
  (ii) a light chain variable (VL) region incorporating the following CDRs:
    LC-CDR1 having the amino acid sequence of SEQ ID NO:41
    LC-CDR2 having the amino acid sequence of SEQ ID NO:308
    LC-CDR3 having the amino acid sequence of SEQ ID NO:43.

In some embodiments the antigen-binding molecule comprises:
  (i) a heavy chain variable (VH) region incorporating the following CDRs:
    HC-CDR1 having the amino acid sequence of SEQ ID NO:244
    HC-CDR2 having the amino acid sequence of SEQ ID NO:34

HC-CDR3 having the amino acid sequence of SEQ ID NO:35; and
(ii) a light chain variable (VL) region incorporating the following CDRs:
LC-CDR1 having the amino acid sequence of SEQ ID NO:41
LC-CDR2 having the amino acid sequence of SEQ ID NO:245
LC-CDR3 having the amino acid sequence of SEQ ID NO:43.

In some embodiments the antigen-binding molecule comprises:
(i) a heavy chain variable (VH) region incorporating the following CDRs:
HC-CDR1 having the amino acid sequence of SEQ ID NO:290
HC-CDR2 having the amino acid sequence of SEQ ID NO:291
HC-CDR3 having the amino acid sequence of SEQ ID NO:278; and
(ii) a light chain variable (VL) region incorporating the following CDRs:
LC-CDR1 having the amino acid sequence of SEQ ID NO:41
LC-CDR2 having the amino acid sequence of SEQ ID NO:309
LC-CDR3 having the amino acid sequence of SEQ ID NO:43.

In some embodiments the antigen-binding molecule comprises:
(i) a heavy chain variable (VH) region incorporating the following CDRs:
HC-CDR1 having the amino acid sequence of SEQ ID NO:290
HC-CDR2 having the amino acid sequence of SEQ ID NO:291
HC-CDR3 having the amino acid sequence of SEQ ID NO:278; and
(ii) a light chain variable (VL) region incorporating the following CDRs:
LC-CDR1 having the amino acid sequence of SEQ ID NO:41
LC-CDR2 having the amino acid sequence of SEQ ID NO:295 or SEQ ID NO:300
LC-CDR3 having the amino acid sequence of SEQ ID NO:43.

In some embodiments the antigen-binding molecule comprises:
(i) a heavy chain variable (VH) region incorporating the following CDRs:
HC-CDR1 having the amino acid sequence of SEQ ID NO:290
HC-CDR2 having the amino acid sequence of SEQ ID NO:291
HC-CDR3 having the amino acid sequence of SEQ ID NO:278; and
(ii) a light chain variable (VL) region incorporating the following CDRs:
LC-CDR1 having the amino acid sequence of SEQ ID NO:41
LC-CDR2 having the amino acid sequence of SEQ ID NO:295
LC-CDR3 having the amino acid sequence of SEQ ID NO:43.

In some embodiments the antigen-binding molecule comprises:
(i) a heavy chain variable (VH) region incorporating the following CDRs:
HC-CDR1 having the amino acid sequence of SEQ ID NO:290
HC-CDR2 having the amino acid sequence of SEQ ID NO:291
HC-CDR3 having the amino acid sequence of SEQ ID NO:278; and
(ii) a light chain variable (VL) region incorporating the following CDRs:
LC-CDR1 having the amino acid sequence of SEQ ID NO:41
LC-CDR2 having the amino acid sequence of SEQ ID NO:300
LC-CDR3 having the amino acid sequence of SEQ ID NO:43.

In some embodiments the antigen-binding molecule comprises:
(i) a heavy chain variable (VH) region incorporating the following CDRs:
HC-CDR1 having the amino acid sequence of SEQ ID NO:33
HC-CDR2 having the amino acid sequence of SEQ ID NO:277
HC-CDR3 having the amino acid sequence of SEQ ID NO:278; and
(ii) a light chain variable (VL) region incorporating the following CDRs:
LC-CDR1 having the amino acid sequence of SEQ ID NO:41
LC-CDR2 having the amino acid sequence of SEQ ID NO:42
LC-CDR3 having the amino acid sequence of SEQ ID NO:43.

In some embodiments the antigen-binding molecule comprises:
(i) a heavy chain variable (VH) region incorporating the following CDRs:
HC-CDR1 having the amino acid sequence of SEQ ID NO:33
HC-CDR2 having the amino acid sequence of SEQ ID NO:286
HC-CDR3 having the amino acid sequence of SEQ ID NO:278; and
(ii) a light chain variable (VL) region incorporating the following CDRs:
LC-CDR1 having the amino acid sequence of SEQ ID NO:41
LC-CDR2 having the amino acid sequence of SEQ ID NO:42
LC-CDR3 having the amino acid sequence of SEQ ID NO:43.

In some embodiments the antigen-binding molecule comprises:
(i) a heavy chain variable (VH) region incorporating the following CDRs:
HC-CDR1 having the amino acid sequence of SEQ ID NO:290
HC-CDR2 having the amino acid sequence of SEQ ID NO:291
HC-CDR3 having the amino acid sequence of SEQ ID NO:278; and
(ii) a light chain variable (VL) region incorporating the following CDRs:
LC-CDR1 having the amino acid sequence of SEQ ID NO:41

LC-CDR2 having the amino acid sequence of SEQ ID NO:42

LC-CDR3 having the amino acid sequence of SEQ ID NO:43.

In some embodiments the antigen-binding molecule comprises:
- (i) a heavy chain variable (VH) region incorporating the following CDRs:
  - HC-CDR1 having the amino acid sequence of SEQ ID NO:290
  - HC-CDR2 having the amino acid sequence of SEQ ID NO:291
  - HC-CDR3 having the amino acid sequence of SEQ ID NO:278; and
- (ii) a light chain variable (VL) region incorporating the following CDRs:
  - LC-CDR1 having the amino acid sequence of SEQ ID NO:41
  - LC-CDR2 having the amino acid sequence of SEQ ID NO:300
  - LC-CDR3 having the amino acid sequence of SEQ ID NO:43.

In some embodiments the antigen-binding molecule comprises:
- (i) a heavy chain variable (VH) region incorporating the following CDRs:
  - HC-CDR1 having the amino acid sequence of SEQ ID NO:33
  - HC-CDR2 having the amino acid sequence of SEQ ID NO:34
  - HC-CDR3 having the amino acid sequence of SEQ ID NO:35; and
- (ii) a light chain variable (VL) region incorporating the following CDRs:
  - LC-CDR1 having the amino acid sequence of SEQ ID NO:41
  - LC-CDR2 having the amino acid sequence of SEQ ID NO:42
  - LC-CDR3 having the amino acid sequence of SEQ ID NO:43.

In some embodiments the antigen-binding molecule comprises:
- (i) a heavy chain variable (VH) region incorporating the following CDRs:
  - HC-CDR1 having the amino acid sequence of SEQ ID NO:33
  - HC-CDR2 having the amino acid sequence of SEQ ID NO:34
  - HC-CDR3 having the amino acid sequence of SEQ ID NO:35; and
- (ii) a light chain variable (VL) region incorporating the following CDRs:
  - LC-CDR1 having the amino acid sequence of SEQ ID NO:41
  - LC-CDR2 having the amino acid sequence of SEQ ID NO:67
  - LC-CDR3 having the amino acid sequence of SEQ ID NO:43.

In some embodiments the antigen-binding molecule comprises:
- (i) a heavy chain variable (VH) region incorporating the following CDRs:
  - HC-CDR1 having the amino acid sequence of SEQ ID NO:53
  - HC-CDR2 having the amino acid sequence of SEQ ID NO:34
  - HC-CDR3 having the amino acid sequence of SEQ ID NO:35; and
- (ii) a light chain variable (VL) region incorporating the following CDRs:
  - LC-CDR1 having the amino acid sequence of SEQ ID NO:41
  - LC-CDR2 having the amino acid sequence of SEQ ID NO:58
  - LC-CDR3 having the amino acid sequence of SEQ ID NO:43.

In some embodiments the antigen-binding molecule comprises:
- (i) a heavy chain variable (VH) region incorporating the following CDRs:
  - HC-CDR1 having the amino acid sequence of SEQ ID NO:72
  - HC-CDR2 having the amino acid sequence of SEQ ID NO:73
  - HC-CDR3 having the amino acid sequence of SEQ ID NO:74; and
- (ii) a light chain variable (VL) region incorporating the following CDRs:
  - LC-CDR1 having the amino acid sequence of SEQ ID NO:80
  - LC-CDR2 having the amino acid sequence of SEQ ID NO:81
  - LC-CDR3 having the amino acid sequence of SEQ ID NO:82.

In some embodiments the antigen-binding molecule comprises:
- (i) a heavy chain variable (VH) region incorporating the following CDRs:
  - HC-CDR1 having the amino acid sequence of SEQ ID NO:88
  - HC-CDR2 having the amino acid sequence of SEQ ID NO:89
  - HC-CDR3 having the amino acid sequence of SEQ ID NO:90; and
- (ii) a light chain variable (VL) region incorporating the following CDRs:
  - LC-CDR1 having the amino acid sequence of SEQ ID NO:96
  - LC-CDR2 having the amino acid sequence of SEQ ID NO:97
  - LC-CDR3 having the amino acid sequence of SEQ ID NO:98.

In some embodiments the antigen-binding molecule comprises:
- (i) a heavy chain variable (VH) region incorporating the following CDRs:
  - HC-CDR1 having the amino acid sequence of SEQ ID NO:88
  - HC-CDR2 having the amino acid sequence of SEQ ID NO:89
  - HC-CDR3 having the amino acid sequence of SEQ ID NO:90; and
- (ii) a light chain variable (VL) region incorporating the following CDRs:
  - LC-CDR1 having the amino acid sequence of SEQ ID NO:137
  - LC-CDR2 having the amino acid sequence of SEQ ID NO:138
  - LC-CDR3 having the amino acid sequence of SEQ ID NO:139.

In some embodiments the antigen-binding molecule comprises:

(i) a heavy chain variable (VH) region incorporating the following CDRs:
HC-CDR1 having the amino acid sequence of SEQ ID NO:33
HC-CDR2 having the amino acid sequence of SEQ ID NO:107
HC-CDR3 having the amino acid sequence of SEQ ID NO:108,
or a variant thereof in which one or two or three amino acids in one or more of HC-CDR1, HC-CDR2, or HC-CDR3 are substituted with another amino acid; and
(ii) a light chain variable (VL) region incorporating the following CDRs:
LC-CDR1 having the amino acid sequence of SEQ ID NO:114
LC-CDR2 having the amino acid sequence of SEQ ID NO:67
LC-CDR3 having the amino acid sequence of SEQ ID NO:115.

In some embodiments the antigen-binding molecule comprises:
(i) a heavy chain variable (VH) region incorporating the following CDRs:
HC-CDR1 having the amino acid sequence of SEQ ID NO:120
HC-CDR2 having the amino acid sequence of SEQ ID NO:121
HC-CDR3 having the amino acid sequence of SEQ ID NO:122; and
(ii) a light chain variable (VL) region incorporating the following CDRs:
LC-CDR1 having the amino acid sequence of SEQ ID NO:127
LC-CDR2 having the amino acid sequence of SEQ ID NO:128
LC-CDR3 having the amino acid sequence of SEQ ID NO:129.

In some embodiments the antigen-binding molecule comprises:
(i) a heavy chain variable (VH) region incorporating the following CDRs:
HC-CDR1 having the amino acid sequence of SEQ ID NO:144
HC-CDR2 having the amino acid sequence of SEQ ID NO:145
HC-CDR3 having the amino acid sequence of SEQ ID NO:146; and
(ii) a light chain variable (VL) region incorporating the following CDRs:
LC-CDR1 having the amino acid sequence of SEQ ID NO:151
LC-CDR2 having the amino acid sequence of SEQ ID NO:152
LC-CDR3 having the amino acid sequence of SEQ ID NO:153.

In some embodiments the antigen-binding molecule comprises:
(i) a heavy chain variable (VH) region incorporating the following CDRs:
HC-CDR1 having the amino acid sequence of SEQ ID NO:158
HC-CDR2 having the amino acid sequence of SEQ ID NO:159
HC-CDR3 having the amino acid sequence of SEQ ID NO:160; and
(ii) a light chain variable (VL) region incorporating the following CDRs:
LC-CDR1 having the amino acid sequence of SEQ ID NO:165
LC-CDR2 having the amino acid sequence of SEQ ID NO:152
LC-CDR3 having the amino acid sequence of SEQ ID NO:153.

In some embodiments the antigen-binding molecule comprises:
(i) a heavy chain variable (VH) region incorporating the following CDRs:
HC-CDR1 having the amino acid sequence of SEQ ID NO:169
HC-CDR2 having the amino acid sequence of SEQ ID NO:170
HC-CDR3 having the amino acid sequence of SEQ ID NO:171; and
(ii) a light chain variable (VL) region incorporating the following CDRs:
LC-CDR1 having the amino acid sequence of SEQ ID NO:177
LC-CDR2 having the amino acid sequence of SEQ ID NO:178
LC-CDR3 having the amino acid sequence of SEQ ID NO:179.

In some embodiments the antigen-binding molecule comprises:
(i) a heavy chain variable (VH) region incorporating the following CDRs:
HC-CDR1 having the amino acid sequence of SEQ ID NO:72
HC-CDR2 having the amino acid sequence of SEQ ID NO:184
HC-CDR3 having the amino acid sequence of SEQ ID NO:246; and
(ii) a light chain variable (VL) region incorporating the following CDRs:
LC-CDR1 having the amino acid sequence of SEQ ID NO:247
LC-CDR2 having the amino acid sequence of SEQ ID NO:178
LC-CDR3 having the amino acid sequence of SEQ ID NO:190.

In some embodiments the antigen-binding molecule comprises:
(i) a heavy chain variable (VH) region incorporating the following CDRs:
HC-CDR1 having the amino acid sequence of SEQ ID NO:72
HC-CDR2 having the amino acid sequence of SEQ ID NO:184
HC-CDR3 having the amino acid sequence of SEQ ID NO:185; and
(ii) a light chain variable (VL) region incorporating the following CDRs:
LC-CDR1 having the amino acid sequence of SEQ ID NO:189
LC-CDR2 having the amino acid sequence of SEQ ID NO:178
LC-CDR3 having the amino acid sequence of SEQ ID NO:190.

In some embodiments the antigen-binding molecule comprises:
(i) a heavy chain variable (VH) region incorporating the following CDRs:
HC-CDR1 having the amino acid sequence of SEQ ID NO:72

HC-CDR2 having the amino acid sequence of SEQ ID NO:184
HC-CDR3 having the amino acid sequence of SEQ ID NO:195; and
(ii) a light chain variable (VL) region incorporating the following CDRs:
LC-CDR1 having the amino acid sequence of SEQ ID NO:197
LC-CDR2 having the amino acid sequence of SEQ ID NO:178
LC-CDR3 having the amino acid sequence of SEQ ID NO:190.

In some embodiments the antigen-binding molecule comprises:
(i) a heavy chain variable (VH) region incorporating the following CDRs:
HC-CDR1 having the amino acid sequence of SEQ ID NO:72
HC-CDR2 having the amino acid sequence of SEQ ID NO:184
HC-CDR3 having the amino acid sequence of SEQ ID NO:200; and
(ii) a light chain variable (VL) region incorporating the following CDRs:
LC-CDR1 having the amino acid sequence of SEQ ID NO:203
LC-CDR2 having the amino acid sequence of SEQ ID NO:178
LC-CDR3 having the amino acid sequence of SEQ ID NO:190.

In some embodiments the antigen-binding molecule comprises:
a VH region comprising an amino acid sequence having at least 70% sequence identity to the amino acid sequence of SEQ ID NO:289; and
a VL region comprising an amino acid sequence having at least 70% sequence identity to the amino acid sequence of SEQ ID NO:310;
or
a VH region comprising an amino acid sequence having at least 70% sequence identity to the amino acid sequence of SEQ ID NO:289; and
a VL region comprising an amino acid sequence having at least 70% sequence identity to the amino acid sequence of one of SEQ ID NO:294, SEQ ID NO:297 or SEQ ID NO:299;
or
a VH region comprising an amino acid sequence having at least 70% sequence identity to the amino acid sequence of SEQ ID NO:289; and
a VL region comprising an amino acid sequence having at least 70% sequence identity to the amino acid sequence of SEQ ID NO:294;
or
a VH region comprising an amino acid sequence having at least 70% sequence identity to the amino acid sequence of SEQ ID NO:289; and
a VL region comprising an amino acid sequence having at least 70% sequence identity to the amino acid sequence of SEQ ID NO:297;
or
a VH region comprising an amino acid sequence having at least 70% sequence identity to the amino acid sequence of SEQ ID NO:289; and
a VL region comprising an amino acid sequence having at least 70% sequence identity to the amino acid sequence of SEQ ID NO:299;
or
a VH region comprising an amino acid sequence having at least 70% sequence identity to the amino acid sequence of SEQ ID NO:289; and
a VL region comprising an amino acid sequence having at least 70% sequence identity to the amino acid sequence of SEQ ID NO:301;
or
a VH region comprising an amino acid sequence having at least 70% sequence identity to the amino acid sequence of SEQ ID NO:289; and
a VL region comprising an amino acid sequence having at least 70% sequence identity to the amino acid sequence of SEQ ID NO:302;
or
a VH region comprising an amino acid sequence having at least 70% sequence identity to the amino acid sequence of SEQ ID NO:289; and
a VL region comprising an amino acid sequence having at least 70% sequence identity to the amino acid sequence of SEQ ID NO:303;
or
a VH region comprising an amino acid sequence having at least 70% sequence identity to the amino acid sequence of SEQ ID NO:276; and
a VL region comprising an amino acid sequence having at least 70% sequence identity to the amino acid sequence of SEQ ID NO:282;
or
a VH region comprising an amino acid sequence having at least 70% sequence identity to the amino acid sequence of SEQ ID NO:285; and
a VL region comprising an amino acid sequence having at least 70% sequence identity to the amino acid sequence of SEQ ID NO:287;
a VH region comprising an amino acid sequence having at least 70% sequence identity to the amino acid sequence of SEQ ID NO:32; and
a VL region comprising an amino acid sequence having at least 70% sequence identity to the amino acid sequence of SEQ ID NO:40;
or
a VH region comprising an amino acid sequence having at least 70% sequence identity to the amino acid sequence of SEQ ID NO:52; and
a VL region comprising an amino acid sequence having at least 70% sequence identity to the amino acid sequence of SEQ ID NO:57;
or
a VH region comprising an amino acid sequence having at least 70% sequence identity to the amino acid sequence of SEQ ID NO:62; and
a VL region comprising an amino acid sequence having at least 70% sequence identity to the amino acid sequence of SEQ ID NO:66;
or
a VH region comprising an amino acid sequence having at least 70% sequence identity to the amino acid sequence of SEQ ID NO:48; and
a VL region comprising an amino acid sequence having at least 70% sequence identity to the amino acid sequence of SEQ ID NO:50;
or.
a VH region comprising an amino acid sequence having at least 70% sequence identity to the amino acid sequence of SEQ ID NO:87; and a VL region comprising an amino acid sequence having at least 70% sequence identity to the amino acid sequence of SEQ ID NO:95;

or a VH region comprising an amino acid sequence having at least 70% sequence identity to the amino acid sequence of SEQ ID NO:106; and a VL region comprising an amino acid sequence having at least 70% sequence identity to the amino acid sequence of SEQ ID NO:113;

or a VH region comprising an amino acid sequence having at least 70% sequence identity to the amino acid sequence of SEQ ID NO:143; and a VL region comprising an amino acid sequence having at least 70% sequence identity to the amino acid sequence of SEQ ID NO:150;

or a VH region comprising an amino acid sequence having at least 70% sequence identity to the amino acid sequence of SEQ ID NO:157; and a VL region comprising an amino acid sequence having at least 70% sequence identity to the amino acid sequence of SEQ ID NO:164;

or a VH region comprising an amino acid sequence having at least 70% sequence identity to the amino acid sequence of SEQ ID NO:71; and a VL region comprising an amino acid sequence having at least 70% sequence identity to the amino acid sequence of SEQ ID NO:79;

or a VH region comprising an amino acid sequence having at least 70% sequence identity to the amino acid sequence of SEQ ID NO:102; and a VL region comprising an amino acid sequence having at least 70% sequence identity to the amino acid sequence of SEQ ID NO:104;

or a VH region comprising an amino acid sequence having at least 70% sequence identity to the amino acid sequence of SEQ ID NO:119; and a VL region comprising an amino acid sequence having at least 70% sequence identity to the amino acid sequence of SEQ ID NO:126;

or a VH region comprising an amino acid sequence having at least 70% sequence identity to the amino acid sequence of SEQ ID NO:183; and a VL region comprising an amino acid sequence having at least 70% sequence identity to the amino acid sequence of SEQ ID NO:188;

or a VH region comprising an amino acid sequence having at least 70% sequence identity to the amino acid sequence of SEQ ID NO:194; and a VL region comprising an amino acid sequence having at least 70% sequence identity to the amino acid sequence of SEQ ID NO:196;

or a VH region comprising an amino acid sequence having at least 70% sequence identity to the amino acid sequence of SEQ ID NO:199; and a VL region comprising an amino acid sequence having at least 70% sequence identity to the amino acid sequence of SEQ ID NO:202;

or a VH region comprising an amino acid sequence having at least 70% sequence identity to the amino acid sequence of SEQ ID NO:133; and a VL region comprising an amino acid sequence having at least 70% sequence identity to the amino acid sequence of SEQ ID NO:136;

or a VH region comprising an amino acid sequence having at least 70% sequence identity to the amino acid sequence of SEQ ID NO:168; and a VL region comprising an amino acid sequence having at least 70% sequence identity to the amino acid sequence of SEQ ID NO:176.

In some embodiments the antigen-binding molecule is capable of binding to human VISTA and one or more of: mouse VISTA and cynomolgus macaque VISTA.

Also provided is an antigen-binding molecule, optionally isolated, comprising (i) an antigen-binding molecule according to the present invention, and (ii) an antigen-binding molecule capable of binding to an antigen other than VISTA.

In some embodiments the antigen-binding molecule is capable of binding to cells expressing VISTA at the cell surface.

In some embodiments the antigen-binding molecule is capable of inhibiting interaction between VISTA and a binding partner for VISTA.

In some embodiments the antigen-binding molecule is capable of inhibiting VISTA-mediated signalling.

In some embodiments the antigen-binding molecule is capable of increasing proliferation and/or cytokine production by effector immune cells.

Also provided is a chimeric antigen receptor (CAR) comprising an antigen-binding molecule according to the present invention.

Also provided is a nucleic acid, or a plurality of nucleic acids, optionally isolated, encoding an antigen-binding molecule or a CAR according to the present invention.

Also provided is an expression vector, or a plurality of expression vectors, comprising a nucleic acid or a plurality of nucleic acids according to the present invention.

Also provided is a cell comprising an antigen-binding molecule, CAR, nucleic acid or a plurality of nucleic acids, expression vector or a plurality of expression vectors according to the present invention.

Also provided is a method comprising culturing a cell comprising a nucleic acid or a plurality of nucleic acids, or an expression vector or a plurality of expression vectors according to the invention, under conditions suitable for expression of the antigen-binding molecule or CAR from the nucleic acid(s) or expression vector(s).

Also provided is a composition comprising an antigen-binding molecule, CAR, nucleic acid or a plurality of nucleic acids, expression vector or plurality of expression vectors, or a cell according to the present invention.

In some embodiments the composition additionally comprises an agent capable of inhibiting signalling mediated by an immune checkpoint molecule other than VISTA, optionally wherein the immune checkpoint inhibitor other than VISTA is selected from PD-1, CTLA-4, LAG-3, TIM-3, TIGIT and BTLA.

Also provided is an antigen-binding molecule, CAR, nucleic acid or a plurality of nucleic acids, expression vector or a plurality of expression vectors, cell, or composition according to the invention for use in a method of medical treatment or prophylaxis.

Also provided is an antigen-binding molecule, CAR, nucleic acid or a plurality of nucleic acids, expression vector or a plurality of expression vectors, cell, or composition of the invention for use in a method of treatment or prevention of a cancer or an infectious disease.

Also provided is the use of an antigen-binding molecule, CAR, nucleic acid or a plurality of nucleic acids, expression vector or a plurality of expression vectors, cell, or composition of the invention in the manufacture of a medicament for use in a method of treatment or prevention of a cancer or an infectious disease.

Also provided is a method of treating or preventing a cancer or an infectious disease, comprising administering to a subject a therapeutically or prophylactically effective amount of an antigen-binding molecule, CAR, nucleic acid or a plurality of nucleic acids, expression vector or a plurality of expression vectors, cell, or composition of the invention.

In some embodiments the cancer is selected from: a cancer comprising cells expressing VISTA, a cancer comprising infiltration of cells expressing VISTA, a cancer comprising cancer cells expressing VISTA, a hematological cancer, leukemia, acute myeloid leukemia, lymphoma, B cell lymphoma, T cell lymphoma, multiple myeloma, mesothelioma, a solid tumor, lung cancer, non-small cell lung carcinoma, gastric cancer, gastric carcinoma, colorectal cancer, colorectal carcinoma, colorectal adenocarcinoma, uterine cancer, uterine corpus endometrial carcinoma, breast cancer, triple negative breast invasive carcinoma, liver cancer, hepatocellular carcinoma, pancreatic cancer, pancreatic ductal adenocarcinoma, thyroid cancer, thymoma, skin cancer, melanoma, cutaneous melanoma, kidney cancer, renal cell carcinoma, renal papillary cell carcinoma, head and neck cancer, squamous cell carcinoma of the head and neck (SCCHN), ovarian cancer, ovarian carcinoma, ovarian serous cystadenocarcinoma, prostate cancer and/or prostate adenocarcinoma.

Also provided is an antigen-binding molecule, CAR, nucleic acid or a plurality of nucleic acids, expression vector or a plurality of expression vectors, cell, or composition of the invention for use in a method of treatment or prevention of a disease in which myeloid-derived suppressor cells (MDSCs) are pathologically implicated.

Also provided is the use of an antigen-binding molecule, CAR, nucleic acid or a plurality of nucleic acids, expression vector or a plurality of expression vectors, cell, or composition of the invention in the manufacture of a medicament for use in a method of treatment or prevention of a disease in which myeloid-derived suppressor cells (MDSCs) are pathologically implicated.

Also provided is a method of treating or preventing a disease in which myeloid-derived suppressor cells (MDSCs) are pathologically implicated, comprising administering to a subject a therapeutically or prophylactically effective amount of an antigen-binding molecule, CAR, nucleic acid or a plurality of nucleic acids, expression vector or a plurality of expression vectors, cell, or composition of the invention.

In some embodiments the methods additionally comprise administration of an agent capable of inhibiting signalling mediated by an immune checkpoint molecule other than VISTA, optionally wherein the immune checkpoint molecule other than VISTA is selected from PD-1, CTLA-4, LAG-3, TIM-3, TIGIT or BTLA.

Also provided is a method of inhibiting VISTA-mediated signalling, comprising contacting VISTA-expressing cells with an antigen-binding molecule according to the invention.

Also provided is a method for inhibiting the activity of myeloid-derived suppressor cells (MDSCs), the method comprising contacting MDSCs with antigen-binding molecule according to the invention.

Also provided is a method for increasing the number or activity of effector immune cells, the method comprising inhibiting the activity of VISTA-expressing cells with an antigen-binding molecule according to the invention.

Also provided is an in vitro complex, optionally isolated, comprising an antigen-binding molecule according to the invention bound to VISTA.

Also provided is a method comprising contacting a sample containing, or suspected to contain, VISTA with an antigen-binding molecule according to the invention, and detecting the formation of a complex of the antigen-binding molecule with VISTA.

Also provided is a method of selecting or stratifying a subject for treatment with a VISTA-targeted agent, the method comprising contacting, in vitro, a sample from the subject with an antigen-binding molecule according to the invention and detecting the formation of a complex of the antigen-binding molecule with VISTA.

Also provided is the use of an antigen-binding molecule according to the invention as an in vitro or in vivo diagnostic or prognostic agent.

Also provided is the use of an antigen-binding molecule according to the invention in a method for detecting, localizing or imaging a cancer, optionally wherein the cancer is selected from: a cancer comprising cells expressing VISTA, a cancer comprising infiltration of cells expressing VISTA, a cancer comprising cancer cells expressing VISTA, a hematological cancer, leukemia, acute myeloid leukemia, lymphoma, B cell lymphoma, T cell lymphoma, multiple myeloma, mesothelioma, a solid tumor, lung cancer, non-small cell lung carcinoma, gastric cancer, gastric carcinoma, colorectal cancer, colorectal carcinoma, colorectal adenocarcinoma, uterine cancer, uterine corpus endometrial carcinoma, breast cancer, triple negative breast invasive carcinoma, liver cancer, hepatocellular carcinoma, pancreatic cancer, pancreatic ductal adenocarcinoma, thyroid cancer, thymoma, skin cancer, melanoma, cutaneous melanoma, kidney cancer, renal cell carcinoma, renal papillary cell carcinoma, head and neck cancer, squamous cell carcinoma of the head and neck (SCCHN), ovarian cancer, ovarian carcinoma, ovarian serous cystadenocarcinoma, prostate cancer and/or prostate adenocarcinoma.

DESCRIPTION

The present invention relates to novel VISTA-binding molecules having novel and/or improved properties as compared to known anti-VISTA antibodies.

The inventors generated antigen-binding molecules which bind to particular regions of interest in the extracellular region of VISTA. The VISTA-binding molecules of the present invention are provided with combinations of desirable biophysical and functional properties as compared to VISTA-binding antigen-binding molecules disclosed in the prior art.

In particular, VISTA-binding molecules described herein are demonstrated to be capable of antagonising VISTA-mediated signalling through a mechanism that does not require Fc-mediated functions. The inventors demonstrate that VISTA-binding molecules described herein comprising Fc which lack the ability to bind to Fcγ receptors and/or C1q are able to provide therapeutic anti-cancer effects in vivo.

The inventors establish for the first time that it is possible to antagonise VISTA-mediated signalling directly through a mechanism that does not require Fc-mediated effector function (e.g. ADCC/ADCP/CDC directed against VISTA-expressing cells).

The VISTA-binding molecules of the present disclosure target a region of VISTA that is different from the region targeted by known anti-VISTA antibodies. Antigen-binding molecules targeting the particular region of VISTA are able to antagonise VISTA-mediated signalling without the requirement for Fc-mediated effector functions.

VISTA-binding molecules disclosed herein are therefore useful for inhibiting VISTA-mediated signalling without depleting VISTA expressing cells. This is important, because VISTA is expressed on cells which it is not desirable to deplete. VISTA-binding molecules disclosed herein are thus able to inhibit VISTA-mediated signalling whilst minimising undesirable side effects.

VISTA-binding molecules disclosed herein are also advantageously shown to be capable of releasing T cells from VISTA-mediated suppression. Specifically, the VISTA-binding molecules disclosed herein are shown to be able to increase T cell proliferation, and production of e.g. IFNγ and TNFa from T cells cultured in the presence of VISTA or VISTA-expressing cells.

VISTA, Binding Partners and VISTA-Mediated Signalling

V-type immunoglobulin domain-containing suppressor of T-cell activation (VISTA; also known e.g. as B7-H5, SISP1, PD-1H) is the protein identified by UniProt Q9H7M9, having the amino acid sequence shown in SEQ ID NO:1 (Q9H7M9-1, v3). The structure and function of VISTA is described e.g. in Lines et al., Cancer Res. (2014) 74(7): 1924-1932, which is hereby incorporated by reference in its entirety. VISTA is a ~50 kDa single-pass type I transmembrane that functions as an immune checkpoint and is encoded by the C10orf54 gene. The extracellular domain of VISTA is homologous to PD-L1.

The N-terminal 32 amino acids of SEQ ID NO:1 constitutes a signal peptide, and so the mature form of VISTA (i.e. after processing to remove the signal peptide) has the amino acid sequence shown in SEQ ID NO:2. Positions 33 to 194 of SEQ ID NO:1 form the extracellular domain (SEQ ID NO:3), positions 195 to 215 form a transmembrane domain (SEQ ID NO:4), and positions 216 to 311 form the cytoplasmic domain (SEQ ID NO:5). The extracellular domain comprises an Ig-like V-type domain (positions 33 to 168 of SEQ ID NO:1, shown in SEQ ID NO:6).

In this specification "VISTA" refers to VISTA from any species and includes VISTA isoforms, fragments, variants (including mutants) or homologues from any species.

As used herein, a "fragment", "variant" or "homologue" of a protein may optionally be characterised as having at least 60%, preferably one of 70%, 75%, 80%, 85%, 90%, 91%, 92%, 93%, 94%, 95%, 96%, 97%, 98%, 99% or 100% amino acid sequence identity to the amino acid sequence of the reference protein (e.g. a reference isoform). In some embodiments fragments, variants, isoforms and homologues of a reference protein may be characterised by ability to perform a function performed by the reference protein.

A "fragment" generally refers to a fraction of the reference protein. A "variant" generally refers to a protein having an amino acid sequence comprising one or more amino acid substitutions, insertions, deletions or other modifications relative to the amino acid sequence of the reference protein, but retaining a considerable degree of sequence identity (e.g. at least 60%) to the amino acid sequence of the reference protein. An "isoform" generally refers to a variant of the reference protein expressed by the same species as the species of the reference protein. A "homologue" generally refers to a variant of the reference protein produced by a different species as compared to the species of the reference protein. Homologues include orthologues.

A "fragment" may be of any length (by number of amino acids), although may optionally be at least 20% of the length of the reference protein (that is, the protein from which the fragment is derived) and may have a maximum length of one of 50%, 75%, 80%, 85%, 90%, 91%, 92%, 93%, 94%, 95%, 96%, 97%, 98%, or 99% of the length of the reference protein. A fragment of VISTA may have a minimum length of one of 10, 20, 30, 40, 50, 100, 150, 200, 250 or 300 amino acids, and may have a maximum length of one of 20, 30, 40, 50, 100, 150, 200, 250 or 300 amino acids.

In some embodiments, the VISTA is VISTA from a mammal (e.g. a primate (rhesus, cynomolgous, non-human primate or human) and/or a rodent (e.g. rat or murine) VISTA). Isoforms, fragments, variants or homologues of VISTA may optionally be characterised as having at least 70%, preferably one of 80%, 85%, 90%, 91%, 92%, 93%, 94%, 95%, 96%, 97%, 98%, 99% or 100% amino acid sequence identity to the amino acid sequence of an immature or mature VISTA isoform from a given species, e.g. human.

Isoforms, fragments, variants or homologues may optionally be functional isoforms, fragments, variants or homologues, e.g. having a functional property/activity of the reference VISTA, as determined by analysis by a suitable assay for the functional property/activity. For example, an isoform, fragment, variant or homologue of VISTA may e.g. display association with VSIG-3 and/or PSGL-1.

In some embodiments, the VISTA comprises, or consists of, an amino acid sequence having at least 70%, preferably one of 80%, 85%, 90%, 91%, 92%, 93%, 94%, 95%, 96%, 97%, 98%, 99% or 100% amino acid sequence identity to SEQ ID NO:1 or 2. In some embodiments, a fragment of VISTA comprises, or consists of, an amino acid sequence having at least 70%, preferably one of 80%, 85%, 90%, 91%, 92%, 93%, 94%, 95%, 96%, 97%, 98%, 99% or 100% amino acid sequence identity to one of SEQ ID NOs:2, 3 or 6.

VISTA is a member of the B7 family of proteins, and is primarily expressed by leukocytes, and in particular CD14+ monocytes (including monocyte-derived suppressor cells (MDSCs)) and CD33+ myeloid cells. VISTA is also expressed by CD56+ NK cells, dendritic cells, and to a lesser extent on CD4+ and CD8+ T cells. VISTA is highly expressed on MDSCs, in particular tumor-infiltrating MDSCs, and also on tumor-infiltrating myeloid DCs (Le Mercier et al, Cancer Res. (2014) 74(7):1933-44), as well as on tumor-associated macrophages (TAMs) and neutrophils.

There is evidence that VISTA can act as both a ligand and a receptor on T cells to inhibit T cell effector function and maintain peripheral tolerance; tumors engineered to overexpress VISTA evade immune control and grow faster than tumors which do not overexpress VISTA (Wang et al., Journal of Experimental Medicine. (2011) 208 (3): 577-92; Lines et al., Cancer Res. (2014) 74(7): 1924-1932). VISTA has been shown to be a co-inhibitory receptor on CD4+ T cells or a co-inhibitory ligand for T cells. VISTA$^{-/-}$ CD4+ T cells have been reported to display stronger antigen-specific proliferation and cytokine production than wildtype CD4+ T cells, suggesting that VISTA functions as an inhibitory receptor on CD4+ T cells. Blocking VISTA function using monoclonal anti-VISTA antibody has been shown to enhance infiltration, proliferation and effector function of tumor-reactive T cells within the tumor microenvironment (Le Mercier et al, Cancer Res. (2014) 74(7):1933-4).

VISTA has been proposed to interact with VSIG-3 (IGSF11)—see e.g. Wang et al., J Immunol (2017), 198 (1 Supplement) 154.1, which is hereby incorporated by reference in its entirety. Engagement of VSIG-3 through VISTA on activated T cells inhibits T cell proliferation, and reduces production of cytokines and chemokines such as IFN-γ, IL-2, IL-17, CCL5/RANTES, CCL3/MIP-1a, and CXCL11/I-TAC.

VSIG-3 is the protein identified by UniProt Q5DX21. Alternative splicing of mRNA encoded by the human IGSF11 gene yields three different isoforms: isoform 1 (UniProt: Q5DX21-1, v3; SEQ ID NO:7); isoform 2 (UniProt: Q5DX21-2; SEQ ID NO:8), which comprises a different sequence to SEQ ID NO:7 at positions 1 to 17; and isoform 3 (UniProt: Q5DX21-3; SEQ ID NO:9), which comprises a different sequence to SEQ ID NO:7 at positions 1 to 17, and which also comprises a different sequence to SEQ ID NO:7 at positions 211-235.

The N-terminal 22 amino acids of SEQ ID NOs:7, 8 and 9 constitute a signal peptide, and so the mature form of VSIG-3 isoforms 1, 2 and 3 (i.e. after processing to remove the signal peptide) have the amino acid sequences shown in SEQ ID NOs:10, 11 and 12, respectively. Positions 23 to 241 of SEQ ID NOs:7, and 8 form the extracellular domain of VSIG-3 isoforms 1 and 2 (SEQ ID NO:13), and positions 23 to 216 of SEQ ID NO:9 form the extracellular domain of VSIG-3 isoform 3 (SEQ ID NO:14). The transmembrane domain of VSIG-3 is shown in SEQ ID NO:15, and the cytoplasmic domain is shown in SEQ ID NO:16. The extracellular domain comprises an Ig-like V-type domain (shown in SEQ ID NO:17), and the extracellular domains of VSIG-3 isoforms 1 and 2 additionally comprise an Ig-like C2-type domain (shown in SEQ ID NO:18).

In this specification "VSIG-3" refers to VSIG-3 from any species and includes VSIG-3 isoforms, fragments, variants (including mutants) or homologues from any species.

A fragment of VSIG-3 may have a minimum length of one of 10, 20, 30, 40, 50, 100, 150, 200, 250, 300, 350 or 400 amino acids, and may have a maximum length of one of 20, 30, 40, 50, 100, 150, 200, 250, 300, 350 or 400 amino acids.

In some embodiments, the VSIG-3 is VSIG-3 from a mammal (e.g. a primate (rhesus, cynomolgus, non-human primate or human) and/or a rodent (e.g. rat or murine) VSIG-3). Isoforms, fragments, variants or homologues of VSIG-3 may optionally be characterised as having at least 70%, preferably one of 80%, 85%, 90%, 91%, 92%, 93%, 94%, 95%, 96%, 97%, 98%, 99% or 100% amino acid sequence identity to the amino acid sequence of an immature or mature VSIG-3 isoform from a given species, e.g. human.

Isoforms, fragments, variants or homologues may optionally be functional isoforms, fragments, variants or homologues, e.g. having a functional property/activity of the reference VSIG-3, as determined by analysis by a suitable assay for the functional property/activity. For example, an isoform, fragment, variant or homologue of VSIG-3 may e.g. display association with VISTA.

In some embodiments, the VSIG-3 comprises, or consists of, an amino acid sequence having at least 70%, preferably one of 80%, 85%, 90%, 91%, 92%, 93%, 94%, 95%, 96%, 97%, 98%, 99% or 100% amino acid sequence identity to one of SEQ ID NOs:7 to 12. In some embodiments, a fragment of VSIG-3 comprises, or consists of, an amino acid sequence having at least 70%, preferably one of 80%, 85%, 90%, 91%, 92%, 93%, 94%, 95%, 96%, 97%, 98%, 99% or 100% amino acid sequence identity to one of SEQ ID NOs:10 to 14, 17 or 18.

VISTA has also been proposed to interact with VSIG-8—see e.g. WO/2016/090347 A1. VSIG-8 is the protein identified by UniProt PODPA2 (SEQ ID NO:19). The N-terminal 21 amino acids of SEQ ID NO:19 constitutes a signal peptide, and so the mature form of VSIG-8 (i.e. after processing to remove the signal peptide) has the amino acid sequence shown in SEQ ID NO:20. Positions 22 to 263 of SEQ ID NO:19 form the extracellular domain of VSIG-8 (SEQ ID NO:21). The transmembrane domain of VSIG-8 is shown in SEQ ID NO:22, and the cytoplasmic domain is shown in SEQ ID NO:23. The extracellular domain comprises an Ig-like V-type domain 1 (shown in SEQ ID NO:24), and an Ig-like V-type domain 2 (shown in SEQ ID NO:25).

In this specification "VSIG-8" refers to VSIG-8 from any species and includes VSIG-8 isoforms, fragments, variants (including mutants) or homologues from any species.

A fragment of VSIG-8 may have a minimum length of one of 10, 20, 30, 40, 50, 100, 150, 200, 250, 300, 350 or 400 amino acids, and may have a maximum length of one of 20, 30, 40, 50, 100, 150, 200, 250, 300, 350 or 400 amino acids.

In some embodiments, the VSIG-8 is VSIG-8 from a mammal (e.g. a primate (rhesus, cynomolgus, non-human primate or human) and/or a rodent (e.g. rat or murine) VSIG-8). Isoforms, fragments, variants or homologues of VSIG-8 may optionally be characterised as having at least 70%, preferably one of 80%, 85%, 90%, 91%, 92%, 93%, 94%, 95%, 96%, 97%, 98%, 99% or 100% amino acid sequence identity to the amino acid sequence of an immature or mature VSIG-8 isoform from a given species, e.g. human.

Isoforms, fragments, variants or homologues may optionally be functional isoforms, fragments, variants or homologues, e.g. having a functional property/activity of the reference VSIG-8, as determined by analysis by a suitable assay for the functional property/activity. For example, an isoform, fragment, variant or homologue of VSIG-8 may e.g. display association with VISTA.

In some embodiments, the VSIG-8 comprises, or consists of, an amino acid sequence having at least 70%, preferably one of 80%, 85%, 90%, 91%, 92%, 93%, 94%, 95%, 96%, 97%, 98%, 99% or 100% amino acid sequence identity to SEQ ID NO:19 or 20. In some embodiments, a fragment of VSIG-8 comprises, or consists of, an amino acid sequence having at least 70%, preferably one of 80%, 85%, 90%, 91%, 92%, 93%, 94%, 95%, 96%, 97%, 98%, 99% or 100% amino acid sequence identity to one of SEQ ID NOs:20, 21, 24 or 25.

VISTA has also been proposed to interact with PSGL-1—see e.g. WO 2018/132476 A1. PSGL-1 isoform 1 is the protein identified by UniProt Q14242-1 (SEQ ID NO:323). PSGL-1 isoform 2 is the protein identified by UniProt Q14242-2 (SEQ ID NO:324), and differs from PSGL-1 isoform 1 in that it comprises an additional 16 amino acids after position 1 of SEQ ID NO:323.

The N-terminal 17 amino acids of SEQ ID NO:323 constitutes a signal peptide, and so the mature form of PSGL-1 (i.e. after processing to remove the signal peptide) has the amino acid sequence shown in SEQ ID NO:325. Positions 18 to 320 of SEQ ID NO:323 form the extracellular domain of PSGL-1 (SEQ ID NO:326). The transmembrane domain of PSGL-1 is shown in SEQ ID NO:327, and the cytoplasmic domain is shown in SEQ ID NO:328. The extracellular domain comprises 12, 10 amino acid tandem repeats; the repeat region is shown in SEQ ID NO:329.

In this specification "PSGL-1" refers to PSGL-1 from any species and includes PSGL-1 isoforms, fragments, variants (including mutants) or homologues from any species.

A fragment of PSGL-1 may have a minimum length of one of 10, 20, 30, 40, 50, 100, 150, 200, 250, 300, 350 or 400 amino acids, and may have a maximum length of one of 20, 30, 40, 50, 100, 150, 200, 250, 300, 350 or 400 amino acids.

In some embodiments, the PSGL-1 is PSGL-1 from a mammal (e.g. a primate (rhesus, cynomolgous, non-human primate or human) and/or a rodent (e.g. rat or murine) PSGL-1). Isoforms, fragments, variants or homologues of PSGL-1 may optionally be characterised as having at least 70%, preferably one of 80%, 85%, 90%, 91%, 92%, 93%, 94%, 95%, 96%, 97%, 98%, 99% or 100% amino acid sequence identity to the amino acid sequence of an immature or mature PSGL-1 isoform from a given species, e.g. human.

Isoforms, fragments, variants or homologues may optionally be functional isoforms, fragments, variants or homologues, e.g. having a functional property/activity of the reference PSGL-1, as determined by analysis by a suitable assay for the functional property/activity. For example, an isoform, fragment, variant or homologue of PSGL-1 may e.g. display association with VISTA.

In some embodiments, the PSGL-1 comprises, or consists of, an amino acid sequence having at least 70%, preferably one of 80%, 85%, 90%, 91%, 92%, 93%, 94%, 95%, 96%, 97%, 98%, 99% or 100% amino acid sequence identity to SEQ ID NO:323 or 324. In some embodiments, a fragment of PSGL-1 comprises, or consists of, an amino acid sequence having at least 70%, preferably one of 80%, 85%, 90%, 91%, 92%, 93%, 94%, 95%, 96%, 97%, 98%, 99% or 100% amino acid sequence identity to one of SEQ ID NOs:325, 326 or 329.

Regions of Particular Interest on the Target Molecule

The antigen-binding molecules of the present invention were specifically designed to target regions of VISTA of particular interest. In a two-step approach, VISTA regions to be targeted were selected following analysis for predicted antigenicity, function and safety. Antibodies specific for the target regions of VISTA were then prepared using peptides corresponding to the target regions as immunogens to raise specific monoclonal antibodies, and subsequent screening to identify antibodies capable of binding to VISTA in the native state. This approach provides exquisite control over the antibody epitope.

The antigen-binding molecules of the present invention may be defined by reference to the region of VISTA which they bind to. The antigen-binding molecules of the present invention may bind to a particular region of interest of VISTA. In some embodiments the antigen-binding molecule may bind to a linear epitope of VISTA, consisting of a contiguous sequence of amino acids (i.e. an amino acid primary sequence). In some embodiments, the antigen-binding molecule may bind to a conformational epitope of VISTA, consisting of a discontinuous sequence of amino acids of the amino acid sequence.

In some embodiments, the antigen-binding molecule of the present invention binds to VISTA. In some embodiments, the antigen-binding molecule binds to the extracellular region of VISTA (e.g. the region shown in SEQ ID NO:3). In some embodiments, the antigen-binding molecule binds to the Ig-like V-type domain of VISTA (e.g. the region shown in SEQ ID NO:6). In some embodiments, the antigen-binding molecule binds to VISTA in the region corresponding to positions 61 to 162 of SEQ ID NO:1 (shown in SEQ ID NO:31).

In some embodiments, the antigen-binding molecule binds to the region of VISTA shown in SEQ ID NO:322. In some embodiments, the antigen-binding molecule binds to the region of VISTA shown in SEQ ID NO:26. In some embodiments, the antigen-binding molecule binds to the region of VISTA shown in SEQ ID NO:27. In some embodiments, the antigen-binding molecule binds to the region of VISTA shown in SEQ ID NO:28. In some embodiments, the antigen-binding molecule binds to the region of VISTA shown in SEQ ID NO:29. In some embodiments, the antigen-binding molecule binds to the region of VISTA shown in SEQ ID NO:30.

In some embodiments, the antigen-binding molecule does not bind to the region of VISTA shown in SEQ ID NO:271. In some embodiments, the antigen-binding molecule does not bind to the region of VISTA shown in SEQ ID NO:272. In some embodiments, the antigen-binding molecule does not bind to the region of VISTA shown in SEQ ID NO:273. In some embodiments, the antigen-binding molecule does not bind to the region of VISTA shown in SEQ ID NO:274. In some embodiments, the antigen-binding molecule does not bind to the region of VISTA shown in SEQ ID NO:275.

The region of a peptide/polypeptide to which an antibody binds can be determined by the skilled person using various methods well known in the art, including X-ray co-crystallography analysis of antibody-antigen complexes, peptide scanning, mutagenesis mapping, hydrogen-deuterium exchange analysis by mass spectrometry, phage display, competition ELISA and proteolysis-based 'protection' methods. Such methods are described, for example, in Gershoni et al., BioDrugs, 2007, 21(3):145-156, which is hereby incorporated by reference in its entirety.

In some embodiments the antigen-binding molecule is capable of binding the same region of VISTA, or an overlapping region of VISTA, to the region of VISTA which is bound by an antibody comprising the VH and VL sequences of one of antibody clones 4M2-C12, 4M2-B4, 4M2-C9, 4M2-D9, 4M2-D5, 4M2-A8, V4H1, V4H2, V4-C1, V4-C9, V4-C24, V4-C26, V4-C27, V4-C28, V4-C30, V4-C31, 2M1-B12, 2M1-D2, 1M2-D2, 13D5p, 13D5-1, 13D5-13, 5M1-A11 or 9M2-C12 described herein.

As used herein, a "peptide" refers to a chain of two or more amino acid monomers linked by peptide bonds. A peptide typically has a length in the region of about 2 to 50 amino acids. A "polypeptide" is a polymer chain of two or more peptides. Polypeptides typically have a length greater than about 50 amino acids.

In some embodiments, the antigen-binding molecule of the present invention is capable of binding to a polypeptide comprising, or consisting of, the amino acid sequence of one of SEQ ID NOs:1, 2, 3, 6 or 31.

In some embodiments, the antigen-binding molecule is capable of binding to a peptide/polypeptide comprising, or consisting of, the amino acid sequence of SEQ ID NO:322. In some embodiments, the antigen-binding molecule is capable of binding to a peptide/polypeptide comprising, or consisting of, the amino acid sequence of SEQ ID NO:26. In some embodiments, the antigen-binding molecule is capable of binding to a peptide/polypeptide comprising, or consisting of, the amino acid sequence of SEQ ID NO:27. In some embodiments, the antigen-binding molecule is capable of binding to a peptide/polypeptide comprising, or consisting of, the amino acid sequence of SEQ ID NO:28. In some embodiments, the antigen-binding molecule is capable of binding to a peptide/polypeptide comprising, or consisting of, the amino acid sequence of SEQ ID NO:29. In some embodiments, the antigen-binding molecule is capable of binding to a peptide/polypeptide comprising, or consisting of, the amino acid sequence of SEQ ID NO:30.

In some embodiments, the antigen-binding molecule is not capable of binding to a peptide consisting of the amino acid sequence of SEQ ID NO:271. In some embodiments, the antigen-binding molecule is not capable of binding to a peptide consisting of the amino acid sequence of SEQ ID NO:272. In some embodiments, the antigen-binding molecule is not capable of binding to a peptide consisting of the amino acid sequence of SEQ ID NO:273. In some embodiments, the antigen-binding molecule is not capable of binding to a peptide consisting of the amino acid sequence of SEQ ID NO:274. In some embodiments, the antigen-binding molecule is not capable of binding to a peptide consisting of the amino acid sequence of SEQ ID NO:275.

The ability of an antigen-binding molecule to bind to a given peptide/polypeptide can be analysed by methods well known to the skilled person, including analysis by ELISA, immunoblot (e.g. western blot), immunoprecipitation, Surface Plasmon Resonance (SPR; see e.g. Hearty et al., Methods Mol Biol (2012) 907:411-442) or Bio-Layer Interferometry (see e.g. Lad et al., (2015) J Biomol Screen 20(4): 498-507).

In embodiments where the antigen binding molecule is capable of binding to a peptide/polypeptide comprising a reference amino acid sequence, the peptide/polypeptide may comprise one or more additional amino acids at one or both ends of the reference amino acid sequence. In some embodiments the peptide/polypeptide comprises e.g. 1-5, 1-10, 1-20, 1-30, 1-40, 1-50, 5-10, 5-20, 5-30, 5-40, 5-50, 10-20, 10-30, 10-40, 10-50, 20-30, 20-40 or 20-50 additional amino acids at one or both ends of the reference amino acid sequence.

In some embodiments the additional amino acid(s) provided at one or both ends (i.e. the N-terminal and C-terminal ends) of the reference sequence correspond to the positions at the ends of the reference sequence in the context of the amino acid sequence of VISTA. By way of example, where the antigen-binding molecule is capable of binding to a peptide/polypeptide comprising the sequence of SEQ ID NO:26, and an additional two amino acids at the C-terminal end of SEQ ID NO:26, the additional two amino acids may be arginine and asparagine, corresponding to positions 90 and 91 of SEQ ID NO:1.

In some embodiments the antigen-binding molecule is capable of binding to a peptide/polypeptide which is bound by an antibody comprising the VH and VL sequences of one of antibody clones 4M2-C12, 4M2-B4, 4M2-C9, 4M2-D9, 4M2-D5, 4M2-A8, V4H1, V4H2, V4-C1, V4-C9, V4-C24, V4-C26, V4-C27, V4-C28, V4-C30, V4-C31, 2M1-B12, 2M1-D2, 1M2-D2, 13D5p, 13D5-1, 13D5-13, 5M1-A11 or 9M2-C12 described herein.

Myeloid-Derived Suppressor Cells (MDSCs)

Myeloid-Derived Suppressor Cells (MDSCs) are a heterogeneous group of immune cells of the myeloid lineage of cells, characterised by an immunosuppressive phenotype. MDSC biology is reviewed in Kumar et al., Trends Immunol. (2016); 37(3): 208-220, which is hereby incorporated by reference in its entirety.

MDSC are characterised by a number of biochemical and genomic features that distinguish these cells from mature myeloid cells (i.e. macrophages, dendritic cells and neutrophils) such as: increased expression of NADPH oxidase (Nox2), increased production of reactive oxygen species (ROS) (such as superoxide anion ($O^{2-}$), hydrogen peroxide ($H_2O_2$), and peroxynitrite (PNT; $ONOO^-$)); increased expression of arginase 1 and nitric oxide synthase 2 (nos2), and increased production of nitric oxide (NO); increased expression of c/EBPβ and STAT3; decreased expression of IRF8; and increased production of S100A8/9 proteins.

There are two different types of MDSC; polymorphonuclear MDSCs (PMN-MDSCs), which are morphologically and phenotypically similar to neutrophils, and monocytic MDSCs (M-MDSCs) which are more similar to monocytes. The morphologic and phenotypic characteristics of MDSCs are described e.g. in Marvel and Gabrilovich J Clin Invest. 2015 Sep. 1; 125(9): 3356-3364, which is hereby incorporated by reference in its entirety. In mice, MDSCs are broadly identified as CD11b$^+$Gr1$^+$ cells. Gr-1$^{hi}$ cells are mostly PMN-MDSCs, and Gr-1$^{lo}$ cells are mostly M-MDSCs. These subsets can be more accurately identified based on Ly6C and Ly6G markers; M-MDSCs are CD11b$^+$Ly6C$^{hi}$Ly6G$^-$, and PMN-MDSCs are CD11b$^+$Ly6C$^{lo}$Ly6G$^+$). In humans, MDSCs are identified in the mononuclear fraction. PMN-MDSCs are CD14$^-$CD11b$^+$CD33$^+$CD15$^+$ or CD66b$^+$ cells, and M-MDSCs are CD14$^+$HLA-DR$^{-/lo}$ cells. Populations of Lin$^-$HLA-DR$^-$CD33$^+$ MDSCs represent a mixed group of cells enriched for myeloid progenitors.

Factors implicated in MDSC-mediated immune suppression include expression of arginase (ARG1), inducible NOS (iNOS), TGF-β, IL-10, and COX2, sequestration of cysteine, decreased expression of I-selectin by T cells, and induction of Tregs. M-MDSCs and PMN-MDSCs employ different mechanisms of immune suppression. M-MDSCs suppress both antigen-specific and non-specific T cell responses through production of NO and cytokines, and are more strongly immunosuppressive than PMN-MDSCs. PMN-MDSCs suppress immune responses in an antigen-specific manner through production of ROS. MDSCs are pathologically implicated in the development and progression of cancer and infectious disease. The role of MDSCs in human disease is reviewed e.g. in Kumar et al., Trends Immunol. (2016); 37(3): 208-220 (incorporated by reference herein) and Greten et al., Int Immunopharmacol. (2011) 11(7):802-807, which is hereby incorporated by reference in its entirety.

MDSCs are abundant in tumor tissues, and contribute to the development and progression of cancer through multiple mechanisms, reviewed e.g. in Umansky et al., Vaccines (Basel) (2016) 4(4):36. MDSCs are recruited to the tumor site through chemokine expression, and proinflammatory factors in the tumor microenvironment result in significant upregulation of immunosuppressive function by MDSCs. MDSCs contribute to tumor development, neovascularization and metastasis through suppression of effector immune cell function (e.g. effector T cell and NK cell function), promotion of regulatory T cell production/activity, production of growth factors such as VEGF and bFGF, and production of ECM-modifying factors such as matrix metalloproteinases.

MDSCs may be characterised by reference to expression of VISTA. In embodiments of the various aspects of the present invention, the MDSCs may be "VISTA-expressing MDSCs" or "VISTA+ MDSCs". The MDSCs may express VISTA at the cell surface (i.e. VISTA may be expressed in or at the cell membrane).

Antigen-Binding Molecules

The present invention provides antigen-binding molecules capable of binding to VISTA.

An "antigen-binding molecule" refers to a molecule which is capable of binding to a target antigen, and encompasses monoclonal antibodies, polyclonal antibodies, monospecific and multispecific antibodies (e.g., bispecific antibodies), and antibody fragments (e.g. Fv, scFv, Fab, scFab, F(ab')$_2$, Fab$_2$, diabodies, triabodies, scFv-Fc, minibodies, single domain antibodies (e.g. VhH), etc.), as long as they display binding to the relevant target molecule(s).

The antigen-binding molecule of the present invention comprises a moiety capable of binding to a target antigen(s). In some embodiments, the moiety capable of binding to a target antigen comprises an antibody heavy chain variable region (VH) and an antibody light chain variable region (VL) of an antibody capable of specific binding to the target antigen. In some embodiments, the moiety capable of binding to a target antigen comprises or consists of an aptamer capable of binding to the target antigen, e.g. a nucleic acid aptamer (reviewed, for example, in Zhou and Rossi Nat Rev Drug Discov. 2017 16(3):181-202). In some embodiments, the moiety capable of binding to a target antigen comprises or consists of a antigen-binding peptide/polypeptide, e.g. a peptide aptamer, thioredoxin, monobody, anticalin, Kunitz domain, avimer, knottin, fynomer, atrimer, DARPin, affibody, nanobody (i.e. a single-domain antibody (sdAb)) affilin, armadillo repeat protein (ArmRP), OBody or fibronectin—reviewed e.g. in Reverdatto et al., Curr Top Med Chem. 2015; 15(12): 1082-1101, which is hereby incorporated by reference in its entirety (see also e.g. Boersma et al., J Biol Chem (2011) 286:41273-85 and Emanuel et al., Mabs (2011) 3:38-48).

The antigen-binding molecules of the present invention generally comprise an antigen-binding domain comprising a VH and a VL of an antibody capable of specific binding to the target antigen. The antigen-binding domain formed by a VH and a VL may also be referred to herein as an Fv region.

An antigen-binding molecule may be, or may comprise, an antigen-binding polypeptide, or an antigen-binding polypeptide complex. An antigen-binding molecule may comprise more than one polypeptide which together form an antigen-binding domain. The polypeptides may associate covalently or non-covalently. In some embodiments the polypeptides form part of a larger polypeptide comprising the polypeptides (e.g. in the case of scFv comprising VH and VL, or in the case of scFab comprising VH-CH1 and VL-CL).

An antigen-binding molecule may refer to a non-covalent or covalent complex of more than one polypeptide (e.g. 2, 3, 4, 6, or 8 polypeptides), e.g. an IgG-like antigen-binding molecule comprising two heavy chain polypeptides and two light chain polypeptides.

The antigen-binding molecules of the present invention may be designed and prepared using the sequences of monoclonal antibodies (mAbs) capable of binding to VISTA. Antigen-binding regions of antibodies, such as single chain variable fragment (scFv), Fab and F(ab')$_2$ fragments may also be used/provided. An "antigen-binding region" is any fragment of an antibody which is capable of binding to the target for which the given antibody is specific.

Antibodies generally comprise six complementarity-determining regions CDRs; three in the heavy chain variable (VH) region: HC-CDR1, HC-CDR2 and HC-CDR3, and three in the light chain variable (VL) region: LC-CDR1, LC-CDR2, and LC-CDR3. The six CDRs together define the paratope of the antibody, which is the part of the antibody which binds to the target antigen.

The VH region and VL region comprise framework regions (FRs) either side of each CDR, which provide a scaffold for the CDRs. From N-terminus to C-terminus, VH regions comprise the following structure: N term-[HC-FR1]-[HC-CDR1]-[HC-FR2]-[HC-CDR2]-[HC-FR3]-[HC-CDR3]-[HC-FR4]-C term; and VL regions comprise the following structure: N term-[LC-FR1]-[LC-CDR1]-[LC-FR2]-[LC-CDR2]-[LC-FR3]-[LC-CDR3]-[LC-FR4]-C term.

There are several different conventions for defining antibody CDRs and FRs, such as those described in Kabat et al., Sequences of Proteins of Immunological Interest, 5th Ed. Public Health Service, National Institutes of Health, Bethesda, Md. (1991), Chothia et al., J. Mol. Biol. 196:901-917 (1987), and VBASE2, as described in Retter et al., Nucl. Acids Res. (2005) 33 (suppl 1): D671-D674. The CDRs and FRs of the VH regions and VL regions of the antibody clones described herein were defined according to the international IMGT (ImMunoGeneTics) information system (LeFranc et al., Nucleic Acids Res. (2015) 43 (Database issue):D413-22), which uses the IMGT V-DOMAIN numbering rules as described in Lefranc et al., Dev. Comp. Immunol. (2003) 27:55-77.

In some embodiments, the antigen-binding molecule comprises the CDRs of an antigen-binding molecule which is capable of binding to VISTA. In some embodiments, the antigen-binding molecule comprises the FRs of an antigen-binding molecule which is capable of binding to VISTA. In some embodiments, the antigen-binding molecule comprises the CDRs and the FRs of an antigen-binding molecule which is capable of binding to VISTA. That is, in some embodiments the antigen-binding molecule comprises the VH region and the VL region of an antigen-binding molecule which is capable of binding to VISTA.

In some embodiments the antigen-binding molecule comprises a VH region and a VL region which is, or which is derived from, the VH/VL region of a VISTA-binding antibody clone described herein (i.e. anti-VISTA antibody clones 4M2-C12, 4M2-B4, 4M2-C9, 4M2-D9, 4M2-D5, 4M2-A8, V4H1, V4H2, V4-C1, V4-C9, V4-C24, V4-C26, V4-C27, V4-C28, V4-C30, V4-C31, 2M1-B12, 2M1-D2, 1M2-D2, 13D5p, 13D5-1, 13D5-13, 5M1-A11 or 9M2-C12).

In some embodiments the antigen-binding molecule comprises a VH region according to one of (1) to (18) below:
(1) (4M2-C12 derived consensus) a VH region incorporating the following CDRs:
  HC-CDR1 having the amino acid sequence of SEQ ID NO:305
  HC-CDR2 having the amino acid sequence of SEQ ID NO:306
  HC-CDR3 having the amino acid sequence of SEQ ID NO:307,
or a variant thereof in which one or two or three amino acids in one or more of HC-CDR1, HC-CDR2, or HC-CDR3 are substituted with another amino acid.
(2) (V4-C24, V4-C26, V4-C27, V4-C28, V4-C30, V4-C31) a VH region incorporating the following CDRs:
  HC-CDR1 having the amino acid sequence of SEQ ID NO:290
  HC-CDR2 having the amino acid sequence of SEQ ID NO:291
  HC-CDR3 having the amino acid sequence of SEQ ID NO:278,
or a variant thereof in which one or two or three amino acids in one or more of HC-CDR1, HC-CDR2, or HC-CDR3 are substituted with another amino acid.
(3) (V4-C1) a VH region incorporating the following CDRs:
  HC-CDR1 having the amino acid sequence of SEQ ID NO:33
  HC-CDR2 having the amino acid sequence of SEQ ID NO:277

HC-CDR3 having the amino acid sequence of SEQ ID NO:278,
or a variant thereof in which one or two or three amino acids in one or more of HC-CDR1, HC-CDR2, or HC-CDR3 are substituted with another amino acid.

(4) (V4-C9) a VH region incorporating the following CDRs:
  HC-CDR1 having the amino acid sequence of SEQ ID NO:33
  HC-CDR2 having the amino acid sequence of SEQ ID NO:286
  HC-CDR3 having the amino acid sequence of SEQ ID NO:278,
  or a variant thereof in which one or two or three amino acids in one or more of HC-CDR1, HC-CDR2, or HC-CDR3 are substituted with another amino acid.

(5) (4M2-C12/V4H1/V4H2 consensus) a VH region incorporating the following CDRs:
  HC-CDR1 having the amino acid sequence of SEQ ID NO:244
  HC-CDR2 having the amino acid sequence of SEQ ID NO:34
  HC-CDR3 having the amino acid sequence of SEQ ID NO:35,
  or a variant thereof in which one or two or three amino acids in one or more of HC-CDR1, HC-CDR2, or HC-CDR3 are substituted with another amino acid.

(6) (4M2-C12, 4M2-B4, V4H2) a VH region incorporating the following CDRs:
  HC-CDR1 having the amino acid sequence of SEQ ID NO:33
  HC-CDR2 having the amino acid sequence of SEQ ID NO:34
  HC-CDR3 having the amino acid sequence of SEQ ID NO:35,
  or a variant thereof in which one or two or three amino acids in one or more of HC-CDR1, HC-CDR2, or HC-CDR3 are substituted with another amino acid.

(7) (V4H1) a VH region incorporating the following CDRs:
  HC-CDR1 having the amino acid sequence of SEQ ID NO:53
  HC-CDR2 having the amino acid sequence of SEQ ID NO:34
  HC-CDR3 having the amino acid sequence of SEQ ID NO:35,
  or a variant thereof in which one or two or three amino acids in one or more of HC-CDR1, HC-CDR2, or HC-CDR3 are substituted with another amino acid.

(8) (2M1-B12, 2M1-D2) a VH region incorporating the following CDRs:
  HC-CDR1 having the amino acid sequence of SEQ ID NO:72
  HC-CDR2 having the amino acid sequence of SEQ ID NO:73
  HC-CDR3 having the amino acid sequence of SEQ ID NO:74,
  or a variant thereof in which one or two or three amino acids in one or more of HC-CDR1, HC-CDR2, or HC-CDR3 are substituted with another amino acid.

(9) (4M2-C9, 5M1-A11) a VH region incorporating the following CDRs:
  HC-CDR1 having the amino acid sequence of SEQ ID NO:88
  HC-CDR2 having the amino acid sequence of SEQ ID NO:89
  HC-CDR3 having the amino acid sequence of SEQ ID NO:90,
  or a variant thereof in which one or two or three amino acids in one or more of HC-CDR1, HC-CDR2, or HC-CDR3 are substituted with another amino acid.

(10) (4M2-D9) a VH region incorporating the following CDRs:
  HC-CDR1 having the amino acid sequence of SEQ ID NO:33
  HC-CDR2 having the amino acid sequence of SEQ ID NO:107
  HC-CDR3 having the amino acid sequence of SEQ ID NO:108,
  or a variant thereof in which one or two or three amino acids in one or more of HC-CDR1, HC-CDR2, or HC-CDR3 are substituted with another amino acid.

(11) (1M2-D2) a VH region incorporating the following CDRs:
  HC-CDR1 having the amino acid sequence of SEQ ID NO:120
  HC-CDR2 having the amino acid sequence of SEQ ID NO:121
  HC-CDR3 having the amino acid sequence of SEQ ID NO:122,
  or a variant thereof in which one or two or three amino acids in one or more of HC-CDR1, HC-CDR2, or HC-CDR3 are substituted with another amino acid.

(12) (4M2-D5) a VH region incorporating the following CDRs:
  HC-CDR1 having the amino acid sequence of SEQ ID NO:144
  HC-CDR2 having the amino acid sequence of SEQ ID NO:145
  HC-CDR3 having the amino acid sequence of SEQ ID NO:146,
  or a variant thereof in which one or two or three amino acids in one or more of HC-CDR1, HC-CDR2, or HC-CDR3 are substituted with another amino acid.

(13) (4M2-A8) a VH region incorporating the following CDRs:
  HC-CDR1 having the amino acid sequence of SEQ ID NO:158
  HC-CDR2 having the amino acid sequence of SEQ ID NO:159
  HC-CDR3 having the amino acid sequence of SEQ ID NO:160,
  or a variant thereof in which one or two or three amino acids in one or more of HC-CDR1, HC-CDR2, or HC-CDR3 are substituted with another amino acid.

(14) (9M2-C12) a VH region incorporating the following CDRs:
  HC-CDR1 having the amino acid sequence of SEQ ID NO:169
  HC-CDR2 having the amino acid sequence of SEQ ID NO:170
  HC-CDR3 having the amino acid sequence of SEQ ID NO:171,
  or a variant thereof in which one or two or three amino acids in one or more of HC-CDR1, HC-CDR2, or HC-CDR3 are substituted with another amino acid.

(15) (13D5 derived) a VH region incorporating the following CDRs:
  HC-CDR1 having the amino acid sequence of SEQ ID NO:72
  HC-CDR2 having the amino acid sequence of SEQ ID NO:184
  HC-CDR3 having the amino acid sequence of SEQ ID NO:246, or a variant thereof in which one or two or three amino acids in one or more of HC-CDR1, HC-CDR2, or HC-CDR3 are substituted with another amino acid.

(16) (13D5p) a VH region incorporating the following CDRs:
HC-CDR1 having the amino acid sequence of SEQ ID NO:72
HC-CDR2 having the amino acid sequence of SEQ ID NO:184
HC-CDR3 having the amino acid sequence of SEQ ID NO:185,
or a variant thereof in which one or two or three amino acids in one or more of HC-CDR1, HC-CDR2, or HC-CDR3 are substituted with another amino acid.

(17) (13D5-1) a VH region incorporating the following CDRs:
HC-CDR1 having the amino acid sequence of SEQ ID NO:72
HC-CDR2 having the amino acid sequence of SEQ ID NO:184
HC-CDR3 having the amino acid sequence of SEQ ID NO:195,
or a variant thereof in which one or two or three amino acids in one or more of HC-CDR1, HC-CDR2, or HC-CDR3 are substituted with another amino acid.

(18) (13D5-13) a VH region incorporating the following CDRs:
HC-CDR1 having the amino acid sequence of SEQ ID NO:72
HC-CDR2 having the amino acid sequence of SEQ ID NO:184
HC-CDR3 having the amino acid sequence of SEQ ID NO:200,
or a variant thereof in which one or two or three amino acids in one or more of HC-CDR1, HC-CDR2, or HC-CDR3 are substituted with another amino acid.

In some embodiments the antigen-binding molecule comprises a VH region according to one of (19) to (35) below:

(19) (V4-C24, V4-C26, V4-C27, V4-C28, V4-C30, V4-C31) a VH region incorporating the following FRs:
HC-FR1 having the amino acid sequence of SEQ ID NO:63
HC-FR2 having the amino acid sequence of SEQ ID NO:292
HC-FR3 having the amino acid sequence of SEQ ID NO:293
HC-FR4 having the amino acid sequence of SEQ ID NO:281,
or a variant thereof in which one or two or three amino acids in one or more of HC-FR1, HC-FR2, HC-FR3, or HC-FR4 are substituted with another amino acid.

(20) (V4-C1, V4-C9) a VH region incorporating the following FRs:
HC-FR1 having the amino acid sequence of SEQ ID NO:63
HC-FR2 having the amino acid sequence of SEQ ID NO:279
HC-FR3 having the amino acid sequence of SEQ ID NO:280
HC-FR4 having the amino acid sequence of SEQ ID NO:281,
or a variant thereof in which one or two or three amino acids in one or more of HC-FR1, HC-FR2, HC-FR3, or HC-FR4 are substituted with another amino acid.

(21) (4M2-C12) a VH region incorporating the following FRs:
HC-FR1 having the amino acid sequence of SEQ ID NO:36
HC-FR2 having the amino acid sequence of SEQ ID NO:37
HC-FR3 having the amino acid sequence of SEQ ID NO:38
HC-FR4 having the amino acid sequence of SEQ ID NO:39,
or a variant thereof in which one or two or three amino acids in one or more of HC-FR1, HC-FR2, HC-FR3, or HC-FR4 are substituted with another amino acid.

(22) (4M2-B4) a VH region incorporating the following FRs:
HC-FR1 having the amino acid sequence of SEQ ID NO:49
HC-FR2 having the amino acid sequence of SEQ ID NO:37
HC-FR3 having the amino acid sequence of SEQ ID NO:38
HC-FR4 having the amino acid sequence of SEQ ID NO:39,
or a variant thereof in which one or two or three amino acids in one or more of HC-FR1, HC-FR2, HC-FR3, or HC-FR4 are substituted with another amino acid.

(23) (V4H1) a VH region incorporating the following FRs:
HC-FR1 having the amino acid sequence of SEQ ID NO:54
HC-FR2 having the amino acid sequence of SEQ ID NO:55
HC-FR3 having the amino acid sequence of SEQ ID NO:56
HC-FR4 having the amino acid sequence of SEQ ID NO:39,
or a variant thereof in which one or two or three amino acids in one or more of HC-FR1, HC-FR2, HC-FR3, or HC-FR4 are substituted with another amino acid.

(24) (V4H2) a VH region incorporating the following FRs:
HC-FR1 having the amino acid sequence of SEQ ID NO:63
HC-FR2 having the amino acid sequence of SEQ ID NO:64
HC-FR3 having the amino acid sequence of SEQ ID NO:65
HC-FR4 having the amino acid sequence of SEQ ID NO:39,
or a variant thereof in which one or two or three amino acids in one or more of HC-FR1, HC-FR2, HC-FR3, or HC-FR4 are substituted with another amino acid.

(25) (2M1-B12) a VH region incorporating the following FRs:
HC-FR1 having the amino acid sequence of SEQ ID NO:75
HC-FR2 having the amino acid sequence of SEQ ID NO:76
HC-FR3 having the amino acid sequence of SEQ ID NO:77
HC-FR4 having the amino acid sequence of SEQ ID NO:78,
or a variant thereof in which one or two or three amino acids in one or more of HC-FR1, HC-FR2, HC-FR3, or HC-FR4 are substituted with another amino acid.

(26) (4M2-C9) a VH region incorporating the following FRs:
HC-FR1 having the amino acid sequence of SEQ ID NO:91

HC-FR2 having the amino acid sequence of SEQ ID NO:92
HC-FR3 having the amino acid sequence of SEQ ID NO:93
HC-FR4 having the amino acid sequence of SEQ ID NO:94,
or a variant thereof in which one or two or three amino acids in one or more of HC-FR1, HC-FR2, HC-FR3, or HC-FR4 are substituted with another amino acid.
(27) (2M1-D2) a VH region incorporating the following FRs:
HC-FR1 having the amino acid sequence of SEQ ID NO:103
HC-FR2 having the amino acid sequence of SEQ ID NO:76
HC-FR3 having the amino acid sequence of SEQ ID NO:77
HC-FR4 having the amino acid sequence of SEQ ID NO:78,
or a variant thereof in which one or two or three amino acids in one or more of HC-FR1, HC-FR2, HC-FR3, or HC-FR4 are substituted with another amino acid.
(28) (4M2-D9) a VH region incorporating the following FRs:
HC-FR1 having the amino acid sequence of SEQ ID NO:109
HC-FR2 having the amino acid sequence of SEQ ID NO:110
HC-FR3 having the amino acid sequence of SEQ ID NO:111
HC-FR4 having the amino acid sequence of SEQ ID NO:112,
or a variant thereof in which one or two or three amino acids in one or more of HC-FR1, HC-FR2, HC-FR3, or HC-FR4 are substituted with another amino acid.
(29) (1M2-D2) a VH region incorporating the following FRs:
HC-FR1 having the amino acid sequence of SEQ ID NO:123
HC-FR2 having the amino acid sequence of SEQ ID NO:124
HC-FR3 having the amino acid sequence of SEQ ID NO:125
HC-FR4 having the amino acid sequence of SEQ ID NO:78,
or a variant thereof in which one or two or three amino acids in one or more of HC-FR1, HC-FR2, HC-FR3, or HC-FR4 are substituted with another amino acid.
(30) (5M1-A11) a VH region incorporating the following FRs:
HC-FR1 having the amino acid sequence of SEQ ID NO:134
HC-FR2 having the amino acid sequence of SEQ ID NO:92
HC-FR3 having the amino acid sequence of SEQ ID NO:93
HC-FR4 having the amino acid sequence of SEQ ID NO:135,
or a variant thereof in which one or two or three amino acids in one or more of HC-FR1, HC-FR2, HC-FR3, or HC-FR4 are substituted with another amino acid.
(31) (4M2-D5) a VH region incorporating the following FRs:
HC-FR1 having the amino acid sequence of SEQ ID NO:147
HC-FR2 having the amino acid sequence of SEQ ID NO:148
HC-FR3 having the amino acid sequence of SEQ ID NO:149
HC-FR4 having the amino acid sequence of SEQ ID NO:135,
or a variant thereof in which one or two or three amino acids in one or more of HC-FR1, HC-FR2, HC-FR3, or HC-FR4 are substituted with another amino acid.
(32) (4M2-A8) a VH region incorporating the following FRs:
HC-FR1 having the amino acid sequence of SEQ ID NO:161
HC-FR2 having the amino acid sequence of SEQ ID NO:162
HC-FR3 having the amino acid sequence of SEQ ID NO:163
HC-FR4 having the amino acid sequence of SEQ ID NO:135,
or a variant thereof in which one or two or three amino acids in one or more of HC-FR1, HC-FR2, HC-FR3, or HC-FR4 are substituted with another amino acid.
(33) (9M2-C12) a VH region incorporating the following FRs:
HC-FR1 having the amino acid sequence of SEQ ID NO:172
HC-FR2 having the amino acid sequence of SEQ ID NO:173
HC-FR3 having the amino acid sequence of SEQ ID NO:174
HC-FR4 having the amino acid sequence of SEQ ID NO:175,
or a variant thereof in which one or two or three amino acids in one or more of HC-FR1, HC-FR2, HC-FR3, or HC-FR4 are substituted with another amino acid.
(34) (13D5p, 13D5-1) a VH region incorporating the following FRs:
HC-FR1 having the amino acid sequence of SEQ ID NO:103
HC-FR2 having the amino acid sequence of SEQ ID NO:186
HC-FR3 having the amino acid sequence of SEQ ID NO:187
HC-FR4 having the amino acid sequence of SEQ ID NO:86,
or a variant thereof in which one or two or three amino acids in one or more of HC-FR1, HC-FR2, HC-FR3, or HC-FR4 are substituted with another amino acid.
(35) (13D5-13) a VH region incorporating the following FRs:
HC-FR1 having the amino acid sequence of SEQ ID NO:103
HC-FR2 having the amino acid sequence of SEQ ID NO:186
HC-FR3 having the amino acid sequence of SEQ ID NO:201
HC-FR4 having the amino acid sequence of SEQ ID NO:86,
or a variant thereof in which one or two or three amino acids in one or more of HC-FR1, HC-FR2, HC-FR3, or HC-FR4 are substituted with another amino acid.

In some embodiments the antigen-binding molecule comprises a VH region comprising the CDRs according to one of (1) to (18) above, and the FRs according to one of (19) to (35) above.

In some embodiments the antigen-binding molecule comprises a VH region according to one of (36) to (57) below:
(36) a VH region comprising the CDRs according to (1) and the FRs according to (19), (20), (21), (22), (23) or (24).

(37) a VH region comprising the CDRs according to (2) and the FRs according to (19).
(38) a VH region comprising the CDRs according to (3) and the FRs according to (20).
(39) a VH region comprising the CDRs according to (4) and the FRs according to (20).
(40) a VH region comprising the CDRs according to (5) and the FRs according to (21), (22), (23) or (24).
(41) a VH region comprising the CDRs according to (6) and the FRs according to (21).
(42) a VH region comprising the CDRs according to (6) and the FRs according to (22).
(43) a VH region comprising the CDRs according to (6) and the FRs according to (24).
(44) a VH region comprising the CDRs according to (7) and the FRs according to (23).
(45) a VH region comprising the CDRs according to (8) and the FRs according to (25).
(46) a VH region comprising the CDRs according to (8) and the FRs according to (27).
(47) a VH region comprising the CDRs according to (9) and the FRs according to (26).
(48) a VH region comprising the CDRs according to (9) and the FRs according to (30).
(49) a VH region comprising the CDRs according to (10) and the FRs according to (28).
(50) a VH region comprising the CDRs according to (11) and the FRs according to (29).
(51) a VH region comprising the CDRs according to (12) and the FRs according to (31).
(52) a VH region comprising the CDRs according to (13) and the FRs according to (32).
(53) a VH region comprising the CDRs according to (14) and the FRs according to (33).
(54) a VH region comprising the CDRs according to (15) and the FRs according to (34) or (35).
(55) a VH region comprising the CDRs according to (16) and the FRs according to (34).
(56) a VH region comprising the CDRs according to (17) and the FRs according to (34).
(57) a VH region comprising the CDRs according to (18) and the FRs according to (35).

In some embodiments the antigen-binding molecule comprises a VH region according to one of (58) to (76) below:
(58) a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:276.
(59) a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:285.
(60) a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:289.
(61) a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:32.
(62) a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:48.
(63) a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:52.
(64) a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:62.
(65) a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:71.
(66) a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:87.
(67) a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:102.
(68) a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:106.
(69) a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:119.
(70) a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:133.
(71) a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:143.
(72) a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:157.

(73) a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:168.

(74) a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:183.

(75) a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:194.

(76) a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:199.

In some embodiments the antigen-binding molecule comprises a VL region according to one of (77) to (96) below:

(77) (4M2-C12 derived consensus) a VL region incorporating the following CDRs:
  LC-CDR1 having the amino acid sequence of SEQ ID NO:41
  LC-CDR2 having the amino acid sequence of SEQ ID NO:308
  LC-CDR3 having the amino acid sequence of SEQ ID NO:43;
  or a variant thereof in which one or two or three amino acids in one or more of LC-CDR1, LC-CDR2 or LC-CDR3 are substituted with another amino acid.

(78) (C24/C26/C27 consensus) a VL region incorporating the following CDRs:
  LC-CDR1 having the amino acid sequence of SEQ ID NO:41
  LC-CDR2 having the amino acid sequence of SEQ ID NO:309
  LC-CDR3 having the amino acid sequence of SEQ ID NO:43;
  or a variant thereof in which one or two or three amino acids in one or more of LC-CDR1, LC-CDR2 or LC-CDR3 are substituted with another amino acid.

(79) (V4-C24, V4-C26) a VL region incorporating the following CDRs:
  LC-CDR1 having the amino acid sequence of SEQ ID NO:41
  LC-CDR2 having the amino acid sequence of SEQ ID NO:295
  LC-CDR3 having the amino acid sequence of SEQ ID NO:43;
  or a variant thereof in which one or two or three amino acids in one or more of LC-CDR1, LC-CDR2 or LC-CDR3 are substituted with another amino acid.

(80) (V4-C27, V4-C30, V4-C31) a VL region incorporating the following CDRs:
  LC-CDR1 having the amino acid sequence of SEQ ID NO:41
  LC-CDR2 having the amino acid sequence of SEQ ID NO:300
  LC-CDR3 having the amino acid sequence of SEQ ID NO:43;
  or a variant thereof in which one or two or three amino acids in one or more of LC-CDR1, LC-CDR2 or LC-CDR3 are substituted with another amino acid.

(81) (4M2-C12/V4H1/V4H2 consensus) a VL region incorporating the following CDRs:
  LC-CDR1 having the amino acid sequence of SEQ ID NO:41
  LC-CDR2 having the amino acid sequence of SEQ ID NO:245
  LC-CDR3 having the amino acid sequence of SEQ ID NO:43;
  or a variant thereof in which one or two or three amino acids in one or more of LC-CDR1, LC-CDR2 or LC-CDR3 are substituted with another amino acid.

(82) (4M2-C12, 4M2-B4, V4-C1, V4-C9, V4-C28) a VL region incorporating the following CDRs:
  LC-CDR1 having the amino acid sequence of SEQ ID NO:41
  LC-CDR2 having the amino acid sequence of SEQ ID NO:42
  LC-CDR3 having the amino acid sequence of SEQ ID NO:43;
  or a variant thereof in which one or two or three amino acids in one or more of LC-CDR1, LC-CDR2 or LC-CDR3 are substituted with another amino acid.

(83) (V4H1) a VL region incorporating the following CDRs:
  LC-CDR1 having the amino acid sequence of SEQ ID NO:41
  LC-CDR2 having the amino acid sequence of SEQ ID NO:58
  LC-CDR3 having the amino acid sequence of SEQ ID NO:43;
  or a variant thereof in which one or two or three amino acids in one or more of LC-CDR1, LC-CDR2 or LC-CDR3 are substituted with another amino acid.

(84) (V4H2) a VL region incorporating the following CDRs:
  LC-CDR1 having the amino acid sequence of SEQ ID NO:41
  LC-CDR2 having the amino acid sequence of SEQ ID NO:67
  LC-CDR3 having the amino acid sequence of SEQ ID NO:43;
  or a variant thereof in which one or two or three amino acids in one or more of LC-CDR1, LC-CDR2 or LC-CDR3 are substituted with another amino acid.

(85) (2M1-B12, 2M1-D2) a VL region incorporating the following CDRs:
  LC-CDR1 having the amino acid sequence of SEQ ID NO:80
  LC-CDR2 having the amino acid sequence of SEQ ID NO:81
  LC-CDR3 having the amino acid sequence of SEQ ID NO:82;
  or a variant thereof in which one or two or three amino acids in one or more of LC-CDR1, LC-CDR2 or LC-CDR3 are substituted with another amino acid.

(86) (4M2-C9) a VL region incorporating the following CDRs:
  LC-CDR1 having the amino acid sequence of SEQ ID NO:96
  LC-CDR2 having the amino acid sequence of SEQ ID NO:97

LC-CDR3 having the amino acid sequence of SEQ ID NO:98;
or a variant thereof in which one or two or three amino acids in one or more of LC-CDR1, LC-CDR2 or LC-CDR3 are substituted with another amino acid.

(87) (4M2-D9) a VH region incorporating the following CDRs:
LC-CDR1 having the amino acid sequence of SEQ ID NO:114
LC-CDR2 having the amino acid sequence of SEQ ID NO:67
LC-CDR3 having the amino acid sequence of SEQ ID NO:115,
or a variant thereof in which one or two or three amino acids in one or more of LC-CDR1, LC-CDR2, or LC-CDR3 are substituted with another amino acid.

(88) (1M2-D2) a VL region incorporating the following CDRs:
LC-CDR1 having the amino acid sequence of SEQ ID NO:127
LC-CDR2 having the amino acid sequence of SEQ ID NO:128
LC-CDR3 having the amino acid sequence of SEQ ID NO:129;
or a variant thereof in which one or two or three amino acids in one or more of LC-CDR1, LC-CDR2 or LC-CDR3 are substituted with another amino acid.

(89) (5M1-A11) a VL region incorporating the following CDRs:
LC-CDR1 having the amino acid sequence of SEQ ID NO:137
LC-CDR2 having the amino acid sequence of SEQ ID NO:138
LC-CDR3 having the amino acid sequence of SEQ ID NO:139;
or a variant thereof in which one or two or three amino acids in one or more of LC-CDR1, LC-CDR2 or LC-CDR3 are substituted with another amino acid.

(90) (4M2-D5) a VL region incorporating the following CDRs:
LC-CDR1 having the amino acid sequence of SEQ ID NO:151
LC-CDR2 having the amino acid sequence of SEQ ID NO:152
LC-CDR3 having the amino acid sequence of SEQ ID NO:153;
or a variant thereof in which one or two or three amino acids in one or more of LC-CDR1, LC-CDR2 or LC-CDR3 are substituted with another amino acid.

(91) (4M2-A8) a VL region incorporating the following CDRs:
LC-CDR1 having the amino acid sequence of SEQ ID NO:165
LC-CDR2 having the amino acid sequence of SEQ ID NO:152
LC-CDR3 having the amino acid sequence of SEQ ID NO:153;
or a variant thereof in which one or two or three amino acids in one or more of LC-CDR1, LC-CDR2 or LC-CDR3 are substituted with another amino acid.

(92) (9M2-C12) a VL region incorporating the following CDRs:
LC-CDR1 having the amino acid sequence of SEQ ID NO:177
LC-CDR2 having the amino acid sequence of SEQ ID NO:178
LC-CDR3 having the amino acid sequence of SEQ ID NO:179;
or a variant thereof in which one or two or three amino acids in one or more of LC-CDR1, LC-CDR2 or LC-CDR3 are substituted with another amino acid.

(93) (13D5p derived) a VL region incorporating the following CDRs:
LC-CDR1 having the amino acid sequence of SEQ ID NO:247
LC-CDR2 having the amino acid sequence of SEQ ID NO:178
LC-CDR3 having the amino acid sequence of SEQ ID NO:190;
or a variant thereof in which one or two or three amino acids in one or more of LC-CDR1, LC-CDR2 or LC-CDR3 are substituted with another amino acid.

(94) (13D5p) a VL region incorporating the following CDRs:
LC-CDR1 having the amino acid sequence of SEQ ID NO:189
LC-CDR2 having the amino acid sequence of SEQ ID NO:178
LC-CDR3 having the amino acid sequence of SEQ ID NO:190;
or a variant thereof in which one or two or three amino acids in one or more of LC-CDR1, LC-CDR2 or LC-CDR3 are substituted with another amino acid.

(95) (13D5-1) a VL region incorporating the following CDRs:
LC-CDR1 having the amino acid sequence of SEQ ID NO:197
LC-CDR2 having the amino acid sequence of SEQ ID NO:178
LC-CDR3 having the amino acid sequence of SEQ ID NO:190;
or a variant thereof in which one or two or three amino acids in one or more of LC-CDR1, LC-CDR2 or LC-CDR3 are substituted with another amino acid.

(96) (13D5-13) a VL region incorporating the following CDRs:
LC-CDR1 having the amino acid sequence of SEQ ID NO:203
LC-CDR2 having the amino acid sequence of SEQ ID NO:178
LC-CDR3 having the amino acid sequence of SEQ ID NO:190;
or a variant thereof in which one or two or three amino acids in one or more of LC-CDR1, LC-CDR2 or LC-CDR3 are substituted with another amino acid.

In some embodiments the antigen-binding molecule comprises a VL region according to one of (97) to (120) below:

(97) (V4-C1) a VL region incorporating the following FRs:
LC-FR1 having the amino acid sequence of SEQ ID NO:59
LC-FR2 having the amino acid sequence of SEQ ID NO:283
LC-FR3 having the amino acid sequence of SEQ ID NO:284
LC-FR4 having the amino acid sequence of SEQ ID NO:47,
or a variant thereof in which one or two or three amino acids in one or more of LC-FR1, LC-FR2, LC-FR3, or LC-FR4 are substituted with another amino acid.

(98) (V4-C9) a VL region incorporating the following FRs:
LC-FR1 having the amino acid sequence of SEQ ID NO:288

LC-FR2 having the amino acid sequence of SEQ ID NO:283
LC-FR3 having the amino acid sequence of SEQ ID NO:284
LC-FR4 having the amino acid sequence of SEQ ID NO:47,
or a variant thereof in which one or two or three amino acids in one or more of LC-FR1, LC-FR2, LC-FR3, or LC-FR4 are substituted with another amino acid.
(99) (V4-C24) a VL region incorporating the following FRs:
LC-FR1 having the amino acid sequence of SEQ ID NO:288
LC-FR2 having the amino acid sequence of SEQ ID NO:283
LC-FR3 having the amino acid sequence of SEQ ID NO:296
LC-FR4 having the amino acid sequence of SEQ ID NO:47,
or a variant thereof in which one or two or three amino acids in one or more of LC-FR1, LC-FR2, LC-FR3, or LC-FR4 are substituted with another amino acid.
(100) (V4-C26) a VL region incorporating the following FRs:
LC-FR1 having the amino acid sequence of SEQ ID NO:288
LC-FR2 having the amino acid sequence of SEQ ID NO:298
LC-FR3 having the amino acid sequence of SEQ ID NO:284
LC-FR4 having the amino acid sequence of SEQ ID NO:47,
or a variant thereof in which one or two or three amino acids in one or more of LC-FR1, LC-FR2, LC-FR3, or LC-FR4 are substituted with another amino acid.
(101) (V4-C27) a VL region incorporating the following FRs:
LC-FR1 having the amino acid sequence of SEQ ID NO:288
LC-FR2 having the amino acid sequence of SEQ ID NO:283
LC-FR3 having the amino acid sequence of SEQ ID NO:284
LC-FR4 having the amino acid sequence of SEQ ID NO:47,
or a variant thereof in which one or two or three amino acids in one or more of LC-FR1, LC-FR2, LC-FR3, or LC-FR4 are substituted with another amino acid.
(102) (V4-C28) a VL region incorporating the following FRs:
LC-FR1 having the amino acid sequence of SEQ ID NO:288
LC-FR2 having the amino acid sequence of SEQ ID NO:283
LC-FR3 having the amino acid sequence of SEQ ID NO:296
LC-FR4 having the amino acid sequence of SEQ ID NO:47,
or a variant thereof in which one or two or three amino acids in one or more of LC-FR1, LC-FR2, LC-FR3, or LC-FR4 are substituted with another amino acid.
(103) (V4-C30) a VL region incorporating the following FRs:
LC-FR1 having the amino acid sequence of SEQ ID NO:288
LC-FR2 having the amino acid sequence of SEQ ID NO:283
LC-FR3 having the amino acid sequence of SEQ ID NO:296
LC-FR4 having the amino acid sequence of SEQ ID NO:47,
or a variant thereof in which one or two or three amino acids in one or more of LC-FR1, LC-FR2, LC-FR3, or LC-FR4 are substituted with another amino acid.
(104) (V4-C31) a VL region incorporating the following FRs:
LC-FR1 having the amino acid sequence of SEQ ID NO:288
LC-FR2 having the amino acid sequence of SEQ ID NO:283
LC-FR3 having the amino acid sequence of SEQ ID NO:304
LC-FR4 having the amino acid sequence of SEQ ID NO:47,
or a variant thereof in which one or two or three amino acids in one or more of LC-FR1, LC-FR2, LC-FR3, or LC-FR4 are substituted with another amino acid.
(105) (4M2-C12) a VL region incorporating the following FRs:
LC-FR1 having the amino acid sequence of SEQ ID NO:44
LC-FR2 having the amino acid sequence of SEQ ID NO:45
LC-FR3 having the amino acid sequence of SEQ ID NO:46
LC-FR4 having the amino acid sequence of SEQ ID NO:47,
or a variant thereof in which one or two or three amino acids in one or more of LC-FR1, LC-FR2, LC-FR3, or LC-FR4 are substituted with another amino acid.
(106) (4M2-B4) a VL region incorporating the following FRs:
LC-FR1 having the amino acid sequence of SEQ ID NO:51
LC-FR2 having the amino acid sequence of SEQ ID NO:45
LC-FR3 having the amino acid sequence of SEQ ID NO:46
LC-FR4 having the amino acid sequence of SEQ ID NO:47,
or a variant thereof in which one or two or three amino acids in one or more of LC-FR1, LC-FR2, LC-FR3, or LC-FR4 are substituted with another amino acid.
(107) (V4H1) a VL region incorporating the following FRs:
LC-FR1 having the amino acid sequence of SEQ ID NO:59
LC-FR2 having the amino acid sequence of SEQ ID NO:60
LC-FR3 having the amino acid sequence of SEQ ID NO:61
LC-FR4 having the amino acid sequence of SEQ ID NO:47,
or a variant thereof in which one or two or three amino acids in one or more of LC-FR1, LC-FR2, LC-FR3, or LC-FR4 are substituted with another amino acid.
(108) (V4H2) a VL region incorporating the following FRs:
LC-FR1 having the amino acid sequence of SEQ ID NO:68
LC-FR2 having the amino acid sequence of SEQ ID NO:69
LC-FR3 having the amino acid sequence of SEQ ID NO:70
LC-FR4 having the amino acid sequence of SEQ ID NO:47, or a variant thereof in which one or two or three amino acids in one or more of LC-FR1, LC-FR2, LC-FR3, or LC-FR4 are substituted with another amino acid.

(109) (2M1-B12) a VL region incorporating the following FRs:
- LC-FR1 having the amino acid sequence of SEQ ID NO:83
- LC-FR2 having the amino acid sequence of SEQ ID NO:84
- LC-FR3 having the amino acid sequence of SEQ ID NO:85
- LC-FR4 having the amino acid sequence of SEQ ID NO:86,
- or a variant thereof in which one or two or three amino acids in one or more of LC-FR1, LC-FR2, LC-FR3, or LC-FR4 are substituted with another amino acid.

(110) (4M2-C9) a VL region incorporating the following FRs:
- LC-FR1 having the amino acid sequence of SEQ ID NO:99
- LC-FR2 having the amino acid sequence of SEQ ID NO:100
- LC-FR3 having the amino acid sequence of SEQ ID NO:101
- LC-FR4 having the amino acid sequence of SEQ ID NO:86,
- or a variant thereof in which one or two or three amino acids in one or more of LC-FR1, LC-FR2, LC-FR3, or LC-FR4 are substituted with another amino acid.

(111) (2M1-D2) a VL region incorporating the following FRs:
- LC-FR1 having the amino acid sequence of SEQ ID NO:105
- LC-FR2 having the amino acid sequence of SEQ ID NO:84
- LC-FR3 having the amino acid sequence of SEQ ID NO:85
- LC-FR4 having the amino acid sequence of SEQ ID NO:86,
- or a variant thereof in which one or two or three amino acids in one or more of LC-FR1, LC-FR2, LC-FR3, or LC-FR4 are substituted with another amino acid.

(112) (4M2-D9) a VL region incorporating the following FRs:
- LC-FR1 having the amino acid sequence of SEQ ID NO:116
- LC-FR2 having the amino acid sequence of SEQ ID NO:117
- LC-FR3 having the amino acid sequence of SEQ ID NO:118
- LC-FR4 having the amino acid sequence of SEQ ID NO:86,
- or a variant thereof in which one or two or three amino acids in one or more of LC-FR1, LC-FR2, LC-FR3, or LC-FR4 are substituted with another amino acid.

(113) (1M2-D2) a VL region incorporating the following FRs:
- LC-FR1 having the amino acid sequence of SEQ ID NO:130
- LC-FR2 having the amino acid sequence of SEQ ID NO:131
- LC-FR3 having the amino acid sequence of SEQ ID NO:132
- LC-FR4 having the amino acid sequence of SEQ ID NO:86,
- or a variant thereof in which one or two or three amino acids in one or more of LC-FR1, LC-FR2, LC-FR3, or LC-FR4 are substituted with another amino acid.

(114) (5M1-A11) a VL region incorporating the following FRs:
- LC-FR1 having the amino acid sequence of SEQ ID NO:140
- LC-FR2 having the amino acid sequence of SEQ ID NO:141
- LC-FR3 having the amino acid sequence of SEQ ID NO:142
- LC-FR4 having the amino acid sequence of SEQ ID NO:86,
- or a variant thereof in which one or two or three amino acids in one or more of LC-FR1, LC-FR2, LC-FR3, or LC-FR4 are substituted with another amino acid.

(115) (4M2-D5) a VL region incorporating the following FRs:
- LC-FR1 having the amino acid sequence of SEQ ID NO:154
- LC-FR2 having the amino acid sequence of SEQ ID NO:155
- LC-FR3 having the amino acid sequence of SEQ ID NO:156
- LC-FR4 having the amino acid sequence of SEQ ID NO:86,
- or a variant thereof in which one or two or three amino acids in one or more of LC-FR1, LC-FR2, LC-FR3, or LC-FR4 are substituted with another amino acid.

(116) (4M2-A8) a VL region incorporating the following FRs:
- LC-FR1 having the amino acid sequence of SEQ ID NO:166
- LC-FR2 having the amino acid sequence of SEQ ID NO:155
- LC-FR3 having the amino acid sequence of SEQ ID NO:167
- LC-FR4 having the amino acid sequence of SEQ ID NO:86,
- or a variant thereof in which one or two or three amino acids in one or more of LC-FR1, LC-FR2, LC-FR3, or LC-FR4 are substituted with another amino acid.

(117) (9M2-C12) a VL region incorporating the following FRs:
- LC-FR1 having the amino acid sequence of SEQ ID NO:180
- LC-FR2 having the amino acid sequence of SEQ ID NO:181
- LC-FR3 having the amino acid sequence of SEQ ID NO:182
- LC-FR4 having the amino acid sequence of SEQ ID NO:86,
- or a variant thereof in which one or two or three amino acids in one or more of LC-FR1, LC-FR2, LC-FR3, or LC-FR4 are substituted with another amino acid.

(118) (13D5p) a VL region incorporating the following FRs:
- LC-FR1 having the amino acid sequence of SEQ ID NO:191
- LC-FR2 having the amino acid sequence of SEQ ID NO:192
- LC-FR3 having the amino acid sequence of SEQ ID NO:193
- LC-FR4 having the amino acid sequence of SEQ ID NO:86,
- or a variant thereof in which one or two or three amino acids in one or more of LC-FR1, LC-FR2, LC-FR3, or LC-FR4 are substituted with another amino acid.

(119) (13D5-1) a VL region incorporating the following FRs:
LC-FR1 having the amino acid sequence of SEQ ID NO:191
LC-FR2 having the amino acid sequence of SEQ ID NO:198
LC-FR3 having the amino acid sequence of SEQ ID NO:193
LC-FR4 having the amino acid sequence of SEQ ID NO:86,
or a variant thereof in which one or two or three amino acids in one or more of LC-FR1, LC-FR2, LC-FR3, or LC-FR4 are substituted with another amino acid.
(120) (13D5-13) a VL region incorporating the following FRs:
LC-FR1 having the amino acid sequence of SEQ ID NO:191
LC-FR2 having the amino acid sequence of SEQ ID NO:192
LC-FR3 having the amino acid sequence of SEQ ID NO:204
LC-FR4 having the amino acid sequence of SEQ ID NO:86,
or a variant thereof in which one or two or three amino acids in one or more of LC-FR1, LC-FR2, LC-FR3, or LC-FR4 are substituted with another amino acid.

In some embodiments the antigen-binding molecule comprises a VL region comprising the CDRs according to one of (77) to (96) above, and the FRs according to one of (97) to (120) above.

In some embodiments the antigen-binding molecule comprises a VL region according to one of (121) to (148) below:
(121) a VL region comprising the CDRs according to (77) and the FRs according to (97), (98), (99), (100), (101), (102), (103), (104), (105), (106), (107) or (108).
(122) a VL region comprising the CDRs according to (78) and the FRs according to (99), (100) or (101).
(123) a VL region comprising the CDRs according to (79) and the FRs according to (99).
(124) a VL region comprising the CDRs according to (79) and the FRs according to (100).
(125) a VL region comprising the CDRs according to (80) and the FRs according to (101).
(126) a VL region comprising the CDRs according to (82) and the FRs according to (97).
(127) a VL region comprising the CDRs according to (82) and the FRs according to (98).
(128) a VL region comprising the CDRs according to (82) and the FRs according to (102).
(129) a VL region comprising the CDRs according to (80) and the FRs according to (103).
(130) a VL region comprising the CDRs according to (80) and the FRs according to (104).
(131) a VL region comprising the CDRs according to (81) and the FRs according to (105), (106), (107) or (108).
(132) a VL region comprising the CDRs according to (82) and the FRs according to (105).
(133) a VL region comprising the CDRs according to (82) and the FRs according to (106).
(134) a VL region comprising the CDRs according to (83) and the FRs according to (107).
(135) a VL region comprising the CDRs according to (84) and the FRs according to (108).
(136) a VL region comprising the CDRs according to (85) and the FRs according to (109).
(137) a VL region comprising the CDRs according to (85) and the FRs according to (111).
(138) a VL region comprising the CDRs according to (86) and the FRs according to (110).
(139) a VL region comprising the CDRs according to (87) and the FRs according to (112).
(140) a VL region comprising the CDRs according to (88) and the FRs according to (113).
(141) a VL region comprising the CDRs according to (89) and the FRs according to (114).
(142) a VL region comprising the CDRs according to (90) and the FRs according to (115).
(143) a VL region comprising the CDRs according to (91) and the FRs according to (116).
(144) a VL region comprising the CDRs according to (92) and the FRs according to (117).
(145) a VL region comprising the CDRs according to (93) and the FRs according to (118), (119) or (120).
(146) a VL region comprising the CDRs according to (94) and the FRs according to (118).
(147) a VL region comprising the CDRs according to (95) and the FRs according to (119).
(148) a VL region comprising the CDRs according to (96) and the FRs according to (120).

In some embodiments the antigen-binding molecule comprises a VL region according to one of (149) to (173) below:
(149) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:310.
(150) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:282.
(151) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:287.
(152) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:294.
(153) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:297.
(154) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:299.
(155) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:301.

(156) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:302.
(157) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:303.
(158) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:40.
(159) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:50.
(160) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:57.
(161) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:66.
(162) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:79.
(163) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:95.
(164) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:104.
(165) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:113.
(166) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:126.
(167) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:136.
(168) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:150.
(169) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:164.
(170) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:176.
(171) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:188.
(172) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:196.
(173) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:202.

In some embodiments the antigen-binding molecule comprises a VH region according to any one of (1) to (76) above, and a VL region according to any one of (77) to (173) above.

In embodiments in accordance with the present invention in which one or more amino acids are substituted with another amino acid, the substitutions may be conservative substitutions, for example according to the following Table. In some embodiments, amino acids in the same block in the middle column are substituted. In some embodiments, amino acids in the same line in the rightmost column are substituted:

| ALIPHATIC | Non-polar | G A P |
| | | I L V |
| | Polar - uncharged | C S T M |
| | | N Q |
| | Polar - charged | D E |
| | | K R |
| AROMATIC | | H F W Y |

In some embodiments, substitution(s) may be functionally conservative. That is, in some embodiments the substitution may not affect (or may not substantially affect) one or more functional properties (e.g. target binding) of the antigen-binding molecule comprising the substitution as compared to the equivalent unsubstituted molecule.

The VH and VL region of an antigen-binding region of an antibody together constitute the Fv region. In some embodiments, the antigen-binding molecule according to the present invention comprises, or consists of, an Fv region which binds to VISTA. In some embodiments the VH and VL regions of the Fv are provided as single polypeptide joined by a linker region, i.e. a single chain Fv (scFv).

In some embodiments the antigen-binding molecule of the present invention comprises one or more regions of an immunoglobulin heavy chain constant sequence. In some embodiments the immunoglobulin heavy chain constant sequence is, or is derived from, the heavy chain constant sequence of an IgG (e.g. IgG1, IgG2, IgG3, IgG4), IgA (e.g. IgA1, IgA2), IgD, IgE or IgM.

In some embodiments the immunoglobulin heavy chain constant sequence is human immunoglobulin G 1 constant (IGHG1; UniProt: P01857-1, v1; SEQ ID NO:205). Positions 1 to 98 of SEQ ID NO:205 form the CH1 region (SEQ ID NO:206). Positions 99 to 110 of SEQ ID NO:205 form a hinge region between CH1 and CH2 regions (SEQ ID NO:207). Positions 111 to 223 of SEQ ID NO:205 form the CH2 region (SEQ ID NO:208). Positions 224 to 330 of SEQ ID NO:205 form the CH3 region (SEQ ID NO:209).

The exemplified antigen-binding molecules may be prepared using pFUSE-CHIg-hG1, which comprises the substitutions D356E, L358M (positions numbered according to EU numbering) in the CH3 region. The amino acid sequence of the CH3 region encoded by pFUSE-CHIg-hG1 is shown in SEQ ID NO:210. It will be appreciated that CH3 regions may be provided with further substitutions in accordance with modification to an Fc region of the antigen-binding molecule as described herein.

In some embodiments a CH1 region comprises or consists of the sequence of SEQ ID NO:206, or a sequence having at least 60%, preferably one of 70%, 75%, 80%, 85%, 90%, 91%, 92%, 93%, 94%, 95%, 96%, 97%, 98%, 99% or 100% amino acid sequence identity to the amino acid sequence of SEQ ID NO:206. In some embodiments a CH1-CH2 hinge region comprises or consists of the sequence of SEQ ID NO:207, or a sequence having at least 60%, preferably one of 70%, 75%, 80%, 85%, 90%, 91%, 92%, 93%, 94%, 95%, 96%, 97%, 98%, 99% or 100% amino acid sequence identity to the amino acid sequence of SEQ ID NO:207. In some embodiments a CH2 region comprises or consists of the sequence of SEQ ID NO:208, or a sequence having at least 60%, preferably one of 70%, 75%, 80%, 85%, 90%, 91%, 92%, 93%, 94%, 95%, 96%, 97%, 98%, 99% or 100% amino acid sequence identity to the amino acid sequence of SEQ ID NO:208. In some embodiments a CH3 region comprises or consists of the sequence of SEQ ID NO:209 or 210, or a sequence having at least 60%, preferably one of 70%, 75%, 80%, 85%, 90%, 91%, 92%, 93%, 94%, 95%, 96%, 97%, 98%, 99% or 100% amino acid sequence identity to the amino acid sequence of SEQ ID NO:209 or 210.

In some embodiments the antigen-binding molecule of the present invention comprises one or more regions of an immunoglobulin light chain constant sequence. In some embodiments the immunoglobulin light chain constant sequence is human immunoglobulin kappa constant (IGKC; Cκ; UniProt: P01834-1, v2; SEQ ID NO:211). In some embodiments the immunoglobulin light chain constant sequence is a human immunoglobulin lambda constant (IGLC; Cλ), e.g. IGLC1, IGLC2, IGLC3, IGLC6 or IGLC7. In some embodiments a CL region comprises or consists of the sequence of SEQ ID NO:211, or a sequence having at least 60%, preferably one of 70%, 75%, 80%, 85%, 90%, 91%, 92%, 93%, 94%, 95%, 96%, 97%, 98%, 99% or 100% amino acid sequence identity to the amino acid sequence of SEQ ID NO:211.

The VL and light chain constant (CL) region, and the VH region and heavy chain constant 1 (CH1) region of an antigen-binding region of an antibody together constitute the Fab region. In some embodiments the antigen-binding molecule comprises a Fab region comprising a VH, a CH1, a VL and a CL (e.g. Cκ or Cλ). In some embodiments the Fab region comprises a polypeptide comprising a VH and a CH1 (e.g. a VH-CH1 fusion polypeptide), and a polypeptide comprising a VL and a CL (e.g. a VL-CL fusion polypeptide). In some embodiments the Fab region comprises a polypeptide comprising a VH and a CL (e.g. a VH-CL fusion polypeptide) and a polypeptide comprising a VL and a CH (e.g. a VL-CH1 fusion polypeptide); that is, in some embodiments the Fab region is a CrossFab region. In some embodiments the VH, CH1, VL and CL regions of the Fab or CrossFab are provided as single polypeptide joined by linker regions, i.e. as a single chain Fab (scFab) or a single chain CrossFab (scCrossFab).

In some embodiments, the antigen-binding molecule of the present invention comprises, or consists of, a Fab region which binds to VISTA.

In some embodiments, the antigen-binding molecule described herein comprises, or consists of, a whole antibody which binds to VISTA. As used herein, "whole antibody" refers to an antibody having a structure which is substantially similar to the structure of an immunoglobulin (Ig). Different kinds of immunoglobulins and their structures are described e.g. in Schroeder and Cavacini J Allergy Clin Immunol. (2010) 125(202): S41-S52, which is hereby incorporated by reference in its entirety.

Immunoglobulins of type G (i.e. IgG) are ~150 kDa glycoproteins comprising two heavy chains and two light chains. From N- to C-terminus, the heavy chains comprise a VH followed by a heavy chain constant region comprising three constant domains (CH1, CH2, and CH3), and similarly the light chain comprise a VL followed by a CL. Depending on the heavy chain, immunoglobulins may be classed as IgG (e.g. IgG1, IgG2, IgG3, IgG4), IgA (e.g. IgA1, IgA2), IgD, IgE, or IgM. The light chain may be kappa (κ) or lambda (λ).

In some embodiments, the antigen-binding molecule described herein comprises, or consists of, an IgG (e.g. IgG1, IgG2, IgG3, IgG4), IgA (e.g. IgA1, IgA2), IgD, IgE, or IgM which binds to VISTA.

In some embodiments, the antigen-binding molecule of the present invention is at least monovalent binding for VISTA. Binding valency refers to the number of binding sites in an antigen-binding molecule for a given antigenic determinant. Accordingly, in some embodiments the antigen-binding molecule comprises at least one binding site for VISTA.

In some embodiments the antigen-binding molecule comprises more than one binding site for VISTA, e.g. 2, 3 or 4 binding sites. The binding sites may be the same or different. In some embodiments the antigen-binding molecule is e.g. bivalent, trivalent or tetravalent for VISTA.

Aspects of the present invention relate to multispecific antigen-binding molecules. By "multispecific" it is meant that the antigen-binding molecule displays specific binding to more than one target. In some embodiments the antigen-binding molecule is a bispecific antigen-binding molecule. In some embodiments the antigen-binding molecule comprises at least two different antigen-binding domains (i.e. at least two antigen-binding domains, e.g. comprising non-identical VHs and VLs).

In some embodiments the antigen-binding molecule binds to VISTA and another target (e.g. an antigen other than VISTA), and so is at least bispecific. The term "bispecific" means that the antigen-binding molecule is able to bind specifically to at least two distinct antigenic determinants.

It will be appreciated that an antigen-binding molecule according to the present invention (e.g. a multispecific antigen-binding molecule) may comprise antigen-binding molecules capable of binding to the targets for which the antigen-binding molecule is specific. For example, an antigen-binding molecule which is capable of binding to VISTA and an antigen other than VISTA may comprise: (i) an antigen-binding molecule which is capable of binding to VISTA, and (ii) an antigen-binding molecule which is capable of binding to an antigen other than VISTA.

It will also be appreciated that an antigen-binding molecule according to the present invention (e.g. a multispecific antigen-binding molecule) may comprise antigen-binding polypeptides or antigen-binding polypeptide complexes capable of binding to the targets for which the antigen-binding molecule is specific. For example, an antigen-binding molecule according to the invention may comprise e.g. (i) an antigen-binding polypeptide complex capable of binding to VISTA, comprising a light chain polypeptide (comprising the structure VL-CL) and a heavy chain polypeptide (comprising the structure VH-CH1-CH2-CH3), and (ii) an antigen-binding polypeptide complex capable of binding to an antigen other than VISTA, comprising a light chain polypeptide (comprising the structure VL-CL) and a heavy chain polypeptide (comprising the structure VH-CH1-CH2-CH3).

In some embodiments, a component antigen-binding molecule of a larger antigen-binding molecule (e.g. a multispecific antigen-biding molecule) may be referred to e.g. as an "antigen-binding domain" or "antigen-binding region" of the larger antigen-binding molecule.

In some embodiments the antigen-binding molecule comprises an antigen-binding molecule capable of binding to VISTA, and an antigen-binding molecule capable of binding to an antigen other than VISTA. In some embodiments, the antigen other than VISTA is an immune cell surface molecule. In some embodiments, the antigen other than VISTA is a cancer cell antigen. In some embodiments the antigen other than VISTA is a receptor molecule, e.g. a cell surface receptor. In some embodiments the antigen other than VISTA is a cell signalling molecule, e.g. a cytokine, chemokine, interferon, interleukin or lymphokine. In some embodiments the antigen other than VISTA is a growth factor or a hormone.

A cancer cell antigen is an antigen which is expressed or over-expressed by a cancer cell. A cancer cell antigen may be any peptide/polypeptide, glycoprotein, lipoprotein, glycan, glycolipid, lipid, or fragment thereof. A cancer cell antigen's expression may be associated with a cancer. A cancer cell antigen may be abnormally expressed by a cancer cell (e.g. the cancer cell antigen may be expressed with abnormal localisation), or may be expressed with an abnormal structure by a cancer cell. A cancer cell antigen may be capable of eliciting an immune response. In some embodiments, the antigen is expressed at the cell surface of the cancer cell (i.e. the cancer cell antigen is a cancer cell surface antigen). In some embodiments, the part of the antigen which is bound by the antigen-binding molecule described herein is displayed on the external surface of the cancer cell (i.e. is extracellular). The cancer cell antigen may be a cancer-associated antigen. In some embodiments the cancer cell antigen is an antigen whose expression is associated with the development, progression or severity of symptoms of a cancer. The cancer-associated antigen may be associated with the cause or pathology of the cancer, or may be expressed abnormally as a consequence of the cancer. In some embodiments, the cancer cell antigen is an antigen whose expression is upregulated (e.g. at the RNA and/or protein level) by cells of a cancer, e.g. as compared to the level of expression of by comparable non-cancerous cells (e.g. non-cancerous cells derived from the same tissue/cell type). In some embodiments, the cancer-associated antigen may be preferentially expressed by cancerous cells, and not expressed by comparable non-cancerous cells (e.g. non-cancerous cells derived from the same tissue/cell type). In some embodiments, the cancer-associated antigen may be the product of a mutated oncogene or mutated tumor suppressor gene. In some embodiments, the cancer-associated antigen may be the product of an overexpressed cellular protein, a cancer antigen produced by an oncogenic virus, an oncofetal antigen, or a cell surface glycolipid or glycoprotein.

An immune cell surface molecule may be any peptide/polypeptide, glycoprotein, lipoprotein, glycan, glycolipid, lipid, or fragment thereof expressed at or on the cell surface of an immune cell. In some embodiments, the part of the immune cell surface molecule which is bound by the antigen-binding molecule of the present invention is on the external surface of the immune cell (i.e. is extracellular). The immune cell surface molecule may be expressed at the cell surface of any immune cell. In some embodiments, the immune cell may be a cell of hematopoietic origin, e.g. a neutrophil, eosinophil, basophil, dendritic cell, lymphocyte, or monocyte. The lymphocyte may be e.g. a T cell, B cell, natural killer (NK) cell, NKT cell or innate lymphoid cell (ILC), or a precursor thereof (e.g. a thymocyte or pre-B cell). In some embodiments the immune cell surface molecule may be a costimulatory molecule (e.g. CD28, OX40, 4-1BB, ICOS or CD27) or a ligand thereof. In some embodiments the immune cell surface molecule may be a checkpoint molecule (e.g. PD-1, CTLA-4, LAG-3, TIM-3, TIGIT or BTLA) or a ligand thereof.

Multispecific antigen-binding molecules according to the invention may be provided in any suitable format, such as those formats described in described in Brinkmann and Kontermann MAbs (2017) 9(2): 182-212, which is hereby incorporated by reference in its entirety. Suitable formats include those shown in FIG. 2 of Brinkmann and Kontermann MAbs (2017) 9(2): 182-212: antibody conjugates, e.g. IgG$_2$, F(ab')$_2$ or CovX-Body; IgG or IgG-like molecules, e.g. IgG, chimeric IgG, κλ-body common HC; CH1/CL fusion proteins, e.g. scFv2-CH1/CL, VHH2-CH1/CL; 'variable domain only' bispecific antigen-binding molecules, e.g. tandem scFv (taFV), triplebodies, diabodies (Db), dsDb, Db(kih), DART, scDB, dsFv-dsFv, tandAbs, triple heads, tandem dAb/VHH, tertravalent dAb.VHH; Non-Ig fusion proteins, e.g. scFv2-albumin, scDb-albumin, taFv-albumin, taFv-toxin, miniantibody, DNL-Fab$_2$, DNL-Fab$_2$-scFv, DNL-Fab$_2$-IgG-cytokine$_2$, ImmTAC (TCR-scFv); modified Fc and CH3 fusion proteins, e.g. scFv-Fc(kih), scFv-Fc(CH3 charge pairs), scFv-Fc (EW-RVT), scFv-fc (HA-TF), scFv-Fc (SEEDbody), taFv-Fc(kih), scFv-Fc(kih)-Fv, Fab-Fc (kih)-scFv, Fab-scFv-Fc(kih), Fab-scFv-Fc(BEAT), Fab-scFv-Fc (SEEDbody), DART-Fc, scFv-CH3(kih), TriFabs; Fc fusions, e.g. Di-diabody, scDb-Fc, taFv-Fc, scFv-Fc-scFv, HCAb-VHH, Fab-scFv-Fc, scFv$_4$-Ig, scFv$_2$-Fcab;

CH3 fusions, e.g. Dia-diabody, scDb-CH3; IgE/IgM CH2 fusions, e.g. scFv-EHD2-scFv, scFvMHD2-scFv; Fab fusion proteins, e.g. Fab-scFv (bibody), Fab-scFv$_2$ (tribody), Fab-Fv, Fab-dsFv, Fab-VHH, orthogonal Fab-Fab; non-Ig fusion proteins, e.g. DNL-Fab$_3$, DNL-Fab$_2$-scFv, DNL-Fab$_2$-IgG-cytokine$_2$; asymmetric IgG or IgG-like molecules, e.g. IgG (kih), IgG(kih) common LC, ZW1 IgG common LC, Biclonics common LC, CrossMab, CrossMab(kih), scFab-IgG (kih), Fab-scFab-IgG(kih), orthogonal Fab IgG(kih), DuetMab, CH3 charge pairs+CH1/CL charge pairs, hinge/CH3 charge pairs, SEED-body, Duobody, four-in-one-CrossMab(kih), LUZ-Y common LC; LUZ-Y scFab-IgG, FcFc*; appended and Fc-modified IgGs, e.g. IgG(kih)-Fv, IgG HA-TF-Fv, IgG(kih)scFab, scFab-Fc(kih)-scFv2, scFab-Fc(kih)-scFv, half DVD-Ig, DVI-Ig (four-in-one), CrossMab-Fab; modified Fc and CH3 fusion proteins, e.g. Fab-Fc(kih)-scFv, Fab-scFv-Fc(kih), Fab-scFv-Fc(BEAT), Fab-scFv-Fc-SEEDbody, TriFab; appended IgGs-HC fusions, e.g. IgG-HC, scFv, IgG-dAb, IgG-taFV, IgG-Cross-Fab, IgG-orthogonal Fab, IgG-(CaCβ) Fab, scFv-HC-IgG, tandem Fab-IgG (orthogonal Fab) Fab-IgG(CaCβ Fab), Fab-IgG(CR3), Fab-hinge-IgG(CR3); appended IgGs-LC fusions, e.g. IgG-scFv(LC), scFv(LC)-IgG, dAb-IgG; appended IgGs-HC and LC fusions, e.g. DVD-Ig, TVD-Ig, CODV-Ig, scFv$_4$-IgG, Zybody; Fc fusions, e.g. Fab-scFv-Fc, scFv$_4$-Ig; F(ab')$_2$ fusions, e.g. F(ab')$_2$-scFv$_2$; CH1/CL fusion proteins e.g. scFv$_2$-CH1-hinge/CL; modified IgGs, e.g. DAF (two-in one-IgG), DutaMab, Mab$^2$; and non-Ig fusions, e.g. DNL-Fab$_4$-IgG.

The skilled person is able to design and prepare bispecific antigen-binding molecules. Methods for producing bispecific antigen-binding molecules include chemically cross-linking of antigen-binding molecules or antibody fragments, e.g. with reducible disulphide or non-reducible thioether bonds, for example as described in Segal and Bast, 2001. Production of Bispecific Antigen-binding molecules. Current Protocols in Immunology. 14:IV:2.13:2.13.1-2.13.16, which is hereby incorporated by reference in its entirety. For example, N-succinimidyl-3-(-2-pyridyldithio)-propionate (SPDP) can be used to chemically crosslink e.g. Fab fragments via hinge region SH-groups, to create disulfide-linked bispecific F(ab)$_2$ heterodimers.

Other methods for producing bispecific antigen-binding molecules include fusing antibody-producing hybridomas e.g. with polyethylene glycol, to produce a quadroma cell capable of secreting bispecific antibody, for example as described in D. M. and Bast, B. J. 2001. Production of Bispecific Antigen-binding molecules. Current Protocols in Immunology. 14:IV:2.13:2.13.1-2.13.16.

Bispecific antigen-binding molecules according to the present invention can also be produced recombinantly, by expression from e.g. a nucleic acid construct encoding polypeptides for the antigen-binding molecules, for example as described in Antibody Engineering: Methods and Protocols, Second Edition (Humana Press, 2012), at Chapter 40: Production of Bispecific Antigen-binding molecules: Diabodies and Tandem scFv (Hornig and Farber-Schwarz), or French, How to make bispecific antigen-binding molecules, Methods Mol. Med. 2000; 40:333-339, the entire contents of both of which are hereby incorporated by reference. For example, a DNA construct encoding the light and heavy chain variable domains for the two antigen-binding fragments (i.e. the light and heavy chain variable domains for the antigen-binding fragment capable of binding VISTA, and the light and heavy chain variable domains for the antigen-binding fragment capable of binding to another target protein), and including sequences encoding a suitable linker or dimerization domain between the antigen-binding fragments can be prepared by molecular cloning techniques. Recombinant bispecific antibody can thereafter be produced by expression (e.g. in vitro) of the construct in a suitable host cell (e.g. a mammalian host cell), and expressed recombinant bispecific antibody can then optionally be purified.

Fc Regions

In some embodiments the antigen-binding molecules of the present invention comprise an Fc region.

In IgG IgA and IgD isotype Fc regions are composed of CH2 and CH3 regions from one polypeptide, and CH2 and CH3 regions from another polypeptide. The CH2 and CH3 regions from the two polypeptides together form the Fc region. In IgM and IgE isotypes the Fc regions contain three constant domains (CH2, CH3 and CH4), and CH2 to CH4 from the two polypeptides together form the Fc region.

Fc regions provide for interaction with Fc receptors and other molecules of the immune system to bring about functional effects. IgG Fc-mediated effector functions are reviewed e.g. in Jefferis et al., Immunol Rev 1998 163:59-76 (hereby incorporated by reference in its entirety), and are brought about through Fc-mediated recruitment and activation of immune cells (e.g. macrophages, dendritic cells, NK cells and T cells) through interaction between the Fc region and Fc receptors expressed by the immune cells, recruitment of complement pathway components through binding of the Fc region to complement protein C1q, and consequent activation of the complement cascade.

Fc-mediated functions include Fc receptor binding, antibody-dependent cellular cytotoxicity (ADCC), antibody-dependent cell-mediated phagocytosis (ADCP), complement-dependent cytotoxicity (CDC), formation of the membrane attack complex (MAC), cell degranulation, cytokine and/or chemokine production, and antigen processing and presentation.

Modifications to antibody Fc regions that influence Fc-mediated functions are known in the art, such as those described e.g. in Wang et al., Protein Cell (2018) 9(1):63-73, which is hereby incorporated by reference in its entirety. In particular, exemplary Fc region modifications known to influence antibody effector function are summarised in Table 1 of Wang et al., Protein Cell (2018) 9(1):63-73. Modifications to Fc regions which influence antibody effector activity are described hereinbelow.

Where an Fc region/CH2/CH3 is described as comprising modification(s) "corresponding to" reference substitution(s), equivalent substitution(s) in the homologous Fc/CH2/CH3 are contemplated. By way of illustration, L234A/L235A substitutions in human IgG1 (numbered according to the EU numbering system as described in Kabat et al., Sequences of Proteins of Immunological Interest, 5th Ed. Public Health Service, National Institutes of Health, Bethesda, Md., 1991) correspond to L to A substitutions at positions 117 and 118 of the mouse Ig gamma-2A chain C region, A allele, numbered according to SEQ ID NO:256.

Where an Fc region is described as comprising a modification, the modification may be present in one or both of the polypeptide chains which together form the Fc region.

In some embodiments, the antigen-binding molecule of the present invention comprises an Fc region comprising modification. In some embodiments, the antigen-binding molecule of the present invention comprises an Fc region comprising modification in one or more of the CH2 and/or CH3 regions.

In some embodiments the Fc region comprises modification to increase an Fc-mediated function. In some embodiments the Fc region comprises modification to increase ADCC. In some embodiments the Fc region comprises modification to increase ADCP. In some embodiments the Fc region comprises modification to increase CDC. An antigen-binding molecule comprising an Fc region comprising modification to increase an Fc-mediated function (e.g. ADCC, ADCP, CDC) induces an increased level of the relevant effector function as compared to an antigen-binding molecule comprising the corresponding unmodified Fc region.

In some embodiments the Fc region comprises modification to increase binding to an Fc receptor. In some embodiments the Fc region comprises modification to increase binding to an Fcγ receptor. In some embodiments the Fc region comprises modification to increase binding to one or more of FcγRI, FcγRIIa, FcγRIIb, FcγRIIc, FcγRIIIa and FcγRIIIb. In some embodiments the Fc region comprises modification to increase binding to FcγRIIIa. In some embodiments the Fc region comprises modification to increase binding to FcγRIIa. In some embodiments the Fc region comprises modification to increase binding to FcγRIIb. In some embodiments the Fc region comprises modification to increase binding to FcRn. In some embodiments the Fc region comprises modification to increase binding to a complement protein. In some embodiments the Fc region comprises modification to increase binding to C1q. In some embodiments the Fc region comprises modification to promote hexamerisation of the antigen-binding molecule. In some embodiments the Fc region comprises modification to increase antigen-binding molecule half-life. In some embodiments the Fc region comprises modification to increase co-engagement.

In some embodiments the Fc region comprises modification corresponding to the combination of substitutions F243L/R292P/Y300L/V305I/P396L as described in Stavenhagen et al. Cancer Res. (2007) 67:8882-8890. In some embodiments the Fc region comprises modification corresponding to the combination of substitutions S239D/I332E or S239D/I332E/A330L as described in Lazar et al., Proc Natl Acad Sci USA. (2006)103:4005-4010. In some embodiments the Fc region comprises modification corresponding to the combination of substitutions S298A/E333A/K334A as described in Shields et al., J Biol Chem. (2001) 276:6591-6604. In some embodiments the Fc region comprises modification to one of heavy chain polypeptides corresponding to the combination of substitutions L234Y/L235Q/G236W/S239M/H268D/D270E/S298A, and modification to the other heavy chain polypeptide corresponding to the combination of substitutions D270E/K326D/A330M/K334E, as described in Mimoto et al., MAbs. (2013): 5:229-236. In some embodiments the Fc region comprises modification corresponding to the combination of substitutions G236A/S239D/I332E as described in Richards et al., Mol Cancer Ther. (2008) 7:2517-2527.

In some embodiments the Fc region comprises modification corresponding to the combination of substitutions K326W/E333S as described in Idusogie et al. J Immunol. (2001) 166(4):2571-5. In some embodiments the Fc region comprises modification corresponding to the combination of substitutions S267E/H268F/S324T as described in Moore et al. MAbs. (2010) 2(2):181-9. In some embodiments the Fc region comprises modification corresponding to the combination of substitutions described in Natsume et al., Cancer Res. (2008) 68(10):3863-72. In some embodiments the Fc region comprises modification corresponding to the combination of substitutions E345R/E430G/S440Y as described in Diebolder et al. Science (2014) 343(6176):1260-3.

In some embodiments the Fc region comprises modification corresponding to the combination of substitutions M252Y/S254T/T256E as described in Dall'Acqua et al. J Immunol. (2002) 169:5171-5180. In some embodiments the Fc region comprises modification corresponding to the combination of substitutions M428L/N434S as described in Zalevsky et al. Nat Biotechnol. (2010) 28:157-159.

In some embodiments the Fc region comprises modification corresponding to the combination of substitutions S267E/L328F as described in Chu et al., Mol Immunol. (2008) 45:3926-3933. In some embodiments the Fc region comprises modification corresponding to the combination of substitutions N325S/L328F as described in Shang et al. Biol Chem. (2014) 289:15309-15318.

In some embodiments the Fc region comprises modification to reduce/prevent an Fc-mediated function. In some embodiments the Fc region comprises modification to reduce/prevent ADCC. In some embodiments the Fc region comprises modification to reduce/prevent ADCP. In some embodiments the Fc region comprises modification to reduce/prevent CDC. An antigen-binding molecule comprising an Fc region comprising modification to reduce/prevent an Fc-mediated function (e.g. ADCC, ADCP, CDC) induces an reduced level of the relevant effector function as compared to an antigen-binding molecule comprising the corresponding unmodified Fc region.

In some embodiments the Fc region comprises modification to reduce/prevent binding to an Fc receptor. In some embodiments the Fc region comprises modification to reduce/prevent binding to an Fcγ receptor. In some embodiments the Fc region comprises modification to reduce/prevent binding to one or more of FcγRI, FcγRIIa, FcγRIIb, FcγRIIc, FcγRIIIa and FcγRIIIb. In some embodiments the Fc region comprises modification to reduce/prevent binding to FcγRIIIa. In some embodiments the Fc region comprises modification to reduce/prevent binding to FcγRIIa. In some embodiments the Fc region comprises modification to reduce/prevent binding to FcγRIIb. In some embodiments the Fc region comprises modification to reduce/prevent binding to a complement protein. In some embodiments the Fc region comprises modification to reduce/prevent binding to C1q. In some embodiments the Fc region comprises modification to reduce/prevent glycosylation of the amino acid residue corresponding to N297.

In some embodiments the Fc region is not able to induce one or more Fc-mediated functions (i.e. lacks the ability to elicit the relevant Fc-mediated function(s)). Accordingly, antigen-binding molecules comprising such Fc regions also lack the ability to induce the relevant function(s). Such antigen-binding molecules may be described as being devoid of the relevant function(s).

In some embodiments the Fc region is not able to induce ADCC. In some embodiments the Fc region is not able to induce ADCP. In some embodiments the Fc region is not able to induce CDC. In some embodiments the Fc region is not able to induce ADCC and/or is not able to induce ADCP and/or is not able to induce CDC.

In some embodiments the Fc region is not able to bind to an Fc receptor. In some embodiments the Fc region is not able to bind to an Fcγ receptor. In some embodiments the Fc region is not able to bind to one or more of FcγRI, FcγRIIa, FcγRIIb, FcγRIIc, FcγRIIIa and FcγRIIIb. In some embodiments the Fc region is not able to bind to FcγRIIIa. In some embodiments the Fc region is not able to bind to FcγRIIa. In some embodiments the Fc region is not able to bind to FcγRIIb. In some embodiments the Fc region is not able to bind to FcRn. In some embodiments the Fc region is not able to bind to a complement protein. In some embodiments the Fc region is not able to bind to C1q. In some embodiments the Fc region is not glycosylated at the amino acid residue corresponding to N297.

In some embodiments the Fc region comprises modification corresponding to N297A or N297Q or N297G as described in Leabman et al., MAbs. (2013) 5:896-903. In some embodiments the Fc region comprises modification corresponding to L235E as described in Alegre et al., J Immunol. (1992) 148:3461-3468. In some embodiments the Fc region comprises modification corresponding to the combination of substitutions L234A/L235A or F234A/L235A as described in Xu et al., Cell Immunol. (2000) 200:16-26. In some embodiments the Fc region comprises modification corresponding to P329A or P329G as described in Schlothauer et al., Protein Engineering, Design and Selection (2016), 29(10):457-466. In some embodiments the Fc region comprises modification corresponding to the combination of substitutions L234A/L235A/P329G as described in Lo et al. J. Biol. Chem (2017) 292(9):3900-3908. In some embodiments the Fc region comprises modification corresponding to the combination of substitutions described in Rother et al., Nat Biotechnol. (2007) 25:1256-1264. In some embodiments the Fc region comprises modification corresponding to the combination of substitutions S228P/L235E as described in Newman et al., Clin. Immunol. (2001) 98:164-174. In some embodiments the Fc region comprises modification corresponding to the combination of substitutions H268Q/V309L/A330S/P331S as described in An et al., MAbs. (2009) 1:572-579. In some embodiments the Fc region comprises modification corresponding to the combination of substitutions V234A/G237A/P238S/H268A/V309L/A330S/P331S as described in Vafa et al., Methods. (2014) 65:114-126. In some embodiments the Fc region comprises modification corresponding to the combination of substitutions L234A/L235E/G237A/A330S/P331S as described in US 2015/0044231 A1.

The combination of substitutions "L234A/L235A" and corresponding substitutions (such as e.g. F234A/L235A in human IgG4) are known to disrupt binding of Fc to Fcγ receptors and inhibit ADCC, ADCP, and also to reduce C1q binding and thus CDC (Schlothauer et al., Protein Engineering, Design and Selection (2016), 29(10):457-466, hereby incorporated by reference in entirety). The substitutions "P329G" and "P329A" reduce C1q binding (and thereby CDC). Substitution of "N297" with "A", "G" or "Q" is known to eliminate glycosylation, and thereby reduce Fc binding to C1q and Fcγ receptors, and thus CDC and ADCC. Lo et al. J. Biol. Chem (2017) 292(9):3900-3908 (hereby incorporated by reference in its entirety) reports that the combination of substitutions L234A/L235A/P329G eliminated complement binding and fixation as well as Fc γ receptor dependent, antibody-dependent, cell-mediated cytotoxicity in both murine IgG2a and human IgG1.

The combination of substitutions L234A/L235E/G237A/A330S/P331S in IgG1 Fc is disclosed in US 2015/0044231 A1 to abolish induction of phagocytosis, ADCC and CDC.

In some embodiments the Fc region comprises modification corresponding to the substitution S228P as described in Silva et al., J Biol Chem. (2015) 290(9):5462-5469. The substitution S228P in IgG4 Fc reduces Fab-arm exchange (Fab arm exchange can be undesirable).

In some embodiments the Fc region comprises modification corresponding to the combination of substitutions L234A/L235A. In some embodiments the Fc region comprises modification corresponding to corresponding to the substitution P329G. In some embodiments the Fc region comprises modification corresponding to corresponding to the substitution N297Q.

In some embodiments the Fc region comprises modification corresponding to corresponding to the combination of substitutions L234A/L235A/P329G.

In some embodiments the Fc region comprises modification corresponding to corresponding to the combination of substitutions L234A/L235A/P329G/N297Q.

In some embodiments the Fc region comprises modification corresponding to corresponding to the combination of substitutions L234A/L235E/G237A/A330S/P331S.

In some embodiments the Fc region comprises modification corresponding to corresponding to the substitution S228P, e.g. in IgG4.

In some embodiments, the antigen-binding molecule of the present invention comprises an Fc region comprising modification in one or more of the CH2 and CH3 regions promoting association of the Fc region. Recombinant co-expression of constituent polypeptides of an antigen-binding molecule and subsequent association leads to several possible combinations. To improve the yield of the desired combinations of polypeptides in antigen-binding molecules in recombinant production, it is advantageous to introduce in the Fc regions modification(s) promoting association of the desired combination of heavy chain polypeptides. Modifications may promote e.g. hydrophobic and/or electrostatic interaction between CH2 and/or CH3 regions of different polypeptide chains. Suitable modifications are described e.g. in Ha et al., Front. Immnol (2016) 7:394, which is hereby incorporated by reference in its entirety.

In some embodiments the antigen antigen-binding molecule of the present invention comprises an Fc region comprising paired substitutions in the CH3 regions of the Fc region according to one of the following formats, as shown in Table 1 of Ha et al., Front. Immnol (2016) 7:394: KiH, KiH$_{s-s}$, HA-TF, ZW1, 7.8.60, DD-KK, EW-RVT, EW-RVT$_{s-s}$, SEED or A107.

In some embodiments, the Fc region comprises the "knob-into-hole" or "KiH" modification, e.g. as described e.g. in U.S. Pat. No. 7,695,936 and Carter, J Immunol Meth 248, 7-15 (2001). In such embodiments, one of the CH3 regions of the Fc region comprises a "knob" modification, and the other CH3 region comprises a "hole" modification. The "knob" and "hole" modifications are positioned within the respective CH3 regions so that the "knob" can be positioned in the "hole" in order to promote heterodimerisation (and inhibit homodimerisation) of the polypeptides and/or stabilise heterodimers. Knobs are constructed by substituting amino acids having small chains with those having larger side chains (e.g. tyrosine or tryptophan). Holes are created by substituting amino acids having large side chains with those having smaller side chains (e.g. alanine or threonine).

In some embodiments, one of the CH3 regions of the Fc region of the antigen-binding molecule of the present invention comprises the substitution (numbering of positions/substitutions in the Fc, CH2 and CH3 regions herein is according to the EU numbering system as described in Kabat et al., Sequences of Proteins of Immunological Interest, 5th Ed. Public Health Service, National Institutes of Health, Bethesda, Md., 1991) T366W, and the other CH3 region of the Fc region comprises the substitution Y407V. In some embodiments, one of the CH3 regions of the Fc region of the antigen-binding molecule comprises the substitution T366W, and the other CH3 region of the Fc region comprises the substitutions T366S and L368A. In some embodiments, one of the CH3 regions of the Fc region of the antigen-binding molecule comprises the substitution T366W, and the other CH3 region of the Fc region comprises the substitutions Y407V, T366S and L368A.

In some embodiments, the Fc region comprises the "DD-KK" modification as described e.g. in WO 2014/131694 A1. In some embodiments, one of the CH3 regions comprises the substitutions K392D and K409D, and the other CH3 region of the Fc region comprises the substitutions E356K and D399K. The modifications promote electrostatic interaction between the CH3 regions.

In some embodiments, the antigen-binding molecule of the present invention comprises an Fc region modified as described in Labrijn et al., Proc Natl Acad Sci USA. (2013) 110(13):5145-50, referred to as 'Duobody' format. In some embodiments one of the CH3 regions comprises the substitution K409R, and the other CH3 region of the Fc region comprises the substitution K405L.

In some embodiments, the antigen-binding molecule of the present invention comprises an Fc region comprising the "EEE-RRR" modification as described in Strop et al., J Mol Biol. (2012) 420(3):204-19. In some embodiments one of the CH3 regions comprises the substitutions D221E, P228E and L368E, and the other CH3 region of the Fc region comprises the substitutions D221R, P228R and K409R.

In some embodiments, the antigen-binding molecule comprises an Fc region comprising the "EW-RVT" modification described in Choi et al., Mol Cancer Ther (2013) 12(12):2748-59. In some embodiments one of the CH3 regions comprises the substitutions K360E and K409W, and the other CH3 region of the Fc region comprises the substitutions Q347R, D399V and F405T.

In some embodiments, one of the CH3 regions comprises the substitution S354C, and the other CH3 region of the Fc region comprises the substitution Y349C. Introduction of these cysteine residues results in formation of a disulphide bridge between the two CH3 regions of the Fc region, further stabilizing the heterodimer (Carter (2001), J Immunol Methods 248, 7-15).

In some embodiments, the Fc region comprises the "KiH$_{S-S}$" modification. In some embodiments one of the CH3 regions comprises the substitutions T366W and S354C, and the other CH3 region of the Fc region comprises the substitutions T366S, L368A, Y407V and Y349C.

In some embodiments, the antigen-binding molecule of the present invention comprises an Fc region comprising the "SEED" modification as described in Davis et al., Protein Eng Des Sel (2010) 23(4):195-202, in which β-strand segments of human IgG1 CH3 and IgA CH3 are exchanged.

In some embodiments, one of the CH3 regions comprises the substitutions S364H and F405A, and the other CH3 region of the Fc region comprises the substitutions Y349T and T394F (see e.g. Moore et al., MAbs (2011) 3(6):546-57).

In some embodiments, one of the CH3 regions comprises the substitutions T350V, L351Y, F405A and Y407V, and the other CH3 region of the Fc region comprises the substitutions T350V, T366L, K392L and T394W (see e.g. Von Kreudenstein et al., MAbs (2013) 5(5):646-54).

In some embodiments, one of the CH3 regions comprises the substitutions K360D, D399M and Y407A, and the other CH3 region of the Fc region comprises the substitutions E345R, Q347R, T366V and K409V (see e.g. Leaver-Fay et al., Structure (2016) 24(4):641-51).

In some embodiments, one of the CH3 regions comprises the substitutions K370E and K409W, and the other CH3 region of the Fc region comprises the substitutions E357N, D399V and F405T (see e.g. Choi et al., PLoS One (2015) 10(12):e0145349).

In some embodiments, the antigen-binding molecule of the present invention comprises an Fc region which does not bind to an Fc γ receptor. In some embodiments, the antigen-binding molecule comprises an Fc region which does not bind to one or more of FcγRI, FcγRIIa, FcγRIIb, FcγRIIc, FcγRIIIa and FcγRIIIb. In some embodiments, the antigen-binding molecule comprises an Fc region which does not bind to one or more of FcγRIIa, FcγRIIb and FcγRIIIa. In some embodiments, the antigen-binding molecule comprises an Fc region which does not bind to one or both of FcγRIIa and FcγRIIb.

The ability of an Fc region, or an antigen-binding molecule comprising an Fc region, to bind to a reference protein (e.g. an Fc receptor) can be analysed according to methods well known in the art, such as ELISA, immunoblot, immunoprecipitation, Surface Plasmon Resonance (SPR; see e.g. Hearty et al., Methods Mol Biol (2012) 907:411-442) or Bio-Layer Interferometry (BLI; see e.g. Lad et al., (2015) J Biomol Screen 20(4): 498-507).

As used herein, an Fc region "which does not bind to" a reference protein may display substantially no binding to the reference protein, e.g. as determined by ELISA, immunoblot (e.g. western blot), immunoprecipitation, SPR or BLI). "Substantially no binding" may be a level of interaction that is not significantly greater than the level of interaction determined for proteins that do not bind to one another in a given assay. "Substantially no binding" may be a level of interaction which is ≤5 times, e.g. ≤4 times, ≤3 times, ≤2.5 times, ≤2 times or ≤1.5 times the level of interaction determined for proteins that do not bind to one another, in a given assay.

In some embodiments, the antigen-binding molecule comprises an Fc region which binds to FcRn.

In some embodiments, the antigen-binding molecule comprises an Fc region which binds to FcRn, and which does not bind to one or more of FcγRIIa, FcγRIIb and FcγRIIIa. In some embodiments, the antigen-binding molecule comprises an Fc region which binds to FcRn, and which does not bind to one or both of FcγRIIa and FcγRIIb.

In some embodiments, the antigen-binding molecule of the present invention comprises an Fc region which does not induce ADCC. In some embodiments, the antigen-binding molecule of the present invention comprises an Fc region which does not induce ADCP. In some embodiments, the antigen-binding molecule of the present invention comprises an Fc region which does not induce CDC. In some embodiments, the antigen-binding molecule of the present invention comprises an Fc region which does not induce ADCC, ADCP or CDC.

As used herein, an Fc region/antigen-binding molecule which does not induce (i.e. is not able to induce) ADCC/ADCP/CDC elicits substantially no ADCC/ADCP/CDC activity, e.g. as determined by analysis in an appropriate assay for the relevant activity. "Substantially no ADCC/ADCP/CDC activity" refers to a level of ADCC/ADCP/CDC that is not significantly greater than ADCC/ADCP/CDC determined for an appropriate negative control molecule in a given assay (e.g. an antigen-binding molecule lacking an Fc region, or an antigen-binding molecule comprising a 'silent' Fc region (e.g. as described in Schlothauer et al., Protein Engineering, Design and Selection (2016), 29(10):457-466, which is incorporated by reference hereinabove)). "Substantially no activity" may be a level of the relevant activity which is ≤5 times, e.g. ≤4 times, ≤3 times, ≤2.5 times, ≤2 times or ≤1.5 times the level of activity determined for an appropriate negative control molecule in a given assay.

The ability of an Fc region, or an antigen-binding molecule comprising an Fc region, to induce ADCC can be analysed e.g. according to the method described in Yamashita et al., Scientific Reports (2016) 6:19772 (hereby incorporated by reference in its entirety), or by $^{51}$Cr release assay as described e.g. in Jedema et al., Blood (2004) 103: 2677-82 (hereby incorporated by reference in its entirety). The ability of an Fc region, or an antigen-binding molecule comprising an Fc region, to induce ADCP can be analysed e.g. according to the method described in Kamen et al., J Immunol (2017) 198 (1 Supplement) 157.17 (hereby incorporated by reference in its entirety). The ability of an Fc region, or an antigen-binding molecule comprising an Fc region, to induce CDC can be analysed e.g. using a C1q binding assay, e.g. as described in Schlothauer et al., Protein Engineering, Design and Selection (2016), 29(10):457-466 (incorporated by reference hereinabove).

In some embodiments, the antigen-binding molecule comprises an Fc region comprising a polypeptide having an amino acid sequence having at least 70%, preferably one of 80%, 85%, 90%, 91%, 92%, 93%, 94%, 95%, 96%, 97%, 98%, 99% or 100% amino acid sequence identity to SEQ ID NO:254. In some embodiments, the antigen-binding molecule comprises an Fc region comprising a polypeptide having an amino acid sequence having at least 70%, preferably one of 80%, 85%, 90%, 91%, 92%, 93%, 94%, 95%, 96%, 97%, 98%, 99% or 100% amino acid sequence identity to SEQ ID NO:257. In some embodiments, the antigen-binding molecule comprises an Fc region comprising a polypeptide having an amino acid sequence having at least 70%, preferably one of 80%, 85%, 90%, 91%, 92%, 93%, 94%, 95%, 96%, 97%, 98%, 99% or 100% amino acid sequence identity to SEQ ID NO:259. In some embodiments, the antigen-binding molecule comprises an Fc region comprising a polypeptide having an amino acid sequence having at least 70%, preferably one of 80%, 85%, 90%, 91%, 92%, 93%, 94%, 95%, 96%, 97%, 98%, 99% or 100% amino acid sequence identity to SEQ ID NO:260.

In some embodiments the antigen-binding molecules of the present invention lack an Fc region.

Fc Receptors

Fc receptors are polypeptides which bind to the Fc region of immunoglobulins. Fc receptor structure and function is reviewed e.g. in Masuda et al., Inflamm Allergy Drug Targets (2009) 8(1): 80-86, and Bruhns, Blood (2012) 119: 5640-5649, both of which are hereby incorporated by reference in their entirety.

Fc receptors are expressed at surface of hematopoietic cells including macrophages, neutrophils, dendritic cells, eosinophils, basophils, mast cells, and NK cells. They include the IgG-binding Fc γ receptors, the high-affinity receptor for IgE (FcεRI), the IgA receptor, and the polymeric Ig receptor for IgA and IgM. The neonatal Fc receptor (FcRn) is a further Fc receptor for IgG, and is involved in IgG transport across epithelial barriers (transcytosis), protecting IgG from degradation, and antigen presentation. Humans have six different classes of Fc γ receptor (mouse orthologues are shown in brackets): FcγRI (mFcγRI), FcγRIIa (mFcγRIII), FcγRIIb (mFcγRIIb), FcγRIIc, FcγRIIIa (mFcγRIV) and FcγRIIIb.

FcγRI, FcγRIIa, FcγRIIc and FcγRIIIa comprise immunoreceptor tyrosine-based activation motifs (ITAMs) in their intracellular domains, and ligation by Fc leads to activation of cells expressing the receptors.

FcγRIIb comprises immunoreceptor tyrosine-based inhibitory motifs (ITIMs) in its intracellular domain, and negatively regulates cell activation and degranulation, cell proliferation, endocytosis, and phagocytosis upon ligation by Fc.

In this specification an "Fcγ receptor" may be from any species, and includes isoforms, fragments, variants (including mutants) or homologues from any species. Similarly, "FcγRI", "FcγRIIa", "FcγRIIb", "FcγRIIc", "FcγRIIIa" and "FcγRIIIb" refer respectively to FcγRI/FcγRIIa/FcγRIIb/FcγRIIc/FcγRIIIa/FcγRIIIb from any species, and include isoforms, fragments, variants (including mutants) or homologues from any species.

In some embodiments, the Fc γ receptor (e.g. FcγRI/FcγRIIa/FcγRIIb/FcγRIIc/FcγRIIIa/FcγRIIIb) is from a mammal (e.g. a primate (rhesus, cynomolgous, non-human primate or human) and/or a rodent (e.g. rat or mouse). Isoforms, fragments, variants or homologues may optionally be characterised as having at least 70%, preferably one of 80%, 85%, 90%, 91%, 92%, 93%, 94%, 95%, 96%, 97%, 98%, 99% or 100% amino acid sequence identity to the amino acid sequence of an immature or mature isoform of an Fc γ receptor (e.g. FcγRI/FcγRIIa/FcγRIIb/FcγRIIc/FcγRIIIa/FcγRIIIb) from a given species, e.g. human.

Isoforms, fragments, variants or homologues may optionally be functional isoforms, fragments, variants or homologues, e.g. having a functional property/activity of the reference Fc γ receptor, as determined by analysis by a suitable assay for the functional property/activity. For example, an isoform, fragment, variant or homologue of FcγRI may e.g. display association with human IgG1 Fc.

In this specification an "FcRn receptor" may be from any species, and includes isoforms, fragments, variants (including mutants) or homologues from any species.

In some embodiments, the FcRn receptor is from a mammal (e.g. a primate (rhesus, cynomolgous, non-human primate or human) and/or a rodent (e.g. rat or mouse). Isoforms, fragments, variants or homologues may optionally be characterised as having at least 70%, preferably one of 80%, 85%, 90%, 91%, 92%, 93%, 94%, 95%, 96%, 97%, 98%, 99% or 100% amino acid sequence identity to the amino acid sequence of an immature or mature isoform of an FcRn receptor from a given species, e.g. human.

Isoforms, fragments, variants or homologues may optionally be functional isoforms, fragments, variants or homologues, e.g. having a functional property/activity of the reference FcRn, as determined by analysis by a suitable assay for the functional property/activity. For example, an isoform, fragment, variant or homologue of FcRn may e.g. display association with human IgG1 Fc.

Polypeptides

The present invention also provides polypeptide constituents of antigen-binding molecules. The polypeptides may be provided in isolated or substantially purified form.

The antigen-binding molecule of the present invention may be, or may comprise, a complex of polypeptides.

In the present specification where a polypeptide comprises more than one domain or region, it will be appreciated that the plural domains/regions are preferably present in the same polypeptide chain. That is, the polypeptide comprises more than one domain or region is a fusion polypeptide comprising the domains/regions.

In some embodiments a polypeptide according to the present invention comprises, or consists of, a VH as described herein. In some embodiments a polypeptide according to the present invention comprises, or consists of, a VL as described herein.

In some embodiments, the polypeptide additionally comprises one or more antibody heavy chain constant regions (CH). In some embodiments, the polypeptide additionally comprises one or more antibody light chain constant regions (CL). In some embodiments, the polypeptide comprises a CH1, CH2 region and/or a CH3 region of an immunoglobulin (Ig).

In some embodiments the polypeptide comprises one or more regions of an immunoglobulin heavy chain constant sequence. In some embodiments the polypeptide comprises a CH1 region as described herein. In some embodiments the polypeptide comprises a CH1-CH2 hinge region as described herein. In some embodiments the polypeptide comprises a CH2 region as described herein. In some embodiments the polypeptide comprises a CH3 region as described herein.

In some embodiments the polypeptide comprises a CH2 and/or CH3 region comprising any one of the following amino acid substitutions/combinations of amino acid substitutions: F243L/R292P/Y300L/V305I/P396L; S239D/I332E; S239D/I332E/A330L; S298A/E333A/K334A; L234Y/L235Q/G236W/S239M/H268D/D270E/S298A; D270E/K326D/A330M/K334E; G236A/S239D/I332E; K326W/E333S; S267E/H268F/S324T; E345R/E430G/S440Y; M252Y/S254T/T256E; M428L/N434S; S267E/L328F; N325S/L328F; N297A; N297Q; N297G; L235E; L234A/L235A; F234A/L235A; P329A; P329G; L234A/L235A/P329G; H268Q/V309L/A330S/P331S; and V234A/G237A/P238S/H268A/V309L/A330S/P331S.

In some embodiments the polypeptide comprises a CH3 region comprising any one of the following amino acid substitutions/combinations of amino acid substitutions (shown e.g. in Table 1 of Ha et al., Front. Immnol (2016) 7:394, incorporated by reference hereinabove): T366W; T366S, L368A and Y407V; T366W and S354C; T366S, L368A, Y407V and Y349C; S364H and F405A; Y349T and T394F; T350V, L351 Y, F405A and Y407V; T350V, T366L, K392L and T394W; K360D, D399M and Y407A; E345R, Q347R, T366V and K409V; K409D and K392D; D399K and E356K; K360E and K409W; Q347R, D399V and F405T; K360E, K409W and Y349C; Q347R, D399V, F405T and S354C; K370E and K409W; and E357N, D399V and F405T.

In some embodiments the CH2 and/or CH3 regions of the polypeptide comprise one or more amino acid substitutions for promoting association of the polypeptide with another polypeptide comprising a CH2 and/or CH3 region.

In some embodiments the polypeptide comprises one or more regions of an immunoglobulin light chain constant sequence. In some embodiments the polypeptide comprises a CL region as described herein.

In some embodiments the polypeptide lacks one or more regions of an immunoglobulin heavy chain constant sequence. In some embodiments the polypeptide lacks a CH2 region. In some embodiments the polypeptide lacks a CH3 region. In some embodiments the polypeptide lacks a CH2 region and also lacks a CH3 region.

In some embodiments, the polypeptide according to the present invention comprises a structure from N- to C-terminus according to one of the following:
(i) VH
(ii) VL
(iii) VH-CH1
(iv) VL-CL
(v) VL-CH1
(vi) VH-CL
(vii) VH-CH1-CH2-CH3
(viii) VL-CL-CH2-CH3
(ix) VL-CH1-CH2-CH3
(x) VH-CL-CH2-CH3

Also provided by the present invention are antigen-binding molecules composed of the polypeptides of the present invention. In some embodiments, the antigen-binding molecule of the present invention comprises one of the following combinations of polypeptides:
(A) VH+VL
(B) VH-CH1+VL-CL
(C) VL-CH1+VH-CL
(D) VH-CH1-CH2-CH3+VL-CL
(E) VH-CL-CH2-CH3+VL-CH1
(F) VL-CH1-CH2-CH3+VH-CL
(G) VL-CL-CH2-CH3+VH-CH1
(H) VH-CH1-CH2-CH3+VL-CL-CH2-CH3
(I) VH-CL-CH2-CH3+VL-CH1-CH2-CH3

In some embodiments the antigen-binding molecule comprises more than one of a polypeptide of the combinations shown in (A) to (I) above. By way of example, with reference to (D) above, in some embodiments the antigen-binding molecule comprises two polypeptides comprising the structure VH-CH1-CH2-CH3, and two polypeptides comprising the structure VL-CL.

In some embodiments, the antigen-binding molecule of the present invention comprises one of the following combinations of polypeptides:
(J) VH (anti-VISTA)+VL (anti-VISTA)
(K) VH (anti-VISTA)-CH1+VL (anti-VISTA)-CL
(L) VL (anti-VISTA)-CH1+VH (anti-VISTA)-CL
(M) VH (anti-VISTA)-CH1-CH2-CH3+VL (anti-VISTA)-CL
(N) VH (anti-VISTA)-CL-CH2-CH3+VL (anti-VISTA)-CH1
(O) VL (anti-VISTA)-CH1-CH2-CH3+VH (anti-VISTA)-CL
(P) VL (anti-VISTA)-CL-CH2-CH3+VH (anti-VISTA)-CH1
(Q) VH (anti-VISTA)-CH1-CH2-CH3+VL (anti-VISTA)-CL-CH2-CH3
(R) VH (anti-VISTA)-CL-CH2-CH3+VL (anti-VISTA)-CH1-CH2-CH3

Wherein: "VH (anti-VISTA)" refers to the VH of an antigen-binding molecule capable of binding to VISTA as described herein, e.g. as defined in one of (1) to (76); "VL (anti-VISTA)" refers to the VL of an antigen-binding molecule capable of binding to VISTA as described herein, e.g. as defined in one of (77) to (173).

In some embodiments the polypeptide comprises or consists of an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of one of SEQ ID NOs:212 to 243, 248 to 250, 258, 266 or 311 to 321.

Linkers and Additional Sequences

In some embodiments the antigen-binding molecules and polypeptides of the present invention comprise a hinge region. In some embodiments a hinge region is provided between a CH1 region and a CH2 region. In some embodiments a hinge region is provided between a CL region and a CH2 region. In some embodiments the hinge region comprises, or consists of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:207.

In some embodiments the antigen-binding molecules and polypeptides of the present invention comprise one or more linker sequences between amino acid sequences. A linker sequence may be provided at one or both ends of one or more of a VH, VL, CH1-CH2 hinge region, CH2 region and a CH3 region of the antigen-binding molecule/polypeptide.

Linker sequences are known to the skilled person, and are described, for example in Chen et al., Adv Drug Deliv Rev (2013) 65(10): 1357-1369, which is hereby incorporated by reference in its entirety. In some embodiments, a linker sequence may be a flexible linker sequence. Flexible linker sequences allow for relative movement of the amino acid sequences which are linked by the linker sequence. Flexible linkers are known to the skilled person, and several are identified in Chen et al., Adv Drug Deliv Rev (2013) 65(10): 1357-1369. Flexible linker sequences often comprise high proportions of glycine and/or serine residues.

In some embodiments, the linker sequence comprises at least one glycine residue and/or at least one serine residue. In some embodiments the linker sequence consists of glycine and serine residues. In some embodiments, the linker sequence has a length of 1-2, 1-3, 1-4, 1-5 or 1-10 amino acids.

The antigen-binding molecules and polypeptides of the present invention may additionally comprise further amino acids or sequences of amino acids. For example, the antigen-binding molecules and polypeptides may comprise amino acid sequence(s) to facilitate expression, folding, trafficking, processing, purification or detection of the antigen-binding molecule/polypeptide. For example, the antigen-binding molecule/polypeptide may comprise a sequence encoding a His, (e.g. 6×His), Myc, GST, MBP, FLAG, HA, E, or Biotin tag, optionally at the N- or C-terminus of the antigen-binding molecule/polypeptide. In some embodiments the antigen-binding molecule/polypeptide comprises a detectable moiety, e.g. a fluorescent, luminescent, immuno-detectable, radio, chemical, nucleic acid or enzymatic label.

The antigen-binding molecules and polypeptides of the present invention may additionally comprise a signal peptide (also known as a leader sequence or signal sequence). Signal peptides normally consist of a sequence of 5-30 hydrophobic amino acids, which form a single alpha helix. Secreted proteins and proteins expressed at the cell surface often comprise signal peptides.

The signal peptide may be present at the N-terminus of the antigen-binding molecule/polypeptide, and may be present in the newly synthesised antigen-binding molecule/polypeptide. The signal peptide provides for efficient trafficking and secretion of the antigen-binding molecule/polypeptide. Signal peptides are often removed by cleavage, and thus are not comprised in the mature antigen-binding molecule/polypeptide secreted from the cell expressing the antigen-binding molecule/polypeptide.

Signal peptides are known for many proteins, and are recorded in databases such as GenBank, UniProt, SwissProt, TrEMBL, Protein Information Resource, Protein Data Bank, Ensembl, and InterPro, and/or can be identified/predicted e.g. using amino acid sequence analysis tools such as SignalP (Petersen et al., 2011 Nature Methods 8: 785-786) or Signal-BLAST (Frank and Sippl, 2008 Bioinformatics 24: 2172-2176).

Labels and Conjugates

In some embodiments the antigen-binding molecules of the present invention additionally comprise a detectable moiety.

In some embodiments the antigen-binding molecule comprises a detectable moiety, e.g. a fluorescent label, phosphorescent label, luminescent label, immuno-detectable label (e.g. an epitope tag), radiolabel, chemical, nucleic acid or enzymatic label. The antigen-binding molecule may be covalently or non-covalently labelled with the detectable moiety.

Fluorescent labels include e.g. fluorescein, rhodamine, allophycocyanin, eosine and NDB, green fluorescent protein (GFP) chelates of rare earths such as europium (Eu), terbium (Tb) and samarium (Sm), tetramethyl rhodamine, Texas Red, 4-methyl umbelliferone, 7-amino-4-methyl coumarin, Cy3, and Cy5. Radiolabels include radioisotopes such as Iodine$^{123}$, Iodine$^{125}$, Iodine$^{126}$, Iodine$^{131}$, Iodine$^{133}$, Bromine$^{77}$, Technetium$^{99m}$, Indium$^{111}$, Indium$^{113m}$, Gallium$^{67}$, Gallium$^{68}$, Ruthenium$^{95}$, Ruthenium$^{97}$, Ruthenium$^{103}$, Ruthenium$^{105}$, Mercury$^{207}$, Mercury$^{203}$, Rhenium$^{99m}$, Rhenium$^{101}$, Rhenium$^{105}$, Scandium$^{47}$, Tellurium$^{121m}$, Tellurium$^{122m}$, Tellurium$^{125m}$, Thulium$^{165}$, Thulium$^{167}$, Thulium$^{168}$, Copper$^{67}$, Fluorine$^{18}$, Yttrium$^{90}$, Palladium$^{100}$, Bismuth$^{217}$ and Antimony$^{211}$. Luminescent labels include as radioluminescent, chemiluminescent (e.g. acridinium ester, luminol, isoluminol) and bioluminescent labels. Immuno-detectable labels include haptens, peptides/polypeptides, antibodies, receptors and ligands such as biotin, avidin, streptavidin or digoxigenin. Nucleic acid labels include aptamers. Enzymatic labels include e.g. peroxidase, alkaline phosphatase, glucose oxidase, beta-galactosidase and luciferase.

In some embodiments the antigen-binding molecules of the present invention are conjugated to a chemical moiety. The chemical moiety may be a moiety for providing a therapeutic effect. Antibody-drug conjugates are reviewed e.g. in Parslow et al., Biomedicines. 2016 September; 4(3): 14. In some embodiments, the chemical moiety may be a drug moiety (e.g. a cytotoxic agent). In some embodiments, the drug moiety may be a chemotherapeutic agent. In some embodiments, the drug moiety is selected from calicheamicin, DM1, DM4, monomethylauristatin E (MMAE), monomethylauristatin F (MMAF), SN-38, doxorubicin, duocarmycin, D6.5 and PBD.

Particular Exemplary Embodiments of the Antigen-Binding Molecules

In some embodiments the antigen-binding molecule comprises, or consists of:
(i) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:212; and
(ii) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:213.

In some embodiments the antigen-binding molecule comprises, or consists of:
(i) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:214; and
(ii) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:215.

In some embodiments the antigen-binding molecule comprises, or consists of:
- (i) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:216; and
- (ii) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:217.

In some embodiments the antigen-binding molecule comprises, or consists of:
- (i) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:218; and
- (ii) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:219.

In some embodiments the antigen-binding molecule comprises, or consists of:
- (i) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:220; and
- (ii) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:221.

In some embodiments the antigen-binding molecule comprises, or consists of:
- (i) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:222; and
- (ii) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:223.

In some embodiments the antigen-binding molecule comprises, or consists of:
- (i) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:224; and
- (ii) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:225.

In some embodiments the antigen-binding molecule comprises, or consists of:
- (i) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:226; and
- (ii) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:227.

In some embodiments the antigen-binding molecule comprises, or consists of:
- (i) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:228; and
- (ii) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:229.

In some embodiments the antigen-binding molecule comprises, or consists of:
- (i) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:230; and
- (ii) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:231.

In some embodiments the antigen-binding molecule comprises, or consists of:
- (i) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:232; and
- (ii) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:233.

In some embodiments the antigen-binding molecule comprises, or consists of:
- (i) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:234; and
(ii) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:235.

In some embodiments the antigen-binding molecule comprises, or consists of:
(i) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:236; and
(ii) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:237.

In some embodiments the antigen-binding molecule comprises, or consists of:
(i) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:238; and
(ii) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:239.

In some embodiments the antigen-binding molecule comprises, or consists of:
(i) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:240; and
(ii) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:241.

In some embodiments the antigen-binding molecule comprises, or consists of:
(i) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:242; and
(ii) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:243.

In some embodiments the antigen-binding molecule comprises, or consists of:
(i) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:248; and
(ii) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:250.

In some embodiments the antigen-binding molecule comprises, or consists of:
(i) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:249; and
(ii) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:250.

In some embodiments the antigen-binding molecule comprises, or consists of:
(i) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:258; and
(ii) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:250.

In some embodiments the antigen-binding molecule comprises, or consists of:
(i) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:266; and
(ii) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:250.

In some embodiments the antigen-binding molecule comprises, or consists of:
(i) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:330; and
(ii) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:213.

Functional Properties of the Antigen-Binding Molecules

The antigen-binding molecules described herein may be characterised by reference to certain functional properties. In some embodiments, the antigen-binding molecule described herein may possess one or more of the following properties:

- binds to VISTA (e.g. human, murine and/or cynomolgus macaque VISTA);
- does not bind to PD-L1 and/or HER3;
- does not bind to an Fcγ receptor;
- does not bind to C1q;
- does not induce ADCC;
- does not induce ADCP;
- does not induce CDC;
- binds to an FcRn receptor;
- binds to VISTA-expressing cells;
- inhibits interaction between VISTA and a binding partner for VISTA (e.g. PSGL-1, VSIG-3 or VSIG-8);
- inhibits VISTA-mediated signalling;
- inhibits VISTA-mediated signalling independently of Fc-mediated function;
- increases killing of VISTA-expressing cells;
- does not induce/increase killing of VISTA-expressing cells;
- reduces the number/proportion of VISTA-expressing cells;
- does not reduce the number/proportion of VISTA-expressing cells;
- increases effector immune cell number/activity;
- reduces suppressor immune cell number/activity;
- reduces suppressor immune cell proliferation;
- decreases immune suppression mediated by VISTA-expressing cells;
- increases antigen presentation by antigen-presenting cells;
- increases production of IL-6 by immune cells;
- increases production of IFN-γ, IL-2 and/or IL-17 in a mixed lymphocyte reaction (MLR) assay; increases T cell proliferation, IFN-γ production and/or TNFa production; and inhibits the development and/or progression of cancer in vivo.

The antigen-binding molecules described herein preferably display specific binding to VISTA. As used herein, "specific binding" refers to binding which is selective for the antigen, and which can be discriminated from non-specific binding to non-target antigen. An antigen-binding molecule that specifically binds to a target molecule preferably binds the target with greater affinity, and/or with greater duration than it binds to other, non-target molecules.

The ability of a given polypeptide to bind specifically to a given molecule can be determined by analysis according to methods known in the art, such as by ELISA, Surface Plasmon Resonance (SPR; see e.g. Hearty et al., Methods Mol Biol (2012) 907:411-442), Bio-Layer Interferometry (see e.g. Lad et al., (2015) J Biomol Screen 20(4): 498-507), flow cytometry, or by a radiolabeled antigen-binding assay (RIA) enzyme-linked immunosorbent assay. Through such analysis binding to a given molecule can be measured and quantified. In some embodiments, the binding may be the response detected in a given assay.

In some embodiments, the extent of binding of the antigen-binding molecule to an non-target molecule is less than about 10% of the binding of the antibody to the target molecule as measured, e.g. by ELISA, SPR, Bio-Layer Interferometry or by RIA. Alternatively, binding specificity may be reflected in terms of binding affinity where the antigen-binding molecule binds with a dissociation constant ($K_D$) that is at least 0.1 order of magnitude (i.e. $0.1 \times 10^n$, where n is an integer representing the order of magnitude) greater than the $K_D$ of the antigen-binding molecule towards a non-target molecule. This may optionally be one of at least 0.2, 0.3, 0.4, 0.5, 0.6, 0.7, 0.8, 0.9, 1.0, 1.5, or 2.0.

In some embodiments, the antigen-binding molecule displays binding to human VISTA, murine (e.g. mouse) VISTA and/or cynomolgus macaque (*Macaca fascicularis*) VISTA. That is, in some embodiments the antigen-binding molecule is cross-reactive for human VISTA and murine VISTA and/or cynomolgus macaque VISTA. In some embodiments the antigen-binding molecule of the present invention displays cross-reactivity with VISTA of a non-human primate. Cross-reactivity to VISTA in model species allows in vivo exploration of efficacy in syngeneic models without relying on surrogate molecules.

In some embodiments, the antigen-binding molecule does not display specific binding to PD-L1 (e.g. human PD-L1). In some embodiments, the antigen-binding molecule does not display specific binding to HER3 (e.g. human HER3). In some embodiments, the antigen-binding molecule does not display specific binding to (i.e. does not cross-react with) another member of the B7 family of proteins. In some embodiments, the antigen-binding molecule does not display specific binding to PD-L1, PD-L2 CD80, CD86, ICOSLG, CD276, VTCN1, NCR3LG1, HHLA2 and/or CTLA4.

In some embodiments, the antigen-binding molecule does not display specific binding to PD-1, PD-L1, B7H3, VTCN1 (B7H4), NCR3LG1 (B7H6), HHLA2 (B7H7) and/or CTLA4.

In some embodiments the antigen-binding molecule is not able to induce one or more Fc-mediated functions (i.e. lacks the ability to elicit the relevant Fc-mediated function(s)). Such antigen-binding molecules may be described as being devoid of the relevant function(s).

As explained hereinabove, an Fc region/antigen-binding molecule which does not induce (i.e. is not able to induce) ADCC/ADCP/CDC elicits substantially no ADCC/ADCP/CDC activity, e.g. as determined by analysis in an appropriate assay for the relevant activity. Similarly, an antigen-binding molecule "which does not bind to" a reference protein (e.g. a given Fc receptor or complement protein) may display substantially no binding to the reference protein in an appropriate assay.

In some embodiments the antigen-binding molecule is not able to induce ADCC. In some embodiments the antigen-binding molecule is not able to induce ADCP. In some embodiments the antigen-binding molecule is not able to induce CDC. In some embodiments the antigen-binding molecule is not able to induce ADCC and/or is not able to induce ADCP and/or is not able to induce CDC.

In some embodiments the antigen-binding molecule is not able to bind to an Fc receptor. In some embodiments the antigen-binding molecule is not able to bind to an Fcγ receptor. In some embodiments the antigen-binding molecule is not able to bind to one or more of FcγRI, FcγRIIa, FcγRIIb, FcγRIIc, FcγRIIIa and FcγRIIIb. In some embodiments the antigen-binding molecule is not able to bind to FcγRIIIa. In some embodiments the antigen-binding molecule is not able to bind to FcγRIIa. In some embodiments the antigen-binding molecule is not able to bind to FcγRIIb. In some embodiments the antigen-binding molecule binds to FcRn. In some embodiments the antigen-binding molecule is not able to bind to a complement protein. In some embodiments the antigen-binding molecule is not able to bind to C1q. In some embodiments the antigen-binding molecule is not glycosylated at the amino acid residue corresponding to N297.

In some embodiments the antigen-binding molecule binds to human VISTA, murine VISTA and/or cynomolgus macaque VISTA; and does not bind to PD-L1, PD-1, B7H3, VTCN1 (B7H4), NCR3LG1 (B7H6), HHLA2 (B7H7) and/or CTLA4 (e.g. human PD-L1/PD-1/B7H3/VTCN1/NCR3LG1/HHLA2/CTLA4).

In some embodiments, the antigen-binding molecule described herein binds to VISTA (e.g. human VISTA, mouse VISTA) with a $K_D$ of 10 μM or less, preferably one of ≤5 μM, ≤2 μM, ≤1 μM, ≤500 nM, ≤100 nM, ≤75 nM, ≤50 nM, ≤40 nM, ≤30 nM, ≤20 nM, ≤15 nM, ≤12.5 nM, ≤10 nM, ≤9 nM, ≤8 nM, ≤7 nM, ≤6 nM, ≤5 nM, ≤4 nM ≤3 nM, ≤2 nM, ≤1 nM or ≤500 pM. In some embodiments, the antigen-binding molecule binds to VISTA (e.g. human VISTA, mouse VISTA) with an affinity of $K_D$=≤10 nM, ≤9 nM, ≤8 nM, ≤7 nM or ≤6 nM, ≤5 nM, ≤4 nM, ≤3 nM, ≤2 nM or ≤1 nM. In some embodiments, the antigen-binding molecule binds to VISTA (e.g. human VISTA, mouse VISTA) with an affinity of $K_D$=≤500 pM, ≤100 pM, ≤90 pM, ≤80 pM, ≤70 pM or ≤60 pM, ≤50 pM, ≤40 pM, ≤30 pM, ≤20 pM, ≤10 pM, ≤9 pM, ≤8 pM, ≤7 pM or ≤6 pM, ≤5 pM, ≤4 pM, ≤3 pM, ≤2 pM or ≤1 pM.

The antigen-binding molecules of the present invention may bind to a particular region of interest of VISTA. The antigen-binding region of an antigen-binding molecule according to the present domain may bind to a linear epitope of VISTA, consisting of a contiguous sequence of amino acids (i.e. an amino acid primary sequence). In some embodiments, the antigen-binding region molecule may bind to a conformational epitope of VISTA, consisting of a discontinuous sequence of amino acids of the amino acid sequence.

In some embodiments, the antigen-binding molecule of the present invention is capable of binding to VISTA. In some embodiments, the antigen-binding molecule is capable of binding to VISTA in an extracellular region of VISTA. In some embodiments, the antigen-binding molecule is capable of binding to VISTA in the Ig-like V-type domain (e.g. the region shown in SEQ ID NO:6). In some embodiments, the antigen-binding molecule is capable of binding to VISTA in the region shown in SEQ ID NO:31.

In some embodiments the antigen-binding molecule is capable of binding to a polypeptide comprising or consisting of the amino acid sequence shown in SEQ ID NO:6. In some embodiments the antigen-binding molecule is capable of binding to a polypeptide comprising or consisting of the amino acid sequence shown in SEQ ID NO:31. In some embodiments the antigen-binding molecule is capable of binding to a peptide or polypeptide comprising or consisting of the amino acid sequence shown in SEQ ID NO:322. In some embodiments the antigen-binding molecule is capable of binding to a peptide or polypeptide comprising or consisting of the amino acid sequence shown in SEQ ID NO:26. In some embodiments the antigen-binding molecule is capable of binding to a peptide or polypeptide comprising or consisting of the amino acid sequence shown in SEQ ID NO:27. In some embodiments the antigen-binding molecule is capable of binding to a peptide or polypeptide comprising or consisting of the amino acid sequence shown in SEQ ID NO:28. In some embodiments the antigen-binding molecule is capable of binding to a peptide or polypeptide comprising or consisting of the amino acid sequence shown in SEQ ID NO:29. In some embodiments the antigen-binding molecule is capable of binding to a peptide or polypeptide comprising or consisting of the amino acid sequence shown in SEQ ID NO:30.

In some embodiments, the antigen-binding molecule does not bind to the region of VISTA bound by IGN175A (described e.g. in WO 2014/197849 A2). In some embodiments, the antigen-binding molecule does not bind to the region of VISTA bound by an antigen-binding molecule comprised of a polypeptide consisting of the sequence of SEQ ID NO:267 and a polypeptide consisting of the sequence of SEQ ID NO:268.

In some embodiments, the antigen-binding molecule does not compete with IGN175A (described e.g. in WO 2014/197849 A2) for binding to VISTA. In some embodiments, the antigen-binding molecule does not compete with an antigen-binding molecule comprised of a polypeptide consisting of the sequence of SEQ ID NO:267 and a polypeptide consisting of the sequence of SEQ ID NO:268 for binding to VISTA.

The ability of a given antigen-binding molecule to compete with IGN175A or the antigen-binding molecule comprised of a polypeptide consisting of the sequence of SEQ ID NO:267 and a polypeptide consisting of the sequence of SEQ ID NO:268 for binding to VISTA can be analysed e.g. by competition ELISA, or by epitope binning as described in Abdiche et al., J Immunol Methods (2012) 382(-2):101-116 (hereby incorporated by reference in its entirety). Epitope binning can be performed e.g. by BLI analysis, e.g. as described in Example 8 of the present application.

In some embodiments the antigen-binding molecule is not capable of binding to a peptide consisting of the amino acid sequence shown in SEQ ID NO:275.

As used herein, a "peptide" refers to a chain of two or more amino acid monomers linked by peptide bonds. A peptide typically has a length in the region of about 2 to 50 amino acids. A "polypeptide" is a polymer chain of two or more peptides. Polypeptides typically have a length greater than about 50 amino acids.

The ability of an antigen-binding molecule to bind to a given peptide/polypeptide can be analysed by methods well known to the skilled person, including analysis by ELISA, immunoblot (e.g. western blot), immunoprecipitation, surface plasmon resonance and biolayer interferometry.

In some embodiments the antigen-binding molecule is capable of binding the same region of VISTA, or an overlapping region of VISTA, to the region of VISTA which is bound by an antibody comprising the VH and VL sequences of one of clones 4M2-C12, 4M2-B4, 4M2-C9, 4M2-D9, 4M2-D5, 4M2-A8, V4H1, V4H2, V4-C1, V4-C9, V4-C24, V4-C26, V4-C27, V4-C28, V4-C30, V4-C31, 2M1-B12, 2M1-D2, 1M2- D2, 13D5p, 13D5-1, 13D5-13, 5M1-A11 or 9M2-C12.

In some embodiments the antigen-binding molecule is capable of binding to a region of VISTA which is different to the region of VISTA bound by IGN175A (described e.g. in WO 2014/197849 A2). In some embodiments the antigen-binding molecule is capable of binding to a region of VISTA which is different to the region of VISTA bound by an antigen-binding molecule comprised of a polypeptide consisting of the sequence of SEQ ID NO:267 and a polypeptide consisting of the sequence of SEQ ID NO:268.

In some embodiments the antigen-binding molecule is capable of binding to a region of VISTA which does not overlap the region of VISTA bound by IGN175A (described e.g. in WO 2014/197849 A2). In some embodiments the antigen-binding molecule is capable of binding to a region of VISTA which does not overlap with the region of VISTA bound by an antigen-binding molecule comprised of a polypeptide consisting of the sequence of SEQ ID NO:267 and a polypeptide consisting of the sequence of SEQ ID NO:268.

In some embodiments, the antigen-binding molecule binds to VISTA through contact with residues of VISTA which are non-identical to the residues of VISTA which are contacted by VSTB112 (described e.g. in WO 2015/097536 A2). In some embodiments, the antigen-binding molecule binds to VISTA through contact with residues of VISTA which are non-identical to the residues of VISTA which are contacted by an antigen-binding molecule comprised of a polypeptide consisting of the sequence of SEQ ID NO:269 and a polypeptide consisting of the sequence of SEQ ID NO:270.

In some embodiments the epitope for the antigen-binding molecule is non-identical to the epitope for VSTB112. In some embodiments the epitope for the antigen-binding molecule is non-identical to the epitope for an antigen-binding molecule comprised of a polypeptide consisting of the sequence of SEQ ID NO:269 and a polypeptide consisting of the sequence of SEQ ID NO:270.

The region of a peptide/polypeptide to which an antibody binds can be determined by the skilled person using various methods well known in the art, including X-ray co-crystallography analysis of antibody-antigen complexes, peptide scanning, mutagenesis mapping, hydrogen-deuterium exchange analysis by mass spectrometry, phage display, competition ELISA and proteolysis-based 'protection' methods. Such methods are described, for example, in Gershoni et al., BioDrugs, 2007, 21(3):145-156, which is hereby incorporated by reference in its entirety.

In some embodiments the antigen-binding molecule of the present invention binds to VISTA in a region which is accessible to an antigen-binding molecule (i.e., an extracellular antigen-binding molecule) when VISTA is expressed at the cell surface (i.e. in or at the cell membrane). In some embodiments the antigen-binding molecule is capable of binding to VISTA expressed at the cell surface of a cell expressing VISTA. In some embodiments the antigen-binding molecule is capable of binding to VISTA-expressing cells (e.g. CD14+ monocytes (such as monocyte-derived suppressor cells (MDSCs)) and/or CD33+ myeloid cells, tumor associated macrophages (TAMs), and neutrophils).

The ability of an antigen-binding molecule to bind to a given cell type can be analysed by contacting cells with the antigen-binding molecule, and detecting antigen-binding molecule bound to the cells, e.g. after a washing step to remove unbound antigen-binding molecule. The ability of an antigen-binding molecule to bind to immune cell surface molecule-expressing cells and/or cancer cell antigen-expressing cells can be analysed by methods such as flow cytometry and immunofluorescence microscopy.

The antigen-binding molecule of the present invention may be an antagonist of VISTA. In some embodiments, the antigen-binding molecule is capable of inhibiting a function or process (e.g. interaction, signalling or other activity) mediated by VISTA and/or a binding partner for VISTA (e.g. PSGL-1, VSIG-3, VSIG-8). Herein, 'inhibition' refers to a reduction, decrease or lessening relative to a control condition.

VISTA-binding antigen-binding molecules described herein are able to inhibit VISTA-mediated functions/processes by a mechanism not requiring Fc-mediated functions such as ADCC, ADCP and CDC. That is, VISTA-binding antigen-binding molecules described herein are able to inhibit the immunosuppressive activity of VISTA-expressing cells without the need to elicit ADCC, ADCP and/or CDC.

In particular, VISTA-binding antigen-binding molecules described herein are able to inhibit VISTA via a mechanism not requiring binding to Fcγ receptors and/or binding to C1q.

In some embodiments the antigen-binding molecule of the present invention is capable of inhibiting interaction between VISTA and a binding partner for VISTA (e.g. PSGL-1, VSIG-3, VSIG-8). In some embodiments the antigen-binding molecule of the present invention is capable of inhibiting interaction between VISTA and PSGL-1. In some embodiments the antigen-binding molecule of the present invention is capable of inhibiting interaction between VISTA and VSIG-3.

The ability of an antigen-binding molecule to inhibit interaction between two factors can be determined for example by analysis of interaction in the presence of, or following incubation of one or both of the interaction partners with, the antibody/fragment. Assays for determining whether a given antigen-binding molecule is capable of inhibiting interaction between two interaction partners include competition ELISA assays and analysis by SPR.

An antigen-binding molecule which is capable of inhibiting a given interaction (e.g. between VISTA and a binding partner for VISTA) is identified by the observation of a reduction/decrease in the level of interaction between the interaction partners in the presence of—or following incubation of one or both of the interaction partners with—the antigen-binding molecule, as compared to the level of interaction in the absence of the antigen-binding molecule (or in the presence of an appropriate control antigen-binding molecule). Suitable analysis can be performed in vitro, e.g. using recombinant interaction partners or using cells expressing the interaction partners. Cells expressing interaction partners may do so endogenously, or may do so from nucleic acid introduced into the cell. For the purposes of such assays, one or both of the interaction partners and/or the antigen-binding molecule may be labelled or used in conjunction with a detectable entity for the purposes of detecting and/or measuring the level of interaction.

The ability of an antigen-binding molecule to inhibit interaction between two binding partners can also be determined by analysis of the downstream functional consequences of such interaction. For example, downstream functional consequences of interaction between VISTA and a binding partner for VISTA may include VISTA-mediated signalling. For example, the ability of an antigen-binding molecule to inhibit interaction of VISTA and a binding partner for VISTA may be determined by analysis of production of IL-2, IFN-γ and/or IL-17 in an MLR assay.

In some embodiments, the antigen-binding molecule of the present invention is capable of inhibiting interaction between VISTA and a binding partner for VISTA (e.g. PSGL-1, VSIG-3, VSIG-8) to less than less than 1 times, e.g. ≤0.99 times, ≤0.95 times, ≤0.9 times, ≤0.85 times, ≤0.8 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times, ≤0.1 times, ≤0.05 times, or ≤0.01 times the level of interaction between VISTA and the binding partner for VISTA in the absence of the antigen-binding molecule (or in the presence of an appropriate control antigen-binding molecule).

In some embodiments the antigen-binding molecule inhibits VISTA-mediated signalling. VISTA-mediated signalling can be analysed e.g. using an assay of effector immune cell number/activity, such as an MLR assay as described in the experimental examples herein. Inhibition of VISTA-mediated signalling can be identified by detection of an increase in the number and/or activity of effector immune cells, as determined e.g. by an increase in production of IL-2, IFN-γ and/or IL-17.

In some embodiments the antigen-binding molecule is able to inhibit VISTA-mediated signalling by a mechanism not requiring or involving Fc-mediated function. In some embodiments the antigen-binding molecule is able to inhibit VISTA-mediated signalling independently of Fc-mediated function. That is, in some embodiments the antigen-binding molecule is able to inhibit VISTA-mediated signalling in an Fc region-independent manner.

The ability of an antigen-binding molecule to inhibit VISTA-mediated signalling by a mechanism not requiring/involving Fc-mediated function can be evaluated e.g. by analysing the ability of the antigen-binding molecule provided in a format lacking a functional Fc region to inhibit VISTA-mediated signalling. For example, the effect on VISTA-mediated signalling can be investigated using an antigen-binding molecule comprising a 'silent' Fc region (e.g. comprising LALA PG substitutions), or using an antigen-binding molecule provided in a format lacking an Fc region (e.g. scFv, Fab etc.).

In some embodiments the antigen-binding molecule is able to inhibit VISTA-mediated signalling by a mechanism not involving ADCC. In some embodiments the antigen-binding molecule is able to inhibit VISTA-mediated signalling by a mechanism not involving ADCP. In some embodiments the antigen-binding molecule is able to inhibit VISTA-mediated signalling by a mechanism not involving CDC.

In some embodiments the antigen-binding molecule is able to inhibit VISTA-mediated signalling by a mechanism not requiring binding of the antigen-binding molecule to an Fc receptor. In some embodiments the antigen-binding molecule is able to inhibit VISTA-mediated signalling by a mechanism not requiring binding of the antigen-binding molecule to an Fcγ receptor. In some embodiments the antigen-binding molecule is able to inhibit VISTA-mediated signalling by a mechanism not requiring binding of the antigen-binding molecule to one or more of FcγRI, FcγRIIa, FcγRIIb, FcγRIIc, FcγRIIIa and FcγRIIIb. In some embodiments the antigen-binding molecule is able to inhibit VISTA-mediated signalling by a mechanism not requiring binding to FcγRIIIa. In some embodiments the antigen-binding molecule is able to inhibit VISTA-mediated signalling by a mechanism not requiring binding to FcγRIIa. In some embodiments the antigen-binding molecule is able to inhibit VISTA-mediated signalling by a mechanism not requiring binding to FcγRIIb. In some embodiments the antigen-binding molecule is able to inhibit VISTA-mediated signalling by a mechanism not requiring binding to a complement protein. In some embodiments the antigen-binding molecule is able to inhibit VISTA-mediated signalling by a mechanism not requiring binding to C1q. In some embodiments the antigen-binding molecule is able to inhibit VISTA-mediated signalling by a mechanism not requiring N297 glycosylation.

In some embodiments, the antigen-binding molecule of the present invention is capable of increasing killing of VISTA-expressing cells. Killing of VISTA-expressing cells may be increased through an effector function of the antigen-binding molecule. In embodiments wherein antigen-binding molecule comprises an Fc region the antigen-binding molecule may increase killing of VISTA-expressing cells through one or more of complement dependent cytotoxicity (CDC), antibody-dependent cell-mediated cytotoxicity (ADCC) and antibody-dependent cellular phagocytosis (ADCP).

An antigen-binding molecule which is capable of increasing killing of VISTA-expressing cells can be identified by observation of an increased level of killing of VISTA-expressing cells in the presence of—or following incubation of the VISTA-expressing cells with—the antigen-binding molecule, as compared to the level of cell killing detected in the absence of the antigen-binding molecule (or in the presence of an appropriate control antigen-binding molecule), in an appropriate assay. Assays of CDC, ADCC and ADCP are well known the skilled person. The level of killing of VISTA-expressing cells can also be determined by measuring the number/proportion of viable and/or non-viable VISTA-expressing cells following exposure to different treatment conditions.

In some embodiments, the antigen-binding molecule of the present invention is capable of increasing killing of VISTA-expressing cells (e.g. VISTA-expressing MDSCs) to more than 1 times, e.g. ≥1.01 times, ≥1.02 times, ≥1.03 times, ≥1.04 times, ≥1.05 times, ≥1.1 times, ≥1.2 times, ≥1.3 times, ≥1.4 times, ≥1.5 times, ≥1.6 times, ≥1.7 times, ≥1.8 times, ≥1.9 times, ≥2 times, ≥3 times, ≥4 times, ≥5 times, ≥6 times, ≥7 times, ≥8 times, ≥9 times or ≥10 times the level of killing observed in the absence of the antigen-binding molecule (or in the presence of an appropriate control antigen-binding molecule).

In some embodiments, the antigen-binding molecule of the present invention is capable of reducing the number of VISTA-expressing cells (e.g. VISTA-expressing MDSCs) to less than less than 1 times, e.g. ≤0.99 times, ≤0.95 times, ≤0.9 times, ≤0.85 times, ≤0.8 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times, ≤0.1 times, ≤0.05 times, or ≤0.01 times the number of VISTA-expressing cells (e.g. VISTA-expressing MDSCs, TAMs, neutrophils) detected following incubation in the absence of the antigen-binding molecule (or following incubation in the presence of an appropriate control antigen-binding molecule), in a comparable assay.

In some embodiments the antigen-binding molecule is a non-depleting antigen-binding molecule. That is, in some embodiments the antigen-binding molecule does not cause substantial depletion of VISTA-expressing cells. In some embodiments the antigen-binding molecule does not elicit/increase ADCC, ADCP and/or CDC against VISTA-expressing cells.

In some embodiments, the antigen-binding molecule of the present invention does not induce/increase killing of VISTA-expressing cells, e.g. in embodiments wherein the antigen-binding molecule lacks an Fc region, or embodiments wherein the antigen-binding molecule comprises an Fc region which is not able to induce an Fc-mediated antibody effector function. In some embodiments, the antigen-binding molecule of the present invention does not reduce the number/proportion of VISTA-expressing cells.

In some embodiments the antigen-binding molecule of the present invention (i) inhibits VISTA-mediated signalling, and (ii) does not induce/increase killing of VISTA-expressing cells. In some embodiments the antigen-binding molecule of the present invention (i) inhibits VISTA-mediated signalling, and (ii) does not reduce the number/proportion of VISTA-expressing cells.

This can be particularly advantageous, because VISTA is expressed by cells that it is not desirable to deplete. For example, VISTA is expressed at low levels by immune cells (e.g. certain types of T cells and dendritic cells) that it is not desirable to kill or reduce the number/proportion of.

In some embodiments, the antigen-binding molecule of the present invention is capable of increasing the number and/or activity of effector immune cells relative to a negative control condition, e.g. in an appropriate in vitro assay, or in vivo. By way of explanation, the antigen-binding molecules of the invention may be capable of releasing effector immune cells from MDSC-mediated suppression of effector immune cell proliferation and function. In some embodiments the effector immune cells may be e.g. CD8+ T cells, CD8+ cytotoxic T lymphocytes (CD8+ CTLs), CD4+ T cells, CD4+ T helper cells, NK cells, IFNγ-producing cells, memory T cells, central memory T cells, antigen-experienced T cells or CD45RO+ T cells.

Cell numbers and proportions can be determined e.g. by flow cytometry analysis using antibodies allowing detection of cell types. Cell division can be analysed, for example, by in vitro analysis of incorporation of $^3$H-thymidine or by CFSE dilution assay, e.g. as described in Fulcher and Wong, Immunol Cell Biol (1999) 77(6): 559-564, hereby incorporated by reference in entirety. Effector immune cell activity can be analysed by measuring a correlate of such activity. In some embodiments effector immune cell activity can be determined e.g. by analysis of production of IL-2, IFN-γ and/or IL-17.

In some embodiments, the antigen-binding molecule of the present invention is capable of increasing the number of an effector immune cell type to more than 1 times, e.g. ≥1.01 times, ≥1.02 times, ≥1.03 times, ≥1.04 times, ≥1.05 times, ≥1.1 times, ≥1.2 times, ≥1.3 times, ≥1.4 times, ≥1.5 times, ≥1.6 times, ≥1.7 times, ≥1.8 times, ≥1.9 times, ≥2 times, ≥3 times, ≥4 times, ≥5 times, ≥6 times, ≥7 times, ≥8 times, ≥9 times or ≥10 times the number observed in the absence of the antigen-binding molecule (or in the presence of an appropriate control antigen-binding molecule). In some embodiments, the antigen-binding molecule of the present invention is capable of increasing the level of a correlate of effector immune cell activity to more than 1 times, e.g. ≥1.01 times, ≥1.02 times, ≥1.03 times, ≥1.04 times, ≥1.05 times, ≥1.1 times, ≥1.2 times, ≥1.3 times, ≥1.4 times, ≥1.5 times, ≥1.6 times, ≥1.7 times, ≥1.8 times, ≥1.9 times, ≥2 times, ≥3 times, ≥4 times, ≥5 times, ≥6 times, ≥7 times, ≥8 times, ≥9 times or ≥10 times the level observed in the absence of the antigen-binding molecule (or in the presence of an appropriate control antigen-binding molecule).

In some embodiments, the antigen-binding molecule of the present invention is capable of decreasing the level of immune suppression mediated by VISTA-expressing cells. A change in the level of immune suppression may be determined using methods to measure the expression of arginase 1 and/or the production of reactive oxygen species (ROS) by VISTA-expressing cells, for example as described in Ochoa et al., Ann Surg. 2001 March; 233(3): 393-399 and Dikalov and Harrison Antioxid Redox Signal. 2014 Jan. 10; 20(2): 372-382.

In some embodiments, the antigen-binding molecule of the present invention is capable of increasing antigen presentation by antigen-presenting cells, e.g. as determined using a suitable assay of antigen presentation. In some embodiments, the antigen-binding molecule of the present invention is capable of increasing phagocytosis by phagocytic cells (e.g. neutrophils, monocytes, macrophages, mast cells, and/or dendritic cells), e.g. as determined using a suitable assay of the level of phagocytosis.

In some embodiments, the antigen-binding molecule of the present invention is capable of increasing production of IL-6 by immune cells. The immune cells may be e.g. PBMCs, lymphocytes, T cells, B cells, NK cells, or monocytes. In some embodiments the immune cells are monocytes. In some embodiments the antigen-binding molecule is capable of increasing production of IL-6 by immune cells following stimulation, e.g. with LPS. The ability of an antigen-binding molecule to increase production of IL-6 by immune cells can be analysed in an in vitro assay e.g. as described in Example 10 herein. Such methods may comprise stimulating monocytes (e.g. THP1 cells) with LPS, and incubating the stimulated cells with the antigen-binding molecule.

In some embodiments, the antigen-binding molecule of the present invention is capable of increasing IL-6 production by immune cells (e.g. LPS-stimulated THP1 cells) to more than 1 times, e.g. ≥1.01 times, ≥1.02 times, ≥1.03 times, ≥1.04 times, ≥1.05 times, ≥1.1 times, ≥1.2 times, ≥1.3 times, ≥1.4 times, ≥1.5 times, ≥1.6 times, ≥1.7 times, ≥1.8 times, ≥1.9 times, ≥2 times, ≥3 times, ≥4 times, ≥5 times, ≥6 times, ≥7 times, ≥8 times, ≥9 times or ≥10 times the level observed in the absence of the antigen-binding molecule (or in the presence of an appropriate control antigen-binding molecule).

In some embodiments, the antigen-binding molecule of the present invention is capable of increasing T cell proliferation, IL-2 production, IFN-γ production and/or IL-17 production in a Mixed Lymphocyte Reaction (MLR) assay. MLR assays may be performed as described in Bromelow et al J. Immunol Methods, 2001 Jan. 1; 247(1-2):1-8, (hereby incorporated by reference in its entirety), or as described in the experimental examples herein. IL-2, IFNγ and/or IL-17 production may be analysed e.g. by antibody-based methods well known to the skilled person, such as western blot, immunohistochemistry, immunocytochemistry, flow cytometry, ELISA, ELISPOT, or by reporter-based methods.

In some embodiments, the antigen-binding molecule of the present invention is capable of increasing T cell proliferation, IL-2 production, IFN-γ production and/or IL-17 production in an MLR assay to more than 1 times, e.g. ≥1.01 times, ≥1.02 times, ≥1.03 times, ≥1.04 times, ≥1.05 times, ≥1.1 times, ≥1.2 times, ≥1.3 times, ≥1.4 times, ≥1.5 times, ≥1.6 times, ≥1.7 times, ≥1.8 times, ≥1.9 times, ≥2 times, ≥3 times, ≥4 times, ≥5 times, ≥6 times, ≥7 times, ≥8 times, ≥9 times or ≥10 times the level observed in the absence of the antigen-binding molecule (or in the presence of an appropriate control antigen-binding molecule).

In some embodiments, the antigen-binding molecule of the present invention is capable of increasing T cell proliferation, IFN-γ production and/or TNFa production, e.g. in the presence of VISTA/VISTA expressing cells. Antigen-binding molecules may be evaluated for such properties e.g. in in vitro assays as described in the experimental examples herein.

In some embodiments, the antigen-binding molecule of the present invention is capable of increasing T cell proliferation, IFN-γ production and/or TNFa production (e.g. in the presence of VISTA/VISTA expressing cells) to more than 1 times, e.g. ≥1.01 times, ≥1.02 times, ≥1.03 times, ≥1.04 times, ≥1.05 times, ≥1.1 times, ≥1.2 times, ≥1.3 times, ≥1.4 times, ≥1.5 times, ≥1.6 times, ≥1.7 times, ≥1.8 times, ≥1.9 times, ≥2 times, ≥3 times, ≥4 times, ≥5 times, ≥6 times, ≥7 times, ≥8 times, ≥9 times or ≥10 times the level observed in the absence of the antigen-binding molecule (or in the presence of an appropriate control antigen-binding molecule).

In some embodiments, the antigen-binding molecule of the present invention is capable of increasing T cell (e.g.

CD4+ T cell and/or CD8+ T cell) proliferation to a greater extent than a VISTA-binding antibody disclosed in the prior art (e.g. VSTB112, described e.g. in WO 2015/097536 A2). T cell proliferation may be evaluated in an in vitro assay e.g. as described in Example 9 herein, and may involve stimulating T cell proliferation by culture in the presence of agonist anti-CD3 antibody. In some embodiments, the antigen-binding molecule of the present invention is capable of increasing T cell proliferation in such an assay to more than 1 times, e.g. ≥1.01 times, ≥1.02 times, ≥1.03 times, ≥1.04 times, ≥1.05 times, ≥1.1 times, ≥1.2 times, ≥1.3 times, ≥1.4 times, ≥1.5 times, ≥1.6 times, ≥1.7 times, ≥1.8 times, ≥1.9 times, ≥2 times, ≥3 times, ≥4 times, ≥5 times, ≥6 times, ≥7 times, ≥8 times, ≥9 times or ≥10 times the level proliferation induced by the prior art VISTA-binding antibody (e.g. VSTB112).

In some embodiments, the antigen-binding molecule of the present invention is capable of increasing IL-6 production by THP1 cells to a greater extent than a VISTA-binding antibody disclosed in the prior art (e.g. VSTB112, described e.g. in WO 2015/097536 A2). IL-6 production by THP1 cells may be evaluated in an in vitro assay e.g. as described in Example 10 herein, and may involve stimulating THP1 cells with LPS. In some embodiments, the antigen-binding molecule of the present invention is capable of increasing IL-6 production in such an assay to more than 1 times, e.g. ≥1.01 times, ≥1.02 times, ≥1.03 times, ≥1.04 times, ≥1.05 times, ≥1.1 times, ≥1.2 times, ≥1.3 times, ≥1.4 times, ≥1.5 times, ≥1.6 times, ≥1.7 times, ≥1.8 times, ≥1.9 times, ≥2 times, ≥3 times, ≥4 times, ≥5 times, ≥6 times, ≥7 times, ≥8 times, ≥9 times or ≥10 times the level induced by the prior art VISTA-binding antibody (e.g. VSTB112).

In some embodiments, the antigen-binding molecule of the present invention is capable of: reducing the number and/or activity of suppressor immune cells, inhibiting proliferation of suppressor immune cells, and/or reducing the proportion of suppressor immune cells within a population of cells (e.g. CD45+ cells, e.g. CD45+ cells obtained from a tumor) relative to control condition, e.g. as determined in an appropriate in vitro assay, or in vivo.

The suppressor immune cells may be e.g. VISTA-expressing cells, Arg1-expressing cells, MDSCs, granulocytic MDSCs (g-MDSCs) or monocytic MDSCs (m-MDSCs).

In some embodiments, the reduction in the number/activity/proliferation/proportion is to less than 1 times, e.g. ≤0.99 times, ≤0.95 times, ≤0.9 times, ≤0.85 times, ≤0.8 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times, ≤0.1 times, ≤0.05 times, or ≤0.01 times the number/activity/proliferation/proportion observed in the absence of the antigen-binding molecule (or in the presence of an appropriate control antigen-binding molecule).

In some embodiments the antigen-binding molecule is able to reduce the number/activity/proliferation/proportion of suppressor immune cells by a mechanism not involving Fc-mediated function. In some embodiments the antigen-binding molecule is able to reduce the number/activity/proliferation/proportion of suppressor immune cells independently of Fc-mediated function (i.e. in an Fc region-independent manner). In some embodiments the antigen-binding molecule is able to reduce the number/activity/proliferation/proportion of suppressor immune cells by a mechanism not involving ADCC, ADCP and/or CDC. In some embodiments the antigen-binding molecule is able to reduce the number/activity/proliferation/proportion of suppressor immune cells by a mechanism not involving depletion of VISTA-expressing cells.

In some embodiments, the antigen-binding molecule of the present invention inhibits the development and/or progression of cancer in vivo.

In some embodiments the antigen-binding molecule causes an increase in the killing of cancer cells, e.g. by effector immune cells. In some embodiments the antigen-binding molecule causes a reduction in the number of cancer cells in vivo, e.g. as compared to an appropriate control condition. In some embodiments the antigen-binding molecule inhibits tumor growth, e.g. as determined by measuring tumor size/volume over time.

In some embodiments, the antigen-binding molecule of the present invention is capable of increasing serum levels of IFN-γ and/or IL-23 in mice treated with the antigen-binding molecule. Serum levels of IFN-γ and/or IL-23 can be analysed e.g. by ELISA of serum derived from blood samples obtained from the mice. In some embodiments, administration of the antigen-binding molecule of the present invention increases serum level of IFN-γ and/or IL-23 to more than 1 times, e.g. ≥1.01 times, ≥1.02 times, ≥1.03 times, ≥1.04 times, ≥1.05 times, ≥1.1 times, ≥1.2 times, ≥1.3 times, ≥1.4 times, ≥1.5 times, ≥1.6 times, ≥1.7 times, ≥1.8 times, ≥1.9 times, ≥2 times, ≥3 times, ≥4 times, ≥5 times, ≥6 times, ≥7 times, ≥8 times, ≥9 times or ≥10 times the level observed in the absence of administration of the antigen-binding molecule (or the level observed following administration of an appropriate control antigen-binding molecule).

The antigen-binding molecule of the present invention may be analysed for the ability to inhibit development and/or progression of cancer in an appropriate in vivo model, e.g. cell line-derived xenograft model such as CT26 cell-derived model, a 4T-1 cell-derived model, an LL2 cell-derived model, a B16 cell-derived model, or an EL4 cell-derived model. The cancer may be a cancer in which VISTA-expressing cells and/or MDSCs (e.g. VISTA-expressing MDSCs, TAMs, neutrophils) are pathologically implicated. Cancers in which MDSCs are 'pathologically implicated' include cancers in which MDSCs, or an increased number/proportion of MDSCs, is positively associated with onset, development or progression of the cancer, and/or severity of one or more symptoms of the cancer, or a cancer for which MDSCs, or an increased number/proportion of MDSCs, is a risk factor for the onset, development or progression of the cancer. The cancer may comprise MDSCs in an organ/tissue which is affected by the disease (e.g. an organ/tissue in which the symptoms of the disease/condition manifest) or in a tumor.

In some embodiments, administration of an antigen-binding molecule according to the present invention may cause one or more of: inhibition of the development/progression of the cancer, a delay to/prevention of onset of the cancer, a reduction in/delay to/prevention of tumor growth, a reduction in/delay to/prevention of metastasis, a reduction in the severity of the symptoms of the cancer, a reduction in the number of cancer cells, a reduction in tumour size/volume, and/or an increase in survival (e.g. progression free survival), e.g. as determined in an CT26 cell, 4T-1 cell, an LL2 cell, a B16 cell, or an EL4 cell-derived xenograft model.

In some embodiments, administration of the antigen-binding molecule of the present invention is capable of inhibiting greater than 5%, e.g. ≥10%, ≥15%, ≥20%, ≥25%, ≥30%, ≥35%, ≥40%, ≥45%, ≥50%, ≥55%, ≥60%, ≥65%, ≥70%, ≥75%, ≥80%, ≥85%, ≥90% or ≥95% of the tumor growth observed in the absence of administration of the antigen-binding molecule (or following administration of an appropriate control antigen-binding molecule).

Chimeric Antigen Receptors (CARs)

The present invention also provides Chimeric Antigen Receptors (CARs) comprising the antigen-binding molecules or polypeptides of the present invention.

CARs are recombinant receptors that provide both antigen-binding and T cell activating functions. CAR structure and engineering is reviewed, for example, in Dotti et al., Immunol Rev (2014) 257(1), hereby incorporated by reference in its entirety. CARs comprise an antigen-binding region linked to a cell membrane anchor region and a signalling region. An optional hinge region may provide separation between the antigen-binding region and cell membrane anchor region, and may act as a flexible linker.

The CAR of the present invention comprises an antigen-binding region which comprises or consists of the antigen-binding molecule of the present invention, or which comprises or consists of a polypeptide according to the invention.

The cell membrane anchor region is provided between the antigen-binding region and the signalling region of the CAR and provides for anchoring the CAR to the cell membrane of a cell expressing a CAR, with the antigen-binding region in the extracellular space, and signalling region inside the cell. In some embodiments, the CAR comprises a cell membrane anchor region comprising or consisting of an amino acid sequence which comprises, consists of, or is derived from, the transmembrane region amino acid sequence for one of CD3-ζ, CD4, CD8 or CD28. As used herein, a region which is 'derived from' a reference amino acid sequence comprises an amino acid sequence having at least 60%, e.g. one of at least 65%, 70%, 75%, 80%, 85%, 90%, 91%, 92%, 93%, 94%, 95%, 96%, 97%, 98%, 99% or 100% sequence identity to the reference sequence.

The signalling region of a CAR allows for activation of the T cell. The CAR signalling regions may comprise the amino acid sequence of the intracellular domain of CD3-', which provides immunoreceptor tyrosine-based activation motifs (ITAMs) for phosphorylation and activation of the CAR-expressing T cell. Signalling regions comprising sequences of other ITAM-containing proteins such as FcγRI have also been employed in CARs (Haynes et al., 2001 J Immunol 166(1):182-187). Signalling regions of CARs may also comprise co-stimulatory sequences derived from the signalling region of co-stimulatory molecules, to facilitate activation of CAR-expressing T cells upon binding to the target protein. Suitable co-stimulatory molecules include CD28, OX40, 4-1BB, ICOS and CD27. In some cases CARs are engineered to provide for co-stimulation of different intracellular signalling pathways. For example, signalling associated with CD28 costimulation preferentially activates the phosphatidylinositol 3-kinase (P13K) pathway, whereas the 4-1 BB-mediated signalling is through TNF receptor associated factor (TRAF) adaptor proteins. Signalling regions of CARs therefore sometimes contain co-stimulatory sequences derived from signalling regions of more than one co-stimulatory molecule. In some embodiments, the CAR of the present invention comprises one or more co-stimulatory sequences comprising or consisting of an amino acid sequence which comprises, consists of, or is derived from, the amino acid sequence of the intracellular domain of one or more of CD28, OX40, 4-1BB, ICOS and CD27.

An optional hinge region may provide separation between the antigen-binding domain and the transmembrane domain, and may act as a flexible linker. Hinge regions may be derived from IgG1. In some embodiments, the CAR of the present invention comprises a hinge region comprising or consisting of an amino acid sequence which comprises, consists of, or is derived from, the amino acid sequence of the hinge region of IgG1.

Also provided is a cell comprising a CAR according to the invention. The CAR according to the present invention may be used to generate CAR-expressing immune cells, e.g. CAR-T or CAR-NK cells. Engineering of CARs into immune cells may be performed during culture, in vitro.

The antigen-binding region of the CAR of the present invention may be provided with any suitable format, e.g. scFv, scFab, etc.

Nucleic Acids and Vectors

The present invention provides a nucleic acid, or a plurality of nucleic acids, encoding an antigen-binding molecule, polypeptide or CAR according to the present invention.

In some embodiments, the nucleic acid is purified or isolated, e.g. from other nucleic acid, or naturally-occurring biological material. In some embodiments the nucleic acid (s) comprise or consist of DNA and/or RNA.

The present invention also provides a vector, or plurality of vectors, comprising the nucleic acid or plurality of nucleic acids according to the present invention.

The nucleotide sequence may be contained in a vector, e.g. an expression vector. A "vector" as used herein is a nucleic acid molecule used as a vehicle to transfer exogenous nucleic acid into a cell. The vector may be a vector for expression of the nucleic acid in the cell. Such vectors may include a promoter sequence operably linked to the nucleotide sequence encoding the sequence to be expressed. A vector may also include a termination codon and expression enhancers. Any suitable vectors, promoters, enhancers and termination codons known in the art may be used to express a peptide or polypeptide from a vector according to the invention.

The term "operably linked" may include the situation where a selected nucleic acid sequence and regulatory nucleic acid sequence (e.g. promoter and/or enhancer) are covalently linked in such a way as to place the expression of nucleic acid sequence under the influence or control of the regulatory sequence (thereby forming an expression cassette). Thus a regulatory sequence is operably linked to the selected nucleic acid sequence if the regulatory sequence is capable of effecting transcription of the nucleic acid sequence. The resulting transcript(s) may then be translated into a desired peptide(s)/polypeptide(s).

Suitable vectors include plasmids, binary vectors, DNA vectors, mRNA vectors, viral vectors (e.g. gammaretroviral vectors (e.g. murine Leukemia virus (MLV)-derived vectors), lentiviral vectors, adenovirus vectors, adeno-associated virus vectors, vaccinia virus vectors and herpesvirus vectors), transposon-based vectors, and artificial chromosomes (e.g. yeast artificial chromosomes).

In some embodiments, the vector may be a eukaryotic vector, e.g. a vector comprising the elements necessary for expression of protein from the vector in a eukaryotic cell. In some embodiments, the vector may be a mammalian vector, e.g. comprising a cytomegalovirus (CMV) or SV40 promoter to drive protein expression.

Constituent polypeptides of an antigen-binding molecule according to the present invention may be encoded by different nucleic acids of the plurality of nucleic acids, or by different vectors of the plurality of vectors.

Cells Comprising/Expressing the Antigen-Binding Molecules and Polypeptides

The present invention also provides a cell comprising or expressing an antigen-binding molecule, polypeptide or CAR according to the present invention. Also provided is a cell comprising or expressing a nucleic acid, a plurality of nucleic acids, a vector or a plurality of vectors according to the invention.

The cell may be a eukaryotic cell, e.g. a mammalian cell. The mammal may be a primate (rhesus, cynomolgous, non-human primate or human) or a non-human mammal (e.g. rabbit, guinea pig, rat, mouse or other rodent (including any animal in the order Rodentia), cat, dog, pig, sheep, goat, cattle (including cows, e.g. dairy cows, or any animal in the order Bos), horse (including any animal in the order Equidae), donkey, and non-human primate).

The present invention also provides a method for producing a cell comprising a nucleic acid(s) or vector(s) according to the present invention, comprising introducing a nucleic acid, a plurality of nucleic acids, a vector or a plurality of vectors according to the present invention into a cell. In some embodiments, introducing an isolated nucleic acid(s) or vector(s) according to the invention into a cell comprises transformation, transfection, electroporation or transduction (e.g. retroviral transduction).

The present invention also provides a method for producing a cell expressing/comprising an antigen-binding molecule, polypeptide or CAR according to the present invention, comprising introducing a nucleic acid, a plurality of nucleic acids, a vector or a plurality of vectors according to the present invention in a cell. In some embodiments, the methods additionally comprise culturing the cell under conditions suitable for expression of the nucleic acid(s) or vector(s) by the cell. In some embodiments, the methods are performed in vitro.

The present invention also provides cells obtained or obtainable by the methods according to the present invention.

Producing the Antigen-Binding Molecules and Polypeptides

Antigen-binding molecules and polypeptides according to the invention may be prepared according to methods for the production of polypeptides known to the skilled person.

Polypeptides may be prepared by chemical synthesis, e.g. liquid or solid phase synthesis. For example, peptides/polypeptides can by synthesised using the methods described in, for example, Chandrudu et al., Molecules (2013), 18: 4373-4388, which is hereby incorporated by reference in its entirety.

Alternatively, antigen-binding molecules and polypeptides may be produced by recombinant expression. Molecular biology techniques suitable for recombinant production of polypeptides are well known in the art, such as those set out in Green and Sambrook, Molecular Cloning: A Laboratory Manual (4th Edition), Cold Spring Harbor Press, 2012, and in Nat Methods. (2008); 5(2): 135-146 both of which are hereby incorporated by reference in their entirety. Methods for the recombinant production of antigen-binding molecules are also described in Frenzel et al., Front Immunol. (2013); 4: 217 and Kunert and Reinhart, Appl Microbiol Biotechnol. (2016) 100: 3451-3461, both of which are hereby incorporated by reference in their entirety.

In some cases the antigen-binding molecule of the present invention are comprised of more than one polypeptide chain. In such cases, production of the antigen-binding molecules may comprise transcription and translation of more than one polypeptide, and subsequent association of the polypeptide chains to form the antigen-binding molecule.

For recombinant production according to the invention, any cell suitable for the expression of polypeptides may be used. The cell may be a prokaryote or eukaryote. In some embodiments the cell is a prokaryotic cell, such as a cell of archaea or bacteria. In some embodiments the bacteria may be Gram-negative bacteria such as bacteria of the family Enterobacteriaceae, for example *Escherichia coli*. In some embodiments, the cell is a eukaryotic cell such as a yeast cell, a plant cell, insect cell or a mammalian cell, e.g. CHO, HEK (e.g. HEK293), HeLa or COS cells. In some embodiments, the cell is a CHO cell that transiently or stably expresses the polypeptides.

In some cases the cell is not a prokaryotic cell because some prokaryotic cells do not allow for the same folding or post-translational modifications as eukaryotic cells. In addition, very high expression levels are possible in eukaryotes and proteins can be easier to purify from eukaryotes using appropriate tags. Specific plasmids may also be utilised which enhance secretion of the protein into the media.

In some embodiments polypeptides may be prepared by cell-free-protein synthesis (CFPS), e.g. according using a system described in Zemella et al. Chembiochem (2015) 16(17): 2420-2431, which is hereby incorporated by reference in its entirety.

Production may involve culture or fermentation of a eukaryotic cell modified to express the polypeptide(s) of interest. The culture or fermentation may be performed in a bioreactor provided with an appropriate supply of nutrients, air/oxygen and/or growth factors. Secreted proteins can be collected by partitioning culture media/fermentation broth from the cells, extracting the protein content, and separating individual proteins to isolate secreted polypeptide(s). Culture, fermentation and separation techniques are well known to those of skill in the art, and are described, for example, in Green and Sambrook, Molecular Cloning: A Laboratory Manual (4th Edition; incorporated by reference herein above).

Bioreactors include one or more vessels in which cells may be cultured. Culture in the bioreactor may occur continuously, with a continuous flow of reactants into, and a continuous flow of cultured cells from, the reactor. Alternatively, the culture may occur in batches. The bioreactor monitors and controls environmental conditions such as pH, oxygen, flow rates into and out of, and agitation within the vessel such that optimum conditions are provided for the cells being cultured.

Following culturing the cells that express the antigen-binding molecule/polypeptide(s), the polypeptide(s) of interest may be isolated. Any suitable method for separating proteins from cells known in the art may be used. In order to isolate the polypeptide it may be necessary to separate the cells from nutrient medium. If the polypeptide(s) are secreted from the cells, the cells may be separated by centrifugation from the culture media that contains the secreted polypeptide(s) of interest. If the polypeptide(s) of interest collect within the cell, protein isolation may comprise centrifugation to separate cells from cell culture medium, treatment of the cell pellet with a lysis buffer, and cell disruption e.g. by sonification, rapid freeze-thaw or osmotic lysis.

It may then be desirable to isolate the polypeptide(s) of interest from the supernatant or culture medium, which may contain other protein and non-protein components. A common approach to separating protein components from a supernatant or culture medium is by precipitation. Proteins of different solubilities are precipitated at different concentrations of precipitating agent such as ammonium sulfate.

For example, at low concentrations of precipitating agent, water soluble proteins are extracted. Thus, by adding different increasing concentrations of precipitating agent, proteins of different solubilities may be distinguished. Dialysis may be subsequently used to remove ammonium sulfate from the separated proteins.

Other methods for distinguishing different proteins are known in the art, for example ion exchange chromatography and size chromatography. These may be used as an alternative to precipitation, or may be performed subsequently to precipitation.

Once the polypeptide(s) of interest have been isolated from culture it may be desired or necessary to concentrate the polypeptide(s). A number of methods for concentrating proteins are known in the art, such as ultrafiltration or lyophilisation.

Compositions

The present invention also provides compositions comprising the antigen-binding molecules, polypeptides, CARs, nucleic acids, expression vectors and cells described herein.

The antigen-binding molecules, polypeptides, CARs, nucleic acids, expression vectors and cells described herein may be formulated as pharmaceutical compositions or medicaments for clinical use and may comprise a pharmaceutically acceptable carrier, diluent, excipient or adjuvant. The composition may be formulated for topical, parenteral, systemic, intracavitary, intravenous, intra-arterial, intramuscular, intrathecal, intraocular, intraconjunctival, intratumoral, subcutaneous, intradermal, intrathecal, oral or transdermal routes of administration which may include injection or infusion.

Suitable formulations may comprise the antigen-binding molecule in a sterile or isotonic medium. Medicaments and pharmaceutical compositions may be formulated in fluid, including gel, form. Fluid formulations may be formulated for administration by injection or infusion (e.g. via catheter) to a selected region of the human or animal body.

In some embodiments the composition is formulated for injection or infusion, e.g. into a blood vessel or tumor.

In accordance with the invention described herein methods are also provided for the production of pharmaceutically useful compositions, such methods of production may comprise one or more steps selected from: producing an antigen-binding molecule, polypeptide, CAR, nucleic acid (or plurality thereof), expression vector (or plurality thereof) or cell described herein; isolating an antigen-binding molecule, polypeptide, CAR, nucleic acid (or plurality thereof), expression vector (or plurality thereof) or cell described herein; and/or mixing an antigen-binding molecule, polypeptide, CAR, nucleic acid (or plurality thereof), expression vector (or plurality thereof) or cell described herein with a pharmaceutically acceptable carrier, adjuvant, excipient or diluent.

For example, a further aspect the invention described herein relates to a method of formulating or producing a medicament or pharmaceutical composition for use in the treatment of a disease/condition (e.g. a cancer), the method comprising formulating a pharmaceutical composition or medicament by mixing an antigen-binding molecule, polypeptide, CAR, nucleic acid (or plurality thereof), expression vector (or plurality thereof) or cell described herein with a pharmaceutically acceptable carrier, adjuvant, excipient or diluent.

Therapeutic and Prophylactic Applications

The antigen-binding molecules, polypeptides, CARs, nucleic acids, expression vectors, cells and compositions described herein find use in therapeutic and prophylactic methods.

The present invention provides an antigen-binding molecule, polypeptide, CAR, nucleic acid (or plurality thereof), expression vector (or plurality thereof), cell or composition described herein for use in a method of medical treatment or prophylaxis. Also provided is the use of an antigen-binding molecule, polypeptide, CAR, nucleic acid (or plurality thereof), expression vector (or plurality thereof), cell or composition described herein in the manufacture of a medicament for treating or preventing a disease or condition. Also provided is a method of treating or preventing a disease or condition, comprising administering to a subject a therapeutically or prophylactically effective amount of an antigen-binding molecule, polypeptide, CAR, nucleic acid (or plurality thereof), expression vector (or plurality thereof), cell or composition described herein.

The methods may be effective to reduce the development or progression of a disease/condition, alleviation of the symptoms of a disease/condition or reduction in the pathology of a disease/condition. The methods may be effective to prevent progression of the disease/condition, e.g. to prevent worsening of, or to slow the rate of development of, the disease/condition. In some embodiments the methods may lead to an improvement in the disease/condition, e.g. a reduction in the symptoms of the disease/condition or reduction in some other correlate of the severity/activity of the disease/condition. In some embodiments the methods may prevent development of the disease/condition to a later stage (e.g. a chronic stage or metastasis).

It will be appreciated that the articles of the present invention may be used for the treatment/prevention of any disease/condition that would derive therapeutic or prophylactic benefit from a reduction in the number and/or activity of cells expressing VISTA (e.g. MDSCs). It will also be clear that the therapeutic and prophylactic utility of the present invention extends to essentially any disease/condition which would benefit from a reduction in the number or activity of MDSCs and/or other cells expressing VISTA, e.g. tumor-associated macrophages (TAMs) and neutrophils. Antagonism of VISTA effectively releases effector immune cells from suppression by MDSCs and/or other cells expressing VISTA.

For example, the disease/condition may be a disease/condition in which cells expressing VISTA (e.g. MDSCs) are pathologically implicated, e.g. a disease/condition in which an increased number/proportion of cells expressing VISTA (e.g. MDSCs) is positively associated with the onset, development or progression of the disease/condition, and/or severity of one or more symptoms of the disease/condition, or for which an increased number/proportion of cells expressing VISTA (e.g. MDSCs), is a risk factor for the onset, development or progression of the disease/condition.

In some embodiments, the disease/condition to be treated/prevented in accordance with the present invention is a disease/condition characterised by an increase in the number/proportion/activity of cells expressing VISTA (e.g. MDSCs), e.g. as compared to the number/proportion/activity of cells expressing VISTA (e.g. MDSCs) in the absence of the disease/condition.

In some embodiments, a subject may be selected for treatment described herein based on the detection of an increase in the number/proportion/activity of cells expressing VISTA (e.g. MDSCs), e.g. in the periphery, or in an organ/tissue which is affected by the disease/condition (e.g.

an organ/tissue in which the symptoms of the disease/condition manifest), or by the presence of cells expressing VISTA (e.g. MDSCs or tumor-associated macrophages) in a tumor. The disease/condition may affect any tissue or organ or organ system. In some embodiments the disease/condition may affect several tissues/organs/organ systems.

In some embodiments a subject may be selected for therapy/prophylaxis in accordance with the present invention based on determination that the subject has an increase in the number/proportion/activity of cells expressing VISTA (e.g. MDSCs) in the periphery or in an organ/tissue relative to the number/proportion/activity of such cells in a healthy subject, or based on determination that the subject has a tumor comprising cells expressing VISTA (e.g. MDSCs).

In some embodiments the disease/condition to be treated/prevented is a cancer.

It will be appreciated that the antigen-binding molecules are useful for the treatment of cancers in general, because antigen-binding molecules of the present invention are useful to release effector immune cells from MDSC-mediated suppression or suppression by cells expressing VISTA, and thereby enhance the anticancer immune response.

The cancer may be any unwanted cell proliferation (or any disease manifesting itself by unwanted cell proliferation), neoplasm or tumor. The cancer may be benign or malignant and may be primary or secondary (metastatic). A neoplasm or tumor may be any abnormal growth or proliferation of cells and may be located in any tissue. The cancer may be of tissues/cells derived from e.g. the adrenal gland, adrenal medulla, anus, appendix, bladder, blood, bone, bone marrow, brain, breast, cecum, central nervous system (including or excluding the brain) cerebellum, cervix, colon, duodenum, endometrium, epithelial cells (e.g. renal epithelia), gallbladder, oesophagus, glial cells, heart, ileum, jejunum, kidney, lacrimal glad, larynx, liver, lung, lymph, lymph node, lymphoblast, maxilla, mediastinum, mesentery, myometrium, nasopharynx, omentum, oral cavity, ovary, pancreas, parotid gland, peripheral nervous system, peritoneum, pleura, prostate, salivary gland, sigmoid colon, skin, small intestine, soft tissues, spleen, stomach, testis, thymus, thyroid gland, tongue, tonsil, trachea, uterus, vulva, and/or white blood cells.

Tumors to be treated may be nervous or non-nervous system tumors. Nervous system tumors may originate either in the central or peripheral nervous system, e.g. glioma, medulloblastoma, meningioma, neurofibroma, ependymoma, Schwannoma, neurofibrosarcoma, astrocytoma and oligodendroglioma. Non-nervous system cancers/tumors may originate in any other non-nervous tissue, examples include melanoma, mesothelioma, lymphoma, myeloma, leukemia, Non-Hodgkin's lymphoma (NHL), Hodgkin's lymphoma, chronic myelogenous leukemia (CML), acute myeloid leukemia (AML), myelodysplastic syndrome (MDS), cutaneous T-cell lymphoma (CTCL), chronic lymphocytic leukemia (CLL), hepatoma, epidermoid carcinoma, prostate carcinoma, breast cancer, lung cancer, colon cancer, ovarian cancer, pancreatic cancer, thymic carcinoma, NSCLC, hematologic cancer and sarcoma.

MDSCs are elevated in advanced colorectal cancer (Toor et al, Front Immunol. 2016; 7:560). MDSCs are also observed in breast cancer, and the percentage of MDSCs in the peripheral blood is increased in patients with later stage breast cancer (Markowitz et al, Breast Cancer Res Treat. 2013 July; 140(1):13-21). MDSC abundance is also correlated with poor prognosis in solid tumors (Charoentong et al, Cell Rep. 2017 Jan. 3; 18(1):248-262), and MDSCs are enriched in liver cancer models (Connolly et al., J Leukoc Biol. (2010) 87(4):713-25). Prostate and breast carcinomas, melanomas, colorectal cancer and Lewis lung carcinoma have been reported to produce chemokines which attract MDSCs and contribute to immune suppression (Umansky et al., Vaccines (Basel) (2016) 4(4):36)), and MDSCs in pancreatic cancer patients have been positively correlated with tumor burden (Xu et al., Hepatobiliary Pancreat Dis Int. (2016) 15(1):99-105). VISTA has also been reported to be a target for the treatment of ovarian cancer (see e.g. U.S. Pat. No. 9,631,018 B2) and lymphoma (see e.g. WO 2017/023749 A1).

Blando et al. Proc Natl Acad Sci USA. (2019) 116(5): 1692-1697 recently reported significant infiltration of VISTA-expressing myeloid cells in pancreatic cancer, and expansion of VISTA-expressing myeloid cells has been observed following treatment with CTLA4 antagonist in prostate cancer, and both pre- and post-treatment with PD-L1 antagonist in melanoma.

In some embodiments, a cancer is selected from: a cancer comprising cells expressing VISTA, a cancer comprising infiltration of cells expressing VISTA, a cancer comprising cancer cells expressing VISTA, a hematological cancer, leukemia, acute myeloid leukemia, lymphoma, B cell lymphoma, T cell lymphoma, multiple myeloma, mesothelioma, a solid tumor, lung cancer, non-small cell lung carcinoma, gastric cancer, gastric carcinoma, colorectal cancer, colorectal carcinoma, colorectal adenocarcinoma, uterine cancer, uterine corpus endometrial carcinoma, breast cancer, triple negative breast invasive carcinoma, liver cancer, hepatocellular carcinoma, pancreatic cancer, pancreatic ductal adenocarcinoma, thyroid cancer, thymoma, skin cancer, melanoma, cutaneous melanoma, kidney cancer, renal cell carcinoma, renal papillary cell carcinoma, head and neck cancer, squamous cell carcinoma of the head and neck (SCCHN), ovarian cancer, ovarian carcinoma, ovarian serous cystadenocarcinoma, prostate cancer and/or prostate adenocarcinoma.

In some embodiments the cancer is colorectal cancer (e.g. colon carcinoma, colon adenocarcinoma), pancreatic cancer, breast cancer, liver cancer, prostate cancer, ovarian cancer, head and neck cancer, leukemia (e.g. T cell leukemia), lymphoma, melanoma, thymoma, lung cancer, non-small cell lung cancer (NSCLC) and/or a solid tumor.

The treatment/prevention may be aimed at one or more of: delaying/preventing the onset/progression of symptoms of the cancer, reducing the severity of symptoms of the cancer, reducing the survival/growth/invasion/metastasis of cells of the cancer, reducing the number of cells of the cancer and/or increasing survival of the subject.

In some embodiments, the cancer to be treated/prevented comprises cells expressing VISTA. In some embodiments, the cancer to be treated/prevented comprises cancer cells expressing VISTA. In some embodiments, the cells expressing VISTA are MDSCs (e.g. g-MDSCs and/or m-MDSCs). In some embodiments, the cancer comprises a tumor comprising cells expressing VISTA (e.g. MDSCs). In some embodiments, the cancer to be treated/prevented comprises a tumor comprising MDSCs. In some embodiments, the cancer to be treated/prevented comprises infiltration of cells expressing VISTA (e.g. MDSCs). In some embodiments, the cancer to be treated/prevented comprises a tumor displaying infiltration of cells expressing VISTA (e.g. MDSCs).

In some embodiments, the cancer to be treated/prevented comprises a tumor comprising a population of CD45+ cells comprising greater than 1%, e.g. ≥2%, ≥5%, ≥10%, ≥15%, ≥20%, ≥25% or ≥30% MDSCs (e.g. as determined by immunoprofiling of the tumor).

In some embodiments, a subject may be selected for treatment described herein based on the detection of a cancer comprising cells expressing VISTA (e.g. MDSCs), or detection of a tumor comprising cells expressing VISTA (e.g. MDSCs), e.g. in a sample obtained from the subject.

In some embodiments the disease/condition in which the VISTA-expressing cells are pathologically implicated is an infectious disease, e.g. bacterial, viral, fungal, or parasitic infection. In some embodiments it may be particularly desirable to treat chronic/persistent infections, e.g. where such infections are associated with T cell dysfunction or T cell exhaustion. It is well established that T cell exhaustion is a state of T cell dysfunction that arises during many chronic infections (including viral, bacterial and parasitic), as well as in cancer (Wherry Nature Immunology Vol. 12, No. 6, p 492-499, June 2011).

Examples of bacterial infections that may be treated include infection by *Bacillus* spp., *Bordetella pertussis*, *Clostridium* spp., *Corynebacterium* spp., *Vibrio chloerae*, *Staphylococcus* spp., *Streptococcus* spp. *Escherichia*, *Klebsiella*, *Proteus*, *Yersinia*, *Erwina*, *Salmonella*, *Listeria* sp, *Helicobacter pylori*, mycobacteria (e.g. *Mycobacterium tuberculosis*) and *Pseudomonas aeruginosa*. For example, the bacterial infection may be sepsis or tuberculosis. Examples of viral infections that may be treated include infection by influenza virus, measles virus, hepatitis B virus (HBV), hepatitis C virus (HCV), human immunodeficiency virus (HIV), lymphocytic choriomeningitis virus (LCMV), Herpes simplex virus and human papilloma virus (HPV). Examples of fungal infections that may be treated include infection by *Alternaria* sp, *Aspergillus* sp, *Candida* sp and *Histoplasma* sp. The fungal infection may be fungal sepsis or histoplasmosis. Examples of parasitic infections that may be treated include infection by *Plasmodium* species (e.g. *Plasmodium falciparum*, *Plasmodium yoeli*, *Plasmodium ovale*, *Plasmodium vivax*, or *Plasmodium chabaudi chabaudi*). The parasitic infection may be a disease such as malaria, leishmaniasis and toxoplasmosis.

In some embodiments the antigen-binding molecule exerts its therapeutic/prophylactic effect via a molecular mechanism which does not involve an Fc region-mediated effector function (e.g. ADCC, ADCP, CDC). In some embodiments the molecular mechanism does not involve binding of the antigen-binding molecule to an Fcγ receptor (e.g. one or more of FcγRI, FcγRIIa, FcγRIIb, FcγRIIc, FcγRIIIa and FcγRIIIb). In some embodiments the molecular mechanism does not involve binding of the antigen-binding molecule to a complement protein (e.g. C1q).

In some embodiments (e.g. embodiments wherein the antigen-binding molecule lacks an Fc region, or embodiments wherein the antigen-binding molecule comprises an Fc region which is not able to induce an Fc-mediated antibody effector function), the treatment does not induce/increase killing of VISTA-expressing cells. In some embodiments the treatment does not reduce the number/proportion of VISTA-expressing cells.

In some embodiments the treatment (i) inhibits VISTA-mediated signalling, and (ii) does not induce/increase killing of VISTA-expressing cells. In some embodiments the treatment (i) inhibits VISTA-mediated signalling, and (ii) does not reduce the number/proportion of VISTA-expressing cells.

Administration of the articles of the present invention is preferably in a "therapeutically effective" or "prophylactically effective" amount, this being sufficient to show therapeutic or prophylactic benefit to the subject. The actual amount administered, and rate and time-course of administration, will depend on the nature and severity of the disease/condition and the particular article administered. Prescription of treatment, e.g. decisions on dosage etc., is within the responsibility of general practitioners and other medical doctors, and typically takes account of the disease/disorder to be treated, the condition of the individual subject, the site of delivery, the method of administration and other factors known to practitioners. Examples of the techniques and protocols mentioned above can be found in Remington's Pharmaceutical Sciences, 20th Edition, 2000, pub. Lippincott, Williams & Wilkins.

Administration may be alone or in combination with other treatments, either simultaneously or sequentially dependent upon the condition to be treated. The antigen-binding molecule or composition described herein and a therapeutic agent may be administered simultaneously or sequentially.

In some embodiments, the methods comprise additional therapeutic or prophylactic intervention, e.g. for the treatment/prevention of a cancer. In some embodiments, the therapeutic or prophylactic intervention is selected from chemotherapy, immunotherapy, radiotherapy, surgery, vaccination and/or hormone therapy. In some embodiments, the therapeutic or prophylactic intervention comprises leukapheresis. In some embodiments the therapeutic or prophylactic intervention comprises a stem cell transplant.

In some embodiments the antigen-binding molecule is administered in combination with an agent capable of inhibiting signalling mediated by an immune checkpoint molecule other than VISTA. In some embodiments the immune checkpoint molecule is e.g. PD-1, CTLA-4, LAG-3, TIM-3, TIGIT or BTLA. In some embodiments the antigen-binding molecule is administered in combination with an agent capable of promoting signalling mediated by a costimulatory receptor. In some embodiments the costimulatory receptor is e.g. CD28, CD80, CD40L, CD86, OX40, 4-1BB, CD27 or ICOS.

Accordingly, the invention provides compositions comprising an article according to the present invention (e.g. an antigen-binding molecule according to the invention) and an agent capable of inhibiting signalling mediated by an immune checkpoint molecule other than VISTA. Also provided are compositions comprising the articles of the present invention and an agent capable of promoting signalling mediated by a costimulatory receptor. Also provided is the use of such compositions in methods of medical treatment and prophylaxis of diseases/conditions described herein.

Also provided are methods for treating/preventing diseases/conditions described herein comprising administering articles of the present invention an article according to the present invention (e.g. an antigen-binding molecule according to the invention) and an agent capable of inhibiting signalling mediated by an immune checkpoint molecule other than VISTA. Also provided are methods for treating/preventing diseases/conditions described herein comprising administering articles of the present invention an article according to the present invention (e.g. an antigen-binding molecule according to the invention) and an agent capable of promoting signalling mediated by a costimulatory receptor.

Agents capable of inhibiting signalling mediated by immune checkpoint molecules are known in the art, and include e.g. antibodies capable of binding to immune checkpoint molecules or their ligands, and inhibiting signalling mediated by the immune checkpoint molecule. Other agents capable of inhibiting signalling mediated by an immune checkpoint molecule include agents capable of reducing gene/protein expression of the immune checkpoint molecule or a ligand for the immune checkpoint molecule (e.g. through inhibiting transcription of the gene(s) encoding the immune checkpoint molecule/ligand, inhibiting post-transcriptional processing of RNA encoding the immune checkpoint molecule/ligand, reducing stability of RNA encoding the immune checkpoint molecule/ligand, promoting degradation of RNA encoding the immune checkpoint molecule/ligand, inhibiting post-translational processing of the immune checkpoint molecule/ligand, reducing stability the immune checkpoint molecule/ligand, or promoting degradation of the immune checkpoint molecule/ligand), and small molecule inhibitors.

Agents capable of promoting signalling mediated by costimulatory receptors are known in the art, and include e.g. agonist antibodies capable of binding to costimulatory receptors and triggering or increasing signalling mediated by the costimulatory receptor. Other agents capable of promoting signalling mediated by costimulatory receptors include agents capable of increasing gene/protein expression of the costimulatory receptor or a ligand for the costimulatory receptor (e.g. through promoting transcription of the gene(s) encoding the costimulatory receptor/ligand, promoting post-transcriptional processing of RNA encoding the costimulatory receptor/ligand, increasing stability of RNA encoding the costimulatory receptor/ligand, inhibiting degradation of RNA encoding the costimulatory receptor/ligand, promoting post-translational processing of the costimulatory receptor/ligand, increasing stability the costimulatory receptor/ligand, or inhibiting degradation of the costimulatory receptor/ligand), and small molecule agonists.

Immune suppression by VISTA-expressing MDSCs has been implicated in the failure of, and development of resistance to, treatment with agents capable of inhibiting signalling mediated by an immune checkpoint molecules. Gao et al., Nature Medicine (2017) 23: 551-555 recently suggested that VISTA may be a compensatory inhibitory pathway in prostate tumors after ipilimumab (i.e. anti-CTLA-4 antibody) therapy.

In particular embodiments the antigen-binding molecule of the present invention is administered in combination with an agent capable of inhibiting signalling mediated by PD-1. The agent capable of inhibiting signalling mediated by PD-1 may be a PD-1- or PD-L1-targeted agent. The agent capable of inhibiting signalling mediated by PD-1 may e.g. be an antibody capable of binding to PD-1 or PD-L1 and inhibiting PD-1-mediated signalling. In some embodiments the agent is an antagonist anti-PD-1 antibody. In some embodiments the agent is an antagonist anti-PD-L1 antibody.

In some embodiments, the antigen-binding molecule of the present invention is administered in combination with an agent capable of inhibiting signalling mediated by CTLA-4. The agent capable of inhibiting signalling mediated by CTLA-4 may be a CTLA-4-targeted agent, or an agent targeted against a ligand for CTLA-4 such as CD80 or CD86. In some embodiments, the agent capable of inhibiting signalling mediated by CTLA-4 may e.g. be an antibody capable of binding to CTLA-4, CD80 or CD86 and inhibiting CTLA-4-mediated signalling.

In some embodiments, the antigen-binding molecule of the present invention is administered in combination with an agent capable of inhibiting signalling mediated by LAG-3. The agent capable of inhibiting signalling mediated by LAG-3 may be a LAG-3-targeted agent, or an agent targeted against a ligand for LAG-3 such as MHC class II. In some embodiments, the agent capable of inhibiting signalling mediated by LAG-3 may e.g. be an antibody capable of binding to LAG-3 or MHC class II and inhibiting LAG-3-mediated signalling.

In some embodiments, the antigen-binding molecule of the present invention is administered in combination with an agent capable of inhibiting signalling mediated by TIM-3. The agent capable of inhibiting signalling mediated by TIM-3 may be a TIM-3-targeted agent, or an agent targeted against a ligand for TIM-3 such as Galectin 9. In some embodiments, the agent capable of inhibiting signalling mediated by TIM-3 may e.g. be an antibody capable of binding to TIM-3 or Galectin 9 and inhibiting TIM-3-mediated signalling.

In some embodiments, the antigen-binding molecule of the present invention is administered in combination with an agent capable of inhibiting signalling mediated by TIGIT. The agent capable of inhibiting signalling mediated by TIGIT may be a TIGIT-targeted agent, or an agent targeted against a ligand for TIGIT such as CD113, CD112 or CD155. In some embodiments, the agent capable of inhibiting signalling mediated by TIGIT may e.g. be an antibody capable of binding to TIGIT, CD113, CD112 or CD155 and inhibiting TIGIT-mediated signalling.

In some embodiments, the antigen-binding molecule of the present invention is administered in combination with an agent capable of inhibiting signalling mediated by BTLA. The agent capable of inhibiting signalling mediated by BTLA may be a BTLA-targeted agent, or an agent targeted against a ligand for BTLA such as HVEM. In some embodiments, the agent capable of inhibiting signalling mediated by BTLA may e.g. be an antibody capable of binding to BTLA or HVEM and inhibiting BTLA-mediated signalling.

In some embodiments methods employing a combination of an antigen-binding molecule of the present invention and an agent capable of inhibiting signalling mediated by an immune checkpoint molecule (e.g. PD-1 and/or PD-L1) provide an improved treatment effect as compared to the effect observed when either agent is used as a monotherapy. In some embodiments the combination of an antigen-binding molecule of the present invention and an agent capable of inhibiting signalling mediated by an immune checkpoint molecule (e.g. PD-1 and/or PD-L1) provide a synergistic (i.e. super-additive) treatment effect.

In some embodiments, treatment with a combination comprising (i) an antigen-binding molecule of the present invention and (ii) an agent capable of inhibiting signalling mediated by an immune checkpoint molecule (e.g. PD-1 and/or PD-L1) may be associated with one or more of:
  an improved treatment effect as compared to the treatment effect observed with either component of the combination used alone;
  a treatment effect which is synergistic (i.e. super-additive) as compared to the treatment effect observed with either component of the combination used alone;
  increased inhibition of tumor growth as compared to inhibition of tumor growth by either component of the combination used alone;
  inhibition of tumor growth which is synergistic (i.e. super-additive) as compared to inhibition of tumor growth by either component of the combination used alone;
  greater reduction in the number/activity of suppressor immune cells as compared to reduction of the number/activity of suppressor immune cells by either component of the combination used alone;
  reduction in the number/activity of suppressor immune cells which is synergistic (i.e. super-additive) as compared to reduction of the number/activity of suppressor immune cells by either component of the combination used alone;

greater reduction of proliferation of suppressor immune cells as compared to reduction proliferation of suppressor immune cells by either component of the combination used alone reduction of proliferation of suppressor immune cells which is synergistic (i.e. super-additive) as compared to reduction proliferation of suppressor immune cells by either component of the combination used alone;

greater reduction in the proportion of suppressor immune cells within a population of cells (e.g. CD45+ cells, e.g. CD45+ cells obtained from a tumor) as compared to the reduction of the proportion of suppressor immune cells by either component of the combination used alone; and reduction in the proportion of suppressor immune cells within a population of cells (e.g. CD45+ cells, e.g. CD45+ cells obtained from a tumor) which is synergistic (i.e. super-additive) as compared to the reduction of the proportion of suppressor immune cells by either component of the combination used alone.

Simultaneous administration refers to administration of the antigen-binding molecule, polypeptide, CAR, nucleic acid (or plurality thereof), expression vector (or plurality thereof), cell or composition and therapeutic agent together, for example as a pharmaceutical composition containing both agents (combined preparation), or immediately after each other and optionally via the same route of administration, e.g. to the same artery, vein or other blood vessel. Sequential administration refers to administration of one of the antigen-binding molecule/composition or therapeutic agent followed after a given time interval by separate administration of the other agent. It is not required that the two agents are administered by the same route, although this is the case in some embodiments. The time interval may be any time interval.

Chemotherapy and radiotherapy respectively refer to treatment of a cancer with a drug or with ionising radiation (e.g. radiotherapy using X-rays or γ-rays). The drug may be a chemical entity, e.g. small molecule pharmaceutical, antibiotic, DNA intercalator, protein inhibitor (e.g. kinase inhibitor), or a biological agent, e.g. antibody, antibody fragment, aptamer, nucleic acid (e.g. DNA, RNA), peptide, polypeptide, or protein. The drug may be formulated as a pharmaceutical composition or medicament. The formulation may comprise one or more drugs (e.g. one or more active agents) together with one or more pharmaceutically acceptable diluents, excipients or carriers.

A treatment may involve administration of more than one drug. A drug may be administered alone or in combination with other treatments, either simultaneously or sequentially dependent upon the condition to be treated. For example, the chemotherapy may be a co-therapy involving administration of two drugs, one or more of which may be intended to treat the cancer.

The chemotherapy may be administered by one or more routes of administration, e.g. parenteral, intravenous injection, oral, subcutaneous, intradermal or intratumoral.

The chemotherapy may be administered according to a treatment regime. The treatment regime may be a predetermined timetable, plan, scheme or schedule of chemotherapy administration which may be prepared by a physician or medical practitioner and may be tailored to suit the patient requiring treatment. The treatment regime may indicate one or more of: the type of chemotherapy to administer to the patient; the dose of each drug or radiation; the time interval between administrations; the length of each treatment; the number and nature of any treatment holidays, if any etc. For a co-therapy a single treatment regime may be provided which indicates how each drug is to be administered.

Chemotherapeutic drugs may be selected from: Abemaciclib, Abiraterone Acetate, Abitrexate (Methotrexate), Abraxane (Paclitaxel Albumin-stabilized Nanoparticle Formulation), ABVD, ABVE, ABVE-PC, AC, Acalabrutinib, AC-T, Adcetris (Brentuximab Vedotin), ADE, Ado-Trastuzumab Emtansine, Adriamycin (Doxorubicin Hydrochloride), Afatinib Dimaleate, Afinitor (Everolimus), Akynzeo (Netupitant and Palonosetron Hydrochloride), Aldara (Imiquimod), Aldesleukin, Alecensa (Alectinib), Alectinib, Alemtuzumab, Alimta (Pemetrexed Disodium), Aliqopa (Copanlisib Hydrochloride), Alkeran for Injection (Melphalan Hydrochloride), Alkeran Tablets (Melphalan), Aloxi (Palonosetron Hydrochloride), Alunbrig (Brigatinib), Ambochlorin (Chlorambucil), Amboclorin (Chlorambucil), Amifostine, Aminolevulinic Acid, Anastrozole, Aprepitant, Aredia (Pamidronate Disodium), Arimidex (Anastrozole), Aromasin (Exemestane), Arranon (Nelarabine), Arsenic Trioxide, Arzerra (Ofatumumab), Asparaginase Erwinia chrysanthemi, Atezolizumab, Avastin (Bevacizumab), Avelumab, Axicabtagene Ciloleucel, Axitinib, Azacitidine, Bavencio (Avelumab), BEACOPP, Becenum (Carmustine), Beleodaq (Belinostat), Belinostat, Bendamustine Hydrochloride, BEP, Besponsa (Inotuzumab Ozogamicin), Bevacizumab, Bexarotene, Bexxar (Tositumomab and Iodine I 131 Tositumomab), Bicalutamide, BiCNU (Carmustine), Bleomycin, Blinatumomab, Blincyto (Blinatumomab), Bortezomib, Bosulif (Bosutinib), Bosutinib, Brentuximab Vedotin, Brigatinib, BuMel, Busulfan, Busulfex (Busulfan), Cabazitaxel, Cabometyx (Cabozantinib-S-Malate), Cabozantinib-S-Malate, CAF, Calquence (Acalabrutinib), Campath (Alemtuzumab), Camptosar (Irinotecan Hydrochloride), Capecitabine, CAPOX, Carac (Fluorouracil—Topical), Carboplatin, CARBOPLATIN-TAXOL, Carfilzomib, Carmubris (Carmustine), Carmustine, Carmustine Implant, Casodex (Bicalutamide), CEM, Ceritinib, Cerubidine (Daunorubicin Hydrochloride), Cervarix (Recombinant HPV Bivalent Vaccine), Cetuximab, CEV, Chlorambucil, CHLORAMBUCIL-PREDNISONE, CHOP, Cisplatin, Cladribine, Clafen (Cyclophosphamide), Clofarabine, Clofarex (Clofarabine), Clolar (Clofarabine), CMF, Cobimetinib, Cometriq (Cabozantinib-S-Malate), Copanlisib Hydrochloride, COPDAC, COPP, COPP-ABV, Cosmegen (Dactinomycin), Cotellic (Cobimetinib), Crizotinib, CVP, Cyclophosphamide, Cyfos (Ifosfamide), Cyramza (Ramucirumab), Cytarabine, Cytarabine Liposome, Cytosar-U (Cytarabine), Cytoxan (Cyclophosphamide), Dabrafenib, Dacarbazine, Dacogen (Decitabine), Dactinomycin, Daratumumab, Darzalex (Daratumumab), Dasatinib, Daunorubicin Hydrochloride, Daunorubicin Hydrochloride and Cytarabine Liposome, Decitabine, Defibrotide Sodium, Defitelio (Defibrotide Sodium), Degarelix, Denileukin Diftitox, Denosumab, DepoCyt (Cytarabine Liposome), Dexamethasone, Dexrazoxane Hydrochloride, Dinutuximab, Docetaxel, Doxil (Doxorubicin Hydrochloride Liposome), Doxorubicin Hydrochloride, Doxorubicin Hydrochloride Liposome, Dox-SL (Doxorubicin Hydrochloride Liposome), DTIC-Dome (Dacarbazine), Durvalumab, Efudex (Fluorouracil—Topical), Elitek (Rasburicase), Ellence (Epirubicin Hydrochloride), Elotuzumab, Eloxatin (Oxaliplatin), Eltrombopag Olamine, Emend (Aprepitant), Empliciti (Elotuzumab), Enasidenib Mesylate, Enzalutamide, Epirubicin Hydrochloride, EPOCH, Erbitux (Cetuximab), Eribulin Mesylate, Erivedge (Vismodegib), Erlotinib Hydrochloride, Erwinaze (Asparaginase *Erwinia chrysanthemi*), Ethyol (Amifostine), Etopophos (Etoposide Phosphate), Etoposide, Etoposide Phosphate, Evacet (Doxorubicin Hydrochloride Liposome), Everolimus, Evista (Raloxifene Hydrochloride), Evomela (Melphalan Hydrochloride), Exemestane, 5-FU (Fluorouracil Injection), 5-FU (Fluorouracil—Topical), Fareston (Toremifene), Farydak (Panobinostat), Faslodex (Fulvestrant), FEC, Femara (Letrozole), Filgrastim, Fludara (Fludarabine Phosphate), Fludarabine Phosphate, Fluoroplex (Fluorouracil—Topical), Fluorouracil Injection, Fluorouracil—Topical, Flutamide, Folex (Methotrexate), Folex PFS (Methotrexate), FOLFIRI, FOLFIRI-BEVACIZUMAB, FOLFIRI-CETUXIMAB, FOLFIRINOX, FOLFOX, Folotyn (Pralatrexate), FU-LV, Fulvestrant, Gardasil (Recombinant HPV Quadrivalent Vaccine), Gardasil 9 (Recombinant HPV Nonavalent Vaccine), Gazyva (Obinutuzumab), Gefitinib, Gemcitabine Hydrochloride, GEMCITABINE-CISPLATIN, GEMCITABINE-OXALIPLATIN, Gemtuzumab Ozogamicin, Gemzar (Gemcitabine Hydrochloride), Gilotrif (Afatinib Dimaleate), Gleevec (Imatinib Mesylate), Gliadel (Carmustine Implant), Gliadel wafer (Carmustine Implant), Glucarpidase, Goserelin Acetate, Halaven (Eribulin Mesylate), Hemangeol (Propranolol Hydrochloride), Herceptin (Trastuzumab), HPV Bivalent Vaccine, Recombinant, HPV Nonavalent Vaccine, Recombinant, HPV Quadrivalent Vaccine, Recombinant, Hycamtin (Topotecan Hydrochloride), Hydrea (Hydroxyurea), Hydroxyurea, Hyper-CVAD, Ibrance (Palbociclib), Ibritumomab Tiuxetan, Ibrutinib, ICE, Iclusig (Ponatinib Hydrochloride), Idamycin (Idarubicin Hydrochloride), Idarubicin Hydrochloride, Idelalisib, Idhifa (Enasidenib Mesylate), Ifex (Ifosfamide), Ifosfamide, Ifosfamidum (Ifosfamide), IL-2 (Aldesleukin), Imatinib Mesylate, Imbruvica (Ibrutinib), Imfinzi (Durvalumab), Imiquimod, Imlygic (Talimogene Laherparepvec), Inlyta (Axitinib), Inotuzumab Ozogamicin, Interferon Alfa-2b, Recombinant, Interleukin-2 (Aldesleukin), Intron A (Recombinant Interferon Alfa-2b), Iodine I 131 Tositumomab and Tositumomab, Ipilimumab, Iressa (Gefitinib), Irinotecan Hydrochloride, Irinotecan Hydrochloride Liposome, Istodax (Romidepsin), Ixabepilone, Ixazomib Citrate, Ixempra (Ixabepilone), Jakafi (Ruxolitinib Phosphate), JEB, Jevtana (Cabazitaxel), Kadcyla (Ado-Trastuzumab Emtansine), Keoxifene (Raloxifene Hydrochloride), Kepivance (Palifermin), Keytruda (Pembrolizumab), Kisqali (Ribociclib), Kymriah (Tisagenlecleucel), Kyprolis (Carfilzomib), Lanreotide Acetate, Lapatinib Ditosylate, Lartruvo (Olaratumab), Lenalidomide, Lenvatinib Mesylate, Lenvima (Lenvatinib Mesylate), Letrozole, Leucovorin Calcium, Leukeran (Chlorambucil), Leuprolide Acetate, Leustatin (Cladribine), Levulan (Aminolevulinic Acid), Linfolizin (Chlorambucil), LipoDox (Doxorubicin Hydrochloride Liposome), Lomustine, Lonsurf (Trifluridine and Tipiracil Hydrochloride), Lupron (Leuprolide Acetate), Lupron Depot (Leuprolide Acetate), Lupron Depot-Ped (Leuprolide Acetate), Lynparza (Olaparib), Marqibo (Vincristine Sulfate Liposome), Matulane (Procarbazine Hydrochloride), Mechlorethamine Hydrochloride, Megestrol Acetate, Mekinist (Trametinib), Melphalan, Melphalan Hydrochloride, Mercaptopurine, Mesna, Mesnex (Mesna), Methazolastone (Temozolomide), Methotrexate, Methotrexate LPF (Methotrexate), Methylnaltrexone Bromide, Mexate (Methotrexate), Mexate-AQ (Methotrexate), Midostaurin, Mitomycin C, Mitoxantrone Hydrochloride, Mitozytrex (Mitomycin C), MOPP, Mozobil (Plerixafor), Mustargen (Mechlorethamine Hydrochloride), Mutamycin (Mitomycin C), Myleran (Busulfan), Mylosar (Azacitidine), Mylotarg (Gemtuzumab Ozogamicin), Nanoparticle Paclitaxel (Paclitaxel Albumin-stabilized Nanoparticle Formulation), Navelbine (Vinorelbine Tartrate), Necitumumab, Nelarabine, Neosar (Cyclophosphamide), Neratinib Maleate, Nerlynx (Neratinib Maleate), Netupitant and Palonosetron Hydrochloride, Neulasta (Pegfilgrastim), Neupogen (Filgrastim), Nexavar (Sorafenib Tosylate), Nilandron (Nilutamide), Nilotinib, Nilutamide, Ninlaro (Ixazomib Citrate), Niraparib Tosylate Monohydrate, Nivolumab, Nolvadex (Tamoxifen Citrate), Nplate (Romiplostim), Obinutuzumab, Odomzo (Sonidegib), OEPA, Ofatumumab, OFF, Olaparib, Olaratumab, Omacetaxine Mepesuccinate, Oncaspar (Pegaspargase), Ondansetron Hydrochloride, Onivyde (Irinotecan Hydrochloride Liposome), Ontak (Denileukin Diftitox), Opdivo (Nivolumab), OPPA, Osimertinib, Oxaliplatin, Paclitaxel, Paclitaxel Albumin-stabilized Nanoparticle Formulation, PAD, Palbociclib, Palifermin, Palonosetron Hydrochloride, Palonosetron Hydrochloride and Netupitant, Pamidronate Disodium, Panitumumab, Panobinostat, Paraplat (Carboplatin), Paraplatin (Carboplatin), Pazopanib Hydrochloride, PCV, PEB, Pegaspargase, Pegfilgrastim, Peginterferon Alfa-2b, PEG-Intron (Peginterferon Alfa-2b), Pembrolizumab, Pemetrexed Disodium, Perjeta (Pertuzumab), Pertuzumab, Platinol (Cisplatin), Platinol-AQ (Cisplatin), Plerixafor, Pomalidomide, Pomalyst (Pomalidomide), Ponatinib Hydrochloride, Portrazza (Necitumumab), Pralatrexate, Prednisone, Procarbazine Hydrochloride, Proleukin (Aldesleukin), Prolia (Denosumab), Promacta (Eltrombopag Olamine), Propranolol Hydrochloride, Provenge (Sipuleucel-T), Purinethol (Mercaptopurine), Purixan (Mercaptopurine), [No Entries], Radium 223 Dichloride, Raloxifene Hydrochloride, Ramucirumab, Rasburicase, R-CHOP, R-CVP, Recombinant Human Papillomavirus (HPV) Bivalent Vaccine, Recombinant Human Papillomavirus (HPV) Nonavalent Vaccine, Recombinant Human Papillomavirus (HPV) Quadrivalent Vaccine, Recombinant Interferon Alfa-2b, Regorafenib, Relistor (Methylnaltrexone Bromide), R-EPOCH, Revlimid (Lenalidomide), Rheumatrex (Methotrexate), Ribociclib, R-ICE, Rituxan (Rituximab), Rituxan Hycela (Rituximab and Hyaluronidase Human), Rituximab, Rituximab and Hyaluronidase Human, Rolapitant Hydrochloride, Romidepsin, Romiplostim, Rubidomycin (Daunorubicin Hydrochloride), Rubraca (Rucaparib Camsylate), Rucaparib Camsylate, Ruxolitinib Phosphate, Rydapt (Midostaurin), Sclerosol Intrapleural Aerosol (Talc), Siltuximab, Sipuleucel-T, Somatuline Depot (Lanreotide Acetate), Sonidegib, Sorafenib Tosylate, Sprycel (Dasatinib), STANFORD V, Sterile Talc Powder (Talc), Steritalc (Talc), Stivarga (Regorafenib), Sunitinib Malate, Sutent (Sunitinib Malate), Sylatron (Peginterferon Alfa-2b), Sylvant (Siltuximab), Synribo (Omacetaxine Mepesuccinate), Tabloid (Thioguanine), TAC, Tafinlar (Dabrafenib), Tagrisso (Osimertinib), Talc, Talimogene Laherparepvec, Tamoxifen Citrate, Tarabine PFS (Cytarabine), Tarceva (Erlotinib Hydrochloride), Targretin (Bexarotene), Tasigna (Nilotinib), Taxol (Paclitaxel), Taxotere (Docetaxel), Tecentriq (Atezolizumab), Temodar (Temozolomide), Temozolomide, Temsirolimus, Thalidomide, Thalomid (Thalidomide), Thioguanine, Thiotepa, Tisagenlecleucel, Tolak (Fluorouracil—Topical), Topotecan Hydrochloride, Toremifene, Torisel (Temsirolimus), Tositumomab and Iodine I 131 Tositumomab, Totect (Dexrazoxane Hydrochloride), TPF, Trabectedin, Trametinib, Trastuzumab, Treanda (Bendamustine Hydrochloride), Trifluridine and Tipiracil Hydrochloride, Trisenox (Arsenic Trioxide), Tykerb (Lapatinib Ditosylate), Unituxin (Dinutuximab), Uridine Triacetate, VAC, Valrubicin, Valstar (Valrubicin), Vandetanib, VAMP, Varubi (Rolapitant Hydrochloride), Vectibix (Panitumumab), VelP, Velban (Vinblastine Sulfate), Velcade (Bortezomib), Velsar (Vinblastine Sulfate), Vemurafenib, Venclexta (Venetoclax), Venetoclax, Verzenio (Abemaciclib), Viadur (Leuprolide Acetate), Vidaza (Azacitidine), Vinblastine Sulfate, Vincasar PFS (Vincristine Sulfate), Vincristine Sulfate, Vincristine Sulfate Liposome, Vinorelbine Tartrate, VIP, Vismodegib, Vistogard (Uridine Triacetate), Voraxaze (Glucarpidase), Vorinostat, Votrient (Pazopanib Hydrochloride), Vyxeos (Daunorubicin Hydrochloride and Cytarabine Liposome), Wellcovorin (Leucovorin Calcium), Xalkori (Crizotinib), Xeloda (Capecitabine), XELIRI, XELOX, Xgeva (Denosumab), Xofigo (Radium 223 Dichloride), Xtandi (Enzalutamide), Yervoy (Ipilimumab), Yescarta (Axicabtagene Ciloleucel), Yondelis (Trabectedin), Zaltrap (Ziv-Aflibercept), Zarxio (Filgrastim), Zejula (Niraparib Tosylate Monohydrate), Zelboraf (Vemurafenib), Zevalin (Ibritumomab Tiuxetan), Zinecard (Dexrazoxane Hydrochloride), Ziv-Aflibercept, Zofran (Ondansetron Hydrochloride), Zoladex (Goserelin Acetate), Zoledronic Acid, Zolinza (Vorinostat), Zometa (Zoledronic Acid), Zydelig (Idelalisib), Zykadia (Ceritinib) and Zytiga (Abiraterone Acetate).

Multiple doses of the antigen-binding molecule, polypeptide, CAR, nucleic acid (or plurality thereof), expression vector (or plurality thereof), cell or composition may be provided. One or more, or each, of the doses may be accompanied by simultaneous or sequential administration of another therapeutic agent.

Multiple doses may be separated by a predetermined time interval, which may be selected to be one of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days, or 1, 2, 3, 4, 5, or 6 months. By way of example, doses may be given once every 7, 14, 21 or 28 days (plus or minus 3, 2, or 1 days).

Methods of Detection

The invention also provides the articles of the present invention for use in methods for detecting, localizing or imaging VISTA, or cells expressing VISTA (e.g. MDSCs). The antigen-binding molecules described herein may be used in methods that involve the antigen-binding molecule to VISTA. Such methods may involve detection of the bound complex of the antigen-binding molecule and VISTA.

In particular, detection of VISTA may be useful in methods of diagnosing/prognosing a disease/condition in which cells expressing VISTA (e.g. MDSCs) are pathologically implicated, identifying subjects at risk of developing such diseases/conditions, and/or may be useful in methods of predicting a subject's response to a therapeutic intervention.

As such, a method is provided, comprising contacting a sample containing, or suspected to contain, VISTA with an antigen-binding molecule as described herein, and detecting the formation of a complex of the antigen-binding molecule and VISTA. Also provided is a method comprising contacting a sample containing, or suspected to contain, a cell expressing VISTA with an antigen-binding molecule as described herein and detecting the formation of a complex of the antigen-binding molecule and a cell expressing VISTA.

A sample may be taken from any tissue or bodily fluid. The sample may comprise or may be derived from: a quantity of blood; a quantity of serum derived from the individual's blood which may comprise the fluid portion of the blood obtained after removal of the fibrin clot and blood cells; a tissue sample or biopsy; pleural fluid; cerebrospinal fluid (CSF); or cells isolated from said individual. In some embodiments, the sample may be obtained or derived from a tissue or tissues which are affected by the disease/condition (e.g. tissue or tissues in which symptoms of the disease manifest, or which are involved in the pathogenesis of the disease/condition).

Suitable method formats are well known in the art, including immunoassays such as sandwich assays, e.g. ELISA. The methods may involve labelling the antigen-binding molecule, or target(s), or both, with a detectable moiety, e.g. a fluorescent label, phosphorescent label, luminescent label, immuno-detectable label, radiolabel, chemical, nucleic acid or enzymatic label as described herein. Detection techniques are well known to those of skill in the art and can be selected to correspond with the labelling agent.

Methods of this kind may provide the basis of methods for the diagnostic and/or prognostic evaluation of a disease or condition, e.g. a cancer. Such methods may be performed in vitro on a patient sample, or following processing of a patient sample. Once the sample is collected, the patient is not required to be present for the in vitro method to be performed, and therefore the method may be one which is not practised on the human or animal body. In some embodiments the method is performed in vivo.

Detection in a sample may be used for the purpose of diagnosis of a disease/condition (e.g. a cancer), predisposition to a disease/condition, or for providing a prognosis (prognosticating) for a disease/condition, e.g. a disease/condition described herein. The diagnosis or prognosis may relate to an existing (previously diagnosed) disease/condition.

The present invention also provides methods for selecting/stratifying a subject for treatment with a VISTA-targeted agent. In some embodiments a subject is selected for treatment/prevention in accordance with the invention, or is identified as a subject which would benefit from such treatment/prevention, based on detection/quantification of VISTA, or cells expressing VISTA, e.g. in a sample obtained from the subject.

Such methods may involve detecting or quantifying VISTA and/or cells expressing VISTA (e.g. MDSCs), e.g. in a patient sample. Where the method comprises quantifying the relevant factor, the method may further comprise comparing the determined amount against a standard or reference value as part of the diagnostic or prognostic evaluation. Other diagnostic/prognostic tests may be used in conjunction with those described herein to enhance the accuracy of the diagnosis or prognosis or to confirm a result obtained by using the tests described herein.

Where an increased level of VISTA is detected, or where the presence of—or an increased number/proportion of—cells expressing VISTA (e.g. MDSCs) is detected in a sample obtained from a subject, the subject may be diagnosed as having a disease/condition in which MDSCs are pathologically implicated, or being at risk of developing such a disease/condition. In such methods, an "increased" level of expression or number/proportion of cells refers to a level/number/proportion which is greater than the level/number/proportion determined for an appropriate control condition, such as the level/number/proportion detected in a comparable sample (e.g. a sample of the same kind, e.g. obtained from the same fluid, tissue, organ etc.), e.g. obtained from a healthy subject.

Where an increased level of VISTA is detected, or where the presence of—or an increased number/proportion of—cells expressing VISTA (e.g. MDSCs) is detected in a sample obtained from a subject, the subject may be determined to have a poorer prognosis as compared to a subject determined to have a lower level of VISTA, or a reduced number/proportion of cells expressing VISTA (e.g. MDSCs) in a comparable sample (e.g. a sample of the same kind, e.g. obtained from the same fluid, tissue, organ etc.).

The antigen-binding molecules of the present invention are also useful in methods for predicting response to immunotherapy. "Immunotherapy" generally refers to therapeutic intervention aimed at harnessing the immune system to treat a disease/condition. Immunotherapy includes therapeutic intervention to increase the number/proportion/activity of effector immune cells (e.g. effector T cells (e.g. antigen-specific T cells, CAR-T cells), NK cells) in a subject. Immunotherapy to increase the number/proportion/activity of effector immune cells includes intervention to promote proliferation and/or survival of effector immune cells, inhibit signalling mediated by immune checkpoint molecules, promote signalling mediated by costimulatory receptors, enhance antigen presentation by antigen-presenting cells, etc. Immunotherapy to increase the number/proportion/activity of effector immune cells also encompasses intervention to increase the frequency of effector immune cells having a desired specificity or activity in a subject e.g. through adoptive cell transfer (ACT). ACT generally involves obtaining immune cells from a subject, typically by drawing a blood sample from which immune cells are isolated. The cells are then typically treated or altered in some way, and then administered either to the same subject or to a different subject. ACT is typically aimed at providing an immune cell population with certain desired characteristics to a subject, or increasing the frequency immune cells with such characteristics in that subject. In some embodiments ACT may e.g. be of cells comprising a chimeric antigen receptor (CAR) specific for a target antigen or cell type of interest. Immunotherapy also includes therapeutic intervention to decrease the number/proportion/activity of suppressor immune cells (e.g. regulatory T cells, MDSCs) in a subject. Immunotherapy to decrease the number/proportion/activity of suppressor immune cells includes intervention to cause or potentiate cell killing of suppressor immune cells, and inhibit signalling mediated by immune checkpoint molecules.

Where an increased level of VISTA is detected, or where the presence of—or an increased number/proportion of—cells expressing VISTA (e.g. MDSCs) is detected in a sample obtained from a subject, the subject may be predicted to have a poorer response to immunotherapy to increase the number/proportion/activity of effector immune cells in the subject as compared to a subject determined to have a lower level of VISTA, or a reduced number/proportion of cells expressing VISTA (e.g. MDSCs) in a comparable sample (e.g. a sample of the same kind, e.g. obtained from the same fluid, tissue, organ etc.). Where an increased level of VISTA is detected, or where the presence of—or an increased number/proportion of—cells expressing VISTA (e.g. MDSCs) is detected in a sample obtained from a subject, the subject may be predicted to have an improved response to immunotherapy aimed at reducing the number/proportion/activity of suppressor immune cells in the subject as compared to a subject determined to have a lower level of VISTA, or a reduced number/proportion of cells expressing VISTA (e.g. MDSCs) in a comparable sample (e.g. a sample of the same kind, e.g. obtained from the same fluid, tissue, organ etc.).

In some embodiments the methods comprise determining the relative size/activity of suppressor immune cell compartment and the effector immune cell compartment. For example, in some embodiments the methods employ the antigen-binding molecules described herein in methods for determining the ratio of VISTA-expressing cells (e.g. MDSCs, TAMs, neutrophils) to effector immune cells. A subject having an increased ratio may be predicted to have an improved response to immunotherapy aimed at reducing the number/proportion/activity of suppressor immune cells, and/or may be predicted to have a poorer response to immunotherapy to increase the number/proportion/activity of effector immune cells as compared to a subject determined to have a lower ratio.

The diagnostic and prognostic methods of the present invention may be performed on samples obtained from a subject at multiple time points throughout the course of the disease and/or treatment, and may be used monitor development of the disease/condition over time, e.g. in response to treatment administered to the subject. The results of characterisation in accordance with the methods may be used to inform clinical decisions as to when and what kind of therapy to administer to a subject.

Methods of diagnosis or prognosis may be performed in vitro on a sample obtained from a subject, or following processing of a sample obtained from a subject. Once the sample is collected, the patient is not required to be present for the in vitro method of diagnosis or prognosis to be performed and therefore the method may be one which is not practised on the human or animal body.

Subjects

The subject in accordance with aspects the invention described herein may be any animal or human. The subject is preferably mammalian, more preferably human. The subject may be a non-human mammal, but is more preferably human. The subject may be male or female. The subject may be a patient. A subject may have been diagnosed with a disease or condition requiring treatment (e.g. a cancer), may be suspected of having such a disease/condition, or may be at risk of developing/contracting such a disease/condition.

In embodiments according to the present invention the subject is preferably a human subject. In some embodiments, the subject to be treated according to a therapeutic or prophylactic method of the invention herein is a subject having, or at risk of developing, a cancer. In embodiments according to the present invention, a subject may be selected for treatment according to the methods based on characterisation for certain markers of such disease/condition.

Kits

In some aspects of the invention described herein a kit of parts is provided. In some embodiments the kit may have at least one container having a predetermined quantity of an antigen-binding molecule, polypeptide, CAR, nucleic acid (or plurality thereof), expression vector (or plurality thereof), cell or composition described herein.

In some embodiments, the kit may comprise materials for producing an antigen-binding molecule polypeptide, CAR, nucleic acid (or plurality thereof), expression vector (or plurality thereof), cell or composition described herein.

The kit may provide the antigen-binding molecule, polypeptide, CAR, nucleic acid (or plurality thereof), expression vector (or plurality thereof), cell or composition together with instructions for administration to a patient in order to treat a specified disease/condition.

In some embodiments the kit may further comprise at least on container having a predetermined quantity of another therapeutic agent (e.g. anti-infective agent of chemotherapy agent). In such embodiments, the kit may also comprise a second medicament or pharmaceutical composition such that the two medicaments or pharmaceutical compositions may be administered simultaneously or separately such that they provide a combined treatment for the specific disease or condition. The therapeutic agent may also be formulated so as to be suitable for injection or infusion to a tumor or to the blood.

Sequence Identity

As used herein, "sequence identity" refers to the percent of nucleotides/amino acid residues in a subject sequence that are identical to nucleotides/amino acid residues in a reference sequence, after aligning the sequences and, if necessary, introducing gaps, to achieve the maximum percent sequence identity between the sequences. Pairwise and multiple sequence alignment for the purposes of determining percent sequence identity between two or more amino acid or nucleic acid sequences can be achieved in various ways known to a person of skill in the art, for instance, using publicly available computer software such as ClustalOmega (Söding, J. 2005, Bioinformatics 21, 951-960), T-coffee (Notredame et al 2000, J. Mol. Biol. (2000) 302, 205-217), Kalign (Lassmann and Sonnhammer 2005, BMC Bioinformatics, 6(298)) and MAFFT (Katoh and Standley 2013, Molecular Biology and Evolution, 30(4) 772-780 software. When using such software, the default parameters, e.g. for gap penalty and extension penalty, are preferably used.

| | | Sequences |
|---|---|---|
| SEQ ID NO: | DESCRIPTION | SEQUENCE |
| 1 | Human VISTA (Q9H7M9-1, v3) | MGVPTALEAGSWRWGSLLFALFLAASLGPVAAFKVATPYSLYVCPEGQNVTLTCRLLGPVDKGH DVTFYKIWYRSSRGEVQTCSERRPIRNLTFQDLHLHHGGHQAANTSHDLAQRHGLESASDHHG NFSITMRNLTLLDSGLYCCLVVEIRHHHSEHRVHGAMELQVQTGKDAPSNCVVYPSSSQDSENIT AAALATGACIVGILCLPLILLLVYKQRQAASNRRAQELVRMDSNIQGIENPGFEASPPAQGIPEAKV RHPLSYVAQRQPSESGRHLLSEPSTPLSPPGPGDVFFPSLDPVPDSPNFEVI |
| 2 | Mature human VISTA (Q9H7M9-1, v3 positions 33 to 311) | FKVATPYSLYVCPEGQNVTLTCRLLGPVDKGHDVTFYKTWYRSSRGEVQTCSERRPIRNLTFQDL HLHHGGHQAANTSHDLAQRHGLESASDHHGNFSITMRNLTLLDSGLYCCLVVEIRHHHSEHRVH GAMELQVQTGKDAPSNCVVYPSSSQDSENITAAALATGACIVGILCLPLILLLVYKQRQAASNRRA QELVRMDSNIQGIENPGFEASPPAQGIPEAKVRHPLSYVAQRQPSESGRHLLSEPSTPLSPPGPG DVFFPSLDPVPDSPNFEVI |
| 3 | Extracellular domain human VISTA (Q9H7M9-1, v3 positions 33 to 194) | FKVATPYSLYVCPEGQNVTLTCRLLGPVDKGHDVTFYKTWYRSSRGEVQTCSERRPIRNLTFQDL HLHHGGHQAANTSHDLAQRHGLESASDHHGNFSITMRNLTLLDSGLYCCLVVEIRHHHSEHRVH GAMELQVQTGKDAPSNCVVYPSSSQDSENITAA |
| 4 | Transmembrane domain human VISTA (Q9H7M9-1, v3 positions 195 to 215) | ALATGACIVGILCLPLILLLV |
| 5 | Cytoplasmic domain human VISTA (Q9H7M9-1, v3 positions 216 to 311) | YKQRQAASNRRAQELVRMDSNIQGIENPGFEASPPAQGIPEAKVRHPLSYVAQRQPSESGRHLL SEPSTPLSPPGPGDVFFPSLDPVPDSPNFEVI |
| 6 | Ig-like V-type domain human VISTA (09H7M9-1, v3 positions 33 to 168) | FKVATPYSLYVCPEGQNVTLTCRLLGPVDKGHDVTFYKTWYRSSRGEVQTCSERRPIRNLTFQDL HLHHGGHQAANTSHDLAQRHGLESASDHHGNFSITMRNLTLLDSGLYCCLVVEIRHHHSEHRVH GAMELQV |
| 7 | Human VSIG-3 isoform 1 (Q5DX21-1, v3) | MTSQRSPLAPLLLLSLHGVAASLEVSESPGSIQVARGQPAVLPCTFTTSAALINLNVIWMVTPLSNA NQPEQVILYQGGQMFDGAPRFHGRVGFTGTMPATNVSIFINNTQLSDTGTYQCLVNNLPDIGGRN IGVTGLTVLVPPSAPHCQIQGSQDIGSDVILLCSSEEGIPRPTYLWEKLDNTLKLPPTATQDQVQGT VTIRNISALSSGLYQCVASNAIGTSTCLLDLQVISPQPRNIGLIAGAIGTGAVIIIFCIALILGAFFYWRS KNKEEEEEIPNEIREDDLPPKCSSAKAFHTEISSSDNNTLTSSNAYNSRYWSNNPKVHRNTESVS HFSDLGQSFSFHSGNANIPSIYANGTHLVPGQHKTLVVTANRGSSPQVMSRSNGSVSRKPRPPH THSYTISHATLERIGAVPVMVPAQSRAGSLV |
| 8 | Human VSIG-3 isoform 2 (Q5DX21-2) | MSLVELLLWWNCFSRTGVAASLEVSESPGSIQVARGQPAVLPCTFTTSAALINLNVIWMVTPLSNA NQPEQVILYQGGQMFDGAPRFHGRVGFTGTMPATNVSIFINNTQLSDTGTYQCLVNNLPDIGGRN IGVTGLTVLVPPSAPHCQIQGSQDIGSDVILLCSSEEGIPRPTYLWEKLDNTLKLPPTATQDQVQGT VTIRNISALSSGLYQCVASNAIGTSTCLLDLQVISPQPRNIGLIAGAIGTGAVIIIFCIALILGAFFYWRS KNKEEEEEIPNEIREDDLPPKCSSAKAFHTEISSSDNNTLTSSNAYNSRYWSNNPKVHRNTESVS HFSDLGQSFSFHSGNANIPSIYANGTHLVPGQHKTLVVTANRGSSPQVMSRSNGSVSRKPRPPH THSYTISHATLERIGAVPVMVPAQSRAGSLV |
| 9 | Human VSIG-3 isoform 3 (Q5DX21-3) | MSLVELLLWWNCFSRTGVAASLEVSESPGSIQVARGQPAVLPCTFTTSAALINLNVIWMVTPLSNA NQPEQVILYQGGQMFDGAPRFHGRVGFTGTMPATNVSIFINNTQLSDTGTYQCLVNNLPDIGGRN IGVTGLTVLVPPSAPHCQIQGSQDIGSDVILLCSSEEGIPRPTYLWEKLDNTLKLPPTATQDQVQGT VTIRNISALSSAQPRNIGLIAGAIGTGAVIIIFCIALILGAFFYWRSKNKEEEEEIPNEIREDDLPPKCS SAKAFHTEISSSDNNTLTSSNAYNSRYWSNNPKVHRNTESVSHFSDLGQSFSFHSGNANIPSIYA NGTHLVPGQHKTLVVTANRGSSPQVMSRSNGSVSRKPRPPHTHSYTISHATLERIGAVPVMVPA QSRAGSLV |
| 10 | Mature human VSIG-3 isoform 1 (Q5DX21-1, v3 positions 23 to 431) | LEVSESPGSIQVARGQPAVLPCTFTTSAALINLNVIWMVTPLSNANQPEQVILYQGGQMFDGAPRF HGRVGFTGTMPATNVSIFINNTQLSDTGTYQCLVNNLPDIGGRNIGVTGLTVLVPPSAPHCQIQGS QDIGSDVILLCSSEEGIPRPTYLWEKLDNTLKLPPTATQDQVQGTVTIRNISALSSGLYQCVASNAI GTSTCLLDLQVISPQPRNIGLIAGAIGTGAVIIIFCIALILGAFFYWRSKNKEEEEEIPNEIREDDLPP KCSSAKAFHTEISSSDNNTLTSSNAYNSRYWSNNPKVHRNTESVSHFSDLGQSFSFHSGNANIPS IYANGTHLVPGQHKTLVVTANRGSSPQVMSRSNGSVSRKPRPPHTHSYTISHATLERIGAVPVMV PAQSRAGSLV |

-continued

Sequences

| SEQ ID NO: | DESCRIPTION | SEQUENCE |
|---|---|---|
| 11 | Mature human VSIG-3 isoform 2 (Q5DX21-2 positions 23 to 431) | LEVSESPGSIQVARGQPAVLPCTFTTSAALINLNVIWMVTPLSNANQPEQVILYQGGQMFDGAPRF HGRVGFTGTMPATNVSIFINNTQLSDTGTYQCLVNNLPDIGGRNIGVTGLTVLVPPSAPHCQIQGS QDIGSDVILLCSSEEGIPRPTYLWEKLDNTLKLPPTATQDQVQGTVTIRNISALSSGLYQCVASNAI GTSTCLLDLQVISPQPRNIGLIAGAIGTGAVIIIFCIALILGAFFYWRSKNKEEEEEEIPNEIREDDLPP KCSSAKAFHTEISSSDNNTLTSSNAYNSRYWSNNPKVHRNTESVSHFSDLGQSFSFHSGNANIPS IYANGTHLVPGQHKTLVVTANRGSSPQVMSRSNGSVSRKPRPPHTHSYTISHATLERIGAVPVMV PAQSRAGSLV |
| 12 | Mature human VSIG-3 isoform 3 (Q5DX21-3 positions 23 to 407) | LEVSESPGSIQVARGQPAVLPCTFTTSAALINLNVIWMVTPLSNANQPEQVILYQGGQMFDGAPRF HGRVGFTGTMPATNVSIFINNTQLSDTGTYQCLVNNLPDIGGRNIGVTGLTVLVPPSAPHCQIQGS QDIGSDVILLCSSEEGIPRPTYLWEKLDNTLKLPPTATQDQVQGTVTIRNISALSSAQPRNIGLIAGAI GTGAVIIIFCIALILGAFFYWRSKNKEEEEEEIPNEIREDDLPPKCSSAKAFHTEISSSDNNTLTSSNA YNSRYWSNNPKVHRNTESVSHFSDLGQSFSFHSGNANIPSIYANGTHLVPGQHKTLVVTANRGS SPQVMSRSNGSVSRKPRPPHTHSYTISHATLERIGAVPVMVPAQSRAGSLV |
| 13 | Extracellular domain human VSIG-3 isoforms 1 and 2 | LEVSESPGSIQVARGQPAVLPCTFTTSAALINLNVIWMVTPLSNANQPEQVILYQGGQMFDGAPRF HGRVGFTGTMPATNVSIFINNTQLSDTGTYQCLVNNLPDIGGRNIGVTGLTVLVPPSAPHCQIQGS QDIGSDVILLCSSEEGIPRPTYLWEKLDNTLKLPPTATQDQVQGTVTIRNISALSSGLYQCVASNAI GTSTCLLDLQVISPQPRNIG |
| 14 | Extracellular domain human VSIG-3 isoform 3 | LEVSESPGSIQVARGQPAVLPCTFTTSAALINLNVIWMVTPLSNANQPEQVILYQGGQMFDGAPRF HGRVGFTGTMPATNVSIFINNTQLSDTGTYQCLVNNLPDIGGRNIGVTGLTVLVPPSAPHCQIQGS QDIGSDVILLCSSEEGIPRPTYLWEKLDNTLKLPPTATQDQVQGTVTIRNISALSSAQPRNIG |
| 15 | Transmembrane domain human VSIG-3 | LIAGAIGTGAVIIIFCIALIL |
| 16 | Cytoplasmic domain human VSIG-3 | GAFFYWRSKNKEEEEEEIPNEIREDDLPPKCSSAKAFHTEISSSDNNTLTSSNAYNSRYWSNNPK VHRNTESVSHFSDLGQSFSFHSGNANIPSIYANGTHLVPGQHKTLVVTANRGSSPQVMSRSNGS VSRKPRPPHTHSYTISHATLERIGAVPVMVPAQSRAGSLV |
| 17 | Ig-like V-type domain human VSIG-3 | LEVSESPGSIQVARGQPAVLPCTFTTSAALINLNVIWMVTPLSNANQPEQVILYQGGQMFDGAPRF HGRVGFTGTMPATNVSIFINNTQLSDTGTYQCLVNNLPDIGGRNIGVT |
| 18 | Ig-like C2-type domain human VSIG-3 | PSAPHCQIQGSQDIGSDVILLCSSEEGIPRPTYLWEKLDNTLKLPPTATQDQVQGTVTIRNISALSS GLYQCVASNAIGTSTCLLDLQVIS |
| 19 | Human VSIG-8 (P0DPA2-1, v1) | MRVGGAFHLLLVCLSPALLSAVRINGDGQEVLYLAEGDNVRLGCPYVLDPEDYGPNGLDIEWMQ VNSDPAHHRENVFLSYQDKRINHGSLPHLQQRVRFAASDPSQYDASINLMNLQVSDTATYECRV KKTTMATRKVIVTVQARPAVPMCWTEGHMTYGNDVVLKCYASGGSQPLSYKWAKISGHHYPYR AGSYTSQHSYHSELSYQESFHSSINQGLNNGDLVLKDISRADDGLYQCTVANNVGYSVCVVEVKV SDSRRIGVIIGIVLGSLLALGCLAVGIWGLVCCCCGGSGAGGARGAFGYGNGGGVGGGACGDLA SEIREDAVAPGCKASGRGSRVTHLLGYPTQNVSRSLRRKYAPPPCGGPEDVALAPCTAAAACEA GPSPVYVKVKSAEPADCAEGPVQCKNGLLV |
| 20 | Mature human VSIG-8 (P0DPA2-1, v1 positions 22 to 414) | VRINGDGQEVLYLAEGDNVRLGCPYVLDPEDYGPNGLDIEWMQVNSDPAHHRENVFLSYQDKRI NHGSLPHLQQRVRFAASDPSQYDASINLMNLQVSDTATYECRVKKTTMATRKVIVTVQARPAVPM CWTEGHMTYGNDWLKCYASGGSQPLSYKWAKISGHHYPYRAGSYTSQHSYHSELSYQESFHS SINQGLNNGDLVLKDISRADDGLYQCTVANNVGYSVCWEVKVSDSRRIGVIIGIVLGSLLALGCLA VGIWGLVCCCCGGSGAGGARGAFGYGNGGGVGGGACGDLASEIREDAVAPGCKASGRGSRVT HLLGYPTQNVSRSLRRKYAPPPCGGPEDVALAPCTAAAACEAGPSPVYVKVKSAEPADCAEGPV QCKNGLLV |
| 21 | Extracellular domain human VSIG-8 (P0DPA2-1, v1 positions 22 to 263) | VRINGDGQEVLYLAEGDNVRLGCPYVLDPEDYGPNGLDIEWMQVNSDPAHHRENVFLSYQDKRI NHGSLPHLQQRVRFAASDPSQYDASINLMNLQVSDTATYECRVKKTTMATRKVIVTVQARPAVPM CWTEGHMTYGNDWLKCYASGGSQPLSYKWAKISGHHYPYRAGSYTSQHSYHSELSYQESFHS SINQGLNNGDLVLKDISRADDGLYQCTVANNVGYSVCWEVKVSDSRRIG |
| 22 | Transmembrane domain human VSIG-8 (P0DPA2-1, v1 positions 264 to 284) | VIIGIVLGSLLALGCLAVGIW |
| 23 | Cytoplasmic domain human VSIG-8 (P0DPA2-1, v1 positions 285 to | GLVCCCCGGSGAGGARGAFGYGNGGGVGGGACGDLASEIREDAVAPGCKASGRGSRVTHLLG YPTQNVSRSLRRKYAPPPCGGPEDVALAPCTAAAACEAGPSPVYVKVKSAEPADCAEGPVQCKN GLLV |
| 24 | Ig-like V-type domain 1 human VSIG-8 (P0DPA2-1, v1 positions 22 to 141) | VRINGDGQEVLYLAEGDNVRLGCPYVLDPEDYGPNGLDIEWMQVNSDPAHHRENVFLSYQDKRI NHGSLPHLQQRVRFAASDPSQYDASINLMNLQVSDTATYECRVKKTTMATRKVIVT |
| 25 | Ig-like V-type domain 2 human VSIG-8 (P0DPA2-1, v1 positions 146 to 257) | PAVPMCWTEGHMTYGNDVVLKCYASGGSQPLSYKWAKISGHHYPYRAGSYTSQHSYHSELSYQ ESFHSSINQGLNNGDLVLKDISRADDGLYQCTVANNVGYSVCVVEVKVS |
| 26 | Epitope recognised by anti-VISTA antibody clones | SRGEVQTCSERRPI |

| SEQ ID NO: | DESCRIPTION | SEQUENCE |
|---|---|---|
| | 4M2-C12, 4M2-B4, 4M2-C9, 4M2-D9, 4M2-D5, 4M2-A8, V4H1, V4H2, V4-C1, V4-C9, V4-C24, V4-C26, V4-C27, V4-C28, V4-C30 and V4-C31 | |
| 27 | Epitope recognised by anti-VISTA antibody clones 2M1-B12 and 2M1-D2 | FQDLHLHHGGHQAA |
| 28 | Epitope recognised by anti-VISTA antibody clones 1M2-D2, 13D5p, 13D5-1 and 13D5-13 | CLVVEIRHHHSEHR |
| 29 | Epitope recognised by anti-VISTA antibody clone 5M1-A11 | DKGHDVTFYKT |
| 30 | Epitope recognised by anti-VISTA antibody clone 9M2-C12 | RHHHSEHRVHG |
| 31 | Positions 61 to 162 of human VISTA (Q9H7M9-1, v3) | DKGHDVTFYKTWYRSSRGEVQTCSERRPIRNLTFQDLHLHHGGHQAANTSHDLAQRHGLESAS DHHGNFSITMRNLTLLDSGLYCCLVVEIRHHHSEHRVHG |
| 32 | 4M2-C12 heavy chain variable region | EVKLVESGPGLVKPSQSLSLTCTVTGYSITSDYAWNWIRQFPGNKLEWMGYITYSGNISYNPSLR SRISITRDTSKNQFFLQLNSVTPEDTATYSCARSLYYPWYFDVWGAGTTVTVSS |
| 33 | 4M2-C12, 4M2-B4, V4H2, 4M2-D9, V4-C1, V4-C9 heavy chain CDR1 | GYSITSDYA |
| 34 | 4M2-C12, 4M2-B4, V4H1, V4H2 heavy chain CDR2 | ITYSGNI |
| 35 | 4M2-C12, 4M2-B4, V4H1, V4H2 heavy chain CDR3 | ARSLYYPWYFDV |
| 36 | 4M2-C12 heavy chain FR1 | EVKLVESGPGLVKPSQSLSLTCTVT |
| 37 | 4M2-C12, 4M2-B4 heavy chain FR2 | WNWIRQFPGNKLEWMGY |
| 38 | 4M2-C12, 4M2-B4 heavy chain FR3 | SYNPSLRSRISITRDTSKNQFFLQLNSVTPEDTATYSC |
| 39 | 4M2-C12, 4M2-B4, V4H1, V4H2, 13D5p, 13D5-1, 13D5-13 heavy chain FR4 | WGAGTTVTVSS |
| 40 | 4M2-C12 light chain variable region | DIVITQTPAILSTSPGEKVTMTCRASSSVGYIHWYQQKPGSSPKPWIYATSNLASGVPARFSGSGS GTSNSLTITRVEAEDAATYYCQQWSSYPPITFGGGTKLEVK |
| 41 | 4M2-C12, 4M2-B4, V4H1, V4H2, V4-C1, V4-C9, V4-C24, V4-C26, V4-C27, V4-C28, V4-C30, V4-C31 light chain CDR1 | SSVGY |
| 42 | 4M2-C12, 4M2-B4, V4-C1, V4-C9, V4-C28 light chain CDR2 | ATS |

-continued

| SEQ ID NO: | DESCRIPTION | SEQUENCE |
|---|---|---|
| 43 | 4M2-C12, 4M2-B4, V4H1, V4H2, V4-C1 V4-C9, V4-C24, V4-C26, V4-C27, V4-C28, V4-C30, V4-C31 light chain CDR3 | QQWSSYPPIT |
| 44 | 4M2-C12 light chain FR1 | DIVITQTPAILSTSPGEKVTMTCRAS |
| 45 | 4M2-C12, 4M2-B4 light chain FR2 | IHWYQQKPGSSPKPWIY |
| 46 | 4M2-C12, 4M2-B4 light chain FR3 | NLASGVPARFSGSGSGTSNSLTITRVEAEDAATYYC |
| 47 | 4M2-C12, 4M2-B4, V4H1, V4H2, V4-C1, V4-C9, V4-C24, V4-C26, V4-C27, V4-C28, V4-C30, V4-C31 light chain FR4 | FGGGTKLEVK |
| 48 | 4M2-B4 heavy chain variable region | EVMLVESGPGLVKPSQSLSLTCTVTGYSITSDYAWNWIRQFPGNKLEWMGYITYSGNISYNPSLR SRISITRDTSKNQFFLQLNSVTPEDTATYSCARSLYYPWYFDVWGAGTTVTVSS |
| 49 | 4M2-B4 heavy chain FR1 | EVMLVESGPGLVKPSQSLSLTCTVT |
| 50 | 4M2-B4 light chain variable region | DIVLTQTTAILSTSPGEKVTMTCRASSSVGYIHWYQQKPGSSPKPWIYATSNLASGVPARFSGSG SGTSNSLTITRVEAEDAATYYCQQWSSYPPITFGGGTKLEVK |
| 51 | 4M2-B4 light chain FR1 | DIVLTQTTAILSTSPGEKVTMTCRA |
| 52 | V4H1 heavy chain variable region | EVQLLESGGGLVQPGGSLRLSCAASGYTITSDYAMSWVRQAPGKGLEWVSVITYSGNISYADSV KGRFTISRDNSKNTLYLQMNSLRAEDTAVYYCARSLYYPWYFDVWGAGTTVTVSS |
| 53 | V4H1 heavy chain CDR1 | GYTITSDYA |
| 54 | V4H1 heavy chain FR1 | EVQLLESGGGLVQPGGSLRLSCAAS |
| 55 | V4H1 heavy chain FR2 | MSWVRQAPGKGLEWVSV |
| 56 | V4H1 heavy chain FR3 | SYADSVKGRFTISRDNSKNTLYLQMNSLRAEDTAVYYC |
| 57 | V4H1 light chain variable region | EIVITQSPATLSLSPGERATLSCRASSSVGYLAWYQQKPGQAPRPLIYDTSNRATGIPARFSGSGS GTDNTLTISSLEPEDFAVYYCQQWSSYPPITFGGGTKLEVK |
| 58 | V4H1 light chain CDR2 | DTS |
| 59 | V4H1, V4-C1 light chain FR1 | EIVITQSPATLSLSPGERATLSCRAS |
| 60 | V4H1 light chain FR2 | LAWYQQKPGQAPRPLIY |
| 61 | V4H1 light chain FR3 | NRATGIPARFSGSGSGTDNTLTISSLEPEDFAVYYC |
| 62 | V4H2 heavy chain variable region | QVQLQESGPGLVKPSDTLSLTCTVSGYSITSDYAWSWIRQPPGKGLEWIGYITYSGNISYNPSLKS RVTISVDTSKNQFSLKLSSVTAADTAVYDCARSLYYPWYFDVWGAGTTVTVSS |
| 63 | V4H2, V4-C1, V4-C9, V4-C24, V4-C26, V4-C27, V4-C28, V4-C30, V4-C31 heavy chain FR1 | QVQLQESGPGLVKPSDTLSLTCTVS |
| 64 | V4H2 heavy chain FR2 | WSWIRQPPGKGLEWIGY |
| 65 | V4H2 heavy chain FR3 | SYNPSLKSRVTISVDTSKNQFSLKLSSVTAADTAVYDC |
| 66 | V4H2 light chain variable region | DIQMTQSPSSLSASVGDRVTITCRASSSVGYLNWYQQKPGKAPKPLIYAASSLQSGVPSRFSGSG SGTDNTLTISSLQPEDFATYYCQQWSSYPPITFGGGTKLEVK |
| 67 | V4H2, 4M2-D9 light chain CDR2 | AAS |
| 68 | V4H2 light chain FR1 | DIQMTQSPSSLSASVGDRVTITCRA |
| 69 | V4H2 light chain FR2 | LNWYQQKPGKAPKPLIY |

-continued

| SEQ ID NO: | DESCRIPTION | SEQUENCE |
|---|---|---|
| 70 | V4H2 light chain FR3 | SLQSGVPSRFSGSGSGTDNTLTISSLQPEDFATYYC |
| 71 | 2M1-B12 heavy chain variable region | EVQLQQSGAELVRPGTSVKTSCKASGYTFTNYWLGWVKERAGHGLEWIGEIFPGGGHTNYKEKF KGKATLTADTSSSTAYMKLSSLTSEDSAVYFCAQIPLYYGHYRSAYWGQGTLVTVSA |
| 72 | 2M1-B12, 2M1-D2, 13D5p, 13D5-1, 13D5-13 heavy chain CDR1 | GYTFTNYW |
| 73 | 2M1-B12, 2M1-D2 heavy chain CDR2 | IFPGGGHT |
| 74 | 2M1-B12, 2M1-D2 heavy chain CDR3 | AQIPLYYGHYRSAY |
| 75 | 2M1-B12 heavy chain FR1 | EVQLQQSGAELVRPGTSVKTSCKAS |
| 76 | 2M1-B12, 2M1-D2 heavy chain FR2 | LGWVKERAGHGLEWIGE |
| 77 | 2M1-B12, 2M1-D2 heavy chain FR3 | NYKEKFKGKATLTADTSSSTAYMKLSSLTSEDSAVYFC |
| 78 | 2M1-B12, 2M1-D2, 1M2-D2 heavy chain FR4 | WGQGTLVTVSA |
| 79 | 2M1-B12 light chain variable region | DIQMMQSPASLSASVGETVAITCGASENIYGALNWYQRKQGKSPQLLIYGATNLADGMSSRFSGS GSGRQYSLKISSLHPDDVATYYCQNVLSTPYTFGGGTKLEIK |
| 80 | 2M1-B12, 2M1-D2 light chain CDR1 | ENIYGA |
| 81 | 2M1-B12, 2M1-D2 light chain CDR2 | GAT |
| 82 | 2M1-B12, 2M1-D2 light chain CDR3 | QNVLSTPYT |
| 83 | 2M1-B12 light chain FR1 | DIQMMQSPASLSASVGETVAITCGAS |
| 84 | 2M1-B12, 2M1-D2 light chain FR2 | LNWYQRKQGKSPQLLIY |
| 85 | 2M1-B12, 2M1-D2 light chain FR3 | NLADGMSSRFSGSGSGRQYSLKISSLHPDDVATYYC |
| 86 | 2M1-B12, 4M2-C9, 2M1-D2, 4M2-D9, 1M2-D2, 5M1-Al 1, 4M2-D5, 4M2-A8, 9M2-C12, 13D5p, 13D5-1, 13d5-13 light chain FR4 | FGGGTKLEIK |
| 87 | 4M2-C9 heavy chain variable region | QVTLKECGPGILQPSQTLSLTCSFSGFSLSTSGMGVSWIRQPSGKGLEWLAHIYWDDDKRYNPSL KSRLTISKDSSSNQVFLKITSVDTADTATYYCARRLDGYNDPYYFDYWGQGTTLTVSS |
| 88 | 4M2-C9, 5M1-A11 heavy chain CDR1 | GFSLSTSGMG |
| 89 | 4M2-C9, 5M1-A11 heavy chain CDR2 | IYWDDDK |
| 90 | 4M2-C9, 5M1-A11 heavy chain CDR3 | ARRLDGYNDPYYFDY |
| 91 | 4M2-C9 heavy chain FR1 | QVTLKECGPGILQPSQTLSLTCSFS |
| 92 | 4M2-C9, 5M1-A11 heavy chain FR2 | VSWIRQPSGKGLEWLAH |
| 93 | 4M2-C9, 5M1-A11 heavy chain FR3 | RYNPSLKSRLTISKDSSSNQVFLKITSVDTADTATYYC |
| 94 | 4M2-C9 heavy chain FR4 | WGQGTTLTVSS |
| 95 | 4M2-C9 light chain variable region | DIVMTQSPSSLSASLGDTVTITCHASQNVNVWLSWYQQKPGNIPKLLIYKASNLHAGVPSRFSGS GSGTGFTLTISSLQPEDIATYYCQQGQSYPLTFGGGTKLEIK |
| 96 | 4M2-C9 light chain CDR1 | QNVNVW |
| 97 | 4M2-C9 light chain CDR2 | KAS |
| 98 | 4M2-C9 light chain CDR3 | QQGQSYPLT |
| 99 | 4M2-C9 light chain FR1 | DIVMTQSPSSLSASLGDTVTITCHAS |

Sequences

| SEQ ID NO: | DESCRIPTION | SEQUENCE |
|---|---|---|
| 100 | 4M2-C9 light chain FR2 | LSWYQQKPGNIPKLLIY |
| 101 | 4M2-C9 light chain FR3 | NLHAGVPSRFSGSGSGTGFTLTISSLQPEDIATYYC |
| 102 | 2M1-D2 heavy chain variable region | QVQLQQSGAELVRPGTSVKISCKASGYTFTNYWLGWVKERAGHGLEWIGEIFPGGGHTNYKEKFKGKATLTADTSSSTAYMKLSSLTSEDSAVYFCAQIPLYYGHYRSAYWGQGTLVTVSA |
| 103 | 2M1-D2, 13D5p, 13D5-1, 13D5-13 heavy chain FR1 | QVQLQQSGAELVRPGTSVKISCKAS |
| 104 | 2M1-D2 light chain variable region | DIVMTQSPASLSASVGETVAITCGASENIYGALNWYQRKQGKSPQLLIYGATNLADGMSSRFSGSGSGRQYSLKISSLHPDDVATYYCQNVLSTPYTFGGGTKLEIK |
| 105 | 2M1-D2 light chain FR1 | DIVMTQSPASLSASVGETVAITCGAS |
| 106 | 4M2-D9 heavy chain variable region | EVQLQESGPGLVKPSQSLSLTCTVTGYSITSDYAWNWIRQFPGNRLEWMGFISYSGFTTYSPSLESRISITRDTSKNQFFLQLISVTTEDTATYYCARNHYGGSYWYFDVWGAGTSVTVSS |
| 107 | 4M2-D9 heavy chain CDR2 | ISYSGFT |
| 108 | 4M2-D9 heavy chain CDR3 | ARNHYGGSYWYFDV |
| 109 | 4M2-D9 heavy chain FR1 | EVQLQESGPGLVKPSQSLSLTCTVT |
| 110 | 4M2-D9 heavy chain FR2 | WNWIRQFPGNRLEWMGF |
| 111 | 4M2-D9 heavy chain FR3 | TYSPSLESRISITRDTSKNQFFLQLISVTTEDTATYYC |
| 112 | 4M2-D9 heavy chain FR4 | WGAGTSVTVSS |
| 113 | 4M2-D9 light chain variable region | DIVMTQSPGSLAVSLGQRATISCRASESVEYYGTSLMQWYLQKPGQPPKLLIYAASNVESGVPDRFRGSGSGTDFSLNIHPVEEDDIAMYFCQQSRKVPWTFGGGTKLEIK |
| 114 | 4M2-D9 light chain CDR1 | ESVEYYGTSL |
| 115 | 4M2-D9 light chain CDR3 | QQSRKVPWT |
| 116 | 4M2-D9 light chain FR1 | DIVMTQSPGSLAVSLGQRATISCRAS |
| 117 | 4M2-D9 light chain FR2 | MQWYLQKPGQPPKLLIY |
| 118 | 4M2-D9 light chain FR3 | NVESGVPDRFRGSGSGTDFSLNIHPVEEDDIAMYFC |
| 119 | 1M2-D2 heavy chain variable region | EVKVEESGGGLVQPGGSMKLSCAASGFTFSDAWMDWVHQSPEKGLEWVAEIRSKANNHATYYVESVEGRFTISRDDSKSSVFLQVNSLRPEDTGIYYCTRRDGYYFAYWGQGTLVTVSA |
| 120 | 1M2-D2 heavy chain CDR1 | GFTFSDAW |
| 121 | 1M2-D2 heavy chain CDR2 | IRSKANNHAT |
| 122 | 1M2-D2 heavy chain CDR3 | TRRDGYYFAY |
| 123 | 1M2-D2 heavy chain FR1 | EVKVEESGGGLVQPGGSMKLSCAAS |
| 124 | 1M2-D2 heavy chain FR2 | MDWVHQSPEKGLEWVAE |
| 125 | 1M2-D2 heavy chain FR3 | YYVESVEGRFTISRDDSKSSVFLQVNSLRPEDTGIYYC |
| 126 | 1M2-D2 light chain variable region | DIVLTQSPAIMSASLGEEITLTCSASSSVRDMHWYQQKSGTSPKVLIYNTFNLASGVPSRFSGSGSGTFYSLTISSVEAGDAAAYYCHQWSSYPTFGGGTKLEIK |
| 127 | 1M2-D2 light chain CDR1 | SSSVRD |
| 128 | 1M2-D2 light chain CDR2 | NTF |
| 129 | 1M2-D2 light chain CDR3 | HQWSSYPT |
| 130 | 1M2-D2 light chain FR1 | DIVLTQSPAIMSASLGEEITLTCSA |
| 131 | 1M2-D2 light chain FR2 | MHWYQQKSGTSPKVLIY |
| 132 | 1M2-D2 light chain FR3 | NLASGVPSRFSGSGSGTFYSLTISSVEAGDAAAYYC |
| 133 | 5M1-A11 heavy chain variable region | QVTLKVSGPGILQPSQTLSLTCSFSGFSLSTSGMGVSWIRQPSGKGLEWLAHIYWDDDKRYNPSLKSRLTISKDSSSNQVFLKITSVDTADTATYYCARRLDGYNDPYYFDYWGQGTTLTVSS |

-continued

| SEQ ID NO: | DESCRIPTION | SEQUENCE |
|---|---|---|
| 134 | 5M1-A11 heavy chain FR1 | QVTLKVSGPGILQPSQTLSLTCSFS |
| 135 | 5M1-A11, 4M2-D5, 4M2-A8 heavy chain FR4 | WGQGTTLTVSS |
| 136 | 5M1-A11 light chain variable region | DVVMTQTPALMSASPGEKVTMTCSASSSVSYMYWYQQKPRSSPKPWIYLTSNLASGVPARFSG SGSGTSYSLTISSMEAEDAATYYCQQWNSNPYTFGGGTKLEIK |
| 137 | 5M1-A11 light chain CDR1 | SSVSY |
| 138 | 5M1-A11 light chain CDR2 | LTS |
| 139 | 5M1-A11 light chain CDR3 | QQWNSNPYT |
| 140 | 5M1-A11 light chain FR1 | DVVMTQTPALMSASPGEKVTMTCSAS |
| 141 | 5M1-A11 light chain FR2 | MYWYQQKPRSSPKPWIY |
| 142 | 5M1-A11 light chain FR3 | NLASGVPARFSGSGSGTSYSLTISSMEAEDAATYYC |
| 143 | 4M2-D5 heavy chain variable region | QVQLQQSGAELARPGASVRMSCKASGYTFTSYTMNWVKQRPGQGLEWIGFINPDSDYTTYDQK FKDKATLTADSSSTAYMQLSSLTYDDSAVYYCTRHSYGNYGDYWGQGTTLTVSS |
| 144 | 4M2-D5 heavy chain CDR1 | GYTFTSYT |
| 145 | 4M2-D5 heavy chain CDR2 | INPDSDYT |
| 146 | 4M2-D5 heavy chain CDR3 | TRHSYGNYGDY |
| 147 | 4M2-D5 heavy chain FR1 | QVQLQQSGAELARPGASVRMSCKAS |
| 148 | 4M2-D5 heavy chain FR2 | MNWVKQRPGQGLEWIGF |
| 149 | 4M2-D5 heavy chain FR3 | TYDQKFKDKATLTADSSSTAYMQLSSLTYDDSAVYYC |
| 150 | 4M2-D5 light chain variable region | DIVLTQSPKFLLVSAGDRVTITCKASQSVTNDVAWYQQKPGQSPKLLIYYASSRYTGVPDRFTGS GFGTDFTFTINTVQAEDLAVYFCQQDYSSPYTFGGGTKLEIK |
| 151 | 4M2-D5 light chain CDR1 | QSVTND |
| 152 | 4M2-D5, 4M2-A8 light chain CDR2 | YAS |
| 153 | 4M2-D5, 4M2-A8 light chain CDR3 | QQDYSSPYT |
| 154 | 4M2-D5 light chain FR1 | DIVLTQSPKFLLVSAGDRVTITCKAS |
| 155 | 4M2-D5, 4M2-A8 light chain FR2 | VAWYQQKPGQSPKLLIY |
| 156 | 4M2-D5 light chain FR3 | SRYTGVPDRFTGSGFGTDFTFTINTVQAEDLAVYFC |
| 157 | 4M2-A8 heavy chain variable region | QVQLQQSGADLARPGASVKMSCKASGYTFIDYTVHWVKQRPGQGLEWIGFINPSNDYTSYNQKF KDKASLTADTSSTAYMQLSSLTSDDSAVYYCARHSYGNYGDYWGQGTTLTVSS |
| 158 | 4M2-A8 heavy chain CDR1 | GYTFIDYT |
| 159 | 4M2-A8 heavy chain CDR2 | INPSNDYT |
| 160 | 4M2-A8 heavy chain CDR3 | ARHSYGNYGDY |
| 161 | 4M2-A8 heavy chain FR1 | QVQLQQSGADLARPGASVKMSCKAS |
| 162 | 4M2-A8 heavy chain FR2 | VHWVKQRPGQGLEWIGF |
| 163 | 4M2-A8 heavy chain FR3 | SYNQKFKDKASLTADTSSTAYMQLSSLTSDDSAVYYC |
| 164 | 4M2-A8 light chain variable region | DIVMTQAPKFLLVSAGDRVTITCKASQSVTNGVAWYQQKPGQSPKLLIYYASNRYTGVPDRFTGS GFGTDFTFTISTVQAEDLAVYFCQQDYSSPYTFGGGTKLEIK |
| 165 | 4M2-A8 light chain CDR1 | QSVTNG |
| 166 | 4M2-A8 light chain FR1 | DIVMTQAPKFLLVSAGDRVTITCKAS |
| 167 | 4M2-A8 light chain FR3 | NRYTGVPDRFTGSGFGTDFTFTISTVQAEDLAVYFC |

-continued

| SEQ ID NO: | DESCRIPTION | SEQUENCE |
|---|---|---|
| 168 | 9M2-C12 heavy chain variable region | QVQLQQSGAELVKPGASVRLSCKASGYTFTSYWMHWVRQRPGLGLEWIGEIDPSDSYTNCNQR FKGKATLTVDKSSSTAYTQLSSLTSEDSAVYYCARWAYGPYAMDYWGQGTSVTVSS |
| 169 | 9M2-C12 heavy chain CDR1 | GYTFTSYW |
| 170 | 9M2-C12 heavy chain CDR2 | IDPSDSYT |
| 171 | 9M2-C12 heavy chain CDR3 | ARWAYGPYAMDY |
| 172 | 9M2-C12 heavy chain FR1 | QVQLQQSGAELVKPGASVRLSCKAS |
| 173 | 9M2-C12 heavy chain FR2 | MHWVRQRPGLGLEWIGE |
| 174 | 9M2-C12 heavy chain FR3 | NCNQRFKGKATLTVDKSSSTAYTQLSSLTSEDSAVYYC |
| 175 | 9M2-C12 heavy chain FR4 | WGQGTSVTVSS |
| 176 | 9M2-C12 light chain variable region | DIVMTQTPLSLPVSLGDQASISCRSSQSLVHSNGNTYLHWYLQKPGQSPKLLIYKVSNRFSGVPD RFSGSGSGTDFTLKISRVEAEDLGVYFCSQSTHVPWTFGGGTKLEIK |
| 177 | 9M2-C12 light chain CDR1 | QSLVHSNGNTY |
| 178 | 9M2-C12, 13D5p, 13D5-1,13D5-13 light chain CDR2 | KVS |
| 179 | 9M2-C12 light chain CD R3 | SQSTHVPWT |
| 180 | 9M2-C12 light chain FR1 | DIVMTQTPLSLPVSLGDQASISCRSS |
| 181 | 9M2-C12 light chain FR2 | LHWYLQKPGQSPKLLIY |
| 182 | 9M2-C12 light chain FR3 | NRFSGVPDRFSGSGSGTDFTLKISRVEAEDLGVYFC |
| 183 | 13D5p heavy chain variable region | QVQLQQSGAELVRPGTSVKISCKASGYTFTNYWLGWVKQRPGHGLEWIGDIYPGGGYTNYNEKF KGKATLTADTSSSTAYMQLSSLTSEDSAVYFCARGGYYYGSSWYFDVWGAGTTVTVSS |
| 184 | 13D5p, 13D5-1, 13D5-13 heavy chain CDR2 | IYPGGGYT |
| 185 | 13D5p heavy chain CDR3 | ARGGYYYGSSWYFDV |
| 186 | 13D5p, 13D5-1, 13D5-13 heavy chain FR2 | LGWVKQRPGHGLEWIGD |
| 187 | 13D5p, 13D5-1 heavy chain FR3 | NYNEKFKGKATLTADTSSSTAYMQLSSLTSEDSAVYFC |
| 188 | 13D5p light chain variable region | DVLMTQTPLSLPVSLGDQASISCRSSQSIVHSNGNTYLEWYLQKPGQSPKLLIYKVSNRFSGVPD RFSGSGSGTDFTLKISRVEAEDLGVYYCFQGSHVPPTFGGGTKLEIK |
| 189 | 13D5p light chain CDR1 | QSIVHSNGNTY |
| 190 | 13D5p, 13D5-1, 13D5-13 light chain CDR3 | FQGSHVPPT |
| 191 | 13D5p, 13D5-1, 13D5-13 light chain FR1 | DVLMTQTPLSLPVSLGDQASISCRSS |
| 192 | 13D5p, 13D5-13 light chain FR2 | LEWYLQKPGQSPKLLIY |
| 193 | 13D5p, 13D5-1 light chain FR3 | NRFSGVPDRFSGSGSGTDFTLKISRVEAEDLGVYYC |
| 194 | 13D5-1 heavy chain variable region | QVQLQQSGAELVRPGTSVKISCKASGYTFTNYWLGWVKQRPGHGLEWIGDIYPGGGYTNYNEKF KGKATLTADTSSSTAYMQLSSLTSEDSAVYFCVRSGYYYGSSWYFDVWGAGTTVTVSS |
| 195 | 13D5-1 heavy chain CDR3 | VRSGYYYGSSWYFDV |
| 196 | 13D5-1 light chain variable region | DVLMTQTPLSLPVSLGDQASISCRSSQSIVHSSGNTYLEWYLQKPDQSPKLLIYKVSNRFSGVPDR FSGSGSGTDFTLKISRVEAEDLGVYYCFQGSHVPPTFGGGTKLEIK |
| 197 | 13D5-1 light chain CDR1 | QSIVHSSGNTY |
| 198 | 13D5-1 light chain FR2 | LEWYLQKPDQSPKLLIY |
| 199 | 13D5-13 heavy chain variable region | QVQLQQSGAELVRPGTSVKISCKASGYTFTNYWLGWVKQRPGHGLEWIGDIYPGGGYTNYNEKF KGKATLTADISSSTAYMQLSSLTSEDSADYFCVRGGYYYGSSWYFDVWGAGTTVTVSS |
| 200 | 13D5-13 heavy chain CDR3 | VRGGYYYGSSWYFDV |

| SEQ ID NO: | DESCRIPTION | SEQUENCE |
|---|---|---|
| 201 | 13D5-13 heavy chain FR3 | NYNEKFKGKATLTADISSSTAYMQLSSLTSEDSADYFC |
| 202 | 13D5-13 light chain variable region | DVLMTQTPLSLPVSLGDQASISCRSSQSTVHSIGNTYLEWYLQKPGQSPKLLIYKVSNRFSGVPDRFSGSESGTDFTLKISRVEAEDLGVYYCFQGSHVPPTFGGGTKLEIK |
| 203 | 13D5-13 light chain CDR1 | QSTVHSIGNTY |
| 204 | 13D5-13 light chain FR3 | NRFSGVPDRFSGSESGTDFTLKISRVEAEDLGVYYC |
| 205 | Human IgG1 constant region (IGHG1; UniProt:P01857-1, v1) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 206 | CH1 IgG1 (positions 1-98 of P01857-1, v1) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKV |
| 207 | Hinge IgG1 (positions 99-110 of P01857-1, v1) | EPKSCDKTHTCP |
| 208 | CH2 IgG1 (positions 111-223 of P01857-1, v1) | PCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAK |
| 209 | CH3 IgG1 (positions 224-330 of P01857-1, v1) | GQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 210 | CH3 (D356E, L358M; positions numbered according to EU numbering) | GQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 211 | $C_K$ CL (IGCK; UniProt: P01834-1, v2) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 212 | 4M2-C12 VH-CH1-CH2-CH3 | EVKLVESGPGLVKPSQSLSLTCTVTGYSITSDYAWNWIRQFPGNKLEWMGYITYSGNISYNPSLRSRISITRDTSKNQFFLQLNSVTPEDTATYSCARSLYYPWYFDVWGAGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 213 | 4M2-C12 VL-$C_K$ | DIVITQTPAILSTSPGEKVTMTCRASSSVGYIHWYQQKPGSSPKPWIYATSNLASGVPARFSGSGSGTSNSLTITRVEAEDAATYYCQQWSSYPPITFGGGTKLEVKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 214 | 4M2-B4 VH-CH1-CH2-CH3 | EVMLVESGPGLVKPSQSLSLTCTVTGYSITSDYAWNWIRQFPGNKLEWMGYITYSGNISYNPSLRSRISITRDTSKNQFFLQLNSVTPEDTATYSCARSLYYPWYFDVWGAGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 215 | 4M2-B4 VL-$C_K$ | DIVLTQTTAILSTSPGEKVTMTCRASSSVGYIHWYQQKPGSSPKPWIYATSNLASGVPARFSGSGSGTSNSLTITRVEAEDAATYYCQQWSSYPPITFGGGTKLEVKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 216 | V4H1 VH-CH1-CH2-CH3 | EVQLLESGGGLVQPGGSLRLSCAASGYTITSDYAMSWVRQAPGKGLEWVSVITYSGNISYADSVKGRFTISRDNSKNTLYLQMNSLRAEDTAVYYCARSLYYPWYFDVWGAGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 217 | V4H1 VL-$C_K$ | EIVITQSPATLSLSPGERATLSCRASSSVGYLAWYQQKPGQAPRPLIYDTSNRATGIPARFSGSGSGTDNTLTISSLEPEDFAVYYCQQWSSYPPITFGGGTKLEVKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |

-continued

Sequences

| SEQ ID NO: | DESCRIPTION | SEQUENCE |
|---|---|---|
| 218 | V4H2 VH-CH1-CH2-CH3 | QVQLQESGPGLVKPSDTLSLTCTVSGYSITSDYAWSWIRQPPGKGLEWIGYITYSGNISYNPSLKS RVTISVDTSKNQFSLKLSSVTAADTAVYDCARSLYYPWYFDVWGAGTTVTVSSASTKGPSVFPLA PSSKSTSGGTAALGCLVKDYFPEPVTVSWNSGALTSGVHTFPAVLQSSGLYSLSSVVTVPSSSLG TQTYICNVNHKPSNTKVDKKVEPKSCDKTHTCPPCPAPELLGGPSVFLFPPKPKDTLMISRTPEVT CVVVDVSHEDPEVKFNWYVDGVEVHNAKTKPREEQYNSTYRVVSVLTVLHQDWLNGKEYKCKV SNKALPAPIEKTISKAKGQPREPQVYTLPPSRDELTKNQVSLTCLVKGFYPSDIAVEWESNGQPEN NYKTTPPVLDSDGSFFLYSKLTVDKSRWQQGNVFSCSVMHEALHNHYTQKSLSLSPGK |
| 219 | V4H2 VL-C$_K$ | DIQMTQSPSSLSASVGDRVTITCRASSSVGYLNWYQQKPGKAPKLIYAASSLQSGVPSRFSGSG SGTDNTLTISSLQPEDFATYYCQQWSSYPPITFGGGTKLEVKRTVAAPSVFIFPPSDEQLKSGTAS VVCLLNNFYPREAKVQWKVDNALQSGNSQESVTEQDSKDSTYSLSSTLTLSKADYEKHKVYACE VTHQGLSSPVTKSFNRGEC |
| 220 | 2M1-B12 VH-CH1-CH2-CH3 | EVQLQQSGAELVRPGTSVKTSCKASGYTFTNYWLGWVKERAGHGLEWIGEIFPGGGHTNYKEKF KGKATLTADTSSSTAYMKLSSLTSEDSAVYFCAQIPLYYGHYRSAYWGQGTLVTVSSASTKGPSV FPLAPSSKSTSGGTAALGCLVKDYFPEPVTVSWNSGALTSGVHTFPAVLQSSGLYSLSSVVTVPS SSLGTQTYICNVNHKPSNTKVDKKVEPKSCDKTHTCPPCPAPELLGGPSVFLFPPKPKDTLMISRT PEVTCVVVDVSHEDPEVKFNWYVDGVEVHNAKTKPREEQYNSTYRVVSVLTVLHQDWLNGKEY KCKVSNKALPAPIEKTISKAKGQPREPQVYTLPPSRDELTKNQVSLTCLVKGFYPSDIAVEWESNG QPENNYKTTPPVLDSDGSFFLYSKLTVDKSRWQQGNVFSCSVMHEALHNHYTQKSLSLSPGK |
| 221 | 2M1-B12 VL-C$_K$ | DIQMMQSPASLSASVGETVAITCGASENIYGALNWYQRKQGKSPQLLIYGATNLADGMSSRFSGS GSGRQYSLKISSLHPDDVATYYCQNVLSTPYTFGGGTKLEIKRTVAAPSVFIFPPSDEQLKSGTAS VVCLLNNFYPREAKVQWKVDNALQSGNSQESVTEQDSKDSTYSLSSTLTLSKADYEKHKVYACE VTHQGLSSPVTKSFNRGEC |
| 222 | 4M2-C9 VH-CH1-CH2-CH3 | QVTLKECGPGILQPSQTLSLTCSFSGFSLSTSGMGVSWIRQPSGKGLEWLAHIYWDDDKRYNPSL KSRLTISKDSSSNQVFLKITSVDTADTATYYCARRLDGYNDPYYFDYWGQGTTLTVSSASTKGPS VFPLAPSSKSTSGGTAALGCLVKDYFPEPVTVSWNSGALTSGVHTFPAVLQSSGLYSLSSVVTVP SSSLGTQTYICNVNHKPSNTKVDKKVEPKSCDKTHTCPPCPAPELLGGPSVFLFPPKPKDTLMISR TPEVTCVVVDVSHEDPEVKFNWYVDGVEVHNAKTKPREEQYNSTYRVVSVLTVLHQDWLNGKE YKCKVSNKALPAPIEKTISKAKGQPREPQVYTLPPSRDELTKNQVSLTCLVKGFYPSDIAVEWESN GQPENNYKTTPPVLDSDGSFFLYSKLTVDKSRWQQGNVFSCSVMHEALHNHYTQKSLSLSPGK |
| 223 | 4M2-C9 VL-C$_K$ | DIVMTQSPSSLSASLGDTVTITCHASQNVNVWLSWYQQKPGNIPKLLIYKASNLHAGVPSRFSGS GSGTGFTLTISSLQPEDIATYYCQQGQSYPLTFGGGTKLEIKRTVAAPSVFIFPPSDEQLKSGTASV VCLLNNFYPREAKVQWKVDNALQSGNSQESVTEQDSKDSTYSLSSTLTLSKADYEKHKVYACEV THQGLSSPVTKSFNRGEC |
| 224 | 2M1-D2 VH-CH1-CH2-CH3 | QVQLQQSGAELVRPGTSVKISCKASGYTFTNYWLGWVKERAGHGLEWIGEIFPGGGHTNYKEKF KGKATLTADTSSSTAYMKLSSLTSEDSAVYFCAQIPLYYGHYRSAYWGQGTLVTVSSASTKGPSV FPLAPSSKSTSGGTAALGCLVKDYFPEPVTVSWNSGALTSGVHTFPAVLQSSGLYSLSSVVTVPS SSLGTQTYICNVNHKPSNTKVDKKVEPKSCDKTHTCPPCPAPELLGGPSVFLFPPKPKDTLMISRT PEVTCVVVDVSHEDPEVKFNWYVDGVEVHNAKTKPREEQYNSTYRVVSVLTVLHQDWLNGKEY KCKVSNKALPAPIEKTISKAKGQPREPQVYTLPPSRDELTKNQVSLTCLVKGFYPSDIAVEWESNG QPENNYKTTPPVLDSDGSFFLYSKLTVDKSRWQQGNVFSCSVMHEALHNHYTQKSLSLSPGK |
| 225 | 2M1-D2 VL-C$_K$ | DIVMTQSPASLSASVGETVAITCGASENIYGALNWYQRKQGKSPQLLIYGATNLADGMSSRFSGS GSGRQYSLKISSLHPDDVATYYCQNVLSTPYTFGGGTKLEIKRTVAAPSVFIFPPSDEQLKSGTAS VVCLLNNFYPREAKVQWKVDNALQSGNSQESVTEQDSKDSTYSLSSTLTLSKADYEKHKVYACE VTHQGLSSPVTKSFNRGEC |
| 226 | 4M2-D9 VH-CH1-CH2-CH3 | EVQLQESGPGLVKPSQSLSLTCTVTGYSITSDYAWNWIRQFPGNRLEWMGFISYSGFTTYSPSLE SRISITRDTSKNQFFLQLISVTTEDTATYYCARNHYGGSYWYFDVWGAGTSVTVSSASTKGPSVF PLAPSSKSTSGGTAALGCLVKDYFPEPVTVSWNSGALTSGVHTFPAVLQSSGLYSLSSVVTVPSS SLGTQTYICNVNHKPSNTKVDKKVEPKSCDKTHTCPPCPAPELLGGPSVFLFPPKPKDTLMISRTP EVTCVVVDVSHEDPEVKFNWYVDGVEVHNAKTKPREEQYNSTYRVVSVLTVLHQDWLNGKEYK CKVSNKALPAPIEKTISKAKGQPREPQVYTLPPSRDELTKNQVSLTCLVKGFYPSDIAVEWESNGQ PENNYKTTPPVLDSDGSFFLYSKLTVDKSRWQQGNVFSCSVMHEALHNHYTQKSLSLSPGK |
| 227 | 4M2-D9 VL-C$_K$ | DIVMTQSPGSLAVSLGQRATISCRASESVEYYGTSLMQWYLQKPGQPPKLLIYAASNVESGVPDR FRGSGSGTDFSLNIHPVEEDDIAMYFCQQSRKVPWTFGGGTKLEIKRTVAAPSVFIFPPSDEQLKS GTASVVCLLNNFYPREAKVQWKVDNALQSGNSQESVTEQDSKDSTYSLSSTLTLSKADYEKHKV YACEVTHQGLSSPVTKSFNRGEC |
| 228 | 1M2-D2 VH-CH1-CH2-CH3 | EVKVEESGGGLVQPGGSMKLSCAASGFTFSDAWMDWVHQSPEKGLEWVAEIRSKANNHATYYV ESVEGRFTISRDDSKSSVFLQVNSLRPEDTGIYYCTRRDGYYFAYWGQGTLVTVSSASTKGPSVF PLAPSSKSTSGGTAALGCLVKDYFPEPVTVSWNSGALTSGVHTFPAVLQSSGLYSLSSVVTVPSS SLGTQTYICNVNHKPSNTKVDKKVEPKSCDKTHTCPPCPAPELLGGPSVFLFPPKPKDTLMISRTP EVTCVVVDVSHEDPEVKFNWYVDGVEVHNAKTKPREEQYNSTYRVVSVLTVLHQDWLNGKEYK CKVSNKALPAPIEKTISKAKGQPREPQVYTLPPSRDELTKNQVSLTCLVKGFYPSDIAVEWESNGQ PENNYKTTPPVLDSDGSFFLYSKLTVDKSRWQQGNVFSCSVMHEALHNHYTQKSLSLSPGK |
| 229 | 1M2-D2 VL-C$_K$ | DIVLTQSPAIMSASLGEEITLTCSASSSVRDMHWYQQKSGTSPKVLIYNTFNLASGVPSRFSGSGS GTFYSLTISSVEAGDAAAYYCHQWSSYPTFGGGTKLEIKRTVAAPSVFIFPPSDEQLKSGTASVVC LLNNFYPREAKVQWKVDNALQSGNSQESVTEQDSKDSTYSLSSTLTLSKADYEKHKVYACEVTH QGLSSPVTKSFNRGEC |
| 230 | 5M1-A11 VH-CH1-CH2-CH3 | QVTLKVSGPGILQPSQTLSLTCSFSGFSLSTSGMGVSWIRQPSGKGLEWLAHIYWDDDKRYNPSL KSRLTISKDSSSNQVFLKITSVDTADTATYYCARRLDGYNDPYYFDYWGQGTTLTVSSASTKGPS VFPLAPSSKSTSGGTAALGCLVKDYFPEPVTVSWNSGALTSGVHTFPAVLQSSGLYSLSSVVTVP SSSLGTQTYICNVNHKPSNTKVDKKVEPKSCDKTHTCPPCPAPELLGGPSVFLFPPKPKDTLMISR TPEVTCVVVDVSHEDPEVKFNWYVDGVEVHNAKTKPREEQYNSTYRVVSVLTVLHQDWLNGKE YKCKVSNKALPAPIEKTISKAKGQPREPQVYTLPPSRDELTKNQVSLTCLVKGFYPSDIAVEWESN GQPENNYKTTPPVLDSDGSFFLYSKLTVDKSRWQQGNVFSCSVMHEALHNHYTQKSLSLSPGK |

Sequences

| SEQ ID NO: | DESCRIPTION | SEQUENCE |
|---|---|---|
| 231 | 5M1-A11 VL-C$_K$ | DVVMTQTPALMSASPGEKVTMTCSASSSVSYMYWYQQKPRSSPKPWIYLTSNLASGVPARFSG SGSGTSYSLTISSMEAEDAATYYCQQWNSNPYTFGGGTKLEIKRTVAAPSVFIFPPSDEQLKSGT ASVVCLLNNFYPREAKVQWKVDNALQSGNSQESVTEQDSKDSTYSLSSTLTLSKADYEKHKVYA CEVTHQGLSSPVTKSFNRGEC |
| 232 | 4M2-D5 VH-CH1-CH2-CH3 | QVQLQQSGAELARPGASVRMSCKASGYTFTSYTMNWVKQRPGQGLEWIGFINPDSDYTTYDQK FKDKATLTADSSSTAYMQLSSLTYDDSAVYYCTRHSYGNYGDYWGQGTTLTVSSASTKGPSVF PLAPSSKSTSGGTAALGCLVKDYFPEPVTVSWNSGALTSGVHTFPAVLQSSGLYSLSSVVTVPSS SLGTQTYICNVNHKPSNTKVDKKVEPKSCDKTHTCPPCPAPELLGGPSVFLFPPKPKDTLMISRTP EVTCVVVDVSHEDPEVKFNWYVDGVEVHNAKTKPREEQYNSTYRVVSVLTVLHQDWLNGKEYK CKVSNKALPAPIEKTISKAKGQPREPQVYTLPPSRDELTKNQVSLTCLVKGFYPSDIAVEWESNGQ PENNYKTTPPVLDSDGSFFLYSKLTVDKSRWQQGNVFSCSVMHEALHNHYTQKSLSLSPGK |
| 233 | 4M2-D5 VL-C$_K$ | DIVLTQSPKFLLVSAGDRVTITCKASQSVTNDVAWYQQKPGQSPKLLIYYASSRYTGVPDRFTGS GFGTDFTFTINTVQAEDLAVYFCQQDYSSPYTFGGGTKLEIKRTVAAPSVFIFPPSDEQLKSGTAS VVCLLNNFYPREAKVQWKVDNALQSGNSQESVTEQDSKDSTYSLSSTLTLSKADYEKHKVYACE VTHQGLSSPVTKSFNRGEC |
| 234 | 4M2-A8 VH-CH1-CH2-CH3 | QVQLQQSGADLARPGASVKMSCKASGYTFIDYTVHWVKQRPGQGLEWIGFINPSNDYTSYNQKF KDKASLTADTSSTTAYMQLSSLTSDDSAVYYCARHSYGNYGDYWGQGTSVTVSSASTKGPSVFP LAPSSKSTSGGTAALGCLVKDYFPEPVTVSWNSGALTSGVHTFPAVLQSSGLYSLSSVVTVPSSS LGTQTYICNVNHKPSNTKVDKKVEPKSCDKTHTCPPCPAPELLGGPSVFLFPPKPKDTLMISRTPE VTCVVVDVSHEDPEVKFNWYVDGVEVHNAKTKPREEQYNSTYRVVSVLTVLHQDWLNGKEYKC KVSNKALPAPIEKTISKAKGQPREPQVYTLPPSRDELTKNQVSLTCLVKGFYPSDIAVEWESNGQP ENNYKTTPPVLDSDGSFFLYSKLTVDKSRWQQGNVFSCSVMHEALHNHYTQKSLSLSPGK |
| 235 | 4M2-A8 VL-C$_K$ | DIVMTQAPKFLLVSAGDRVTITCKASQSVTNGVAWYQQKPGQSPKLLIYYASNRYTGVPDRFTGS GFGTDFTFTISTVQAEDLAVYFCQQDYSSPYTFGGGTKLEIKRTVAAPSVFIFPPSDEQLKSGTAS VVCLLNNFYPREAKVQWKVDNALQSGNSQESVTEQDSKDSTYSLSSTLTLSKADYEKHKVYACE VTHQGLSSPVTKSFNRGEC |
| 236 | 9M2-C12 VH-CH1-CH2-CH3 | QVQLQQSGAELVKPGASVRLSCKASGYTFTSYWMHWVRQRPGLGLEWIGEIDPSDSYTNCNQR FKGKATLTVDKSSSTAYTQLSSLTSEDSAVYYCARWAYGPYAMDYWGQGTSVTVSSASTKGPSV FPLAPSSKSTSGGTAALGCLVKDYFPEPVTVSWNSGALTSGVHTFPAVLQSSGLYSLSSVVTVPS SSLGTQTYICNVNHKPSNTKVDKKVEPKSCDKTHTCPPCPAPELLGGPSVFLFPPKPKDTLMISRT PEVTCVVVDVSHEDPEVKFNWYVDGVEVHNAKTKPREEQYNSTYRVVSVLTVLHQDWLNGKEY KCKVSNKALPAPIEKTISKAKGQPREPQVYTLPPSRDELTKNQVSLTCLVKGFYPSDIAVEWESNG QPENNYKTTPPVLDSDGSFFLYSKLTVDKSRWQQGNVFSCSVMHEALHNHYTQKSLSLSPGK |
| 237 | 9M2-C12 VL-C$_K$ | DIVMTQTPLSLPVSLGDQASISCRSSQSLVHSNGNTYLHWYLQKPGQSPKLLIYKVSNRFSGVPD RFSGSGSGTDFTLKISRVEAEDLGVYFCSQSTHVPWTFGGGTKLEIKRTVAAPSVFIFPPSDEQLK SGTASVVCLLNNFYPREAKVQWKVDNALQSGNSQESVTEQDSKDSTYSLSSTLTLSKADYEKHK VYACEVTHQGLSSPVTKSFNRGEC |
| 238 | 13D5p VH-CH1-CH2-CH3 | QVQLQQSGAELVRPGTSVKISCKASGYTFTNYWLGWVKQRPGHGLEWIGDIYPGGGYTNYNEKF KGKATLTADTSSSTAYMQLSSLTSEDSAVYFCARGGYYYGSSWYFDVWGAGTTVTVSSASTKGP SVFPLAPSSKSTSGGTAALGCLVKDYFPEPVTVSWNSGALTSGVHTFPAVLQSSGLYSLSSVVTV PSSSLGTQTYICNVNHKPSNTKVDKKVEPKSCDKTHTCPPCPAPELLGGPSVFLFPPKPKDTLMIS RTPEVTCVVVDVSHEDPEVKFNWYVDGVEVHNAKTKPREEQYNSTYRVVSVLTVLHQDWLNGK EYKCKVSNKALPAPIEKTISKAKGQPREPQVYTLPPSRDELTKNQVSLTCLVKGFYPSDIAVEWES NGQPENNYKTTPPVLDSDGSFFLYSKLTVDKSRWQQGNVFSCSVMHEALHNHYTQKSLSLSPGK |
| 239 | 13D5p VL-C$_K$ | DVLMTQTPLSLPVSLGDQASISCRSSQSIVHSNGNTYLEWYLQKPGQSPKLLIYKVSNRFSGVPD RFSGSGSGTDFTLKISRVEAEDLGVYYCFQGSHVPPTFGGGTKLEIKRTVAAPSVFIFPPSDEQLK SGTASVVCLLNNFYPREAKVQWKVDNALQSGNSQESVTEQDSKDSTYSLSSTLTLSKADYEKHK VYACEVTHQGLSSPVTKSFNRGEC |
| 240 | 13D5-1 VH-CH1-CH2-CH3 | QVQLQQSGAELVRPGTSVKISCKASGYTFTNYWLGWVKQRPGHGLEWIGDIYPGGGYTNYNEKF KGKATLTADTSSSTAYMQLSSLTSEDSAVYFCVRSGYYYGSSWYFDVWGAGTTVTVSSASTKGP SVFPLAPSSKSTSGGTAALGCLVKDYFPEPVTVSWNSGALTSGVHTFPAVLQSSGLYSLSSVVTV PSSSLGTQTYICNVNHKPSNTKVDKKVEPKSCDKTHTCPPCPAPELLGGPSVFLFPPKPKDTLMIS RTPEVTCVVVDVSHEDPEVKFNWYVDGVEVHNAKTKPREEQYNSTYRVVSVLTVLHQDWLNGK EYKCKVSNKALPAPIEKTISKAKGQPREPQVYTLPPSRDELTKNQVSLTCLVKGFYPSDIAVEWES NGQPENNYKTTPPVLDSDGSFFLYSKLTVDKSRWQQGNVFSCSVMHEALHNHYTQKSLSLSPGK |
| 241 | 13D5-1 VL-C$_K$ | DVLMTQTPLSLPVSLGDQASISCRSSQSIVHSSGNTYLEWYLQKPDQSPKLLIYKVSNRFSGVPDR FSGSGSGTDFTLKISRVEAEDLGVYYCFQGSHVPPTFGGGTKLEIKRTVAAPSVFIFPPSDEQLKS GTASVVCLLNNFYPREAKVQWKVDNALQSGNSQESVTEQDSKDSTYSLSSTLTLSKADYEKHKV YACEVTHQGLSSPVTKSFNRGEC |
| 242 | 13D5-13 VH-CH1-CH2-CH3 | QVQLQQSGAELVRPGTSVKISCKASGYTFTNYWLGWVKQRPGHGLEWIGDIYPGGGYTNYNEKF KGKATLTADISSSTAYMQLSSLTSEDSADYFCVRGGYYYGSSWYFDVWGAGTTVTVSSASTKGP SVFPLAPSSKSTSGGTAALGCLVKDYFPEPVTVSWNSGALTSGVHTFPAVLQSSGLYSLSSVVTV PSSSLGTQTYICNVNHKPSNTKVDKKVEPKSCDKTHTCPPCPAPELLGGPSVFLFPPKPKDTLMIS RTPEVTCVVVDVSHEDPEVKFNWYVDGVEVHNAKTKPREEQYNSTYRVVSVLTVLHQDWLNGK EYKCKVSNKALPAPIEKTISKAKGQPREPQVYTLPPSRDELTKNQVSLTCLVKGFYPSDIAVEWES NGQPENNYKTTPPVLDSDGSFFLYSKLTVDKSRWQQGNVFSCSVMHEALHNHYTQKSLSLSPGK |
| 243 | 13D5-13 VL-C$_K$ | DVLMTQTPLSLPVSLGDQASISCRSSQSTVHSIGNTYLEWYLQKPGQSPKLLIYKVSNRFSGVPDR FSGSESGTDFTLKISRVEAEDLGVYYCFQGSHVPPTFGGGTKLEIKRTVAAPSVFIFPPSDEQLKS GTASVVCLLNNFYPREAKVQWKVDNALQSGNSQESVTEQDSKDSTYSLSSTLTLSKADYEKHKV YACEVTHQGLSSPVTKSFNRGEC |

-continued

| SEQ ID NO: | DESCRIPTION | SEQUENCE |
|---|---|---|
| 244 | 4M2-C12/V4H1/V4H2 heavy chain CDR1 consensus | GYX1ITSDYA<br>wherein X1 = S or T |
| 245 | 4M2-C12/V4H1/V4H2 light chain CDR2 consensus | X2X3S<br>wherein X2 = A or D; X3 = T or A |
| 246 | 13D5p derived heavy chain CDR3 consensus | X4RX5GYYYGSSWYFDV<br>wherein X4 = V or A; X5 = G or S |
| 247 | 13D5p derived light chain CDR1 consensus | QSX6VHSX7GNTY<br>wherein X6 = I or T; X7 = N, S or I |
| 248 | 4M2-C12 mIgG2a HC | EVKLVESGPGLVKPSQSLSLTCTVTGYSITSDYAWNWIRQFPGNKLEWMGYITYSGNISYNPSLR<br>SRISITRDTSKNQFFLQLNSVTPEDTATYSCARSLYYPWYFDVWGAGTTVTVSSAKTTAPSVYPLA<br>PVCGDTTGSSVTLGCLVKGYFPEPVTLTWNSGSLSSGVHTFPAVLQSDLYTLSSSVTVTSSTWPS<br>QSITCNVAHPASSTKVDKKIEPRGPTIKPCPPCKCPAPNLLGGPSVFIFPPKIKDVLMISLSPIVTCV<br>VVDVSEDDPDVQISWFVNNVEVHTAQTQTHREDYNSTLRVVSALPIQHQDWMSGKEFKCKVNNK<br>DLPAPIERTISKPKGSVRAPQVYVLPPPEEEMTKKQVTLTCMVTDFMPEDIYVEWTNNGKTELNYK<br>NTEPVLDSDGSYFMYSKLRVEKKNWVERNSYSCSVVHEGLHNHHTTKSFSRTPGK |
| 249 | 4M2-C12 mIaG2a LALA PG HC | EVKLVESGPGLVKPSQSLSLTCTVTGYSITSDYAWNWIRQFPGNKLEWMGYITYSGNISYNPSLR<br>SRISITRDTSKNQFFLQLNSVTPEDTATYSCARSLYYPWYFDVWGAGTTVTVSSAKTTAPSVYPLA<br>PVCGDTTGSSVTLGCLVKGYFPEPVTLTWNSGSLSSGVHTFPAVLQSDLYTLSSSVTVTSSTWPS<br>QSITCNVAHPASSTKVDKKIEPRGPTIKPCPPCKCPAPNAAGGPSVFIFPPKIKDVLMISLSPIVTCV<br>VVDVSEDDPDVQISWFVNNVEVHTAQTQTHREDYNSTLRVVSALPIQHQDWMSGKEFKCKVNNK<br>DLGAPIERTISKPKGSVRAPQVYVLPPPEEEMTKKQVTLTCMVTDFMPEDIYVEWTNNGKTELNY<br>KNTEPVLDSDGSYFMYSKLRVEKKNWVERNSYSCSVVHEGLHNHHTTKSFSRTPGK |
| 250 | 4M2-C12 LC | DIVITQTPAILSTSPGEKVTMTCRASSSVGYIHWYQQKPGSSPKPWIYATSNLASGVPARFSGSGS<br>GTSNSLTITRVEAEDAATYYCQQWSSYPPITFGGGTKLEVKRADAAPTVSIFPPSSEQLTSGGASV<br>VCFLNNFYPKDINVKWKIDGSERQNGVLNSWTDQDSKDSTYSMSSTLTLTKDEYERHNSYTCEA<br>THKTSTSPIVKSFNRNEC |
| 251 | mIgG2a CH1 | AKTTAPSVYPLAPVCGDTTGSSVTLGCLVKGYFPEPVTLTWNSGSLSSGVHTFPAVLQSDLYTLS<br>SSVTVTSSIWPSQSITCNVAHPASSTKVDKKI |
| 252 | mIgG2a Hinge | EPRGPTIKPCPPCKCP |
| 253 | mIgG2a CH2 | APNLLGGPSVFIFPPKIKDVLMISLSPIVTCVVVDSEDDPDVQISWFVNNVEVHTAQTQTHREDYN<br>STLRVVSALPIQHQDWMSGKEFKCKVNNKDLPAPIERTISKPK |
| 254 | mIgG2a CH2 LALA PG | APNAAGGPSVFIFPPKIKDVLMISLSPIVTCVVVDSEDDPDVQISWFVNNVEVHTAQTQTHREDY<br>NSTLRVVSALPIQHQDWMSGKEFKCKVNNKDLGAPIERTISKPK |
| 255 | mIgG2a CH3 | GSVRAPQVYVLPPPEEEMTKKQVTLTCMVTDFMPEDIYVEWTNNGKTELNYKNTEPVLDSDGSY<br>FMYSKLRVEKKNWVERNSYSCSVVHEGLHNHHTTKSFSRTPGK |
| 256 | Mouse Ig gamma-2A chain C region, A allele | AKTTAPSVYPLAPVCGDTTGSSVTLGCLVKGYFPEPVTLTWNSGSLSSGVHTFPAVLQSDLYTLS<br>SSVTVTSSIWPSQSITCNVAHPASSTKVDKKIEPRGPTIKPCPPCKCPAPNLLGGPSVFIFPPKIKD<br>VLMISLSPIVTCVVVDSEDDPDVQISWFVNNVEVHTAQTQTHREDYNSTLRVVSALPIQHQDWM<br>SGKEFKCKVNNKDLPAPIERTISKPKGSVRAPQVYVLPPPEEEMTKKQVTLTCMVTDFMPEDIYVE<br>WTNNGKTELNYKNTEPVLDSDGSYFMYSKLRVEKKNWVERNSYSCSVVHEGLHNHHTTKSFSR<br>TPGK |
| 257 | mIgG2a CH2, CH3 LALA PG | APNAAGGPSVFIFPPKIKDVLMISLSPIVTCVVVDSEDDPDVQISWFVNNVEVHTAQTQTHREDY<br>NSTLRVVSALPIQHQDWMSGKEFKCKVNNKDLGAPIERTISKPKGSVRAPQVYVLPPPEEEMTKK<br>QVTLTCMVTDFMPEDIYVEWTNNGKTELNYKNTEPVLDSDGSYFMYSKLRVEKKNWVERNSYSC<br>SVVHEGLHNHHTTKSFSRTPGK |
| 258 | 4M2-C12 mIgG2a NQ HC | EVKLVESGPGLVKPSQSLSLTCTVTGYSITSDYAWNWIRQFPGNKLEWMGYITYSGNISYNPSLR<br>SRISITRDTSKNQFFLQLNSVTPEDTATYSCARSLYYPWYFDVWGAGTTVTVSSAKTTAPSVYPLA<br>PVCGDTTGSSVTLGCLVKGYFPEPVTLTWNSGSLSSGVHTFPAVLQSDLYTLSSSVTVTSSTWPS<br>QSITCNVAHPASSTKVDKKIEPRGPTIKPCPPCKCPAPNLLGGPSVFIFPPKIKDVLMISLSPIVTCV<br>VVDVSEDDPDVQISWFVNNVEVHTAQTQTHREDYQSTLRVVSALPIQHQDWMSGKEFKCKVNN<br>KDLPAPIERTISKPKGSVRAPQVYVLPPPEEEMTKKQVTLTCMVTDFMPEDIYVEWTNNGKTELNY<br>KNTEPVLDSDGSYFMYSKLRVEKKNWVERNSYSCSVVHEGLHNHHTTKSFSRTPGK |
| 259 | mIgG2a CH2 NQ | APNLLGGPSVFIFPPKIKDVLMISLSPIVTCVVVDSEDDPDVQISWFVNNVEVHTAQTQTHREDY<br>QSTLRVVSALPIQHQDWMSGKEFKCKVNNKDLPAPIERTISKPK |
| 260 | mIgG2a CH2, CH3 NQ | APNLLGGPSVFIFPPKIKDVLMISLSPIVTCVVVDSEDDPDVQISWFVNNVEVHTAQTQTHREDY<br>QSTLRVVSALPIQHQDWMSGKEFKCKVNNKDLPAPIERTISKPKGSVRAPQVYVLPPPEEEMTKK<br>QVTLTCMVTDFMPEDIYVEWTNNGKTELNYKNTEPVLDSDGSYFMYSKLRVEKKNWVERNSYSC<br>SVVHEGLHNHHTTKSFSRTPGK |
| 261 | Mouse IGHG1 | AKTTPPSVYPLAPGSAAQTNSMVTLGCLVKGYFPEPVTVTWNSGSLSSGVHTFPAVLQSDLYTLS<br>SSVTVPSSTWPSETVTCNVAHPASSTKVDKKIVPRDCGCKPCICTVPEVSSVFIFPPKPKDVLTITL<br>TPKVTCVVVDISKDDPEVQFSWFVDDVEVHTAQTQPREEQFNSTFRSVSELPIMHQDWLNGKEF<br>KCRVNSAAFPAPIEKTISKTKGRPKAPQVYTIPPPKEQMAKDKVSLTCMITDFFPEDITVEWQWNG<br>QPAENYKNTQPIMNTNGSYFVYSKLNVQKSNWEAGNTFTCSVLHEGLHNHHTEKSLSHSPGK |
| 262 | mIgG1 CH1 | AKTTPPSVYPLAPGSAAQTNSMVTLGCLVKGYFPEPVTVTWNSGSLSSGVHTFPAVLQSDLYTLS<br>SSVTVPSSTWPSETVTCNVAHPASSTKVDKKI |

-continued

Sequences

| SEQ ID NO: | DESCRIPTION | SEQUENCE |
|---|---|---|
| 263 | mIgG1 Hinge | VPRDCGCKPCICT |
| 264 | mIgG1 CH2 | VPEVSSVFIFPPKPKDVLTITLTPKVTCVVVDISKDDPEVQFSWFVDDVEVHTAQTQPREEQFNST FRSVSELPIMHQDWLNGKEFKCRVNSAAFPAPIEKTISKTK |
| 265 | mIgG1 CH3 | GRPKAPQVYTIPPPKEQMAKDKVSLTCMITDFFPEDITVEWQWNGQPAENYKNTQPIMNTNGSYF VYSKLNVQKSNWEAGNTFTCSVLHEGLHNHHTEKSLSHSPGK |
| 266 | 4M2-C12 mIgG1 HC | EVKLVESGPGLVKPSQSLSLTCTVTGYSITSDYAWNWIRQFPGNKLEWMGYITYSGNISYNPSLR SRISITRDTSKNQFFLQLNSVTPEDTATYSCARSLYYPWYFDVWGAGTTVTVSSAKTTPPSVYPLA PGSAAQTNSMVTLGCLVKGYFPEPVTVTWNSGSLSSGVHTFPAVLQSDLYTLSSSVTVPSSTWP SETVTCNVAHPASSTKVDKKIVPRDCGCKPCICTVPEVSSVFIFPPKPKDVLTITLTPKVTCVVVDIS KDDPEVQFSWFVDDVEVHTAQTQPREEQFNSTFRSVSELPIMHQDWLNGKEFKCRVNSAAFPA PIEKTISKTKGRPKAPQVYTIPPPKEQMAKDKVSLTCMITDFFPEDITVEWQWNGQPAENYKNTQP IMNTNGSYFVYSKLNVQKSNWEAGNTFTCSVLHEGLHNHHTEKSLSHSPGK |
| 267 | IGN175A HC | QVQLQQSGAELMKPGASVKISCKATGYTFSTHWIEWVKQRPGHGLEWIGEILPGSGSTSYNEKF KGKATFTADTSSNTAYMQLSSLTSEDSAVYYCARWLLYYYAMDYWGQGTSVTVSSASTKGPSVF PLAPSSKSTSGGTAALGCLVKDYFPEPVTVSWNSGALTSGVHTFPAVLQSSGLYSLSSVVTVPSS SLGTQTYICNVNHKPSNTKVDKKVEPKSCDKTHTCPPCPAPELLGGPSVFLFPPKPKDTLMISRTP EVTCVVVDVSHEDPEVKFNWYVDGVEVHNAKTKPREEQYNSTYRVVSVLTVLHQDWLNGKEYK CKVSNKALPAPIEKTISKAKGQPREPQVYTLPPSRDELTKNQVSLTCLVKGFYPSDIAVEWESNGQ PENNYKTTPPVLDSDGSFFLYSKLTVDKSRWQQGNVFSCSVMHEALHNHYTQKSLSLSPGK |
| 268 | IGN175A LC | DVLMTQTPLSLPVSLGDQASISCRSSQSIVHSNGNTYLEWYLQKPGQSPKLLIYKLSNRFSGVPDR FSGSGSGTDFTLKISRVEAEDLGVYYCFQGSHFPYTFGGGTKLEIKRTVAAPSVFIFPPSDEQLKS GTASVVCLLNNFYPREAKVQWKVDNALQSGNSQESVTEQDSKDSTYSLSSTLTLSKADYEKHKV YACEVTHQGLSSPVTKSFNRGEC |
| 269 | VSTB112 HC | QVQLVQSGAEVKKPGSSVKVSCKASGGTFSSYAISWVRQAPGQGLEWMGGIIPIFGTANYAQKF QGRVTITADESTSTAYMELSSLRSEDTAVYYCARSSYGWSYEFDYWGQGTLVTVSSASTKGPSV FPLAPSSKSTSGGTAALGCLVKDYFPEPVTVSWNSGALTSGVHTFPAVLQSSGLYSLSSVVTVPS SSLGTQTYICNVNHKPSNTKVDKKVEPKSCDKTHTCPPCPAPELLGGPSVFLFPPKPKDTLMISRT PEVTCVVVDVSHEDPEVKFNWYVDGVEVHNAKTKPREEQYNSTYRVVSVLTVLHQDWLNGKEY KCKVSNKALPAPIEKTISKAKGQPREPQVYTLPPSRDELTKNQVSLTCLVKGFYPSDIAVEWESNG QPENNYKTTPPVLDSDGSFFLYSKLTVDKSRWQQGNVFSCSVMHEALHNHYTQKSLSLSPGK |
| 270 | VSTB112 LC | DIQMTQSPSSLSASVGDRVTITCRASQSIDTRLNWYQQKPGKAPKLLIYSASSLQSGVPSRFSGS GSGTDFTLTISSLQPEDFATYYCQQSAYNPITFGQGTKVEIKRTVAAPSVFIFPPSDEQLKSGTASV VCLLNNFYPREAKVQWKVDNALQSGNSQESVTEQDSKDSTYSLSSTLTLSKADYEKHKVYACEV THQGLSSPVTKSFNRGEC |
| 271 | VSTB112 major epitope 1 | PVDKGHDVTF |
| 272 | VSTB112 major epitope 2 | RRPIRNLTFQDL |
| 273 | VSTB112 minor epitope 1 | TWYRSSRGEVQTCS |
| 274 | VSTB112 minor epitope 2 | EIRHHHSEHRVHGAMEL |
| 275 | IGN175A epitope | FKVATPYSLYVCPEGQNVTLTCRLLGPVDKGH |
| 276 | V4-C1 heavy chain variable region | QVQLQESGPGLVKPSDTLSLTCTVSGYSITSDYAWNWIRQTPGKGLEWIGYITYSGYISYNPSLRS RVTISRDTSKNQFSLKLSSVTAADTAVYSCARALYYPWYFDVWGTGTTVTVSS |
| 277 | V4-C1 heavy chain CDR2 | ITYSGYI |
| 278 | V4-C1, V4-C9, V4-C24, V4-C26, V4-C27, V4-C28, V4-C30, V4-C31 heavy chain CDR3 | ARALYYPWYFDV |
| 279 | V4-C1, V4-C9 heavy chain FR2 | WNWIRQTPGKGLEWIGY |
| 280 | V4-C1, V4-C9 heavy chain FR3 | SYNPSLRSRVTISRDTSKNQFSLKLSSVTAADTAVYSC |
| 281 | V4-C1, V4-C9, V4-C24, V4-C26, V4-C27, V4-C28, V4-C30, V4-C31 heavy chain FR4 | WGTGTTVTVSS |
| 282 | V4-C1 light chain variable region | EIVITQSPATLSLSPGERATLSCRASSSVGYIHWYQQKPGQAPRPLIYATSNRATGIPARFSGSGS GTDNTLTISSLEPEDSAVYYCQQWSSYPPITFGGGTKLEVK |
| 283 | V4-C1, V4-C9, V4-C24, V4-C27, V4-C28, V4-C30, V4-C31 light chain FR2 | IHWYQQKPGQAPRPLIY |
| 284 | V4-C1, V4-C9, V4-C26, V4-C27 light chain FR3 | NRATGIPARFSGSGSGTDNTLTISSLEPEDSAVYYC |
| 285 | V4-C9 heavy chain variable region | QVQLQESGPGLVKPSDTLSLTCTVSGYSITSDYAWNWIRQTPGKGLEWIGYITYSGYVSYNPSLR SRVTISRDTSKNQFSLKLSSVTAADTAVYSCARALYYPWYFDVWGTGTTVTVSS |

| SEQ ID NO: | DESCRIPTION | SEQUENCE |
|---|---|---|
| 286 | V4-C9 heavy chain CDR2 | ITYSGYV |
| 287 | V4-C9 light chain variable region | EIVLTQSPATLSLSPGERATLSCRASSSVGYIHWYQQKPGQAPRPLIYATSNRATGIPARFSGSGS GTDNTLTISSLEPEDSAVYYCQQWSSYPPITFGGGTKLEVK |
| 288 | V4-C9, C26, V4-C27, V4-C28, V4-C30, V4-C31 light chain FR1 | V4-C24, V4- EIVLTQSPATLSLSPGERATLSCRAS |
| 289 | V4-C24, V4-C26, V4-C27, V4-C28, V4-C30, V4-C31 heavy chain variable region | QVQLQESGPGLVKPSDTLSLTCTVSGYSITSDYTWNWIRQTPGKGLEWIGHITYSGSVSYNPSLR SRVTISRDTSKNQFSLKLSSVTAADTATYSCARALYYPWYFDVWGTGTTVTVSS |
| 290 | V4-C24, V4-C26, V4-C27, V4-C28, V4-C30, V4-C31 heavy chain CDR1 | GYSITSDYT |
| 291 | V4-C24, V4-C26, V4-C27, V4-C28, V4-C30, V4-C31 heavy chain CDR2 | ITYSGSV |
| 292 | V4-C24, V4-C26, V4-C27, V4-C28, V4-C30, V4-C31 heavy chain FR2 | WNWIRQTPGKGLEWIGH |
| 293 | V4-C24, V4-C26, V4-C27, V4-C28, V4-C30, V4-C31 heavy chain FR3 | SYNPSLRSRVTISRDTSKNQFSLKLSSVTAADTATYSC |
| 294 | V4-C24 light chain variable region | EIVLTQSPATLSLSPGERATLSCRASSSVGYIHWYQQKPGQAPRPLIYTTSYRATGIPARFSGSGS GTDNTLTISSLEPEDSAVYYCQQWSSYPPITFGGGTKLEVK |
| 295 | V4-C24, V4-C26 light chain CDR2 | TTS |
| 296 | V4-C24, V4-C28, V4-C30 light chain FR3 | YRATGIPARFSGSGSGTDNTLTISSLEPEDSAVYYC |
| 297 | V4-C26 light chain variable region | EIVLTQSPATLSLSPGERATLSCRASSSVGYIHWYQQKPGQAPRPIIYTTSNRATGIPARFSGSGS GTDNTLTISSLEPEDSAVYYCQQWSSYPPITFGGGTKLEVK |
| 298 | V4-C26 light chain FR2 | IHWYQQKPGQAPRPIIY |
| 299 | V4-C27 light chain variable region | EIVLTQSPATLSLSPGERATLSCRASSSVGYIHWYQQKPGQAPRPLIYATYNRATGIPARFSGSGS GTDNTLTISSLEPEDSAVYYCQQWSSYPPITFGGGTKLEVK |
| 300 | V4-C27, V4-C30, V4-C31 light chain CDR2 | ATY |
| 301 | V4-C28 light chain variable region | EIVLTQSPATLSLSPGERATLSCRASSSVGYIHWYQQKPGQAPRPLIYATSYRATGIPARFSGSGS GTDNTLTISSLEPEDSAVYYCQQWSSYPPITFGGGTKLEVK |
| 302 | V4-C30 light chain variable region | EIVLTQSPATLSLSPGERATLSCRASSSVGYIHWYQQKPGQAPRPLIYATYYRATGIPARFSGSGS GTDNTLTISSLEPEDSAVYYCQQWSSYPPITFGGGTKLEVK |
| 303 | V4-C31 light chain variable region | EIVLTQSPATLSLSPGERATLSCRASSSVGYIHWYQQKPGQAPRPLIYATYYRTTGIPARFSGSGS GTDNTLTISSLEPEDSAVYYCQQWSSYPPITFGGGTKLEVK |
| 304 | V4-C31 light chain FR3 | YRTTGIPARFSGSGSGTDNTLTISSLEPEDSAVYYC |
| 305 | 4M2-C12 derived heavy chain CDR1 consensus | GYX$_8$ITSDYX3 wherein X$_8$ = S or T; X$_9$ = T or A |
| 306 | 4M2-C12 derived heavy chain CDR2 consensus | ITYSGX$_{10}$X$_{11}$ wherein X$_{10}$ = S, N or Y; X$_{11}$ = V or I |
| 307 | 4M2-C12 derived heavy chain CDR3 consensus | ARX$_{12}$LYYPWYFDV wherein X$_{12}$ = A or S |
| 308 | 4M2-C12 derived light chain CDR2 consensus | X$_{13}$X$_{14}$X$_{15}$ wherein X$_{13}$ = A, T or D; X$_{14}$ = T or A; X$_{15}$ = S or Y |
| 309 | C24/C26/C27 light chain CDR2 consensus | X$_{16}$TX$_{17}$ wherein X$_{16}$ = T or A; X$_{17}$ = S or Y |

-continued

Sequences

| SEQ ID NO: | DESCRIPTION | SEQUENCE |
|---|---|---|
| 310 | C24/C26/C27 light chain variable region consensus | EIVLTQSPATLSLSPGERATLSCRASSSVGYIHWYQQKPGQAPRPX17YX18TX19X20YNRATGIPAR FSGSGSGTDNTLTISSLEPEDSAVYYCQQWSSYPPITFGGGTKLEVK<br><br>wherein $X_{17}$ = L or I; $X_{18}$ = T or A; $X_{19}$ = S or Y; $X_{20}$ = N or Y |
| 311 | V4-C1 VH-CH1-CH2-CH3 | QVQLQESGPGLVKPSDTLSLTCTVSGYSITSDYAWNWIRQTPGKGLEWIGYITYSGYISYNPSLRS RVTISRDTSKNQFSLKLSSVTAADTAVYSCARALYYPWYFDVWGTGTTVTVSSASTKGPSVFPLA PSSKSTSGGTAALGCLVKDYFPEPVTVSWNSGALTSGVHTFPAVLQSSGLYSLSSVVTVPSSSLG TQTYICNVNHKPSNTKVDKKVEPKSCDKTHTCPPCPAPELLGGPSVFLFPPKPKDTLMISRTPEVT CVVVDVSHEDPEVKFNWYVDGVEVHNAKTKPREEQYNSTYRVVSVLTVLHQDWLNGKEYKCKV SNKALPAPIEKTISKAKGQP REPQVYTLPPSRDELTKNQVSLTCLVKGFYPSDIAVEWESNGQPEN NYKTTPPVLDSDGSFFLYSKLTVDKSRWQQGNVFSCSVMHEALHNHYTQKSLSLSPGK |
| 312 | V4-C1 VL-$C_K$ | EIVLTQSPATLSLSPGERATLSCRASSSVGYIHWYQQKPGQAPRPLIYATSNRATGIPARFSGSGS GTDNTLTISSLEPEDSAVYYCQQWSSYPPITFGGGTKLEVKRTVAAPSVFIFPPSDEQLKSGTASV VCLLNNFYPREAKVQWKVDNALQSGNSQESVTEQDSKDSTYSLSSTLTLSKADYEKHKVYACEV THQGLSSPVTKSFNRGEC |
| 313 | V4-C9 VH-CH1-CH2-CH3 | QVQLQESGPGLVKPSDTLSLTCTVSGYSITSDYAWNWIRQTPGKGLEWIGYITYSGYVSYNPSLR SRVTISRDTSKNQFSLKLSSVTAADTAVYSCARALYYPWYFDVWGTGTTVTVSSASTKGPSVFPL APSSKSTSGGTAALGCLVKDYFPEPVTVSWNSGALTSGVHTFPAVLQSSGLYSLSSVVTVPSSSL GTQTYICNVNHKPSNTKVDKKVEPKSCDKTHTCPPCPAPELLGGPSVFLFPPKPKDTLMISRTPEV TCVVVDVSHEDPEVKFNWYVDGVEVHNAKTKPREEQYNSTYRVVSVLTVLHQDWLNGKEYKCK VSNKALPAPIEKTISKAKGQP REPQVYTLPPSRDELTKNQVSLTCLVKGFYPSDIAVEWESNGQPE NNYKTTPPVLDSDGSFFLYSKLTVDKSRWQQGNVFSCSVMHEALHNHYTQKSLSLSPGK |
| 314 | V4-C9 VL-$C_K$ | EIVLTQSPATLSLSPGERATLSCRASSSVGYIHWYQQKPGQAPRPLIYATSNRATGIPARFSGSGS GTDNTLTISSLEPEDSAVYYCQQWSSYPPITFGGGTKLEVKRTVAAPSVFIFPPSDEQLKSGTASV VCLLNNFYPREAKVQWKVDNALQSGNSQESVTEQDSKDSTYSLSSTLTLSKADYEKHKVYACEV THQGLSSPVTKSFNRGEC |
| 315 | V4-C24/C26/C27/C28/C30/C31 VH-CH1-CH2-CH3 | QVQLQESGPGLVKPSDTLSLTCTVSGYSITSDYTWNWIRQTPGKGLEWIGHITYSGSVSYNPSLR SRVTISRDTSKNQFSLKLSSVTAADTATYSCARALYYPWYFDVWGTGTTVTVSSASTKGPSVFPL APSSKSTSGGTAALGCLVKDYFPEPVTVSWNSGALTSGVHTFPAVLQSSGLYSLSSVVTVPSSSL GTQTYICNVNHKPSNTKVDKKVEPKSCDKTHTCPPCPAPELLGGPSVFLFPPKPKDTLMISRTPEV TCVVVDVSHEDPEVKFNWYVDGVEVHNAKTKPREEQYNSTYRVVSVLTVLHQDWLNGKEYKCK VSNKALPAPIEKTISKAKGQP REPQVYTLPPSRDELTKNQVSLTCLVKGFYPSDIAVEWESNGQPE NNYKTTPPVLDSDGSFFLYSKLTVDKSRWQQGNVFSCSVMHEALHNHYTQKSLSLSPGK |
| 316 | V4-C24 VL-$C_K$ | EIVLTQSPATLSLSPGERATLSCRASSSVGYIHWYQQKPGQAPRPLIYTTSYRATGIPARFSGSGS GTDNTLTISSLEPEDSAVYYCQQWSSYPPITFGGGTKLEVKRTVAAPSVFIFPPSDEQLKSGTASV VCLLNNFYPREAKVQWKVDNALQSGNSQESVTEQDSKDSTYSLSSTLTLSKADYEKHKVYACEV THQGLSSPVTKSFNRGEC |
| 317 | V4-C26 VL-$C_K$ | EIVLTQSPATLSLSPGERATLSCRASSSVGYIHWYQQKPGQAPRPIIYTTSNRATGIPARFSGSGS GTDNTLTISSLEPEDSAVYYCQQWSSYPPITFGGGTKLEVKRTVAAPSVFIFPPSDEQLKSGTASV VCLLNNFYPREAKVQWKVDNALQSGNSQESVTEQDSKDSTYSLSSTLTLSKADYEKHKVYACEV THQGLSSPVTKSFNRGEC |
| 183 | V4-C27 VL-$C_K$ | EIVLTQSPATLSLSPGERATLSCRASSSVGYIHWYQQKPGQAPRPLIYATYNRATGIPARFSGSGS GTDNTLTISSLEPEDSAVYYCQQWSSYPPITFGGGTKLEVKRTVAAPSVFIFPPSDEQLKSGTASV VCLLNNFYPREAKVQWKVDNALQSGNSQESVTEQDSKDSTYSLSSTLTLSKADYEKHKVYACEV THQGLSSPVTKSFNRGEC |
| 319 | V4-C28 VL-$C_K$ | EIVLTQSPATLSLSPGERATLSCRASSSVGYIHWYQQKPGQAPRPLIYATSYRATGIPARFSGSGS GTDNTLTISSLEPEDSAVYYCQQWSSYPPITFGGGTKLEVKRTVAAPSVFIFPPSDEQLKSGTASV VCLLNNFYPREAKVQWKVDNALQSGNSQESVTEQDSKDSTYSLSSTLTLSKADYEKHKVYACEV THQGLSSPVTKSFNRGEC |
| 320 | V4-C30 VL-$C_K$ | EIVLTQSPATLSLSPGERATLSCRASSSVGYIHWYQQKPGQAPRPLIYATYYRATGIPARFSGSGS GTDNTLTISSLEPEDSAVYYCQQWSSYPPITFGGGTKLEVKRTVAAPSVFIFPPSDEQLKSGTASV VCLLNNFYPREAKVQWKVDNALQSGNSQESVTEQDSKDSTYSLSSTLTLSKADYEKHKVYACEV THQGLSSPVTKSFNRGEC |
| 321 | V4-C31 VL-$C_K$ | EIVLTQSPATLSLSPGERATLSCRASSSVGYIHWYQQKPGQAPRPLIYATYYRTTGIPARFSGSGS GTDNTLTISSLEPEDSAVYYCQQWSSYPPITFGGGTKLEVKRTVAAPSVFIFPPSDEQLKSGTASV VCLLNNFYPREAKVQWKVDNALQSGNSQESVTEQDSKDSTYSLSSTLTLSKADYEKHKVYACEV THQGLSSPVTKSFNRGEC |
| 322 | VISTA sequence to which 4M2-C12 and derivatives bind | SRGEVQ |
| 323 | Human PSGL-1 isoform 1 (UniProt: Q14242-1, v1) | MPLQLLLLLILLGPGNSLQLWDTWADEAEKALGPLLARDRRQATEYEYLDYDFLPETEPPEMLRN STDTTPLTGPGTPESTTVEPAARRSTGLDAGGAVTELTTELANMGNLSTDSAAMEIQTTQPAATE AQTTQPVPTEAQTTPLAATEAQTTRLTATEAQTTPLAATEAQTTPPAATEAQTTQPTGLEAQTTAP AAMEAQTTAPAAMEAQTTPPAAMEAQTTQTTAMEAQTTAPEATEAQTTQPTATEAQTTPLAAME ALSTEPSATEALSMEPTTKRGLFIPFSVSSVTHKGIPMAASNLSVNYPVGAPDHISVKQCLLAILILA LVATIFFVCTVVLAVRLSRKGHMYPVRNYSPTEMVCISSLLPDGGEGPSATANGGLSKAKSPGLTP EPREDREGDDLTLHSFLP |

Sequences

| SEQ ID NO: | DESCRIPTION | SEQUENCE |
|---|---|---|
| 324 | Human PSGL-1 isoform 2 (UniProt: Q14242-2) | MAVGASGLEGDKMAGAMPLQLLLLLILLGPGNSLQLWDTWADEAEKALGPLLARDRRQATEYEY LDYDFLPETEPPEMLRNSTDTTPLTGPGTPESTTVEPAARRSTGLDAGGAVTELTTELANMGNLS TDSAAMEIQTTQPAATEAQTTQPVPTEAQTTPLAATEAQTTRLTATEAQTTPLAATEAQTTPPAAT EAQTTQPTGLEAQTTAPAAMEAQTTAPAAMEAQTTPPAAMEAQTTQTTAMEAQTTAPEATEAQT TQPTATEAQTTPLAAMEALSTEPSATEALSMEPTTKRGLFIPFSVSSVTHKGIPMAASNLSVNYPV GAPDH ISVKQCLLAI LILALVATIFFVCTVVLAVRLSRKGH MYPVRNYSPTEMVCISSLLPDGGEGP SATANGG LSKAKS PG LTP EP RED REGDD LTLHS FLP |
| 325 | Mature human PSGL-1 isoform 1 (Q14242-1, v1 positions 18 to 412) | LQLWD-RNADEAEKALGPLLARDRRQATEYEYLDYDFLPETEPPEMLRNSTDTTPLTGPGTPESTT VEPAARRSTGLDAGGAVTELTTELANMGNLSTDSAAMEIQTTQPAATEAQTTQPVPTEAQTTPLA ATEAQTTRLTATEAQTTPLAATEAQTTPPAATEAQTTQPTGLEAQTTAPAAMEAQTTAPAAMEAQ TTPPAAMEAQTTQTTAMEAQTTAPEATEAQTTQPTATEAQTTPLAAMEALSTEPSATEALSMEPT TKRGLFI PFSVSSVTHKG IP MAASNLSVNYPVGAPDH ISVKQCLLAILI LALVATI FFVCTVVLAVRLS RKGHMYPVRNYSPTEMVCISSLLPDGGEGPSATANGGLSKAKSPGLTPEPREDREGDDLTLHSF LP |
| 326 | PSGL-1 extracellular domain (Q14242-1, v1 positions 18 to 320) | LQLWD-RNADEAEKALGPLLARDRRQATEYEYLDYDFLPETEPPEMLRNSTDTTPLTGPGTPESTT VEPAARRSTGLDAGGAVTELTTELANMGNLSTDSAAMEIQTTQPAATEAQTTQPVPTEAQTTPLA ATEAQTTRLTATEAQTTPLAATEAQTTPPAATEAQTTQPTGLEAQTTAPAAMEAQTTAPAAMEAQ TTPPAAMEAQTTQTTAMEAQTTAPEATEAQTTQPTATEAQTTPLAAMEALSTEPSATEALSMEPT TKRGLFI PFSVSSVTHKGIP MAASNLSVNYPVGAPDH ISVKQC |
| 327 | PSGL-1 transmembrane domain (014242-1, v1 positions 321 to 341) | LLAI LI LALVATIFFVCTVVL |
| 328 | PSGL-1 cytoplasmic domain (Q14242-1, v1 positions 342 to 412) | AVRLSRKGHMYPVRNYSPTEMVCISSLLPDGGEGPSATANGGLSKAKSPGLTPEPREDREGDDL TLHSFLP |
| 329 | PSGL-1 extracellular domain repeat region (014242-1, v1 positions 122 to 261) | QTTQPAATEAQTTQPVPTEAQTTPLAATEAQTTRLTATEAQTTPLAATEAQTTPPAATEAQTTQPT GLEAQTTAPAAMEAQTTAPAAMEAQTTPPAAMEAQTTQTTAMEAQTTAPEATEAQTTQPTATEA QTTPLAAMEA |
| 330 | 4M2-C12 VH-CH1-CH2-CH3 IgG4 | EVKLVESGPGLVKPSQSLSLTCTVTGYSITSDYAWNW I RQFPGNKLEWMGYITYSGN ISYNPSLR SRISITRDTSKNQFFLQLNSVTPEDTATYSCARSLYYPWYFDVWGAGTTVTVSSASTKGPSVFPLA PCSRSTSESTAALGCLVKDYFPEPVTVSWNSGALTSGVHTFPAVLQSSGLYSLSSVVTVPSSSLG TKTYTCNVDHKPSNTKVDKRVESKYGPPCPSCPAPEFLGGPSVFLFPPKPKDTLMISRTPEVTCV VVDVSQEDPEVQFNWYVDGVEVHNAKTKPREEQFNSTYRVVSVLTVLHQDWLNGKEYKCKVSN KGLPSS IEKTISKAKGQP REPQVYTLPPSQEEMTKNQVSLTCLVKGFYPSD IAVEWESNGQPENN YKTTPPVLDSDGSFFLYSRLTVDKSRWQEGNVFSCSVMHEALHNHYTQKSLSLSLGK |

Numbered Paragraphs

The following numbered paragraphs (paras) provide further statements of features and combinations of features which are contemplated in connection with the present invention:

1. An antigen-binding molecule, optionally isolated, which is capable of binding to VISTA and inhibiting VISTA-mediated signalling, independently of Fc-mediated function.
2. The antigen-binding molecule according to para 1, which is capable of binding to VISTA in the Ig-like V-type domain.
3. The antigen-binding molecule according to para 1 or para 2, wherein the antigen-binding molecule is capable of binding to a polypeptide comprising or consisting of the amino acid sequence of SEQ ID NO:6.
4. The antigen-binding molecule according to any one of paras 1 to 3, wherein the antigen-binding molecule is capable of binding to a polypeptide comprising or consisting of the amino acid sequence of SEQ ID NO:31.
5. The antigen-binding molecule according to any one of paras 1 to 4, wherein the antigen-binding molecule does not compete with IGN175A for binding to VISTA.
6. The antigen-binding molecule according to any one of paras 1 to 5, wherein the antigen-binding molecule is not capable of binding to a peptide consisting of the amino acid sequence of SEQ ID NO:275.
7. The antigen-binding molecule according to any one of paras 1 to 6, wherein the antigen-binding molecule comprises:
   (i) a heavy chain variable (VH) region incorporating the following CDRs:
   HC-CDR1 having the amino acid sequence of SEQ ID NO:305
   HC-CDR2 having the amino acid sequence of SEQ ID NO:306
   HC-CDR3 having the amino acid sequence of SEQ ID NO:307; and
   (ii) a light chain variable (VL) region incorporating the following CDRs:
   LC-CDR1 having the amino acid sequence of SEQ ID NO:41
   LC-CDR2 having the amino acid sequence of SEQ ID NO:308
   LC-CDR3 having the amino acid sequence of SEQ ID NO:43.
8. The antigen-binding molecule according to any one of paras 1 to 7, wherein the antigen-binding molecule comprises:
   (i) a heavy chain variable (VH) region incorporating the following CDRs:

HC-CDR1 having the amino acid sequence of SEQ ID NO:290
HC-CDR2 having the amino acid sequence of SEQ ID NO:291
HC-CDR3 having the amino acid sequence of SEQ ID NO:278; and
(ii) a light chain variable (VL) region incorporating the following CDRs:
LC-CDR1 having the amino acid sequence of SEQ ID NO:41
LC-CDR2 having the amino acid sequence of SEQ ID NO:309
LC-CDR3 having the amino acid sequence of SEQ ID NO:43.

9. The antigen-binding molecule according to any one of paras 1 to 8, wherein the antigen-binding molecule comprises:
(i) a heavy chain variable (VH) region incorporating the following CDRs:
HC-CDR1 having the amino acid sequence of SEQ ID NO:290
HC-CDR2 having the amino acid sequence of SEQ ID NO:291
HC-CDR3 having the amino acid sequence of SEQ ID NO:278; and
(ii) a light chain variable (VL) region incorporating the following CDRs:
LC-CDR1 having the amino acid sequence of SEQ ID NO:41
LC-CDR2 having the amino acid sequence of SEQ ID NO:295
LC-CDR3 having the amino acid sequence of SEQ ID NO:43.

10. The antigen-binding molecule according to any one of paras 1 to 8, wherein the antigen-binding molecule comprises:
(i) a heavy chain variable (VH) region incorporating the following CDRs:
HC-CDR1 having the amino acid sequence of SEQ ID NO:290
HC-CDR2 having the amino acid sequence of SEQ ID NO:291
HC-CDR3 having the amino acid sequence of SEQ ID NO:278; and
(ii) a light chain variable (VL) region incorporating the following CDRs:
LC-CDR1 having the amino acid sequence of SEQ ID NO:41
LC-CDR2 having the amino acid sequence of SEQ ID NO:300
LC-CDR3 having the amino acid sequence of SEQ ID NO:43.

11. The antigen-binding molecule according to any one of paras 1 to 8, wherein the antigen-binding molecule comprises:
(i) a heavy chain variable (VH) region incorporating the following CDRs:
HC-CDR1 having the amino acid sequence of SEQ ID NO:33
HC-CDR2 having the amino acid sequence of SEQ ID NO:277
HC-CDR3 having the amino acid sequence of SEQ ID NO:278; and
(ii) a light chain variable (VL) region incorporating the following CDRs:
LC-CDR1 having the amino acid sequence of SEQ ID NO:41
LC-CDR2 having the amino acid sequence of SEQ ID NO:42
LC-CDR3 having the amino acid sequence of SEQ ID NO:43.

12. The antigen-binding molecule according to any one of paras 1 to 8, wherein the antigen-binding molecule comprises:
(i) a heavy chain variable (VH) region incorporating the following CDRs:
HC-CDR1 having the amino acid sequence of SEQ ID NO:33
HC-CDR2 having the amino acid sequence of SEQ ID NO:286
HC-CDR3 having the amino acid sequence of SEQ ID NO:278; and
(ii) a light chain variable (VL) region incorporating the following CDRs:
LC-CDR1 having the amino acid sequence of SEQ ID NO:41
LC-CDR2 having the amino acid sequence of SEQ ID NO:42
LC-CDR3 having the amino acid sequence of SEQ ID NO:43.

13. The antigen-binding molecule according to any one of paras 1 to 8, wherein the antigen-binding molecule comprises:
(i) a heavy chain variable (VH) region incorporating the following CDRs:
HC-CDR1 having the amino acid sequence of SEQ ID NO:290
HC-CDR2 having the amino acid sequence of SEQ ID NO:291
HC-CDR3 having the amino acid sequence of SEQ ID NO:278; and
(ii) a light chain variable (VL) region incorporating the following CDRs:
LC-CDR1 having the amino acid sequence of SEQ ID NO:41
LC-CDR2 having the amino acid sequence of SEQ ID NO:42
LC-CDR3 having the amino acid sequence of SEQ ID NO:43.

14. The antigen-binding molecule according to any one of paras 1 to 8, wherein the antigen-binding molecule comprises:
(i) a heavy chain variable (VH) region incorporating the following CDRs:
HC-CDR1 having the amino acid sequence of SEQ ID NO:290
HC-CDR2 having the amino acid sequence of SEQ ID NO:291
HC-CDR3 having the amino acid sequence of SEQ ID NO:278; and
(ii) a light chain variable (VL) region incorporating the following CDRs:
LC-CDR1 having the amino acid sequence of SEQ ID NO:41
LC-CDR2 having the amino acid sequence of SEQ ID NO:300
LC-CDR3 having the amino acid sequence of SEQ ID NO:43.

15. The antigen-binding molecule according to any one of paras 1 to 7, wherein the antigen-binding molecule comprises:
(i) a heavy chain variable (VH) region incorporating the following CDRs:

HC-CDR1 having the amino acid sequence of SEQ ID NO:33
HC-CDR2 having the amino acid sequence of SEQ ID NO:34
HC-CDR3 having the amino acid sequence of SEQ ID NO:35; and
(ii) a light chain variable (VL) region incorporating the following CDRs:
LC-CDR1 having the amino acid sequence of SEQ ID NO:41
LC-CDR2 having the amino acid sequence of SEQ ID NO:42
LC-CDR3 having the amino acid sequence of SEQ ID NO:43.

16. The antigen-binding molecule according to any one of paras 1 to 7, wherein the antigen-binding molecule comprises:
(i) a heavy chain variable (VH) region incorporating the following CDRs:
HC-CDR1 having the amino acid sequence of SEQ ID NO:33
HC-CDR2 having the amino acid sequence of SEQ ID NO:34
HC-CDR3 having the amino acid sequence of SEQ ID NO:35; and
(ii) a light chain variable (VL) region incorporating the following CDRs:
LC-CDR1 having the amino acid sequence of SEQ ID NO:41
LC-CDR2 having the amino acid sequence of SEQ ID NO:67
LC-CDR3 having the amino acid sequence of SEQ ID NO:43.

17. The antigen-binding molecule according to any one of paras 1 to 7, wherein the antigen-binding molecule comprises:
(i) a heavy chain variable (VH) region incorporating the following CDRs:
HC-CDR1 having the amino acid sequence of SEQ ID NO:53
HC-CDR2 having the amino acid sequence of SEQ ID NO:34
HC-CDR3 having the amino acid sequence of SEQ ID NO:35; and
(ii) a light chain variable (VL) region incorporating the following CDRs:
LC-CDR1 having the amino acid sequence of SEQ ID NO:41
LC-CDR2 having the amino acid sequence of SEQ ID NO:58
LC-CDR3 having the amino acid sequence of SEQ ID NO:43.

18. The antigen-binding molecule according to any one of paras 1 to 6, wherein the antigen-binding molecule comprises:
(i) a heavy chain variable (VH) region incorporating the following CDRs:
HC-CDR1 having the amino acid sequence of SEQ ID NO:72
HC-CDR2 having the amino acid sequence of SEQ ID NO:73
HC-CDR3 having the amino acid sequence of SEQ ID NO:74; and
(ii) a light chain variable (VL) region incorporating the following CDRs:
LC-CDR1 having the amino acid sequence of SEQ ID NO:80
LC-CDR2 having the amino acid sequence of SEQ ID NO:81
LC-CDR3 having the amino acid sequence of SEQ ID NO:82.

19. The antigen-binding molecule according to any one of paras 1 to 6, wherein the antigen-binding molecule comprises:
(i) a heavy chain variable (VH) region incorporating the following CDRs:
HC-CDR1 having the amino acid sequence of SEQ ID NO:88
HC-CDR2 having the amino acid sequence of SEQ ID NO:89
HC-CDR3 having the amino acid sequence of SEQ ID NO:90; and
(ii) a light chain variable (VL) region incorporating the following CDRs:
LC-CDR1 having the amino acid sequence of SEQ ID NO:96
LC-CDR2 having the amino acid sequence of SEQ ID NO:97
LC-CDR3 having the amino acid sequence of SEQ ID NO:98.

20. The antigen-binding molecule according to any one of paras 1 to 6, wherein the antigen-binding molecule comprises:
(i) a heavy chain variable (VH) region incorporating the following CDRs:
HC-CDR1 having the amino acid sequence of SEQ ID NO:88
HC-CDR2 having the amino acid sequence of SEQ ID NO:89
HC-CDR3 having the amino acid sequence of SEQ ID NO:90; and
(ii) a light chain variable (VL) region incorporating the following CDRs:
LC-CDR1 having the amino acid sequence of SEQ ID NO:137
LC-CDR2 having the amino acid sequence of SEQ ID NO:138
LC-CDR3 having the amino acid sequence of SEQ ID NO:139.

21. The antigen-binding molecule according to any one of paras 1 to 6, wherein the antigen-binding molecule comprises:
(i) a heavy chain variable (VH) region incorporating the following CDRs:
HC-CDR1 having the amino acid sequence of SEQ ID NO:33
HC-CDR2 having the amino acid sequence of SEQ ID NO:107
HC-CDR3 having the amino acid sequence of SEQ ID NO:108,
or a variant thereof in which one or two or three amino acids in one or more of HC-CDR1, HC-CDR2, or HC-CDR3 are substituted with another amino acid; and
(ii) a light chain variable (VL) region incorporating the following CDRs:
LC-CDR1 having the amino acid sequence of SEQ ID NO:114
LC-CDR2 having the amino acid sequence of SEQ ID NO:67
LC-CDR3 having the amino acid sequence of SEQ ID NO:115.

22. The antigen-binding molecule according to any one of paras 1 to 6, wherein the antigen-binding molecule comprises:

(i) a heavy chain variable (VH) region incorporating the following CDRs:
    HC-CDR1 having the amino acid sequence of SEQ ID NO:120
    HC-CDR2 having the amino acid sequence of SEQ ID NO:121
    HC-CDR3 having the amino acid sequence of SEQ ID NO:122; and
(ii) a light chain variable (VL) region incorporating the following CDRs:
    LC-CDR1 having the amino acid sequence of SEQ ID NO:127
    LC-CDR2 having the amino acid sequence of SEQ ID NO:128
    LC-CDR3 having the amino acid sequence of SEQ ID NO:129.

23. The antigen-binding molecule according to any one of paras 1 to 6, wherein the antigen-binding molecule comprises:
(i) a heavy chain variable (VH) region incorporating the following CDRs:
    HC-CDR1 having the amino acid sequence of SEQ ID NO:144
    HC-CDR2 having the amino acid sequence of SEQ ID NO:145
    HC-CDR3 having the amino acid sequence of SEQ ID NO:146; and
(ii) a light chain variable (VL) region incorporating the following CDRs:
    LC-CDR1 having the amino acid sequence of SEQ ID NO:151
    LC-CDR2 having the amino acid sequence of SEQ ID NO:152
    LC-CDR3 having the amino acid sequence of SEQ ID NO:153.

24. The antigen-binding molecule according to any one of paras 1 to 6, wherein the antigen-binding molecule comprises:
(i) a heavy chain variable (VH) region incorporating the following CDRs:
    HC-CDR1 having the amino acid sequence of SEQ ID NO:158
    HC-CDR2 having the amino acid sequence of SEQ ID NO:159
    HC-CDR3 having the amino acid sequence of SEQ ID NO:160; and
(ii) a light chain variable (VL) region incorporating the following CDRs:
    LC-CDR1 having the amino acid sequence of SEQ ID NO:165
    LC-CDR2 having the amino acid sequence of SEQ ID NO:152
    LC-CDR3 having the amino acid sequence of SEQ ID NO:153.

25. The antigen-binding molecule according to any one of paras 1 to 6, wherein the antigen-binding molecule comprises:
(i) a heavy chain variable (VH) region incorporating the following CDRs:
    HC-CDR1 having the amino acid sequence of SEQ ID NO:169
    HC-CDR2 having the amino acid sequence of SEQ ID NO:170
    HC-CDR3 having the amino acid sequence of SEQ ID NO:171; and
(ii) a light chain variable (VL) region incorporating the following CDRs:
    LC-CDR1 having the amino acid sequence of SEQ ID NO:177
    LC-CDR2 having the amino acid sequence of SEQ ID NO:178
    LC-CDR3 having the amino acid sequence of SEQ ID NO:179.

26. The antigen-binding molecule according to any one of paras 1 to 6, wherein the antigen-binding molecule comprises:
(i) a heavy chain variable (VH) region incorporating the following CDRs:
    HC-CDR1 having the amino acid sequence of SEQ ID NO:72
    HC-CDR2 having the amino acid sequence of SEQ ID NO:184
    HC-CDR3 having the amino acid sequence of SEQ ID NO:246; and
(ii) a light chain variable (VL) region incorporating the following CDRs:
    LC-CDR1 having the amino acid sequence of SEQ ID NO:247
    LC-CDR2 having the amino acid sequence of SEQ ID NO:178
    LC-CDR3 having the amino acid sequence of SEQ ID NO:190.

27. The antigen-binding molecule according to any one of paras 1 to 6 or para 26, wherein the antigen-binding molecule comprises:
(i) a heavy chain variable (VH) region incorporating the following CDRs:
    HC-CDR1 having the amino acid sequence of SEQ ID NO:72
    HC-CDR2 having the amino acid sequence of SEQ ID NO:184
    HC-CDR3 having the amino acid sequence of SEQ ID NO:185; and
(ii) a light chain variable (VL) region incorporating the following CDRs:
    LC-CDR1 having the amino acid sequence of SEQ ID NO:189
    LC-CDR2 having the amino acid sequence of SEQ ID NO:178
    LC-CDR3 having the amino acid sequence of SEQ ID NO:190.

28. The antigen-binding molecule according to any one of paras 1 to 6 or para 26, wherein the antigen-binding molecule comprises:
(i) a heavy chain variable (VH) region incorporating the following CDRs:
    HC-CDR1 having the amino acid sequence of SEQ ID NO:72
    HC-CDR2 having the amino acid sequence of SEQ ID NO:184
    HC-CDR3 having the amino acid sequence of SEQ ID NO:195; and
(ii) a light chain variable (VL) region incorporating the following CDRs:
    LC-CDR1 having the amino acid sequence of SEQ ID NO:197
    LC-CDR2 having the amino acid sequence of SEQ ID NO:178
    LC-CDR3 having the amino acid sequence of SEQ ID NO:190.

29. The antigen-binding molecule according to any one of paras 1 to 6 or para 26, wherein the antigen-binding molecule comprises:

(i) a heavy chain variable (VH) region incorporating the following CDRs:
    HC-CDR1 having the amino acid sequence of SEQ ID NO:72
    HC-CDR2 having the amino acid sequence of SEQ ID NO:184
    HC-CDR3 having the amino acid sequence of SEQ ID NO:200; and
(ii) a light chain variable (VL) region incorporating the following CDRs:
    LC-CDR1 having the amino acid sequence of SEQ ID NO:203
    LC-CDR2 having the amino acid sequence of SEQ ID NO:178
    LC-CDR3 having the amino acid sequence of SEQ ID NO:190.

30. The antigen-binding molecule according to any one of paras 1 to 6, wherein the antigen-binding molecule comprises:
    a VH region comprising an amino acid sequence having at least 70% sequence identity to the amino acid sequence of SEQ ID NO:289; and
    a VL region comprising an amino acid sequence having at least 70% sequence identity to the amino acid sequence of SEQ ID NO:310;
or
    a VH region comprising an amino acid sequence having at least 70% sequence identity to the amino acid sequence of SEQ ID NO:289; and
    a VL region comprising an amino acid sequence having at least 70% sequence identity to the amino acid sequence of SEQ ID NO:294;
or
    a VH region comprising an amino acid sequence having at least 70% sequence identity to the amino acid sequence of SEQ ID NO:289; and
    a VL region comprising an amino acid sequence having at least 70% sequence identity to the amino acid sequence of SEQ ID NO:297;
or
    a VH region comprising an amino acid sequence having at least 70% sequence identity to the amino acid sequence of SEQ ID NO:289; and
    a VL region comprising an amino acid sequence having at least 70% sequence identity to the amino acid sequence of SEQ ID NO:299;
or
    a VH region comprising an amino acid sequence having at least 70% sequence identity to the amino acid sequence of SEQ ID NO:289; and
    a VL region comprising an amino acid sequence having at least 70% sequence identity to the amino acid sequence of SEQ ID NO:301;
or
    a VH region comprising an amino acid sequence having at least 70% sequence identity to the amino acid sequence of SEQ ID NO:289; and
    a VL region comprising an amino acid sequence having at least 70% sequence identity to the amino acid sequence of SEQ ID NO:302;
or
    a VH region comprising an amino acid sequence having at least 70% sequence identity to the amino acid sequence of SEQ ID NO:289; and
    a VL region comprising an amino acid sequence having at least 70% sequence identity to the amino acid sequence of SEQ ID NO:303;
or
    a VH region comprising an amino acid sequence having at least 70% sequence identity to the amino acid sequence of SEQ ID NO:276; and
    a VL region comprising an amino acid sequence having at least 70% sequence identity to the amino acid sequence of SEQ ID NO:282;
or
    a VH region comprising an amino acid sequence having at least 70% sequence identity to the amino acid sequence of SEQ ID NO:285; and
    a VL region comprising an amino acid sequence having at least 70% sequence identity to the amino acid sequence of SEQ ID NO:287;
    a VH region comprising an amino acid sequence having at least 70% sequence identity to the amino acid sequence of SEQ ID NO:32; and
    a VL region comprising an amino acid sequence having at least 70% sequence identity to the amino acid sequence of SEQ ID NO:40;
or
    a VH region comprising an amino acid sequence having at least 70% sequence identity to the amino acid sequence of SEQ ID NO:52; and
    a VL region comprising an amino acid sequence having at least 70% sequence identity to the amino acid sequence of SEQ ID NO:57;
or
    a VH region comprising an amino acid sequence having at least 70% sequence identity to the amino acid sequence of SEQ ID NO:62; and
    a VL region comprising an amino acid sequence having at least 70% sequence identity to the amino acid sequence of SEQ ID NO:66;
or
    a VH region comprising an amino acid sequence having at least 70% sequence identity to the amino acid sequence of SEQ ID NO:48; and
    a VL region comprising an amino acid sequence having at least 70% sequence identity to the amino acid sequence of SEQ ID NO:50;
or.
    a VH region comprising an amino acid sequence having at least 70% sequence identity to the amino acid sequence of SEQ ID NO:87; and
    a VL region comprising an amino acid sequence having at least 70% sequence identity to the amino acid sequence of SEQ ID NO:95;
or
    a VH region comprising an amino acid sequence having at least 70% sequence identity to the amino acid sequence of SEQ ID NO:106; and
    a VL region comprising an amino acid sequence having at least 70% sequence identity to the amino acid sequence of SEQ ID NO:113;
or
    a VH region comprising an amino acid sequence having at least 70% sequence identity to the amino acid sequence of SEQ ID NO:143; and
    a VL region comprising an amino acid sequence having at least 70% sequence identity to the amino acid sequence of SEQ ID NO:150;
or
    a VH region comprising an amino acid sequence having at least 70% sequence identity to the amino acid sequence of SEQ ID NO:157; and a VL region comprising an amino acid sequence having at least 70% sequence identity to the amino acid sequence of SEQ ID NO:164;
or
a VH region comprising an amino acid sequence having at least 70% sequence identity to the amino acid sequence of SEQ ID NO:71; and
a VL region comprising an amino acid sequence having at least 70% sequence identity to the amino acid sequence of SEQ ID NO:79;
or
a VH region comprising an amino acid sequence having at least 70% sequence identity to the amino acid sequence of SEQ ID NO:102; and
a VL region comprising an amino acid sequence having at least 70% sequence identity to the amino acid sequence of SEQ ID NO:104;
or
a VH region comprising an amino acid sequence having at least 70% sequence identity to the amino acid sequence of SEQ ID NO:119; and
a VL region comprising an amino acid sequence having at least 70% sequence identity to the amino acid sequence of SEQ ID NO:126;
or
a VH region comprising an amino acid sequence having at least 70% sequence identity to the amino acid sequence of SEQ ID NO:183; and
a VL region comprising an amino acid sequence having at least 70% sequence identity to the amino acid sequence of SEQ ID NO:188;
or
a VH region comprising an amino acid sequence having at least 70% sequence identity to the amino acid sequence of SEQ ID NO:194; and
a VL region comprising an amino acid sequence having at least 70% sequence identity to the amino acid sequence of SEQ ID NO:196;
or
a VH region comprising an amino acid sequence having at least 70% sequence identity to the amino acid sequence of SEQ ID NO:199; and
a VL region comprising an amino acid sequence having at least 70% sequence identity to the amino acid sequence of SEQ ID NO:202;
or
a VH region comprising an amino acid sequence having at least 70% sequence identity to the amino acid sequence of SEQ ID NO:133; and
a VL region comprising an amino acid sequence having at least 70% sequence identity to the amino acid sequence of SEQ ID NO:136;
or
a VH region comprising an amino acid sequence having at least 70% sequence identity to the amino acid sequence of SEQ ID NO:168; and
a VL region comprising an amino acid sequence having at least 70% sequence identity to the amino acid sequence of SEQ ID NO:176.

31. The antigen-binding molecule according to any one of paras 1 to 30, wherein the antigen-binding molecule is capable of binding to human VISTA and one or more of: mouse VISTA and cynomolgus macaque VISTA.

32. An antigen-binding molecule, optionally isolated, comprising (i) an antigen-binding molecule according to any one of paras 1 to 31, and (ii) an antigen-binding molecule capable of binding to an antigen other than VISTA.

33. The antigen-binding molecule according to any one of paras 1 to 32, wherein the antigen-binding molecule is capable of binding to cells expressing VISTA at the cell surface.

34. The antigen-binding molecule according to any one of paras 1 to 33, wherein the antigen-binding molecule is capable of inhibiting interaction between VISTA and a binding partner for VISTA.

35. The antigen-binding molecule according to any one of paras 1 to 34, wherein the antigen-binding molecule is capable of inhibiting VISTA-mediated signalling.

36. The antigen-binding molecule according to any one of paras 1 to 35, wherein the antigen-binding molecule is capable of increasing proliferation and/or cytokine production by effector immune cells.

37. A chimeric antigen receptor (CAR) comprising an antigen-binding molecule according to any one of paras 1 to 36.

38. A nucleic acid, or a plurality of nucleic acids, optionally isolated, encoding an antigen-binding molecule according to any one of paras 1 to 36 or a CAR according to para 37.

39. An expression vector, or a plurality of expression vectors, comprising a nucleic acid or a plurality of nucleic acids according to para 38.

40. A cell comprising an antigen-binding molecule according to any one of paras 1 to 36, a CAR according to para 37, a nucleic acid or a plurality of nucleic acids according to para 38, or an expression vector or a plurality of expression vectors according to para 39.

41. A method comprising culturing a cell comprising a nucleic acid or a plurality of nucleic acids according to para 38, or an expression vector or a plurality of expression vectors according to para 39, under conditions suitable for expression of the antigen-binding molecule or CAR from the nucleic acid(s) or expression vector(s).

42. A composition comprising an antigen-binding molecule according to any one of paras 1 to 36, a CAR according to para 37, a nucleic acid or a plurality of nucleic acids according to para 38, an expression vector or a plurality of expression vectors according to para 39, or a cell according to para 40.

43. The composition according to para 42, additionally comprising an agent capable of inhibiting signalling mediated by an immune checkpoint molecule other than VISTA, optionally wherein the immune checkpoint molecule other than VISTA is selected from PD-1, CTLA-4, LAG-3, TIM-3, TIGIT and BTLA.

44. An antigen-binding molecule according to any one of paras 1 to 36, a CAR according to para 37, a nucleic acid or a plurality of nucleic acids according to para 38, an expression vector or a plurality of expression vectors according to para 39, a cell according to para 40, or a composition according to para 42 or para 43 for use in a method of medical treatment or prophylaxis.

45. An antigen-binding molecule according to any one of paras 1 to 36, a CAR according to para 37, a nucleic acid or a plurality of nucleic acids according to para 38, an expression vector or a plurality of expression vectors according to para 39, a cell according to para 40, or a composition according to para 42 or para 43, for use in a method of treatment or prevention of a cancer or an infectious disease.

46. Use of an antigen-binding molecule according to any one of paras 1 to 36, a CAR according to para 37, a nucleic acid or a plurality of nucleic acids according to para 38, an expression vector or a plurality of expression vectors according to para 39, a cell according to para 40, or a composition according to para 42 or para 43, in the manufacture of a medicament for use in a method of treatment or prevention of a cancer or an infectious disease.

47. A method of treating or preventing a cancer or an infectious disease, comprising administering to a subject a therapeutically or prophylactically effective amount of an antigen-binding molecule according to any one of paras 1 to 36, a CAR according to para 37, a nucleic acid or a plurality of nucleic acids according to para 38, an expression vector or a plurality of expression vectors according to para 39, a cell according to para 40, or a composition according to para 42 or para 43.

48. The antigen-binding molecule, CAR, nucleic acid or plurality of nucleic acids, expression vector or plurality of expression vectors, cell or composition for use according to para 45, the use according to para 46 or the method according to para 47, wherein the cancer is selected from: colorectal cancer, pancreatic cancer, breast cancer, liver cancer, prostate cancer, ovarian cancer, head and neck cancer, leukemia, lymphoma, melanoma, thymoma, lung cancer, non-small cell lung cancer (NSCLC) and a solid tumor.

49. An antigen-binding molecule according to any one of paras 1 to 36, a CAR according to para 37, a nucleic acid or a plurality of nucleic acids according to para 38, an expression vector or a plurality of expression vectors according to para 39, a cell according to para 40, or a composition according to para 42 or para 43, for use in a method of treatment or prevention of a disease in which myeloid-derived suppressor cells (MDSCs) are pathologically implicated.

50. Use of an antigen-binding molecule according to any one of paras 1 to 36, a CAR according to para 37, a nucleic acid or a plurality of nucleic acids according to para 38, an expression vector or a plurality of expression vectors according to para 39, a cell according to para 40, or a composition according to para 42 or para 43, in the manufacture of a medicament for use in a method of treatment or prevention of a disease in which myeloid-derived suppressor cells (MDSCs) are pathologically implicated.

51. A method of treating or preventing a disease in which myeloid-derived suppressor cells (MDSCs) are pathologically implicated, comprising administering to a subject a therapeutically or prophylactically effective amount of an antigen-binding molecule according to any one of paras 1 to 36, a CAR according to para 37, a nucleic acid or a plurality of nucleic acids according to para 38, an expression vector or a plurality of expression vectors according to para 39, a cell according to para 40, or a composition according to para 42 or para 43.

52. The antigen-binding molecule, CAR, nucleic acid or plurality of nucleic acids, expression vector or plurality of expression vectors, cell or composition for use, the use, or the method according to any one of paras 45 to 51, wherein the method additionally comprises administration of an agent capable of inhibiting signalling mediated by an immune checkpoint molecule other than VISTA, optionally wherein the immune checkpoint molecule other than VISTA is selected from PD-1, CTLA-4, LAG-3, TIM-3, TIGIT or BTLA.

53. A method of inhibiting VISTA-mediated signalling, comprising contacting VISTA-expressing cells with an antigen-binding molecule according to any one of paras 1 to 36.

54. A method for inhibiting the activity of myeloid-derived suppressor cells (MDSCs), the method comprising contacting MDSCs with an antigen-binding molecule according to any one of paras 1 to 36.

55. A method for increasing the number or activity of effector immune cells, the method comprising inhibiting the activity of VISTA-expressing cells with an antigen-binding molecule according to any one of paras 1 to 36.

56. An in vitro complex, optionally isolated, comprising an antigen-binding molecule according to any one of paras 1 to 36 bound to VISTA.

57. A method comprising contacting a sample containing, or suspected to contain, VISTA with an antigen-binding molecule according to any one of paras 1 to 36, and detecting the formation of a complex of the antigen-binding molecule with VISTA.

58. A method of selecting or stratifying a subject for treatment with a VISTA-targeted agent, the method comprising contacting, in vitro, a sample from the subject with an antigen-binding molecule according to any one of paras 1 to 36 and detecting the formation of a complex of the antigen-binding molecule with VISTA.

59. Use of an antigen-binding molecule according to any one of paras 1 to 36 as an in vitro or in vivo diagnostic or prognostic agent.

60. Use of an antigen-binding molecule according to any one of paras 1 to 36 in a method for detecting, localizing or imaging a cancer, optionally wherein the cancer is selected from: colorectal cancer, pancreatic cancer, breast cancer, liver cancer, prostate cancer, ovarian cancer, head and neck cancer, leukemia, lymphoma, melanoma, thymoma, lung cancer, non-small cell lung cancer (NSCLC) and a solid tumor.

The invention includes the combination of the aspects and preferred features described except where such a combination is clearly impermissible or expressly avoided.

The section headings used herein are for organizational purposes only and are not to be construed as limiting the subject matter described.

Aspects and embodiments of the present invention will now be illustrated, by way of example, with reference to the accompanying figures. Further aspects and embodiments will be apparent to those skilled in the art. All documents mentioned in this text are incorporated herein by reference.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

Where a nucleic acid sequence is disclosed herein, the reverse complement thereof is also expressly contemplated.

Methods described herein may preferably performed in vitro. The term "in vitro" is intended to encompass procedures performed with cells in culture whereas the term "in vivo" is intended to encompass procedures with/on intact multi-cellular organisms.

BRIEF DESCRIPTION OF THE FIGURES

Embodiments and experiments illustrating the principles of the invention will now be discussed with reference to the accompanying figures.

FIGS. 4A to 4B. Graphs showing the results of analysis of binding of anti-VISTA antibodies to different proteins. 4A shows binding to human, cynomolgus monkey and murine VISTA, human PD-L1 and human HER3 by anti-VISTA antibody clone V4, as determined by ELISA. 4B shows binding of anti-VISTA antibody clone V4 to human VISTA, PD-1, PD-L1, B7H3, B7H4, B7H6, B7H7, CTLA4 and an irrelevant antigen.

FIGS. 29A to 29C. Tables summarising the results of analysis of binding of 4M2-C12 mIgG1, 4M2-C12 mIgG2a, 4M2-C12 mIgG2a LALA PG and 4M2-C12 mIgG2a to mouse FcγRIV, mouse FcγRIII, mouse FcγRIIb, and mouse FcRn. 29A shows calculated $K_{on}$ values, 29B shows calculated $K_{dis}$ values and 29C shows calculated $K_D$ values.

FIGS. 33A and 33C show results obtained from conditions using wells coated with a 1:1 ratio of agonist anti-CD3 antibody and VISTA-Ig, and FIGS. 33B and 33D show results obtained from conditions using wells coated with a 2:1 ratio of agonist anti-CD3 antibody and VISTA-Ig. FIGS. 33A and 33B show the percentages of CFSE-low CD4+ T cells, and FIGS. 33C and 33D show the percentages of CFSE-low CD8+ T cells.

FIG. 34A shows the results obtained using 4M2-C12, and FIG. 34B shows the results obtained using VSTB112.

FIGS. 45A to 45D. Sensorgrams and table showing the results of analysis of binding of different anti-VISTA antibodies to human VISTA (45A) mouse VISTA (45B) and human PD-L1 (45C), as determined by Biolayer Interferometry. 45D summarises the kinetic and thermodynamic constants calculated from the sensorgrams of 45A and 45B.

FIGS. 46A and 46B. Sensorgrams and table showing the results of analysis of binding of different anti-VISTA antibodies to mouse VISTA, as determined by Biolayer Interferometry. 45B summarises the kinetic and thermodynamic constants calculated from the sensorgrams of 46A.

FIG. 47A to 47C. Sensorgrams and table showing the results of analysis of binding of different anti-VISTA antibodies to human VISTA (47A) and mouse VISTA (47B), as determined by Biolayer Interferometry. 47C summarises the kinetic and thermodynamic constants calculated from the sensorgrams of 47A and 47B.

FIGS. 51A to 51C. Concentration-response graphs and table showing the results of analysis of binding of different antibodies to human VISTA (51A) and mouse VISTA (51B), as determined by ELISA. 51C shows EC50 values (nM) for binding of the different antibodies to the indicated proteins.

FIGS. 52A to 52J. Melting graphs and table showing the results of analysis of stability of different anti-VISTA antibodies by Differential Scanning Fluorimetry analysis. 52A to 52I show the first derivate of the raw data obtained for test antibody preparations and no protein control (NPC) preparations, in triplicate. 52J summarises the results of 52A to 52I.

FIGS. 59A and 59B. Images showing immunohistochemical staining of human tissue using anti-VISTA antibody. 59A shows staining of normal human spleen tissue by 4M2-C12 mIgG2a, and 59B shows staining of normal human ovary tissue by 4M2-C12 mIgG2a, at the indicated magnifications.

FIGS. 64A to 64C. Tables showing representative hematological profiles in BALB/C mice 96 hours after administration of 50 mg/kg 4M2-C12-hIgG1 or an equal volume of PBS. 64A shows results of analysis of the red blood cell compartment, 64B shows results of analysis of the white blood cell compartment, and 64C shows results of analysis of correlates of liver and kidney function. RBC=red blood cell, MVC=mean corpuscular volume, MCH=mean corpuscular haemoglobin, MCHC=mean corpuscular haemoglobin concentration, WBC=white blood cell, ALT=alanine aminotransferase, ALP=alkaline phosphatase, CREA=creatinine, and BUN=blood urea nitrogen.

FIGS. 65A to 65C. Tables showing representative hematological profiles of SD rats following administration of 250 mg/kg 4M2-C12-hIgG1, 250 mg/kg 4M2-C12-hIgG4 or an equal volume of PBS. 65A shows results of analysis of the red blood cell compartment, 65B shows results of analysis of the white blood cell compartment, and 65C shows results of analysis of correlates of liver, kidney and pancreas function, and levels of electrolytes. RBC=red blood cell, MVC=mean corpuscular volume, MCH=mean corpuscular haemoglobin, MCHC=mean corpuscular haemoglobin concentration, WBC=white blood cell, ALT=alanine aminotransferase, ALP=alkaline phosphatase, CREA=creatinine, BUN=blood urea nitrogen, GLU=glucagon, AMY=amylase, NA=sodium, K=potassium, P=phosphorus and CA=calcium.

EXAMPLES

Figure 1A:
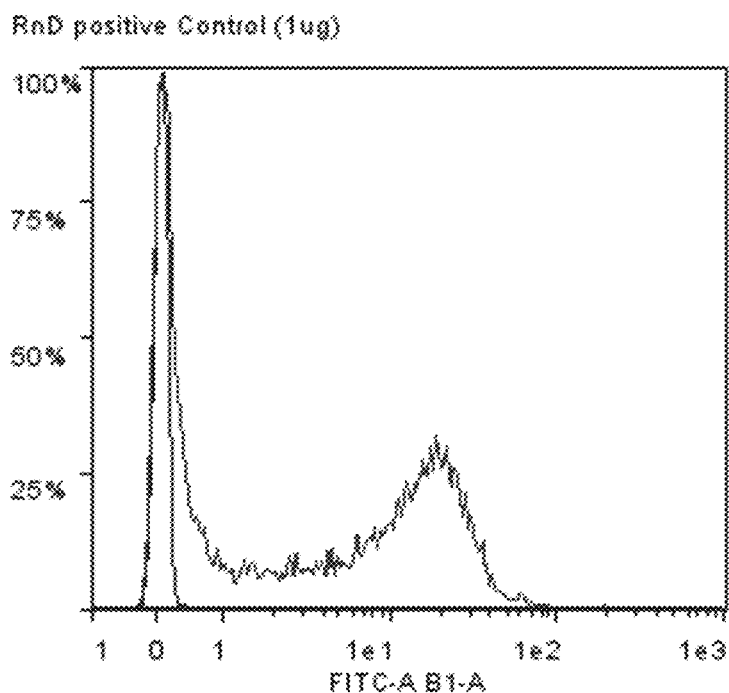
FIGS. 1A to 1D. Histograms showing staining of cells by anti-VISTA antibodies as determined by flow cytometry. Histograms show staining of HEK293 cells (which do not express VISTA), or HEK293 VISTA overexpressing cells (HEK293 VISTA O/E) by anti-VISTA antibody clone (1A) VSTB112 (positive control; WO 2015/097536), (1B) 4-M2-D5, (1C) 9M2-C12 or (1D) 4M2-C12 (also referred to herein as "V4").
Figure 1B:
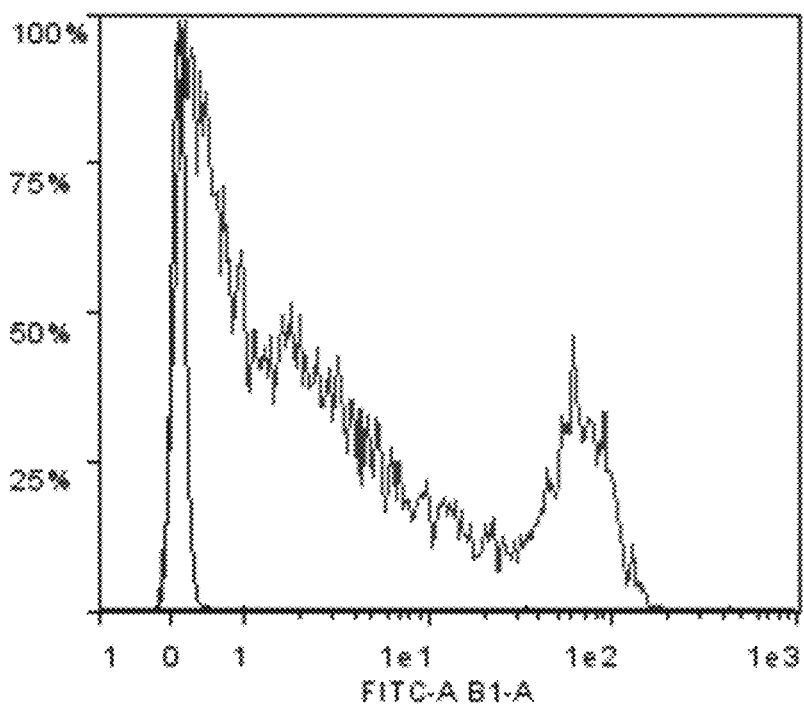
Figure 1C:
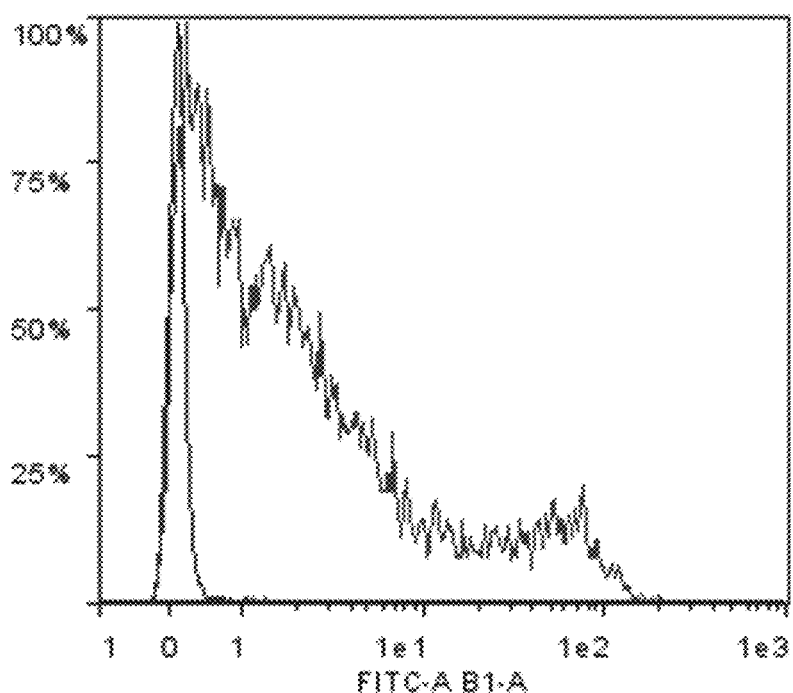
Figure 1D:
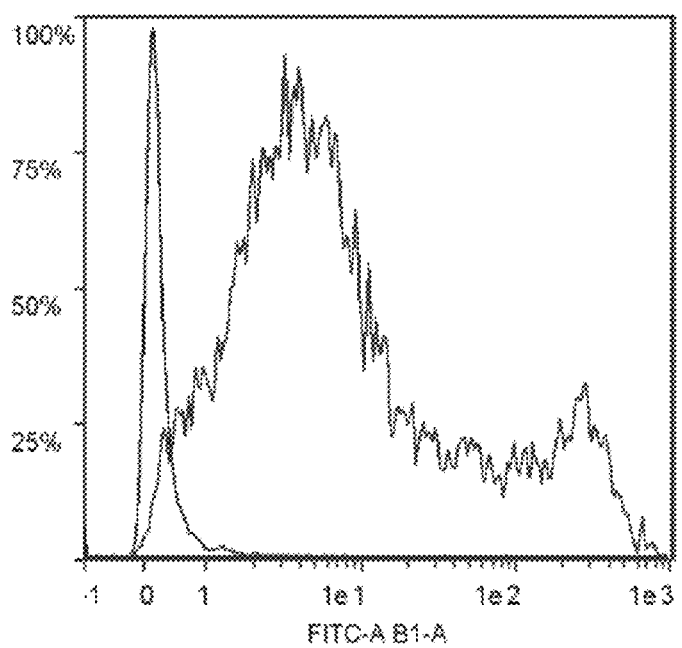
Figure 2:
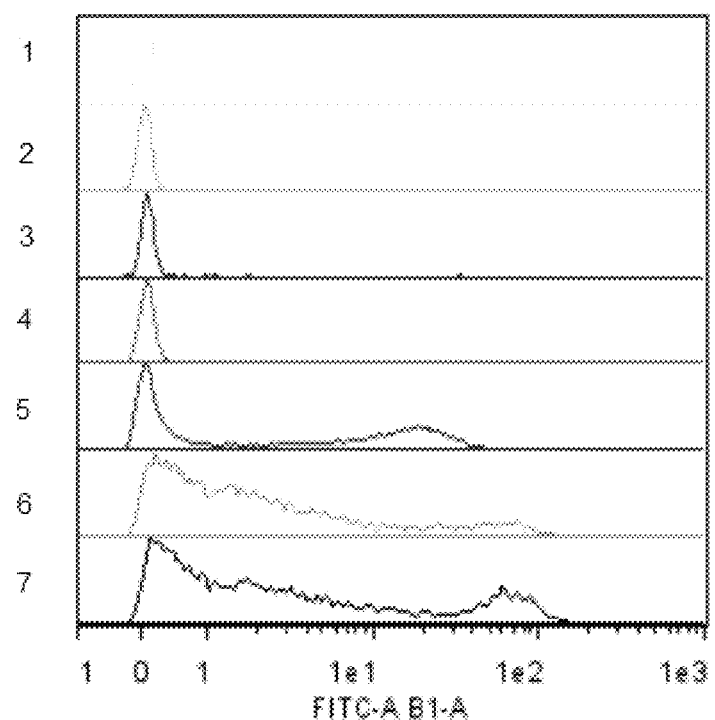
FIG. 2. Histograms showing staining of cells by anti-VISTA antibodies as determined by flow cytometry. Histograms show staining of HEK293 cells (which do not express VISTA), or HEK293 VISTA overexpressing cells (HEK293 VISTA O/E) by anti-VISTA antibody clones 9M2C12, V4 and clone VSTB112, or an isotype control antibody. Unstained cells were analysed as a negative control.

In the following Examples, the inventors describe the generation of novel anti-VISTA antibody clones targeted to specific regions of interest in the VISTA molecule, and the biophysical and functional characterisation and therapeutic evaluation of these antigen-binding molecules.

Example 1: VISTA Target Design and Anti-VISTA Antibody Hybridoma Production

The inventors selected regions in the extracellular region of human VISTA (SEQ ID NO:3) for raising VISTA-binding monoclonal antibodies.

The FG loop region was targeted because this region of VISTA has been proposed to be important for VISTA's inhibitory function (Vigdorovich et al., Structure. 2013; 21(5):707-717). The front-facing β-sheet region of VISTA was also targeted.

1.1 Hybridoma Production

Approximately 6 week old female BALB/c mice were obtained from InVivos (Singapore). Animals were housed under specific pathogen-free conditions and were treated in compliance with the Institutional Animal Care and Use Committee (IACUC) guidelines.

For hybridoma production, mice were immunized with proprietary mixtures of antigenic peptide, recombinant target protein or cells expressing the target protein.

Prior to harvesting the spleen for fusion, mice were boosted with antigen mixture for three consecutive days. 24 h after the final boost total splenocytes were isolated and fused with the myeloma cell line P3X63.Ag8.653 (ATCC, USA), with PEG using ClonaCell-HY Hybridoma Cloning Kit, in accordance with the manufacturer's instructions (Stemcell Technologies, Canada).

Fused cells were cultured in ClonaCell-HY Medium C (Stemcell Technologies, Canada) overnight at 37° C. in a 5% $CO_2$ incubator. The next day, fused cells were centrifuged and resuspended in 10 ml of ClonaCell-HY Medium C and then gently mixed with 90 ml of semisolid methylcellulose-based ClonaCell-HY Medium D (StemCell Technologies, Canada) containing HAT components, which combines the hybridoma selection and cloning into one step.

The fused cells were then plated into 96 well plates and allowed to grow at 37° C. in a 5% $CO_2$ incubator. After 7-10 days, single hybridoma clones were isolated and antibody producing hybridomas were selected by screening the supernatants by Enzyme-linked immunosorbent assay (ELISA) and Fluorescence-activated cell sorting (FACs).

1.2 Antibody Variable Region Amplification and Sequencing

Total RNA was extracted from hybridoma cells using TRIzol reagent (Life Technologies, Inc., USA) using manufacturer's protocol. Double-stranded cDNA was synthesized using SMARTer RACE 5'/3' Kit (Clontech™, USA) in accordance with the manufacturer's instructions. Briefly, 1 µg total RNA was used to generate full-length cDNA using 5'-RACE CDS primer (provided in the kit), and the 5' adaptor (SMARTer II A primer) was then incorporated into each cDNA according to manufacturer's instructions. cDNA synthesis reactions contained: 5× First-Strand Buffer, DTT (20 mM), dNTP Mix (10 mM), RNase Inhibitor (40 U/µl) and SMARTScribe Reverse Transcriptase (100 U/µl).

The race-ready cDNAs were amplified using SeqAmp DNA Polymerase (Clontech™, USA). Amplification reactions contained SeqAmp DNA Polymerase, 2× Seq AMP buffer, 5' universal primer provided in the 5' SMARTer Race kit, that is complement to the adaptor sequence, and 3' primers that anneal to respective heavy chain or light chain constant region primer. The 5' constant region were designed based on previously reported primer mix either by Krebber et al. J. Immunol. Methods 1997; 201: 35-55, Wang et al. Journal of Immunological Methods 2000, 233; 167-177 or Tiller et al. Journal of Immunological Methods 2009; 350: 183-193. The following thermal protocol was used: pre-denature cycle at 94° C. for 1 min; 35 cycles of 94° C., 30 s, 55° C., 30 s and 72° C., 45 s; final extension at 72° C. for 3 min.

The resulting VH and VL PCR products, approximately 550 bp, were cloned into pJET1.2/blunt vector using Clone-JET PCR Cloning Kit (Thermo Scientific, USA) and used to transform highly competent E. coli DH5a. From the resulting transformants, plasmid DNA was prepared using Miniprep Kit (Qiagene, Germany) and sequenced. DNA sequencing was carried out by AITbiotech. These sequencing data were analyzed using the international IMGT (ImMunoGeneTics) information system (LeFranc et al., Nucleic Acids Res. (2015) 43 (Database issue):D413-22) to characterize the individual CDRs and framework sequences. The signal peptide at 5' end of the VH and VL was identified by SignalP (v 4.1; Nielsen, in Kihara, D (ed): Protein Function Prediction (Methods in Molecular Biology vol. 1611) 59-73, Springer 2017).

Monoclonal anti-VISTA antibody clones were then selected for further development and characterisation. Humanised versions of antibody clone 4M2-C12 (also referred to herein as "V4") were also prepared according to standard methods by cloning the CDRs of antibodies into VH and VL comprising human antibody framework regions.

| Antibody clone | VH/VL sequence | Peptide immunogen used to raise the antibody |
|---|---|---|
| 4M2-C12 (also referred to herein as "V4") | VH = SEQ ID NO: 32<br>VL = SEQ ID NO: 40 | SEQ ID NO: 26 |
| V4H1 | VH = SEQ ID NO: 52<br>VL = SEQ ID NO: 57 | |
| V4H2 | VH = SEQ ID NO: 62<br>VL = SEQ ID NO: 66 | |
| 4M2-B4 | VH = SEQ ID NO: 48<br>VL = SEQ ID NO: 50 | |
| 4M2-C9 | VH = SEQ ID NO: 87<br>VL = SEQ ID NO: 95 | |
| 4M2-D9 | VH = SEQ ID NO: 106<br>VL = SEQ ID NO: 113 | |
| 4M2-D5 | VH = SEQ ID NO: 143<br>VL = SEQ ID NO: 150 | |
| 4M2-A8 | VH = SEQ ID NO: 157<br>VL = SEQ ID NO: 164 | |
| 2M1-B12 | VH = SEQ ID NO: 71<br>VL = SEQ ID NO: 79 | SEQ ID NO: 27 |
| 2M1-D2 | VH = SEQ ID NO: 102<br>VL = SEQ ID NO: 104 | |
| 1M2-D2 | VH = SEQ ID NO: 119<br>VL = SEQ ID NO: 126 | SEQ ID NO: 28 |
| 13D5p | VH = SEQ ID NO: 183<br>VL = SEQ ID NO: 188 | |
| 13D5-1 | VH = SEQ ID NO: 194<br>VL = SEQ ID NO: 196 | |
| 13D5-13 | VH = SEQ ID NO: 199<br>VL = SEQ ID NO: 202 | |

-continued

| Antibody clone | VH/VL sequence | Peptide immunogen used to raise the antibody |
|---|---|---|
| 5M1-A11 | VH = SEQ ID NO: 133<br>VL = SEQ ID NO: 136 | SEQ ID NO: 29 |
| 9M2-C12 | VH = SEQ ID NO: 168<br>VL = SEQ ID NO: 176 | SEQ ID NO: 30 |

Example 2: Antibody Production and Purification 2.1 Cloning VH and VL into Expression Vectors:

DNA sequences encoding the heavy and light chain variable regions of the anti-VISTA antibody clones were subcloned into the pmAbDZ_IgG1_CH and pmAbDZ_IgG1_CL (InvivoGen, USA) eukaryotic expression vectors for construction of human-mouse chimeric antibodies.

Alternatively, DNA sequence encoding the heavy and light chain variable regions of the anti-VISTA antibody clones were subcloned into the pFUSE-CHIg-hG1 and pFUSE2ss-CLIg-hk (InvivoGen, USA) eukaryotic expression vectors for construction of human-mouse chimeric antibodies. Human IgG1 constant region encoded by pFUSE-CHIg-hG1 comprises the substitutions D356E, L358M (positions numbered according to EU numbering) in the CH3 region relative to Human IgG1 constant region (IGHG1; UniProt:P01857-1, v1; SEQ ID NO:210). pFUSE2ss-CLIg-hk encodes human IgG1 light chain kappa constant region (IGCK; UniProt: P01834-1, v2).

Variable regions along with the signal peptides were amplified from the cloning vector using SeqAmp enzyme (Clontech™, USA) following the manufacturer's protocol. Forward and reverse primers having 15-20 bp overlap with the appropriate regions within VH or VL plus 6 bp at 5' end as restriction sites were used. The DNA insert and the pFuse vector were digested with restriction enzyme recommended by the manufacturer to ensure no frameshift was introduced (e.g., EcoRI and NheI for VH, AgeI and BsiWI for VL,) and ligated into its respective plasmid using T4 ligase enzyme (Thermo Scientific, USA). The molar ratio of 3:1 of DNA insert to vector was used for ligation.

2.2 Expression of Antibodies in Mammalian Cells

Antibodies were expressed using either 1) Expi293 Transient Expression System Kit (Life Technologies, USA), or 2) HEK293-6E Transient Expression System (CNRC-NRC, Canada) following the manufacturer's instructions.

1) Expi293 Transient Expression System:

Cell Line Maintenance:

HEK293F cells (Expi293F) were obtained from Life Technologies, Inc (USA). Cells were cultured in serum-free, protein-free, chemically defined medium (Expi293 Expression Medium, Thermo Fisher, USA), supplemented with 50 IU/ml penicillin and 50 µg/ml streptomycine (Gibco, USA) at 37° C., in 8% $CO_2$ and 80% humidified incubators with shaking platform.

Transfection:

Expi293F cells were transfected with expression plasmids using ExpiFectamine 293 Reagent kit (Gibco, USA) according to its manufacturer's protocol. Briefly, cells at maintenance were subjected to a media exchange to remove antibiotics by spinning down the culture, cell pellets were re-suspended in fresh media without antibiotics at 1 day before transfection. On the day of transfection, $2.5 \times 10^6$/ml of viable cells were seeded in shaker flasks for each transfection. DNA-ExpiFectamine complexes were formed in serum-reduced medium, Opti-MEM (Gibco, USA), for 25 min at room temperature before being added to the cells. Enhancers were added to the transfected cells at 16-18 h post transfection. An equal amount of media was topped up to the transfectants at day 4 post-transfection to prevent cell aggregation. Transfectants were harvested at day 7 by centrifugation at 4000×g for 15 min, and filtered through 0.22 µm sterile filter units.

2) HEK293-6E Transient Expression System

Cell Line Maintenance: HEK293-6E cells were obtained from National Research Council Canada. Cells were cultured in serum-free, protein-free, chemically defined Freestyle F17 Medium (Invitrogen, USA), supplemented with 0.1% Kolliphor-P188 and 4 mM L-Glutamine (Gibco, USA) and 25 µg/ml G-418 at 37° C., in 5% $CO_2$ and 80% humidified incubators with shaking platform.

Transfection:

HEK293-6E cells were transfected with expression plasmids using PEIpro™ (Polyplus, USA) according to its manufacturer's protocol. Briefly, cells at maintenance were subjected to a media exchange to remove antibiotics by centrifugation, cell pellets were re-suspended with fresh media without antibiotics at 1 day before transfection. On the day of transfection, $1.5-2 \times 10^6$ cells/ml of viable cells were seeded in shaker flasks for each transfection. DNA and PEIpro™ were mixed to a ratio of 1:1 and the complexes were allowed to form in F17 medium for 5 min at RT before adding to the cells. 0.5% (w/v) of Tryptone N1 was fed to transfectants at 24-48 h post transfection. Transfectants were harvested at day 6-7 by centrifugation at 4000×g for 15 min and the supernatant was filtered through 0.22 µm sterile filter units.

Cells were transfected with vectors encoding the following combinations of polypeptides:

| Antigen-biding molecule | Polypeptides | Antibody |
|---|---|---|
| [1] | 4M2-C12 VH-CH1-CH2-CH3 (SEQ ID NO: 212) +<br>4M2-C12 VL-$C_K$ (SEQ ID NO: 213) | anti-VISTA clone 4M2-C12 IgG1 |
| [2] | 4M2-B4 VH-CH1-CH2-CH3 (SEQ ID NO: 214) +<br>4M2-B4 VL-$C_K$ (SEQ ID NO: 215) | anti-VISTA clone 4M2-B4 IgG1 |
| [3] | V4H1 VH-CH1-CH2-CH3 (SEQ ID NO: 216) +<br>V4H1 VL-$C_K$ (SEQ ID NO: 217) | anti-VISTA clone V4H1 IgG1 |
| [4] | V4H2 VH-CH1-CH2-CH3 (SEQ ID NO: 218) +<br>V4H2 VL-$C_K$ (SEQ ID NO: 219) | anti-VISTA clone V4H2 IgG1 |
| [5] | 2M1-B12 VH-CH1-CH2-CH3 (SEQ ID NO: 220) +<br>2M1-B12 VL-$C_K$ (SEQ ID NO: 221) | anti-VISTA clone 2M1-B12 IgG1 |
| [6] | 4M2-C9 VH-CH1-CH2-CH3 (SEQ ID NO: 222) +<br>4M2-C9 VL-$C_K$ (SEQ ID NO: 223) | anti-VISTA clone 4M2-C9 IgG1 |
| [7] | 2M1-D2 VH-CH1-CH2-CH3 (SEQ ID NO: 224) +<br>2M1-D2 VL-$C_K$ (SEQ ID NO: 225) | anti-VISTA clone 2M1-D2 IgG1 |
| [8] | 4M2-D9 VH-CH1-CH2-CH3 (SEQ ID NO: 226) +<br>4M2-D9 VL-$C_K$ (SEQ ID NO: 227) | anti-VISTA clone 4M2-D9 IgG1 |
| [9] | 1M2-D2 VH-CH1-CH2-CH3 (SEQ ID NO: 228) +<br>1M2-D2 VL-$C_K$ (SEQ ID NO: 229) | anti-VISTA clone 1M2-D2 IgG1 |
| [10] | 5M1-A11 VH-CH1-CH2-CH3 (SEQ ID NO: 230) +<br>5M1-A11 VL-$C_K$ (SEQ ID NO: 231) | anti-VISTA clone 5M1-A11 IgG1 |
| [11] | 4M2-D5 VH-CH1-CH2-CH3 (SEQ ID NO: 232) +<br>4M2-D5 VL-$C_K$ (SEQ ID NO: 233) | anti-VISTA clone 4M2-D5 IgG1 |

-continued

| Antigen-biding molecule | Polypeptides | Antibody |
|---|---|---|
| [12] | 4M2-A8 VH-CH1-CH2-CH3 (SEQ ID NO: 234) + 4M2-A8 VL-C$_K$ (SEQ ID NO: 235) | anti-VISTA clone 4M2-A8 IgG1 |
| +13] | 9M2-C12 VH-CH1-CH2-CH3 (SEQ ID NO: 236) + 9M2-C12 VL-C$_K$ (SEQ ID NO: 237) | anti-VISTA clone 9M2-C12 IgG1 |
| [14] | 13D5p VH-CH1-CH2-CH3 (SEQ ID NO: 238) + 13D5p VL-C$_K$ (SEQ ID NO: 239) | anti-VISTA clone 13D5p IgG1 |
| [15] | 13D5-1 VH-CH1-CH2-CH3 (SEQ ID NO: 240) + 13D5-1 VL-C$_K$ (SEQ ID NO: 241) | anti-VISTA clone 13D5-1 IgG1 |
| [16] | 13D5-13 VH-CH1-CH2-CH3 (SEQ ID NO: 242) + 13D5-13 VL-C$_K$ (SEQ ID NO: 243) | anti-VISTA clone 13D5-13 IgG1 |

2.3 Antibody Purification
Affinity Purification, Buffer Exchange and Storage:

Antibodies secreted by the transfected cells into the culture supernatant were purified using liquid chromatography system AKTA Start (GE Healthcare, UK). Specifically, supernatants were loaded onto HiTrap Protein G column (GE Healthcare, UK) at a binding rate of 5 ml/min, followed by washing the column with 10 column volumes of washing buffer (20 mM sodium phosphate, pH 7.0). Bound mAbs were eluted with elution buffer (0.1 M glycine, pH 2.7) and the eluents were fractionated to collection tubes which contain appropriate amount of neutralization buffer (1 M Tris, pH 9). Neutralised elution buffer containing purified mAb were exchanged into PBS using 30K MWCO protein concentrators (Thermo Fisher, USA) or 3.5K MWCO dialysis cassettes (Thermo Fisher, USA). Monoclonal antibodies were sterilized by passing through 0.22 µm filter, aliquoted and snap-frozen in −80° C. for storage.

2.4 Antibody-Purity Analysis
Size Exclusion Chromatography (SEC):

Antibody purity was analysed by size exclusion chromatography (SEC) using Superdex 200 10/30 GL columns (GE Healthcare, UK) in PBS running buffer, on a AKTA Explorer liquid chromatography system (GE Healthcare, UK). 150 µg of antibody in 500 µl PBS pH 7.2 was injected to the column at a flow rate of 0.75 ml/min at room temperature. Proteins were eluted according to their molecular weights.

Figure 10:
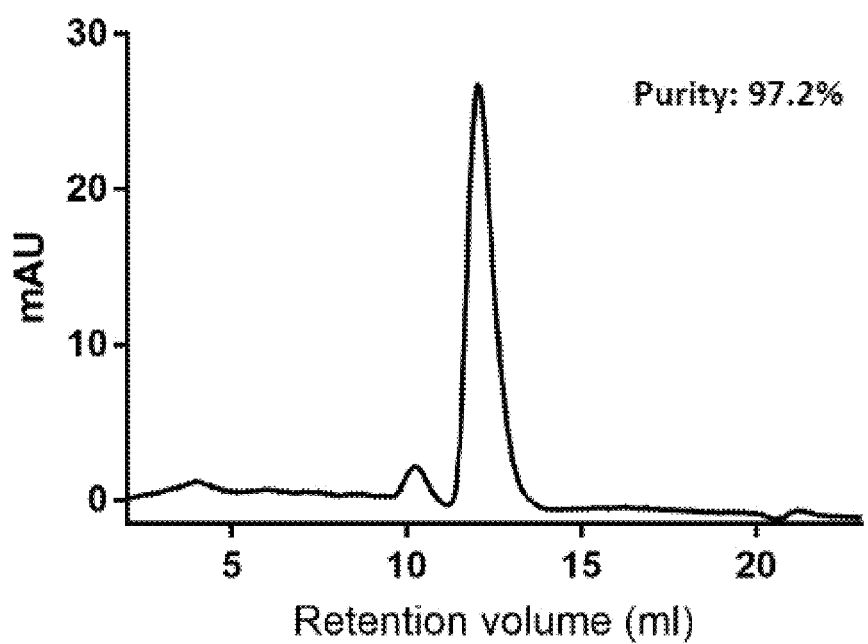
FIG. 10. Graph showing the results of analysis of anti-VISTA antibody clone V4 by size exclusion chromatography.

The result for anti-VISTA antibody clone V4 ([1] of Example 2.2) is shown in FIG. 10.

Sodium-Dodecyl Sulfate Polyacrylamide Gel Electrophoresis (SDS-PAGE):

Antibody purity was also analysed by SDS-PAGE under reducing and non-reducing conditions according to standard methods. Briefly, 4%-20% TGX protein gels (Bio-Rad, USA) were used to resolve proteins using a Mini-Protean Electrophoresis System (Bio-Rad, USA). For non-reducing condition, protein samples were denatured by mixing with 2× Laemmli sample buffer (Bio-Rad, USA) and boiled at 95° C. for 5-10 min before loading to the gel. For reducing conditions, 2× sample buffer containing 5% of 3-mercaptoethanol (P3ME), or 40 mM DTT (dithiothreitol) was used. Electrophoresis was carried out at a constant voltage of 150V for 1 h in SDS running buffer (25 mM Tris, 192 mM glycine, 1% SDS, pH 8.3).

Western Blot:

Protein samples (30 µg) were fractionated by SDS-PAGE as described above and transferred to nitrocellulose membranes. Membranes were then blocked and immunoblotted with antibodies overnight at 4° C. After washing three times in PBS-Tween the membranes were then incubated for 1 h at room temperature with horseradish peroxidase (HRP)-conjugated secondary antibodies. The results were visualized via a chemiluminescent Pierce ECL Substrate Western blot detection system (Thermo Scientific, USA) and exposure to autoradiography film (Kodak XAR film).

The primary antibody used for detection was goat anti-mouse IgG (H+L) Antibody (LI-COR, Cat. No. 926-32210).

Figure 11:
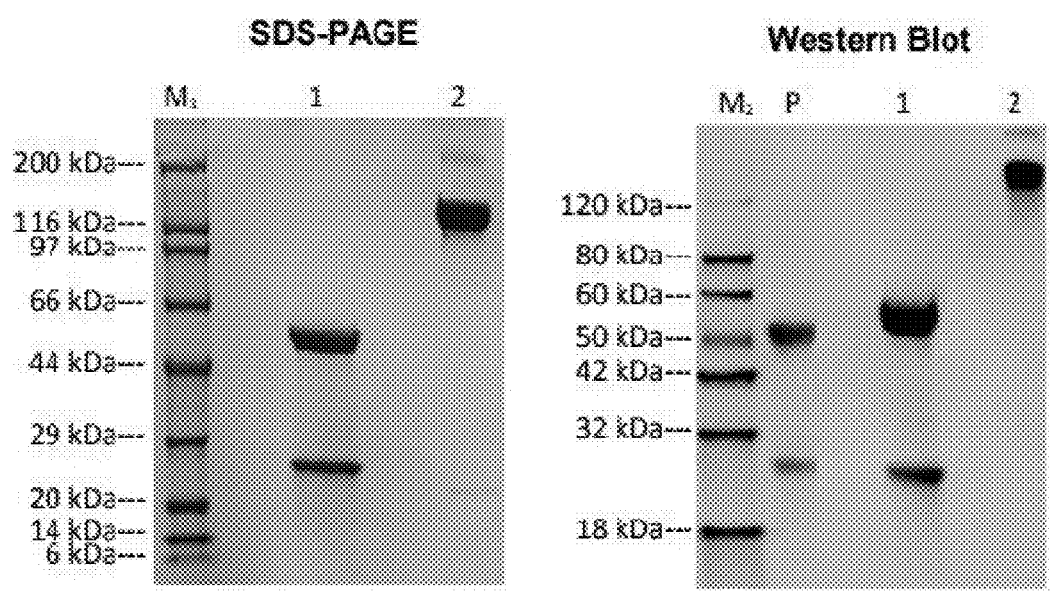
FIG. 11. Images showing the results of the analysis of anti-VISTA antibody clone V4 expression by SDS-PAGE and western blot. Lanes: M1=TaKaRa protein marker Cat. No. 3452; M2=GenScript protein marker Cat. No. M00521; 1=reducing conditions; 2=non-reducing conditions; P=positive control: mouse IgG1, Kappa (Sigma Cat. No. M9269). For western blot, the primary antibody used was goat anti-mouse IgG (H+L) antibody (LI-COR, Cat. No. 926-32210).

The result for anti-VISTA antibody clone V4 ([1] of Example 2.2) is shown in FIG. 11. V4 was easily expressed, purified and processed at high concentrations.

Example 3: Biophysical Characterisation 3.1 Analysis of Cell Surface Antigen-Binding by Flow Cytometry Wildtype HEK293T cells (which do not express high levels of VISTA) and cells of HEK293T cells transfected with vector encoding human VISTA (i.e. HEK 293 HER O/E cells) were incubated with 20 µg/ml of anti-VISTA antibody or isotype control antibody at 4° C. for 1 hr. The anti-VISTA antibody clone VSTB112, as described in WO 2015/097536, was included in the analysis as a positive control.

The cells were washed thrice with FACS buffer (PBS with 5 mM EDTA and 0.5% BSA) and resuspended in FITC-conjugated anti-FC antibody (Invitrogen, USA) for 40 min at 2-8° C. Cells were washed again and resuspended in 200 µL of FACS flow buffer (PBS with 5 mM EDTA) for flow cytometric analysis using MACSQuant 10 (Miltenyi Biotec, Germany). After acquisition, all raw data were analyzed using Flowlogic software. Cells were gated using forward and side scatter profile and Median of Fluorescence Intensity (MFI) value was determined for native and overexpressing cell populations.

The results are shown in FIGS. 1A to 1D, FIG. 2 and FIG. 24. The anti-VISTA antibodies were shown to bind to human VISTA with high specificity.

In a separate experiment 13D5p ([14] of Example 2.2) was analysed for its ability to bind to cells transfected with vector encoding cynomolgus macaque VISTA or murine VISTA. 13D5p was found to display cross-reactivity with cynomolgus macaque VISTA and murine VISTA.

3.2 Global Affinity Study Using Octet QK384 System

Bio-Layer Interferometry (BLI) experiments were performed using the Octet QK384 system (ForteBio). anti-Penta-HIS (HIS1K) coated biosensor tips (Pall ForteBio, USA) were used to capture His-tagged human, cynomolgus macaque or murine VISTA (270 nM). All measurements were performed at 25° C. with agitation at 1000 rpm. Kinetic measurements for antigen binding were performed by loading anti-VISTA antibody at different concentrations (indicated in the Figures) for 120 s, followed by a 120 s dissociation time by transferring the biosensors into assay buffer containing wells. Sensograms were referenced for buffer effects and then fitted using the Octet QK384 user software (Pall ForteBio, USA). Kinetic responses were subjected to a global fitting using a one site binding model to obtain values for association (kon), dissociation (koff) rate constants and the equilibrium dissociation constant ($K_D$). Only curves that could be reliably fitted with the software ($R^2 > 0.90$) were included in the analysis.

Figure 3A:
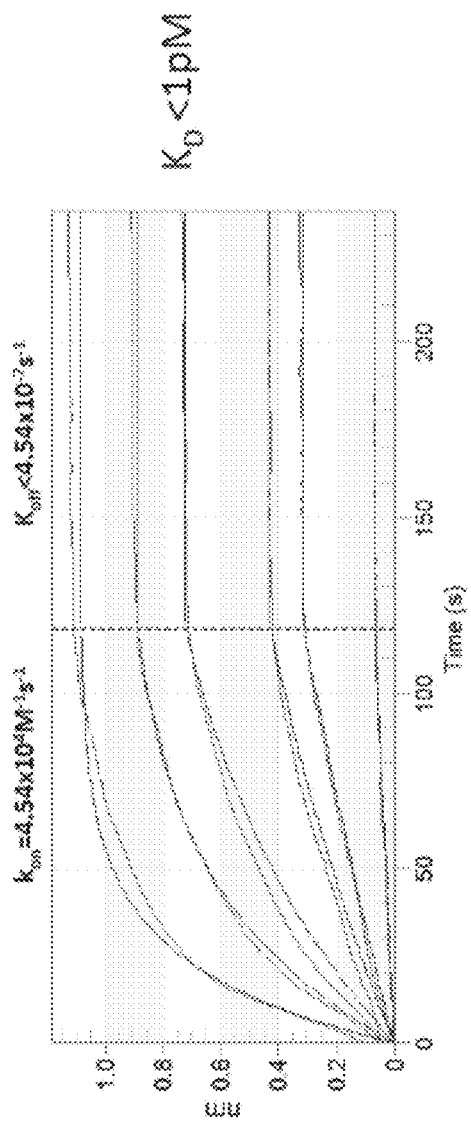
FIGS. 3A to 3C. Sensorgrams showing the results of analysis of affinity of binding to human, cynomolgus monkey and murine VISTA by anti-VISTA antibody clone V4. (3A) shows binding to human VISTA, (3B) shows binding to cynomolgus monkey VISTA, and (3C) shows binding to murine VISTA. Kon, Koff and $K_D$ are shown.
Figure 3B:
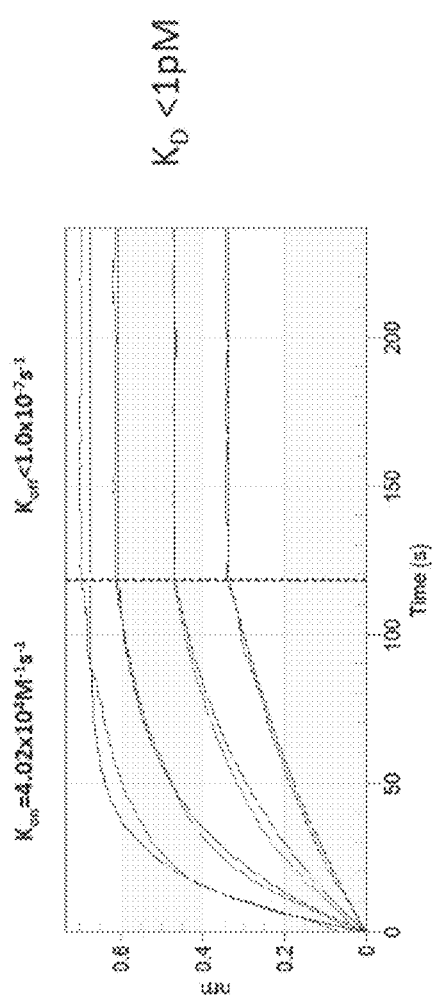
Figure 3C:
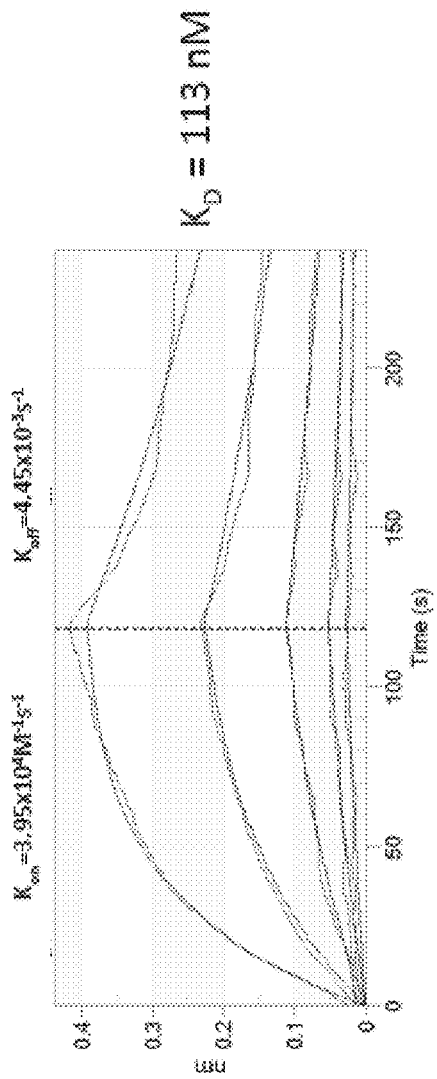

Representative sensorgrams for analysis of binding by anti-VISTA antibody clone V4 (i.e. [1] of example 2.2) are shown in FIGS. 3A to 3C.

Anti-VISTA antibody clone V4 was found to bind to human and cynomolgus macaque VISTA with an affinity of $K_D$=<1 pM, and to bind to murine VISTA with an affinity of $K_D$=113 nM.

3.3 ELISAs for Determining Antibody Specificity

ELISAs were used to determine the binding specificity of the antibodies. Anti-VISTA antibodies were analysed for binding to human VISTA polypeptide, respective mouse and cynomolgus macaque homologues, as well as human PD-L1 and human HER3 (Sino Biological Inc., China).

ELISAs were carried out according to standard protocols. Briefly, 96-well plates (Nunc, Denmark) were coated with 1 µg/ml of target protein in phosphate-buffered saline (PBS) for 2 h at 37° C. After blocking for 1 h with 10% BSA in Tris buffer saline (TBS) at room temperature, the test antibody was serially diluted (12 point serial dilution) with the highest concentration being 30 µg/ml and added to the plate, in the. Post 1 h incubation at room temperature, plates were washed three times with TBS containing 0.05% Tween 20 (TBS-T) and were then incubated with a HRP-conjugated anti-mouse IgG antibody (Life Technologies, Inc., USA) for 1 h at room temperature. After washing, plates were developed with colorimetric detection substrate 3,3',5,5'-tetramethylbenzidine (Turbo-TMB; Pierce, USA) for 15 min at room temperature. The reaction was stopped with 2M $H_2SO_4$, and OD was measured at 450 nM within 30 min.

The results obtained with anti-VISTA antibody clone V4 ([1] of Example 2.2) are shown in FIG. 4A. Clone V4 was found to be able to bind to human, cynomolgus macaque and murine VISTA, but did not display cross-reactivity with human PD-L1 or human HER3 (even at very high concentrations).

Figure 20:
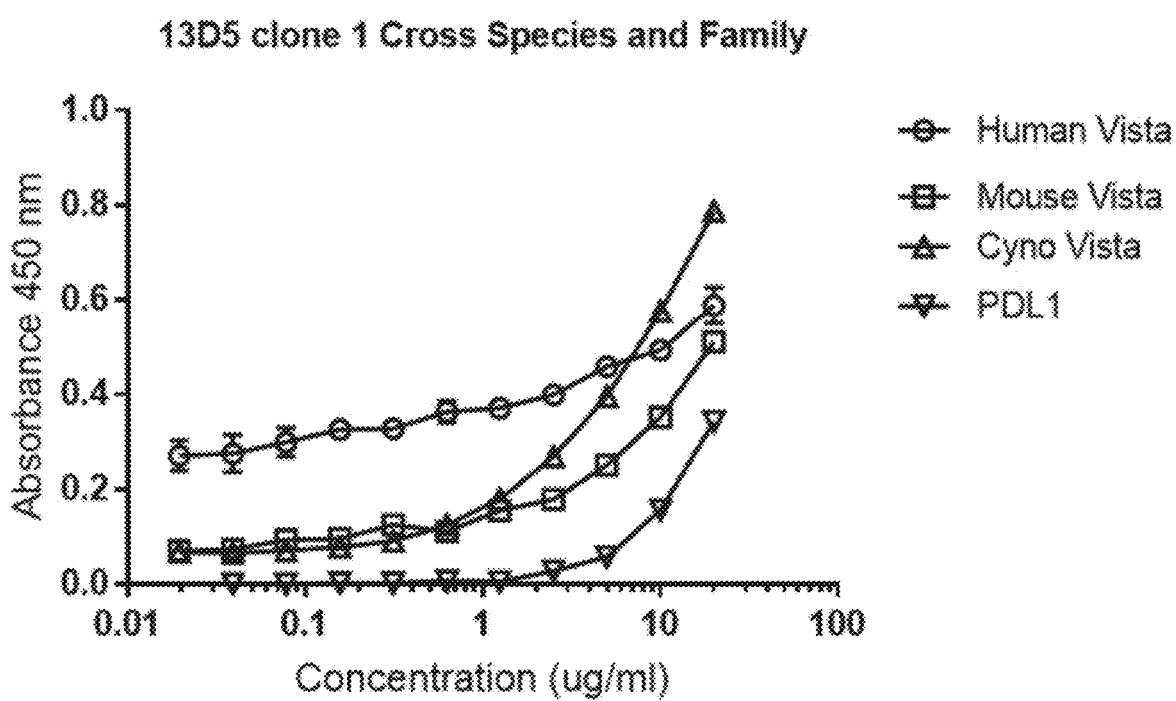
FIG. 20. Graph showing the results of analysis of binding to human, cynomolgus monkey and mouse VISTA and human PD-L1 by anti-VISTA antibody clone 13D5-1, as determined by ELISA.
Figure 21:
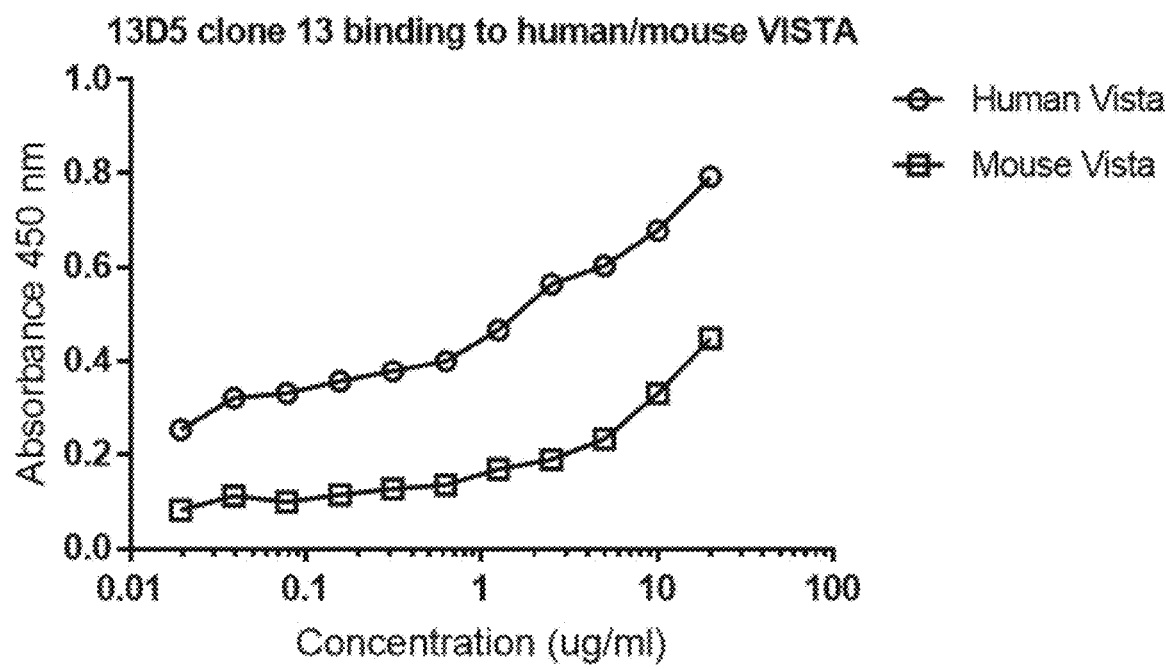
FIG. 21. Graph showing the results of analysis of binding to human and mouse VISTA by anti-VISTA antibody clone 13D5-13, as determined by ELISA.

The results obtained with anti-VISTA antibody clone 13D5-1 ([15] of Example 2.2) are shown in FIG. 20. Clone 13D5-1 was found to be able to bind to human, cynomolgus macaque and mouse VISTA. The results obtained with anti-VISTA antibody clone 13D5-13 ([16] of Example 2.2) are shown in FIG. 21. Clone 13D5-13 was found to be able to bind to human and mouse VISTA.

In a further experiment, anti-VISTA antibody clone V4 ([1] of Example 2.2) was analysed by ELISA for ability to bind to human VISTA, PD-1, PD-L1, B7H3, B7H4, B7H6, B7H7 and CTLA4. The results are shown in FIG. 4C. Clone V4 was found not to cross-react with any of PD-1, PD-L1, B7H3, B7H4, B7H6, B7H7 or CTLA4.

3.4 Analysis of Thermostability by Differential Scanning Fluorimetry

Briefly, triplicate reaction mixes of antibodies at 0.2 mg/mL and SYPRO Orange dye (ThermoFisher) were prepared in 25 µL of PBS, transferred to wells of MicroAmp Optical 96-Well Reaction Plates (ThermoFisher), and sealed with MicroAmp Optical Adhesive Film (ThermoFisher). Melting curves were run in a 7500 fast Real-Time PCR system (Applied Biosystems) selecting TAMRA as reporter and ROX as passive reference. The thermal profile included an initial step of 2 min at 25° C. and a final step of 2 min at 99° C., with a ramp rate of 1.2%. The first derivative of the raw data was plotted as a function of temperature to obtain the derivative melting curves. Melting temperatures (Tm) of the antibodies were extracted from the peaks of the derivative curves.

Figure 9:
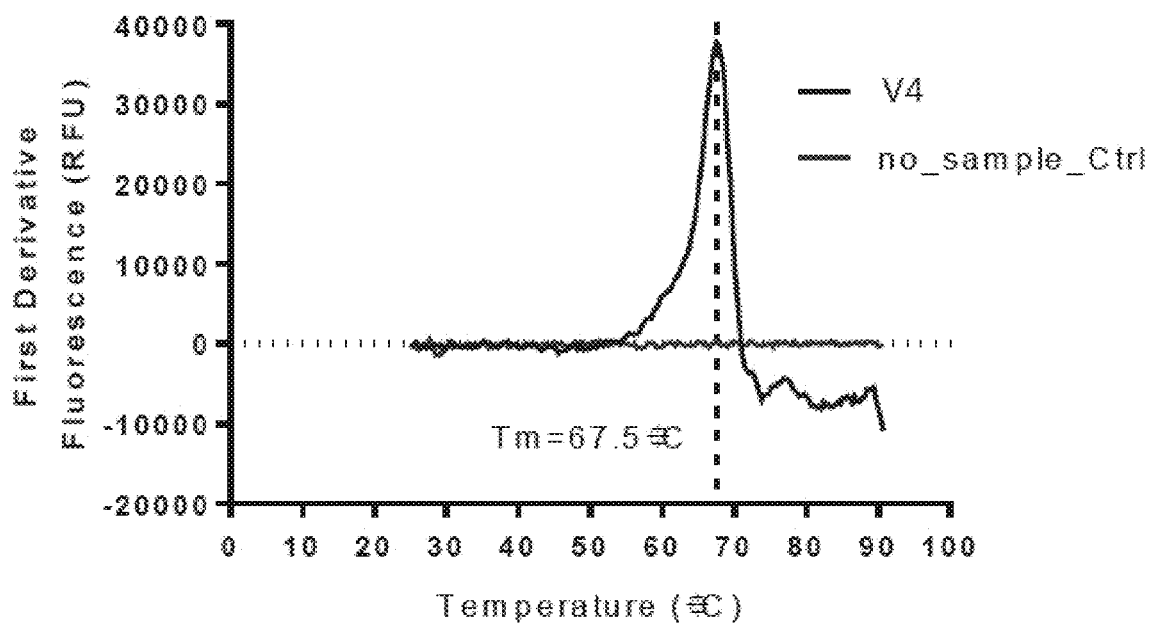
FIG. 9. Graph showing the results of analysis of stability of anti-VISTA antibody clone V4 by Differential Scanning Fluorimetry analysis.

The first derivative of the raw data obtained for Differential Scanning Fluorimetry analysis of the thermostability of antibody clone V4 IgG1 format (i.e. [1] of Example 2.2) is shown in FIG. 9. The Tm was determined to be 67.5° C.

Example 4: Functional Characterisation 4.1 Interaction Between VISTA and VSIG-3

The inventors investigated whether VSIG-3 behaves as a ligand for VISTA by Bio-Layer Interferometry (BLI) analysis using the Octet QK384 system (ForteBio). Briefly, an anti-human Fc capture biosensor was used to capture Fc-tagged VSIG-3 at concentration 100 nM, and association of captured VSIG-3 with VISTA applied at concentrations starting from 3000 nM followed by 3 serial dilutions were measured, and compared to PBS control.

Figure 5:
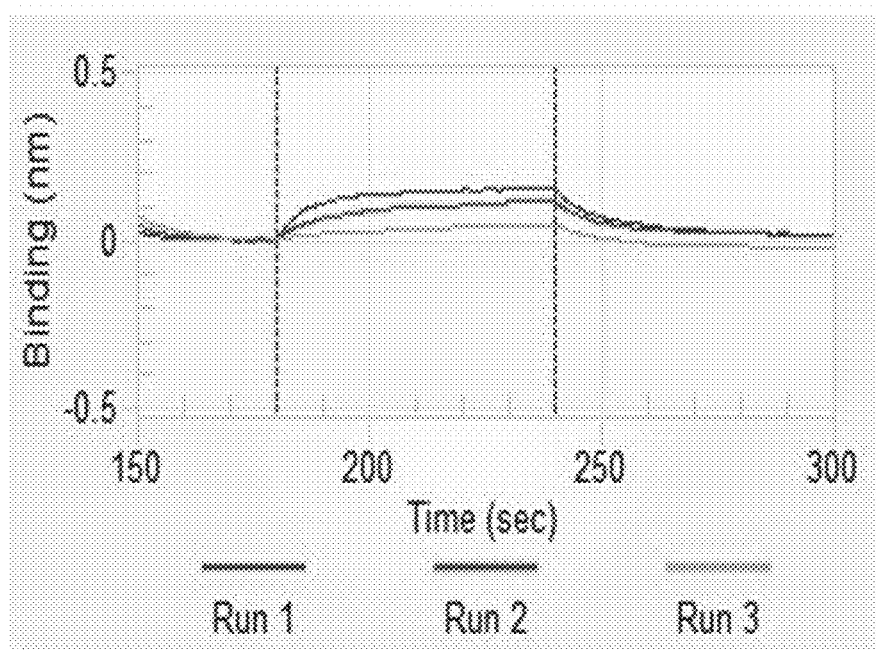
FIG. 5. Sensorgrams showing the results of analysis of binding between VISTA and VSIG-3.

Representative sensorgrams are shown in FIG. 5. The affinity of association between VSIG-3 and VISTA was calculated to be $\sim K_D$=5.28 µM.

The inventors next analysed the ability of anti-VISTA antibodies to inhibit interaction between VISTA and VSIG-3.

Briefly, 96-well plates (Nunc, Denmark) were coated with 1 µg/ml of untagged or Fc-tagged VSIG-3 (R&D Systems, USA) in 1×PBS for 16 h at 4° C. After blocking for 1 h with 1% BSA in TBS at room temperature, 15 µg/ml of VISTA/ human His-tagged fusion protein (Sinobiological Inc, China) was added in the presence or absence of increasing concentrations of anti-VISTA antibody, and incubated for 1 hr at room temperature. Plates were subsequently washed three times with TBS-T and incubated with an HRP-conjugated anti-his secondary antibody for 1 h at room temperature. After washing, plates were developed with colorimetric detection substrate Turbo-TMB (Pierce, USA). The reaction was stopped with 2M $H_2SO_4$, and OD was measured at 450 nM.

Figure 6:
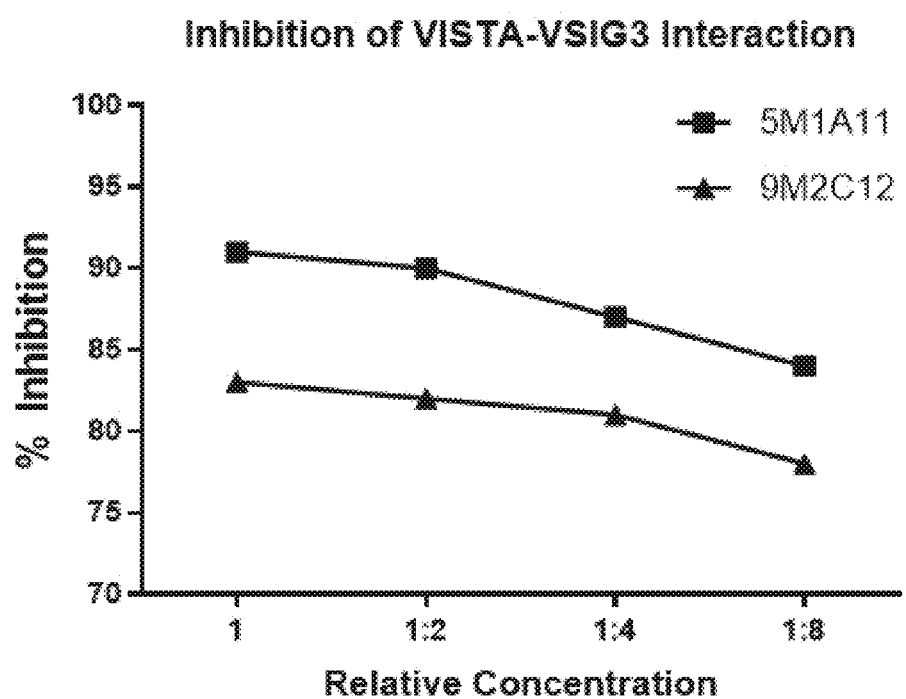
FIG. 6. Graph showing the results of analysis of inhibition of binding between VISTA and VSIG-3 by anti-VISTA antibody clones 5M1-A11 and 9M2-C12.

The results obtained for anti-VISTA antibody clones 5M1-A11 and 9M2-C12 ([10] and [13] of Example 2.2) are shown in FIG. 6. The anti-VISTA antibodies displayed dose-dependent inhibition of interaction between VISTA and VSIG-3.

Figure 32:
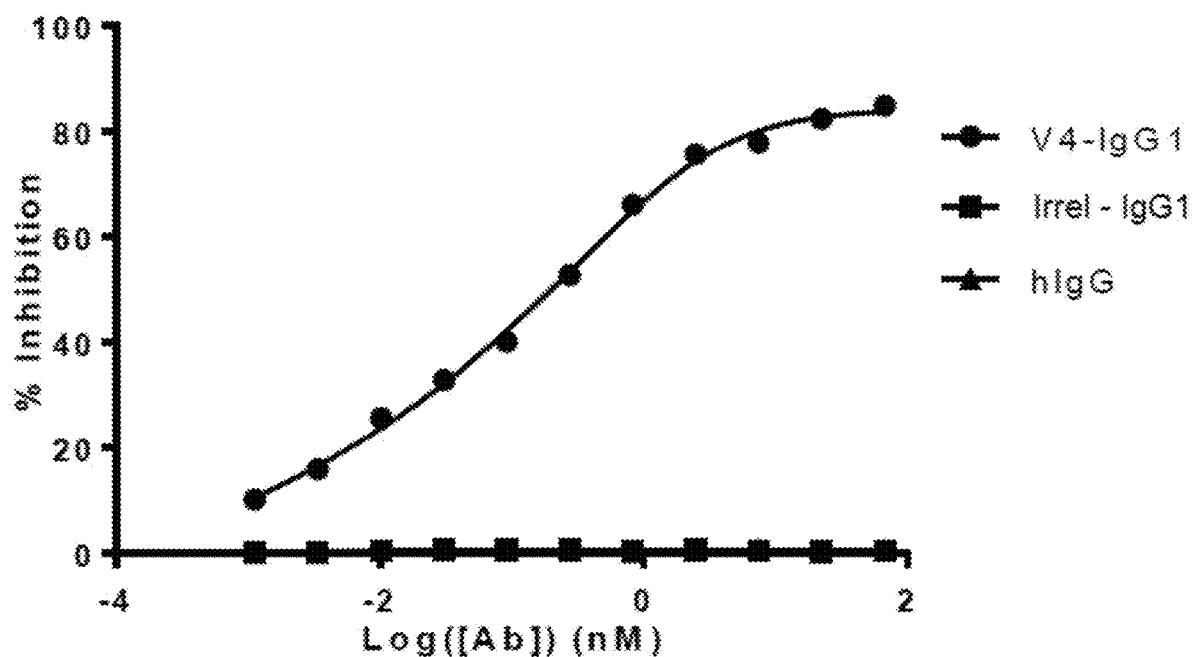
FIG. 32. Graph showing the results of analysis of inhibition of binding between VISTA and VSIG-3 by anti-VISTA antibody 4M2-C12.
Figure 33A:
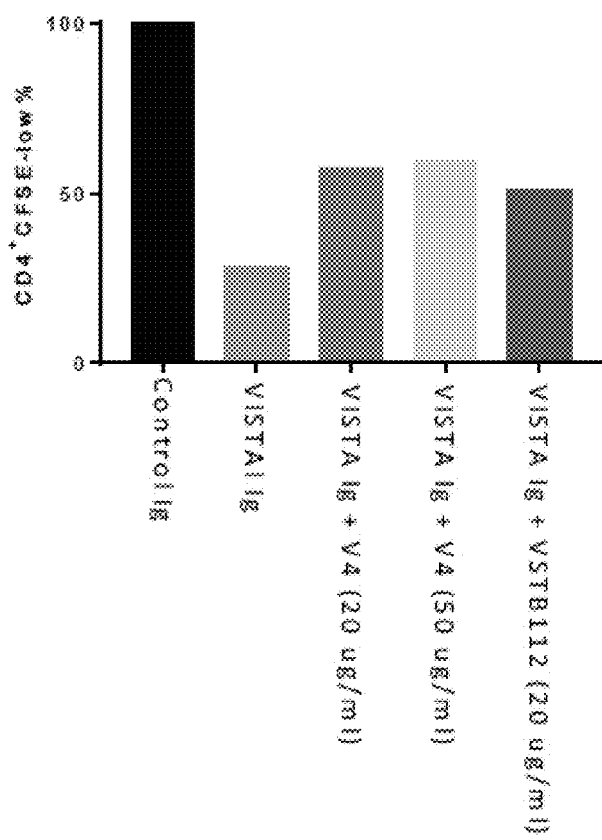
FIGS. 33A to 33D. Bar charts showing the results of analysis of the ability of anti-VISTA antibodies to restore T cell proliferation to T cells treated with VISTA-Ig, as determined by CFSE dilution assay.
Figure 33B:
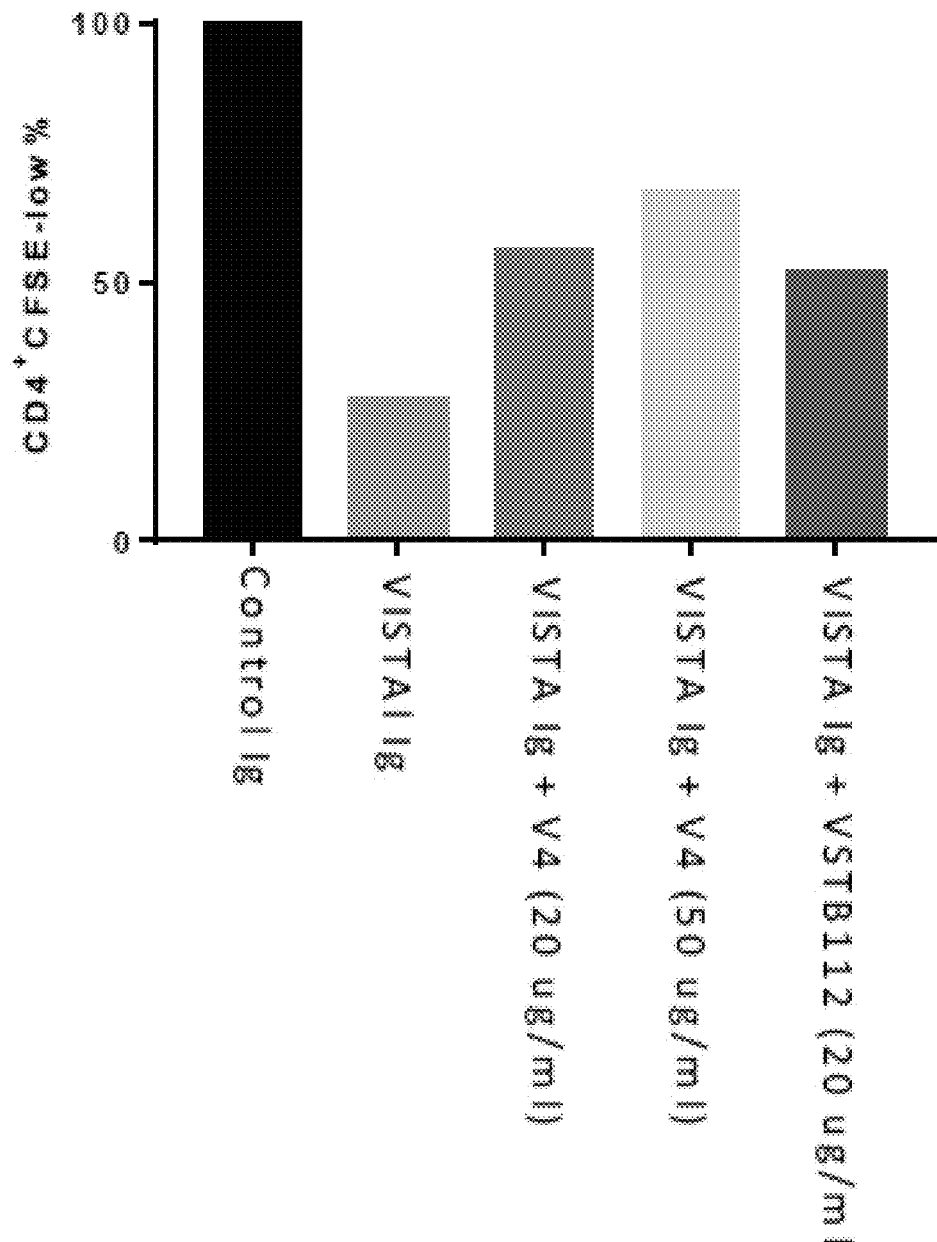
Figure 33C:
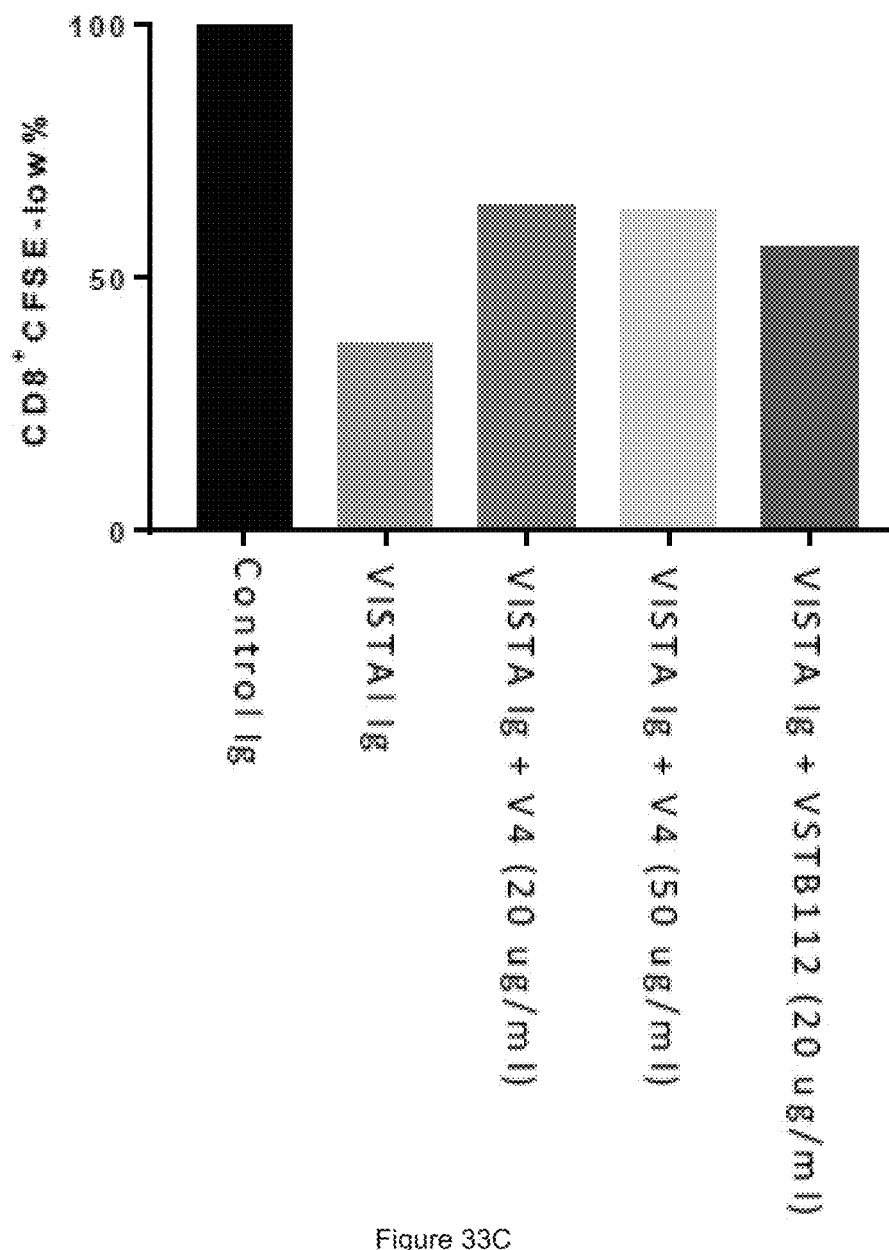
Figure 33D:
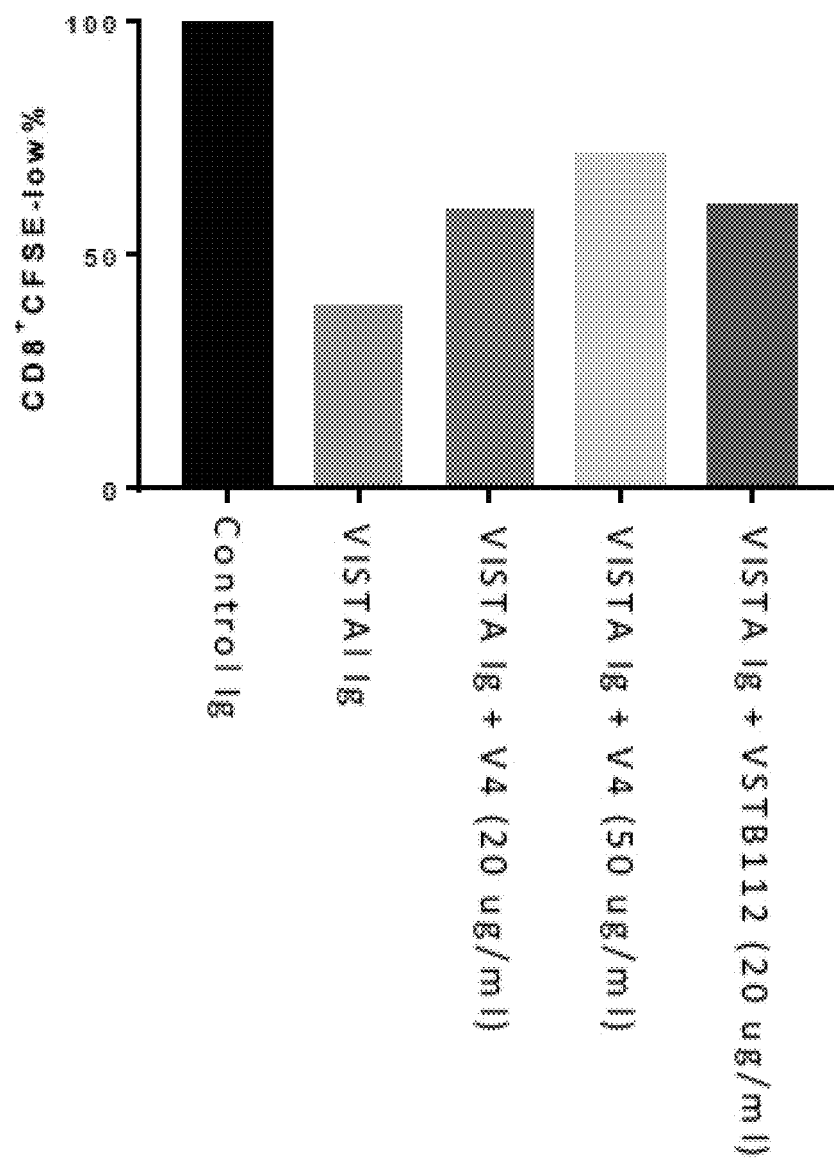

In a further experiment, inhibition by 4M2-C12 IgG1 ([1] of Example 2.2) of interaction between VISTA and VSIG-3 was analysed. Inhibition of VISTA:VSIG-3 interaction by an antibody specific for an irrelevant target antigen and by human IgG1 isotype control were also analysed as control conditions. The results are shown in FIG. 32. 4M2-C12 IgG1 was found to inhibit VISTA:VSIG-3 interaction in a dose-dependent manner.

In a further experiment, inhibition by 4M2-C12 IgG1 ([1] of Example 2.2) of interaction between VISTA and VSIG-3 was analysed in an assay in which VISTA-Fc was used as the capture agent. Briefly, wells of 384-well plates were coated with 30 µl of 0.5 µg/ml of VISTA-Fc for 1 h at room temperature. Plates were washed with PBS-T and blocked for 1 h with 1% BSA in TBS at room temperature. Serial dilutions of 4M2-C12 IgG1 or human IgG1 isotype control antibodies were added to plates, together with 0.3 µg/ml of VISG3-His. After 1 h of incubation at room temperature plates were washed five times with PBS-T, and incubated with goat anti-HIS-HRP for 1 h at room temperature. Plates were washed five times with PBS-T and, developed with Turbo-TMB. The reaction was stopped with 2M $H_2SO_4$, and OD was measured at 450 nM.

Figures 53, 54:
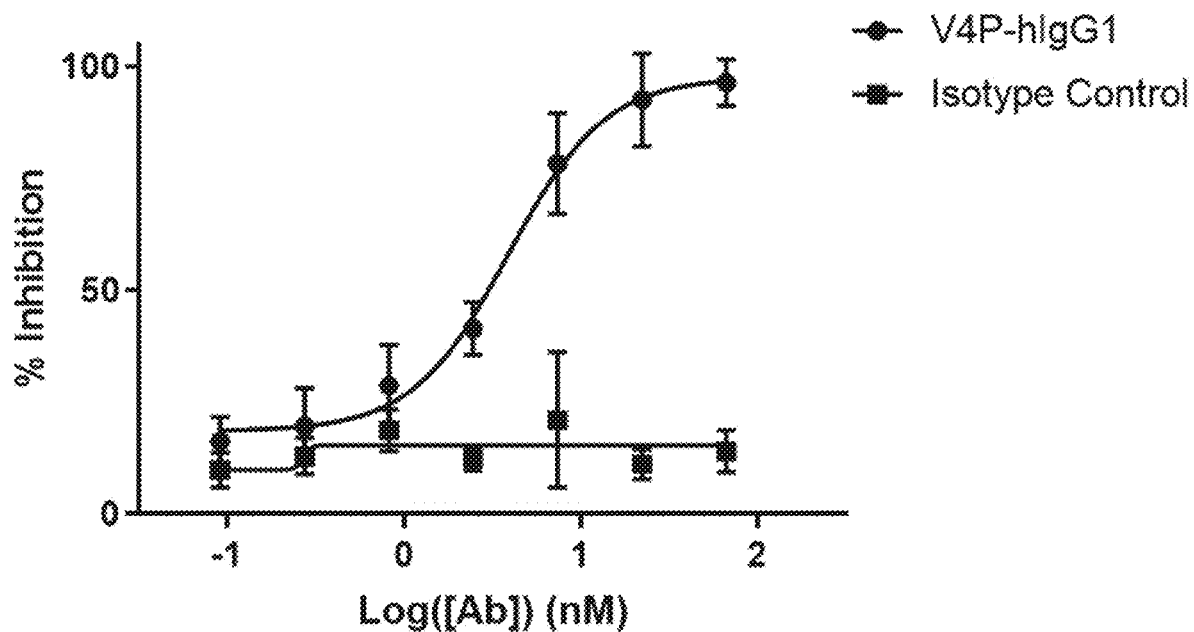
FIG. 53. Table summarising the results of in silico analysis of different anti-VISTA antibodies for safety and immunogenicity.
FIG. 54. Graph showing the results of analysis of inhibition of binding between VISTA and VSIG-3 by anti-VISTA antibody 4M2-C12.

The results are shown in FIG. 54. 4M2-C12 IgG1 was found to inhibit VISTA:VSIG-3 interaction in a dose-dependent manner.

4.2 Interaction Between VISTA and PSGL-1

The inventors next investigated whether PSGL-1 behaves as a ligand for VISTA in a flow cytometry-based assay.

Briefly, 100,000 HEK293T cells modified to overexpress human VISTA protein (by transfection with a construct encoding human VISTA) were co-incubated with 4M2-C12-hIgG1 ([1] of Example 2.2) or an isotype-matched control antibody at concentrations of 20 µg/ml, 40 µg/ml or 80 µg/ml for 15 min at 4° C., in buffer comprising HBSS, 0.5% BSA and 2 mM EDTA pH 6.0. 15 µg/ml of Fc-tagged human PSGL1 (R&D Systems, Cat No: 3345-PS) or the same amount of an Fc-tagged irrelevant antigen was then added to the cells, which were then incubated for a further 45 min at 4° C. Cells were subsequently washed three times with buffer, and then FITC-conjugated anti-PSGL1 antibody (Miltenyi Biotec Cat No: 130-104-706) was added at a dilution factor of (1:11) or Alex488-conjugated anti-Fc antibody was added at a dilution factor of 1:200, and the cells were incubated for 15 min at 4° C. Cells were then washed three times with buffer and analysed by flow cytometry.

Figure 55:
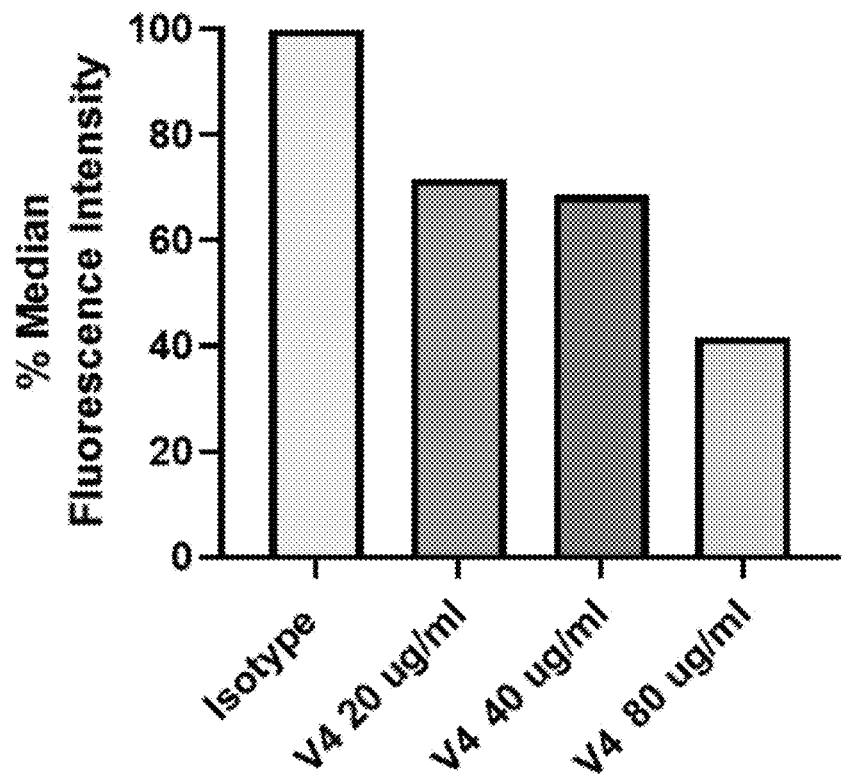
FIG. 55. Bar chart showing the results of analysis of inhibition of binding between VISTA and PSGL-1 by anti-VISTA antibody clone 4M2-C12 (V4).
Figure 56A:
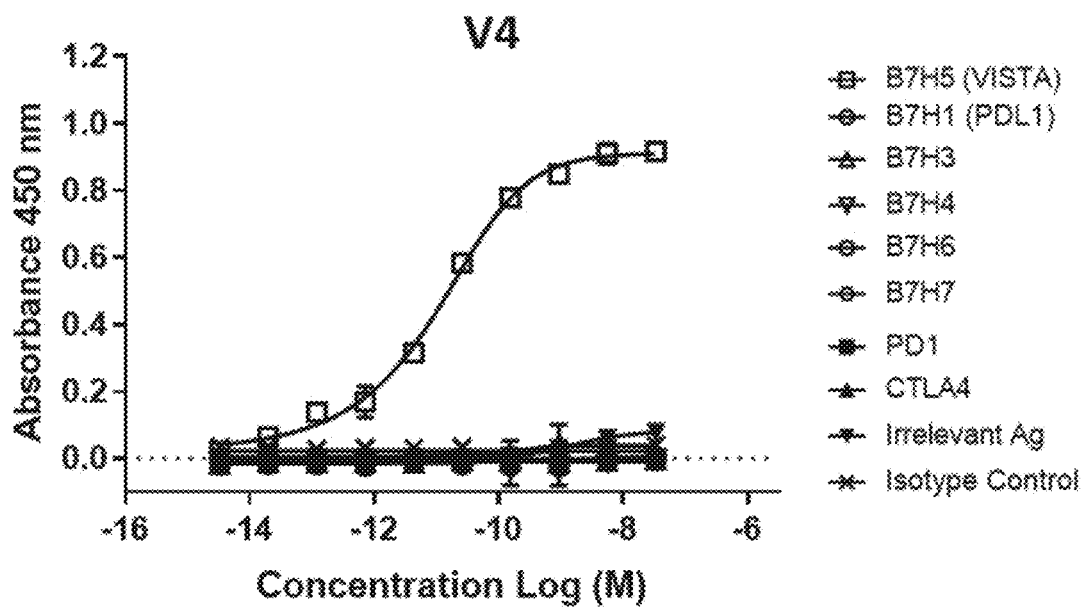
FIGS. 56A to 56G. Concentration-response graphs showing the results of analysis of binding of (56A) V4, (56B) V4-C24, (56C) V4-C26, (56D) V4-C27, (56E) V4-C28, (56F) V4-C30 and (56G) V4-C31 to human VISTA, PD-L1, B7H3, B7H4, B7H6, B7H7, PD-1 and CTLA-4, as determined by ELISA.
Figure 56B:
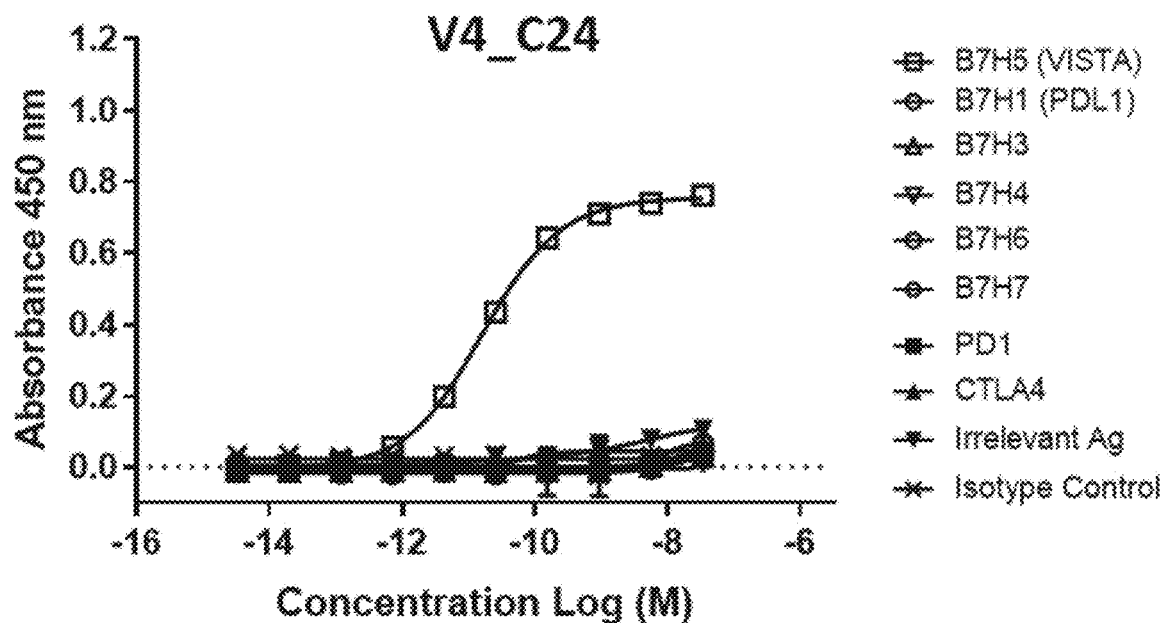
Figure 56C:
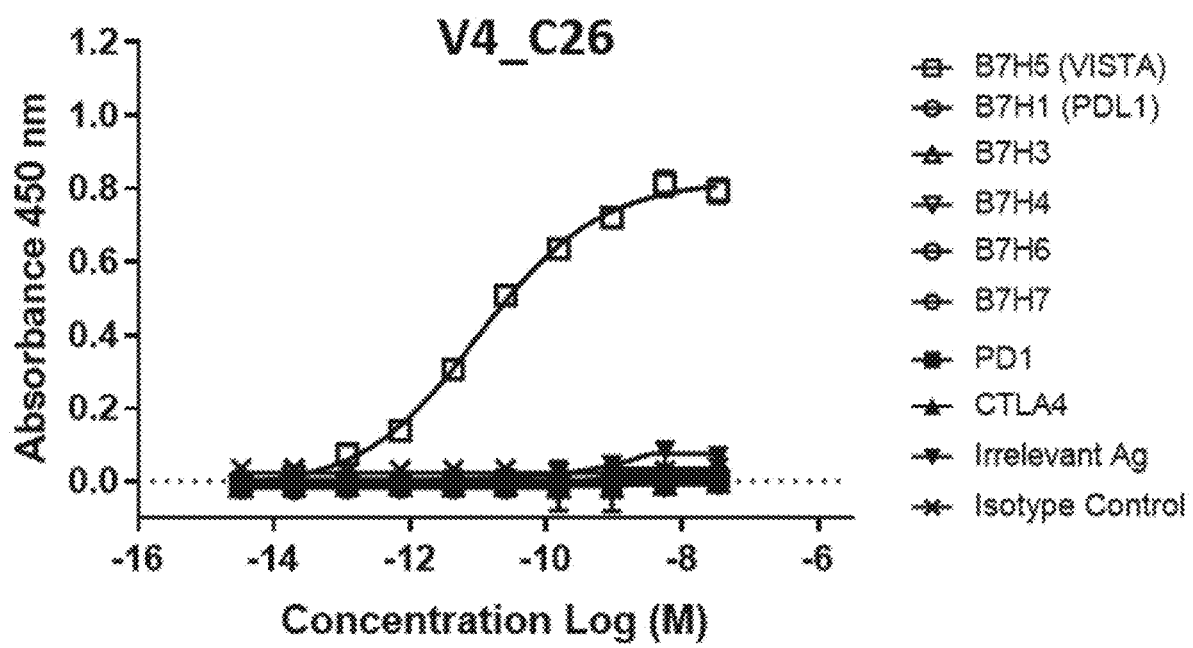
Figure 56D:
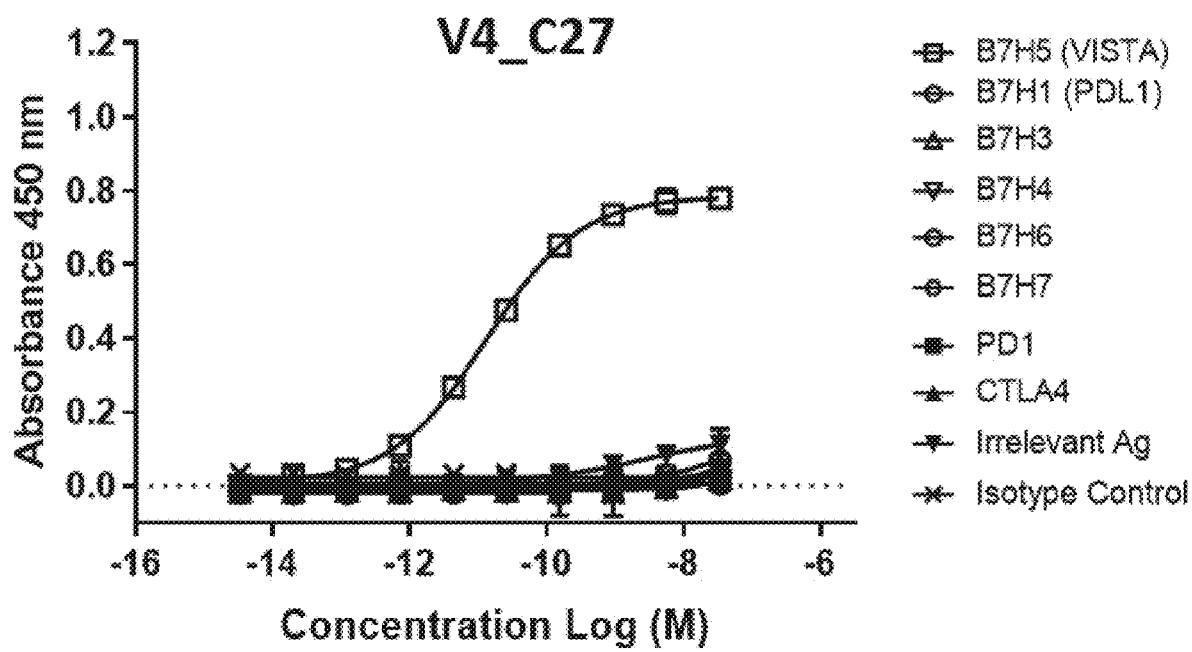
Figure 56E:
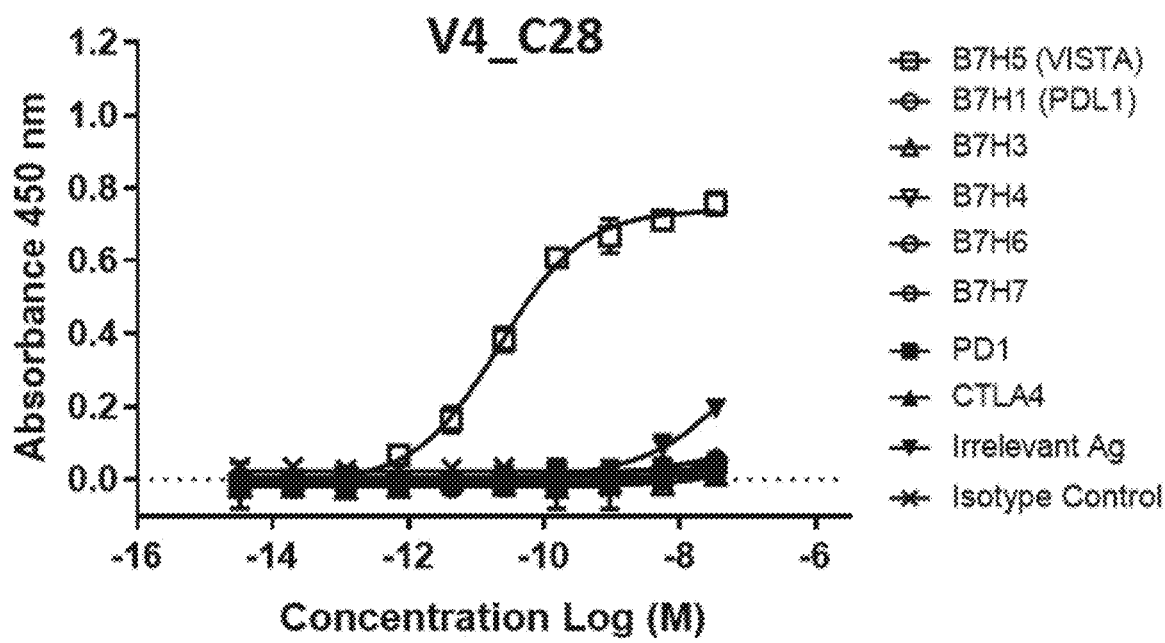
Figure 56F:
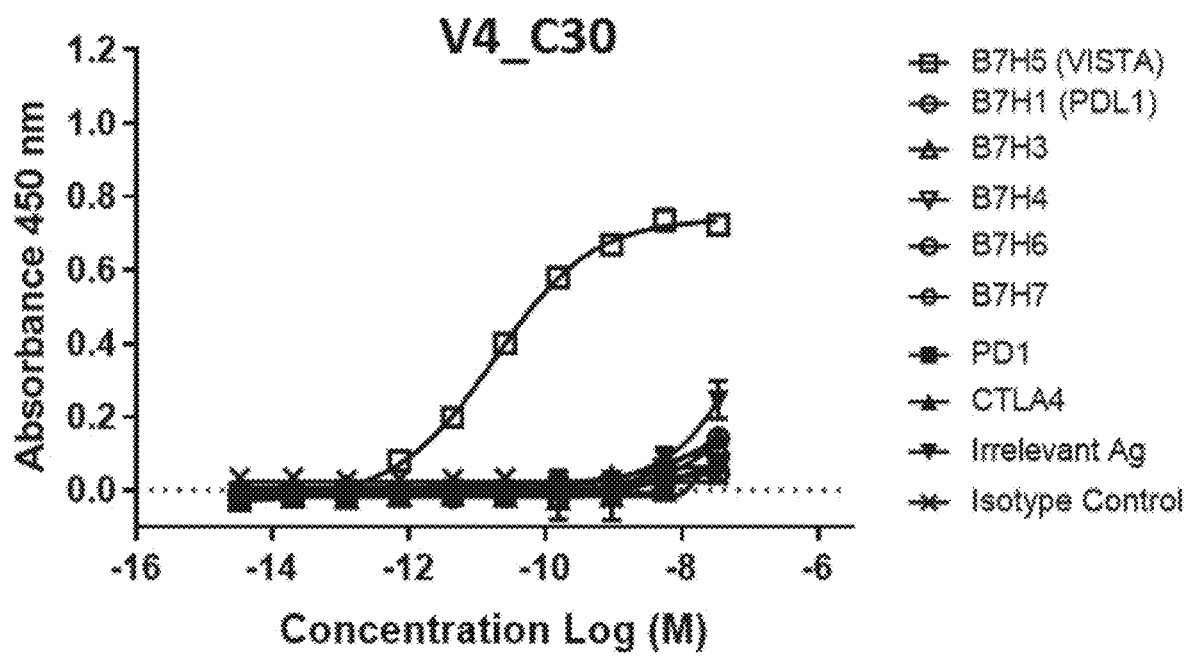
Figure 56G:
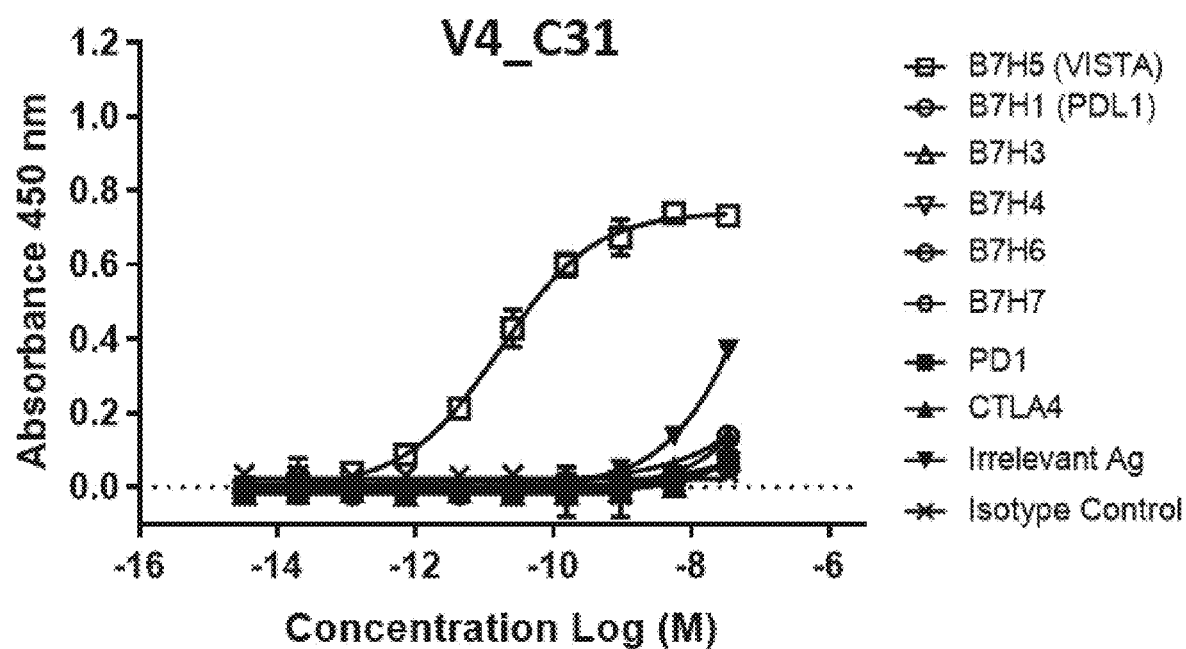

The results are shown in FIG. 55. 4M2-C12-hIgG1 was found to inhibit binding of PSGL-1 to VISTA in a dose-dependent manner.

4.3 Inhibition of VISTA-Mediated Signalling

The inventors investigated whether anti-VISTA antibody clone 13D5p could inhibit VISTA-mediated signalling by analysis using a mixed lymphocyte reaction (MLR) assay.

Figure 7A:
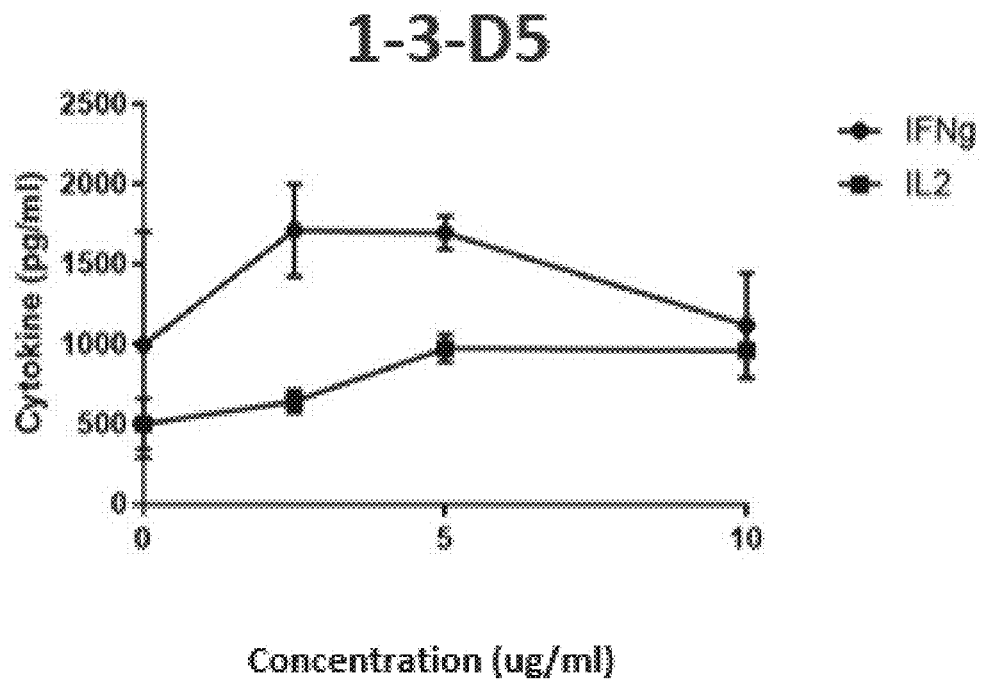
FIGS. 7A and 7B. Graph and bar chart showing results of the analysis of the effect of treatment with anti-VISTA antibody clone 13D5p on production of IFN-γ, IL-2 and IL-17A in a mixed lymphocyte reaction (MLR) assay. (7A) shows the level of cytokine detected in the cell culture supernatant at the end of the assay, and (7B) shows the fold-change ("FC") in the level of the indicated cytokines.
Figure 7B:
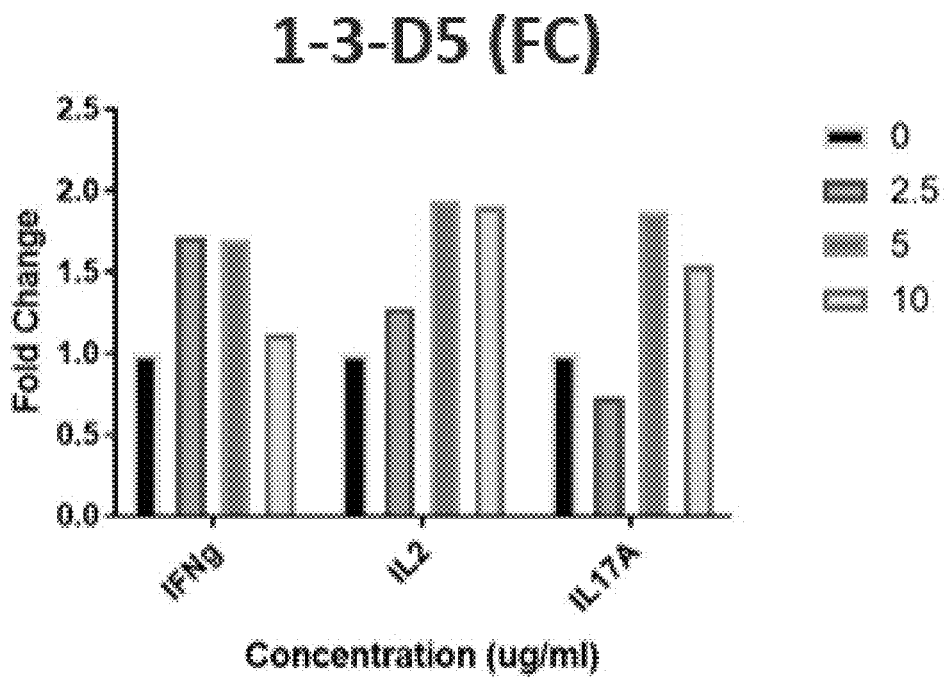
Figure 8A:
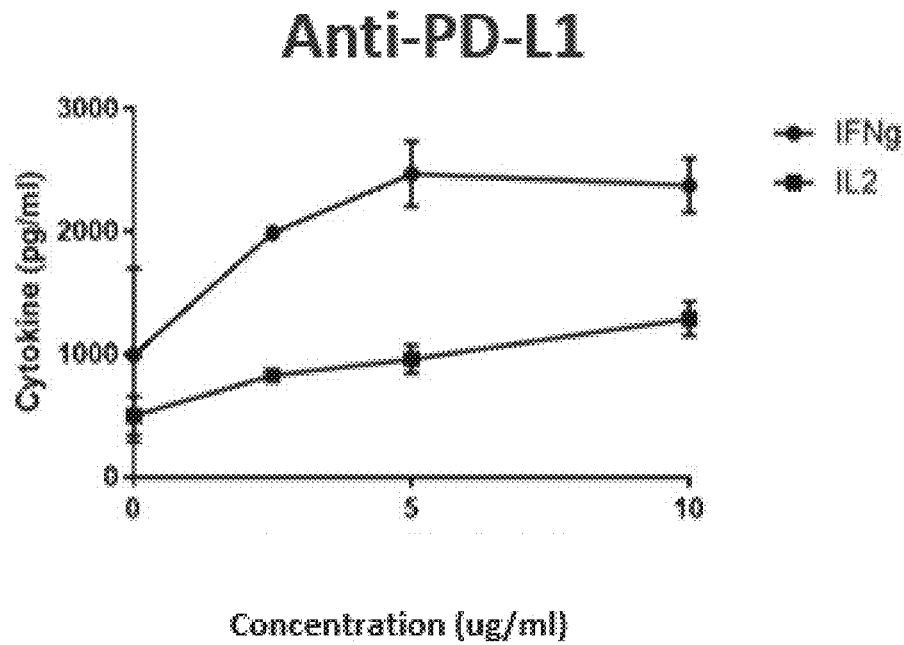
FIGS. 8A and 8B. Graph and bar chart showing results of the analysis of the effect of treatment with anti-PD-L1 antibody clone MIH5 (ThermoFisher Scientific) on production of IFN-γ, IL-2 and IL-17A in a mixed lymphocyte reaction (MLR) assay. (8A) shows the level of cytokine detected in the cell culture supernatant at the end of the assay, and (8B) shows the fold-change ("FC") in the level of the indicated cytokines.
Figure 8B:
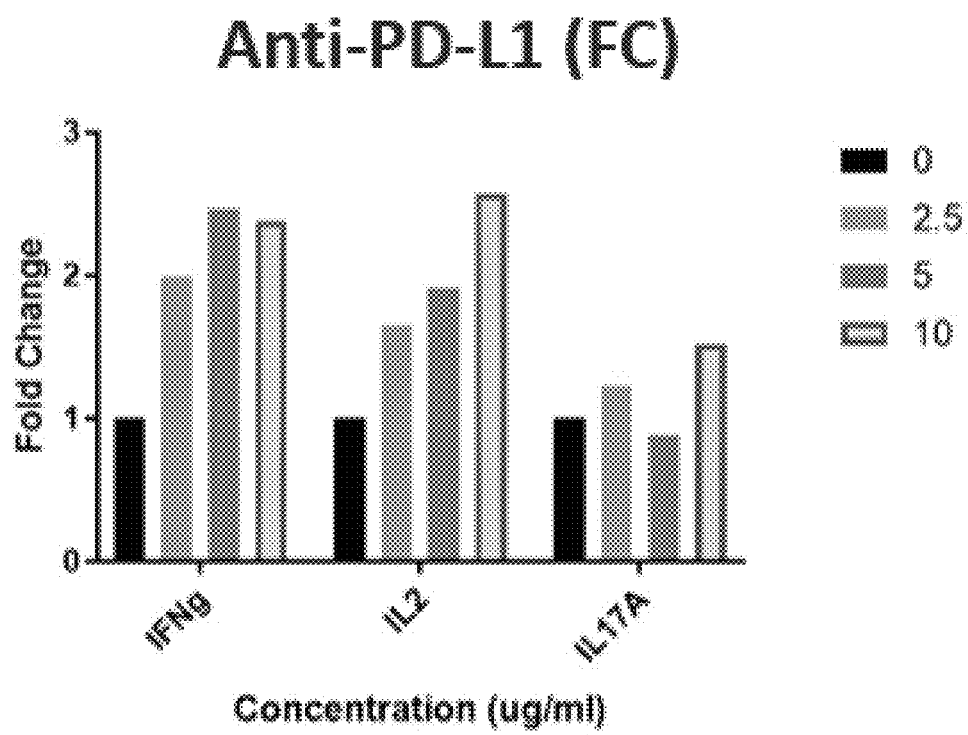

Briefly, PBMCs were isolated from unrelated donors (to obtain stimulator and effector populations) using Septamate kit (Stemcell Technologies, Canada), according to the manufacturer's instructions. Stimulator cells were treated with 50 µg/mL of mitomycin C (Sigma Aldrich, USA) for 20 minutes at 37° C. and used after 5 washes with ix PBS. The stimulator population was seeded at $0.5 \times 10^5$ cells/well and responder population at $1.0 \times 10^5$ cells per well in the presence or absence of increasing concentrations of the test antibody, starting at a highest concentration of 20 µg/ml. After 5 days, the supernatant was harvested and the levels of IL-17, IL-2A and IFN-γ were determined by ELISA following the standard protocol. The results are shown in FIGS. 7A and 7B. Anti-VISTA antibody 13D5p was found to result in an increase in the levels of IL-17, IL-2 and IFN-γ. FIGS. 8A and 8B show results obtained in the same assay using anti-PD-L1 antibody clone MIH5 (ThermoFisher Scientific).

Example 5: Analysis In Vivo

For in vivo studies, 4M2-C12 was produced in mouse IgG2a format. The molecule is a heteromer of the heavy chain polypeptide having the sequence shown in SEQ ID NO:248, and the light chain polypeptide having the sequence shown in SEQ ID NO:250. 4M2-C12 mIgG2a was produced by co-expression of nucleic acids encoding the heavy and light chains polypeptides in CHO cells, and was subsequently purified.

| Antigen-biding molecule | Polypeptides | Antibody |
|---|---|---|
| [17] | 4M2-C12 mIgG2a HC (SEQ ID NO: 248) + 4M2-C12 CL (SEQ ID NO: 250) | 4M2-C12 mIgG2a |

5.1 Pharmacokinetic Analysis

C57BL/6 mice approximately 6-8 weeks old were housed under specific pathogen-free conditions and were treated in compliance with the Institutional Animal Care and Use Committee (IACUC) guidelines.

600 µg anti-VISTA antibody was administered and blood was obtained from 3 mice by cardiac puncture at baseline (−2 hr), 0.5 hr, 6 hr, 24 hr, 96 hr, 168 hr and 336 hr after administration. Antibody in the serum was quantified be ELISA.

The parameters for the pharmacokinetic analysis were derived from a non-compartmental model: maximum concentration ($C_{max}$), AUC (0-336 hr), AUC (0-infinity), Half-life (t½), Clearance (CL), Volume of distribution at steady state ($V_{ss}$).

Figure 12:
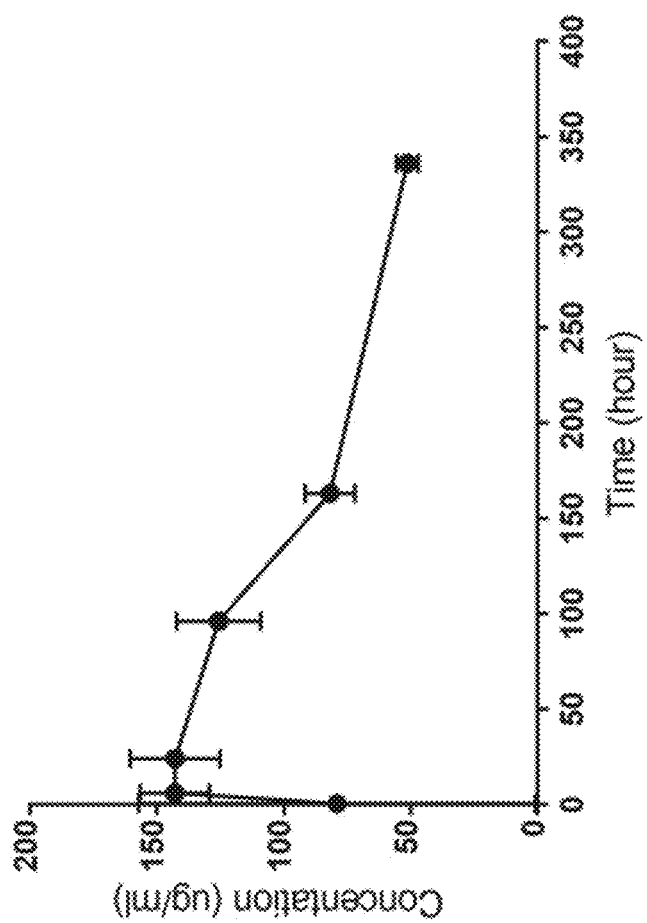
FIG. 12. Graph and table showing the results of the pharmacokinetics analysis of anti-VISTA antibody clone V4 by ELISA analysis of antibody serum.

The results obtained for anti-VISTA antibody clone V4 ([17] of Example 5) are shown in FIG. 12. This antibody clone was found to have a half-life of 11.7 days.

5.2 Analysis of Efficacy to Treat Cancer In Vivo

Female BALB/c or C57BL/6 mice approximately 6-8 weeks old were purchased from InVivos (Singapore). Animals were housed under specific pathogen-free conditions and were treated in compliance with the Institutional Animal Care and Use Committee (IACUC) guidelines.

Cell lines used in the studies included LL2 cells (Lewis Lung carcinoma), 4T1 cells (breast cancer), CT26 cells (colon carcinoma), Clone-M3 cells (melanoma) and EL4 cells (T cell leukemia/lymphoma) obtained from ATCC. B16-BL6 cells (melanoma) were obtained from Creative Bioarray. The cell lines were maintained in accordance with the supplier's instructions; LL2 cells, B16-BL6 cells and EL4 cells were cultured in DMEM supplemented with 10% fetal bovine serum (FBS) and 1% Pen/Strep, and 4T1 cells and CT26 cells were cultured in RPMI-1640 supplemented with 10% FBS and 1 and 1% Pen/Strep. Clone-M3 cells were grown in F12-K medium supplemented with 2.5% FBS, 15% Horse serum and 1% Pen/Strep. All cells were cultured at 37° C. in a 5% $CO_2$ incubator.

Syngeneic tumor models were generated by injecting either LL2 ($2 \times 10^5$), 4T1 ($5 \times 10^5$), CT26 ($1 \times 10^5$-$1 \times 10^6$), Clone-M3 ($5 \times 10^5$), EL4 ($2 \times 10^5$) or B16-BL6 ($1 \times 10^5$) cells subcutaneously into the right flank of mice. 3 days post-implantation anti-VISTA antibodies were administered intraperitoneally every 3 days for a total of 6 doses. Control groups received vehicle treatment at the same dose interval.

Tumor volume was measured 3 times a week using a digital caliper and calculated using the formula [L×W2/2]. Study End point was considered to have been reached once the tumors of the control arm measured >1.5 cm in length.

5.2.1 CT26 Cell Model

Figure 13:
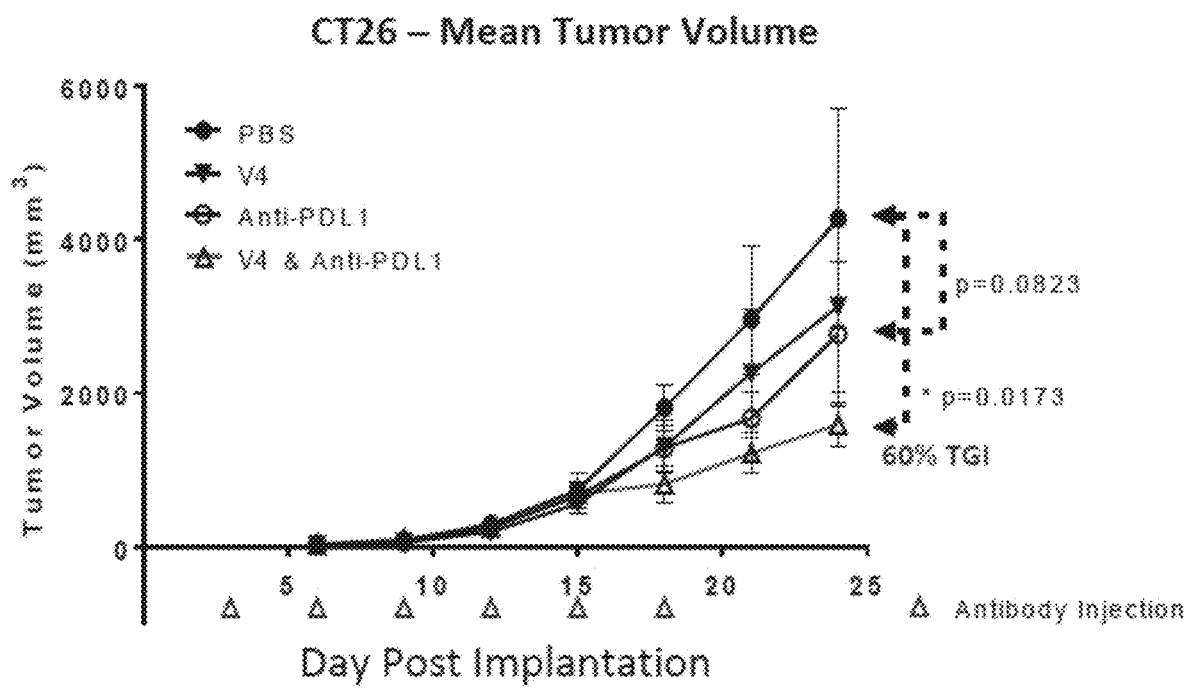
FIG. 13. Graph showing the results of the analysis of anti-cancer activity of anti-VISTA antibody clone V4 in vivo in a syngeneic cell-line derived mouse model of colon carcinoma.

FIG. 13 shows the results obtained in an experiment wherein the anti-cancer effect of anti-VISTA antibody clone V4 ([17] of Example 5) was compared to that of anti-PD-L1 antibody clone 10F.9G2 in a CT26 cell-line derived syngeneic mouse colon carcinoma model. The model was established by subcutaneous injection of 100,000 CT26 cells into the right flank of Balb/c mice (n=8 mice per treatment group).

V4 or anti-PD-L1 antibody were administered at 300 µg per dose every 3 days from day 3. A combination treatment of 300 µg V4+300 µg anti-PD-L1 antibody per dose was also included in the analysis.

Anti-VISTA antibody clone V4 was found to be highly potent in this model, and capable of inhibiting tumor growth by ~60%.

Figure 39:
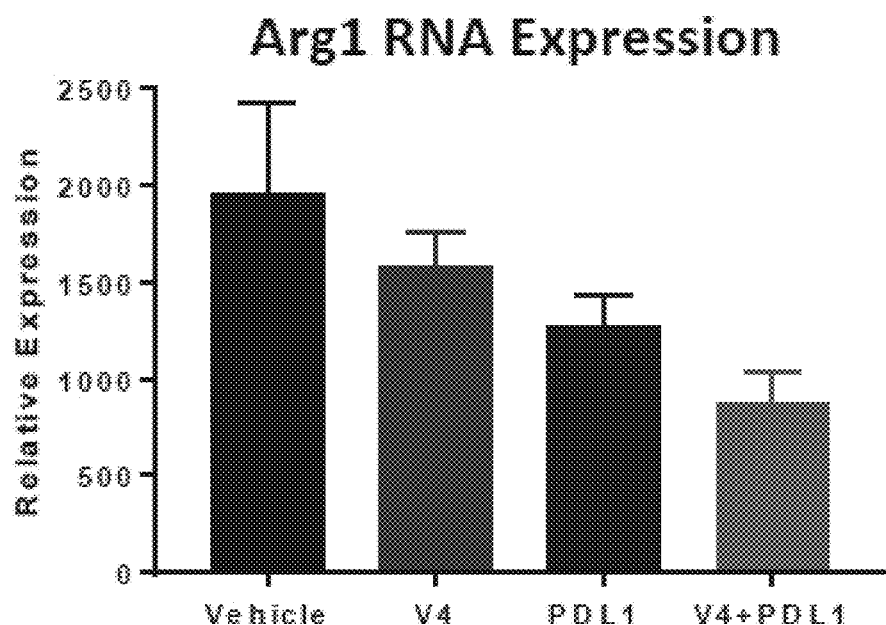
FIG. 39. Bar chart showing the level of Arg1 RNA expression in tumors at day 21 of a cell-line derived mouse model of colon carcinoma, obtained from mice treated with PBS (Vehicle), anti-VISTA antibody 4M2-C12 mIgG2a (V4), anti-PD-L1 antibody (PDL1) or combination treatment with 4M2-C12 mIgG2a and anti-PD-1 antibody (V4+PDL1).

At day 21 tumors were harvested and evaluated for Arg1 RNA expression by RNA-seq analysis, according to the method described in Newman et al. Nat Methods. (2015) 12(5):453-457. The results are shown in FIG. 39. Treatment with 4M2-C12 was associated with a significant reduction in Arg1 expression in tumors at day 21.

In another experiment a CT26 cell-line derived syngeneic mouse colon carcinoma model was established by subcutaneous injection of 100,000 CT26 cells into the right flank of Balb/c mice (n=8 mice per treatment group), and mic were treated by administration of 300 µg per dose every 3 days from day 3 of an isotype control antibody, anti-PD-L1 antibody clone 10F.9G2, anti-VISTA antibody clone V4 ([17] of Example 5), anti-TIGIT antibody clone 1G9, anti-LAG-3 antibody clone C9B7W, anti-TIM-3 antibody clone RMT3-23, or combination treatments of 300 µg anti-PD-L1 antibody clone 10F.9G2 with 300 µg of each of the other of antibodies per dose was also included in the analysis.

Figure 14:
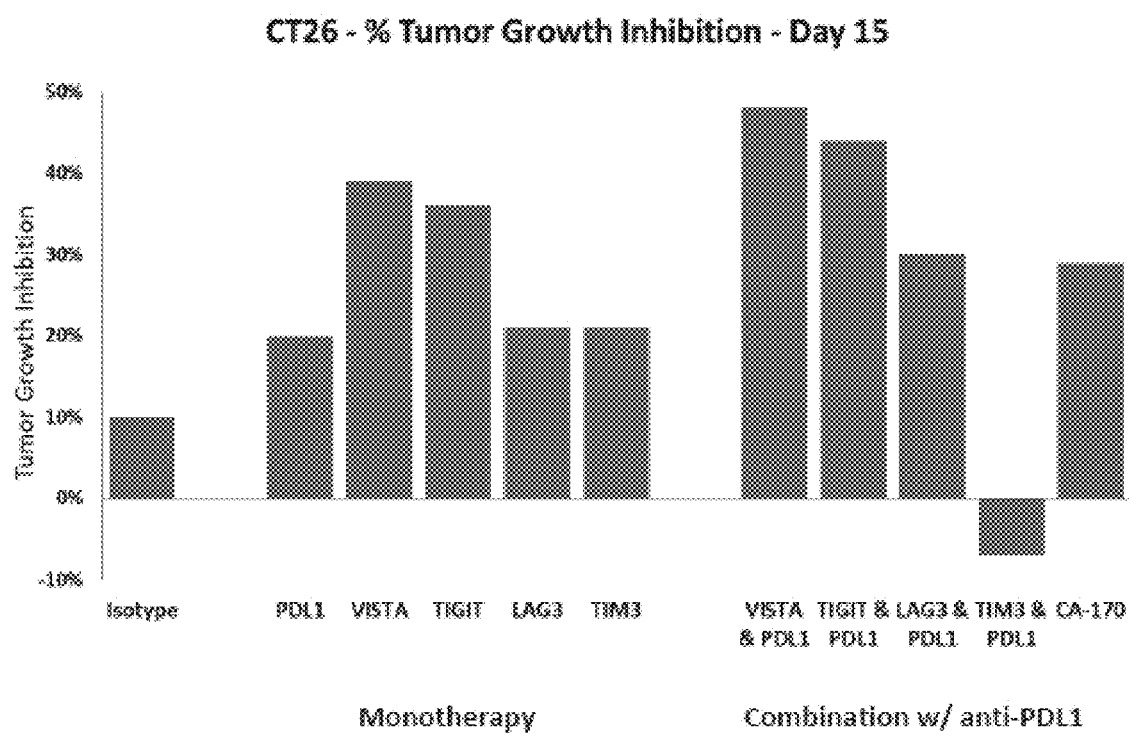
FIG. 14. Bar chart showing inhibition of tumor growth at day 15 in a syngeneic cell-line derived mouse model of colon carcinoma following treatment with monotherapy or combination therapy targeting the indicated checkpoint molecules. The antibodies used in this study were as follows: anti-VISTA=clone V4, anti-PD-L1=clone 10F.9G2, anti-TIGIT=clone 1G9, anti-LAG-3=clone C9B7W, and anti-TIM-3=clone RMT3-23.

The results of the calculated inhibition of tumor growth detected at day 15 are shown in FIG. 14. In this experiment anti-VISTA antibody clone V4 was found to be a more potent inhibitor of tumor growth than any other monotherapies directed against immune checkpoint molecules, and was found to perform better in combination with anti-PD-L1 therapy.

The inventors performed a further experiment in which CT26 tumors were established in the same way, and mice were then administered biweekly with 300 µg anti-VISTA antibody clone V4, 200 µg anti-PD-L1 antibody clone 10F.9G2, 300 µg anti-VISTA antibody clone V4+200 µg anti-PD-L1 antibody clone 10F.9G2, or PBS as a control condition. At the end of the experiment tumors were analysed by RNA-Seq to determine the relative numbers of MDSCs, CD8+ T cell and Tregs, according to the method described in Newman et al. Nat Methods. (2015) 12(5):453-457 which is hereby incorporated by reference in its entirety.

Figure 15:
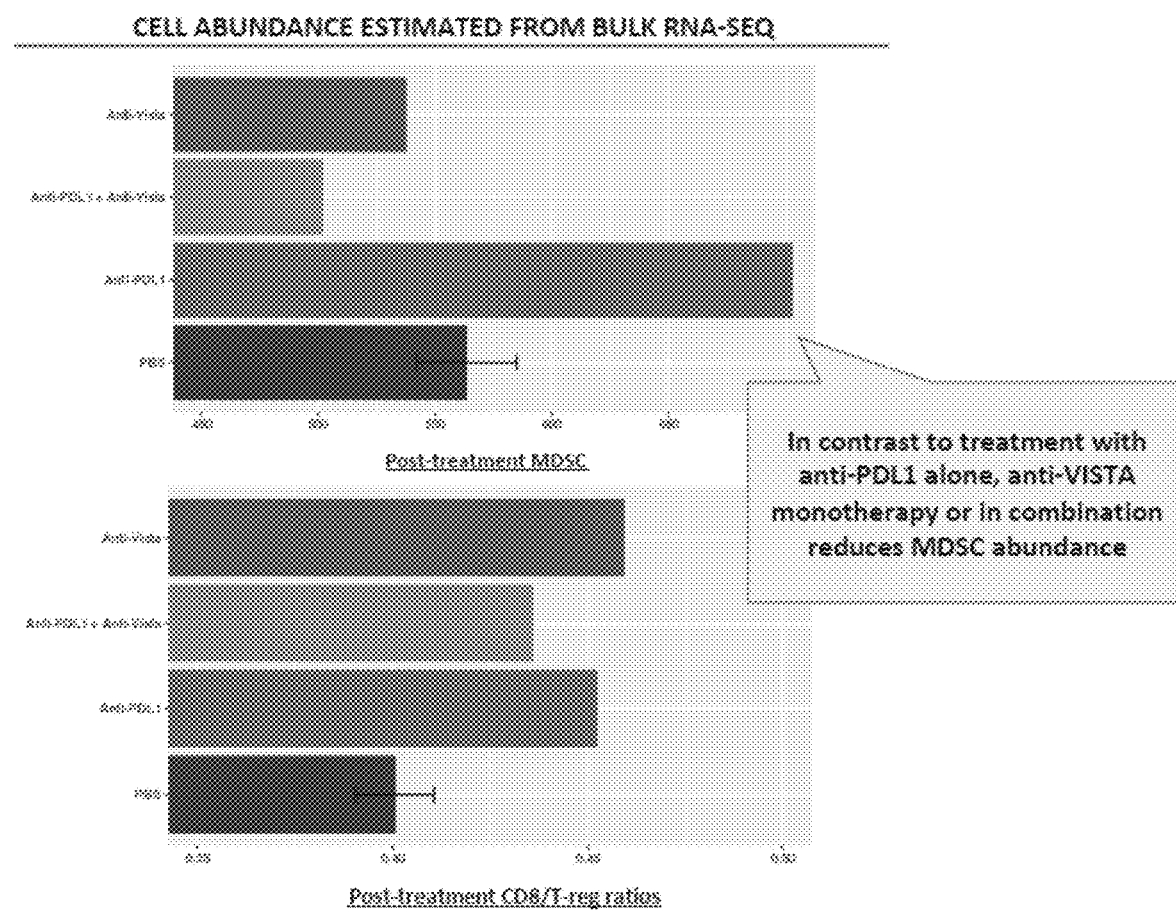
FIG. 15. Bar chart showing the number of MDSCs per 100,000 cells, and the ratio of CD8+ T cell:Tregs, in the tumor bulk of a syngeneic cell-line derived mouse model of colon carcinoma, as determined by RNA-Seq analysis of bulk tumor following treatment with anti-VISTA antibody clone V4 alone, anti-PD-L1 antibody clone 10F.9G2 alone, combination treatment with anti-VISTA antibody clone V4 and anti-PD-L1 antibody clone 10F.9G2, or treatment with PBS (negative control).

The results are shown in FIG. 15. Treatment with anti-VISTA antibody clone V4 (either alone or in combination with anti-PD-L1 treatment) was found to reduce the numbers of MDSCs, and to increase the CD8 T cell: Treg ratio. Analysis of changes in gene expression in the tumor microenvironment associated with anti-VISTA antibody treatment also revealed upregulation of expression of genes involved in phagocytic processes (e.g. actin filament-based movement), and downregulation of expression of arginase 1 (resulting in a less immunosuppressive environment).

In a further experiment, a CT26 cell-line derived syngeneic mouse colon carcinoma model was established in Balb/C mice as described above, and mice were administered from day 3 and every 3 days with: (i) 600 µg anti-VISTA antibody clone 13D5-1, (ii) 200 µg anti-PD-L1 antibody clone 10F.9G2, (iii) 600 µg anti-VISTA antibody clone 13D5-1+200 µg anti-PD-L1 antibody clone 10F.9G2, or (iv) an equal volume of PBS (as a negative control).

Figure 22:
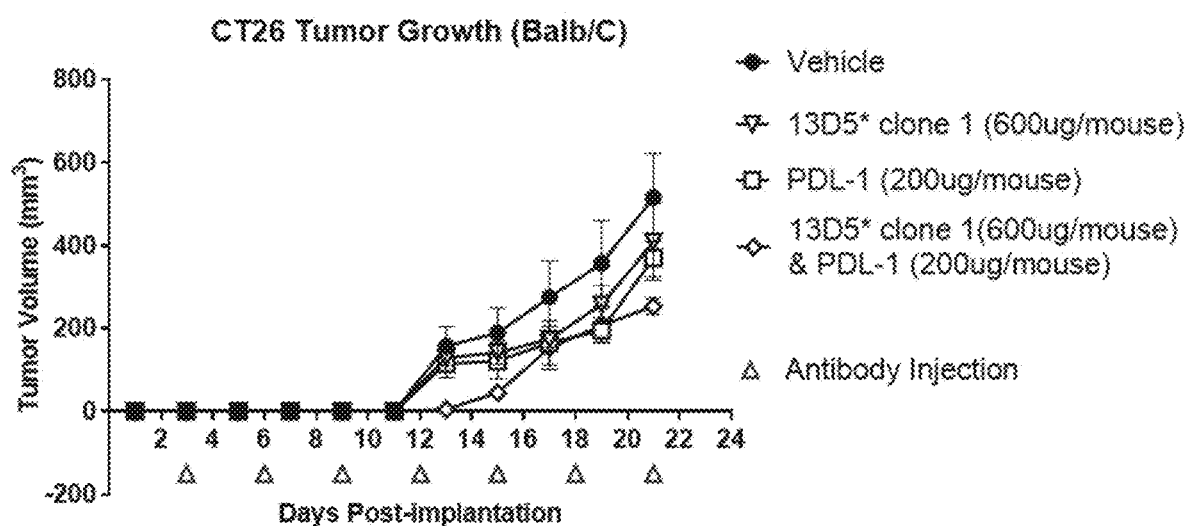
FIG. 22. Graph showing the results of the analysis of anti-cancer activity of anti-VISTA antibody clone 13D5-1 in vivo in a cell-line derived mouse model of colon carcinoma, alone or in combination with anti-PD-L1.

The results are shown in FIG. 22. Anti-VISTA antibody clone 13D5-1 (either alone or in combination with anti-PD-L1 treatment) was found to be able to inhibit tumor growth in this model.

5.2.2 LL2 Cell Model

The LL2 model was established by subcutaneous injection of 200,000 LL2 cells into the right flank of Balb/c mice (n=8 mice per treatment group), and mice were subsequently administered biweekly with 600 µg anti-VISTA antibody clone V4 ([17] of Example 5) or an equal volume of vehicle as a negative control.

Figure 16:
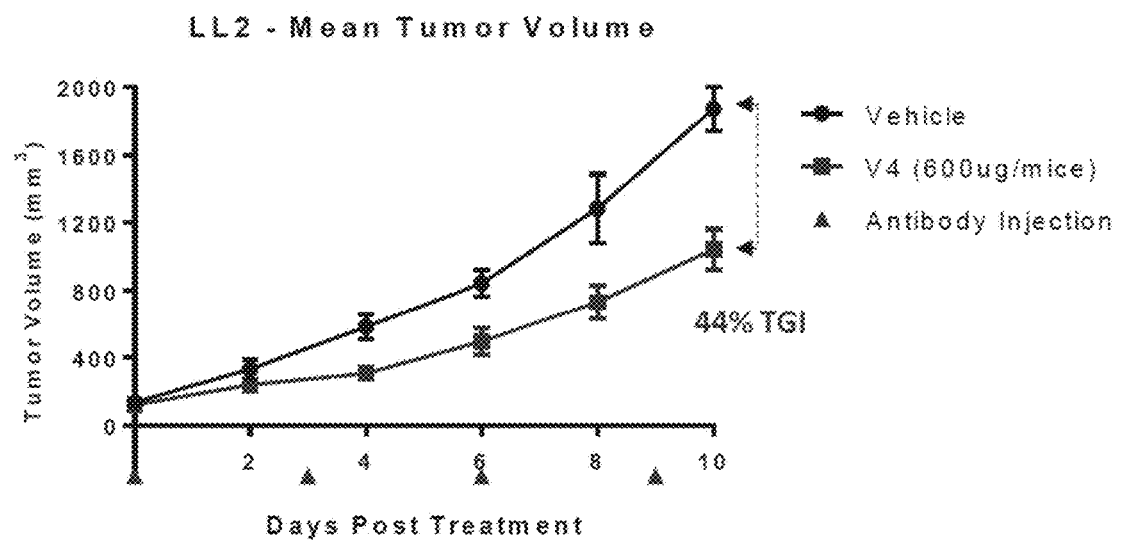
FIG. 16. Graph showing the results of the analysis of anti-cancer activity of anti-VISTA antibody clone V4 in vivo in a syngeneic cell-line derived mouse model of Lewis lung carcinoma.

The results of the experiment are shown in FIG. 16. Anti-VISTA antibody clone V4 was found to be highly potent in this model—capable of inhibiting tumor growth by 44%.

5.2.3 B16-BL6 Cell Model

The B16-BL6 model was established by subcutaneous injection of 200,000 B16-BL6 cells into the right flank of C57BL/6 mice (n=8 mice per treatment group), and mice were subsequently administered biweekly (for a total of 6 doses) with 600 µg anti-VISTA antibody clone V4 ([17] of Example 5), 200 µg of anti-PD-1 antibody RMP1-14 (Bio X Cell), 600 µg anti-VISTA antibody clone V4+200 µg anti-PD-1 antibody, or an equal volume of vehicle as a negative control.

Figure 17:
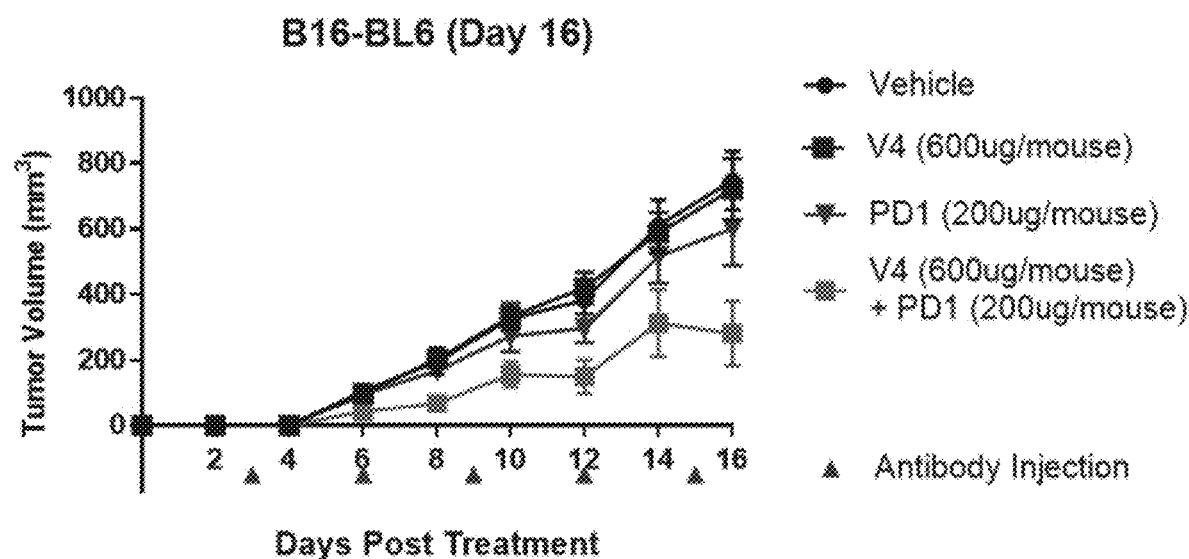
FIG. 17. Graph showing the results of the analysis of anti-cancer activity of anti-VISTA antibody clone V4 in vivo in a syngeneic cell-line derived mouse model of melanoma, as a monotherapy, or in combination with an anti-PD-1 antibody RMP1-14 (Bio X Cell).

The results of the experiment are shown in FIG. 17. Anti-VISTA antibody clone V4 was found to be highly potent in combination with anti-PD-1 antibody treatment in this model.

5.2.4 4T1 Cell Model

The 4T1 cell-line derived syngeneic mouse mammary carcinoma model was established in Balb/c mice by subcutaneous injection of 250,000 4T1 cells into the right flank.

Mice were subsequently administered from day 3 and every 3 days (for a total of 6 doses) with either 300 or 600 µg of anti-VISTA antibody clone 13D5-1, isotype control antibody or an equal volume of vehicle as a negative control.

Figure 23:
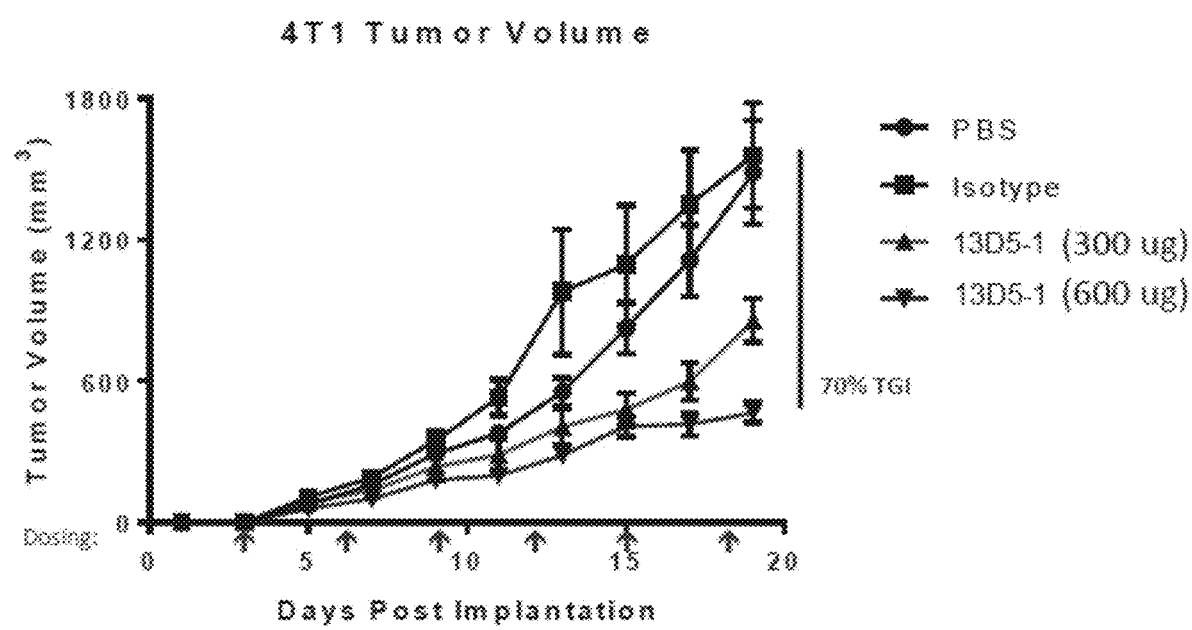
FIG. 23. Graph showing the results of the analysis of anti-cancer activity of anti-VISTA antibody clone 13D5-1 in vivo in a cell-line derived mouse model of mammary carcinoma.
Figure 24:
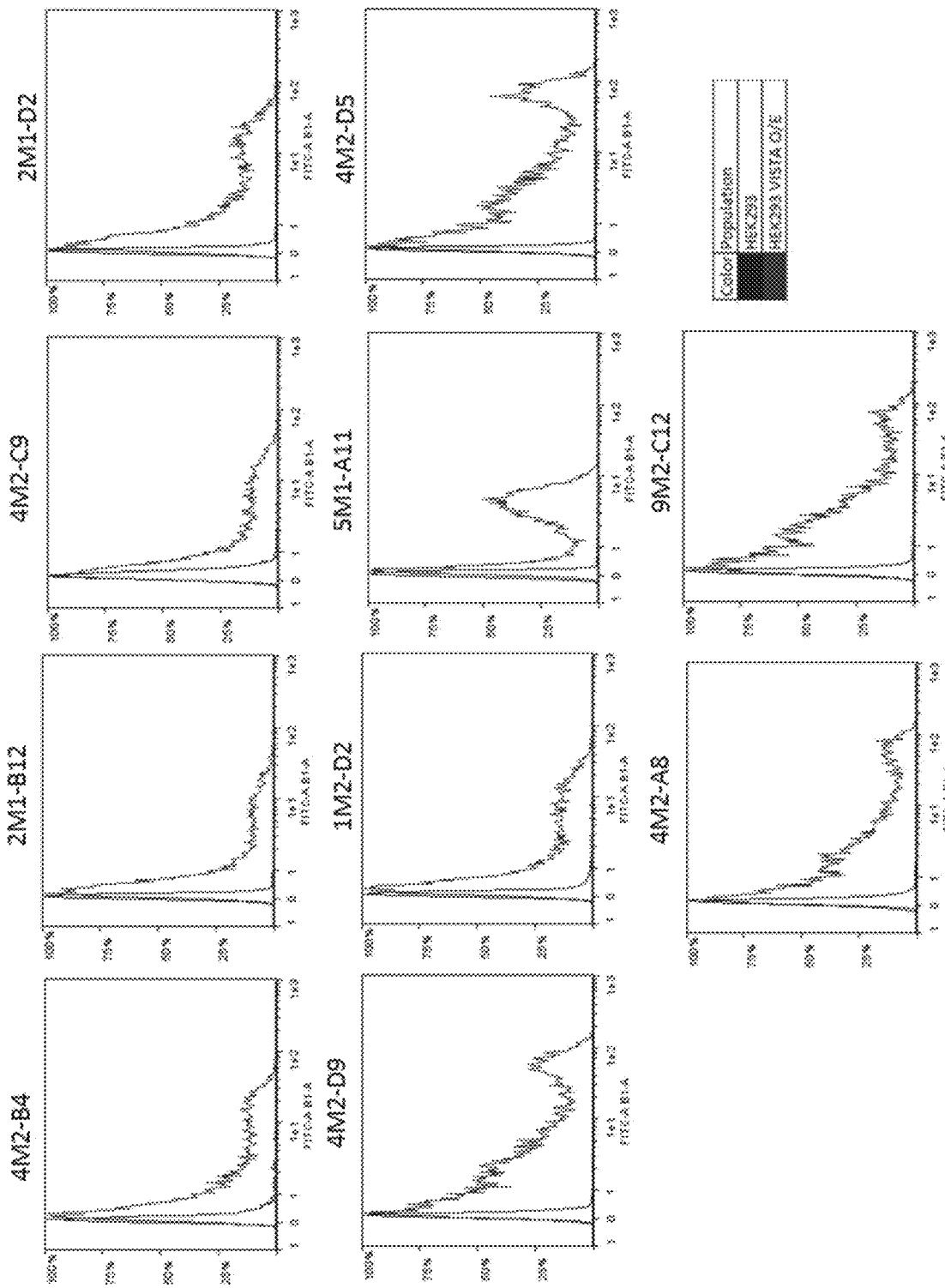
FIG. 24. Histograms showing staining of cells by anti-VISTA antibodies as determined by flow cytometry. Histograms show staining of HEK293 cells (which do not express VISTA), or HEK293 VISTA overexpressing cells (HEK293 VISTA O/E) by anti-VISTA antibody clones 4M2-B4, 2M1-B12, 4M2-C9, 2M1-D2, 4M2-D9, 1M2-D2, 5M1-A11, 4M2-D5, 4M2-A8 and 9M2-C12.
Figure 25A:
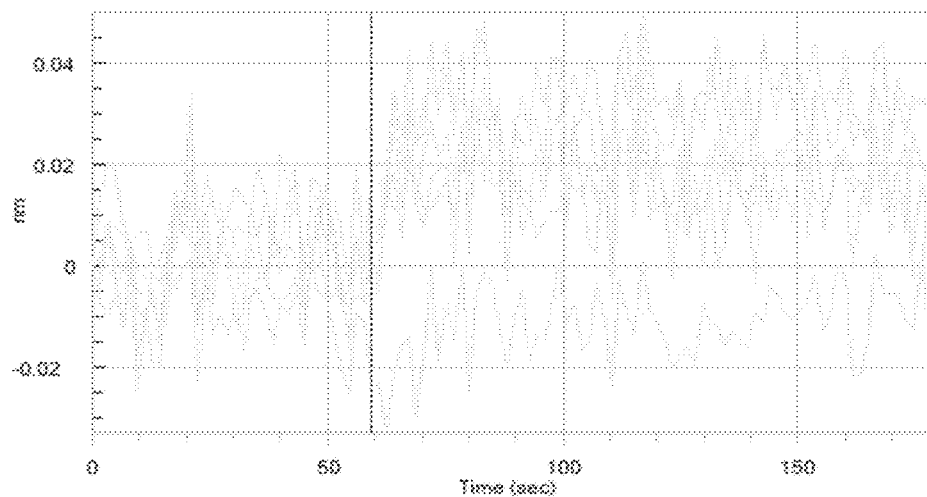
FIGS. 25A to 25D. Sensorgrams showing the results of analysis of binding of 4M2-C12 mIgG1 to 30 (25A) mouse FcγRIV, (25B) mouse FcγRIII, (25C) mouse FcγRIIb, and (25D) mouse FcRn.
Figure 25B:
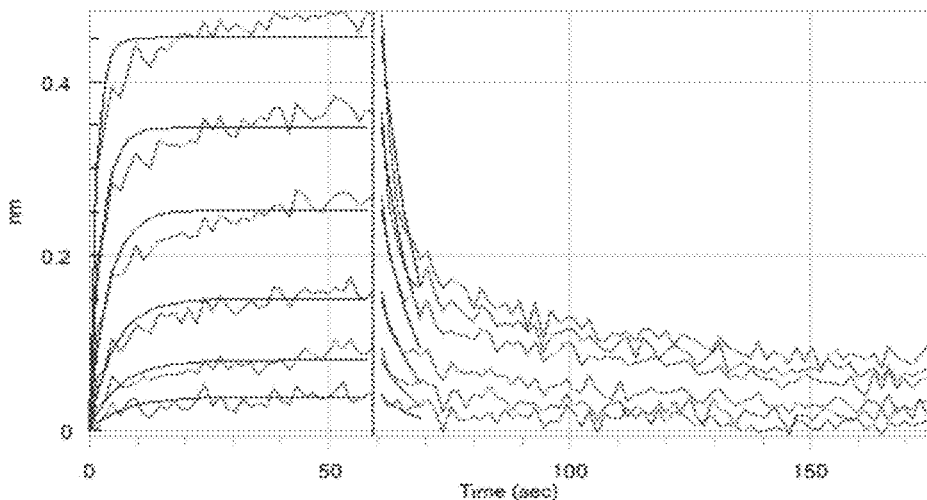
Figure 25C:
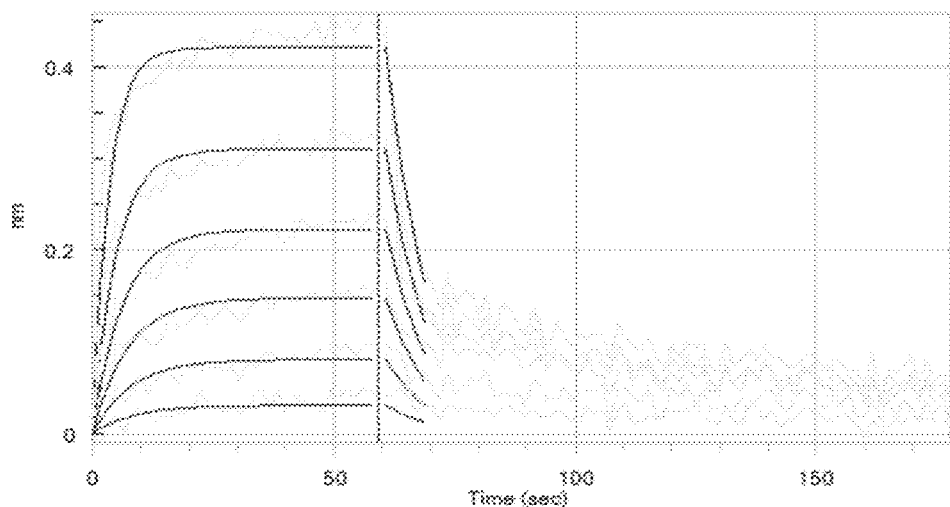
Figure 25D:
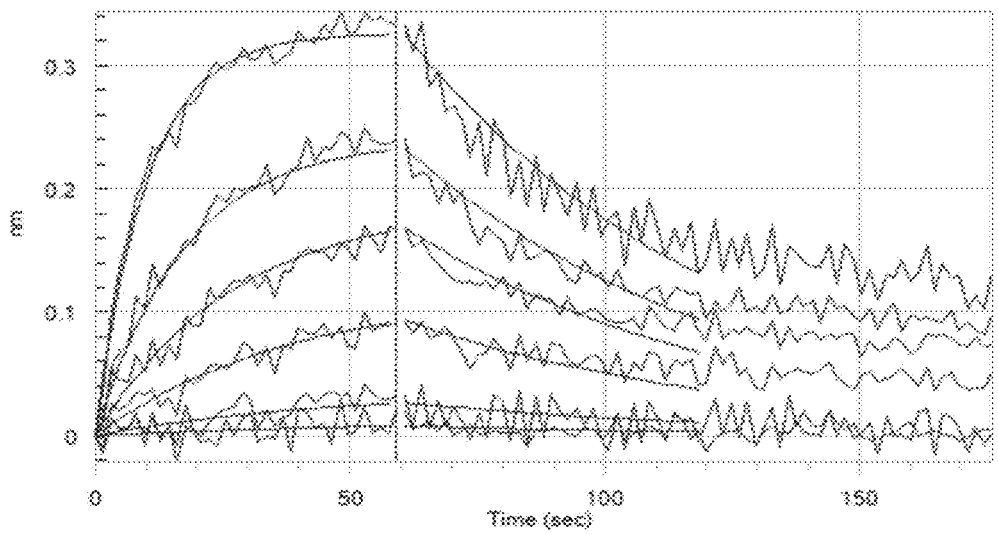
Figure 26A:
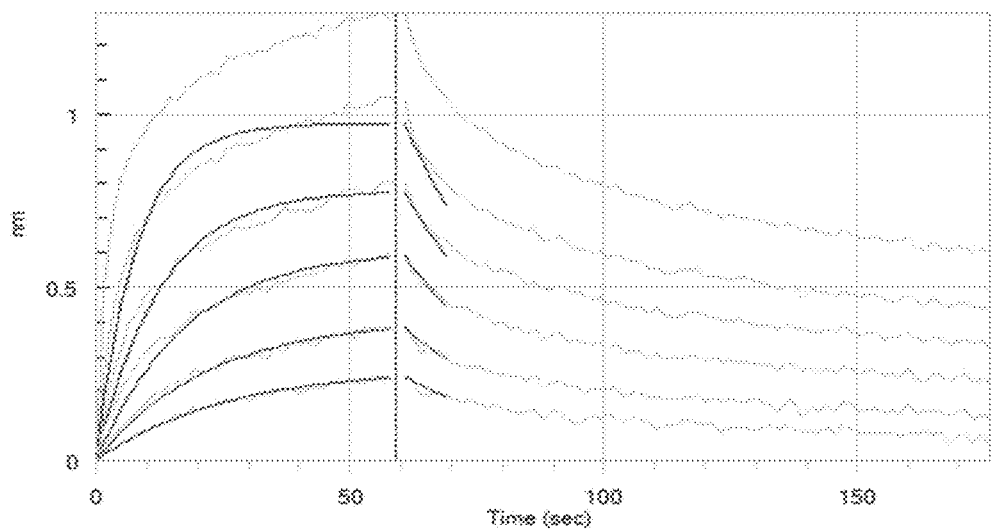
FIGS. 26A to 26D. Sensorgrams showing the results of analysis of binding of 4M2-C12 mIgG2a to (26A) mouse FcγRIV, (26B) mouse FcγRIII, (26C) mouse FcγRIIb, and (26D) mouse FcRn.
Figure 26B:
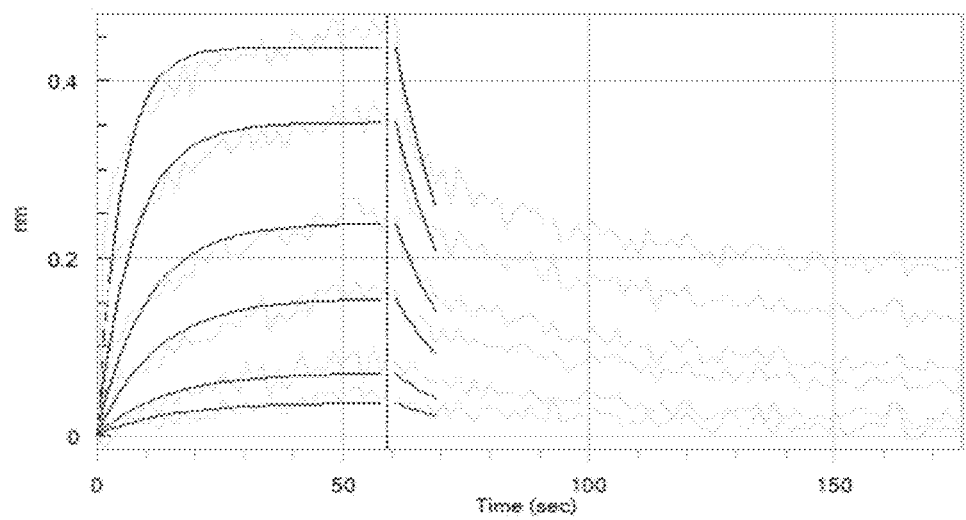
Figure 26C:
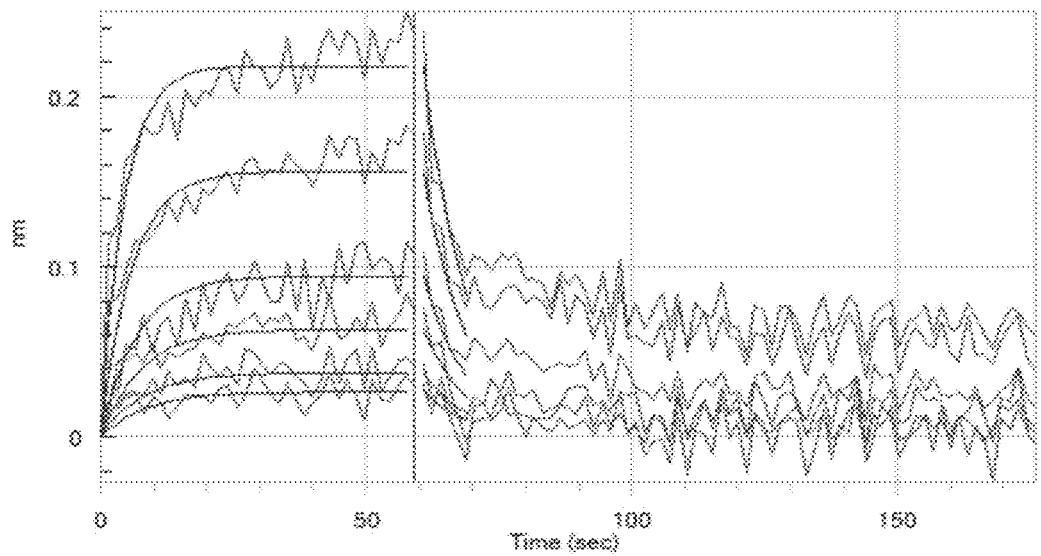
Figure 26D:
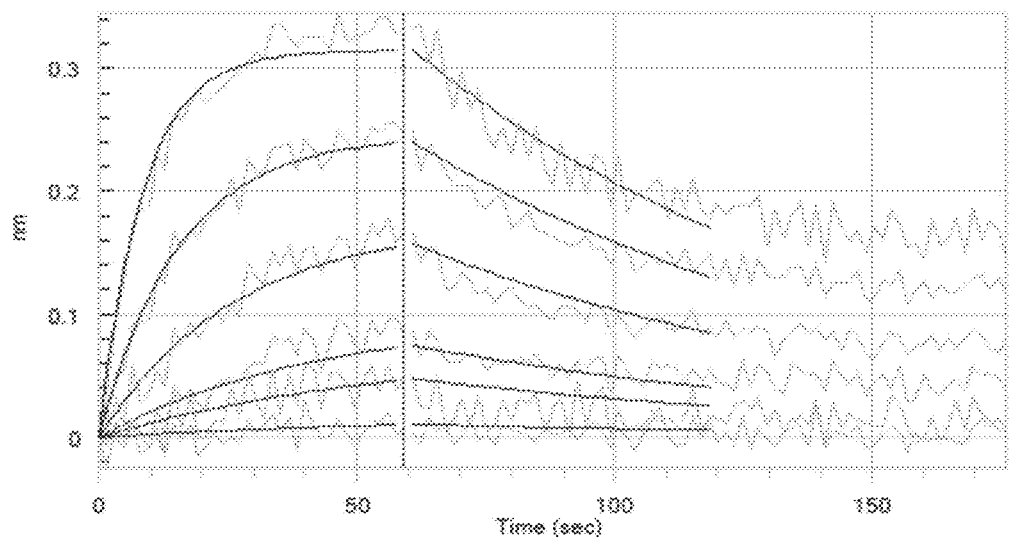
Figure 27A:
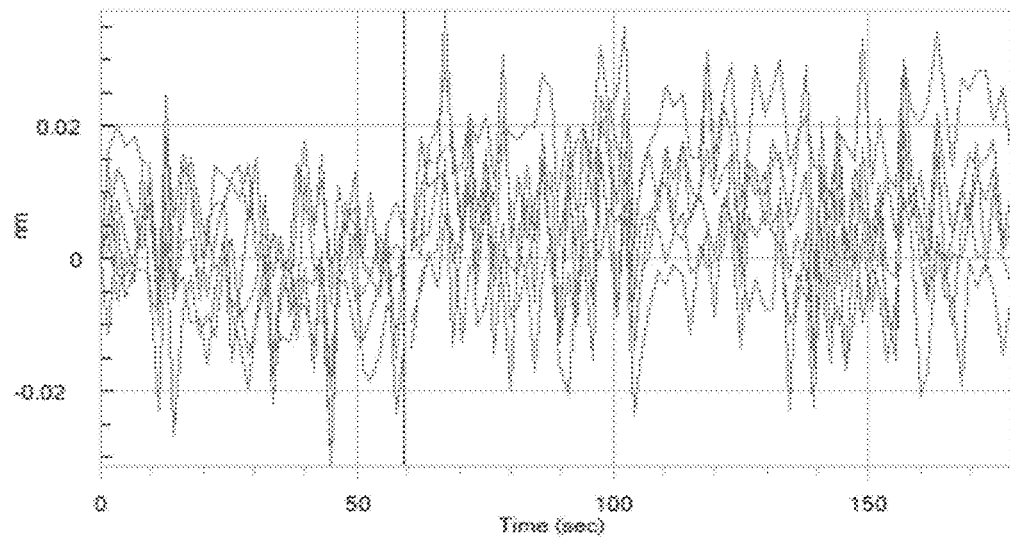
FIGS. 27A to 27D. Sensorgrams showing the results of analysis of binding of 4M2-C12 mIgG2a LALA PG to (27A) mouse FcγRIV, (27B) mouse FcγRIII, (27C) mouse FcγRIIb, and (27D) mouse FcRn.
Figure 27B:
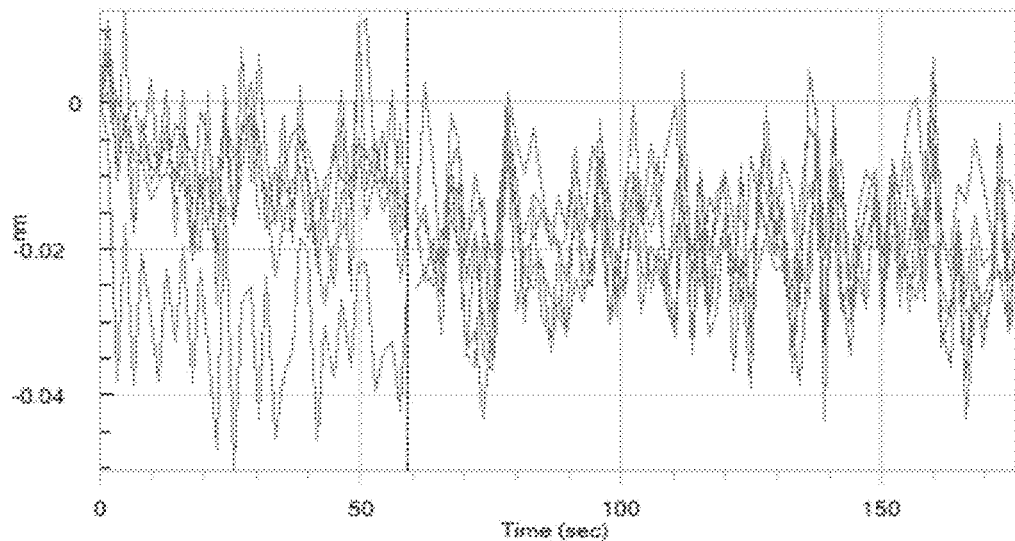
Figure 27C:
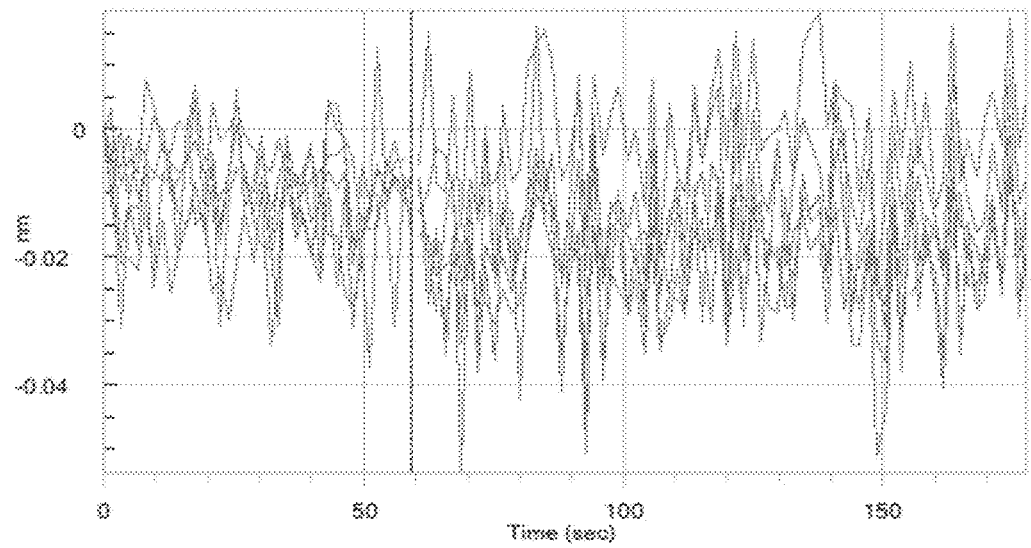
Figure 27D:
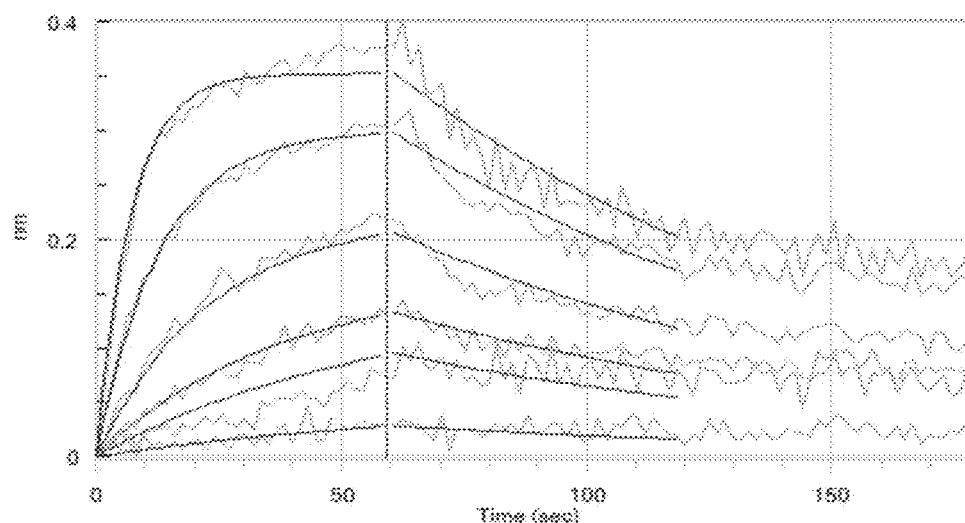
Figure 28A:
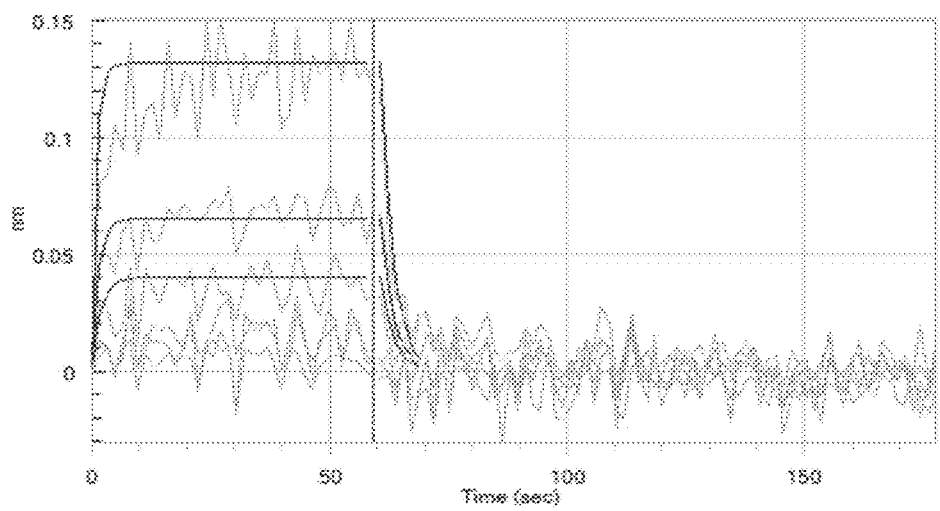
FIGS. 28A to 28D. Sensorgrams showing the results of analysis of binding of 4M2-C12 mIgG2a NQ to (28A) mouse FcγRIV, (28B) mouse FcγRIII, (28C) mouse FcγRIIb, and (28D) mouse FcRn.
Figure 28B:
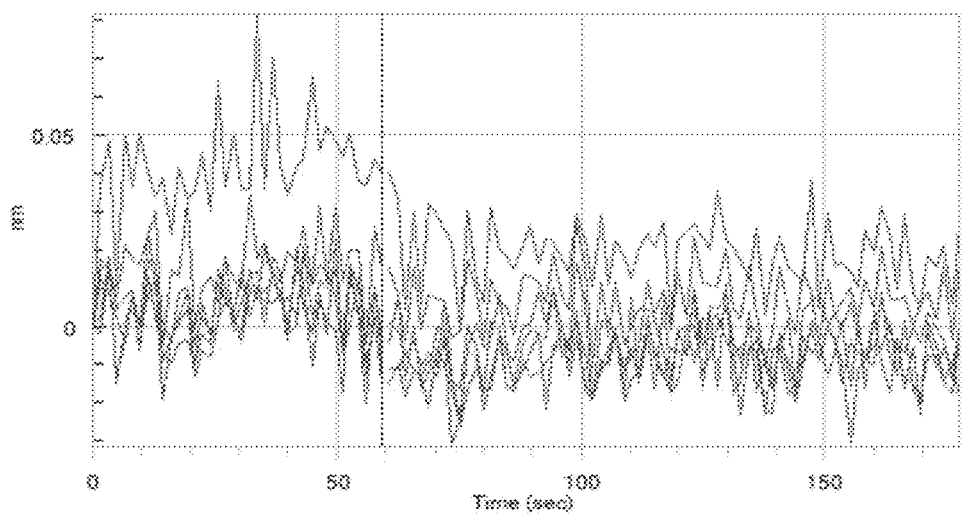
Figure 28C:
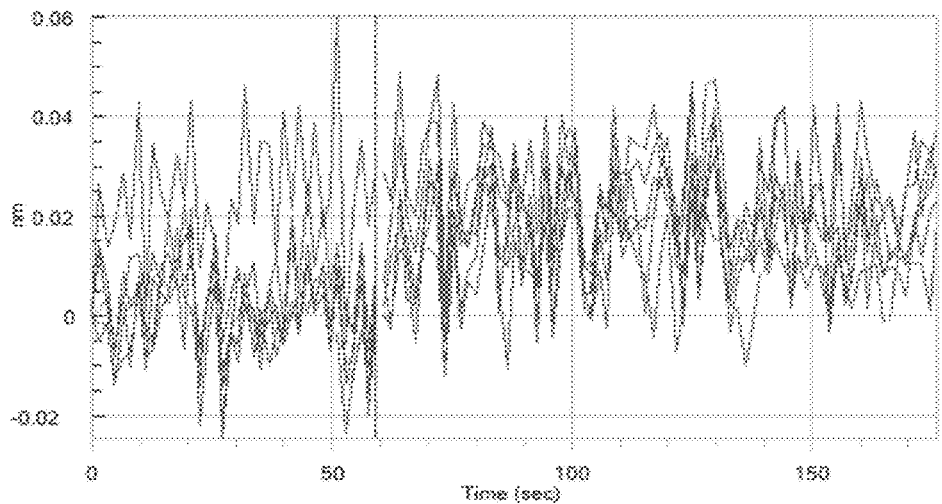
Figure 28D:
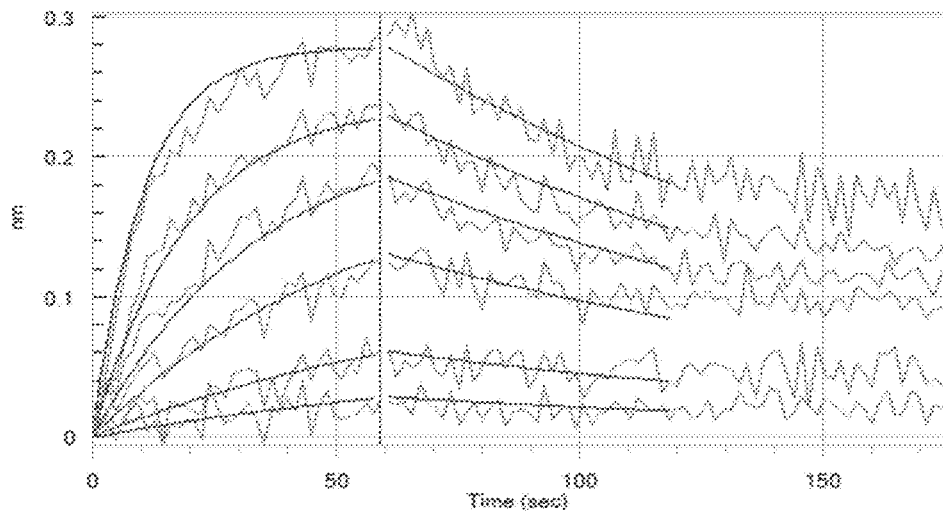

The results of the experiment are shown in FIG. 23. Anti-VISTA antibody clone 13D5-1 was found to be highly potent in this model—capable of inhibiting tumor growth by 70%.

5.3 Safety Pharmacology, Toxicology and Immunotoxicity

Anti-VISTA antibody clone V4 and humanized versions V4H1 and V4H2 were analysed in silico for safety and immunogenicity using IMGT DomainGapAlign (Ehrenmann et al., Nucleic Acids Res., 38, D301-307 (2010)) and IEDB deimmunization (Dhanda et al., Immunology. (2018) 153(1):118-132) tools.

Anti-VISTA antibody clones V4H1 and V4H2 had sufficient homology to human heavy and light chains to be considered humanized (i.e. >85%), had numbers of potential immunogenic peptides few enough to be considered safe, and did not possess any other properties that could cause potential developability issues.

Figure 44:
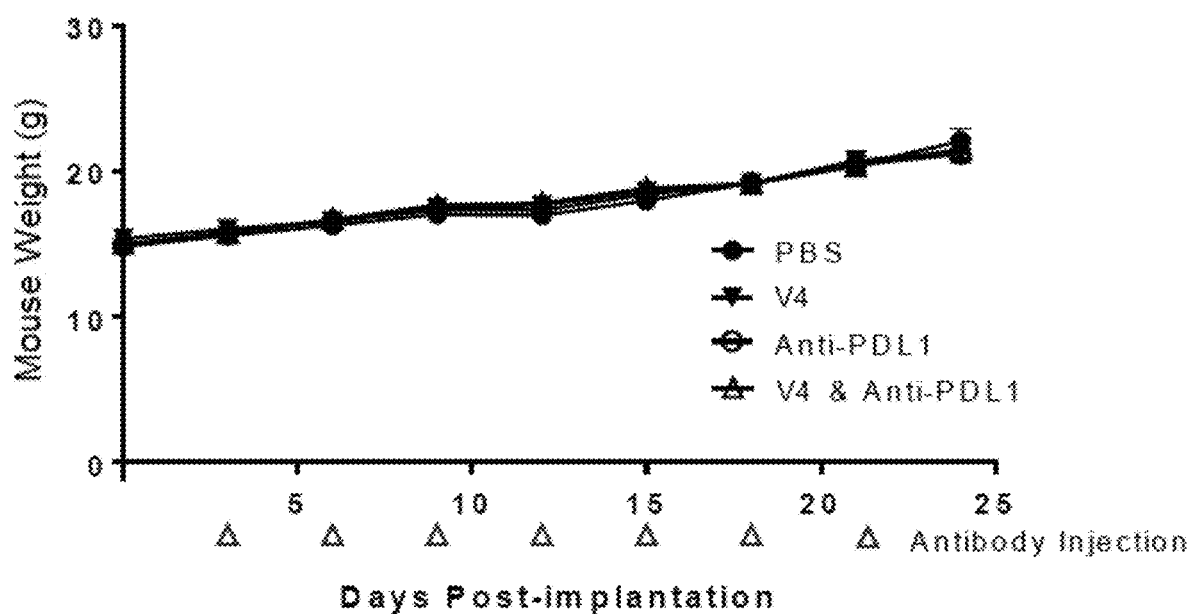
FIG. 44. Graph showing the weights of mice during the course of treatment of a cell-line derived mouse model of colon carcinoma with PBS (Vehicle), anti-VISTA antibody 4M2-C12 mIgG2a (V4), anti-PD-L1 antibody (Anti-PDL1) or combination treatment with 4M2-C12 mIgG2a and anti-PD-1 antibody (V4+Anti-PDL1).

The inventors also weighed and analysed mice for signs of gross necroscopy during the course of the experiments described in Example 5.2; mice treated with anti-VISTA antibody clone V4 did not display any differences from PBS-treated control mice. FIG. 44 shows the results obtained during the course of the study described in Example 5.2.1.

The inventors further investigated hemotoxicity in an experiment in which mice were injected with a single dose of 900 µg anti-VISTA antibody clone V4 or an equal volume of PBS.

Figure 18:
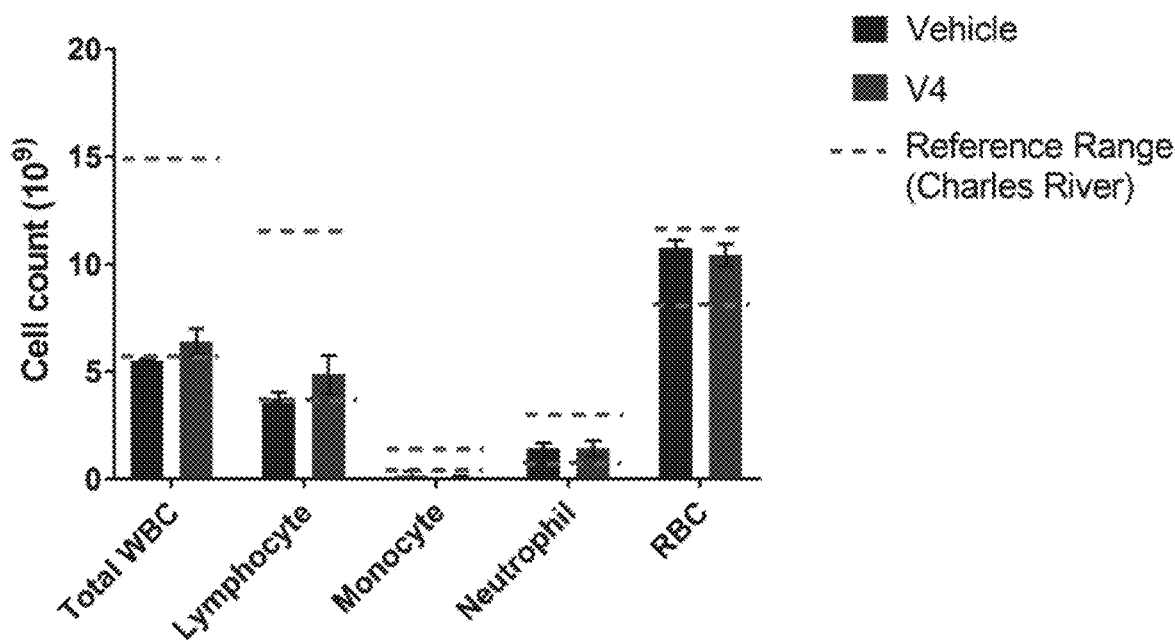
FIG. 18. Bar chart showing numbers or different types of white blood cells after administration of a single dose of 900 μg of anti-VISTA antibody clone V4, or an equal volume of vehicle (PBS) as a negative control.

Blood samples were obtained and analysed for numbers of different types of white blood cells using HM5 Hematology Analyser. The results are shown in FIG. 18; the numbers of the different cell types were within the Charles River reference range and did not differ between the V4 and PBS-treated groups, and no differences in clinical signs, gross necroscopy or weight were detected between the different groups.

Figure 19A:
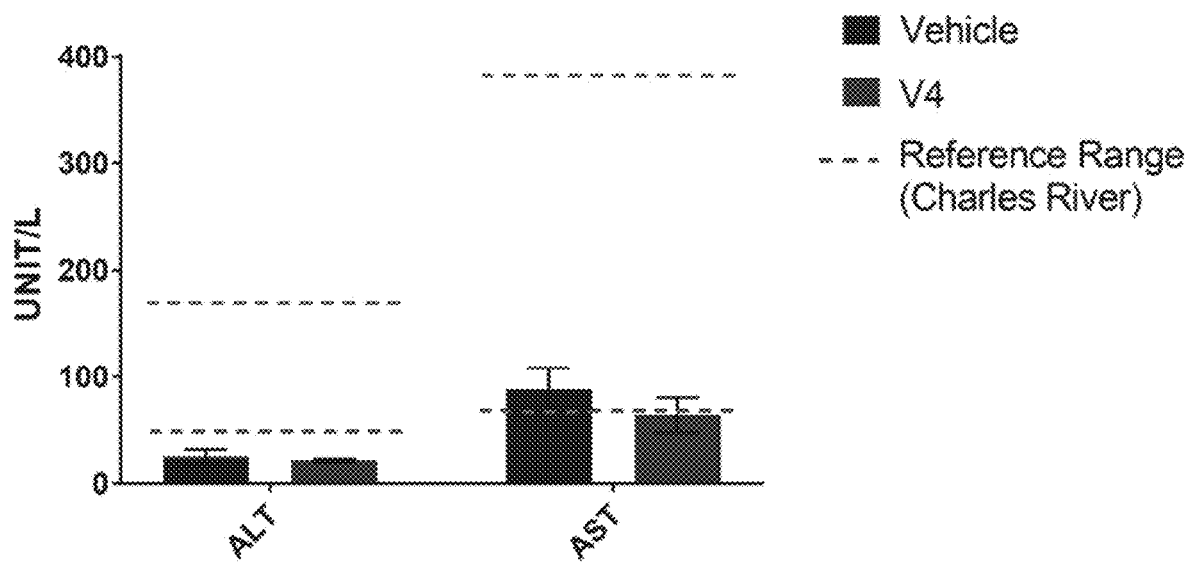
FIGS. 19A and 19B. Bar charts showing analysis of hepatotoxicity and nephrotoxicity, by evaluation of correlates of (9A) liver and (9B) kidney function following administration of a single dose of 900 μg of anti-VISTA antibody clone V4, or an equal volume of vehicle (PBS) as a negative control. (9A) shows levels of alanine aminotransferase (ALT) and aspartate transaminase (AST), and (9B) shows level of blood urea nitrogen (BUN) and creatinine (CREA).
Figure 19B:
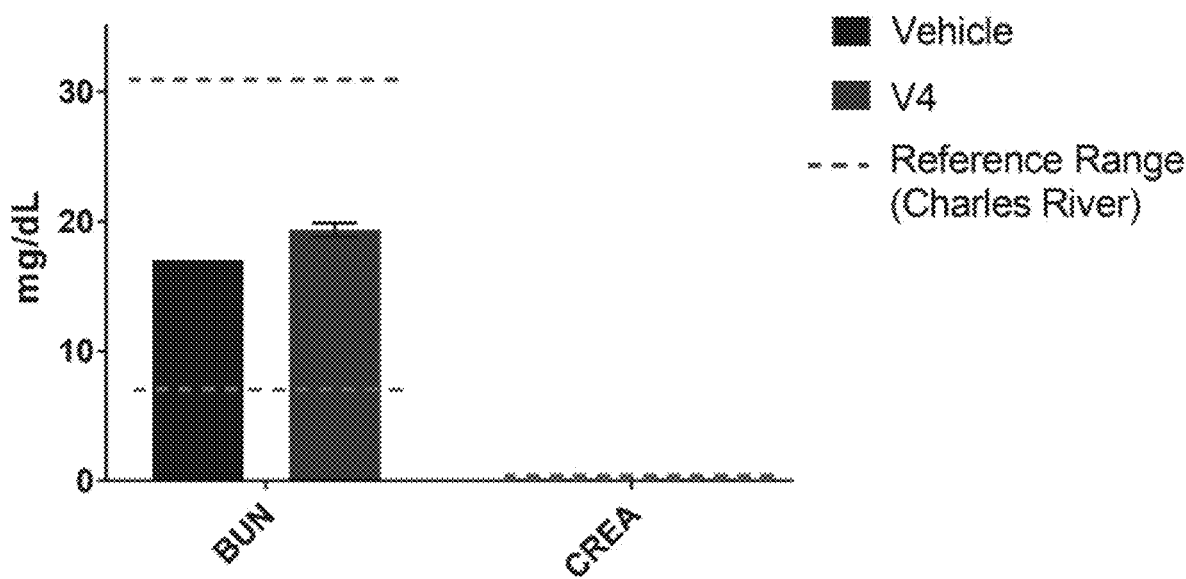

The mice were also analysed for correlates hepatotoxicity and nephrotoxicity, and the results are shown in FIG. 19. The levels detected were within the Charles River reference range and did not differ between the V4 and PBS-treated groups.

5.4 Treatment of Advanced Solid Tumors

First in Human

Patients with advanced or metastatic solid tumors with disease progression or treatment intolerance after treatment with standard therapies and with adequate organ function and ECOG status are treated by intravenous injection of anti-VISTA antibody V4 ([1] of Example 2.2), V4H1 ([3] of Example 2.2) or V4H2 ([4] of Example 2.2), at a dose calculated in accordance with safety-adjusted 'Minimal Anticipated Biological Effect Level' (MABEL) approach. Patients are monitored for 28 days post-administration.

The patients are then evaluated according to the Common Terminology Criteria for Adverse Events (CTCAE), to determine the safety and tolerability of the treatment, and to determine the pharmacokinetics of the molecules.

Treatment with the anti-VISTA antibodies is found to be safe and tolerable.

Dose Escalation—Monotherapy

Patients with advanced or metastatic solid tumors with disease progression or treatment intolerance after treatment with standard therapies and with adequate organ function and ECOG status (n=18-24) are treated by intravenous injection of anti-VISTA antibody V4 ([1] of Example 2.2), V4H1 ([3] of Example 2.2) or V4H2 ([4] of Example 2.2), in accordance with a 3+3 model based escalation with overdose control (EWOC) dose escalation.

The patients are then evaluated according to the Common Terminology Criteria for Adverse Events (CTCAE) to determine the safety and tolerability of the treatment, and the pharmacokinetics of the molecules and efficacy of the treatment is evaluated. The maximum tolerated dose (MTD) and maximum administered dose (MAD) are also determined.

Dose Escalation—Combination Therapy

Patients with advanced or metastatic solid tumors with disease progression or treatment intolerance after treatment with standard therapies and with adequate organ function and ECOG status (n=9) are treated with anti-VISTA antibody V4 ([1] of Example 2.2), V4H1 ([3] of Example 2.2) or V4H2 ([4] of Example 2.2), in accordance with a 3+3 model based escalation with anti-PD-1 or anti-PD-L1 antibody (3 mg/kg).

The patients are then evaluated according to the Common Terminology Criteria for Adverse Events (CTCAE) to determine the safety and tolerability of the treatment, and the pharmacokinetics of the molecules and efficacy of the treatment is evaluated.

Dose Expansion

Treated patients are analysed for overall response rate, expression of tumor markers, circulating tumor cells, progression-free survival, overall survival, safety and tolerability.

The anti-VISTA antibodies are found to be safe and tolerable, to be able to reduce the number/proportion of cancer cells, reduce tumor cell marker expression, increase progression-free survival and increase overall survival.

5.5 Treatment of Lymphoma

First in Human

Patients with lymphoma (NHL and HL) who did not benefit from 1 line of chemotherapy, who have not received allogeneic stem cell transplantation and are likely to respond to rituximab (NHL) and nivolumab or pembrolizumab (HL) are treated by intravenous injection of anti-VISTA antibody V4 ([1] of Example 2.2), V4H1 ([3] of Example 2.2) or V4H2 ([4] of Example 2.2), at a dose calculated in accordance with safety-adjusted 'Minimal Anticipated Biological Effect Level' (MABEL) approach. Patients are monitored for 28 days post-administration.

The patients are then evaluated according to the Common Terminology Criteria for Adverse Events (CTCAE), to determine the safety and tolerability of the treatment, and to determine the pharmacokinetics of the molecules.

Treatment with the anti-VISTA antibodies is found to be safe and tolerable.

Dose Escalation—Monotherapy

Patients with lymphoma (NHL and HL) who did not benefit from 1 line of chemotherapy, who have not received allogeneic stem cell transplantation and are likely to respond to rituximab (NHL) and nivolumab or pembrolizumab (HL) are treated by intravenous injection of anti-VISTA antibody V4 ([1] of Example 2.2), V4H1 ([3] of Example 2.2) or V4H2 ([4] of Example 2.2), in accordance with a 3+3 model based escalation with overdose control (EWOC) dose escalation.

The patients are then evaluated according to the Common Terminology Criteria for Adverse Events (CTCAE) to determine the safety and tolerability of the treatment, and the pharmacokinetics of the molecules and efficacy of the treatment is evaluated. The maximum tolerated dose (MTD) and maximum administered dose (MAD) are also determined.

Dose Escalation—Combination Therapy

Patients with lymphoma (NHL and HL) who did not benefit from 1 line of chemotherapy, who have not received allogeneic stem cell transplantation and are likely to respond to rituximab (NHL) and nivolumab or pembrolizumab (HL) are treated by intravenous injection of anti-VISTA antibody V4 ([1] of Example 2.2), V4H1 ([3] of Example 2.2) or V4H2 ([4] of Example 2.2), in accordance with a 3+3 model based escalation with anti-PD-L1 antibody.

The patients are then evaluated according to the Common Terminology Criteria for Adverse Events (CTCAE) to determine the safety and tolerability of the treatment, and the pharmacokinetics of the molecules and efficacy of the treatment is evaluated.

Dose Expansion

Treated patients are analysed for overall response rate, expression of cancer cell markers, circulating cancer cells, progression-free survival, overall survival, safety and tolerability.

The anti-VISTA antibodies are found to be safe and tolerable, to be able to reduce the number/proportion of cancer cells, reduce tumor cell marker expression, increase progression-free survival and increase overall survival.

Example 6: Production and Characterisation of VISTA-Binding Antibodies Comprising Different Fc Regions 6.1 Production and Characterisation of VISTA-Binding Antibodies Comprising Different Fc Regions 4M2-C12 was produced in mouse IgG2a LALA PG format. The molecule is a heteromer of the heavy chain polypeptide having the sequence shown in SEQ ID NO:249, and the light chain polypeptide having the sequence shown in SEQ ID NO:250. The heavy chain sequence comprises leucine (L) to alanine (A) substitutions in the CH2 region, at positions 4 and 5 numbered according to SEQ ID NO:253, and a proline (P) to glycine (G) substitution at position 99 numbered according to SEQ ID NO:253. These substitutions are referred to in the literature as L234A, L235A and P329G, and are described in mouse IgG2a Fc e.g. in Lo et al. J. Biol. Chem (2017) 292(9):3900-3908, which is hereby incorporated by reference in its entirety. 4M2-C12 mIgG2a LALA PG was produced by co-expression of nucleic acids encoding the heavy and light chain polypeptides in CHO cells, and was subsequently purified.

| Antigen-biding molecule | Polypeptides | Antibody |
| --- | --- | --- |
| [18] | 4M2-C12 mIgG2a LALA PG HC (SEQ ID NO: 249) + 4M2-C12 CL (SEQ ID NO: 250) | 4M2-C12 mIgG2a LALA PG |

4M2-C12 was also produced in mouse IgG2a NQ format. The molecule is a heteromer of the heavy chain polypeptide having the sequence shown in SEQ ID NO:258, and the light chain polypeptide having the sequence shown in SEQ ID NO:250. The heavy chain sequence comprises an asparagine (N) to glutamine (Q) substitution in the CH2 region, at position 67 according to SEQ ID NO:253. This substitution is referred to in the literature as N297Q, and is described in mouse IgG2a Fc e.g. in Lo et al. J. Biol. Chem (2017) 292(9):3900-3908. 4M2-C12 mIgG2a NQ was produced by co-expression of nucleic acids encoding the heavy and light chain polypeptides in CHO cells, and was subsequently purified.

| Antigen-biding molecule | Polypeptides | Antibody |
|---|---|---|
| [19] | 4M2-C12 mIgG2a NQ HC (SEQ ID NO: 258) + 4M2-C12 CL (SEQ ID NO: 250) | 4M2-C12 mIgG2a NQ |

4M2-C12 was produced in mouse IgG1 format. The molecule is a heteromer of the heavy chain polypeptide having the sequence shown in SEQ ID NO:266, and the light chain polypeptide having the sequence shown in SEQ ID NO:250. 4M2-C12 mIgG1 was produced by co-expression of nucleic acids encoding the heavy and light chains polypeptides in CHO cells, and was subsequently purified.

| Antigen-biding molecule | Polypeptides | Antibody |
|---|---|---|
| [20] | 4M2-C12 mIgG1 HC (SEQ ID NO: 266) + 4M2-C12 CL (SEQ ID NO: 250) | 4M2-C12 mIgG1 |

6.2 Analysis of Binding of VISTA-Binding Antibodies Comprising Different Fc Regions to Fc Receptors Binding of 4M2-C12 in different antibody formats to human, cynomolgus and murine VISTA protein was assessed via ELISA, and binding to mouse Fcγ receptors and mouse FcRn was assessed by BLI using a Pall ForteBio Octet QK 384 system.

Histidine-tagged mFcγRIV (50036-M08H), mFcγRIII (50326-M08H), mFcγRIIb (50030-M08H), and mFcRn (CT009-H08H) were obtained from Sino Biological. Anti-Penta-HIS (HIS1K) biosensors were purchased from Forte Bio (18-5120).

For the kinetic experiment, anti-Penta-HIS biosensors were incubated for 60 sec in PBS buffer (pH 7.2) to obtain the first baseline, and were subsequently loaded for 120 sec with 200 nM mFcγRIV (orthologue of hFcγRIIIa), 160 nM mFcγRIII (orthologue of hFcγRIIa), 75 nM mFcγRIIb (orthologue of hFcγRIIb) or 120 nM mFcRn in PBS (pH 7.2). After loading, biosensors were incubated for 60 sec in PBS buffer (pH 7.2 for Fcγ receptors and pH 5.8 for FcRn) to obtain the second baseline, and for 60 sec with a 6 point 2-fold dilution series of the test antibodies (2000 nM-62.5 nM for mFcγ receptor binding, and 500 nM-15.6 nM for FcRn binding) in PBS (pH 7.2 for Fcγ receptors and pH 5.8 for FcRn) to obtain the association curves. Finally, the biosensors were incubated for 120 sec in PBS (pH 7.2 for mFcγR and pH 5.8 for mFcRn) to obtain the dissociation curves. Kinetic and affinity constants were calculated by global fitting of the association and dissociation data to a 1:1 binding model.

The results for analysis of binding of 4M2-C12-mIgG1 to different mouse Fcγ receptors and mouse FcRn are shown in FIGS. 25A to 25D.

The results for analysis of binding of 4M2-C12-mIgG2a to different mouse Fcγ receptors and mouse FcRn are shown in FIGS. 26A to 26D. Two separate experiments were performed (1 and 2; see FIGS. 29A to 29C); FIGS. 26A to 26D show the results obtained in experiment 2. The level of binding detected for the different Fcγ receptors was comparable to the level reported in the scientific literature.

The results for analysis of binding of 4M2-C12-mIgG2a LALA PG to different mouse Fcγ receptors and mouse FcRn are shown in FIGS. 27A to 27D. The level of binding to mFcγRIV, mFcγRIII and mFcγRIIb was neglibible/undetectable, and the level of binding to mFcRn was similar to the level of binding to mFcRn by 4M2-C12-mIgG2a.

The results for analysis of binding of 4M2-C12-mIgG2a NQ to different mouse Fcγ receptors and mouse FcRn are shown in FIGS. 28A to 28D.

The $K_{on}$, $K_{dis}$ and $K_D$ values for binding to different Fc receptors determined for 4M2-C12-mIgG1, 4M2-C12-mIgG2a, 4M2-C12-mIgG2a LALA PG and 4M2-C12-mIgG2a NQ are summarised in the tables of FIGS. 29A to 29C.

Example 7: Analysis In Vivo of VISTA-Binding Antibodies Comprising Different Fc Regions 4M2-C12-mIgG2a and 4M2-C12-mIgG2a LALA PG (see Example 6.1) were evaluated for efficacy to treat cancer in vivo in a syngeneic EL4 T-cell leukemia/lymphoma model.

EL4 cells cultured in DMEM supplemented with 10% Horse serum (FBS) and 1% Pen/Strep. Cells were cultured at 37° C. in a 5% $CO_2$ incubator.

C57BL/6 mice, approximately 6 weeks old were obtained from InVivos (Singapore). Animals were housed under specific pathogen-free conditions and were treated in compliance with the Institutional Animal Care and Use Committee (IACUC) guidelines. C57BL/6 mice were inoculated with $2\times10^5$ EL4 T-cell leukemia/lymphoma cells on the right flank. Post tumor implantation, when tumors reached 350 to 400 mm$^3$ in size, mice were randomized to the following treatment groups: a) vehicle control (PBS), b) 4M2-C12 mIgG2a ([17] of Example 5), or c) 4M2-C12 mIgG2a-LALA PG ([18] of Example 6), at a dose of 25 mg/kg. The treatments were administered intraperitoneally every 3 days for a total of 5 doses.

Tumor volume was measured 3 times a week using a digital caliper, and calculated using the formula [L×W2/2]. Study End point was considered to have been reached once the tumors of the vehicle control treatment group measured >1.5 cm in length.

Figure 30A:
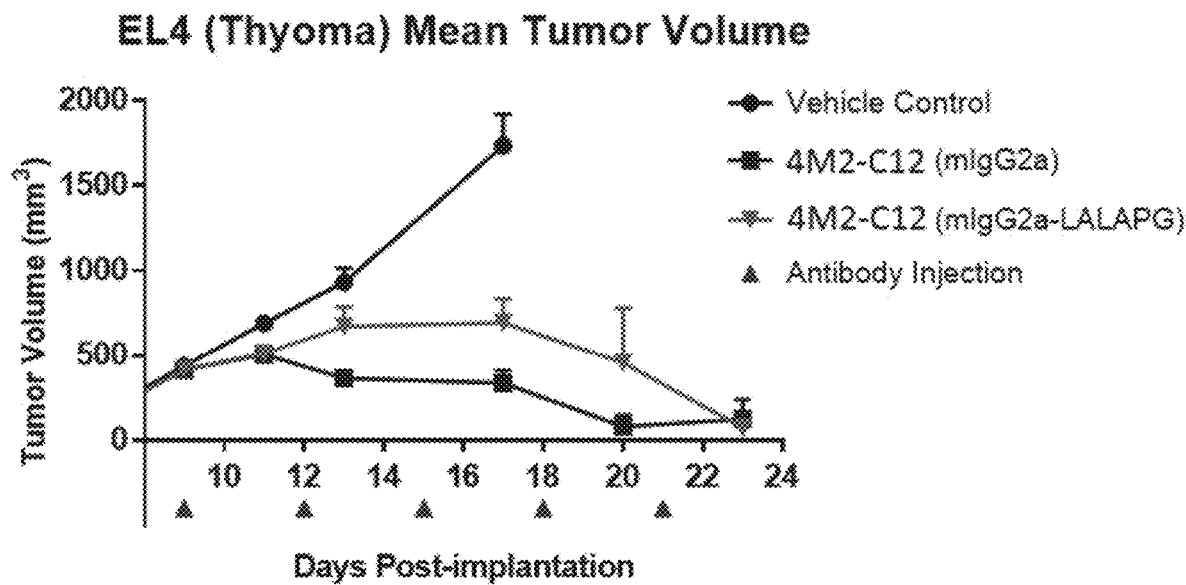
FIGS. 30A to 30C. Graphs showing the results of the analysis of anti-cancer activity in vivo of anti-VISTA antibody clone 4M2-C12 in mIgG2a and mIgG2a LALA PG formats, in a cell-line derived mouse model of T cell lymphoma. 30A shows data for the different treatment groups, 30B shows the data obtained for individual mice in the vehicle control and 4M2-C12 mIgG2a treatment groups, and 30C shows the data obtained for individual mice in the vehicle control and 4M2-C12 mIgG2a LALA PG treatment groups.
Figure 30B:
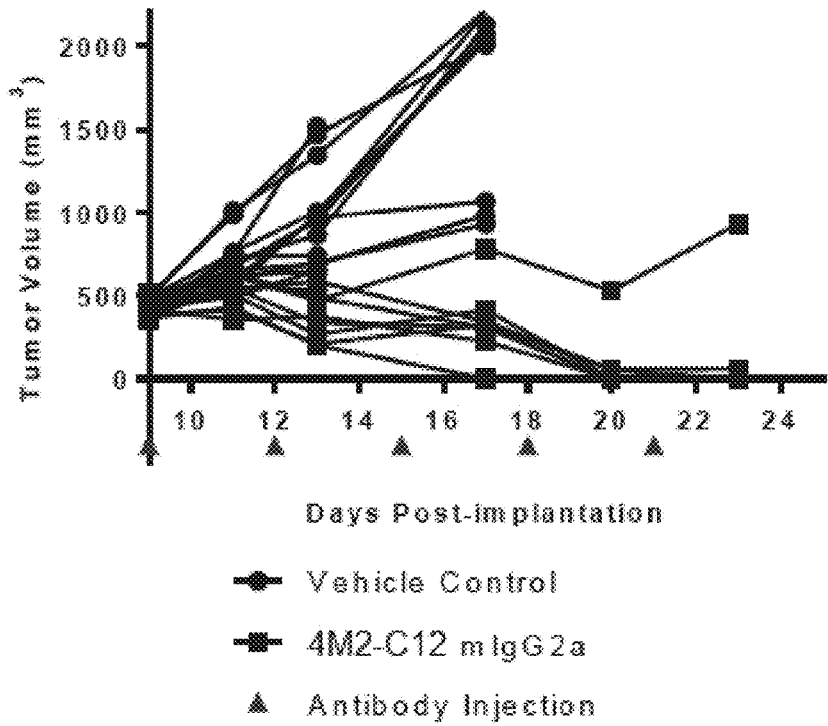
Figure 30C:
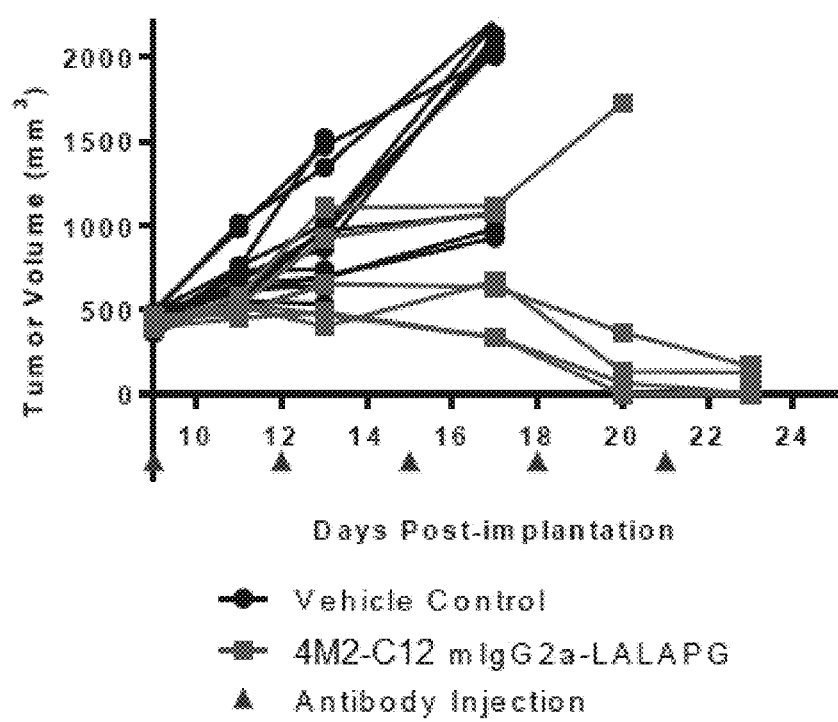

The results are shown in FIGS. 30A to 30C. By the final day of the study (Day 23 post implantation), the mean tumor volume in both the 4M2-C12 IgG2a and 4M2-C12 IgG2a LALA PG treatment groups was below the size for reliable measurement (<30 mm$^3$). By contrast, the average tumor volume in mice in the vehicle (PBS) treatment group exceeded 2000 mm$^3$ by Day 18 and all animals were euthanized.

Thus 4M2-C12 was found to display potent inhibition of tumor growth in both IgG2a and IgG2a LALA PG formats.

Treatment of highly established EL4 tumor-bearing mice with anti-VISTA antibody 4M2-C12 was found to be very effective as a monotherapy, and resulted in tumor clearance.

The biological activity of 4M2-C12 was found not to be dependent on engagement of murine Fcγ receptors, strongly suggesting that 4M2-C12 exerts its biological activity through inhibition of VISTA-mediated signalling.

Example 8: Analysis of the Epitope of VISTA Bound by the Antibodies

Anti-VISTA antibodies were evaluated to determine whether they compete with one another for binding to VISTA.

VSTB112 has previously been suggested to bind VISTA in several regions. The major epitopes have been proposed to correspond to positions 59 to 68 and positions 86 to 97 of SEQ ID NO:1 (i.e. SEQ ID NOs:271 and 272). The minor epitopes have been proposed to correspond to positions 71 to 84 and positions 150 to 166 of SEQ ID NO:1 (i.e. SEQ ID NOs:273 and 274); see e.g. WO 2017/137830 A1, e.g. at paragraph [0302]. VSTB112 is described e.g. in WO 2015/097536 A2, which is hereby incorporated by reference in its entirety.

IGN175A is thought to bind to VISTA within the first 32 amino acids of the mature protein (i.e. within positions 33 to 64 of SEQ ID NO:1 (i.e. SEQ ID NO:275)). IGN175A is described e.g. in WO 2014/197849 A2, which is hereby incorporated by reference in its entirety.

Epitope binning experiments were performed by BLI using the Octet QK384 system (ForteBio). Briefly, human VISTA-His recombinant protein in PBS (4.7 µg/ml) was immobilized to Anti-Penta His sensor (HIS1K, ForteBio), for 5 mins. Baseline signals in PBS were measured for 30s before loading of 400 nM saturating antibody in PBS for 10 mins, and at a shake speed of 1000 rpm, followed by a 120 s dissociation step using PBS. Biosensors were subsequently treated with 300 nM competing antibody in PBS for 5 mins, at a shake speed of 1000 rpm, followed by a 120 s dissociation step using PBS. The following antigen-binding molecules were analysed in the experiment:

4M2-C12 (V4) in IgG1 format ([1] of Example 2.2)

A humanised and affinity-matured variant of 4M2-C12 (V4-C1) in IgG1 format ([21] of Example 13)

IGN175A IgG1 (comprising IGN175A HC (SEQ ID NO: 267)+IGN175A LC (SEQ ID NO: 268))

VSTB112 IgG1 (comprising VSTB112 HC (SEQ ID NO: 269)+VSTB112 LC (SEQ ID NO: 270))

The following antigen/saturating antibody/competing antibody combinations were investigated:

| Antigen | Saturating Antibody | Competing Antibody |
|---|---|---|
| human VISTA | V4-C1 IgG1 | IGN175A IgG1 |
| human VISTA | V4-C1 IgG1 | V4-C1 IgG1 |
| human VISTA | V4-C1 IgG1 | VSTB112 IgG1 |
| human VISTA | VSTB112 IgG1 | IGN175A IgG1 |
| human VISTA | IGN175A IgG1 | V4-C1 IgG1 |
| human VISTA | VSTB112 IgG1 | V4-C1 IgG1 |
| human VISTA | IGN175A IgG1 | IGN175A IgG1 |
| None (PBS) | V4-C1 IgG1 | IGN175A IgG1 |

Figure 31A:
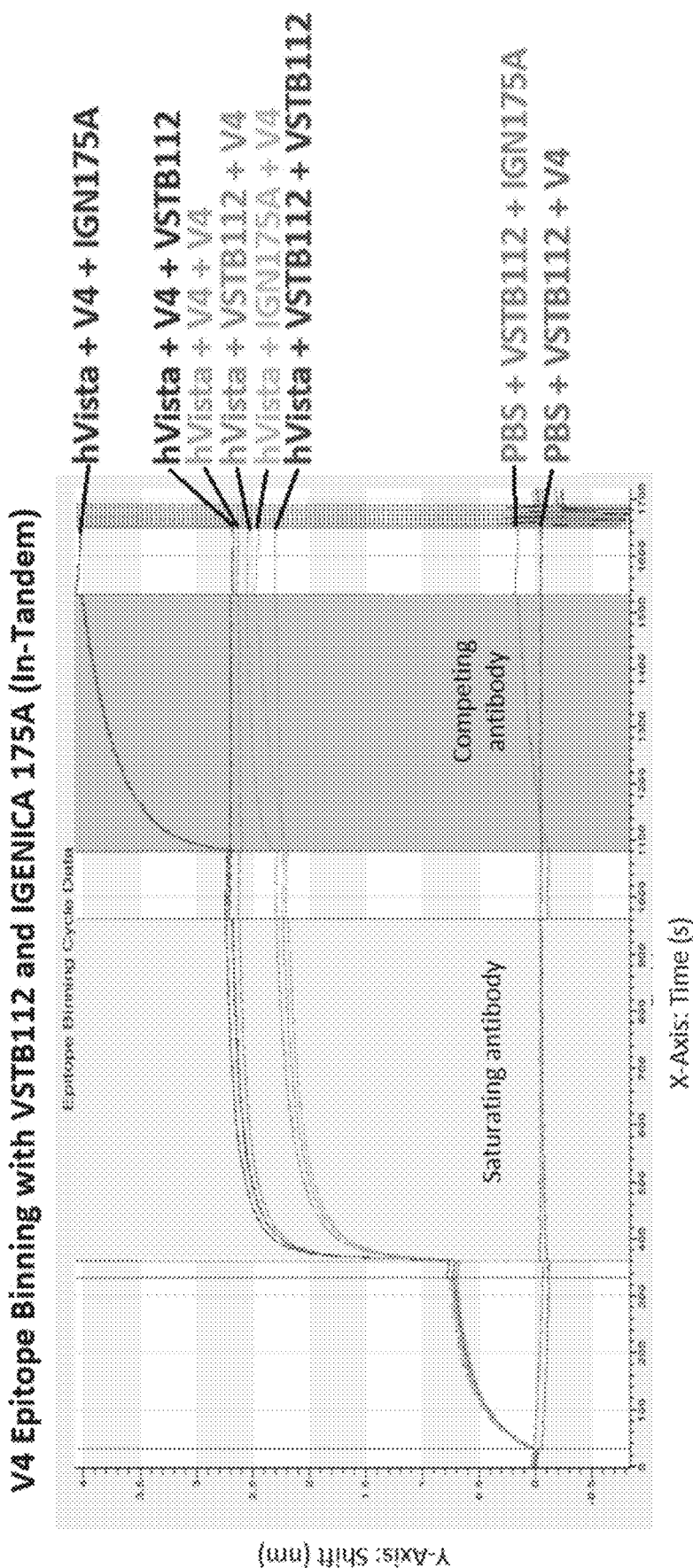
FIGS. 31A and 31B. Sensorgram showing the results of analysis of competition between different anti-VISTA antibodies for binding to human VISTA by BLI.
Figure 31B:
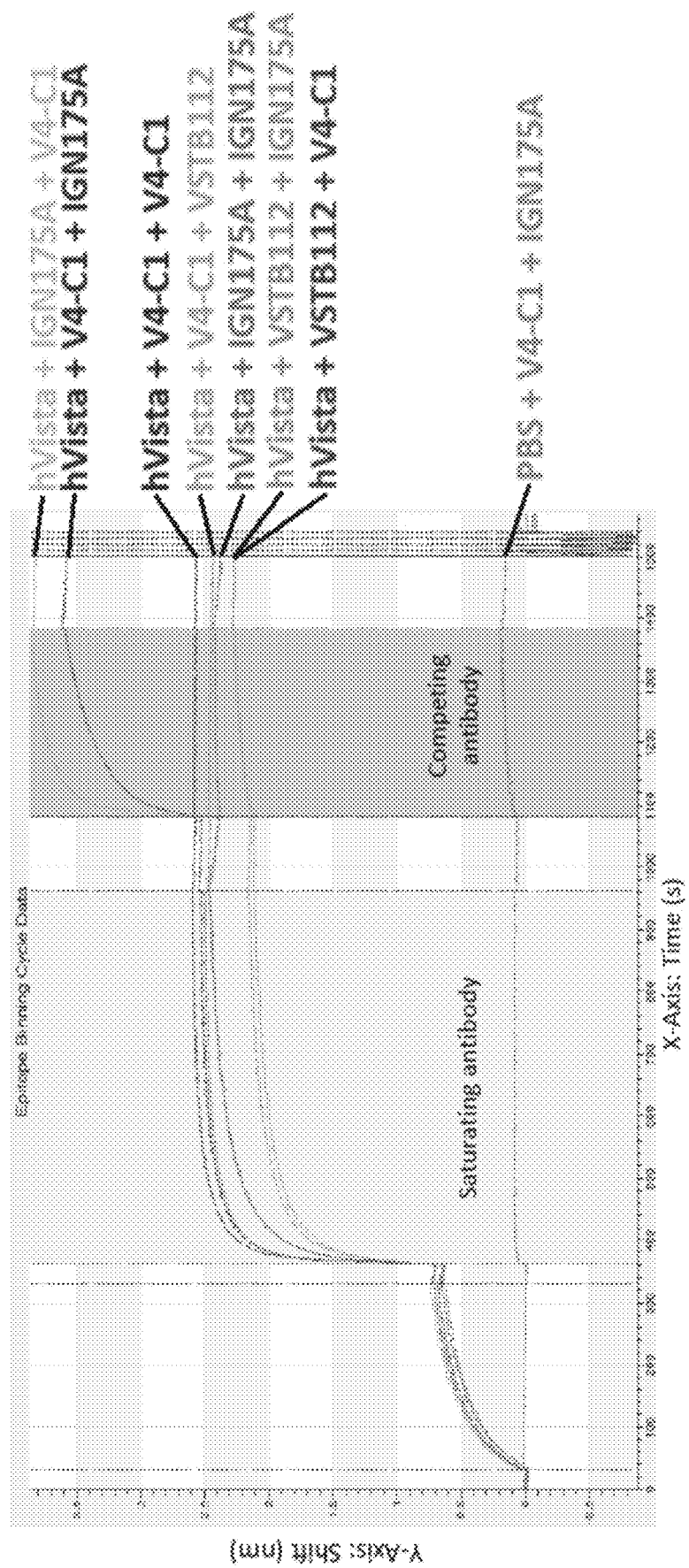

The results are shown in FIGS. 31A and 31B.

V4 and V4-C1 IgG1 were found not to compete with IGN175A for binding to VISTA. VSTB112 was found to partially compete with V4, V4-C1 and IGN175A for binding to VISTA. Changes in response (in nm) upon addition of the competing antibody are shown below.

| Saturating Antibody | Competing Antibody | | |
|---|---|---|---|
| | IGN175A | V4-C1 IgG1 | VSTB112 |
| IGN175A | 0.0454 | 1.4362 | — |
| V4-C1 IgG1 | 1.0661 | −0.0158 | −0.0124 |
| VSTB112 | 0.1392 | 0.1579 | — |

The results indicate that 4M2-C12 and IGN175A bind to topically distant regions of VISTA, and that VSTB112 binds to VISTA in regions which are proximal to 4M2-C12 and IGN175A.

The fact that V1-C1 and IGN175A do not compete for binding to VISTA taken together with the observation that VSTB112 competes with IGN175A for binding to VISTA indicates that antibodies comprising the CDRs of 4M2-C12 bind to an epitope of VISTA which is non-identical to the epitope of VISTA bound by IGN175A, and which is also non-identical to the epitope of VISTA bound by VSTB112.

From analysis of the sequence for VISTA, the immunogen used to raise 4M2-C12 and species cross-reactivity data, the inventors concluded that 4M2-C12 and derivatives thereof bind to the sequence shown in SEQ ID NO:322 (which corresponds to positions 76 to 81 of SEQ ID NO:1).

Example 9: Analysis of the Ability of VISTA-Binding Antibodies to Rescue VISTA-Mediated Inhibition of T Cell Proliferation The ability of anti-VISTA antibodies to rescue the inhibitory effects of VISTA-mediated signalling was analysed in an in vitro assay.

Briefly, 96-well plates were coated with anti-CD3 and VISTA-Ig or control-Ig at concentration ratios of either 1:1 (2.5 µg/ml anti-CD3:2.5 µg/ml of VISTA/control Ig) or 2:1 (2.5 µg/ml anti-CD3: 1.25 µg/ml VISTA/control Ig). Irrelevant antigen-Ig was used as control condition. Plates were incubated overnight at 4° C.

PBMCs were purified from freshly collected blood samples and further enriched for T cells using human Pan T Cell Isolated Kit (Miltenyi Biotec). The enriched T cell populations were then labelled with CFSE.

Wells were washed three times with PBS, and 100,000 CFSE-labelled T cells were added to each well, in complete RPMI 1640 medium supplemented with 10% FBS, in the presence of 4M2-C12 IgG1 ([1] of Example 2.2) at a final concentration of 20 µg/ml or 50 µg/ml, or in the presence of VSTB 112 at a final concentration of 20 µg/ml, or in the absence of added antibody.

After 5 days, cells were harvested, labelled with fluorescently conjugated anti-CD4 and anti-CD8 antibodies, and analysed by flow cytometry using a Macsquant Analyzer 10.

The results of the experiments are shown in FIGS. 33A to 33D. 4M2-C12 was found to restore the ability of both CD4+ T cells and CD8+ T cells to proliferate.

Importantly, 4M2-C12 was found to be more effective at restoring proliferation of T cells than VSTB112.

Example 10: Analysis of the Ability of VISTA-Binding Antibodies to Promote Production of IL-6 by THP1 Cells in Response to LPS The ability of anti-VISTA antibodies to promote production of IL-6 by THP-1 cells in response to LPS stimulation was analysed in an in vitro assay.

Briefly, undifferentiated THP1 cells were seeded in 96 well plates in duplicate (100,000 cells/well), in RPMI media without FBS or pen/strep. Cells subsequently treated with LPS (final concentration of 100 µg/ml) and $MnCl_2$ (100 µM), in the presence of different concentrations of 4M2-C12 IgG1 ([1] of Example 2.2) ranging from 2000 µg/ml to 7.8 µg/ml, or different concentrations of VSTB112 ranging from 1000 µg/ml to 7.8 µg/ml. After 3 days, the cell culture supernatant was collected and analysed by ELISA to determine the level of IL-6, using the IL-6 Human ELISA Kit (Invitrogen).

Figure 34A:
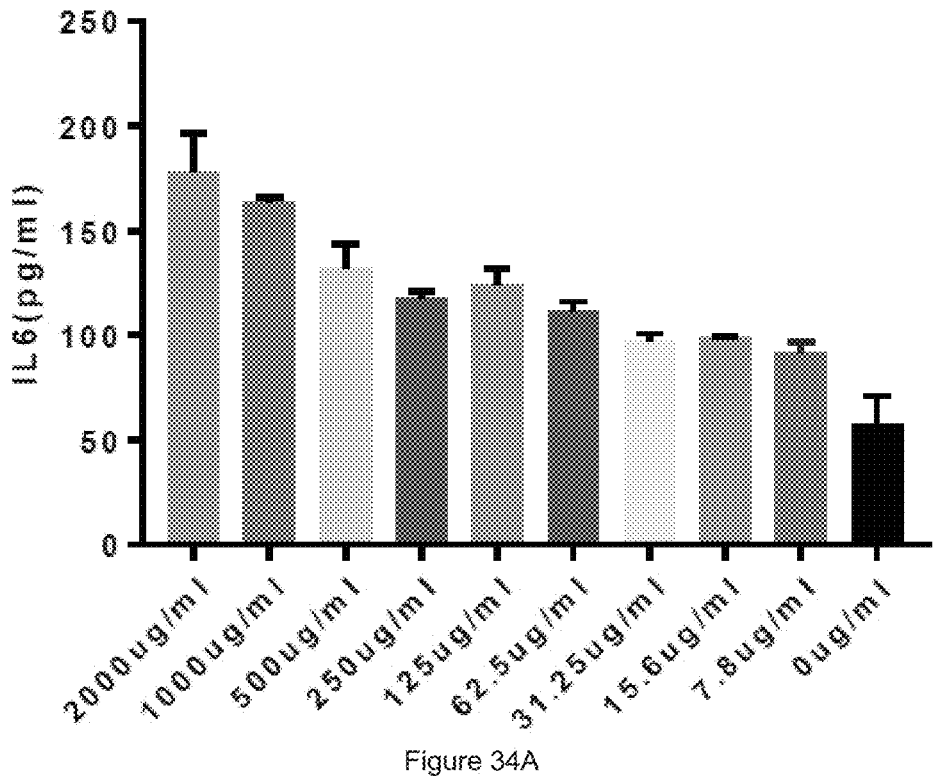
FIGS. 34A and 34B. Bar charts showing the results of analysis of the ability of anti-VISTA antibodies to promote the production of IL-6 by LPS-stimulated THP-1 cells.
Figure 34B:
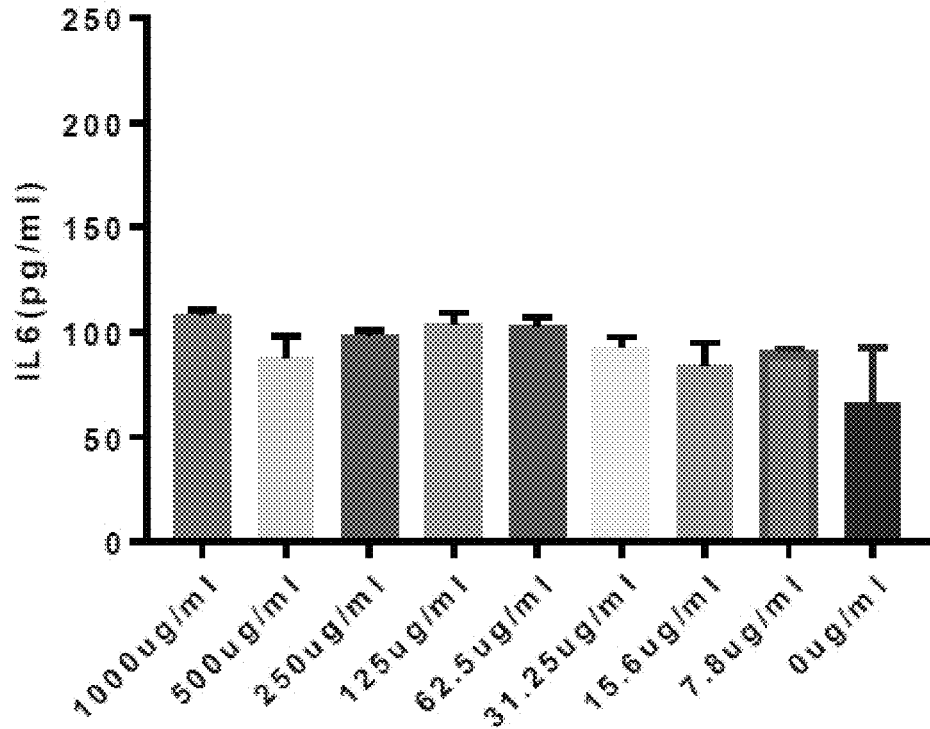

The results are shown in FIGS. 34A and 34B. 4M2-C12 was found to promote the production of more IL-6 by LPS-stimulated THP1 cells than VSTB112.

Example 11: Analysis of the Ability of VISTA-Binding Antibodies to Promote Production of IL-6 In Vivo IL-6 production in response to treatment with 4M2-C12 was investigated in vivo.

Briefly, C57BL/6 mice (n=3) were administered with a single 600 µg dose of 4M2-C12 mIgG2a ([17] of Example 5), and blood samples were harvested from mice at 2 hr before administration, and 0.5 hr, 6 hr, 24 hr, 96 hr, 168 hr and 336 hr post-administration.

The serum was analysed for IL-6 content using the Mouse IL-6 ELISA Kit (Abcam, ab100712).

Figure 35:
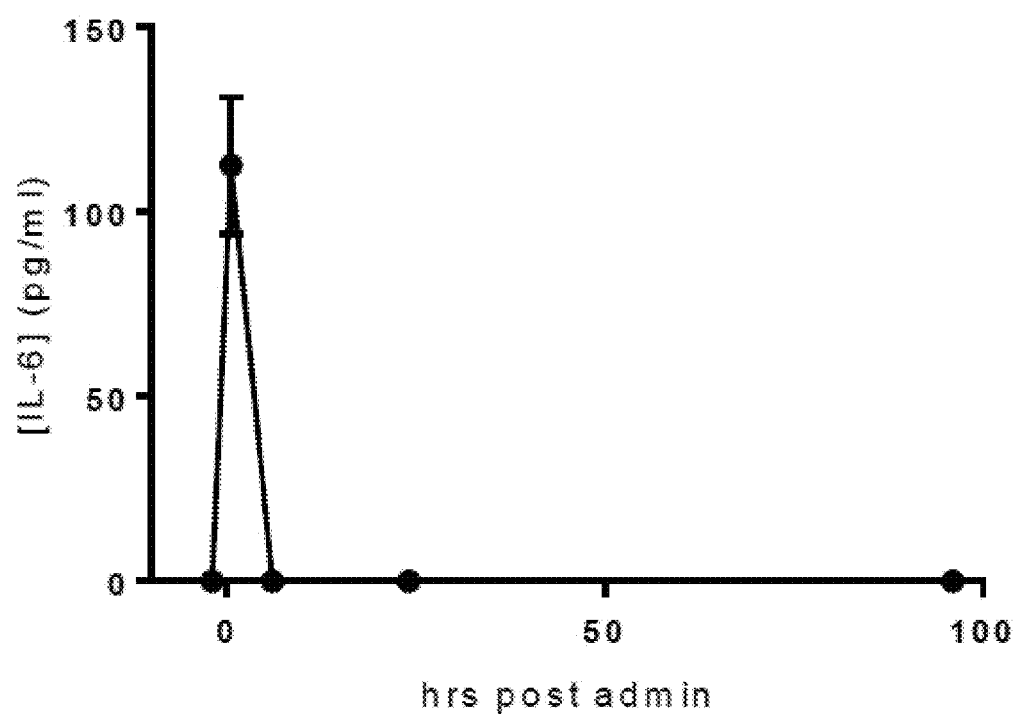
FIG. 35. Bar chart showing the level of IL-6 detected in blood samples obtained from mice administered with anti-VISTA antibody 4M2-C12, at 2h prior to administration, and at 0.5 hr, 6 hr, 24 hr and 96 hr after administration.

The results are shown in FIG. 35. IL-6 was detected in the serum at 0.5 hr after administration of 4M2-C12 mIgG2a.

Example 12: Analysis In Vivo of VISTA-Binding Antibodies Alone or in Combination with Anti-PD-1/PD-L1 Antibody 12.1 CT26 Cell Model A syngeneic model of T cell leukemia/lymphoma was generated by injecting $1\times10^5$ CT26 cells subcutaneously into the right flank of Balb/c mice.

Mice (7 per treatment group) were administered intraperitoneally every 3 days for a total of 7 doses with:
600 µg of 4M2-C12 IgG2a ([17] of Example 5)
200 µg of anti-PD-1 antibody (clone RMP1-14 (Bioxcell))
600 µg of 4M2-C12 IgG2a+200 µg of anti-PD-1 antibody
PBS only Tumor volume was measured 3 times a week using a digital caliper and calculated using the formula [L×W2/2]. Study End point was considered to have been reached once the tumors of the control arm measured >1.5 cm in length.

Figure 36A:
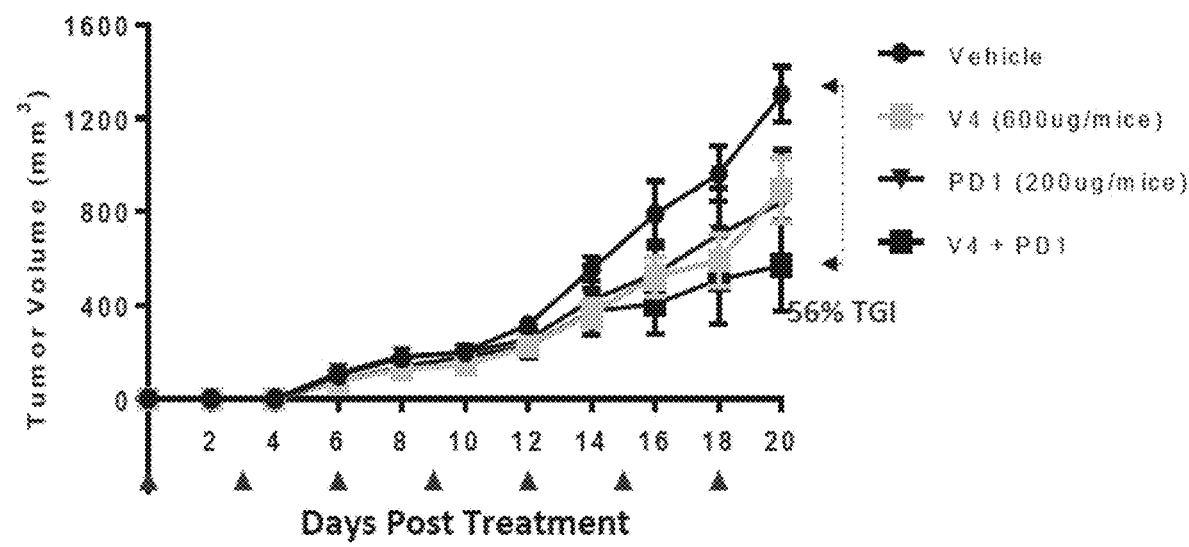
FIGS. 36A and 36B. Graphs showing the results of the analysis of anti-cancer activity in vivo of anti-VISTA antibody 4M2-C12 mIgG2a (V4), anti-PD-1 antibody (PD1) or combination treatment with 4M2-C12 mIgG2a and anti-PD-1 antibody, in a cell-line derived mouse model of colon carcinoma. 36A shows data for the different treatment groups, 36B shows the data obtained for individual mice in the vehicle control and 4M2-C12 mIgG2a+anti-PD-1 treatment groups.
Figure 36B:
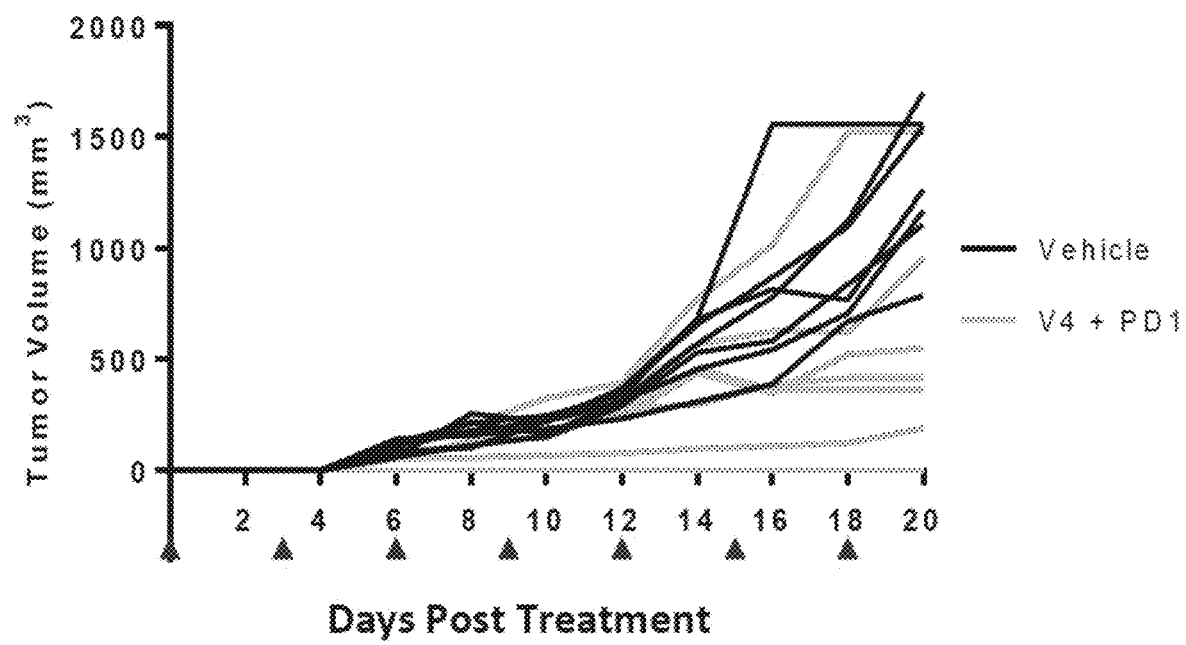

The results are shown in FIGS. 36A and 36B. Combination therapy with anti-VISTA antibody 4M2-C12 and anti-PD-1 inhibited tumor growth to a greater extent than either agent used alone.

Immunoprofiling of the tumor-infiltrating CD45+ cells was undertaken. Briefly, at day 22 of the experiment tumors were harvested, processed into single cell suspensions and stained with antibodies specific for immune cell surface proteins (CD45, CD4, CD8, CD25, CD11b, Ly6G, and Ly6C).

Samples were analysed by flow cytometry, and were classified into the following immune cell subsets based on their staining for the different immune cell surface proteins as follows:
CD4 cells: $CD45^+CD4^+$;
CD8 T cells: $CD45^+CD8^+$;
Treg cells: $CD45^+CD4^+CD25^+$;
Granulocytic MDSC (g-MDSC): $CD45^+CD11b^+Ly6G^+Ly6C^{lo/-}$
Monocytic MDSC (m-MDSC): $CD45^+CD11b^+Ly6G^-Ly6C^{hi/+}$ The percentage of tumor-infiltrating CD45+ cells having the indicated phenotypes are summarised below:

| Treatment Group | CD4 cells | CD8 cells | Treg | g-MDSC | m-MDSC |
|---|---|---|---|---|---|
| PBS | 1.03% | 5.99% | 0.09% | 33.08% | 9.8% |
| 4M2-C12 IgG2a | 1.66% | 6.51% | 0.11% | 26.4% | 8.34% |
| anti-PD-1 antibody | 1.05% | 7.21% | 0.14% | 46.2% | 15.25% |
| 4M2-C12 IgG2a + anti-PD-1 antibody | 1.55% | 9.98% | 0.22% | 15.66% | 14.04% |

Figure 37:
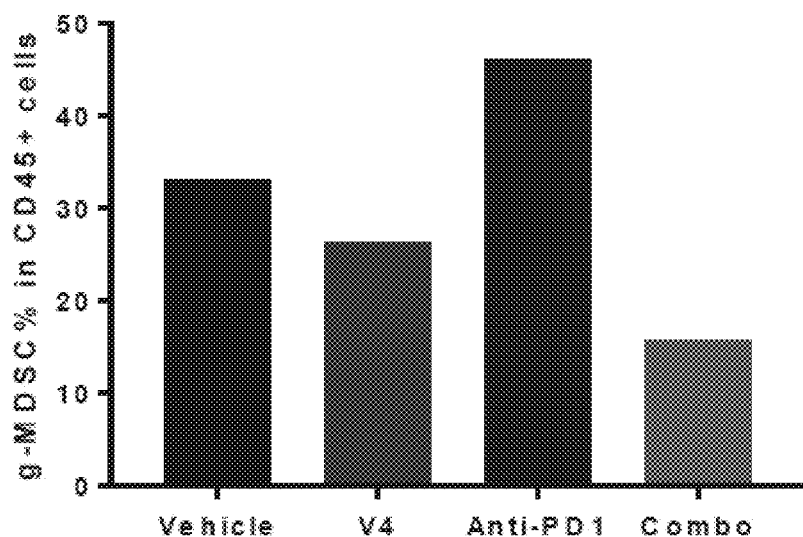
FIG. 37. Bar chart showing the percentage of tumor-infiltrating CD45+ cells which are g-MDSCs of day 22 tumors of a cell-line derived mouse model of colon carcinoma, obtained from mice treated with PBS (Vehicle), anti-VISTA antibody 4M2-C12 mIgG2a (V4), anti-PD-1 antibody (Anti-PD1) or combination treatment with 4M2-C12 mIgG2a and anti-PD-1 antibody (Combo).
Figure 38A:
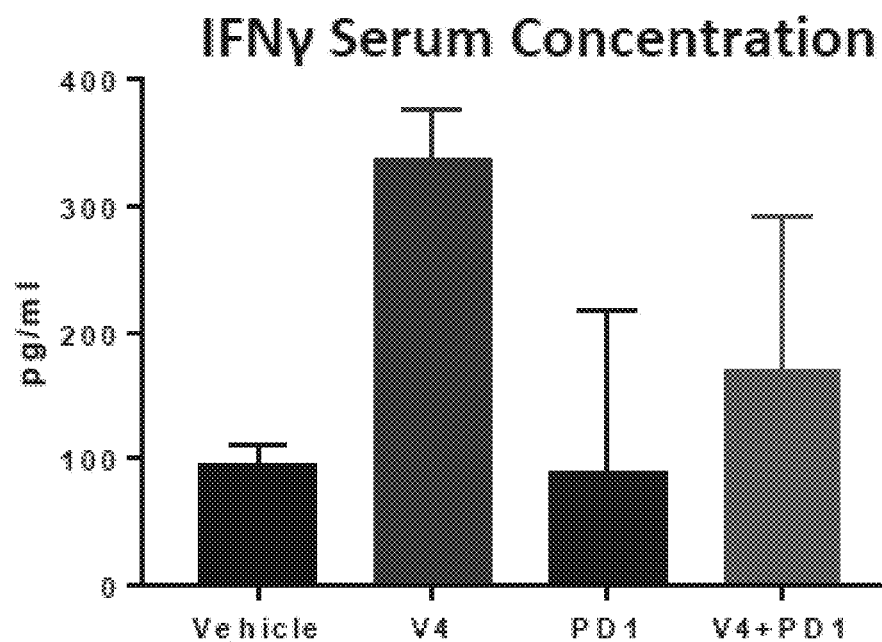
FIGS. 38A to 38E. Bar charts showing levels of (38A) IFNγ, (38B) IL-23, (38C) IL-10, (38D) IL-4, and (38E) IL-5 in serum obtained at day 18 of a cell-line derived mouse model of colon carcinoma, obtained from mice treated with PBS (Vehicle), anti-VISTA antibody 4M2-C12 mIgG2a (V4), anti-PD-1 antibody (PD1) or combination treatment with 4M2-C12 mIgG2a and anti-PD-1 antibody (V4+PD1).
Figure 38B:
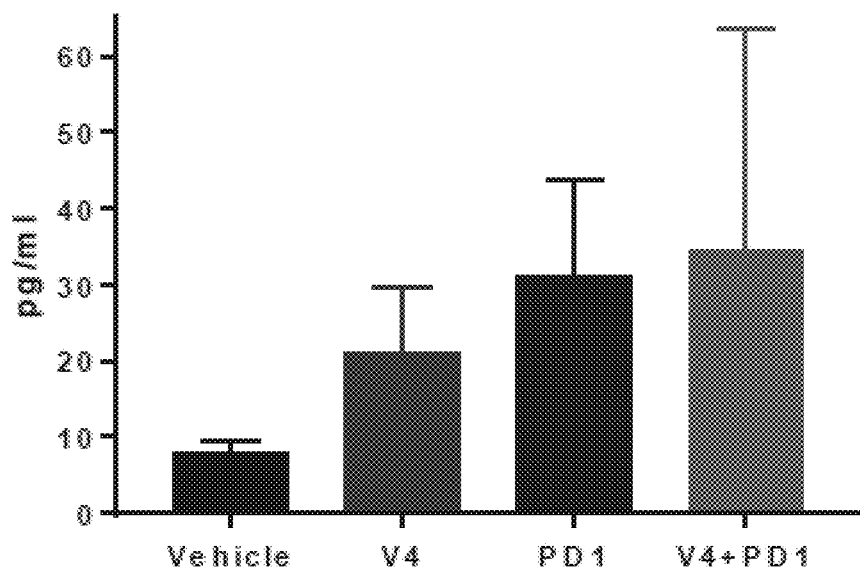
Figure 38C:
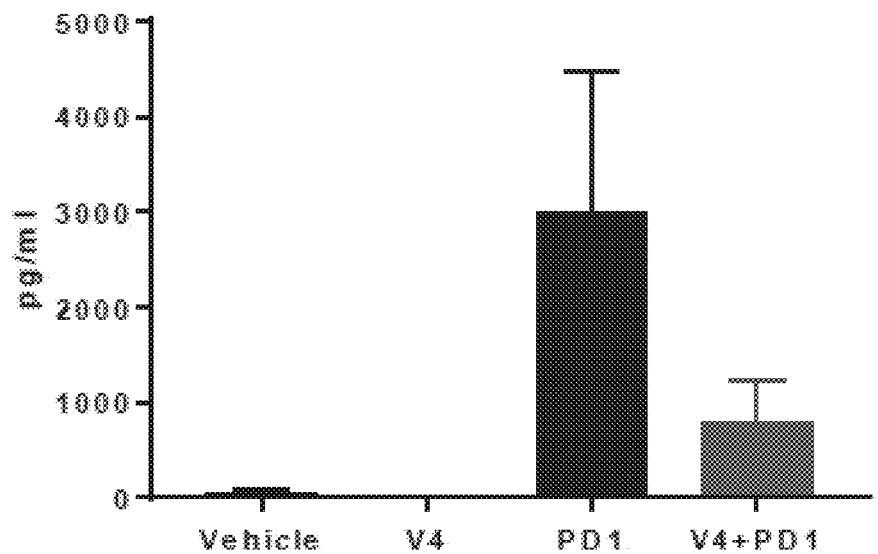
Figure 38D:
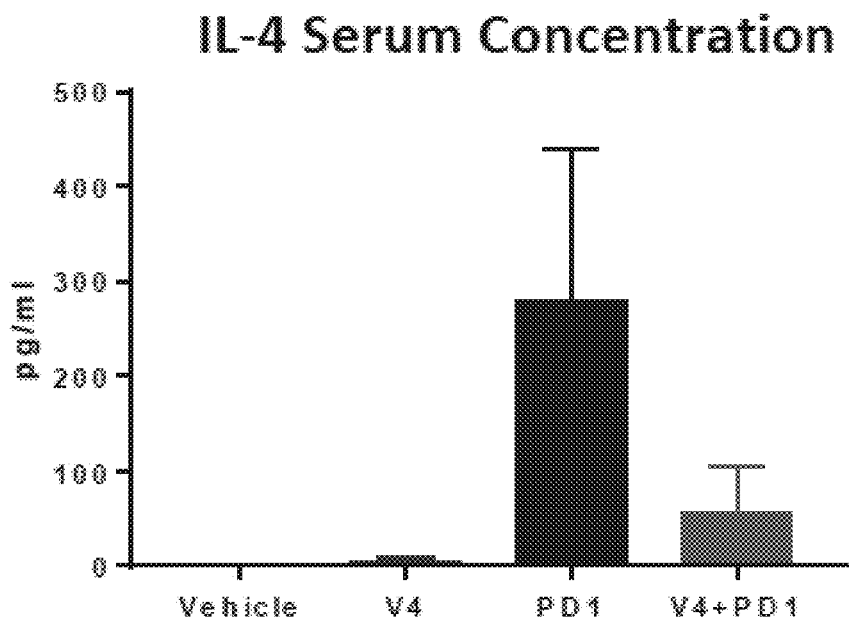
Figure 38E:
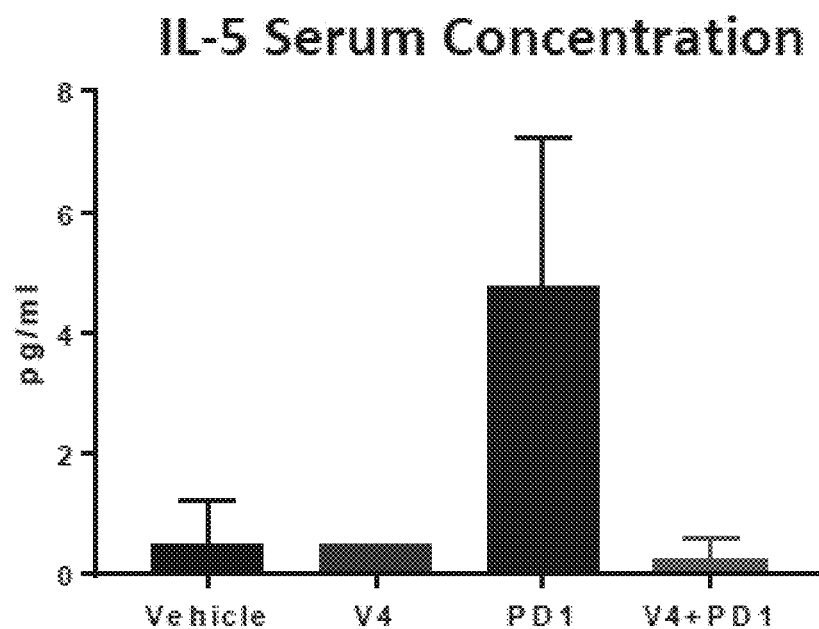

The percentage of tumor-infiltrating CD45+ cells which were g-MDSC is shown in FIG. 37. Treatment with 4M2-C12 (either alone, or in combination with anti-PD-1) significantly reduced the proportion of g-MDSCs amongst the tumor-infiltrating CD45+ cells.

Blood was obtained from mice at day 18, and serum was analysed for the levels of various different cytokines by analysis using the MACSPlex cytokine 10 Kit for mouse (Miltenyi Biotec).

The results are shown in FIGS. 38A to 38E.

12.2 B16-BL6 Cell Model

Figure 40A:
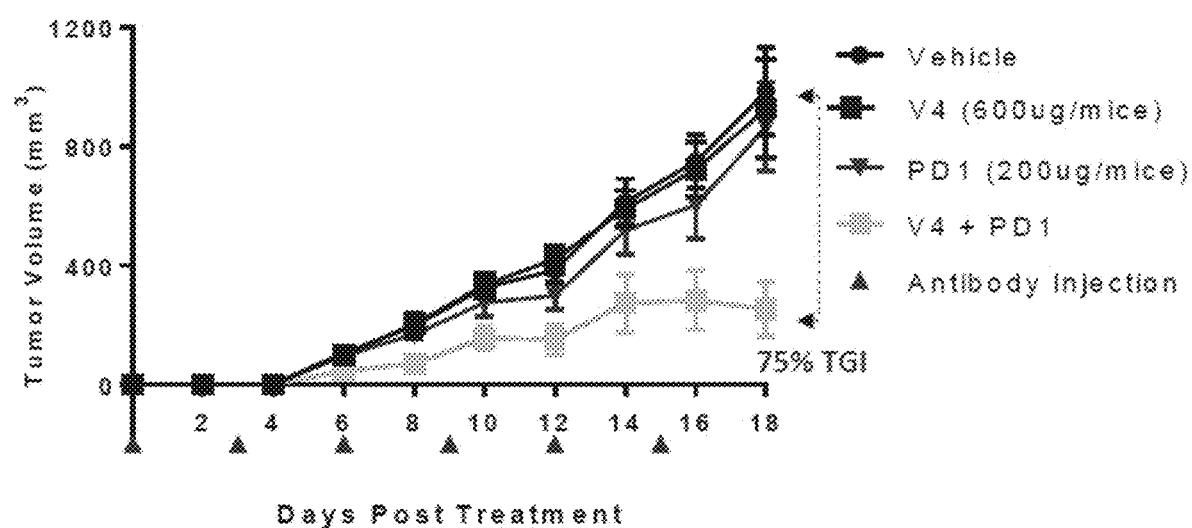
FIGS. 40A and 40B. Graphs showing the results of the analysis of anti-cancer activity in vivo of anti-VISTA antibody 4M2-C12 mIgG2a (V4), anti-PD-1 antibody (PD1) or combination treatment with 4M2-C12 mIgG2a and anti-PD-1 antibody, in a cell-line derived mouse model of melanoma. 40A shows data for the different treatment groups, 40B shows the data obtained for individual mice in the vehicle control and 4M2-C12 mIgG2a+anti-PD-1 treatment groups.
Figure 40B:
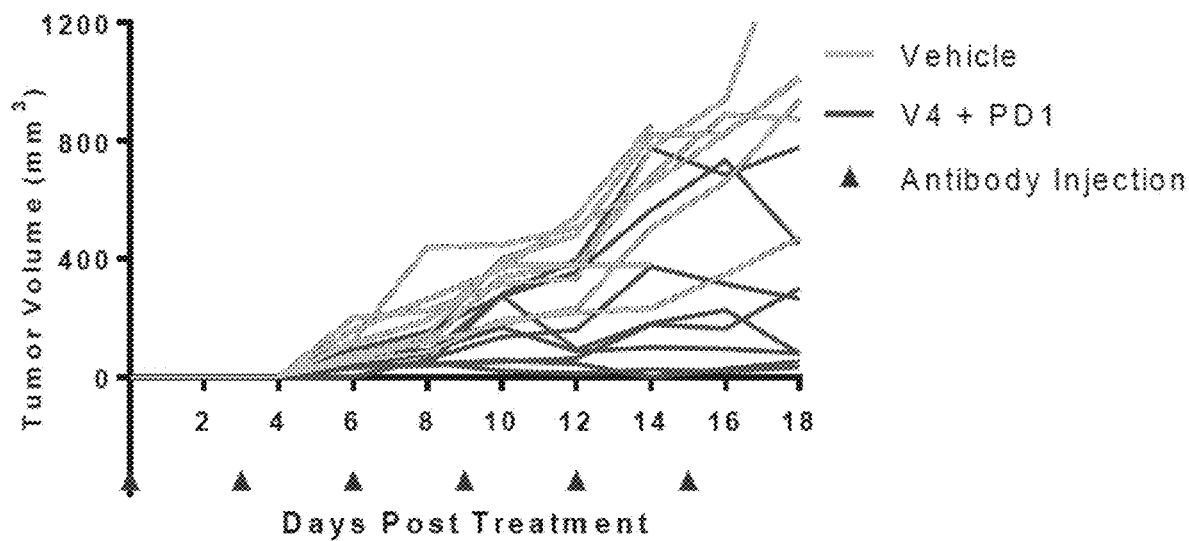

FIGS. 40A and 40B show the results of the study described in Example 5.2.3 above (results shown in FIG. 17), extended to 18 days. Combination therapy with anti-VISTA antibody 4M2-C12 and anti-PD-1 inhibited tumor growth to a greater extent than either agent used alone.

Immunoprofiling of the tumor-infiltrating CD45+ cells was undertaken. Briefly, at day 18 of the experiment tumors were harvested, processed into single cell suspensions, stained with antibodies and specific for immune cell surface, analysed by flow cytometry and cells were classified into immune cell subsets as described in Example 12.1 above.

The percentage of tumor-infiltrating CD45+ cells having the indicated phenotypes are summarised below:

| Treatment Group | CD4 cells | CD8 cells | Treg | g-MDSC | m-MDSC |
|---|---|---|---|---|---|
| PBS | 2.72% | 8.79% | 1.42% | 2.06% | 6.68% |
| 4M2-C12 IgG2a | 2.84% | 10.7% | 1.58% | 1.65% | 13.94% |
| anti-PD-1 antibody | 0.95% | 3.43% | 0.51% | 36.65% | 14.12% |
| 4M2-C12 IgG2a + anti-PD-1 antibody | 3.58% | 10.6% | 0.82% | 5.45% | 14.44% |

Figure 41:
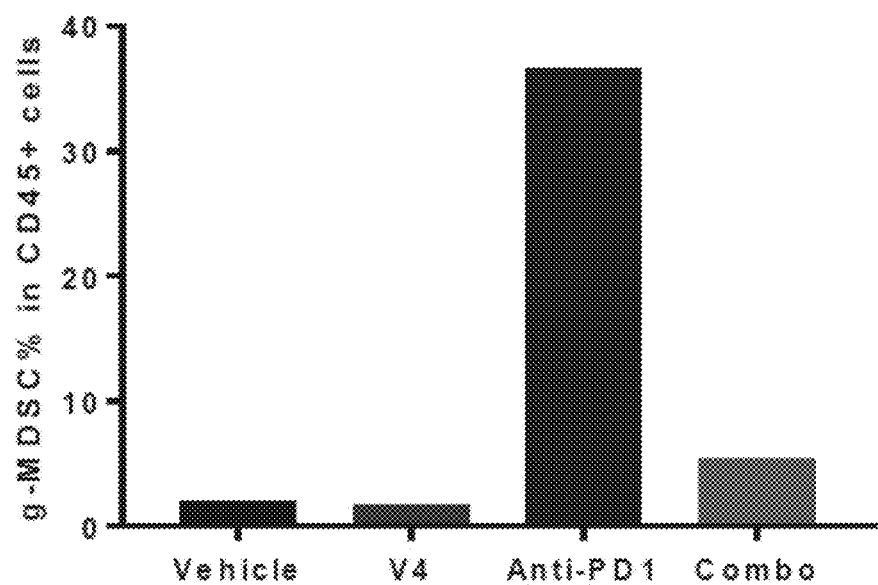
FIG. 41. Bar chart showing the percentage of tumor-infiltrating CD45+ cells which are g-MDSCs of day 18 tumors of a cell-line derived mouse model of melanoma, obtained from mice treated with PBS (Vehicle), anti-VISTA antibody 4M2-C12 mIgG2a (V4), anti-PD-1 antibody (Anti-PD1) or combination treatment with 4M2-C12 mIgG2a and anti-PD-1 antibody (Combo).

The percentage of tumor-infiltrating CD45+ cells which were g-MDSC is shown in FIG. 41.

12.3 EL4 Cell Model

A syngeneic model of T cell leukemia/lymphoma was established by injecting $2\times10^5$ EL4 cells subcutaneously into the right flank of C57BL/6 mice.

Mice (7 per treatment group) were administered intraperitoneally every 3 days for a total of 5 doses with:
600 µg of 4M2-C12 IgG2a ([17] of Example 5)
200 µg of anti-PD-1 antibody (clone RMP1-14 (Bioxcell))
600 µg of 4M2-C12 IgG2a+200 µg of anti-PD-1 antibody
PBS only Tumor volume was measured 3 times a week using a digital caliper and calculated using the formula [L×W2/2]. Study End point was considered to have been reached once the tumors of the control arm measured >1.5 cm in length.

Figure 42:
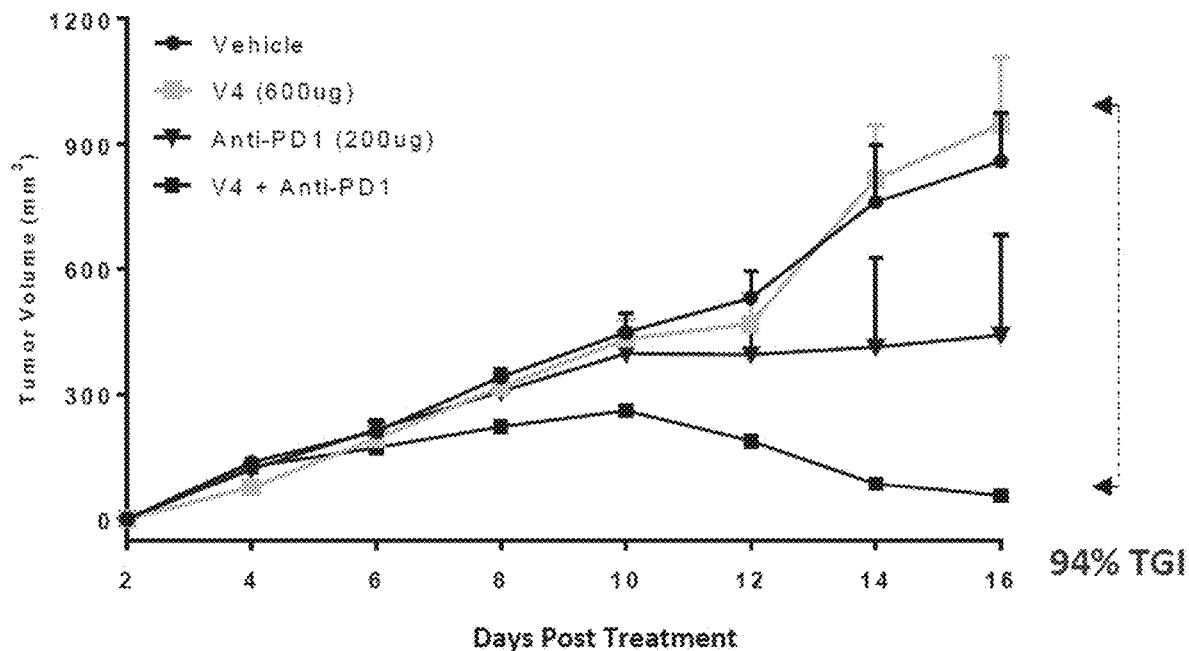
FIG. 42. Graph showing the results of the analysis of anti-cancer activity in vivo of anti-VISTA antibody 4M2-C12 mIgG2a (V4), anti-PD-1 antibody (Anti-PD1) or combination treatment with 4M2-C12 mIgG2a and anti-PD-1 antibody (V4+Anti-PD1), in a cell-line derived mouse model of T cell leukemia/lymphoma.

The results are shown in FIG. 42. Combination therapy with anti-VISTA antibody 4M2-C12 and anti-PD-1 inhibited tumor growth to a greater extent than either agent used alone.

Immunoprofiling of the tumor-infiltrating CD45+ cells was undertaken. Briefly, at day 16 of the experiment tumors were harvested, processed into single cell suspensions, stained with antibodies and specific for immune cell surface, analysed by flow cytometry and cells were classified into immune cell subsets as described in Example 12.1 above.

The percentage of tumor-infiltrating CD45+ cells having the indicated phenotypes are summarised below:

| Treatment Group | CD4 cells | CD8 cells | Treg | g-MDSC | m-MDSC |
|---|---|---|---|---|---|
| PBS | 3.71% | 0.55% | 0.18% | 19.41% | 0.88% |
| 4M2-C12 IgG2a | 7.4% | 1.84% | 0.19% | 14.51% | 0.94% |
| anti-PD-1 antibody | 4.35% | 3.04% | 0.09% | 20.91% | 0.81% |
| 4M2-C12 IgG2a + anti-PD-1 antibody | 6.53% | 2.18% | 0.35% | 10.16% | 0.33% |

Figure 43:
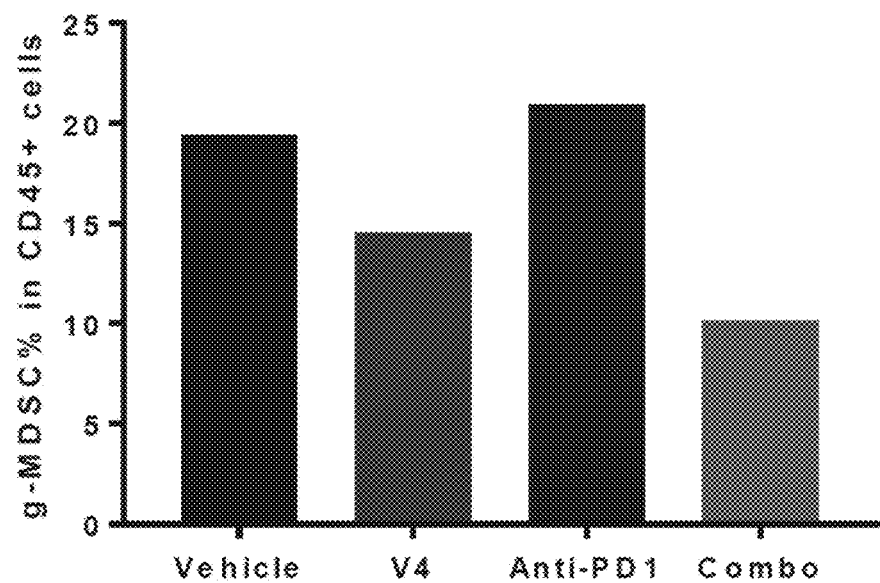
FIG. 43. Bar chart showing the percentage of tumor-infiltrating CD45+ cells which are g-MDSCs of day 16 tumors of a cell-line derived mouse model of T cell leukemia/lymphoma, obtained from mice treated with PBS (Vehicle), anti-VISTA antibody 4M2-C12 mIgG2a (V4), anti-PD-1 antibody (Anti-PD1) or combination treatment with 4M2-C12 mIgG2a and anti-PD-1 antibody (Combo).

The percentage of tumor-infiltrating CD45+ cells which were g-MDSC is shown in FIG. 43. Treatment with 4M2-C12 (either alone, or in combination with anti-PD-1) significantly reduced the proportion of g-MDSCs amongst the tumor-infiltrating CD45+ cells.

12.4 Conclusions

Inhibition of PD-1/PD-L1 signalling increases the proportion of g-MDSCs amongst the tumor-infiltrating CD45+ cells in the CT26, B16-BL6 and EL4 models, whereas treatment with 4M2-C12 suppresses g-MDSC expansion.

Example 13: Further Characterisation of VISTA-Binding Antibodies

Further VISTA-binding antigen-binding molecules were produced:

| Antigen-biding molecule | Polypeptides | Antibody |
|---|---|---|
| [21] | V4-C1 VH-CH1-CH2-CH3 (SEQ ID NO: 311) + V4-C1 VL-$C_K$ (SEQ ID NO: 312) | anti-VISTA clone V4-C1 IgG1 |
| [22] | V4-C9 VH-CH1-CH2-CH3 (SEQ ID NO: 313) + V4-C9 VL-$C_K$ (SEQ ID NO: 314) | anti-VISTA clone V4-C9 IgG1 |
| [23] | V4-C24/C26/C27/C28/C30/C31 VH-CH1-CH2-CH3 (SEQ ID NO: 315) + V4-C24 VL-$C_K$ (SEQ ID NO: 316) | anti-VISTA clone V4-C24 IgG1 |
| [24] | V4-C24/C26/C27/C28/C30/C31 VH-CH1-CH2-CH3 (SEQ ID NO: 315) + V4-C26 VL-$C_K$ (SEQ ID NO: 317) | anti-VISTA clone V4-C26 IgG1 |
| [25] | V4-C24/C26/C27/C28/C30/C31 VH-CH1-CH2-CH3 (SEQ ID NO: 315) + V4-C27 VL-$C_K$ (SEQ ID NO: 318) | anti-VISTA clone V4-C27 IgG1 |
| [26] | V4-C24/C26/C27/C28/C30/C31 VH-CH1-CH2-CH3 (SEQ ID NO: 315) + V4-C28 VL-$C_K$ (SEQ ID NO: 319) | anti-VISTA clone V4-C28 IgG1 |
| [27] | V4-C24/C26/C27/C28/C30/C31 VH-CH1-CH2-CH3 (SEQ ID NO: 315) + V4-C30 VL-$C_K$ (SEQ ID NO: 320) | anti-VISTA clone V4-C30 IgG1 |
| [28] | V4-C24/C26/C27/C28/C30/C31 VH-CH1-CH2-CH3 (SEQ ID NO: 315) + V4-C31 VL-$C_K$ (SEQ ID NO: 321) | anti-VISTA clone V4-C31 IgG1 |

V4-C1, V4-C9, V4-C24, V4-C26, V4-C27, V4-C28, V4-C30 and V4-C31 were analysed in silico for safety and immunogenicity using IMGT DomainGapAlign (Ehrenmann et al., Nucleic Acids Res., 38, D301-307 (2010)) and IEDB deimmunization (Dhanda et al., Immunology. (2018) 153(1):118-132) tools.

V4-C1, V4-C9, V4-C24, V4-C26, V4-C27, V4-C28, V4-C30 and V4-C31 had sufficient homology to human heavy and light chains to be considered humanized (i.e. >85%), had numbers of potentially immunogenic peptides few enough to be considered safe (see FIG. 53), and did not possess any other properties that could cause potential developability issues.

13.1 Analysis of Binding Affinity by BLI

Binding of V4-C1, V4-C9, V4-C24, V4-C26, V4-C27, V4-C28, V4-C30 and V4-C31 (i.e. [21] to [28]) to human and mouse VISTA proteins and human PD-L1 was assessed by BLI using a Pall ForteBio Octet QK 384 system.

Briefly, anti-Penta-HIS biosensors were incubated for 60 sec in PBS buffer (pH 7.2) to obtain the first baseline, and were subsequently loaded for 120 sec with 180 nM hVISTA, 180 nM mVISTA or 250 nM hPD-L1 in PBS (pH 7.2). After loading, biosensors were incubated for 60 sec in PBS buffer pH 7.2 to obtain the second baseline, and for 120 sec or 900 sec with a 6 point, 2 fold dilution series of the test antibodies (500 nM-15.6 nM) in PBS pH 7.2 to obtain the association curves. Finally, the biosensors were incubated for 120 sec in PBS pH 7.2 to obtain the dissociation curves. Kinetic and affinity constants were calculated by global fitting of the association and dissociation data to a 1:1 binding model.

Figure 45A:
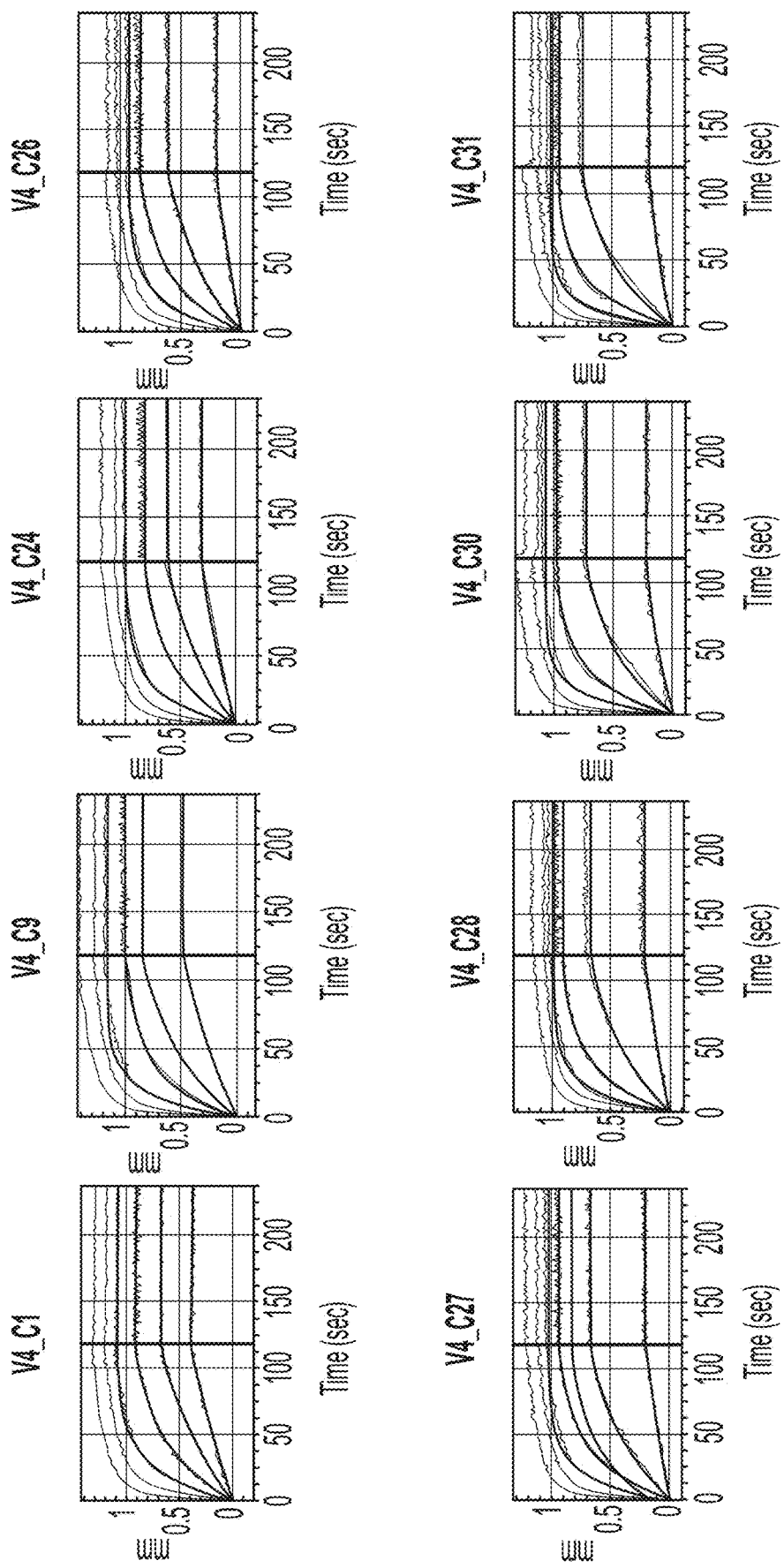
Figure 45B:
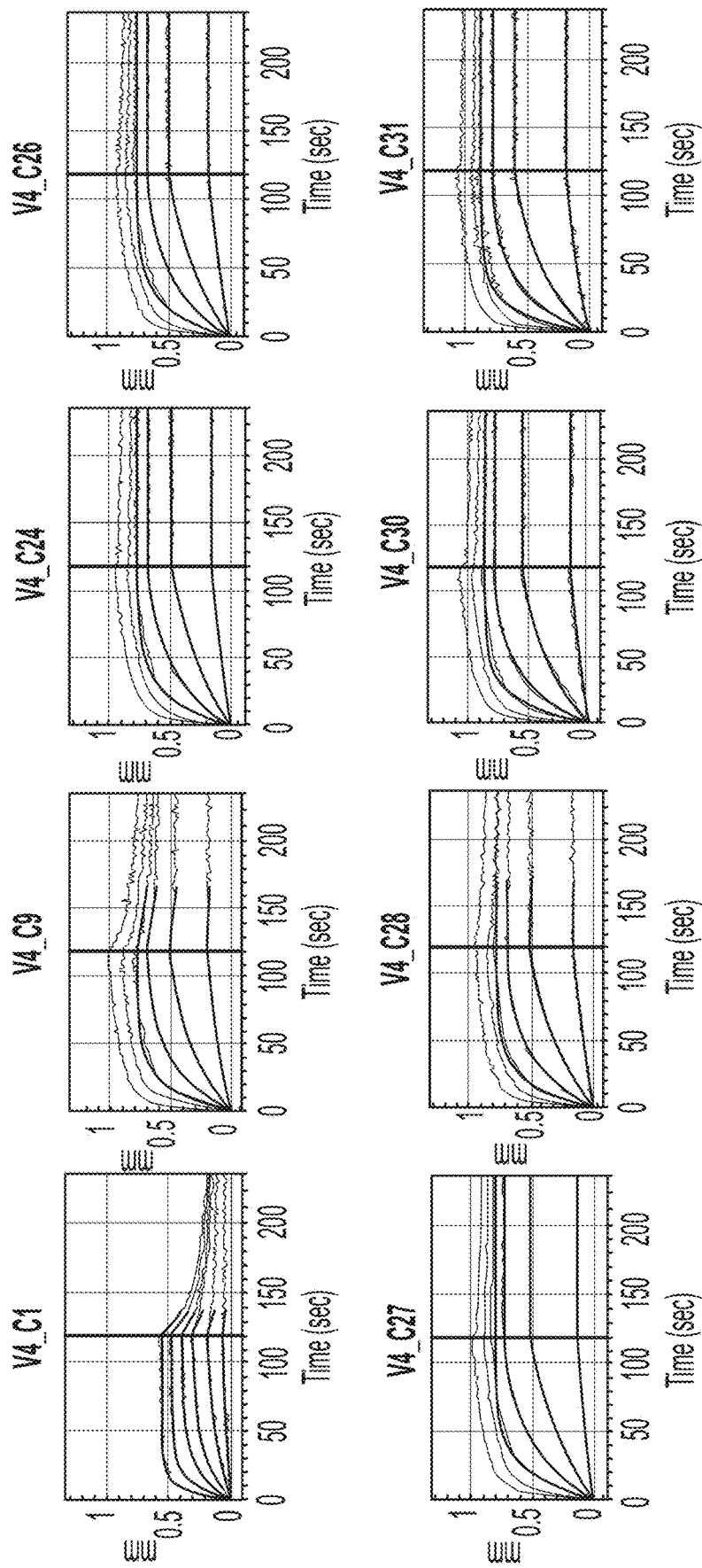
Figure 45C:
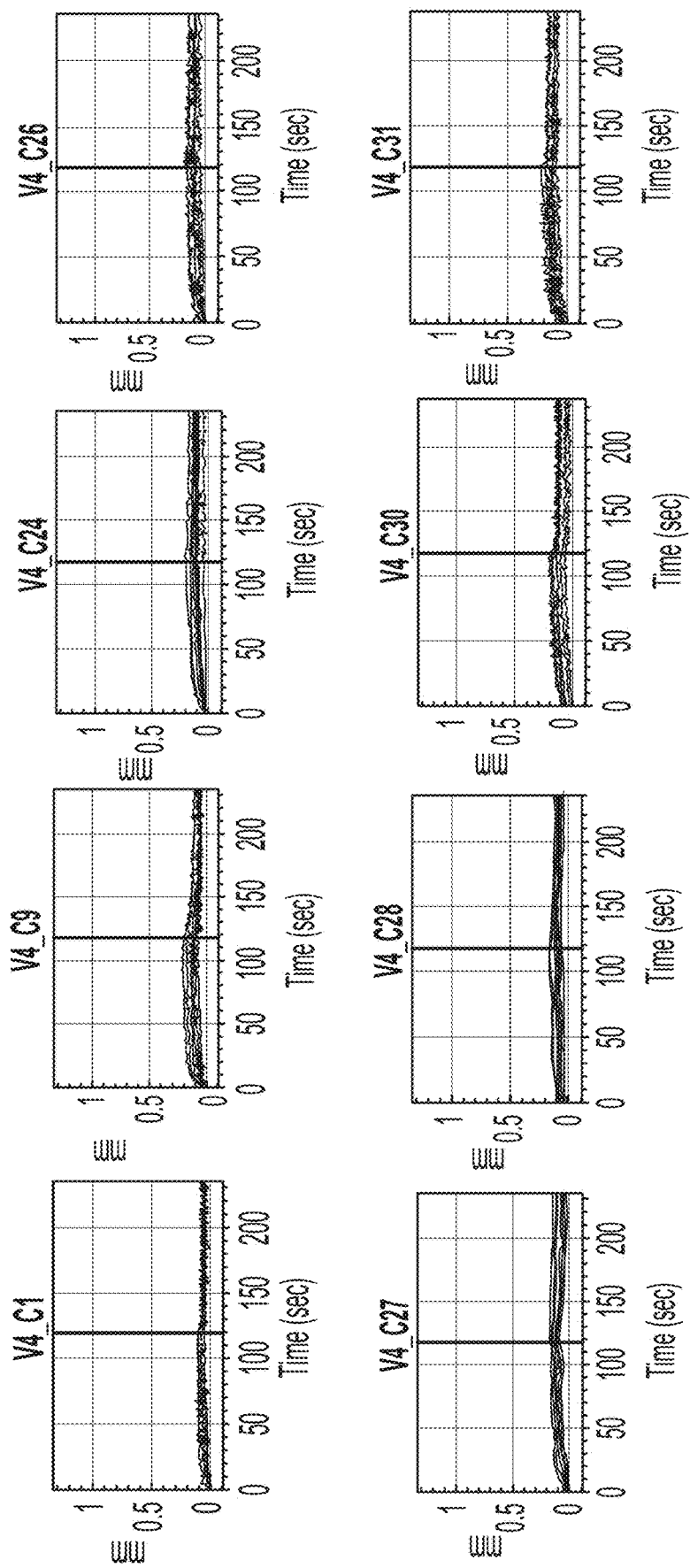

None of V4-C1, V4-C9, V4-C24, V4-C26, V4-C27, V4-C28, V4-C30 or V4-C31 displayed significant binding to human PD-L1 (FIG. 45C).

The kinetic and thermodynamic constants calculated for binding of V4-C1, V4-C9, V4-C24, V4-C26, V4-C27, V4-C28, V4-C30 and V4-C31 to human VISTA and mouse VISTA in this experiment are shown in FIG. 45D.

Binding to mouse VISTA protein by V4-C1, V4-C9, V4-C24, V4-C26, V4-C27, V4-C28, V4-C30 and V4-C31 was analysed in a separate experiment, which included evaluation of VSTB112 IgG1 (comprising VSTB112 HC (SEQ ID NO: 269)+VSTB112 LC (SEQ ID NO: 270)).

Figure 46A:
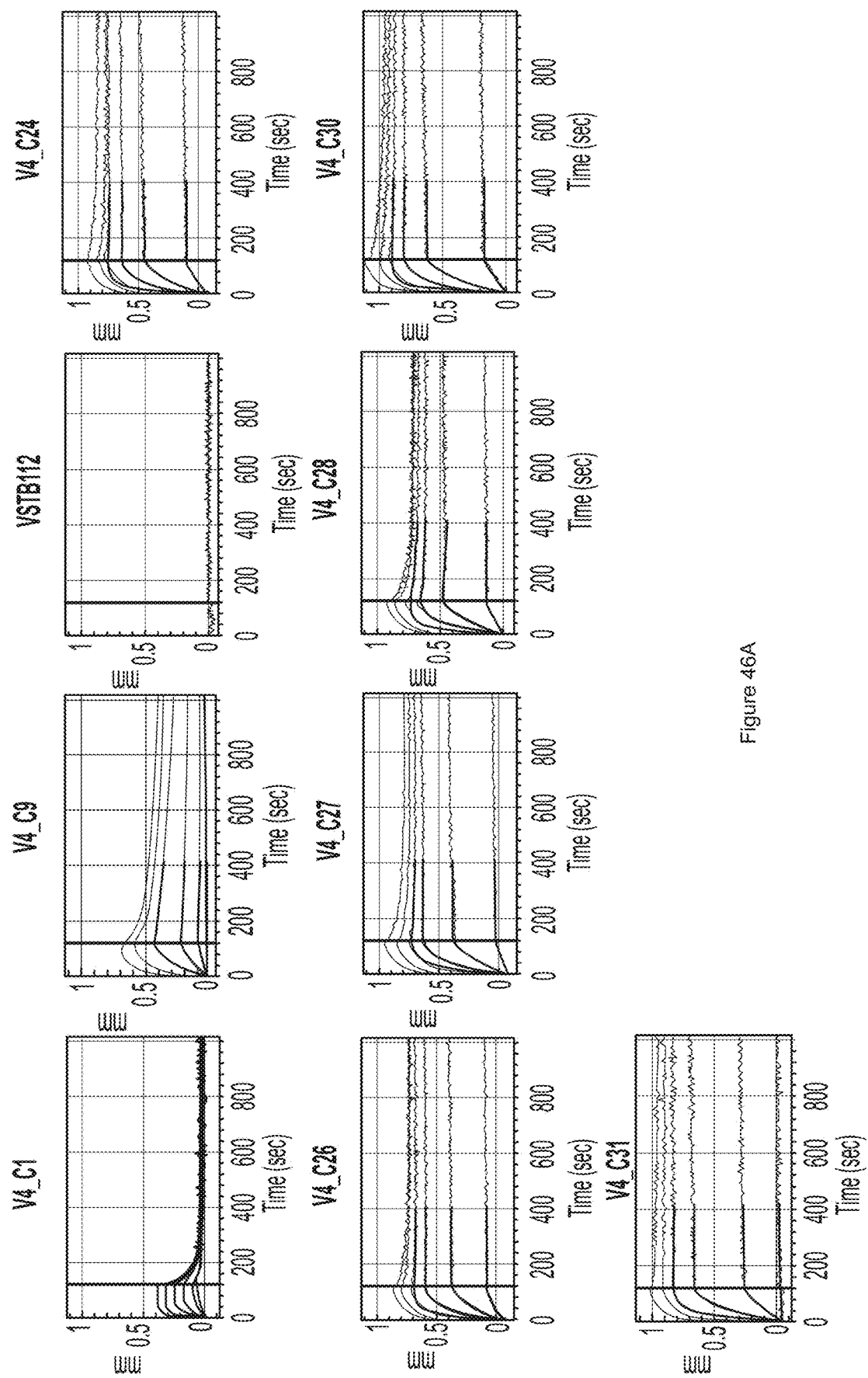

VSTB112 did not display significant binding to mouse VISTA protein (FIG. 46A). The kinetic and thermodynamic constants calculated for binding of V4-C1, V4-C9, V4-C24, V4-C26, V4-C27, V4-C28, V4-C30 and V4-C31 to mouse VISTA in this experiment are shown in FIG. 46B.

Figure 47A:
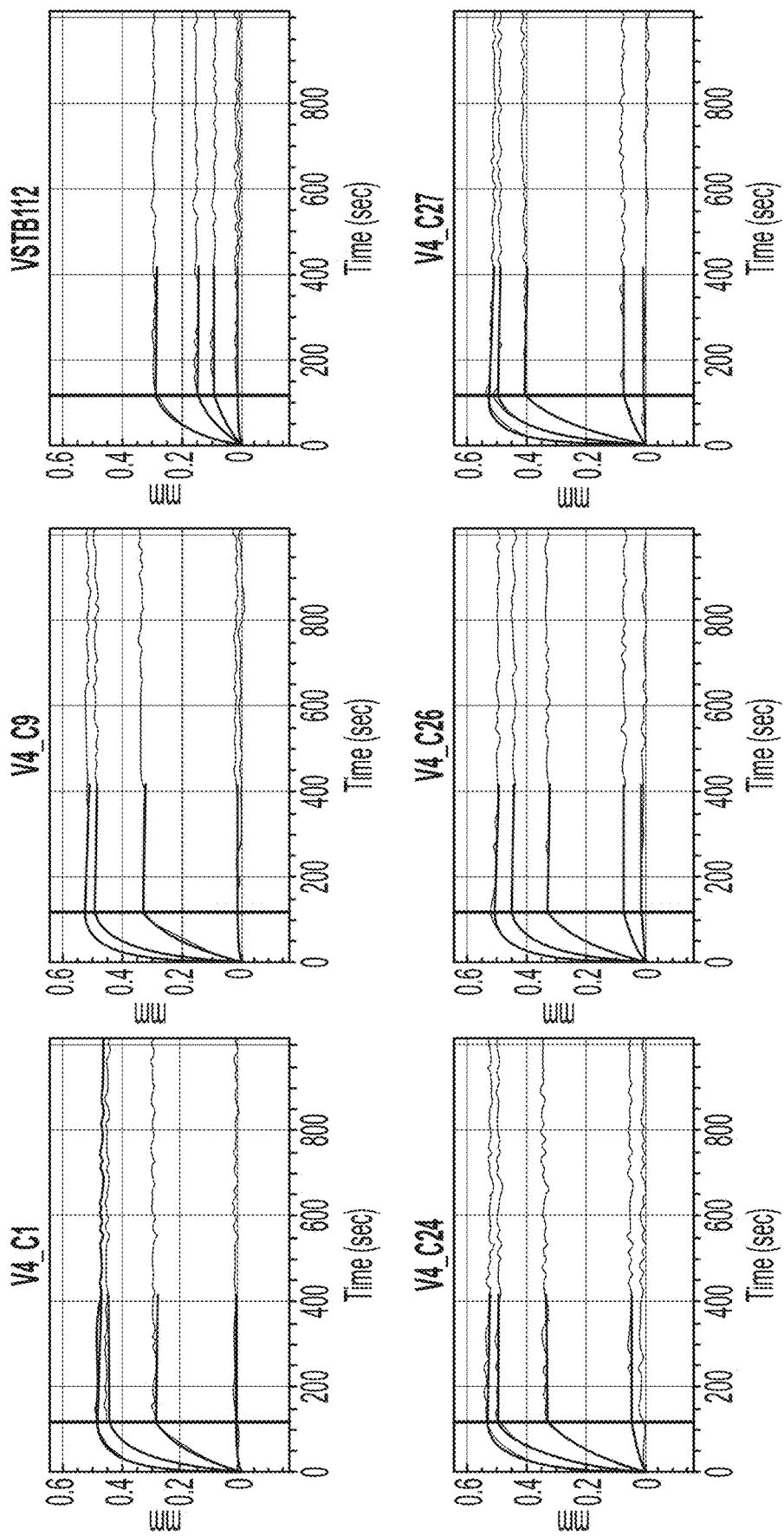
Figure 47B:
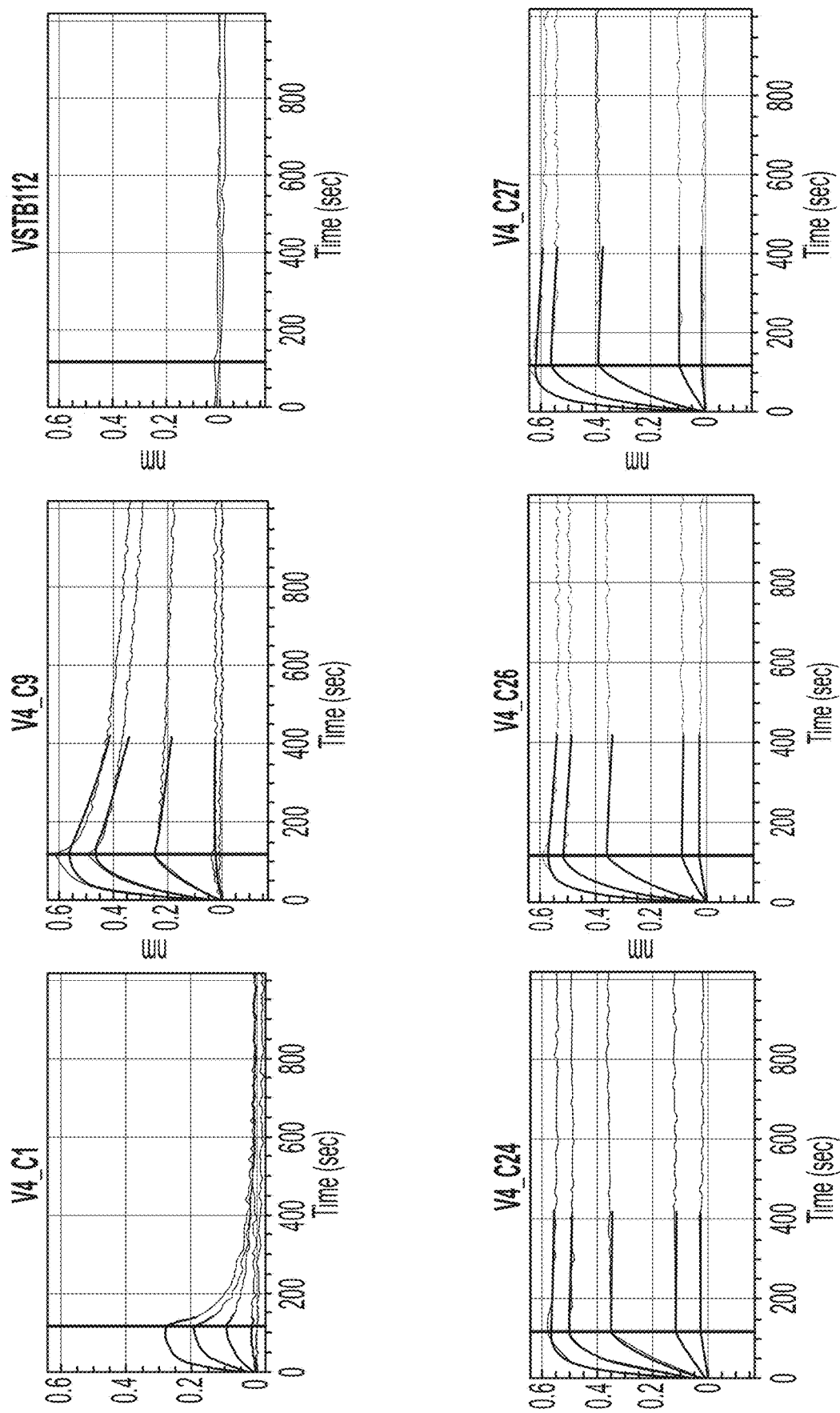

In a further experiment, binding of V4-C1, V4-C9, V4-C24, V4-C26, V4-C27 and VSTB112 IgG1 to human VISTA and mouse VISTA was analysed, and the calculated kinetic and thermodynamic constants are shown in FIG. 47C.

In another experiment, binding of V4 ([1] of Example 2.2) and VSTB112 IgG1 (comprising VSTB112 HC (SEQ ID NO: 269)+VSTB112 LC (SEQ ID NO: 270)) to human VISTA, mouse VISTA and human CD47 was analysed. Anti-Penta-HIS biosensors were incubated for 60 sec in PBS buffer (pH 7.2) to obtain the first baseline, and were subsequently loaded for 120 sec with 180 nM hVISTA, 180 nM mVISTA or 300 nM hCD47 in PBS (pH 7.2). After loading, biosensors were incubated for 60 sec in PBS buffer pH 7.2 to obtain the second baseline, and for 120 sec with a dilution series of the test antibodies (1500 nM-46.9 nM) in PBS pH 7.2 to obtain the association curves. Finally, the biosensors were incubated for 120 sec in PBS pH 7.2 to obtain the dissociation curves. Kinetic and affinity constants were calculated by global fitting of the association and dissociation data to a 1:1 binding model.

Neither V4 nor VSTB112 displayed binding to human CD47. VSTB112 did not display significant binding to mouse VISTA protein, whereas V4 did. The calculated kinetic and thermodynamic constants are shown in FIG. 48B.

13.2 Analysis of Binding Affinity by ELISA

ELISAs were used to evaluate binding of different antibodies to human VISTA and mouse VISTA. The ELISAs were performed as described in Example 3.3 above.

Figure 48A:
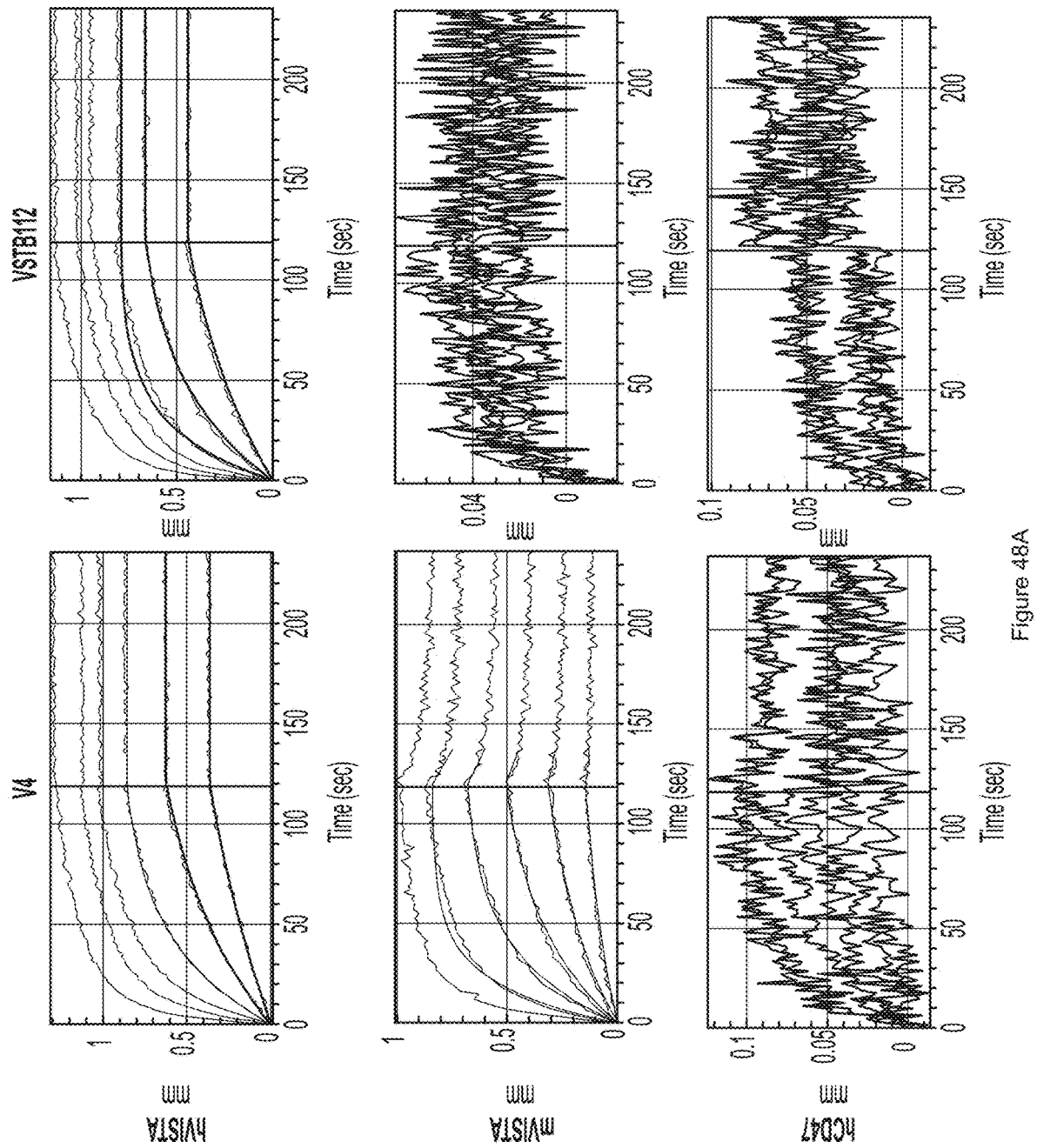
FIGS. 48A and 48B. Sensorgrams and table showing the results of analysis of binding of different anti-VISTA antibodies to human VISTA, and mouse VISTA and human CD47, as determined by Biolayer Interferometry. 48B summarises the kinetic and thermodynamic constants calculated from the sensorgrams of 48A.
Figures 48B, 49A:
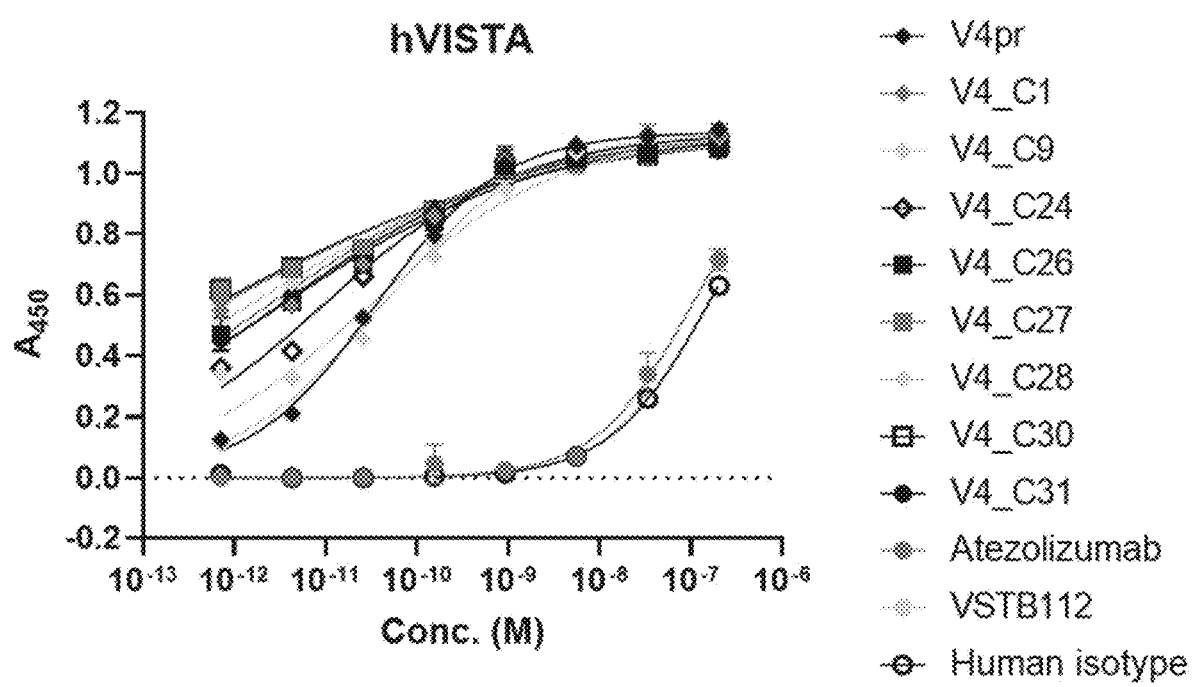
FIGS. 49A to 49C. Concentration-response graphs and table showing the results of analysis of binding of different antibodies to human VISTA (49A) or mouse VISTA (49B), as determined by ELISA. 49C shows EC50 values (nM) for binding of the different antibodies to the indicated proteins.
Figures 49B, 49C:
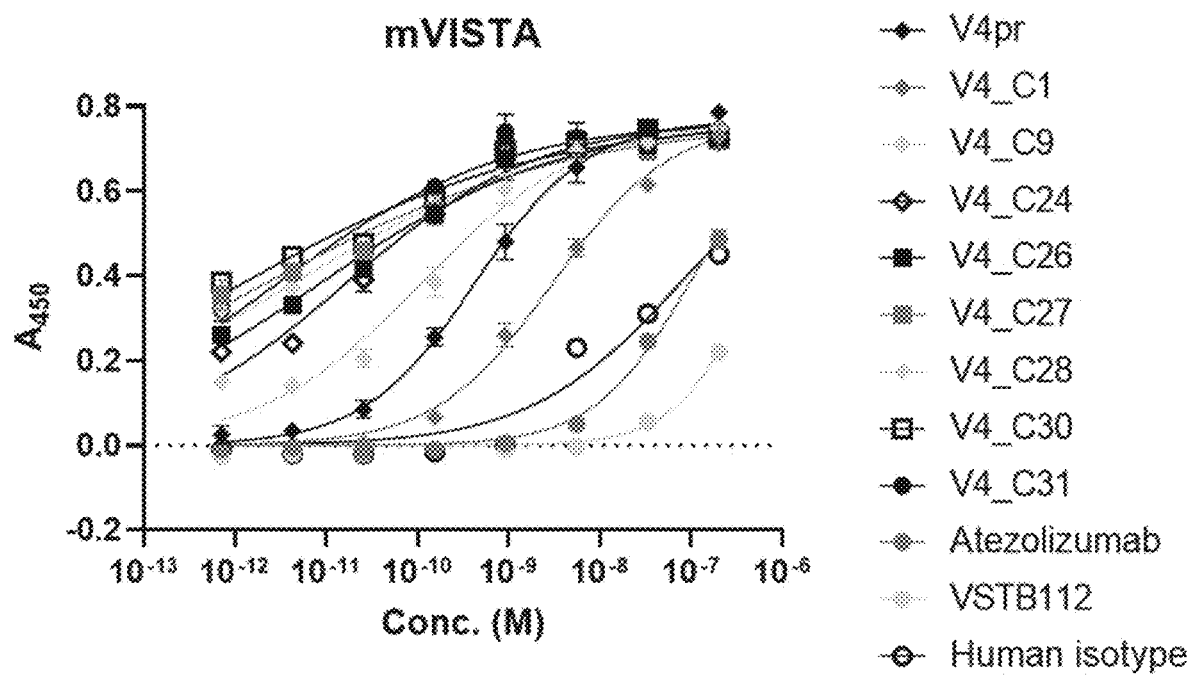

The following antibodies were analysed in the experiments:
- 4M2-C12 IgG1 ([1] of Example 2.2; referred to as "V4pr" in the Figures)
- V4-C1 IgG1 ([21] of Example 13)
- V4-C9 IgG1 ([22] of Example 13)
- V4-C24 IgG1 ([23] of Example 13)
- V4-C26 IgG1 ([24] of Example 13)
- V4-C27 IgG1 ([25] of Example 13)
- V4-C28 IgG1 ([26] of Example 13)
- V4-C30 IgG1 ([27] of Example 13)
- V4-C31 IgG1 ([28] of Example 13)
- VSTB112 IgG1 (comprising VSTB112 HC (SEQ ID NO: 269)+VSTB112 LC (SEQ ID NO: 270))
- Atezolizumab
- Human IgG1 Isotype control The results obtained are shown in FIGS. 49A and 49B, and the EC50 (nM) values calculated from the ELISAs for binding of the antibodies to the indicated proteins are summarised in FIG. 49C.

Figure 50A:
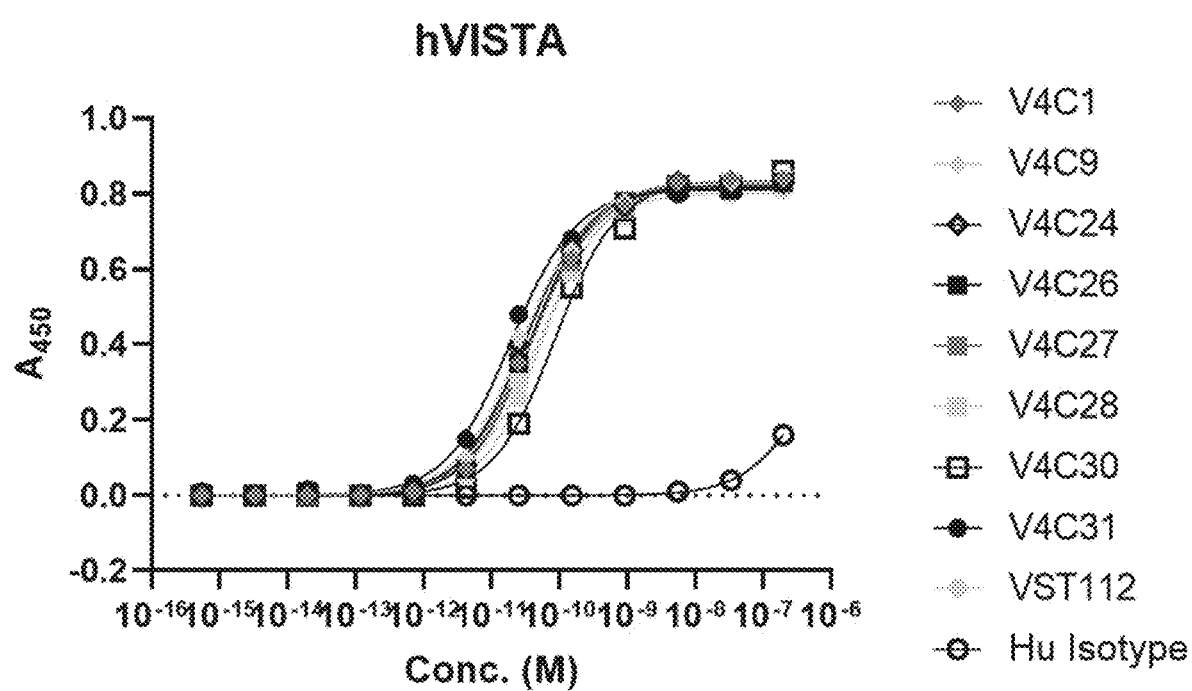
FIGS. 50A to 50C. Concentration-response graphs and table showing the results of analysis of binding of different antibodies to human VISTA (50A) and mouse VISTA (50B), as determined by ELISA. 50C shows EC50 values (nM) for binding of the different antibodies to the indicated proteins.
Figures 50B, 50C:
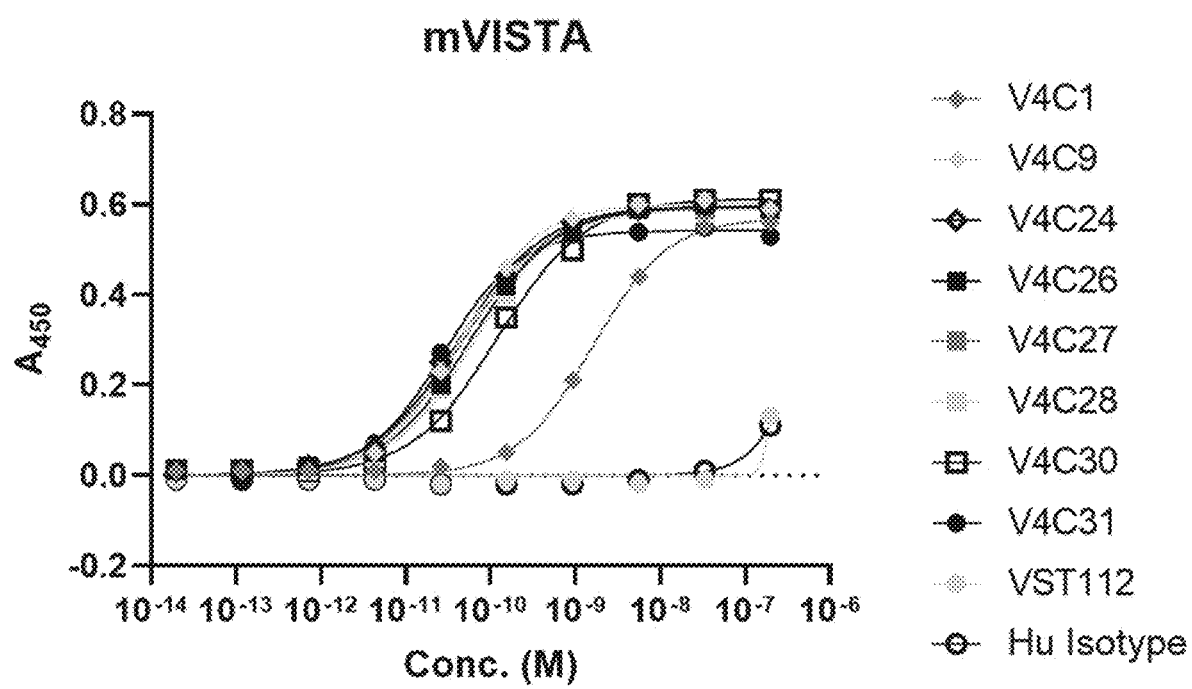

A further experiment was performed in which binding of V4-C1, V4-C9, V4-C24, V4-C26, V4-C27, V4-C28, V4-C30, V4-C31, VSTB112 and isotype control antibody to human VISTA or mouse VISTA was analysed. The results are shown in FIGS. 50A and 50B, and the EC50 (nM) values calculated from the ELISAs for binding of the antibodies to the indicated proteins are summarised in FIG. 50C.

Figure 51A:
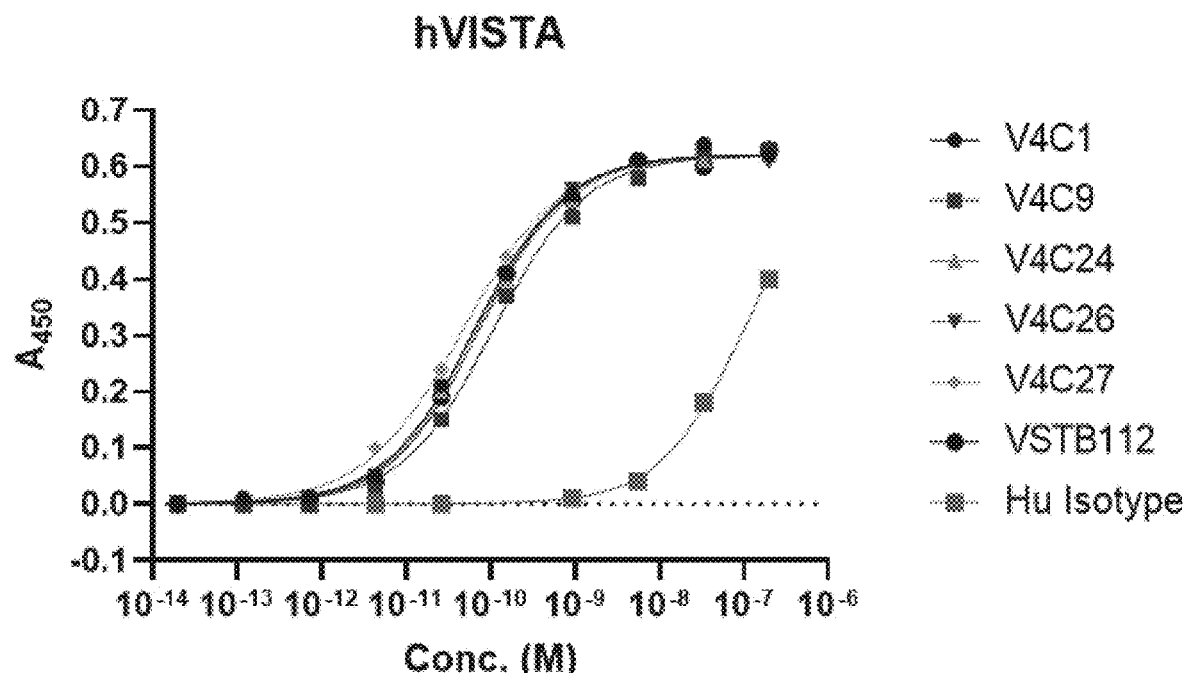
Figure 51B:
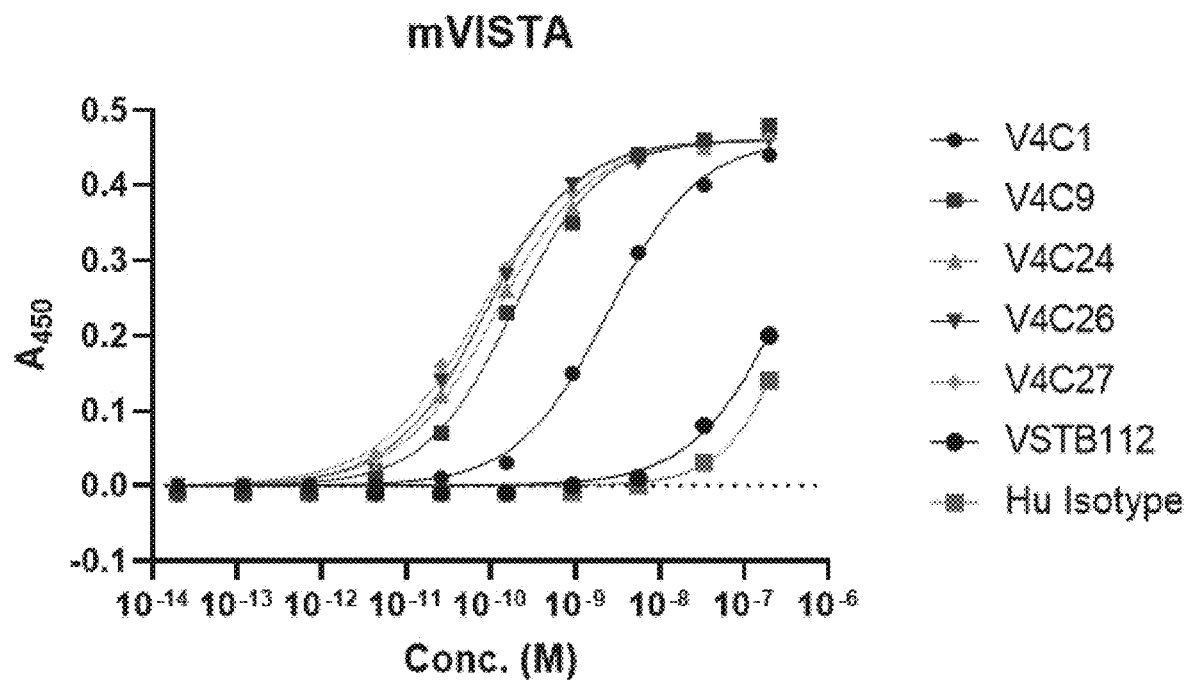

A further experiment was performed in which binding of V4-C1, V4-C9, V4-C24, V4-C26, V4-C27, VSTB112 and isotype control antibody to human VISTA or mouse VISTA was analysed. The results are shown in FIGS. 51A and 51B, and the EC50 (nM) values calculated from the ELISAs for binding of the antibodies to the indicated proteins are summarised in FIG. 51C.

A further experiment was performed in which binding of V4, V4-C24, V4-C26, V4-C27, V4-C28, V4-C30 and V4-C31 and isotype control antibody to human VISTA, PD-L1, B7H3, B7H4, B7H6, B7H7, PD-1 and CTLA-4 was analysed. The results are shown in FIGS. 56A to 56G. Each of V4-C24, V4-C26, V4-C27, V4-C28, V4-C30 and V4-C31 displayed strong binding to human VISTA, and no cross-reactivity for other members of the B7 family of proteins.

In a further experiment, V4 (referred to in FIG. 57 as "V4P"), V4-C24, V4-C26, V4-C27, V4-C28, V4-C30 and V4-C31 were analysed for binding to human VISTA, mouse VISTA, rat VISTA and cyno VISTA. The results obtained are shown in FIGS. 57A to 57H, and the EC50 (M) values calculated from the ELISAs for binding of the antibodies to the indicated proteins are summarised in FIG. 57I.

V4 and all of the V4-derived clones V4-C24, V4-C26, V4-C27, V4-C28, V4-C30 and V4-C31 were found to bind to human VISTA, mouse VISTA, rat VISTA and cyno VISTA.

13.3 Analysis of Binding to VISTA-Expressing Cells by Flow Cytometry

Anti-VISTA antibodies were analysed for their ability to bind to VISTA-expressing cells essentially as described in Example 3.1 above.

Briefly, transfected cells, or HEK293 cells transfected with vector encoding human VISTA or mouse VISTA were incubated with 1 µg/ml of anti-VISTA antibody or isotype control antibody at 4° C. for 1 hr. Cells were then washed, and incubated with 10 µg/ml FITC-conjugated anti-human Fc antibody at 4° C. for 1 hr. Cells were washed again, and then analysed by flow cytometry.

Figure 57A:
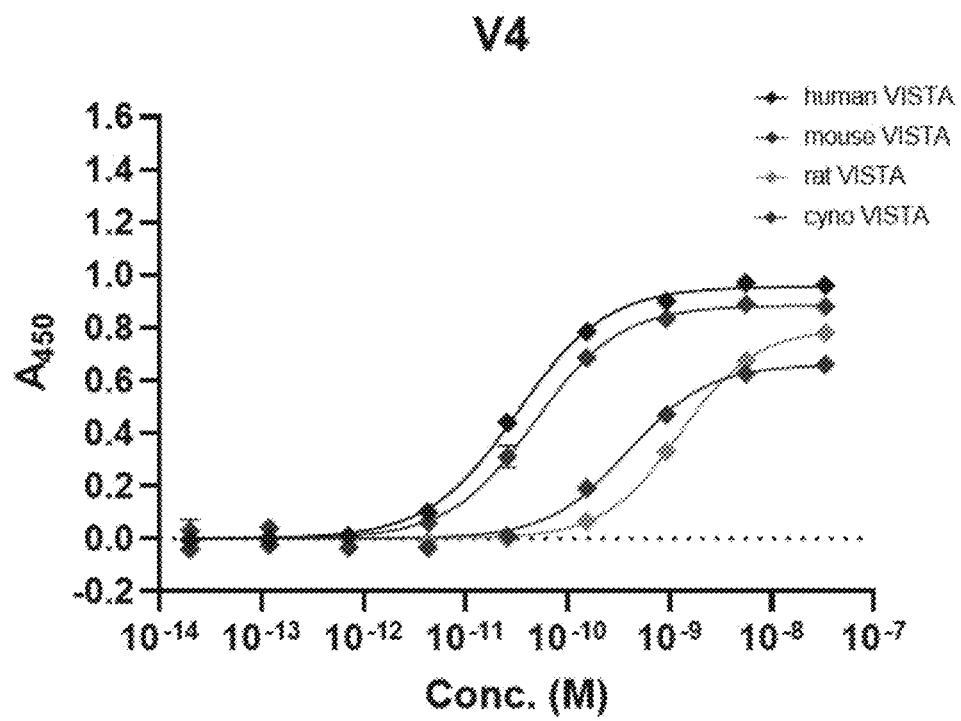
FIGS. 57A to 57I. Concentration-response graphs showing the results of analysis of binding of (57A) V4, (57B) V4-C24, (57C) V4-C26, (57D) V4-C27, (57E) V4-C28, (57F) V4-C30 (57G) V4-C31 and (57H) isotype-matched control antibody to human VISTA, mouse VISTA, rat VISTA and cyno VISTA, as determined by ELISA. 57I shows EC50 values (M) for binding of the different antibodies to the indicated proteins.
Figure 57B:
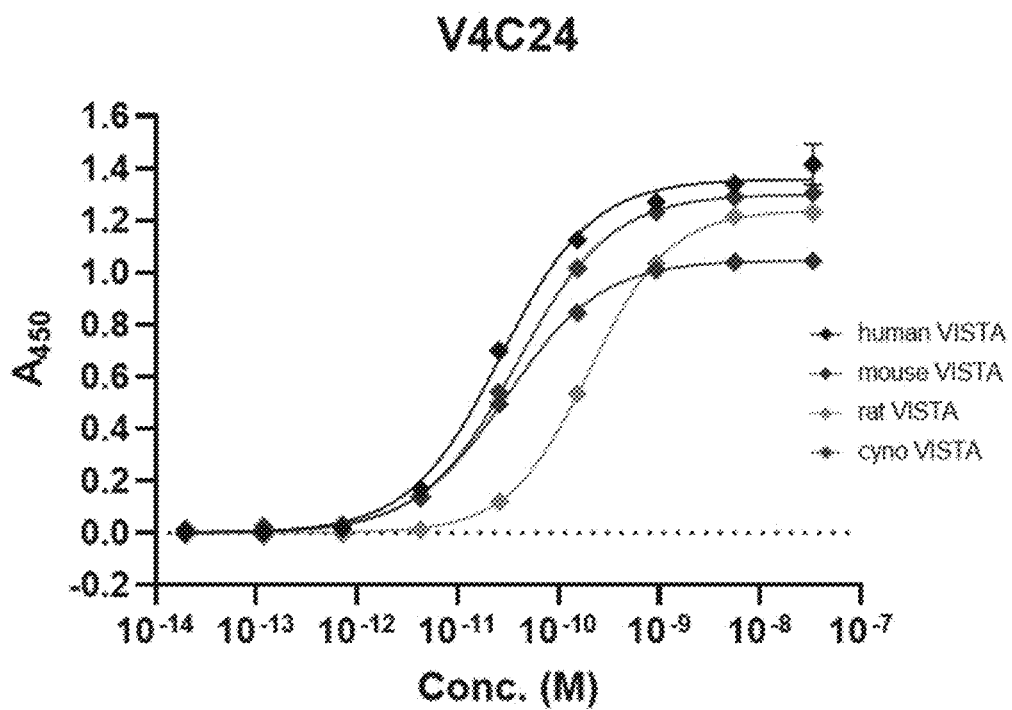
Figure 57C:
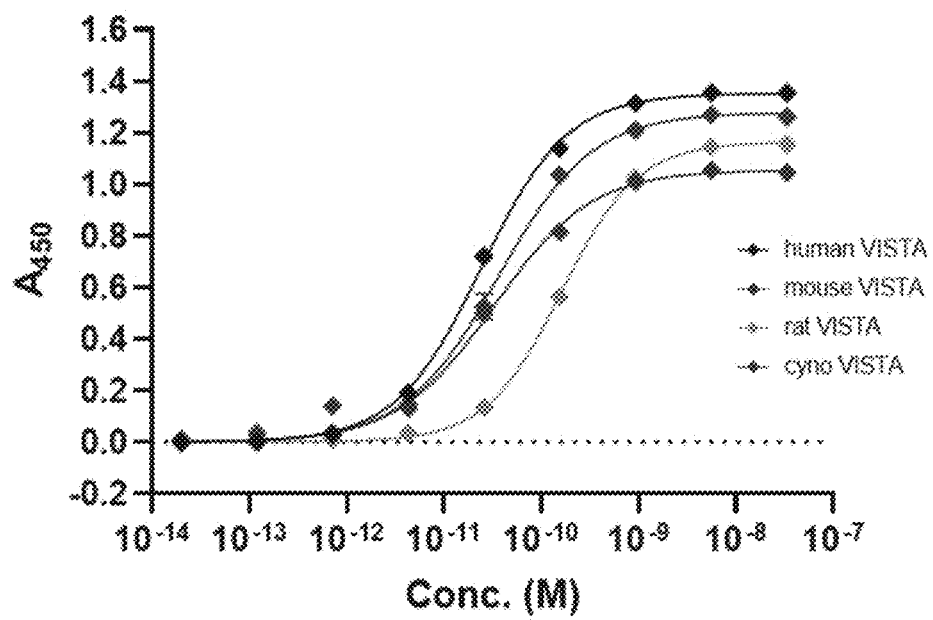
Figure 57D:
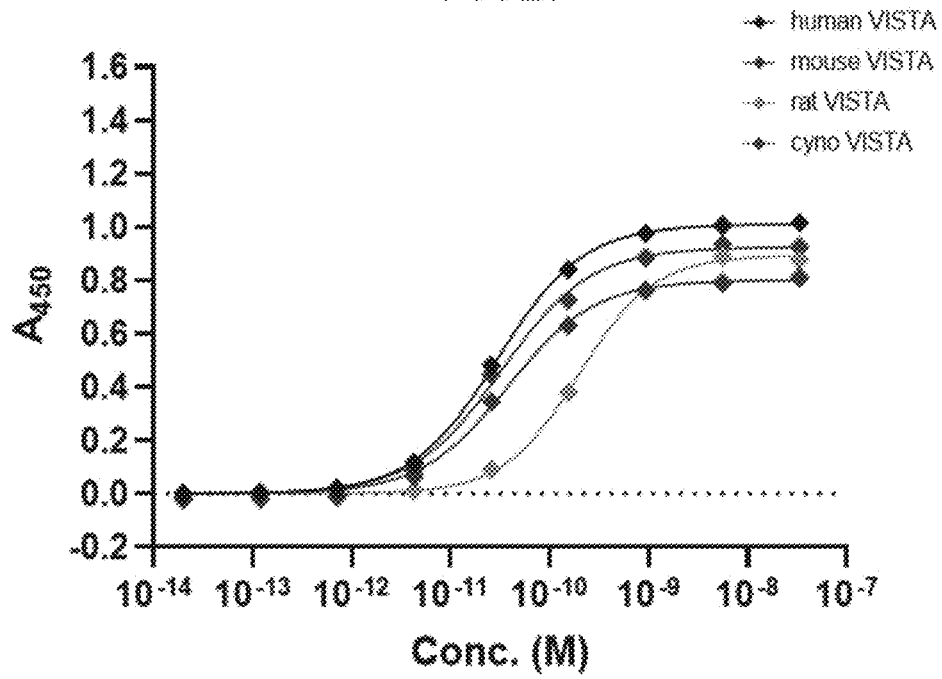
Figure 57E:
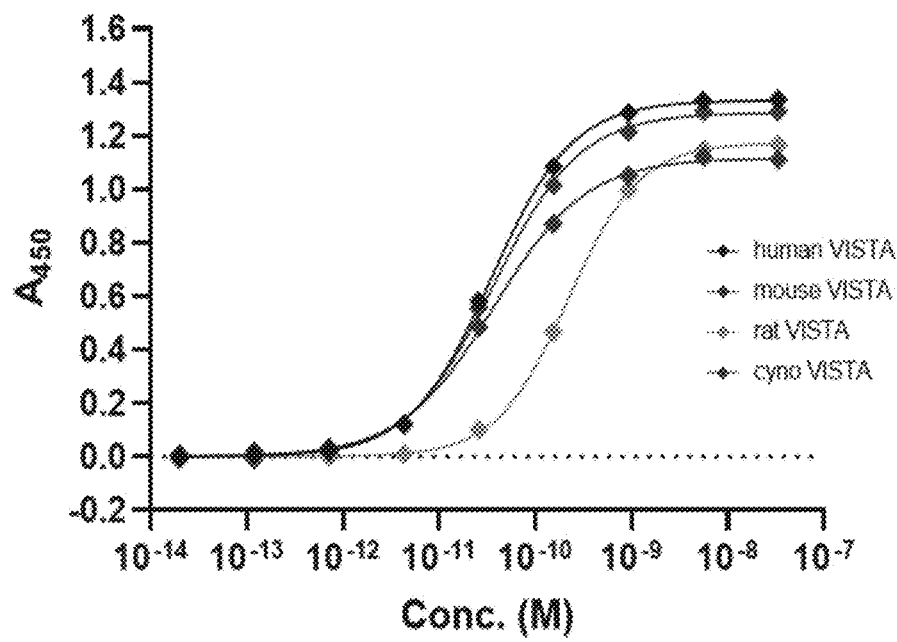
Figure 57F:
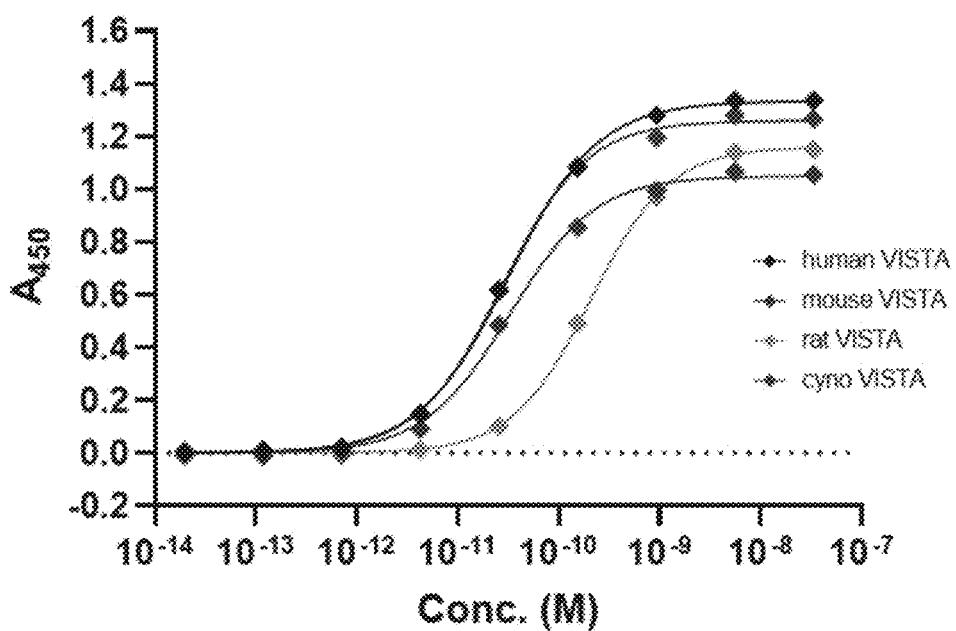
Figure 57G:
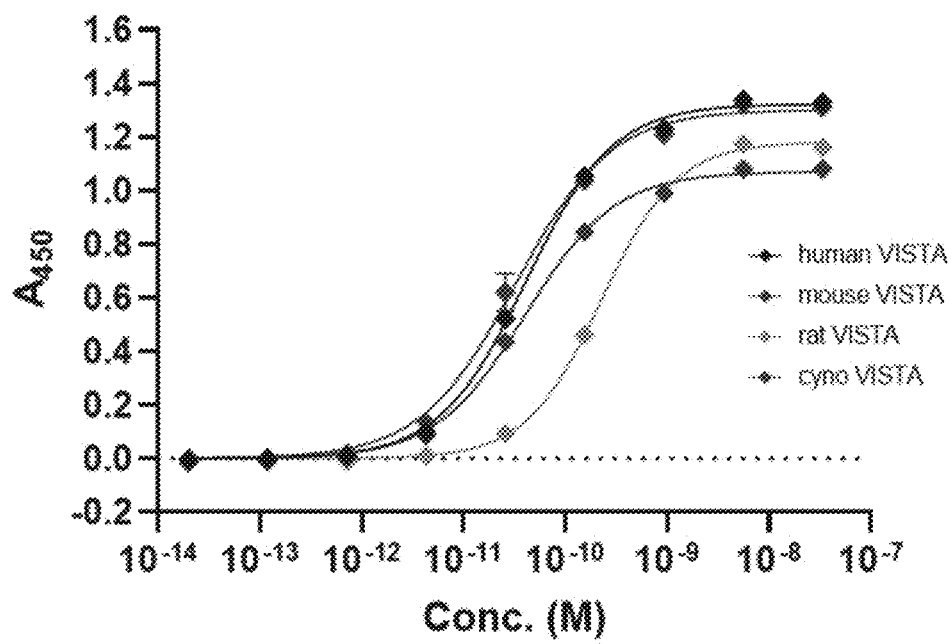
Figure 57H:
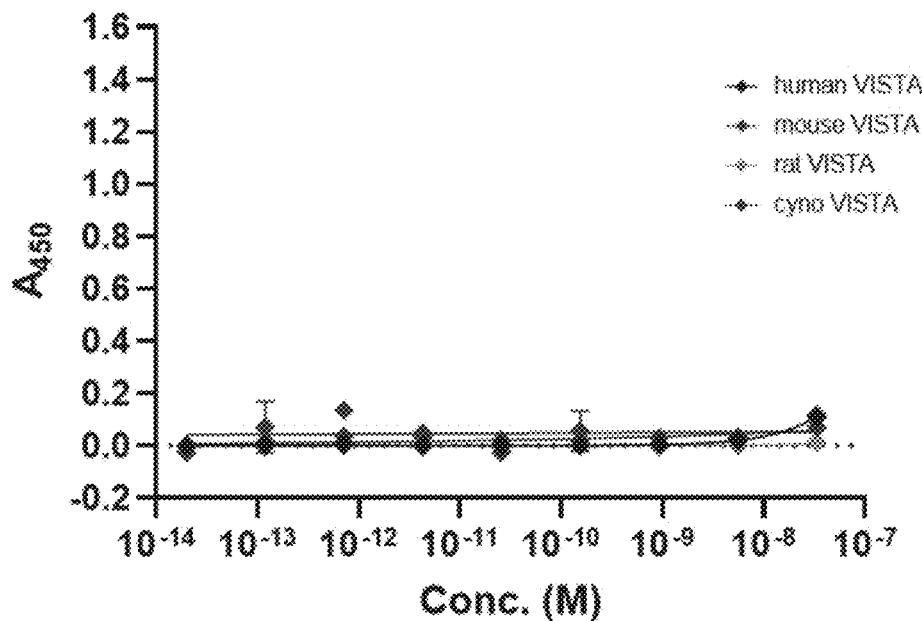
Figures 57I, 58A:
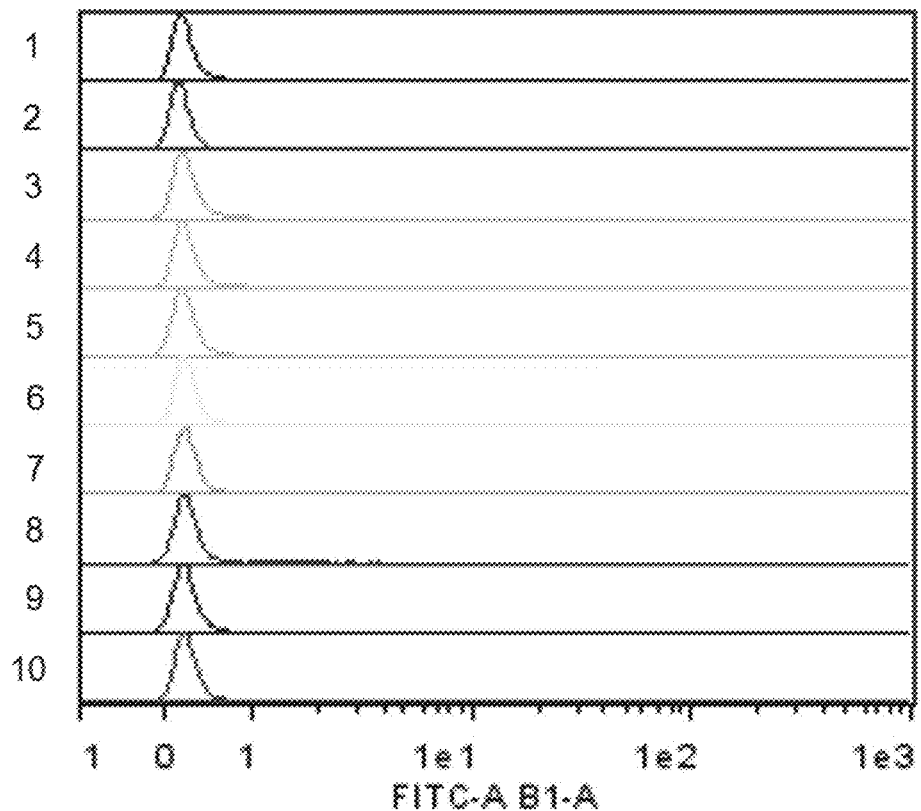
FIGS. 58A to 58C. Histograms showing staining of cells by different anti-VISTA antibodies or isotype control antibody as determined by flow cytometry. 58A shows binding of antibodies to wildtype, non-transfected HEK293-6E cells. 58B shows binding of antibodies to HEK293-6E cells overexpressing human VISTA protein. 58C shows binding of antibodies to HEK293-6E cells overexpressing mouse VISTA protein. 1=no antibody (unstained), 2=human IgG1 Isotype control antibody, 3=VSTB112 IgG1, 4=4M2-C12 IgG1, 5=V4-C24 IgG1, 6=V4-C26 IgG1, 7=V4-C27 IgG1, 8=V4-C28 IgG1, 9=V4-C30 IgG1, and 10=V4-C31 IgG1.
Figure 58B:
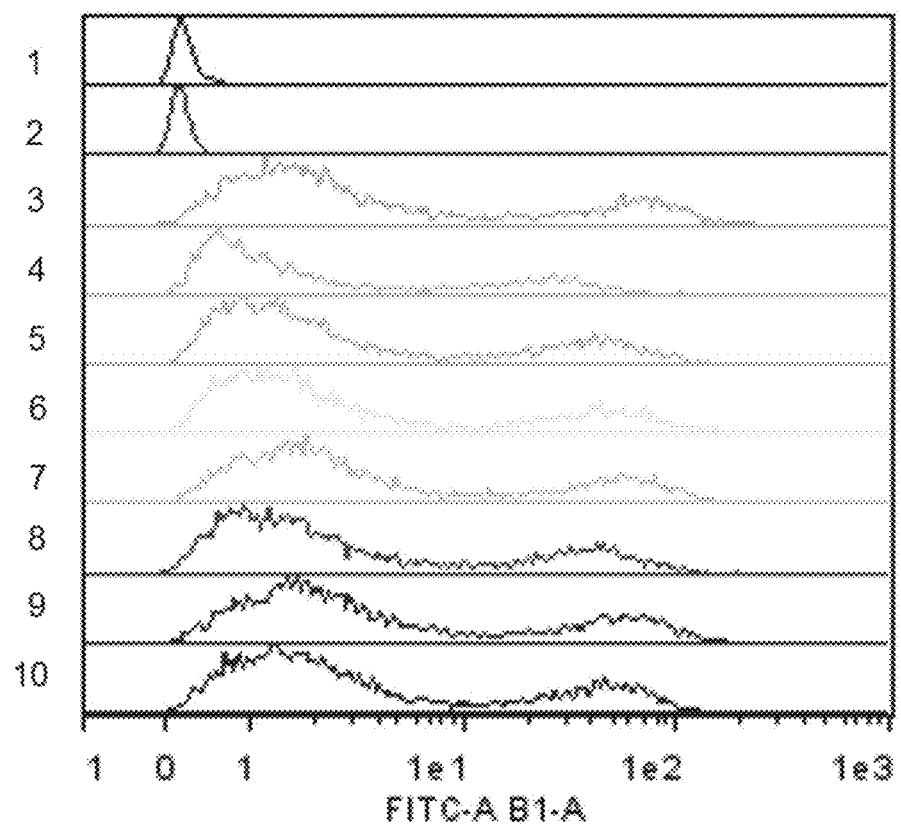
Figure 58C:
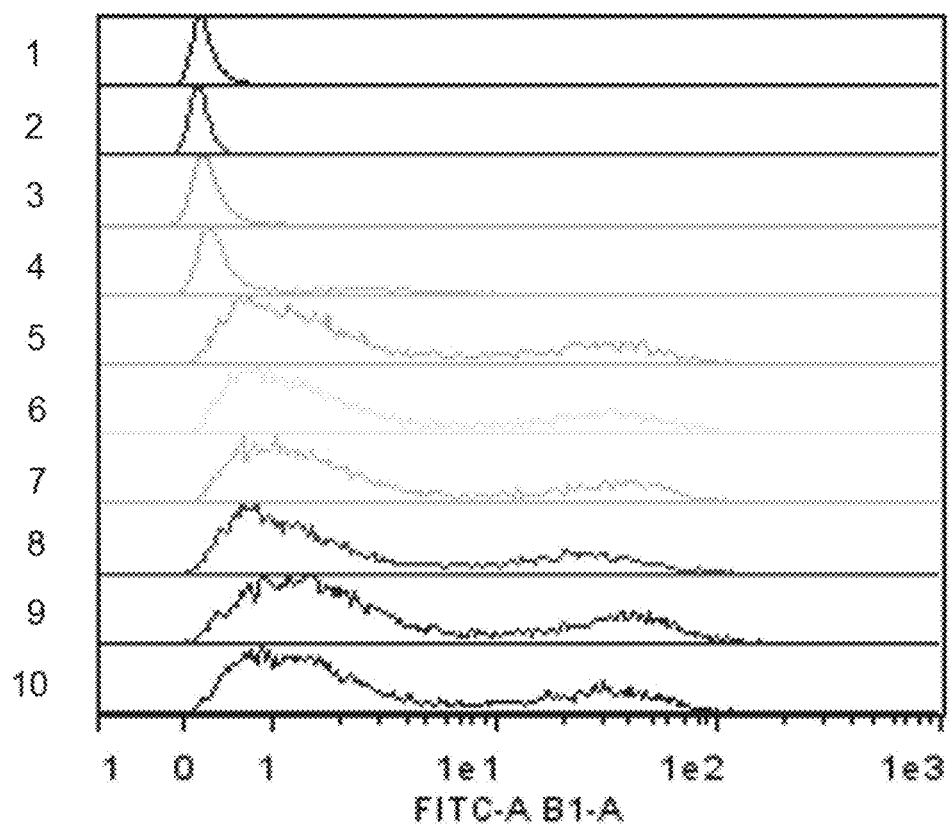

The following antibodies were analysed in the experiments:
- 4M2-C12 IgG1 ([1] of Example 2.2; referred to as "V4P" in the Figures)
- V4-C24 IgG1 ([23] of Example 13)
- V4-C26 IgG1 ([24] of Example 13)
- V4-C27 IgG1 ([25] of Example 13)
- V4-C28 IgG1 ([26] of Example 13)
- V4-C30 IgG1 ([27] of Example 13)
- V4-C31 IgG1 ([28] of Example 13)
- VSTB112 IgG1 (comprising VSTB112 HC (SEQ ID NO: 269)+VSTB112 LC (SEQ ID NO: 270))
- Human IgG1 Isotype control The results are shown in FIGS. 58A to 58C.

13.4 Analysis of Thermostability by Differential Scanning Fluorimetry

Thermostability of different antibodies was evaluated by Differential Scanning Fluorimetry analysis, as described in Example 3.4 above.

Figure 52C:
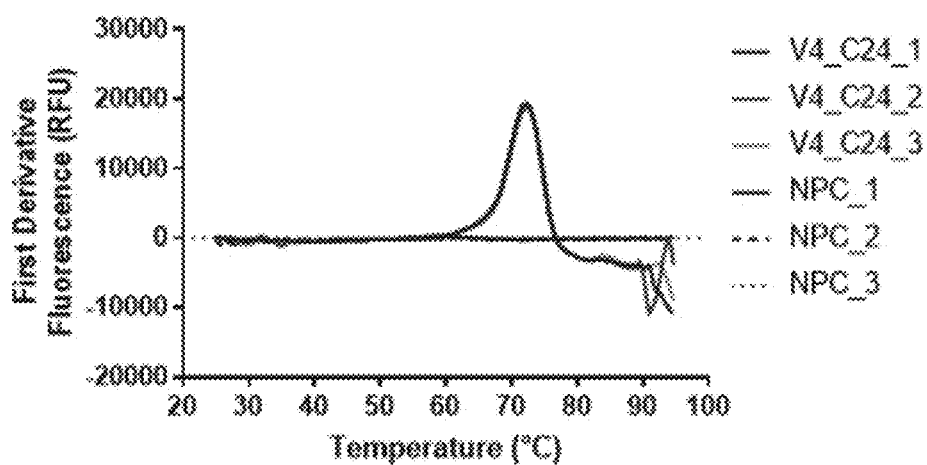
Figure 52D:
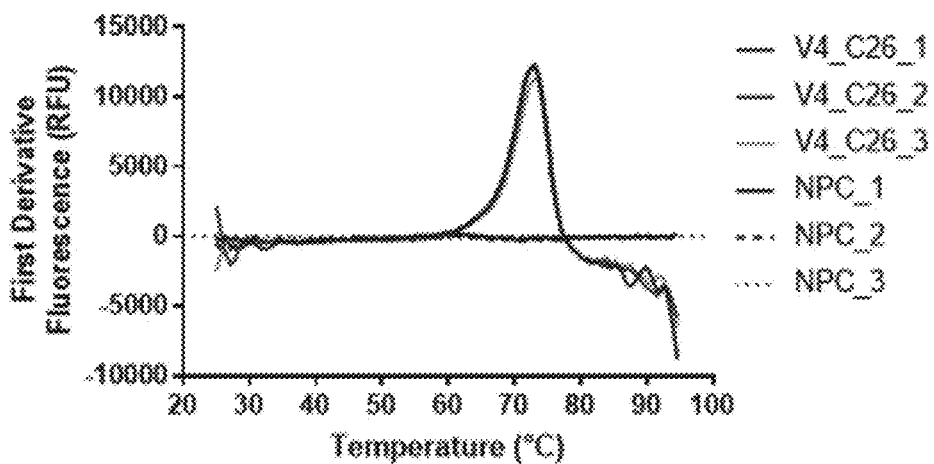
Figure 52E:
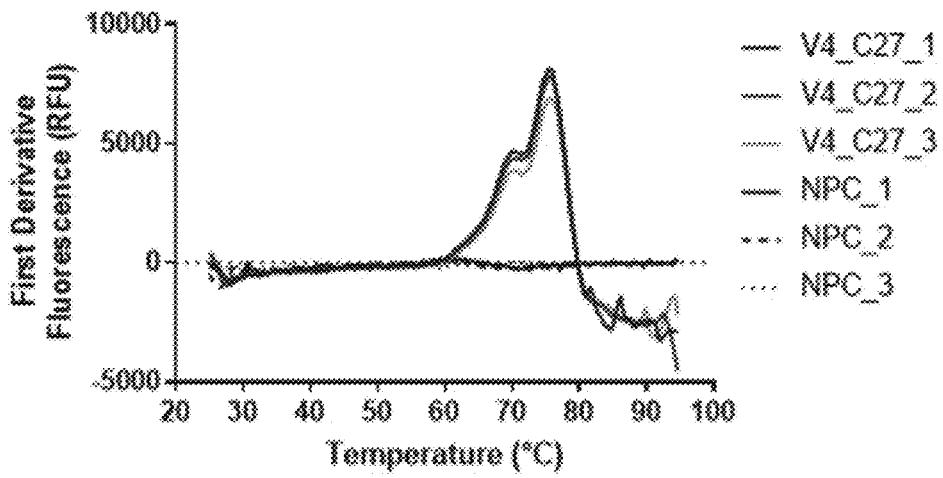
Figure 52F:
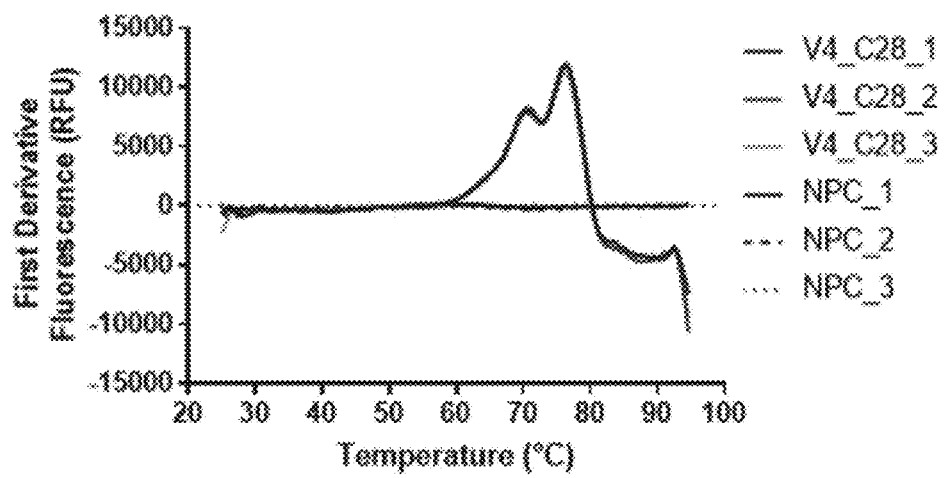
Figure 52G:
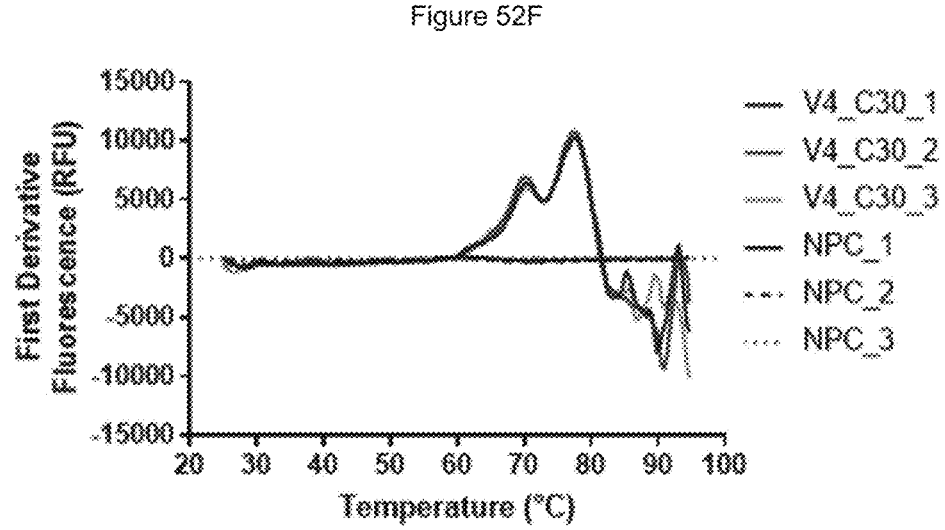
Figure 52H:
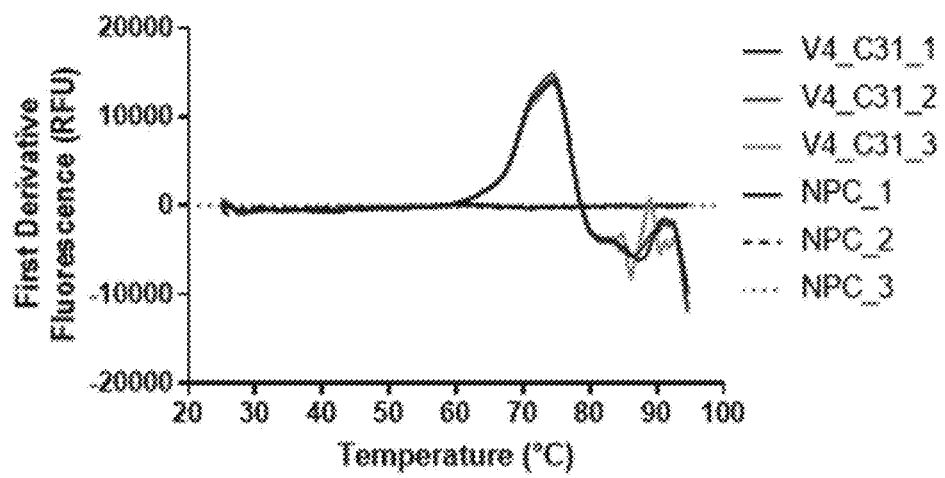
Figures 52I, 52J:
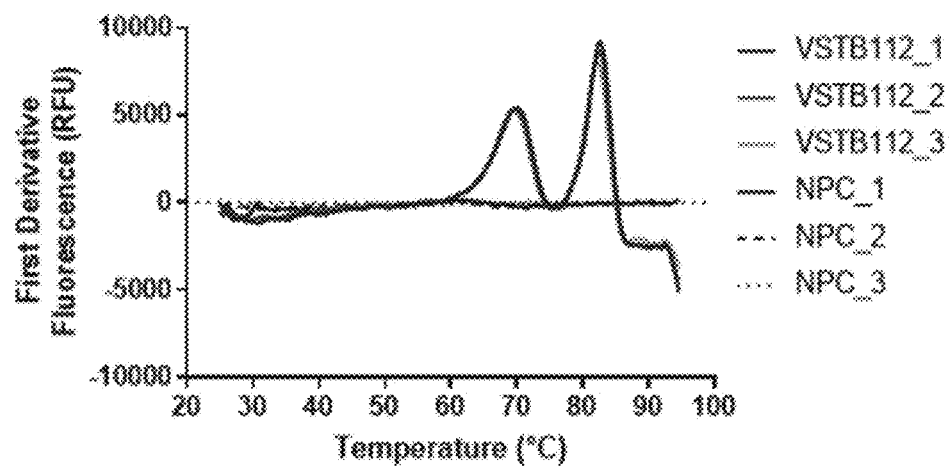

The first derivative of the raw data obtained for Differential Scanning Fluorimetry analysis of the thermostability of V4-C1, V4-C9, V4-C24, V4-C26, V4-C27, V4-C28, V4-C30, V4-C31 (i.e. [21] to [28]) and VSTB112 (in triplicate) is shown in FIGS. 52A to 52I, and the results are summarised in FIG. 52J.

V4-C1, V4-C9, V4-C24, V4-C26, V4-C27, V4-C28, V4-C30 and V4-C31 were found to have a higher melting temperature (Tm) for the Fab region as compared to V4 (67.5° C.), and thus improved thermal stability.

Example 14: Use of VISTA-Binding Antibodies in Immunohistochemistry

Anti-VISTA antibody 4M2-C12 mIgG2a ([17] of Example 5) was evaluated for its ability to be used in immunohistochemistry for the detection of human VISTA protein.

Processing of sections was performed using Bond reagents (Leica Biosystems). Commercial paraffin sections from normal human spleen or normal human ovary were de-paraffinized in Bond Dewax solution, and rehydrated using. Sections were then subjected to the following treatments with 4-5 rinses of 1× Bond Wash between steps: (i) antigen exposure by treatment with Bond Epitope Retrieval Solution for 40 min at 100° C., (ii) endogenous peroxidase blocking by treatment with 3.5% (v/v) $H_2O_2$ for 15 min at room temperature, (iii) blocking by treatment with 10% goat serum for 30 min at room temperature, (iv) incubation with 4M2-C12 mIgG2a at 1:50 dilution of a 9.37 mg/mL solution overnight at 4° C., (v) incubation with HRP-polymer conjugated goat anti-mouse antibody for 5 min at room temperature, and (vi) development with Bond Mixed DAB Refine for 7 min at room temperature, followed by rinsing with deionised water to stop the reaction.

Sections were counterstained with haematoxylin for 5 min at room temperature and rinsed with deionised water and 1× Bond Wash solution, and were then dehydrated, mounted in synthetic mounting media and scanned with high resolution.

The results are shown in FIGS. 59A and 59B. The anti-VISTA antibody stained cytoplasm of cells of the spleen, but not cells in normal ovary sections (control).

Example 15: Further Analysis of the Ability of VISTA-Binding Antibodies to Rescue VISTA-Mediated Inhibition of T Cell Proliferation and Production of Proinflammatory Cytokines Anti-VISTA antibodies were characterised for the ability to release T cells from VISTA-mediated suppression.

96-well plates were coated with anti-CD3 at concentration of 2.5 µg/ml and incubated overnight at 4° C. PBMCs were isolated from blood samples, T cells were enriched from the PBMCs and labelled with CSFE as above, and the CFSE-labelled T cell were then co-cultured at a ratio of 2:1 with HEK293-6E cells transfected with a construct encoding human VISTA, in RPMI 1640 medium supplemented with 2% FBS.

Cells were then treated with 4M2-C12-hIgG1 ([1] of Example 2.2) or VSTB112 at concentrations of 0 µg/ml (control), 20 µg/ml or 50 µg/ml.

After 5 days, cells were harvested and analysed by flow cytometry to determine cell proliferation by CSFE dilution profile. Cell culture supernatants were also harvested, and INFγ and TNFa levels was analysed by ELISA.

Figure 60A:
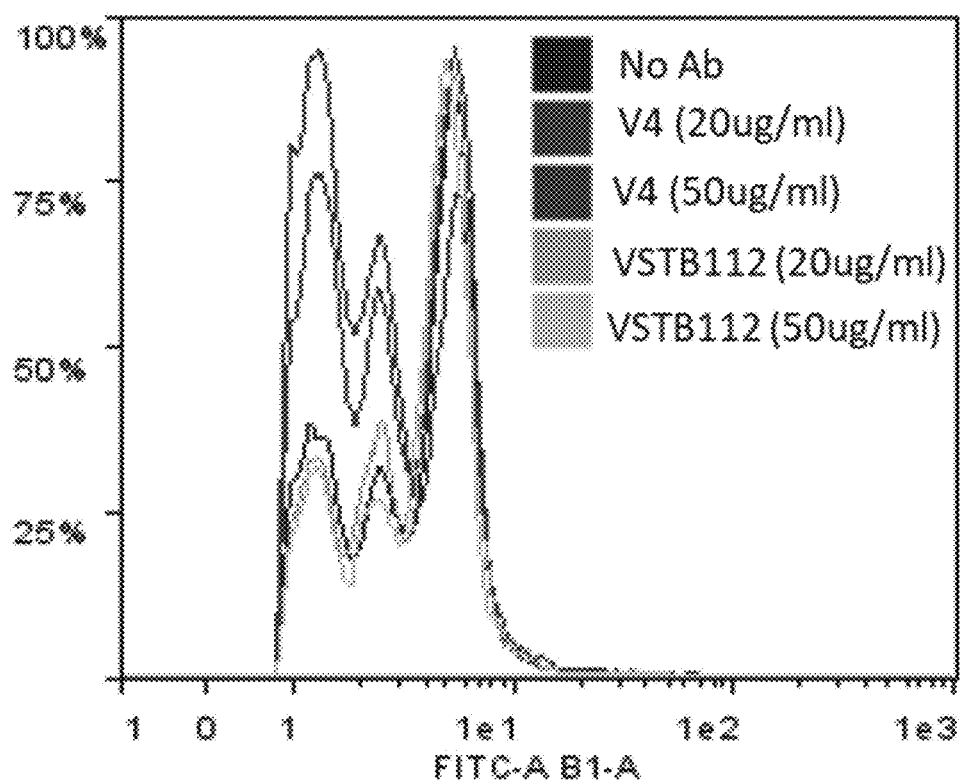
FIGS. 60A to 60D. Histogram and bar charts showing the results of analysis of the ability of anti-VISTA antibodies 4M2-C12-hIgG1 (V4) or VSTB112 to release activated T cells from suppression by VISTA-expressing cells. 60A and 60B show the results of CFSE dilution analysis of T cell proliferation in the presence of VISTA-expressing cells and the indicated quantities of anti-VISTA antibodies, for 5 days. 60C and 60D show the concentration of IFNγ (60C) and TNFa (60D) detected in the cell culture supernatant after 5 days.
Figure 60B:
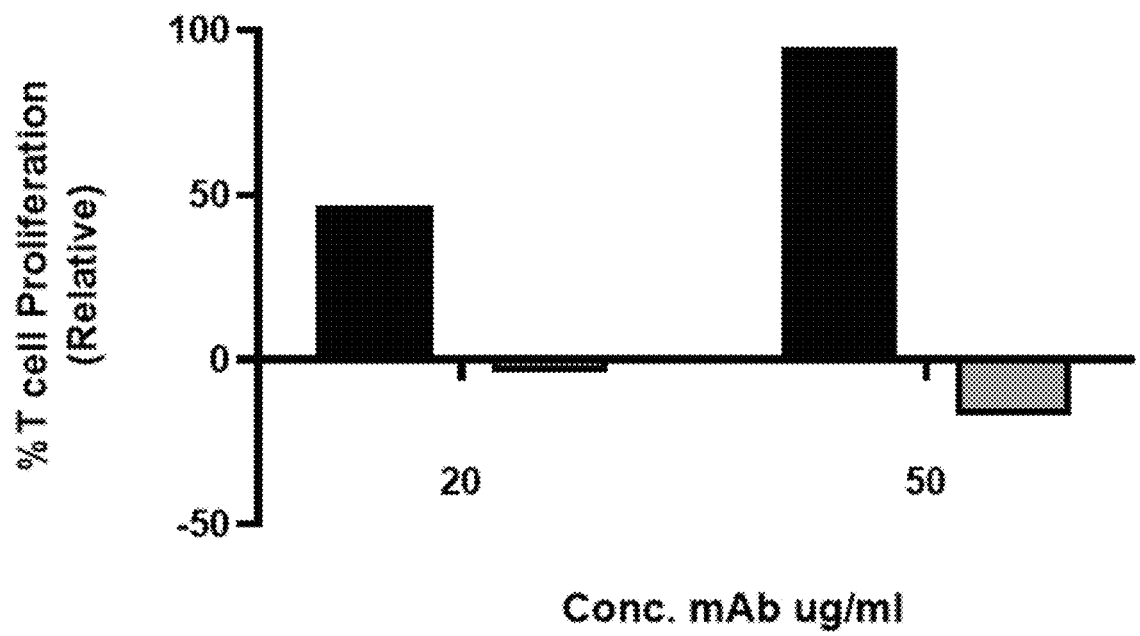
Figure 60C:
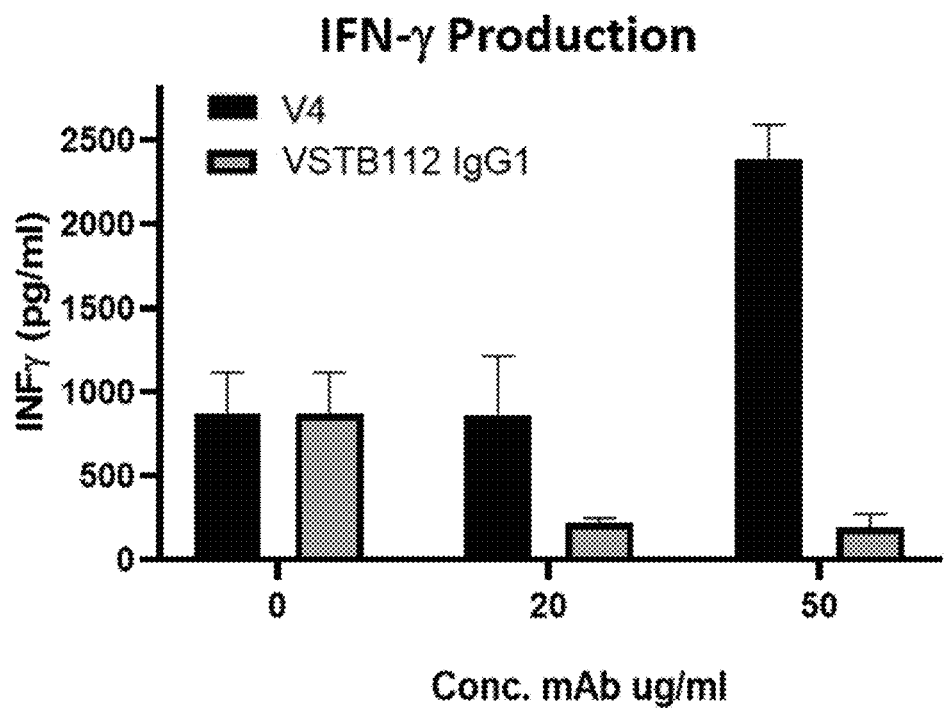
Figure 60D:
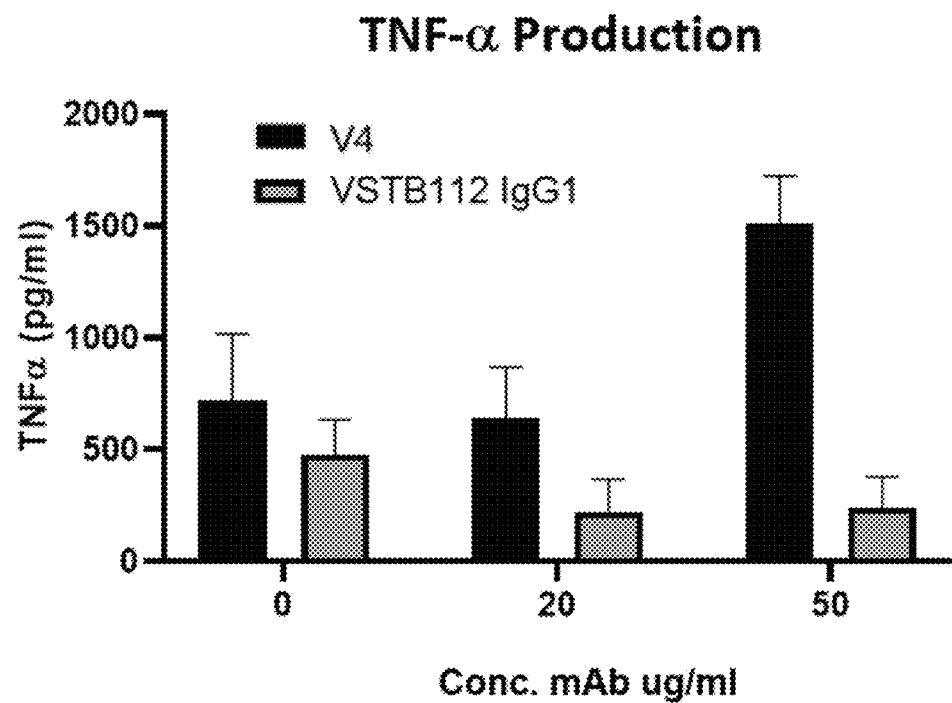

The results are shown in FIGS. 60A to 60D. FIGS. 60A and 60B show that 4M2-C12-hIgG1 released T cells from VISTA-mediated inhibition of proliferation in a dose-dependent fashion. FIGS. 60C and 60D show that 4M2-C12-hIgG1 released T cells from VISTA-mediated inhibition of production of INFγ and TNFa.

In further experiments, undifferentiated THP1 cells were seeded in wells of 96 well plates in duplicate, in RPMI media without FBS or pen/strep (100,000 cells/well), and cells were stimulated with LPS (100 µg/ml) in the presence of serially diluted concentrations of 4M2-C12-hIgG1 ([1] of Example 2.2) or VSTB112, at concentrations ranging from 2000 µg/ml to 7.8 µg/ml.

After 24 h cell culture supernatant was collected and analyzed by ELISA for IL-6 and TNFa. Cells were also fixed and permeabilized, and analyzed for the presence of VISTA via flow cytometry.

Figure 61A:
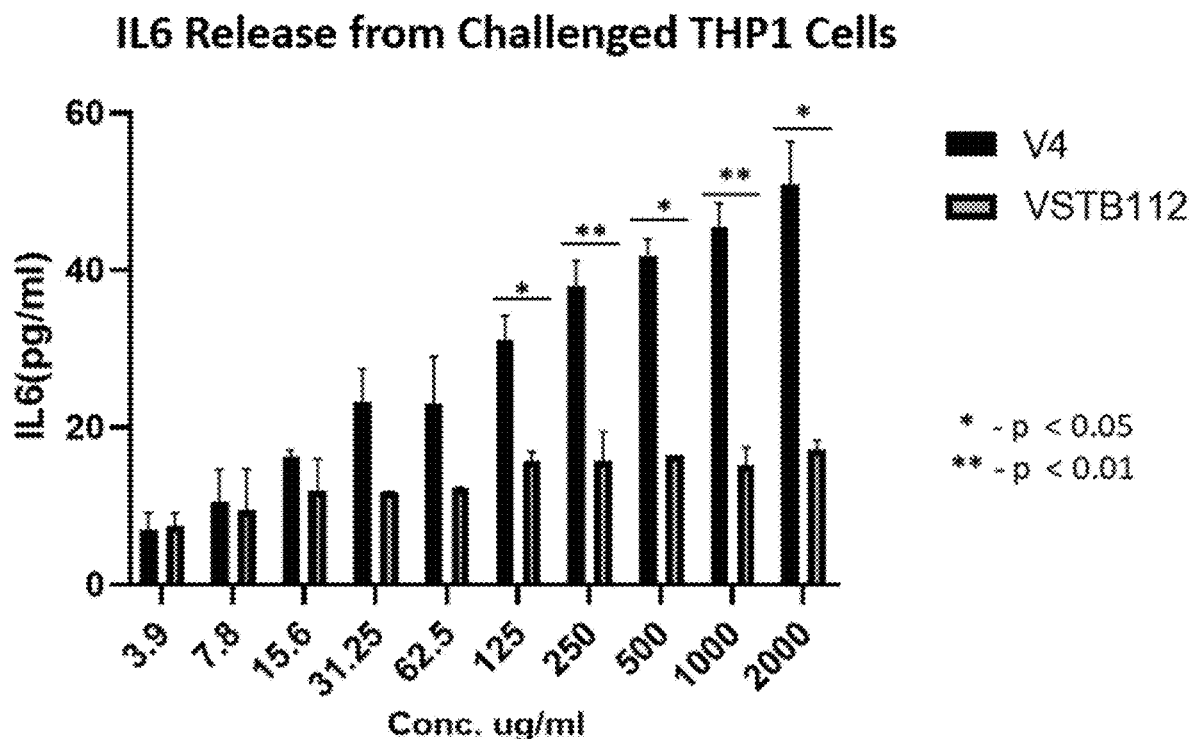
FIGS. 61A to 61C. Bar charts showing the results of analysis of the ability of anti-VISTA antibodies 4M2-C12-hIgG1 (V4) or VSTB112 to promote the production of cytokines by LPS-stimulated THP-1 cells. 61A shows the concentration of IL-6 detected in the cell culture supernatant, and 61B shows the concentration of TNFa detected in the cell culture supernatant of cells for 24 hours in the presence of the indicated quantities of anti-VISTA antibodies. 61C shows that the THP1 cells are VISTA-expressing cells; the percentage of the cells in culture determined to express VISTA is shown. 1=unstained, 2=cells stained with isotype-matched control antibody, 3=cells stained with 20 μg V4, 4=cells stained with 40 μg V4, and 5=cells stained with 20 μg VSTB112.
Figure 61B:
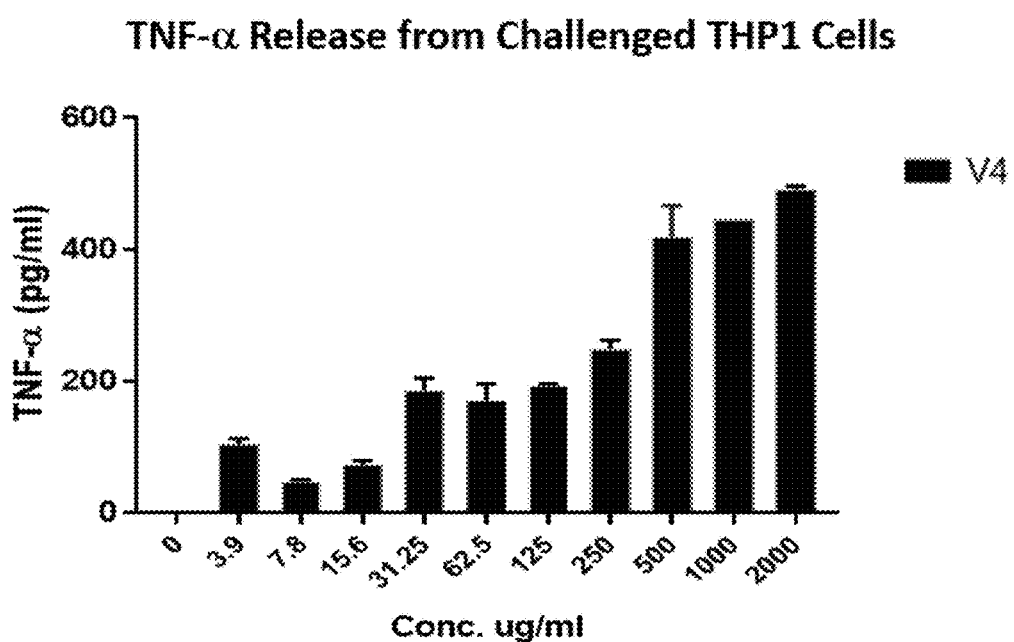
Figure 61C:
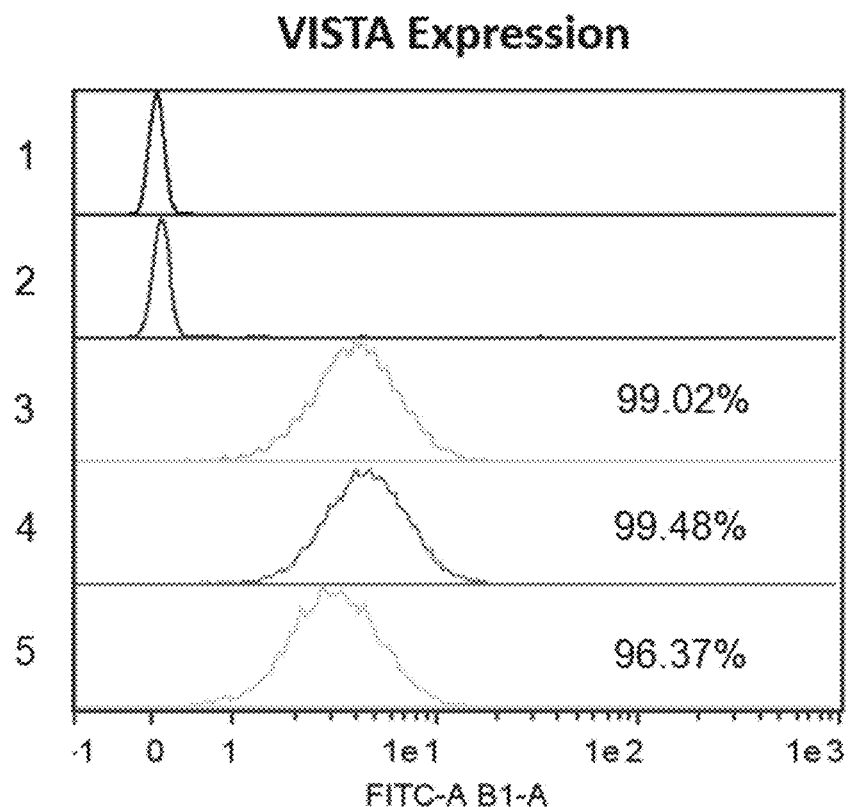

The results are shown in FIGS. 61A to 61C. 4M2-C12-hIgG1 was found to increase IL-6 and TNFa production from LPS-stimulated THP1 cells in a dose-dependent fashion, and to a much greater extent than VSTB112.

In a further experiment, undifferentiated THP1 cells were seeded in wells of 96 well plates in duplicate, in RPMI media without FBS or pen/strep (100,000 cells/well), and cells were stimulated with LPS (100 µg/ml) and $MnCl_2$ (100 µM) in the presence of 4M2-C12-hIgG1 ([1] of Example 2.2) or 4M2-C12-hIgG4 ([29] shown below), at concentrations ranging from 2000 µg/ml to 7.8 µg/ml. After 24 h cell culture supernatant was collected and analyzed by ELISA for IL-6.

| Antigen-biding molecule | Polypeptides | Antibody |
|---|---|---|
| [29] | 4M2-C12 VH-CH1-CH2-CH3 IgG4 (SEQ ID NO: 330) + 4M2-C12 VL-C$_K$ (SEQ ID NO: 213) | anti-VISTA clone 4M2-C12 IgG4 |

Figure 62:
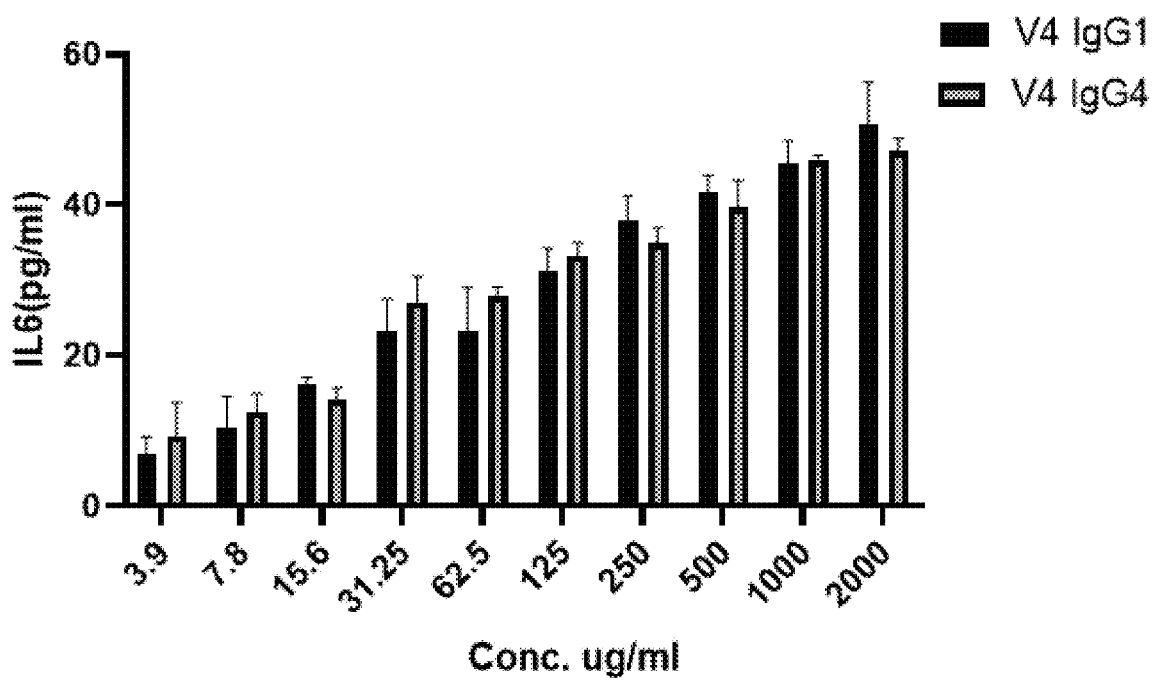
FIG. 62. Bar chart showing the results of analysis of the ability of anti-VISTA antibodies 4M2-C12-hIgG1 or 4M2-C12-hIgG4 to promote the production of IL-6 by LPS-stimulated THP-1 cells. The concentration of IL-6 detected in the cell culture supernatant is shown.
Figure 63A:
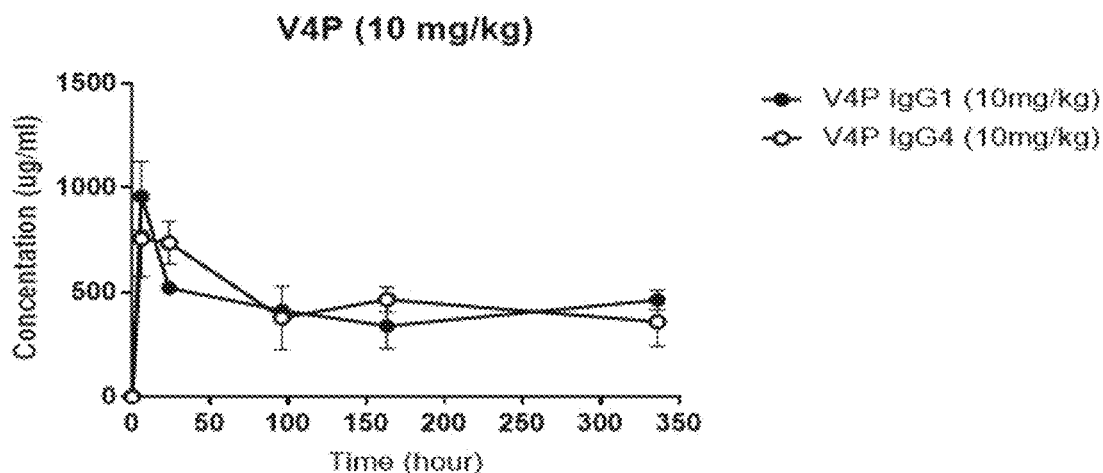
FIGS. 63A to 63D. Graphs and tables showing the results of the pharmacokinetics analysis of anti-VISTA antibodies 4M2-C12-hIgG1 and 4M2-C12-hIgG4 by ELISA analysis of antibody serum. Results are shown following administration of (63A) 10 mg/kg, (63B) 25 mg/kg, (63C) 100 mg/kg, or (63D) 250 mg/kg of antibody.
Figure 63B:
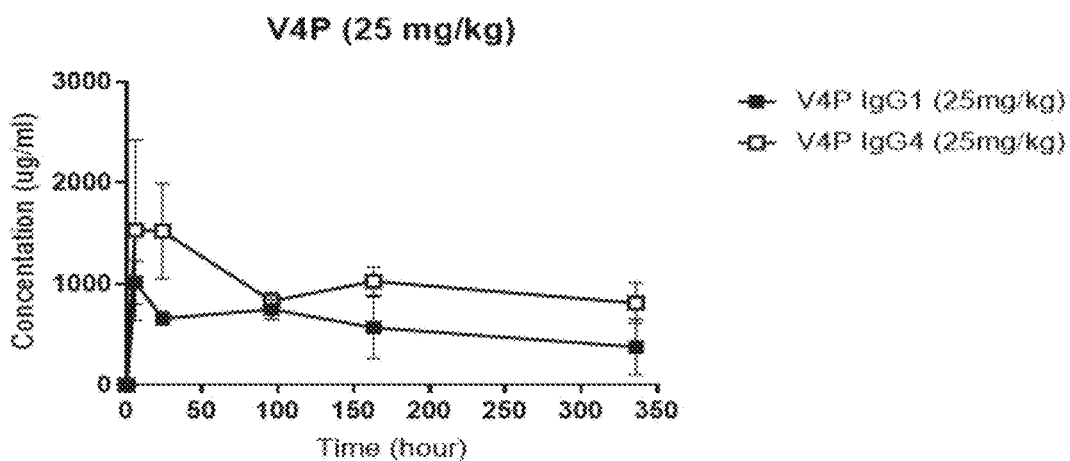
Figure 63C:
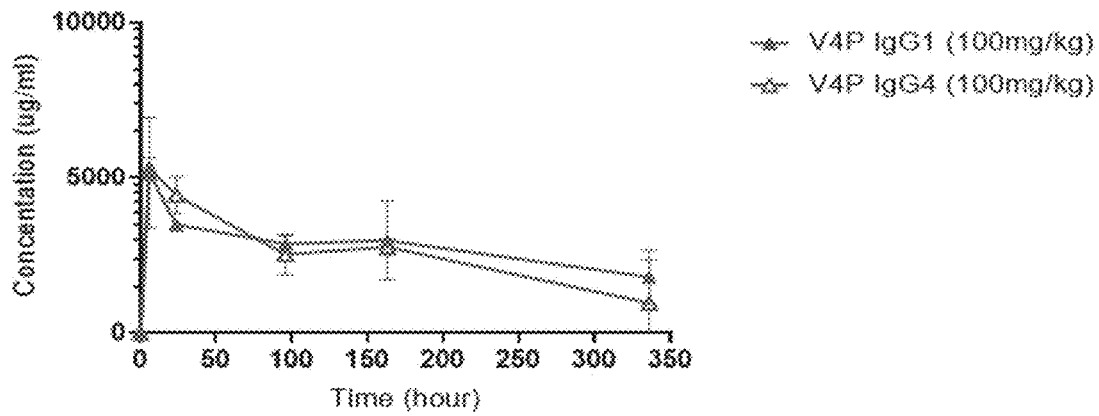
Figure 63D:
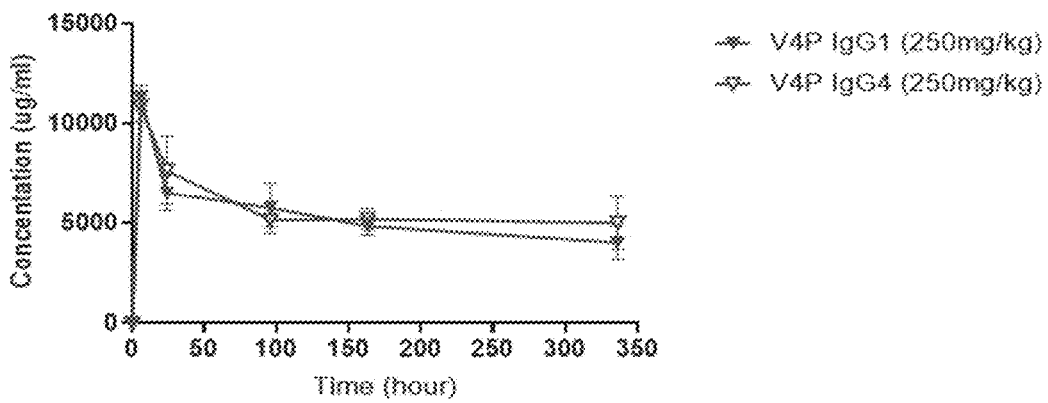

The results are shown in FIG. 62. Increased production of IL-6 by LPS-stimulated THP1 cells was found to be independent of Fc-independent, as no significant difference was observed between the level of IL6 induced by treatment with 4M2-C12 in human IgG1 or IgG4 formats.

Example 16: Further Analysis of Pharmacology, Toxicology and Immunotoxicity

In an acute dose study, rats were administered with a single dose of 10 mg/kg, 25 mg/kg, 100 mg/kg or 250 mg/kg of 4M2-C12-hIgG1 ([1] of Example 2.2) or 4M2-C12-hIgG4 ([29] of Example 15).

Blood was obtained from the rats at baseline (−2 hr), 0.5 hr, 6 hr, 24 hr, 96 hr, 168 hr and 336 hr after administration. Antibody in the serum was quantified be ELISA.

The parameters for the pharmacokinetic analysis were derived from a non-compartmental model: maximum concentration ($C_{max}$), AUC (0-336 hr), AUC (0-infinity), Half-life (t½), Clearance (CL), Volume of distribution at steady state ($V_{ss}$).

The results are shown in FIGS. 63A to 63D.

In separate experiments, BALB/C mice were administered with a single dose of 50 mg/kg 4M2-C12-hIgG1 ([1] of Example 2.2) or an equal volume of PBS. Blood samples were obtained after 96 hours, and analysed for numbers of different types of white blood cells using HM5 Hematology Analyser. Blood samples were also analysed for correlates hepatotoxicity and nephrotoxicity.

Representative results are shown in the tables of FIGS. 64A to 64C.

In further experiments, Sprague Dawley rats were administered with a single dose of 250 mg/kg 4M2-C12-hIgG1 ([1] of Example 2.2) or an equal volume of PBS. Blood samples were obtained at 6, 24, 96 and 168 hours, and analysed for numbers of different types of white blood cells using HM5 Hematology Analyser. Blood samples were also analysed for correlates hepatotoxicity, nephrotoxicity and pancreas toxicity.

Representative results are shown in the tables of FIGS. 65A to 65C.

Administration of 4M2-C12-hIgG1 was not found to be associated with significant toxicity, and did not significantly alter numbers of cell types in blood.

The invention claimed is:

1. An antigen-binding molecule that specifically binds to VISTA, comprising:
   (i) a heavy chain variable (VH) region having the following CDRs:
      HC-CDR1 having the amino acid sequence of SEQ ID NO:290
      HC-CDR2 having the amino acid sequence of SEQ ID NO:291
      HC-CDR3 having the amino acid sequence of SEQ ID NO:278; and
   (ii) a light chain variable (VL) region having the following CDRs:
      LC-CDR1 having the amino acid sequence of SEQ ID NO:41
      LC-CDR2 having the amino acid sequence of SEQ ID NO:295
      LC-CDR3 having the amino acid sequence of SEQ ID NO:43.

2. The antigen-binding molecule according to claim 1, wherein the antigen-binding molecule comprises:
   a VH region comprising an amino acid sequence having at least 70% sequence identity to the amino acid sequence of SEQ ID NO:289; and
   a VL region comprising an amino acid sequence having at least 70% sequence identity to the amino acid sequence of SEQ ID NO:297.

3. The antigen-binding molecule according to claim 1, wherein the antigen-binding molecule comprises:
   a VH region having the following framework regions (FRs):
   HC-FR1 having the amino acid sequence of SEQ ID NO:63
   HC-FR2 having the amino acid sequence of SEQ ID NO:292
   HC-FR3 having the amino acid sequence of SEQ ID NO:293
   HC-FR4 having the amino acid sequence of SEQ ID NO:281.

4. The antigen-binding molecule according to claim 1, wherein the antigen-binding molecule comprises:
   a VL region having the following framework regions (FRs):
   LC-FR1 having the amino acid sequence of SEQ ID NO:288
   LC-FR2 having the amino acid sequence of SEQ ID NO:298
   LC-FR3 having the amino acid sequence of SEQ ID NO:284
   LC-FR4 having the amino acid sequence of SEQ ID NO:47.

5. The antigen-binding molecule according to claim 1, wherein the antigen-binding molecule comprises a heavy chain comprising the CH1, CH2 and CH3 region sequences of human IgG4.

6. The antigen-binding molecule according to claim 1, wherein the antigen-binding molecule comprises a light chain comprising the amino acid sequence of SEQ ID NO:211.

7. A nucleic acid, or a plurality of nucleic acids, encoding an antigen-binding molecule that specifically binds to VISTA, wherein the antigen-binding molecule comprises:
   (i) a heavy chain variable (VH) region having the following CDRs:
      HC-CDR1 having the amino acid sequence of SEQ ID NO:290
      HC-CDR2 having the amino acid sequence of SEQ ID NO:291
      HC-CDR3 having the amino acid sequence of SEQ ID NO:278; and
   (ii) a light chain variable (VL) region having the following CDRs:
      LC-CDR1 having the amino acid sequence of SEQ ID NO:41
      LC-CDR2 having the amino acid sequence of SEQ ID NO:295
      LC-CDR3 having the amino acid sequence of SEQ ID NO:43.

8. The nucleic acid or plurality of nucleic acids according to claim 7, wherein the antigen-binding molecule comprises:
   a VH region comprising an amino acid sequence having at least 70% sequence identity to the amino acid sequence of SEQ ID NO:289; and a VL region comprising an amino acid sequence having at least 70% sequence identity to the amino acid sequence of SEQ ID NO:297.

9. The nucleic acid or plurality of nucleic acids according to claim 7, wherein the antigen-binding molecule comprises:
a VH region having the following framework regions (FRs):
HC-FR1 having the amino acid sequence of SEQ ID NO:63
HC-FR2 having the amino acid sequence of SEQ ID NO:292
HC-FR3 having the amino acid sequence of SEQ ID NO:293
HC-FR4 having the amino acid sequence of SEQ ID NO:281.

10. The nucleic acid or plurality of nucleic acids according to claim 7, wherein the antigen-binding molecule comprises:
a VL region having the following framework regions (FRs):
LC-FR1 having the amino acid sequence of SEQ ID NO:288
LC-FR2 having the amino acid sequence of SEQ ID NO:298
LC-FR3 having the amino acid sequence of SEQ ID NO:284
LC-FR4 having the amino acid sequence of SEQ ID NO:47.

11. The nucleic acid or plurality of nucleic acids according to claim 7, wherein the antigen-binding molecule comprises a heavy chain comprising the CH1, CH2 and CH3 region sequences of human IgG4.

12. The nucleic acid or plurality of nucleic acids according to claim 7, wherein the antigen-binding molecule comprises a light chain comprising the amino acid sequence of SEQ ID NO:211.

13. A cell comprising a nucleic acid, or a plurality of nucleic acids, encoding an antigen-binding molecule that specifically binds to VISTA, wherein the antigen-binding molecule comprises:
(i) a heavy chain variable (VH) region having the following CDRs:
HC-CDR1 having the amino acid sequence of SEQ ID NO:290
HC-CDR2 having the amino acid sequence of SEQ ID NO:291
HC-CDR3 having the amino acid sequence of SEQ ID NO:278; and
(ii) a light chain variable (VL) region having the following CDRs:
LC-CDR1 having the amino acid sequence of SEQ ID NO:41
LC-CDR2 having the amino acid sequence of SEQ ID NO:295
LC-CDR3 having the amino acid sequence of SEQ ID NO:43.

14. The cell according to claim 13, wherein the antigen-binding molecule comprises:
a VH region comprising an amino acid sequence having at least 70% sequence identity to the amino acid sequence of SEQ ID NO:289; and
a VL region comprising an amino acid sequence having at least 70% sequence identity to the amino acid sequence of SEQ ID NO:297.

15. The cell according to claim 13, wherein the antigen-binding molecule comprises:
a VH region having the following framework regions (FRs):
HC-FR1 having the amino acid sequence of SEQ ID NO:63
HC-FR2 having the amino acid sequence of SEQ ID NO:292
HC-FR3 having the amino acid sequence of SEQ ID NO:293
HC-FR4 having the amino acid sequence of SEQ ID NO:281.

16. The cell according to claim 13, wherein the antigen-binding molecule comprises:
a VL region having the following framework regions (FRs):
LC-FR1 having the amino acid sequence of SEQ ID NO:288
LC-FR2 having the amino acid sequence of SEQ ID NO:298
LC-FR3 having the amino acid sequence of SEQ ID NO:284
LC-FR4 having the amino acid sequence of SEQ ID NO:47.

17. The cell according to claim 13, wherein the antigen-binding molecule comprises a heavy chain comprising the CH1, CH2 and CH3 region sequences of human IgG4.

18. The cell according to claim 13, wherein the antigen-binding molecule comprises a light chain comprising the amino acid sequence of SEQ ID NO:211.

19. A method of treating a cancer in a subject, comprising administering to a subject a therapeutically or prophylactically effective amount of an antigen-binding molecule that specifically binds to VISTA, wherein the antigen-binding molecule comprises:
(i) a heavy chain variable (VH) region having the following CDRs:
HC-CDR1 having the amino acid sequence of SEQ ID NO:290
HC-CDR2 having the amino acid sequence of SEQ ID NO:291
HC-CDR3 having the amino acid sequence of SEQ ID NO:278; and
(ii) a light chain variable (VL) region having the following CDRs:
LC-CDR1 having the amino acid sequence of SEQ ID NO:41
LC-CDR2 having the amino acid sequence of SEQ ID NO:295
LC-CDR3 having the amino acid sequence of SEQ ID NO:43.

20. The method according to claim 19, wherein the antigen-binding molecule comprises:
a VH region comprising an amino acid sequence having at least 70% sequence identity to the amino acid sequence of SEQ ID NO:289; and
a VL region comprising an amino acid sequence having at least 70% sequence identity to the amino acid sequence of SEQ ID NO:297.

21. The method according to claim 19, wherein the antigen-binding molecule comprises:
a VH region having the following framework regions (FRs):
HC-FR1 having the amino acid sequence of SEQ ID NO:63
HC-FR2 having the amino acid sequence of SEQ ID NO:292
HC-FR3 having the amino acid sequence of SEQ ID NO:293

HC-FR4 having the amino acid sequence of SEQ ID NO:281.

22. The method according to claim 19, wherein the antigen-binding molecule comprises:
  a VL region having the following framework regions (FRs):
  LC-FR1 having the amino acid sequence of SEQ ID NO:288
  LC-FR2 having the amino acid sequence of SEQ ID NO:298
  LC-FR3 having the amino acid sequence of SEQ ID NO:284
  LC-FR4 having the amino acid sequence of SEQ ID NO:47.

23. The method according to claim 19, wherein the antigen-binding molecule comprises a heavy chain comprising the CH1, CH2 and CH3 region sequences of human IgG4.

24. The method according to claim 19, wherein the antigen-binding molecule comprises a light chain comprising the amino acid sequence of SEQ ID NO:211.

25. The method according to claim 19, wherein the cancer is selected from: a cancer comprising cells expressing VISTA, a cancer comprising infiltration of cells expressing VISTA, a cancer comprising cancer cells expressing VISTA, a hematological cancer, leukemia, acute myeloid leukemia, lymphoma, B cell lymphoma, T cell lymphoma, multiple myeloma, mesothelioma, a solid tumor, lung cancer, non-small cell lung carcinoma, gastric cancer, gastric carcinoma, colorectal cancer, colorectal carcinoma, colorectal adenocarcinoma, uterine cancer, uterine corpus endometrial carcinoma, breast cancer, triple negative breast invasive carcinoma, liver cancer, hepatocellular carcinoma, pancreatic cancer, pancreatic ductal adenocarcinoma, thyroid cancer, thymoma, skin cancer, melanoma, cutaneous melanoma, kidney cancer, renal cell carcinoma, renal papillary cell carcinoma, head and neck cancer, squamous cell carcinoma of the head and neck (SCCHN), ovarian cancer, ovarian carcinoma, ovarian serous cystadenocarcinoma, prostate cancer and/or prostate adenocarcinoma.

\* \* \* \* \*

UNITED STATES PATENT AND TRADEMARK OFFICE
CERTIFICATE OF CORRECTION

| | | |
|---|---|---|
| PATENT NO. | : 10,633,456 B1 | Page 1 of 1 |
| APPLICATION NO. | : 16/596739 | |
| DATED | : April 28, 2020 | |
| INVENTOR(S) | : Jerome Douglas Boyd-Kirkup et al. | |

It is certified that error appears in the above-identified patent and that said Letters Patent is hereby corrected as shown below:

On the Title Page

The Assignee section, reading:
(73) Hummingbird Bioscience Holdings Pte. Ltd., Singapore (KR)
"(KR)" should read --(SG)--

Signed and Sealed this
Twenty-third Day of June, 2020

Andrei Iancu
*Director of the United States Patent and Trademark Office*

SEQUENCE LISTING

```
<160> NUMBER OF SEQ ID NOS: 330

<210> SEQ ID NO 1
<211> LENGTH: 311
<212> TYPE: PRT
<213> ORGANISM: Homo sapiens
<220> FEATURE:
<221> NAME/KEY: misc_feature
<222> LOCATION: (1)..(311)
<223> OTHER INFORMATION: VISTA

<400> SEQUENCE: 1
```

-continued

```
Met Gly Val Pro Thr Ala Leu Glu Ala Gly Ser Trp Arg Trp Gly Ser
1               5                   10                  15

Leu Leu Phe Ala Leu Phe Leu Ala Ala Ser Leu Gly Pro Val Ala Ala
            20                  25                  30

Phe Lys Val Ala Thr Pro Tyr Ser Leu Tyr Val Cys Pro Glu Gly Gln
        35                  40                  45

Asn Val Thr Leu Thr Cys Arg Leu Leu Gly Pro Val Asp Lys Gly His
    50                  55                  60

Asp Val Thr Phe Tyr Lys Thr Trp Tyr Arg Ser Arg Gly Glu Val
65                  70                  75                  80

Gln Thr Cys Ser Glu Arg Arg Pro Ile Arg Asn Leu Thr Phe Gln Asp
                85                  90                  95

Leu His Leu His His Gly Gly His Gln Ala Ala Asn Thr Ser His Asp
            100                 105                 110

Leu Ala Gln Arg His Gly Leu Glu Ser Ala Ser Asp His His Gly Asn
        115                 120                 125

Phe Ser Ile Thr Met Arg Asn Leu Thr Leu Leu Asp Ser Gly Leu Tyr
    130                 135                 140

Cys Cys Leu Val Val Glu Ile Arg His His Ser Glu His Arg Val
145                 150                 155                 160

His Gly Ala Met Glu Leu Gln Val Gln Thr Gly Lys Asp Ala Pro Ser
                165                 170                 175

Asn Cys Val Val Tyr Pro Ser Ser Ser Gln Asp Ser Glu Asn Ile Thr
            180                 185                 190

Ala Ala Ala Leu Ala Thr Gly Ala Cys Ile Val Gly Ile Leu Cys Leu
        195                 200                 205

Pro Leu Ile Leu Leu Val Tyr Lys Gln Arg Gln Ala Ala Ser Asn
    210                 215                 220

Arg Arg Ala Gln Glu Leu Val Arg Met Asp Ser Asn Ile Gln Gly Ile
225                 230                 235                 240

Glu Asn Pro Gly Phe Glu Ala Ser Pro Pro Ala Gln Gly Ile Pro Glu
                245                 250                 255

Ala Lys Val Arg His Pro Leu Ser Tyr Val Ala Gln Arg Gln Pro Ser
            260                 265                 270

Glu Ser Gly Arg His Leu Leu Ser Glu Pro Ser Thr Pro Leu Ser Pro
        275                 280                 285

Pro Gly Pro Gly Asp Val Phe Phe Pro Ser Leu Asp Pro Val Pro Asp
    290                 295                 300

Ser Pro Asn Phe Glu Val Ile
305                 310

<210> SEQ ID NO 2
<211> LENGTH: 279
<212> TYPE: PRT
<213> ORGANISM: Homo sapiens
<220> FEATURE:
<221> NAME/KEY: misc_feature
<222> LOCATION: (1)..(279)
<223> OTHER INFORMATION: VISTA

<400> SEQUENCE: 2

Phe Lys Val Ala Thr Pro Tyr Ser Leu Tyr Val Cys Pro Glu Gly Gln
1               5                   10                  15

Asn Val Thr Leu Thr Cys Arg Leu Leu Gly Pro Val Asp Lys Gly His
            20                  25                  30
```

Asp Val Thr Phe Tyr Lys Thr Trp Tyr Arg Ser Ser Arg Gly Glu Val
            35                  40                  45

Gln Thr Cys Ser Glu Arg Arg Pro Ile Arg Asn Leu Thr Phe Gln Asp
 50                  55                  60

Leu His Leu His His Gly Gly His Gln Ala Ala Asn Thr Ser His Asp
 65                  70                  75                  80

Leu Ala Gln Arg His Gly Leu Glu Ser Ala Ser Asp His His Gly Asn
                85                  90                  95

Phe Ser Ile Thr Met Arg Asn Leu Thr Leu Leu Asp Ser Gly Leu Tyr
            100                 105                 110

Cys Cys Leu Val Val Glu Ile Arg His His Ser Glu His Arg Val
            115                 120                 125

His Gly Ala Met Glu Leu Gln Val Gln Thr Gly Lys Asp Ala Pro Ser
130                 135                 140

Asn Cys Val Val Tyr Pro Ser Ser Gln Asp Ser Glu Asn Ile Thr
145                 150                 155                 160

Ala Ala Ala Leu Ala Thr Gly Ala Cys Ile Val Gly Ile Leu Cys Leu
                165                 170                 175

Pro Leu Ile Leu Leu Val Tyr Lys Gln Arg Gln Ala Ala Ser Asn
            180                 185                 190

Arg Arg Ala Gln Glu Leu Val Arg Met Asp Ser Asn Ile Gln Gly Ile
            195                 200                 205

Glu Asn Pro Gly Phe Glu Ala Ser Pro Pro Ala Gln Gly Ile Pro Glu
            210                 215                 220

Ala Lys Val Arg His Pro Leu Ser Tyr Val Ala Gln Arg Gln Pro Ser
225                 230                 235                 240

Glu Ser Gly Arg His Leu Leu Ser Glu Pro Ser Thr Pro Leu Ser Pro
                245                 250                 255

Pro Gly Pro Gly Asp Val Phe Phe Pro Ser Leu Asp Pro Val Pro Asp
            260                 265                 270

Ser Pro Asn Phe Glu Val Ile
            275

<210> SEQ ID NO 3
<211> LENGTH: 162
<212> TYPE: PRT
<213> ORGANISM: Homo sapiens
<220> FEATURE:
<221> NAME/KEY: misc_feature
<222> LOCATION: (1)..(162)
<223> OTHER INFORMATION: extracellular domain

<400> SEQUENCE: 3

Phe Lys Val Ala Thr Pro Tyr Ser Leu Tyr Val Cys Pro Glu Gly Gln
 1               5                   10                  15

Asn Val Thr Leu Thr Cys Arg Leu Leu Gly Pro Val Asp Lys Gly His
            20                  25                  30

Asp Val Thr Phe Tyr Lys Thr Trp Tyr Arg Ser Ser Arg Gly Glu Val
            35                  40                  45

Gln Thr Cys Ser Glu Arg Arg Pro Ile Arg Asn Leu Thr Phe Gln Asp
 50                  55                  60

Leu His Leu His His Gly Gly His Gln Ala Ala Asn Thr Ser His Asp
 65                  70                  75                  80

Leu Ala Gln Arg His Gly Leu Glu Ser Ala Ser Asp His His Gly Asn
                85                  90                  95

Phe Ser Ile Thr Met Arg Asn Leu Thr Leu Leu Asp Ser Gly Leu Tyr

```
                  100                 105                 110
Cys Cys Leu Val Val Glu Ile Arg His His His Ser Glu His Arg Val
            115                 120                 125

His Gly Ala Met Glu Leu Gln Val Gln Thr Gly Lys Asp Ala Pro Ser
            130                 135                 140

Asn Cys Val Val Tyr Pro Ser Ser Ser Gln Asp Ser Glu Asn Ile Thr
145                 150                 155                 160

Ala Ala

<210> SEQ ID NO 4
<211> LENGTH: 21
<212> TYPE: PRT
<213> ORGANISM: Homo sapiens
<220> FEATURE:
<221> NAME/KEY: misc_feature
<222> LOCATION: (1)..(21)
<223> OTHER INFORMATION: VISTA transmembrane domain

<400> SEQUENCE: 4

Ala Leu Ala Thr Gly Ala Cys Ile Val Gly Ile Leu Cys Leu Pro Leu
1               5                   10                  15

Ile Leu Leu Leu Val
            20

<210> SEQ ID NO 5
<211> LENGTH: 96
<212> TYPE: PRT
<213> ORGANISM: Homo sapiens
<220> FEATURE:
<221> NAME/KEY: misc_feature
<222> LOCATION: (1)..(96)
<223> OTHER INFORMATION: VISTA cytoplasmic domain

<400> SEQUENCE: 5

Tyr Lys Gln Arg Gln Ala Ala Ser Asn Arg Arg Ala Gln Glu Leu Val
1               5                   10                  15

Arg Met Asp Ser Asn Ile Gln Gly Ile Glu Asn Pro Gly Phe Glu Ala
            20                  25                  30

Ser Pro Pro Ala Gln Gly Ile Pro Glu Ala Lys Val Arg His Pro Leu
        35                  40                  45

Ser Tyr Val Ala Gln Arg Gln Pro Ser Glu Ser Gly Arg His Leu Leu
    50                  55                  60

Ser Glu Pro Ser Thr Pro Leu Ser Pro Pro Gly Pro Gly Asp Val Phe
65                  70                  75                  80

Phe Pro Ser Leu Asp Pro Val Pro Asp Ser Pro Asn Phe Glu Val Ile
                85                  90                  95

<210> SEQ ID NO 6
<211> LENGTH: 136
<212> TYPE: PRT
<213> ORGANISM: Homo sapiens
<220> FEATURE:
<221> NAME/KEY: misc_feature
<222> LOCATION: (1)..(136)
<223> OTHER INFORMATION: VISTA Ig-like V-type domain

<400> SEQUENCE: 6

Phe Lys Val Ala Thr Pro Tyr Ser Leu Tyr Val Cys Pro Glu Gly Gln
1               5                   10                  15

Asn Val Thr Leu Thr Cys Arg Leu Leu Gly Pro Val Asp Lys Gly His
            20                  25                  30
```

```
Asp Val Thr Phe Tyr Lys Thr Trp Tyr Arg Ser Ser Arg Gly Glu Val
            35                  40                  45

Gln Thr Cys Ser Glu Arg Arg Pro Ile Arg Asn Leu Thr Phe Gln Asp
 50                  55                  60

Leu His Leu His His Gly Gly His Gln Ala Ala Asn Thr Ser His Asp
 65                  70                  75                  80

Leu Ala Gln Arg His Gly Leu Glu Ser Ala Ser Asp His His Gly Asn
                 85                  90                  95

Phe Ser Ile Thr Met Arg Asn Leu Thr Leu Leu Asp Ser Gly Leu Tyr
            100                 105                 110

Cys Cys Leu Val Val Glu Ile Arg His His Ser Glu His Arg Val
            115                 120                 125

His Gly Ala Met Glu Leu Gln Val
        130                 135
```

<210> SEQ ID NO 7
<211> LENGTH: 431
<212> TYPE: PRT
<213> ORGANISM: Homo sapiens
<220> FEATURE:
<221> NAME/KEY: misc_feature
<222> LOCATION: (1)..(431)
<223> OTHER INFORMATION: HVSIG 3 isoform 1

<400> SEQUENCE: 7

```
Met Thr Ser Gln Arg Ser Pro Leu Ala Pro Leu Leu Leu Leu Ser Leu
 1               5                  10                  15

His Gly Val Ala Ala Ser Leu Glu Val Ser Glu Ser Pro Gly Ser Ile
             20                  25                  30

Gln Val Ala Arg Gly Gln Pro Ala Val Leu Pro Cys Thr Phe Thr Thr
             35                  40                  45

Ser Ala Ala Leu Ile Asn Leu Asn Val Ile Trp Met Val Thr Pro Leu
 50                  55                  60

Ser Asn Ala Asn Gln Pro Glu Gln Val Ile Leu Tyr Gln Gly Gly Gln
 65                  70                  75                  80

Met Phe Asp Gly Ala Pro Arg Phe His Gly Arg Val Gly Phe Thr Gly
             85                  90                  95

Thr Met Pro Ala Thr Asn Val Ser Ile Phe Ile Asn Asn Thr Gln Leu
            100                 105                 110

Ser Asp Thr Gly Thr Tyr Gln Cys Leu Val Asn Asn Leu Pro Asp Ile
            115                 120                 125

Gly Gly Arg Asn Ile Gly Val Thr Gly Leu Thr Val Leu Val Pro Pro
            130                 135                 140

Ser Ala Pro His Cys Gln Ile Gln Gly Ser Gln Asp Ile Gly Ser Asp
145                 150                 155                 160

Val Ile Leu Leu Cys Ser Ser Glu Glu Gly Ile Pro Arg Pro Thr Tyr
                165                 170                 175

Leu Trp Glu Lys Leu Asp Asn Thr Leu Lys Leu Pro Pro Thr Ala Thr
            180                 185                 190

Gln Asp Gln Val Gln Gly Thr Val Thr Ile Arg Asn Ile Ser Ala Leu
            195                 200                 205

Ser Ser Gly Leu Tyr Gln Cys Val Ala Ser Asn Ala Ile Gly Thr Ser
            210                 215                 220

Thr Cys Leu Leu Asp Leu Gln Val Ile Ser Pro Gln Pro Arg Asn Ile
225                 230                 235                 240

Gly Leu Ile Ala Gly Ala Ile Gly Thr Gly Ala Val Ile Ile Ile Phe
```

```
            245                 250                 255
Cys Ile Ala Leu Ile Leu Gly Ala Phe Phe Tyr Trp Arg Ser Lys Asn
            260                 265                 270
Lys Glu Glu Glu Glu Glu Ile Pro Asn Glu Ile Arg Glu Asp Asp
        275                 280                 285
Leu Pro Pro Lys Cys Ser Ser Ala Lys Ala Phe His Thr Glu Ile Ser
        290                 295                 300
Ser Ser Asp Asn Asn Thr Leu Thr Ser Ser Asn Ala Tyr Asn Ser Arg
305                 310                 315                 320
Tyr Trp Ser Asn Asn Pro Lys Val His Arg Asn Thr Glu Ser Val Ser
                325                 330                 335
His Phe Ser Asp Leu Gly Gln Ser Phe Ser Phe His Ser Gly Asn Ala
                340                 345                 350
Asn Ile Pro Ser Ile Tyr Ala Asn Gly Thr His Leu Val Pro Gly Gln
                355                 360                 365
His Lys Thr Leu Val Val Thr Ala Asn Arg Gly Ser Ser Pro Gln Val
                370                 375                 380
Met Ser Arg Ser Asn Gly Ser Val Ser Arg Lys Pro Arg Pro His
385                 390                 395                 400
Thr His Ser Tyr Thr Ile Ser His Ala Thr Leu Glu Arg Ile Gly Ala
                    405                 410                 415
Val Pro Val Met Val Pro Ala Gln Ser Arg Ala Gly Ser Leu Val
                420                 425                 430
```

<210> SEQ ID NO 8
<211> LENGTH: 430
<212> TYPE: PRT
<213> ORGANISM: Homo sapiens
<220> FEATURE:
<221> NAME/KEY: misc_feature
<222> LOCATION: (1)..(430)
<223> OTHER INFORMATION: VSIG-3 isoform 2

<400> SEQUENCE: 8

```
Met Ser Leu Val Glu Leu Leu Trp Trp Asn Cys Phe Ser Arg Thr
1               5                   10                  15
Gly Val Ala Ala Ser Leu Glu Val Ser Glu Ser Pro Gly Ser Ile Gln
                20                  25                  30
Val Ala Arg Gly Gln Pro Ala Val Leu Pro Cys Thr Phe Thr Thr Ser
            35                  40                  45
Ala Ala Leu Ile Asn Leu Asn Val Ile Trp Met Val Thr Pro Leu Ser
        50                  55                  60
Asn Ala Asn Gln Pro Glu Gln Val Ile Leu Tyr Gln Gly Gly Gln Met
65                  70                  75                  80
Phe Asp Gly Ala Pro Arg Phe His Gly Arg Val Gly Phe Thr Gly Thr
                85                  90                  95
Met Pro Ala Thr Asn Val Ser Ile Phe Ile Asn Asn Thr Gln Leu Ser
                100                 105                 110
Asp Thr Gly Thr Tyr Gln Cys Leu Val Asn Asn Leu Pro Asp Ile Gly
            115                 120                 125
Gly Arg Asn Ile Gly Val Thr Gly Leu Thr Val Leu Val Pro Pro Ser
        130                 135                 140
Ala Pro His Cys Gln Ile Gln Gly Ser Gln Asp Ile Gly Ser Asp Val
145                 150                 155                 160
Ile Leu Leu Cys Ser Ser Glu Glu Gly Ile Pro Arg Pro Thr Tyr Leu
                165                 170                 175
```

-continued

```
Trp Glu Lys Leu Asp Asn Thr Leu Lys Leu Pro Pro Thr Ala Thr Gln
            180                 185                 190

Asp Gln Val Gln Gly Thr Val Thr Ile Arg Asn Ile Ser Ala Leu Ser
        195                 200                 205

Ser Gly Leu Tyr Gln Cys Val Ala Ser Asn Ala Ile Gly Thr Ser Thr
210                 215                 220

Cys Leu Leu Asp Leu Gln Val Ile Ser Pro Gln Pro Arg Asn Ile Gly
225                 230                 235                 240

Leu Ile Ala Gly Ala Ile Gly Thr Gly Ala Val Ile Ile Phe Cys
                245                 250                 255

Ile Ala Leu Ile Leu Gly Ala Phe Phe Tyr Trp Arg Ser Lys Asn Lys
            260                 265                 270

Glu Glu Glu Glu Glu Glu Ile Pro Asn Glu Ile Arg Glu Asp Asp Leu
        275                 280                 285

Pro Pro Lys Cys Ser Ser Ala Lys Ala Phe His Thr Glu Ile Ser Ser
290                 295                 300

Ser Asp Asn Asn Thr Leu Thr Ser Ser Asn Ala Tyr Asn Ser Arg Tyr
305                 310                 315                 320

Trp Ser Asn Asn Pro Lys Val His Arg Asn Thr Glu Ser Val Ser His
                325                 330                 335

Phe Ser Asp Leu Gly Gln Ser Phe Ser Phe His Ser Gly Asn Ala Asn
            340                 345                 350

Ile Pro Ser Ile Tyr Ala Asn Gly Thr His Leu Val Pro Gly Gln His
        355                 360                 365

Lys Thr Leu Val Val Thr Ala Asn Arg Gly Ser Ser Pro Gln Val Met
370                 375                 380

Ser Arg Ser Asn Gly Ser Val Ser Arg Lys Pro Arg Pro His Thr
385                 390                 395                 400

His Ser Tyr Thr Ile Ser His Ala Thr Leu Glu Arg Ile Gly Ala Val
                405                 410                 415

Pro Val Met Val Pro Ala Gln Ser Arg Ala Gly Ser Leu Val
            420                 425                 430
```

<210> SEQ ID NO 9
<211> LENGTH: 406
<212> TYPE: PRT
<213> ORGANISM: Homo sapiens
<220> FEATURE:
<221> NAME/KEY: misc_feature
<222> LOCATION: (1)..(406)
<223> OTHER INFORMATION: HVSIG-3 isoform 3

<400> SEQUENCE: 9

```
Met Ser Leu Val Glu Leu Leu Trp Trp Asn Cys Phe Ser Arg Thr
1               5                   10                  15

Gly Val Ala Ala Ser Leu Glu Val Ser Glu Ser Pro Gly Ser Ile Gln
            20                  25                  30

Val Ala Arg Gly Gln Pro Ala Val Leu Pro Cys Thr Phe Thr Thr Ser
        35                  40                  45

Ala Ala Leu Ile Asn Leu Asn Val Ile Trp Met Val Thr Pro Leu Ser
50                  55                  60

Asn Ala Asn Gln Pro Glu Gln Val Ile Leu Tyr Gln Gly Gly Gln Met
65                  70                  75                  80

Phe Asp Gly Ala Pro Arg Phe His Gly Arg Val Gly Phe Thr Gly Thr
                85                  90                  95
```

```
Met Pro Ala Thr Asn Val Ser Ile Phe Ile Asn Asn Thr Gln Leu Ser
             100                 105                 110

Asp Thr Gly Thr Tyr Gln Cys Leu Val Asn Asn Leu Pro Asp Ile Gly
        115                 120                 125

Gly Arg Asn Ile Gly Val Thr Gly Leu Thr Val Leu Val Pro Pro Ser
    130                 135                 140

Ala Pro His Cys Gln Ile Gln Gly Ser Gln Asp Ile Gly Ser Asp Val
145                 150                 155                 160

Ile Leu Leu Cys Ser Ser Glu Glu Gly Ile Pro Arg Pro Thr Tyr Leu
                165                 170                 175

Trp Glu Lys Leu Asp Asn Thr Leu Lys Leu Pro Pro Thr Ala Thr Gln
            180                 185                 190

Asp Gln Val Gln Gly Thr Val Thr Ile Arg Asn Ile Ser Ala Leu Ser
        195                 200                 205

Ser Ala Gln Pro Arg Asn Ile Gly Leu Ile Ala Gly Ala Ile Gly Thr
210                 215                 220

Gly Ala Val Ile Ile Ile Phe Cys Ile Ala Leu Ile Leu Gly Ala Phe
225                 230                 235                 240

Phe Tyr Trp Arg Ser Lys Asn Lys Glu Glu Glu Glu Ile Pro
                245                 250                 255

Asn Glu Ile Arg Glu Asp Asp Leu Pro Pro Lys Cys Ser Ser Ala Lys
                260                 265                 270

Ala Phe His Thr Glu Ile Ser Ser Asp Asn Asn Thr Leu Thr Ser
                275                 280                 285

Ser Asn Ala Tyr Asn Ser Arg Tyr Trp Ser Asn Pro Lys Val His
            290                 295                 300

Arg Asn Thr Glu Ser Val Ser His Phe Ser Asp Leu Gly Gln Ser Phe
305                 310                 315                 320

Ser Phe His Ser Gly Asn Ala Asn Ile Pro Ser Ile Tyr Ala Asn Gly
                325                 330                 335

Thr His Leu Val Pro Gly Gln His Lys Thr Leu Val Val Thr Ala Asn
            340                 345                 350

Arg Gly Ser Ser Pro Gln Val Met Ser Arg Ser Asn Gly Ser Val Ser
        355                 360                 365

Arg Lys Pro Arg Pro Pro His Thr His Ser Tyr Thr Ile Ser His Ala
370                 375                 380

Thr Leu Glu Arg Ile Gly Ala Val Pro Val Met Val Pro Ala Gln Ser
385                 390                 395                 400

Arg Ala Gly Ser Leu Val
                405

<210> SEQ ID NO 10
<211> LENGTH: 409
<212> TYPE: PRT
<213> ORGANISM: Homo sapiens
<220> FEATURE:
<221> NAME/KEY: misc_feature
<222> LOCATION: (1)..(409)
<223> OTHER INFORMATION: VSIG-3 isoform 1

<400> SEQUENCE: 10

Leu Glu Val Ser Glu Ser Pro Gly Ser Ile Gln Val Ala Arg Gly Gln
1               5                   10                  15

Pro Ala Val Leu Pro Cys Thr Phe Thr Thr Ser Ala Ala Leu Ile Asn
            20                  25                  30

Leu Asn Val Ile Trp Met Val Thr Pro Leu Ser Asn Ala Asn Gln Pro
```

```
                35                  40                  45
Glu Gln Val Ile Leu Tyr Gln Gly Gly Gln Met Phe Asp Gly Ala Pro
 50                  55                  60

Arg Phe His Gly Arg Val Gly Phe Thr Gly Thr Met Pro Ala Thr Asn
 65                  70                  75                  80

Val Ser Ile Phe Ile Asn Asn Thr Gln Leu Ser Asp Thr Gly Thr Tyr
                 85                  90                  95

Gln Cys Leu Val Asn Asn Leu Pro Asp Ile Gly Gly Arg Asn Ile Gly
                100                 105                 110

Val Thr Gly Leu Thr Val Leu Val Pro Pro Ser Ala Pro His Cys Gln
                115                 120                 125

Ile Gln Gly Ser Gln Asp Ile Gly Ser Asp Val Ile Leu Leu Cys Ser
130                 135                 140

Ser Glu Glu Gly Ile Pro Arg Pro Thr Tyr Leu Trp Glu Lys Leu Asp
145                 150                 155                 160

Asn Thr Leu Lys Leu Pro Pro Thr Ala Thr Gln Asp Gln Val Gln Gly
                165                 170                 175

Thr Val Thr Ile Arg Asn Ile Ser Ala Leu Ser Ser Gly Leu Tyr Gln
                180                 185                 190

Cys Val Ala Ser Asn Ala Ile Gly Thr Ser Thr Cys Leu Leu Asp Leu
                195                 200                 205

Gln Val Ile Ser Pro Gln Pro Arg Asn Ile Gly Leu Ile Ala Gly Ala
210                 215                 220

Ile Gly Thr Gly Ala Val Ile Ile Phe Cys Ile Ala Leu Ile Leu
225                 230                 235                 240

Gly Ala Phe Phe Tyr Trp Arg Ser Lys Asn Lys Glu Glu Glu Glu Glu
                245                 250                 255

Glu Ile Pro Asn Glu Ile Arg Glu Asp Asp Leu Pro Pro Lys Cys Ser
                260                 265                 270

Ser Ala Lys Ala Phe His Thr Glu Ile Ser Ser Ser Asp Asn Asn Thr
                275                 280                 285

Leu Thr Ser Ser Asn Ala Tyr Asn Ser Arg Tyr Trp Ser Asn Asn Pro
290                 295                 300

Lys Val His Arg Asn Thr Glu Ser Val Ser His Phe Ser Asp Leu Gly
305                 310                 315                 320

Gln Ser Phe Ser Phe His Ser Gly Asn Ala Asn Ile Pro Ser Ile Tyr
                325                 330                 335

Ala Asn Gly Thr His Leu Val Pro Gly Gln His Lys Thr Leu Val Val
                340                 345                 350

Thr Ala Asn Arg Gly Ser Ser Pro Gln Val Met Ser Arg Ser Asn Gly
                355                 360                 365

Ser Val Ser Arg Lys Pro Arg Pro Pro His Thr His Ser Tyr Thr Ile
                370                 375                 380

Ser His Ala Thr Leu Glu Arg Ile Gly Ala Val Pro Val Met Val Pro
385                 390                 395                 400

Ala Gln Ser Arg Ala Gly Ser Leu Val
                405

<210> SEQ ID NO 11
<211> LENGTH: 409
<212> TYPE: PRT
<213> ORGANISM: Homo sapiens
<220> FEATURE:
<221> NAME/KEY: misc_feature
<222> LOCATION: (1)..(409)
```

<223> OTHER INFORMATION: VSIG-3 isoform 2

<400> SEQUENCE: 11

```
Leu Glu Val Ser Glu Ser Pro Gly Ser Ile Gln Val Ala Arg Gly Gln
1               5                   10                  15

Pro Ala Val Leu Pro Cys Thr Phe Thr Thr Ser Ala Ala Leu Ile Asn
            20                  25                  30

Leu Asn Val Ile Trp Met Val Thr Pro Leu Ser Asn Ala Asn Gln Pro
        35                  40                  45

Glu Gln Val Ile Leu Tyr Gln Gly Gly Gln Met Phe Asp Gly Ala Pro
    50                  55                  60

Arg Phe His Gly Arg Val Gly Phe Thr Gly Thr Met Pro Ala Thr Asn
65              70                  75                  80

Val Ser Ile Phe Ile Asn Asn Thr Gln Leu Ser Asp Thr Gly Thr Tyr
            85                  90                  95

Gln Cys Leu Val Asn Asn Leu Pro Asp Ile Gly Gly Arg Asn Ile Gly
        100                 105                 110

Val Thr Gly Leu Thr Val Leu Val Pro Pro Ser Ala Pro His Cys Gln
    115                 120                 125

Ile Gln Gly Ser Gln Asp Ile Gly Ser Asp Val Ile Leu Leu Cys Ser
130                 135                 140

Ser Glu Glu Gly Ile Pro Arg Pro Thr Tyr Leu Trp Glu Lys Leu Asp
145                 150                 155                 160

Asn Thr Leu Lys Leu Pro Pro Thr Ala Thr Gln Asp Gln Val Gln Gly
            165                 170                 175

Thr Val Thr Ile Arg Asn Ile Ser Ala Leu Ser Ser Gly Leu Tyr Gln
        180                 185                 190

Cys Val Ala Ser Asn Ala Ile Gly Thr Ser Thr Cys Leu Leu Asp Leu
    195                 200                 205

Gln Val Ile Ser Pro Gln Pro Arg Asn Ile Gly Leu Ile Ala Gly Ala
210                 215                 220

Ile Gly Thr Gly Ala Val Ile Ile Phe Cys Ile Ala Leu Ile Leu
225                 230                 235                 240

Gly Ala Phe Phe Tyr Trp Arg Ser Lys Asn Lys Glu Glu Glu Glu
            245                 250                 255

Glu Ile Pro Asn Glu Ile Arg Glu Asp Asp Leu Pro Pro Lys Cys Ser
        260                 265                 270

Ser Ala Lys Ala Phe His Thr Glu Ile Ser Ser Ser Asp Asn Asn Thr
    275                 280                 285

Leu Thr Ser Ser Asn Ala Tyr Asn Ser Arg Tyr Trp Ser Asn Asn Pro
290                 295                 300

Lys Val His Arg Asn Thr Glu Ser Val Ser His Phe Ser Asp Leu Gly
305                 310                 315                 320

Gln Ser Phe Ser Phe His Ser Gly Asn Ala Asn Ile Pro Ser Ile Tyr
            325                 330                 335

Ala Asn Gly Thr His Leu Val Pro Gly Gln His Lys Thr Leu Val Val
        340                 345                 350

Thr Ala Asn Arg Gly Ser Ser Pro Gln Val Met Ser Arg Ser Asn Gly
    355                 360                 365

Ser Val Ser Arg Lys Pro Arg Pro Pro His Thr His Ser Tyr Thr Ile
370                 375                 380

Ser His Ala Thr Leu Glu Arg Ile Gly Ala Val Pro Val Met Val Pro
385                 390                 395                 400
```

Ala Gln Ser Arg Ala Gly Ser Leu Val
            405

<210> SEQ ID NO 12
<211> LENGTH: 385
<212> TYPE: PRT
<213> ORGANISM: Homo sapiens
<220> FEATURE:
<221> NAME/KEY: misc_feature
<222> LOCATION: (1)..(385)
<223> OTHER INFORMATION: VSIG-3 isoform 3

<400> SEQUENCE: 12

Leu Glu Val Ser Glu Ser Pro Gly Ser Ile Gln Val Ala Arg Gly Gln
1               5                   10                  15

Pro Ala Val Leu Pro Cys Thr Phe Thr Thr Ser Ala Ala Leu Ile Asn
            20                  25                  30

Leu Asn Val Ile Trp Met Val Thr Pro Leu Ser Asn Ala Asn Gln Pro
        35                  40                  45

Glu Gln Val Ile Leu Tyr Gln Gly Gly Gln Met Phe Asp Gly Ala Pro
    50                  55                  60

Arg Phe His Gly Arg Val Gly Phe Thr Gly Thr Met Pro Ala Thr Asn
65                  70                  75                  80

Val Ser Ile Phe Ile Asn Asn Thr Gln Leu Ser Asp Thr Gly Thr Tyr
                85                  90                  95

Gln Cys Leu Val Asn Asn Leu Pro Asp Ile Gly Gly Arg Asn Ile Gly
            100                 105                 110

Val Thr Gly Leu Thr Val Leu Val Pro Pro Ser Ala Pro His Cys Gln
        115                 120                 125

Ile Gln Gly Ser Gln Asp Ile Gly Ser Asp Val Ile Leu Leu Cys Ser
    130                 135                 140

Ser Glu Glu Gly Ile Pro Arg Pro Thr Tyr Leu Trp Glu Lys Leu Asp
145                 150                 155                 160

Asn Thr Leu Lys Leu Pro Pro Thr Ala Thr Gln Asp Gln Val Gln Gly
                165                 170                 175

Thr Val Thr Ile Arg Asn Ile Ser Ala Leu Ser Ser Ala Gln Pro Arg
            180                 185                 190

Asn Ile Gly Leu Ile Ala Gly Ala Ile Gly Thr Gly Ala Val Ile Ile
        195                 200                 205

Ile Phe Cys Ile Ala Leu Ile Leu Gly Ala Phe Phe Tyr Trp Arg Ser
    210                 215                 220

Lys Asn Lys Glu Glu Glu Glu Glu Ile Pro Asn Glu Ile Arg Glu
225                 230                 235                 240

Asp Asp Leu Pro Pro Lys Cys Ser Ser Ala Lys Ala Phe His Thr Glu
                245                 250                 255

Ile Ser Ser Ser Asp Asn Asn Thr Leu Thr Ser Ser Asn Ala Tyr Asn
            260                 265                 270

Ser Arg Tyr Trp Ser Asn Asn Pro Lys Val His Arg Asn Thr Glu Ser
        275                 280                 285

Val Ser His Phe Ser Asp Leu Gly Gln Ser Phe Ser Phe His Ser Gly
    290                 295                 300

Asn Ala Asn Ile Pro Ser Ile Tyr Ala Asn Gly Thr His Leu Val Pro
305                 310                 315                 320

Gly Gln His Lys Thr Leu Val Val Thr Ala Asn Arg Gly Ser Ser Pro
                325                 330                 335

Gln Val Met Ser Arg Ser Asn Gly Ser Val Ser Arg Lys Pro Arg Pro

```
                    340                 345                 350
Pro His Thr His Ser Tyr Thr Ile Ser His Ala Thr Leu Glu Arg Ile
                355                 360                 365

Gly Ala Val Pro Val Met Val Pro Ala Gln Ser Arg Ala Gly Ser Leu
            370                 375                 380

Val
385

<210> SEQ ID NO 13
<211> LENGTH: 219
<212> TYPE: PRT
<213> ORGANISM: Homo sapiens
<220> FEATURE:
<221> NAME/KEY: misc_feature
<222> LOCATION: (1)..(219)
<223> OTHER INFORMATION: VSIG-3 isoforms 1 and 2 extracellular domain

<400> SEQUENCE: 13

Leu Glu Val Ser Glu Ser Pro Gly Ser Ile Gln Val Ala Arg Gly Gln
1               5                   10                  15

Pro Ala Val Leu Pro Cys Thr Phe Thr Thr Ser Ala Ala Leu Ile Asn
            20                  25                  30

Leu Asn Val Ile Trp Met Val Thr Pro Leu Ser Asn Ala Asn Gln Pro
        35                  40                  45

Glu Gln Val Ile Leu Tyr Gln Gly Gly Gln Met Phe Asp Gly Ala Pro
    50                  55                  60

Arg Phe His Gly Arg Val Gly Phe Thr Gly Thr Met Pro Ala Thr Asn
65                  70                  75                  80

Val Ser Ile Phe Ile Asn Asn Thr Gln Leu Ser Asp Thr Gly Thr Tyr
                85                  90                  95

Gln Cys Leu Val Asn Asn Leu Pro Asp Ile Gly Gly Arg Asn Ile Gly
            100                 105                 110

Val Thr Gly Leu Thr Val Leu Val Pro Pro Ser Ala Pro His Cys Gln
        115                 120                 125

Ile Gln Gly Ser Gln Asp Ile Gly Ser Asp Val Ile Leu Leu Cys Ser
    130                 135                 140

Ser Glu Glu Gly Ile Pro Arg Pro Thr Tyr Leu Trp Glu Lys Leu Asp
145                 150                 155                 160

Asn Thr Leu Lys Leu Pro Pro Thr Ala Thr Gln Asp Gln Val Gln Gly
                165                 170                 175

Thr Val Thr Ile Arg Asn Ile Ser Ala Leu Ser Ser Gly Leu Tyr Gln
            180                 185                 190

Cys Val Ala Ser Asn Ala Ile Gly Thr Ser Thr Cys Leu Leu Asp Leu
        195                 200                 205

Gln Val Ile Ser Pro Gln Pro Arg Asn Ile Gly
    210                 215

<210> SEQ ID NO 14
<211> LENGTH: 195
<212> TYPE: PRT
<213> ORGANISM: Homo sapiens
<220> FEATURE:
<221> NAME/KEY: misc_feature
<222> LOCATION: (1)..(195)
<223> OTHER INFORMATION: VSIG-3 isoform 3 extracellular domain

<400> SEQUENCE: 14

Leu Glu Val Ser Glu Ser Pro Gly Ser Ile Gln Val Ala Arg Gly Gln
1               5                   10                  15
```

```
Pro Ala Val Leu Pro Cys Thr Phe Thr Thr Ser Ala Ala Leu Ile Asn
            20                  25                  30

Leu Asn Val Ile Trp Met Val Thr Pro Leu Ser Asn Ala Asn Gln Pro
        35                  40                  45

Glu Gln Val Ile Leu Tyr Gln Gly Gly Gln Met Phe Asp Gly Ala Pro
 50                  55                  60

Arg Phe His Gly Arg Val Gly Phe Thr Gly Thr Met Pro Ala Thr Asn
 65                  70                  75                  80

Val Ser Ile Phe Ile Asn Asn Thr Gln Leu Ser Asp Thr Gly Thr Tyr
                85                  90                  95

Gln Cys Leu Val Asn Asn Leu Pro Asp Ile Gly Gly Arg Asn Ile Gly
            100                 105                 110

Val Thr Gly Leu Thr Val Leu Val Pro Pro Ser Ala Pro His Cys Gln
        115                 120                 125

Ile Gln Gly Ser Gln Asp Ile Gly Ser Asp Val Ile Leu Leu Cys Ser
    130                 135                 140

Ser Glu Glu Gly Ile Pro Arg Pro Thr Tyr Leu Trp Glu Lys Leu Asp
145                 150                 155                 160

Asn Thr Leu Lys Leu Pro Pro Thr Ala Thr Gln Asp Gln Val Gln Gly
                165                 170                 175

Thr Val Thr Ile Arg Asn Ile Ser Ala Leu Ser Ser Ala Gln Pro Arg
            180                 185                 190

Asn Ile Gly
        195

<210> SEQ ID NO 15
<211> LENGTH: 21
<212> TYPE: PRT
<213> ORGANISM: Homo sapiens
<220> FEATURE:
<221> NAME/KEY: misc_feature
<222> LOCATION: (1)..(21)
<223> OTHER INFORMATION: VSIG-3 transmembrane domain

<400> SEQUENCE: 15

Leu Ile Ala Gly Ala Ile Gly Thr Gly Ala Val Ile Ile Ile Phe Cys
1               5                   10                  15

Ile Ala Leu Ile Leu
            20

<210> SEQ ID NO 16
<211> LENGTH: 169
<212> TYPE: PRT
<213> ORGANISM: Homo sapiens
<220> FEATURE:
<221> NAME/KEY: misc_feature
<222> LOCATION: (1)..(169)
<223> OTHER INFORMATION: VSIG-3 cytoplasmic domain

<400> SEQUENCE: 16

Gly Ala Phe Phe Tyr Trp Arg Ser Lys Asn Lys Glu Glu Glu Glu Glu
1               5                   10                  15

Glu Ile Pro Asn Glu Ile Arg Glu Asp Asp Leu Pro Pro Lys Cys Ser
            20                  25                  30

Ser Ala Lys Ala Phe His Thr Glu Ile Ser Ser Ser Asp Asn Asn Thr
        35                  40                  45

Leu Thr Ser Ser Asn Ala Tyr Asn Ser Arg Tyr Trp Ser Asn Asn Pro
 50                  55                  60
```

Lys Val His Arg Asn Thr Glu Ser Val Ser His Phe Ser Asp Leu Gly
65                  70                  75                  80

Gln Ser Phe Ser Phe His Ser Gly Asn Ala Asn Ile Pro Ser Ile Tyr
            85                  90                  95

Ala Asn Gly Thr His Leu Val Pro Gly Gln His Lys Thr Leu Val Val
            100                 105                 110

Thr Ala Asn Arg Gly Ser Ser Pro Gln Val Met Ser Arg Ser Asn Gly
        115                 120                 125

Ser Val Ser Arg Lys Pro Arg Pro His Thr His Ser Tyr Thr Ile
    130                 135                 140

Ser His Ala Thr Leu Glu Arg Ile Gly Ala Val Pro Val Met Val Pro
145                 150                 155                 160

Ala Gln Ser Arg Ala Gly Ser Leu Val
            165

<210> SEQ ID NO 17
<211> LENGTH: 114
<212> TYPE: PRT
<213> ORGANISM: Homo sapiens
<220> FEATURE:
<221> NAME/KEY: misc_feature
<222> LOCATION: (1)..(114)
<223> OTHER INFORMATION: VSIG-3 Ig-like V-type domain

<400> SEQUENCE: 17

Leu Glu Val Ser Glu Ser Pro Gly Ser Ile Gln Val Ala Arg Gly Gln
1               5                   10                  15

Pro Ala Val Leu Pro Cys Thr Phe Thr Thr Ser Ala Ala Leu Ile Asn
            20                  25                  30

Leu Asn Val Ile Trp Met Val Thr Pro Leu Ser Asn Ala Asn Gln Pro
        35                  40                  45

Glu Gln Val Ile Leu Tyr Gln Gly Gly Gln Met Phe Asp Gly Ala Pro
    50                  55                  60

Arg Phe His Gly Arg Val Gly Phe Thr Gly Thr Met Pro Ala Thr Asn
65                  70                  75                  80

Val Ser Ile Phe Ile Asn Asn Thr Gln Leu Ser Asp Thr Gly Thr Tyr
            85                  90                  95

Gln Cys Leu Val Asn Asn Leu Pro Asp Ile Gly Gly Arg Asn Ile Gly
            100                 105                 110

Val Thr

<210> SEQ ID NO 18
<211> LENGTH: 91
<212> TYPE: PRT
<213> ORGANISM: Homo sapiens
<220> FEATURE:
<221> NAME/KEY: misc_feature
<222> LOCATION: (1)..(91)
<223> OTHER INFORMATION: VSIG-3 Ig-like V-type domain

<400> SEQUENCE: 18

Pro Ser Ala Pro His Cys Gln Ile Gln Gly Ser Gln Asp Ile Gly Ser
1               5                   10                  15

Asp Val Ile Leu Leu Cys Ser Ser Glu Glu Gly Ile Pro Arg Pro Thr
            20                  25                  30

Tyr Leu Trp Glu Lys Leu Asp Asn Thr Leu Lys Leu Pro Pro Thr Ala
        35                  40                  45

Thr Gln Asp Gln Val Gln Gly Thr Val Thr Ile Arg Asn Ile Ser Ala
    50                  55                  60

```
Leu Ser Ser Gly Leu Tyr Gln Cys Val Ala Ser Asn Ala Ile Gly Thr
 65                  70                  75                  80

Ser Thr Cys Leu Leu Asp Leu Gln Val Ile Ser
                 85                  90

<210> SEQ ID NO 19
<211> LENGTH: 414
<212> TYPE: PRT
<213> ORGANISM: Homo sapiens
<220> FEATURE:
<221> NAME/KEY: misc_feature
<222> LOCATION: (1)..(414)
<223> OTHER INFORMATION: VSIG-8

<400> SEQUENCE: 19

Met Arg Val Gly Gly Ala Phe His Leu Leu Val Cys Leu Ser Pro
 1               5                  10                  15

Ala Leu Leu Ser Ala Val Arg Ile Asn Gly Asp Gly Gln Glu Val Leu
                 20                  25                  30

Tyr Leu Ala Glu Gly Asp Asn Val Arg Leu Gly Cys Pro Tyr Val Leu
                 35                  40                  45

Asp Pro Glu Asp Tyr Gly Pro Asn Gly Leu Asp Ile Glu Trp Met Gln
 50                  55                  60

Val Asn Ser Asp Pro Ala His His Arg Glu Asn Val Phe Leu Ser Tyr
 65                  70                  75                  80

Gln Asp Lys Arg Ile Asn His Gly Ser Leu Pro His Leu Gln Arg
                 85                  90                  95

Val Arg Phe Ala Ala Ser Asp Pro Ser Gln Tyr Asp Ala Ser Ile Asn
                 100                 105                 110

Leu Met Asn Leu Gln Val Ser Asp Thr Ala Thr Tyr Glu Cys Arg Val
                 115                 120                 125

Lys Lys Thr Thr Met Ala Thr Arg Lys Val Ile Val Thr Val Gln Ala
                 130                 135                 140

Arg Pro Ala Val Pro Met Cys Trp Thr Glu Gly His Met Thr Tyr Gly
 145                 150                 155                 160

Asn Asp Val Val Leu Lys Cys Tyr Ala Ser Gly Gly Ser Gln Pro Leu
                 165                 170                 175

Ser Tyr Lys Trp Ala Lys Ile Ser Gly His His Tyr Pro Tyr Arg Ala
                 180                 185                 190

Gly Ser Tyr Thr Ser Gln His Ser Tyr His Ser Glu Leu Ser Tyr Gln
                 195                 200                 205

Glu Ser Phe His Ser Ser Ile Asn Gln Gly Leu Asn Asn Gly Asp Leu
                 210                 215                 220

Val Leu Lys Asp Ile Ser Arg Ala Asp Asp Gly Leu Tyr Gln Cys Thr
 225                 230                 235                 240

Val Ala Asn Asn Val Gly Tyr Ser Val Cys Val Val Glu Val Lys Val
                 245                 250                 255

Ser Asp Ser Arg Arg Ile Gly Val Ile Gly Ile Val Leu Gly Ser
                 260                 265                 270

Leu Leu Ala Leu Gly Cys Leu Ala Val Gly Ile Trp Gly Leu Val Cys
                 275                 280                 285

Cys Cys Cys Gly Gly Ser Gly Ala Gly Ala Arg Gly Ala Phe Gly
                 290                 295                 300

Tyr Gly Asn Gly Gly Gly Val Gly Gly Gly Ala Cys Gly Asp Leu Ala
 305                 310                 315                 320
```

```
Ser Glu Ile Arg Glu Asp Ala Val Ala Pro Gly Cys Lys Ala Ser Gly
                325                 330                 335

Arg Gly Ser Arg Val Thr His Leu Leu Gly Tyr Pro Thr Gln Asn Val
            340                 345                 350

Ser Arg Ser Leu Arg Arg Lys Tyr Ala Pro Pro Cys Gly Gly Pro
        355                 360                 365

Glu Asp Val Ala Leu Ala Pro Cys Thr Ala Ala Ala Cys Glu Ala
370                 375                 380

Gly Pro Ser Pro Val Tyr Val Lys Val Lys Ser Ala Glu Pro Ala Asp
385                 390                 395                 400

Cys Ala Glu Gly Pro Val Gln Cys Lys Asn Gly Leu Leu Val
                405                 410
```

<210> SEQ ID NO 20
<211> LENGTH: 393
<212> TYPE: PRT
<213> ORGANISM: Homo sapiens VSIG-8
<220> FEATURE:
<221> NAME/KEY: misc_feature
<222> LOCATION: (1)..(393)
<223> OTHER INFORMATION: VSIG-8

<400> SEQUENCE: 20

```
Val Arg Ile Asn Gly Asp Gly Gln Glu Val Leu Tyr Leu Ala Glu Gly
1               5                   10                  15

Asp Asn Val Arg Leu Gly Cys Pro Tyr Val Leu Asp Pro Glu Asp Tyr
            20                  25                  30

Gly Pro Asn Gly Leu Asp Ile Glu Trp Met Gln Val Asn Ser Asp Pro
        35                  40                  45

Ala His His Arg Glu Asn Val Phe Leu Ser Tyr Gln Asp Lys Arg Ile
    50                  55                  60

Asn His Gly Ser Leu Pro His Leu Gln Gln Arg Val Arg Phe Ala Ala
65                  70                  75                  80

Ser Asp Pro Ser Gln Tyr Asp Ala Ser Ile Asn Leu Met Asn Leu Gln
                85                  90                  95

Val Ser Asp Thr Ala Thr Tyr Glu Cys Arg Val Lys Lys Thr Thr Met
            100                 105                 110

Ala Thr Arg Lys Val Ile Val Thr Val Gln Ala Arg Pro Ala Val Pro
        115                 120                 125

Met Cys Trp Thr Glu Gly His Met Thr Tyr Gly Asn Asp Val Val Leu
    130                 135                 140

Lys Cys Tyr Ala Ser Gly Gly Ser Gln Pro Leu Ser Tyr Lys Trp Ala
145                 150                 155                 160

Lys Ile Ser Gly His His Tyr Pro Tyr Arg Ala Gly Ser Tyr Thr Ser
                165                 170                 175

Gln His Ser Tyr His Ser Glu Leu Ser Tyr Gln Glu Ser Phe His Ser
            180                 185                 190

Ser Ile Asn Gln Gly Leu Asn Asn Gly Asp Leu Val Leu Lys Asp Ile
        195                 200                 205

Ser Arg Ala Asp Asp Gly Leu Tyr Gln Cys Thr Val Ala Asn Asn Val
    210                 215                 220

Gly Tyr Ser Val Cys Val Glu Val Lys Val Ser Asp Ser Arg Arg
225                 230                 235                 240

Ile Gly Val Ile Ile Gly Ile Val Leu Gly Ser Leu Leu Ala Leu Gly
                245                 250                 255

Cys Leu Ala Val Gly Ile Trp Gly Leu Val Cys Cys Cys Cys Gly Gly
```

```
                260                 265                 270
Ser Gly Ala Gly Gly Ala Arg Gly Ala Phe Gly Tyr Gly Asn Gly Gly
            275                 280                 285

Gly Val Gly Gly Gly Ala Cys Gly Asp Leu Ala Ser Glu Ile Arg Glu
            290                 295                 300

Asp Ala Val Ala Pro Gly Cys Lys Ala Ser Gly Arg Gly Ser Arg Val
305                 310                 315                 320

Thr His Leu Leu Gly Tyr Pro Thr Gln Asn Val Ser Arg Ser Leu Arg
                325                 330                 335

Arg Lys Tyr Ala Pro Pro Cys Gly Pro Glu Asp Val Ala Leu
            340                 345                 350

Ala Pro Cys Thr Ala Ala Ala Cys Glu Ala Gly Pro Ser Pro Val
            355                 360                 365

Tyr Val Lys Val Lys Ser Ala Glu Pro Ala Asp Cys Ala Glu Gly Pro
            370                 375                 380

Val Gln Cys Lys Asn Gly Leu Leu Val
385                 390

<210> SEQ ID NO 21
<211> LENGTH: 242
<212> TYPE: PRT
<213> ORGANISM: Homo sapiens
<220> FEATURE:
<221> NAME/KEY: misc_feature
<222> LOCATION: (1)..(242)
<223> OTHER INFORMATION: VSIG-8 extracellular domain

<400> SEQUENCE: 21

Val Arg Ile Asn Gly Asp Gly Gln Glu Val Leu Tyr Leu Ala Glu Gly
1               5                   10                  15

Asp Asn Val Arg Leu Gly Cys Pro Tyr Val Leu Asp Pro Glu Asp Tyr
            20                  25                  30

Gly Pro Asn Gly Leu Asp Ile Glu Trp Met Gln Val Asn Ser Asp Pro
        35                  40                  45

Ala His His Arg Glu Asn Val Phe Leu Ser Tyr Gln Asp Lys Arg Ile
    50                  55                  60

Asn His Gly Ser Leu Pro His Leu Gln Gln Arg Val Arg Phe Ala Ala
65                  70                  75                  80

Ser Asp Pro Ser Gln Tyr Asp Ala Ser Ile Asn Leu Met Asn Leu Gln
                85                  90                  95

Val Ser Asp Thr Ala Thr Tyr Glu Cys Arg Val Lys Lys Thr Thr Met
            100                 105                 110

Ala Thr Arg Lys Val Ile Val Thr Val Gln Ala Arg Pro Ala Val Pro
        115                 120                 125

Met Cys Trp Thr Glu Gly His Met Thr Tyr Gly Asn Asp Val Val Leu
    130                 135                 140

Lys Cys Tyr Ala Ser Gly Gly Ser Gln Pro Leu Ser Tyr Lys Trp Ala
145                 150                 155                 160

Lys Ile Ser Gly His His Tyr Pro Tyr Arg Ala Gly Ser Tyr Thr Ser
                165                 170                 175

Gln His Ser Tyr His Ser Glu Leu Ser Tyr Gln Glu Ser Phe His Ser
            180                 185                 190

Ser Ile Asn Gln Gly Leu Asn Asn Gly Asp Leu Val Leu Lys Asp Ile
        195                 200                 205

Ser Arg Ala Asp Asp Gly Leu Tyr Gln Cys Thr Val Ala Asn Asn Val
    210                 215                 220
```

-continued

```
Gly Tyr Ser Val Cys Val Val Glu Val Lys Val Ser Asp Ser Arg Arg
225                 230                 235                 240

Ile Gly

<210> SEQ ID NO 22
<211> LENGTH: 21
<212> TYPE: PRT
<213> ORGANISM: Homo sapiens
<220> FEATURE:
<221> NAME/KEY: misc_feature
<222> LOCATION: (1)..(21)
<223> OTHER INFORMATION: VSIG-8 transmembrane domain

<400> SEQUENCE: 22

Val Ile Ile Gly Ile Val Leu Gly Ser Leu Leu Ala Leu Gly Cys Leu
1               5                   10                  15

Ala Val Gly Ile Trp
            20

<210> SEQ ID NO 23
<211> LENGTH: 130
<212> TYPE: PRT
<213> ORGANISM: Homo sapiens
<220> FEATURE:
<221> NAME/KEY: misc_feature
<222> LOCATION: (1)..(130)
<223> OTHER INFORMATION: VSIG-8 cytoplasmic domain

<400> SEQUENCE: 23

Gly Leu Val Cys Cys Cys Cys Gly Gly Ser Gly Ala Gly Gly Ala Arg
1               5                   10                  15

Gly Ala Phe Gly Tyr Gly Asn Gly Gly Val Gly Gly Gly Ala Cys
            20                  25                  30

Gly Asp Leu Ala Ser Glu Ile Arg Glu Asp Ala Val Ala Pro Gly Cys
            35                  40                  45

Lys Ala Ser Gly Arg Gly Ser Arg Val Thr His Leu Leu Gly Tyr Pro
    50                  55                  60

Thr Gln Asn Val Ser Arg Ser Leu Arg Arg Lys Tyr Ala Pro Pro Pro
65                  70                  75                  80

Cys Gly Gly Pro Glu Asp Val Ala Leu Ala Pro Cys Thr Ala Ala Ala
                85                  90                  95

Ala Cys Glu Ala Gly Pro Ser Pro Val Tyr Val Lys Val Lys Ser Ala
            100                 105                 110

Glu Pro Ala Asp Cys Ala Glu Gly Pro Val Gln Cys Lys Asn Gly Leu
        115                 120                 125

Leu Val
    130

<210> SEQ ID NO 24
<211> LENGTH: 120
<212> TYPE: PRT
<213> ORGANISM: Homo sapiens
<220> FEATURE:
<221> NAME/KEY: misc_feature
<222> LOCATION: (1)..(120)
<223> OTHER INFORMATION: VSIG-8 Ig-like V-type domain

<400> SEQUENCE: 24

Val Arg Ile Asn Gly Asp Gly Gln Glu Val Leu Tyr Leu Ala Glu Gly
1               5                   10                  15

Asp Asn Val Arg Leu Gly Cys Pro Tyr Val Leu Asp Pro Glu Asp Tyr
```

```
                      20                  25                  30

Gly Pro Asn Gly Leu Asp Ile Glu Trp Met Gln Val Asn Ser Asp Pro
                  35                  40                  45

Ala His His Arg Glu Asn Val Phe Leu Ser Tyr Gln Asp Lys Arg Ile
 50                  55                  60

Asn His Gly Ser Leu Pro His Leu Gln Gln Arg Val Arg Phe Ala Ala
 65                  70                  75                  80

Ser Asp Pro Ser Gln Tyr Asp Ala Ser Ile Asn Leu Met Asn Leu Gln
                  85                  90                  95

Val Ser Asp Thr Ala Thr Tyr Glu Cys Arg Val Lys Lys Thr Thr Met
                 100                 105                 110

Ala Thr Arg Lys Val Ile Val Thr
                 115                 120

<210> SEQ ID NO 25
<211> LENGTH: 112
<212> TYPE: PRT
<213> ORGANISM: Homo sapiens
<220> FEATURE:
<221> NAME/KEY: misc_feature
<222> LOCATION: (1)..(112)
<223> OTHER INFORMATION: VSIG-8 Ig-like V-type domain

<400> SEQUENCE: 25

Pro Ala Val Pro Met Cys Trp Thr Glu Gly His Met Thr Tyr Gly Asn
 1               5                  10                  15

Asp Val Val Leu Lys Cys Tyr Ala Ser Gly Gly Ser Gln Pro Leu Ser
                 20                  25                  30

Tyr Lys Trp Ala Lys Ile Ser Gly His His Tyr Pro Tyr Arg Ala Gly
                 35                  40                  45

Ser Tyr Thr Ser Gln His Ser Tyr His Ser Glu Leu Ser Tyr Gln Glu
 50                  55                  60

Ser Phe His Ser Ser Ile Asn Gln Gly Leu Asn Asn Gly Asp Leu Val
 65                  70                  75                  80

Leu Lys Asp Ile Ser Arg Ala Asp Asp Gly Leu Tyr Gln Cys Thr Val
                 85                  90                  95

Ala Asn Asn Val Gly Tyr Ser Val Cys Val Val Glu Val Lys Val Ser
                 100                 105                 110

<210> SEQ ID NO 26
<211> LENGTH: 14
<212> TYPE: PRT
<213> ORGANISM: Artificial Sequence
<220> FEATURE:
<223> OTHER INFORMATION: Epitope recognised by anti-VISTA antibody
      clones 4M2-C12, 4M2-B4, 4M2-C9, 4M2-D9, 4M2-D5, 4M2-A8, V4H1 and
      V4H2

<400> SEQUENCE: 26

Ser Arg Gly Glu Val Gln Thr Cys Ser Glu Arg Arg Pro Ile
 1               5                  10

<210> SEQ ID NO 27
<211> LENGTH: 14
<212> TYPE: PRT
<213> ORGANISM: Artificial Sequence
<220> FEATURE:
<223> OTHER INFORMATION: Epitope recognised by anti-VISTA antibody
      clones 2M1-B12 and 2M1-D2

<400> SEQUENCE: 27
```

```
Phe Gln Asp Leu His Leu His His Gly Gly His Gln Ala Ala
1               5                   10
```

<210> SEQ ID NO 28
<211> LENGTH: 14
<212> TYPE: PRT
<213> ORGANISM: Artificial Sequence
<220> FEATURE:
<223> OTHER INFORMATION: Epitope recognised by anti-VISTA antibody
      clones 1M2-D2, 13D5p, 13D5-1 and 13D5-13

<400> SEQUENCE: 28

```
Cys Leu Val Val Glu Ile Arg His His His Ser Glu His Arg
1               5                   10
```

<210> SEQ ID NO 29
<211> LENGTH: 11
<212> TYPE: PRT
<213> ORGANISM: Artificial Sequence
<220> FEATURE:
<223> OTHER INFORMATION: Epitope recognised by anti-VISTA antibody
      clone 5M1-A11

<400> SEQUENCE: 29

```
Asp Lys Gly His Asp Val Thr Phe Tyr Lys Thr
1               5                   10
```

<210> SEQ ID NO 30
<211> LENGTH: 11
<212> TYPE: PRT
<213> ORGANISM: Artificial Sequence
<220> FEATURE:
<223> OTHER INFORMATION: Epitope recognised by anti-VISTA antibody
      clone 9M2-C12

<400> SEQUENCE: 30

```
Arg His His His Ser Glu His Arg Val His Gly
1               5                   10
```

<210> SEQ ID NO 31
<211> LENGTH: 102
<212> TYPE: PRT
<213> ORGANISM: Artificial Sequence
<220> FEATURE:
<223> OTHER INFORMATION: Positions 61 to 162 of human VISTA
      (Q9H7M9-1, v3)

<400> SEQUENCE: 31

```
Asp Lys Gly His Asp Val Thr Phe Tyr Lys Thr Trp Tyr Arg Ser Ser
1               5                   10                  15

Arg Gly Glu Val Gln Thr Cys Ser Glu Arg Arg Pro Ile Arg Asn Leu
            20                  25                  30

Thr Phe Gln Asp Leu His Leu His His Gly Gly His Gln Ala Ala Asn
        35                  40                  45

Thr Ser His Asp Leu Ala Gln Arg His Gly Leu Glu Ser Ala Ser Asp
    50                  55                  60

His His Gly Asn Phe Ser Ile Thr Met Arg Asn Leu Thr Leu Leu Asp
65                  70                  75                  80

Ser Gly Leu Tyr Cys Cys Leu Val Val Glu Ile Arg His His His Ser
                85                  90                  95

Glu His Arg Val His Gly
            100
```

<210> SEQ ID NO 32

```
<211> LENGTH: 119
<212> TYPE: PRT
<213> ORGANISM: Artificial Sequence
<220> FEATURE:
<223> OTHER INFORMATION: 4M2-C12 heavy chain variable region

<400> SEQUENCE: 32

Glu Val Lys Leu Val Glu Ser Gly Pro Gly Leu Val Lys Pro Ser Gln
1               5                   10                  15

Ser Leu Ser Leu Thr Cys Thr Val Thr Gly Tyr Ser Ile Thr Ser Asp
            20                  25                  30

Tyr Ala Trp Asn Trp Ile Arg Gln Phe Pro Gly Asn Lys Leu Glu Trp
        35                  40                  45

Met Gly Tyr Ile Thr Tyr Ser Gly Asn Ile Ser Tyr Asn Pro Ser Leu
    50                  55                  60

Arg Ser Arg Ile Ser Ile Thr Arg Asp Thr Ser Lys Asn Gln Phe Phe
65                  70                  75                  80

Leu Gln Leu Asn Ser Val Thr Pro Glu Asp Thr Ala Thr Tyr Ser Cys
                85                  90                  95

Ala Arg Ser Leu Tyr Tyr Pro Trp Tyr Phe Asp Val Trp Gly Ala Gly
            100                 105                 110

Thr Thr Val Thr Val Ser Ser
        115

<210> SEQ ID NO 33
<211> LENGTH: 9
<212> TYPE: PRT
<213> ORGANISM: Artificial Sequence
<220> FEATURE:
<223> OTHER INFORMATION: 4M2-C12, 4M2-B4, V4H2, 4M2-D9 heavy chain CDR1

<400> SEQUENCE: 33

Gly Tyr Ser Ile Thr Ser Asp Tyr Ala
1               5

<210> SEQ ID NO 34
<211> LENGTH: 7
<212> TYPE: PRT
<213> ORGANISM: Artificial Sequence
<220> FEATURE:
<223> OTHER INFORMATION: 4M2-C12, 4M2-B4, V4H1, V4H2 heavy chain CDR2

<400> SEQUENCE: 34

Ile Thr Tyr Ser Gly Asn Ile
1               5

<210> SEQ ID NO 35
<211> LENGTH: 12
<212> TYPE: PRT
<213> ORGANISM: Artificial Sequence
<220> FEATURE:
<223> OTHER INFORMATION: 4M2-C12, 4M2-B4, V4H1, V4H2 heavy chain CDR3

<400> SEQUENCE: 35

Ala Arg Ser Leu Tyr Tyr Pro Trp Tyr Phe Asp Val
1               5                   10

<210> SEQ ID NO 36
<211> LENGTH: 25
<212> TYPE: PRT
<213> ORGANISM: Artificial Sequence
<220> FEATURE:
<223> OTHER INFORMATION: 4M2-C12 heavy chain FR1
```

<400> SEQUENCE: 36

Glu Val Lys Leu Val Glu Ser Gly Pro Gly Leu Val Lys Pro Ser Gln
1               5                   10                  15

Ser Leu Ser Leu Thr Cys Thr Val Thr
            20                  25

<210> SEQ ID NO 37
<211> LENGTH: 17
<212> TYPE: PRT
<213> ORGANISM: Artificial Sequence
<220> FEATURE:
<223> OTHER INFORMATION: 4M2-C12, 4M2-B4 heavy chain FR2

<400> SEQUENCE: 37

Trp Asn Trp Ile Arg Gln Phe Pro Gly Asn Lys Leu Glu Trp Met Gly
1               5                   10                  15

Tyr

<210> SEQ ID NO 38
<211> LENGTH: 38
<212> TYPE: PRT
<213> ORGANISM: Artificial Sequence
<220> FEATURE:
<223> OTHER INFORMATION: 4M2-C12, 4M2-B4 heavy chain FR3

<400> SEQUENCE: 38

Ser Tyr Asn Pro Ser Leu Arg Ser Arg Ile Ser Ile Thr Arg Asp Thr
1               5                   10                  15

Ser Lys Asn Gln Phe Phe Leu Gln Leu Asn Ser Val Thr Pro Glu Asp
            20                  25                  30

Thr Ala Thr Tyr Ser Cys
        35

<210> SEQ ID NO 39
<211> LENGTH: 11
<212> TYPE: PRT
<213> ORGANISM: Artificial Sequence
<220> FEATURE:
<223> OTHER INFORMATION: 4M2-C12, 4M2-B4, V4H1, V4H2, 13D5p, 13D5-1,
    13D5-13 heavy chain FR4

<400> SEQUENCE: 39

Trp Gly Ala Gly Thr Thr Val Thr Val Ser Ser
1               5                   10

<210> SEQ ID NO 40
<211> LENGTH: 107
<212> TYPE: PRT
<213> ORGANISM: Artificial Sequence
<220> FEATURE:
<223> OTHER INFORMATION: 4M2-C12 light chain variable region

<400> SEQUENCE: 40

Asp Ile Val Ile Thr Gln Thr Pro Ala Ile Leu Ser Thr Ser Pro Gly
1               5                   10                  15

Glu Lys Val Thr Met Thr Cys Arg Ala Ser Ser Ser Val Gly Tyr Ile
            20                  25                  30

His Trp Tyr Gln Gln Lys Pro Gly Ser Ser Pro Lys Pro Trp Ile Tyr
        35                  40                  45

Ala Thr Ser Asn Leu Ala Ser Gly Val Pro Ala Arg Phe Ser Gly Ser
    50                  55                  60

Gly Ser Gly Thr Ser Asn Ser Leu Thr Ile Thr Arg Val Glu Ala Glu

```
              65                  70                  75                  80
Asp Ala Ala Thr Tyr Tyr Cys Gln Gln Trp Ser Ser Tyr Pro Pro Ile
                    85                  90                  95

Thr Phe Gly Gly Gly Thr Lys Leu Glu Val Lys
            100                 105

<210> SEQ ID NO 41
<211> LENGTH: 5
<212> TYPE: PRT
<213> ORGANISM: Artificial Sequence
<220> FEATURE:
<223> OTHER INFORMATION: 4M2-C12, 4M2-B4, V4H1, V4H2 light chain CDR1

<400> SEQUENCE: 41

Ser Ser Val Gly Tyr
1               5

<210> SEQ ID NO 42
<211> LENGTH: 3
<212> TYPE: PRT
<213> ORGANISM: Artificial Sequence
<220> FEATURE:
<223> OTHER INFORMATION: 4M2-C12, 4M2-B4 light chain CDR2

<400> SEQUENCE: 42

Ala Thr Ser
1

<210> SEQ ID NO 43
<211> LENGTH: 10
<212> TYPE: PRT
<213> ORGANISM: Artificial Sequence
<220> FEATURE:
<223> OTHER INFORMATION: 4M2-C12, 4M2-B4, V4H1, V4H2 light chain CDR3

<400> SEQUENCE: 43

Gln Gln Trp Ser Ser Tyr Pro Pro Ile Thr
1               5                   10

<210> SEQ ID NO 44
<211> LENGTH: 26
<212> TYPE: PRT
<213> ORGANISM: Artificial Sequence
<220> FEATURE:
<223> OTHER INFORMATION: 4M2-C12 light chain FR1

<400> SEQUENCE: 44

Asp Ile Val Ile Thr Gln Thr Pro Ala Ile Leu Ser Thr Ser Pro Gly
1               5                   10                  15

Glu Lys Val Thr Met Thr Cys Arg Ala Ser
            20                  25

<210> SEQ ID NO 45
<211> LENGTH: 17
<212> TYPE: PRT
<213> ORGANISM: Artificial Sequence
<220> FEATURE:
<223> OTHER INFORMATION: 4M2-C12, 4M2-B4 light chain FR2

<400> SEQUENCE: 45

Ile His Trp Tyr Gln Gln Lys Pro Gly Ser Ser Pro Lys Pro Trp Ile
1               5                   10                  15

Tyr
```

-continued

```
<210> SEQ ID NO 46
<211> LENGTH: 36
<212> TYPE: PRT
<213> ORGANISM: Artificial Sequence
<220> FEATURE:
<223> OTHER INFORMATION: 4M2-C12, 4M2-B4 light chain FR3

<400> SEQUENCE: 46

Asn Leu Ala Ser Gly Val Pro Ala Arg Phe Ser Gly Ser Gly Ser Gly
1               5                   10                  15

Thr Ser Asn Ser Leu Thr Ile Thr Arg Val Glu Ala Glu Asp Ala Ala
            20                  25                  30

Thr Tyr Tyr Cys
        35

<210> SEQ ID NO 47
<211> LENGTH: 10
<212> TYPE: PRT
<213> ORGANISM: Artificial Sequence
<220> FEATURE:
<223> OTHER INFORMATION: 4M2-C12, 4M2-B4, V4H1, V4H2 light chain FR4

<400> SEQUENCE: 47

Phe Gly Gly Gly Thr Lys Leu Glu Val Lys
1               5                   10

<210> SEQ ID NO 48
<211> LENGTH: 119
<212> TYPE: PRT
<213> ORGANISM: Artificial Sequence
<220> FEATURE:
<223> OTHER INFORMATION: 4M2-B4 heavy chain variable region

<400> SEQUENCE: 48

Glu Val Met Leu Val Glu Ser Gly Pro Gly Leu Val Lys Pro Ser Gln
1               5                   10                  15

Ser Leu Ser Leu Thr Cys Thr Val Thr Gly Tyr Ser Ile Thr Ser Asp
            20                  25                  30

Tyr Ala Trp Asn Trp Ile Arg Gln Phe Pro Gly Asn Lys Leu Glu Trp
        35                  40                  45

Met Gly Tyr Ile Thr Tyr Ser Gly Asn Ile Ser Tyr Asn Pro Ser Leu
    50                  55                  60

Arg Ser Arg Ile Ser Ile Thr Arg Asp Thr Ser Lys Asn Gln Phe Phe
65                  70                  75                  80

Leu Gln Leu Asn Ser Val Thr Pro Glu Asp Thr Ala Thr Tyr Ser Cys
                85                  90                  95

Ala Arg Ser Leu Tyr Tyr Pro Trp Tyr Phe Asp Val Trp Gly Ala Gly
            100                 105                 110

Thr Thr Val Thr Val Ser Ser
        115

<210> SEQ ID NO 49
<211> LENGTH: 25
<212> TYPE: PRT
<213> ORGANISM: Artificial Sequence
<220> FEATURE:
<223> OTHER INFORMATION: 4M2-B4 heavy chain FR1

<400> SEQUENCE: 49

Glu Val Met Leu Val Glu Ser Gly Pro Gly Leu Val Lys Pro Ser Gln
1               5                   10                  15

Ser Leu Ser Leu Thr Cys Thr Val Thr
            20                  25
```

<210> SEQ ID NO 50
<211> LENGTH: 107
<212> TYPE: PRT
<213> ORGANISM: Artificial Sequence
<220> FEATURE:
<223> OTHER INFORMATION: 4M2-B4 light chain variable region

<400> SEQUENCE: 50

```
Asp Ile Val Leu Thr Gln Thr Thr Ala Ile Leu Ser Thr Ser Pro Gly
1               5                   10                  15

Glu Lys Val Thr Met Thr Cys Arg Ala Ser Ser Val Gly Tyr Ile
            20                  25                  30

His Trp Tyr Gln Gln Lys Pro Gly Ser Ser Pro Lys Pro Trp Ile Tyr
        35                  40                  45

Ala Thr Ser Asn Leu Ala Ser Gly Val Pro Ala Arg Phe Ser Gly Ser
    50                  55                  60

Gly Ser Gly Thr Ser Asn Ser Leu Thr Ile Thr Arg Val Glu Ala Glu
65                  70                  75                  80

Asp Ala Ala Thr Tyr Tyr Cys Gln Gln Trp Ser Ser Tyr Pro Pro Ile
                85                  90                  95

Thr Phe Gly Gly Gly Thr Lys Leu Glu Val Lys
            100                 105
```

<210> SEQ ID NO 51
<211> LENGTH: 25
<212> TYPE: PRT
<213> ORGANISM: Artificial Sequence
<220> FEATURE:
<223> OTHER INFORMATION: 4M2-B4 light chain FR1

<400> SEQUENCE: 51

```
Asp Ile Val Leu Thr Gln Thr Thr Ala Ile Leu Ser Thr Ser Pro Gly
1               5                   10                  15

Glu Lys Val Thr Met Thr Cys Arg Ala
            20                  25
```

<210> SEQ ID NO 52
<211> LENGTH: 119
<212> TYPE: PRT
<213> ORGANISM: Artificial Sequence
<220> FEATURE:
<223> OTHER INFORMATION: V4H1 heavy chain variable region

<400> SEQUENCE: 52

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Tyr Thr Ile Thr Ser Asp
            20                  25                  30

Tyr Ala Met Ser Trp Val Arg Gln Ala Pro Gly Lys Gly Leu Glu Trp
        35                  40                  45

Val Ser Val Ile Thr Tyr Ser Gly Asn Ile Ser Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Tyr Tyr Pro Trp Tyr Phe Asp Val Trp Gly Ala Gly
            100                 105                 110
```

-continued

Thr Thr Val Thr Val Ser Ser
        115

<210> SEQ ID NO 53
<211> LENGTH: 9
<212> TYPE: PRT
<213> ORGANISM: Artificial Sequence
<220> FEATURE:
<223> OTHER INFORMATION: V4H1 heavy chain CDR1

<400> SEQUENCE: 53

Gly Tyr Thr Ile Thr Ser Asp Tyr Ala
1               5

<210> SEQ ID NO 54
<211> LENGTH: 25
<212> TYPE: PRT
<213> ORGANISM: Artificial Sequence
<220> FEATURE:
<223> OTHER INFORMATION: V4H1 heavy chain FR1

<400> SEQUENCE: 54

Glu Val Gln Leu Leu Glu Ser Gly Gly Gly Leu Val Gln Pro Gly Gly
1               5                   10                  15

Ser Leu Arg Leu Ser Cys Ala Ala Ser
            20                  25

<210> SEQ ID NO 55
<211> LENGTH: 17
<212> TYPE: PRT
<213> ORGANISM: Artificial Sequence
<220> FEATURE:
<223> OTHER INFORMATION: V4H1 heavy chain FR2

<400> SEQUENCE: 55

Met Ser Trp Val Arg Gln Ala Pro Gly Lys Gly Leu Glu Trp Val Ser
1               5                   10                  15

Val

<210> SEQ ID NO 56
<211> LENGTH: 38
<212> TYPE: PRT
<213> ORGANISM: Artificial Sequence
<220> FEATURE:
<223> OTHER INFORMATION: V4H1 heavy chain FR3

<400> SEQUENCE: 56

Ser Tyr Ala Asp Ser Val Lys Gly Arg Phe Thr Ile Ser Arg Asp Asn
1               5                   10                  15

Ser Lys Asn Thr Leu Tyr Leu Gln Met Asn Ser Leu Arg Ala Glu Asp
            20                  25                  30

Thr Ala Val Tyr Tyr Cys
        35

<210> SEQ ID NO 57
<211> LENGTH: 107
<212> TYPE: PRT
<213> ORGANISM: Artificial Sequence
<220> FEATURE:
<223> OTHER INFORMATION: V4H1 light chain variable region

<400> SEQUENCE: 57

Glu Ile Val Ile Thr Gln Ser Pro Ala Thr Leu Ser Leu Ser Pro Gly
1               5                   10                  15

```
Glu Arg Ala Thr Leu Ser Cys Arg Ala Ser Ser Val Gly Tyr Leu
         20                  25                  30

Ala Trp Tyr Gln Gln Lys Pro Gly Gln Ala Pro Arg Pro Leu Ile Tyr
         35                  40                  45

Asp Thr Ser Asn Arg Ala Thr Gly Ile Pro Ala Arg Phe Ser Gly Ser
     50                  55                  60

Gly Ser Gly Thr Asp Asn Thr Leu Thr Ile Ser Ser Leu Glu Pro Glu
65                  70                  75                  80

Asp Phe Ala Val Tyr Tyr Cys Gln Gln Trp Ser Ser Tyr Pro Pro Ile
                 85                  90                  95

Thr Phe Gly Gly Gly Thr Lys Leu Glu Val Lys
            100                 105
```

```
<210> SEQ ID NO 58
<211> LENGTH: 3
<212> TYPE: PRT
<213> ORGANISM: Artificial Sequence
<220> FEATURE:
<223> OTHER INFORMATION: V4H1 light chain CDR2

<400> SEQUENCE: 58

Asp Thr Ser
1
```

```
<210> SEQ ID NO 59
<211> LENGTH: 25
<212> TYPE: PRT
<213> ORGANISM: Artificial Sequence
<220> FEATURE:
<223> OTHER INFORMATION: V4H1 light chain FR1

<400> SEQUENCE: 59

Glu Ile Val Ile Thr Gln Ser Pro Ala Thr Leu Ser Leu Ser Pro Gly
1               5                   10                  15

Glu Arg Ala Thr Leu Ser Cys Arg Ala
            20                  25
```

```
<210> SEQ ID NO 60
<211> LENGTH: 17
<212> TYPE: PRT
<213> ORGANISM: Artificial Sequence
<220> FEATURE:
<223> OTHER INFORMATION: V4H1 light chain FR2

<400> SEQUENCE: 60

Leu Ala Trp Tyr Gln Gln Lys Pro Gly Gln Ala Pro Arg Pro Leu Ile
1               5                   10                  15

Tyr
```

```
<210> SEQ ID NO 61
<211> LENGTH: 36
<212> TYPE: PRT
<213> ORGANISM: Artificial Sequence
<220> FEATURE:
<223> OTHER INFORMATION: V4H1 light chain FR3

<400> SEQUENCE: 61

Asn Arg Ala Thr Gly Ile Pro Ala Arg Phe Ser Gly Ser Gly Ser Gly
1               5                   10                  15

Thr Asp Asn Thr Leu Thr Ile Ser Ser Leu Glu Pro Glu Asp Phe Ala
            20                  25                  30
```

```
Val Tyr Tyr Cys
        35
```

<210> SEQ ID NO 62
<211> LENGTH: 119
<212> TYPE: PRT
<213> ORGANISM: Artificial Sequence
<220> FEATURE:
<223> OTHER INFORMATION: V4H2 heavy chain variable region

<400> SEQUENCE: 62

```
Gln Val Gln Leu Gln Glu Ser Gly Pro Gly Leu Val Lys Pro Ser Asp
1               5                   10                  15

Thr Leu Ser Leu Thr Cys Thr Val Ser Gly Tyr Ser Ile Thr Ser Asp
            20                  25                  30

Tyr Ala Trp Ser Trp Ile Arg Gln Pro Pro Gly Lys Gly Leu Glu Trp
        35                  40                  45

Ile Gly Tyr Ile Thr Tyr Ser Gly Asn Ile Ser Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Asp Cys
                85                  90                  95

Ala Arg Ser Leu Tyr Tyr Pro Trp Tyr Phe Asp Val Trp Gly Ala Gly
            100                 105                 110

Thr Thr Val Thr Val Ser Ser
        115
```

<210> SEQ ID NO 63
<211> LENGTH: 25
<212> TYPE: PRT
<213> ORGANISM: Artificial Sequence
<220> FEATURE:
<223> OTHER INFORMATION: V4H2 heavy chain FR1

<400> SEQUENCE: 63

```
Gln Val Gln Leu Gln Glu Ser Gly Pro Gly Leu Val Lys Pro Ser Asp
1               5                   10                  15

Thr Leu Ser Leu Thr Cys Thr Val Ser
            20                  25
```

<210> SEQ ID NO 64
<211> LENGTH: 17
<212> TYPE: PRT
<213> ORGANISM: Artificial Sequence
<220> FEATURE:
<223> OTHER INFORMATION: V4H2 heavy chain FR2

<400> SEQUENCE: 64

```
Trp Ser Trp Ile Arg Gln Pro Pro Gly Lys Gly Leu Glu Trp Ile Gly
1               5                   10                  15

Tyr
```

<210> SEQ ID NO 65
<211> LENGTH: 38
<212> TYPE: PRT
<213> ORGANISM: Artificial Sequence
<220> FEATURE:
<223> OTHER INFORMATION: V4H2 heavy chain FR3

<400> SEQUENCE: 65

```
Ser Tyr Asn Pro Ser Leu Lys Ser Arg Val Thr Ile Ser Val Asp Thr
```

```
                1               5                  10                 15
Ser Lys Asn Gln Phe Ser Leu Lys Leu Ser Ser Val Thr Ala Ala Asp
                20                 25                 30

Thr Ala Val Tyr Asp Cys
            35

<210> SEQ ID NO 66
<211> LENGTH: 107
<212> TYPE: PRT
<213> ORGANISM: Artificial Sequence
<220> FEATURE:
<223> OTHER INFORMATION: V4H2 light chain variable region

<400> SEQUENCE: 66

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Ser Val Gly Tyr Leu
                20                  25                  30

Asn Trp Tyr Gln Gln Lys Pro Gly Lys Ala Pro Lys Pro Leu Ile Tyr
            35                  40                  45

Ala Ala Ser Ser Leu Gln Ser Gly Val Pro Ser Arg Phe Ser Gly Ser
        50                  55                  60

Gly Ser Gly Thr Asp Asn Thr Leu Thr Ile Ser Ser Leu Gln Pro Glu
65                  70                  75                  80

Asp Phe Ala Thr Tyr Tyr Cys Gln Gln Trp Ser Ser Tyr Pro Pro Ile
                85                  90                  95

Thr Phe Gly Gly Gly Thr Lys Leu Glu Val Lys
            100                 105

<210> SEQ ID NO 67
<211> LENGTH: 3
<212> TYPE: PRT
<213> ORGANISM: Artificial Sequence
<220> FEATURE:
<223> OTHER INFORMATION: V4H2, 4M2-D9 light chain CDR2

<400> SEQUENCE: 67

Ala Ala Ser
1

<210> SEQ ID NO 68
<211> LENGTH: 25
<212> TYPE: PRT
<213> ORGANISM: Artificial Sequence
<220> FEATURE:
<223> OTHER INFORMATION: V4H2 light chain FR1

<400> SEQUENCE: 68

Asp Ile Gln Met Thr Gln Ser Pro Ser Ser Leu Ser Ala Ser Val Gly
1               5                   10                  15

Asp Arg Val Thr Ile Thr Cys Arg Ala
                20                  25

<210> SEQ ID NO 69
<211> LENGTH: 17
<212> TYPE: PRT
<213> ORGANISM: Artificial Sequence
<220> FEATURE:
<223> OTHER INFORMATION: V4H2 light chain FR2

<400> SEQUENCE: 69

Leu Asn Trp Tyr Gln Gln Lys Pro Gly Lys Ala Pro Lys Pro Leu Ile
```

```
1               5                   10                  15
Tyr

<210> SEQ ID NO 70
<211> LENGTH: 36
<212> TYPE: PRT
<213> ORGANISM: Artificial Sequence
<220> FEATURE:
<223> OTHER INFORMATION: V4H2 light chain FR3

<400> SEQUENCE: 70

Ser Leu Gln Ser Gly Val Pro Ser Arg Phe Ser Gly Ser Gly Ser Gly
1               5                   10                  15

Thr Asp Asn Thr Leu Thr Ile Ser Ser Leu Gln Pro Glu Asp Phe Ala
            20                  25                  30

Thr Tyr Tyr Cys
            35

<210> SEQ ID NO 71
<211> LENGTH: 121
<212> TYPE: PRT
<213> ORGANISM: Artificial Sequence
<220> FEATURE:
<223> OTHER INFORMATION: 2M1-B12 heavy chain variable region

<400> SEQUENCE: 71

Glu Val Gln Leu Gln Gln Ser Gly Ala Glu Leu Val Arg Pro Gly Thr
1               5                   10                  15

Ser Val Lys Thr Ser Cys Lys Ala Ser Gly Tyr Thr Phe Thr Asn Tyr
            20                  25                  30

Trp Leu Gly Trp Val Lys Glu Arg Ala Gly His Gly Leu Glu Trp Ile
        35                  40                  45

Gly Glu Ile Phe Pro Gly Gly His Thr Asn Tyr Lys Glu Lys Phe
    50                  55                  60

Lys Gly Lys Ala Thr Leu Thr Ala Asp Thr Ser Ser Thr Ala Tyr
65                  70                  75                  80

Met Lys Leu Ser Ser Leu Thr Ser Glu Asp Ser Ala Val Tyr Phe Cys
            85                  90                  95

Ala Gln Ile Pro Leu Tyr Tyr Gly His Tyr Arg Ser Ala Tyr Trp Gly
            100                 105                 110

Gln Gly Thr Leu Val Thr Val Ser Ala
        115                 120

<210> SEQ ID NO 72
<211> LENGTH: 8
<212> TYPE: PRT
<213> ORGANISM: Artificial Sequence
<220> FEATURE:
<223> OTHER INFORMATION: 2M1-B12, 2M1-D2, 13D5p, 13D5-1, 13D5-13 heavy
      chain CDR1

<400> SEQUENCE: 72

Gly Tyr Thr Phe Thr Asn Tyr Trp
1               5

<210> SEQ ID NO 73
<211> LENGTH: 8
<212> TYPE: PRT
<213> ORGANISM: Artificial Sequence
<220> FEATURE:
<223> OTHER INFORMATION: 2M1-B12, 2M1-D2 heavy chain CDR2
```

```
<400> SEQUENCE: 73

Ile Phe Pro Gly Gly His Thr
1               5

<210> SEQ ID NO 74
<211> LENGTH: 14
<212> TYPE: PRT
<213> ORGANISM: Artificial Sequence
<220> FEATURE:
<223> OTHER INFORMATION: 2M1-B12, 2M1-D2 heavy chain CDR3

<400> SEQUENCE: 74

Ala Gln Ile Pro Leu Tyr Tyr Gly His Tyr Arg Ser Ala Tyr
1               5                   10

<210> SEQ ID NO 75
<211> LENGTH: 25
<212> TYPE: PRT
<213> ORGANISM: Artificial Sequence
<220> FEATURE:
<223> OTHER INFORMATION: 2M1-B12 heavy chain FR1

<400> SEQUENCE: 75

Glu Val Gln Leu Gln Gln Ser Gly Ala Glu Leu Val Arg Pro Gly Thr
1               5                   10                  15

Ser Val Lys Thr Ser Cys Lys Ala Ser
            20                  25

<210> SEQ ID NO 76
<211> LENGTH: 17
<212> TYPE: PRT
<213> ORGANISM: Artificial Sequence
<220> FEATURE:
<223> OTHER INFORMATION: 2M1-B12, 2M1-D2 heavy chain FR2

<400> SEQUENCE: 76

Leu Gly Trp Val Lys Glu Arg Ala Gly His Gly Leu Glu Trp Ile Gly
1               5                   10                  15

Glu

<210> SEQ ID NO 77
<211> LENGTH: 38
<212> TYPE: PRT
<213> ORGANISM: Artificial Sequence
<220> FEATURE:
<223> OTHER INFORMATION: 2M1-B12, 2M1-D2 heavy chain FR3

<400> SEQUENCE: 77

Asn Tyr Lys Glu Lys Phe Lys Gly Lys Ala Thr Leu Thr Ala Asp Thr
1               5                   10                  15

Ser Ser Ser Thr Ala Tyr Met Lys Leu Ser Ser Leu Thr Ser Glu Asp
            20                  25                  30

Ser Ala Val Tyr Phe Cys
                35

<210> SEQ ID NO 78
<211> LENGTH: 11
<212> TYPE: PRT
<213> ORGANISM: Artificial Sequence
<220> FEATURE:
<223> OTHER INFORMATION: 2M1-B12, 2M1-D2, 1M2-D2 heavy chain FR4

<400> SEQUENCE: 78

Trp Gly Gln Gly Thr Leu Val Thr Val Ser Ala
```

<210> SEQ ID NO 79
<211> LENGTH: 107
<212> TYPE: PRT
<213> ORGANISM: Artificial Sequence
<220> FEATURE:
<223> OTHER INFORMATION: 2M1-B12 light chain variable region

<400> SEQUENCE: 79

```
Asp Ile Gln Met Met Gln Ser Pro Ala Ser Leu Ser Ala Ser Val Gly
 1               5                  10                  15
Glu Thr Val Ala Ile Thr Cys Gly Ala Ser Glu Asn Ile Tyr Gly Ala
             20                  25                  30
Leu Asn Trp Tyr Gln Arg Lys Gln Gly Lys Ser Pro Gln Leu Leu Ile
         35                  40                  45
Tyr Gly Ala Thr Asn Leu Ala Asp Gly Met Ser Ser Arg Phe Ser Gly
     50                  55                  60
Ser Gly Ser Gly Arg Gln Tyr Ser Leu Lys Ile Ser Ser Leu His Pro
 65                  70                  75                  80
Asp Asp Val Ala Thr Tyr Tyr Cys Gln Asn Val Leu Ser Thr Pro Tyr
                 85                  90                  95
Thr Phe Gly Gly Gly Thr Lys Leu Glu Ile Lys
            100                 105
```

<210> SEQ ID NO 80
<211> LENGTH: 6
<212> TYPE: PRT
<213> ORGANISM: Artificial Sequence
<220> FEATURE:
<223> OTHER INFORMATION: 2M1-B12, 2M1-D2 light chain CDR1

<400> SEQUENCE: 80

```
Glu Asn Ile Tyr Gly Ala
 1               5
```

<210> SEQ ID NO 81
<211> LENGTH: 3
<212> TYPE: PRT
<213> ORGANISM: Artificial Sequence
<220> FEATURE:
<223> OTHER INFORMATION: 2M1-B12, 2M1-D2 light chain CDR2

<400> SEQUENCE: 81

```
Gly Ala Thr
 1
```

<210> SEQ ID NO 82
<211> LENGTH: 9
<212> TYPE: PRT
<213> ORGANISM: Artificial Sequence
<220> FEATURE:
<223> OTHER INFORMATION: 2M1-B12, 2M1-D2 light chain CDR3

<400> SEQUENCE: 82

```
Gln Asn Val Leu Ser Thr Pro Tyr Thr
 1               5
```

<210> SEQ ID NO 83
<211> LENGTH: 26
<212> TYPE: PRT
<213> ORGANISM: Artificial Sequence
<220> FEATURE:
<223> OTHER INFORMATION: 2M1-B12 light chain FR1

```
<400> SEQUENCE: 83

Asp Ile Gln Met Met Gln Ser Pro Ala Ser Leu Ser Ala Ser Val Gly
1               5                   10                  15

Glu Thr Val Ala Ile Thr Cys Gly Ala Ser
            20                  25

<210> SEQ ID NO 84
<211> LENGTH: 17
<212> TYPE: PRT
<213> ORGANISM: Artificial Sequence
<220> FEATURE:
<223> OTHER INFORMATION: 2M1-B12, 2M1-D2 light chain FR2

<400> SEQUENCE: 84

Leu Asn Trp Tyr Gln Arg Lys Gln Gly Lys Ser Pro Gln Leu Leu Ile
1               5                   10                  15

Tyr

<210> SEQ ID NO 85
<211> LENGTH: 36
<212> TYPE: PRT
<213> ORGANISM: Artificial Sequence
<220> FEATURE:
<223> OTHER INFORMATION: 2M1-B12, 2M1-D2 light chain FR3

<400> SEQUENCE: 85

Asn Leu Ala Asp Gly Met Ser Ser Arg Phe Ser Gly Ser Gly Ser Gly
1               5                   10                  15

Arg Gln Tyr Ser Leu Lys Ile Ser Ser Leu His Pro Asp Asp Val Ala
            20                  25                  30

Thr Tyr Tyr Cys
        35

<210> SEQ ID NO 86
<211> LENGTH: 10
<212> TYPE: PRT
<213> ORGANISM: Artificial Sequence
<220> FEATURE:
<223> OTHER INFORMATION: 2M1-B12, 4M2-C9, 2M1-D2, 4M2-D9, 1M2-D2,
      5M1-A11, 4M2-D5, 4M2-A8, 9M2-C12, 13D5p, 13D5-1, 13d5-13 light
      chain FR4

<400> SEQUENCE: 86

Phe Gly Gly Gly Thr Lys Leu Glu Ile Lys
1               5                   10

<210> SEQ ID NO 87
<211> LENGTH: 123
<212> TYPE: PRT
<213> ORGANISM: Artificial Sequence
<220> FEATURE:
<223> OTHER INFORMATION: 4M2-C9 heavy chain variable region

<400> SEQUENCE: 87

Gln Val Thr Leu Lys Glu Cys Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Gly Met Gly Val Ser Trp Ile Arg Gln Pro Ser Gly Lys Gly Leu Glu
        35                  40                  45

Trp Leu Ala His Ile Tyr Trp Asp Asp Lys Arg Tyr Asn Pro Ser
    50                  55                  60
```

```
Leu Lys Ser Arg Leu Thr Ile Ser Lys Asp Ser Ser Asn Gln Val
 65                  70                  75                  80

Phe Leu Lys Ile Thr Ser Val Asp Thr Ala Asp Thr Ala Thr Tyr Tyr
                 85                  90                  95

Cys Ala Arg Arg Leu Asp Gly Tyr Asn Asp Pro Tyr Tyr Phe Asp Tyr
            100                 105                 110

Trp Gly Gln Gly Thr Thr Leu Thr Val Ser Ser
        115                 120
```

<210> SEQ ID NO 88
<211> LENGTH: 10
<212> TYPE: PRT
<213> ORGANISM: Artificial Sequence
<220> FEATURE:
<223> OTHER INFORMATION: 4M2-C9, 5M1-A11 heavy chain CDR1

<400> SEQUENCE: 88

```
Gly Phe Ser Leu Ser Thr Ser Gly Met Gly
 1               5                   10
```

<210> SEQ ID NO 89
<211> LENGTH: 7
<212> TYPE: PRT
<213> ORGANISM: Artificial Sequence
<220> FEATURE:
<223> OTHER INFORMATION: 4M2-C9, 5M1-A11 heavy chain CDR2

<400> SEQUENCE: 89

```
Ile Tyr Trp Asp Asp Asp Lys
 1               5
```

<210> SEQ ID NO 90
<211> LENGTH: 15
<212> TYPE: PRT
<213> ORGANISM: Artificial Sequence
<220> FEATURE:
<223> OTHER INFORMATION: 4M2-C9, 5M1-A11 heavy chain CDR3

<400> SEQUENCE: 90

```
Ala Arg Arg Leu Asp Gly Tyr Asn Asp Pro Tyr Tyr Phe Asp Tyr
 1               5                   10                  15
```

<210> SEQ ID NO 91
<211> LENGTH: 25
<212> TYPE: PRT
<213> ORGANISM: Artificial Sequence
<220> FEATURE:
<223> OTHER INFORMATION: 4M2-C9 heavy chain FR1

<400> SEQUENCE: 91

```
Gln Val Thr Leu Lys Glu Cys Gly Pro Gly Ile Leu Gln Pro Ser Gln
 1               5                   10                  15

Thr Leu Ser Leu Thr Cys Ser Phe Ser
                20                  25
```

<210> SEQ ID NO 92
<211> LENGTH: 17
<212> TYPE: PRT
<213> ORGANISM: Artificial Sequence
<220> FEATURE:
<223> OTHER INFORMATION: 4M2-C9, 5M1-A11 heavy chain FR2

<400> SEQUENCE: 92

```
Val Ser Trp Ile Arg Gln Pro Ser Gly Lys Gly Leu Glu Trp Leu Ala
 1               5                   10                  15
```

His

<210> SEQ ID NO 93
<211> LENGTH: 38
<212> TYPE: PRT
<213> ORGANISM: Artificial Sequence
<220> FEATURE:
<223> OTHER INFORMATION: 4M2-C9, 5M1-A11 heavy chain FR3

<400> SEQUENCE: 93

Arg Tyr Asn Pro Ser Leu Lys Ser Arg Leu Thr Ile Ser Lys Asp Ser
1               5                   10                  15

Ser Ser Asn Gln Val Phe Leu Lys Ile Thr Ser Val Asp Thr Ala Asp
            20                  25                  30

Thr Ala Thr Tyr Tyr Cys
        35

<210> SEQ ID NO 94
<211> LENGTH: 11
<212> TYPE: PRT
<213> ORGANISM: Artificial Sequence
<220> FEATURE:
<223> OTHER INFORMATION: 4M2-C9 heavy chain FR4

<400> SEQUENCE: 94

Trp Gly Gln Gly Thr Thr Leu Thr Val Ser Ser
1               5                   10

<210> SEQ ID NO 95
<211> LENGTH: 107
<212> TYPE: PRT
<213> ORGANISM: Artificial Sequence
<220> FEATURE:
<223> OTHER INFORMATION: 4M2-C9 light chain variable region

<400> SEQUENCE: 95

Asp Ile Val Met Thr Gln Ser Pro Ser Ser Leu Ser Ala Ser Leu Gly
1               5                   10                  15

Asp Thr Val Thr Ile Thr Cys His Ala Ser Gln Asn Val Asn Val Trp
            20                  25                  30

Leu Ser Trp Tyr Gln Gln Lys Pro Gly Asn Ile Pro Lys Leu Leu Ile
        35                  40                  45

Tyr Lys Ala Ser Asn Leu His Ala Gly Val Pro Ser Arg Phe Ser Gly
    50                  55                  60

Ser Gly Ser Gly Thr Gly Phe Thr Leu Thr Ile Ser Ser Leu Gln Pro
65                  70                  75                  80

Glu Asp Ile Ala Thr Tyr Tyr Cys Gln Gln Gly Gln Ser Tyr Pro Leu
                85                  90                  95

Thr Phe Gly Gly Gly Thr Lys Leu Glu Ile Lys
            100                 105

<210> SEQ ID NO 96
<211> LENGTH: 6
<212> TYPE: PRT
<213> ORGANISM: Artificial Sequence
<220> FEATURE:
<223> OTHER INFORMATION: 4M2-C9 light chain CDR1

<400> SEQUENCE: 96

Gln Asn Val Asn Val Trp
1               5

<210> SEQ ID NO 97
<211> LENGTH: 3
<212> TYPE: PRT
<213> ORGANISM: Artificial Sequence
<220> FEATURE:
<223> OTHER INFORMATION: 4M2-C9 light chain CDR2

<400> SEQUENCE: 97

Lys Ala Ser
1

<210> SEQ ID NO 98
<211> LENGTH: 9
<212> TYPE: PRT
<213> ORGANISM: Artificial Sequence
<220> FEATURE:
<223> OTHER INFORMATION: 4M2-C9 light chain CDR3

<400> SEQUENCE: 98

Gln Gln Gly Gln Ser Tyr Pro Leu Thr
1               5

<210> SEQ ID NO 99
<211> LENGTH: 26
<212> TYPE: PRT
<213> ORGANISM: Artificial Sequence
<220> FEATURE:
<223> OTHER INFORMATION: 4M2-C9 light chain FR1

<400> SEQUENCE: 99

Asp Ile Val Met Thr Gln Ser Pro Ser Ser Leu Ser Ala Ser Leu Gly
1               5                   10                  15

Asp Thr Val Thr Ile Thr Cys His Ala Ser
            20                  25

<210> SEQ ID NO 100
<211> LENGTH: 17
<212> TYPE: PRT
<213> ORGANISM: Artificial Sequence
<220> FEATURE:
<223> OTHER INFORMATION: 4M2-C9 light chain FR2

<400> SEQUENCE: 100

Leu Ser Trp Tyr Gln Gln Lys Pro Gly Asn Ile Pro Lys Leu Leu Ile
1               5                   10                  15

Tyr

<210> SEQ ID NO 101
<211> LENGTH: 36
<212> TYPE: PRT
<213> ORGANISM: Artificial Sequence
<220> FEATURE:
<223> OTHER INFORMATION: 4M2-C9 light chain FR3

<400> SEQUENCE: 101

Asn Leu His Ala Gly Val Pro Ser Arg Phe Ser Gly Ser Gly Ser Gly
1               5                   10                  15

Thr Gly Phe Thr Leu Thr Ile Ser Ser Leu Gln Pro Glu Asp Ile Ala
            20                  25                  30

Thr Tyr Tyr Cys
            35

<210> SEQ ID NO 102

<211> LENGTH: 121
<212> TYPE: PRT
<213> ORGANISM: Artificial Sequence
<220> FEATURE:
<223> OTHER INFORMATION: 2M1-D2 heavy chain variable region

<400> SEQUENCE: 102

```
Gln Val Gln Leu Gln Gln Ser Gly Ala Glu Leu Val Arg Pro Gly Thr
  1               5                  10                  15
Ser Val Lys Ile Ser Cys Lys Ala Ser Gly Tyr Thr Phe Thr Asn Tyr
             20                  25                  30
Trp Leu Gly Trp Val Lys Glu Arg Ala Gly His Gly Leu Glu Trp Ile
         35                  40                  45
Gly Glu Ile Phe Pro Gly Gly His Thr Asn Tyr Lys Glu Lys Phe
     50                  55                  60
Lys Gly Lys Ala Thr Leu Thr Ala Asp Thr Ser Ser Thr Ala Tyr
 65                  70                  75                  80
Met Lys Leu Ser Ser Leu Thr Ser Glu Asp Ser Ala Val Tyr Phe Cys
                 85                  90                  95
Ala Gln Ile Pro Leu Tyr Tyr Gly His Tyr Arg Ser Ala Tyr Trp Gly
            100                 105                 110
Gln Gly Thr Leu Val Thr Val Ser Ala
            115                 120
```

<210> SEQ ID NO 103
<211> LENGTH: 25
<212> TYPE: PRT
<213> ORGANISM: Artificial Sequence
<220> FEATURE:
<223> OTHER INFORMATION: 2M1-D2, 13D5p, 13D5-1, 13D5-13 heavy chain FR1

<400> SEQUENCE: 103

```
Gln Val Gln Leu Gln Gln Ser Gly Ala Glu Leu Val Arg Pro Gly Thr
  1               5                  10                  15
Ser Val Lys Ile Ser Cys Lys Ala Ser
             20                  25
```

<210> SEQ ID NO 104
<211> LENGTH: 107
<212> TYPE: PRT
<213> ORGANISM: Artificial Sequence
<220> FEATURE:
<223> OTHER INFORMATION: 2M1-D2 light chain variable region

<400> SEQUENCE: 104

```
Asp Ile Val Met Thr Gln Ser Pro Ala Ser Leu Ser Ala Ser Val Gly
  1               5                  10                  15
Glu Thr Val Ala Ile Thr Cys Gly Ala Ser Glu Asn Ile Tyr Gly Ala
             20                  25                  30
Leu Asn Trp Tyr Gln Arg Lys Gln Gly Lys Ser Pro Gln Leu Leu Ile
         35                  40                  45
Tyr Gly Ala Thr Asn Leu Ala Asp Gly Met Ser Ser Arg Phe Ser Gly
     50                  55                  60
Ser Gly Ser Gly Arg Gln Tyr Ser Leu Lys Ile Ser Ser Leu His Pro
 65                  70                  75                  80
Asp Asp Val Ala Thr Tyr Tyr Cys Gln Asn Val Leu Ser Thr Pro Tyr
                 85                  90                  95
Thr Phe Gly Gly Gly Thr Lys Leu Glu Ile Lys
            100                 105
```

<210> SEQ ID NO 105
<211> LENGTH: 26
<212> TYPE: PRT
<213> ORGANISM: Artificial Sequence
<220> FEATURE:
<223> OTHER INFORMATION: 2M1-D2 light chain FR1

<400> SEQUENCE: 105

Asp Ile Val Met Thr Gln Ser Pro Ala Ser Leu Ser Ala Ser Val Gly
1               5                   10                  15

Glu Thr Val Ala Ile Thr Cys Gly Ala Ser
            20                  25

<210> SEQ ID NO 106
<211> LENGTH: 121
<212> TYPE: PRT
<213> ORGANISM: Artificial Sequence
<220> FEATURE:
<223> OTHER INFORMATION: 4M2-D9 heavy chain variable region

<400> SEQUENCE: 106

Glu Val Gln Leu Gln Glu Ser Gly Pro Gly Leu Val Lys Pro Ser Gln
1               5                   10                  15

Ser Leu Ser Leu Thr Cys Thr Val Thr Gly Tyr Ser Ile Thr Ser Asp
            20                  25                  30

Tyr Ala Trp Asn Trp Ile Arg Gln Phe Pro Gly Asn Arg Leu Glu Trp
        35                  40                  45

Met Gly Phe Ile Ser Tyr Ser Gly Phe Thr Thr Tyr Ser Pro Ser Leu
    50                  55                  60

Glu Ser Arg Ile Ser Ile Thr Arg Asp Thr Ser Lys Asn Gln Phe Phe
65                  70                  75                  80

Leu Gln Leu Ile Ser Val Thr Thr Glu Asp Thr Ala Thr Tyr Tyr Cys
                85                  90                  95

Ala Arg Asn His Tyr Gly Gly Ser Tyr Trp Tyr Phe Asp Val Trp Gly
            100                 105                 110

Ala Gly Thr Ser Val Thr Val Ser Ser
        115                 120

<210> SEQ ID NO 107
<211> LENGTH: 7
<212> TYPE: PRT
<213> ORGANISM: Artificial Sequence
<220> FEATURE:
<223> OTHER INFORMATION: 4M2-D9 heavy chain CDR2

<400> SEQUENCE: 107

Ile Ser Tyr Ser Gly Phe Thr
1               5

<210> SEQ ID NO 108
<211> LENGTH: 14
<212> TYPE: PRT
<213> ORGANISM: Artificial Sequence
<220> FEATURE:
<223> OTHER INFORMATION: 4M2-D9 heavy chain CDR3

<400> SEQUENCE: 108

Ala Arg Asn His Tyr Gly Gly Ser Tyr Trp Tyr Phe Asp Val
1               5                   10

<210> SEQ ID NO 109
<211> LENGTH: 25

```
<212> TYPE: PRT
<213> ORGANISM: Artificial Sequence
<220> FEATURE:
<223> OTHER INFORMATION: 4M2-D9 heavy chain FR1

<400> SEQUENCE: 109

Glu Val Gln Leu Gln Glu Ser Gly Pro Gly Leu Val Lys Pro Ser Gln
1               5                   10                  15

Ser Leu Ser Leu Thr Cys Thr Val Thr
            20                  25

<210> SEQ ID NO 110
<211> LENGTH: 17
<212> TYPE: PRT
<213> ORGANISM: Artificial Sequence
<220> FEATURE:
<223> OTHER INFORMATION: 4M2-D9 heavy chain FR2

<400> SEQUENCE: 110

Trp Asn Trp Ile Arg Gln Phe Pro Gly Asn Arg Leu Glu Trp Met Gly
1               5                   10                  15

Phe

<210> SEQ ID NO 111
<211> LENGTH: 38
<212> TYPE: PRT
<213> ORGANISM: Artificial Sequence
<220> FEATURE:
<223> OTHER INFORMATION: 4M2-D9 heavy chain FR3

<400> SEQUENCE: 111

Thr Tyr Ser Pro Ser Leu Glu Ser Arg Ile Ser Ile Thr Arg Asp Thr
1               5                   10                  15

Ser Lys Asn Gln Phe Phe Leu Gln Leu Ile Ser Val Thr Thr Glu Asp
            20                  25                  30

Thr Ala Thr Tyr Tyr Cys
        35

<210> SEQ ID NO 112
<211> LENGTH: 11
<212> TYPE: PRT
<213> ORGANISM: Artificial Sequence
<220> FEATURE:
<223> OTHER INFORMATION: 4M2-D9 heavy chain FR4

<400> SEQUENCE: 112

Trp Gly Ala Gly Thr Ser Val Thr Val Ser Ser
1               5                   10

<210> SEQ ID NO 113
<211> LENGTH: 111
<212> TYPE: PRT
<213> ORGANISM: Artificial Sequence
<220> FEATURE:
<223> OTHER INFORMATION: 4M2-D9 light chain variable region

<400> SEQUENCE: 113

Asp Ile Val Met Thr Gln Ser Pro Gly Ser Leu Ala Val Ser Leu Gly
1               5                   10                  15

Gln Arg Ala Thr Ile Ser Cys Arg Ala Ser Glu Ser Val Glu Tyr Tyr
            20                  25                  30

Gly Thr Ser Leu Met Gln Trp Tyr Leu Gln Lys Pro Gly Gln Pro Pro
        35                  40                  45
```

```
Lys Leu Leu Ile Tyr Ala Ala Ser Asn Val Glu Ser Gly Val Pro Asp
         50                  55                  60

Arg Phe Arg Gly Ser Gly Ser Gly Thr Asp Phe Ser Leu Asn Ile His
 65                  70                  75                  80

Pro Val Glu Glu Asp Asp Ile Ala Met Tyr Phe Cys Gln Gln Ser Arg
                 85                  90                  95

Lys Val Pro Trp Thr Phe Gly Gly Gly Thr Lys Leu Glu Ile Lys
                100                 105                 110
```

<210> SEQ ID NO 114
<211> LENGTH: 10
<212> TYPE: PRT
<213> ORGANISM: Artificial Sequence
<220> FEATURE:
<223> OTHER INFORMATION: 4M2-D9 light chain CDR1

<400> SEQUENCE: 114

```
Glu Ser Val Glu Tyr Tyr Gly Thr Ser Leu
 1               5                  10
```

<210> SEQ ID NO 115
<211> LENGTH: 9
<212> TYPE: PRT
<213> ORGANISM: Artificial Sequence
<220> FEATURE:
<223> OTHER INFORMATION: 4M2-D9 light chain CDR3

<400> SEQUENCE: 115

```
Gln Gln Ser Arg Lys Val Pro Trp Thr
 1               5
```

<210> SEQ ID NO 116
<211> LENGTH: 26
<212> TYPE: PRT
<213> ORGANISM: Artificial Sequence
<220> FEATURE:
<223> OTHER INFORMATION: 4M2-D9 light chain FR1

<400> SEQUENCE: 116

```
Asp Ile Val Met Thr Gln Ser Pro Gly Ser Leu Ala Val Ser Leu Gly
 1               5                  10                  15

Gln Arg Ala Thr Ile Ser Cys Arg Ala Ser
                20                  25
```

<210> SEQ ID NO 117
<211> LENGTH: 17
<212> TYPE: PRT
<213> ORGANISM: Artificial Sequence
<220> FEATURE:
<223> OTHER INFORMATION: 4M2-D9 light chain FR2

<400> SEQUENCE: 117

```
Met Gln Trp Tyr Leu Gln Lys Pro Gly Gln Pro Pro Lys Leu Leu Ile
 1               5                  10                  15

Tyr
```

<210> SEQ ID NO 118
<211> LENGTH: 36
<212> TYPE: PRT
<213> ORGANISM: Artificial Sequence
<220> FEATURE:
<223> OTHER INFORMATION: 4M2-D9 light chain FR3

<400> SEQUENCE: 118

Asn Val Glu Ser Gly Val Pro Asp Arg Phe Arg Gly Ser Gly Ser Gly
1               5                   10                  15

Thr Asp Phe Ser Leu Asn Ile His Pro Val Glu Glu Asp Ile Ala
            20                  25                  30

Met Tyr Phe Cys
        35

<210> SEQ ID NO 119
<211> LENGTH: 119
<212> TYPE: PRT
<213> ORGANISM: Artificial Sequence
<220> FEATURE:
<223> OTHER INFORMATION: 1M2-D2 heavy chain variable region

<400> SEQUENCE: 119

Glu Val Lys Val Glu Glu Ser Gly Gly Gly Leu Val Gln Pro Gly Gly
1               5                   10                  15

Ser Met Lys Leu Ser Cys Ala Ala Ser Gly Phe Thr Phe Ser Asp Ala
            20                  25                  30

Trp Met Asp Trp Val His Gln Ser Pro Glu Lys Gly Leu Glu Trp Val
        35                  40                  45

Ala Glu Ile Arg Ser Lys Ala Asn Asn His Ala Thr Tyr Tyr Val Glu
    50                  55                  60

Ser Val Glu Gly Arg Phe Thr Ile Ser Arg Asp Asp Ser Lys Ser Ser
65                  70                  75                  80

Val Phe Leu Gln Val Asn Ser Leu Arg Pro Glu Asp Thr Gly Ile Tyr
                85                  90                  95

Tyr Cys Thr Arg Arg Asp Gly Tyr Tyr Phe Ala Tyr Trp Gly Gln Gly
            100                 105                 110

Thr Leu Val Thr Val Ser Ala
        115

<210> SEQ ID NO 120
<211> LENGTH: 8
<212> TYPE: PRT
<213> ORGANISM: Artificial Sequence
<220> FEATURE:
<223> OTHER INFORMATION: 1M2-D2 heavy chain CDR1

<400> SEQUENCE: 120

Gly Phe Thr Phe Ser Asp Ala Trp
1               5

<210> SEQ ID NO 121
<211> LENGTH: 10
<212> TYPE: PRT
<213> ORGANISM: Artificial Sequence
<220> FEATURE:
<223> OTHER INFORMATION: 1M2-D2 heavy chain CDR2

<400> SEQUENCE: 121

Ile Arg Ser Lys Ala Asn Asn His Ala Thr
1               5                   10

<210> SEQ ID NO 122
<211> LENGTH: 10
<212> TYPE: PRT
<213> ORGANISM: Artificial Sequence
<220> FEATURE:
<223> OTHER INFORMATION: 1M2-D2 heavy chain CDR3

<400> SEQUENCE: 122

```
Thr Arg Arg Asp Gly Tyr Tyr Phe Ala Tyr
1               5                   10
```

<210> SEQ ID NO 123
<211> LENGTH: 25
<212> TYPE: PRT
<213> ORGANISM: Artificial Sequence
<220> FEATURE:
<223> OTHER INFORMATION: 1M2-D2 heavy chain FR1

<400> SEQUENCE: 123

```
Glu Val Lys Val Glu Ser Gly Gly Gly Leu Val Gln Pro Gly Gly
1               5                   10                  15

Ser Met Lys Leu Ser Cys Ala Ala Ser
            20                  25
```

<210> SEQ ID NO 124
<211> LENGTH: 17
<212> TYPE: PRT
<213> ORGANISM: Artificial Sequence
<220> FEATURE:
<223> OTHER INFORMATION: 1M2-D2 heavy chain FR2

<400> SEQUENCE: 124

```
Met Asp Trp Val His Gln Ser Pro Glu Lys Gly Leu Glu Trp Val Ala
1               5                   10                  15

Glu
```

<210> SEQ ID NO 125
<211> LENGTH: 38
<212> TYPE: PRT
<213> ORGANISM: Artificial Sequence
<220> FEATURE:
<223> OTHER INFORMATION: 1M2-D2 heavy chain FR3

<400> SEQUENCE: 125

```
Tyr Tyr Val Glu Ser Val Glu Gly Arg Phe Thr Ile Ser Arg Asp Asp
1               5                   10                  15

Ser Lys Ser Ser Val Phe Leu Gln Val Asn Ser Leu Arg Pro Glu Asp
            20                  25                  30

Thr Gly Ile Tyr Tyr Cys
            35
```

<210> SEQ ID NO 126
<211> LENGTH: 105
<212> TYPE: PRT
<213> ORGANISM: Artificial Sequence
<220> FEATURE:
<223> OTHER INFORMATION: 1M2-D2 light chain variable region

<400> SEQUENCE: 126

```
Asp Ile Val Leu Thr Gln Ser Pro Ala Ile Met Ser Ala Ser Leu Gly
1               5                   10                  15

Glu Glu Ile Thr Leu Thr Cys Ser Ala Ser Ser Val Arg Asp Met
            20                  25                  30

His Trp Tyr Gln Gln Lys Ser Gly Thr Ser Pro Lys Val Leu Ile Tyr
            35                  40                  45

Asn Thr Phe Asn Leu Ala Ser Gly Val Pro Ser Arg Phe Ser Gly Ser
            50                  55                  60

Gly Ser Gly Thr Phe Tyr Ser Leu Thr Ile Ser Ser Val Glu Ala Gly
65                  70                  75                  80

Asp Ala Ala Ala Tyr Tyr Cys His Gln Trp Ser Ser Tyr Pro Thr Phe
```

```
                    85                  90                  95

Gly Gly Gly Thr Lys Leu Glu Ile Lys
            100                 105
```

<210> SEQ ID NO 127
<211> LENGTH: 6
<212> TYPE: PRT
<213> ORGANISM: Artificial Sequence
<220> FEATURE:
<223> OTHER INFORMATION: 1M2-D2 light chain CDR1

<400> SEQUENCE: 127

```
Ser Ser Ser Val Arg Asp
1               5
```

<210> SEQ ID NO 128
<211> LENGTH: 3
<212> TYPE: PRT
<213> ORGANISM: Artificial Sequence
<220> FEATURE:
<223> OTHER INFORMATION: 1M2-D2 light chain CDR2

<400> SEQUENCE: 128

```
Asn Thr Phe
1
```

<210> SEQ ID NO 129
<211> LENGTH: 8
<212> TYPE: PRT
<213> ORGANISM: Artificial Sequence
<220> FEATURE:
<223> OTHER INFORMATION: 1M2-D2 light chain CDR3

<400> SEQUENCE: 129

```
His Gln Trp Ser Ser Tyr Pro Thr
1               5
```

<210> SEQ ID NO 130
<211> LENGTH: 25
<212> TYPE: PRT
<213> ORGANISM: Artificial Sequence
<220> FEATURE:
<223> OTHER INFORMATION: 1M2-D2 light chain FR1

<400> SEQUENCE: 130

```
Asp Ile Val Leu Thr Gln Ser Pro Ala Ile Met Ser Ala Ser Leu Gly
1               5                   10                  15

Glu Glu Ile Thr Leu Thr Cys Ser Ala
            20                  25
```

<210> SEQ ID NO 131
<211> LENGTH: 17
<212> TYPE: PRT
<213> ORGANISM: Artificial Sequence
<220> FEATURE:
<223> OTHER INFORMATION: 1M2-D2 light chain FR2

<400> SEQUENCE: 131

```
Met His Trp Tyr Gln Gln Lys Ser Gly Thr Ser Pro Lys Val Leu Ile
1               5                   10                  15

Tyr
```

<210> SEQ ID NO 132
<211> LENGTH: 36
<212> TYPE: PRT

<213> ORGANISM: Artificial Sequence
<220> FEATURE:
<223> OTHER INFORMATION: 1M2-D2 light chain FR3

<400> SEQUENCE: 132

Asn Leu Ala Ser Gly Val Pro Ser Arg Phe Ser Gly Ser Gly Ser Gly
1               5                   10                  15

Thr Phe Tyr Ser Leu Thr Ile Ser Ser Val Glu Ala Gly Asp Ala Ala
            20                  25                  30

Ala Tyr Tyr Cys
        35

<210> SEQ ID NO 133
<211> LENGTH: 123
<212> TYPE: PRT
<213> ORGANISM: Artificial Sequence
<220> FEATURE:
<223> OTHER INFORMATION: 5M1-A11 heavy chain variable region

<400> SEQUENCE: 133

Gln Val Thr Leu Lys Val Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Gly Met Gly Val Ser Trp Ile Arg Gln Pro Ser Gly Lys Gly Leu Glu
        35                  40                  45

Trp Leu Ala His Ile Tyr Trp Asp Asp Lys Arg Tyr Asn Pro Ser
    50                  55                  60

Leu Lys Ser Arg Leu Thr Ile Ser Lys Asp Ser Ser Asn Gln Val
65                  70                  75                  80

Phe Leu Lys Ile Thr Ser Val Asp Thr Ala Asp Thr Ala Thr Tyr Tyr
                85                  90                  95

Cys Ala Arg Arg Leu Asp Gly Tyr Asn Asp Pro Tyr Tyr Phe Asp Tyr
            100                 105                 110

Trp Gly Gln Gly Thr Thr Leu Thr Val Ser Ser
        115                 120

<210> SEQ ID NO 134
<211> LENGTH: 25
<212> TYPE: PRT
<213> ORGANISM: Artificial Sequence
<220> FEATURE:
<223> OTHER INFORMATION: 5M1-A11 heavy chain FR1

<400> SEQUENCE: 134

Gln Val Thr Leu Lys Val Ser Gly Pro Gly Ile Leu Gln Pro Ser Gln
1               5                   10                  15

Thr Leu Ser Leu Thr Cys Ser Phe Ser
            20                  25

<210> SEQ ID NO 135
<211> LENGTH: 11
<212> TYPE: PRT
<213> ORGANISM: Artificial Sequence
<220> FEATURE:
<223> OTHER INFORMATION: 5M1-A11, 4M2-D5, 4M2-A8 heavy chain FR4

<400> SEQUENCE: 135

Trp Gly Gln Gly Thr Thr Leu Thr Val Ser Ser
1               5                   10

<210> SEQ ID NO 136
<211> LENGTH: 106
<212> TYPE: PRT
<213> ORGANISM: Artificial Sequence
<220> FEATURE:
<223> OTHER INFORMATION: 5M1-A11 light chain variable region

<400> SEQUENCE: 136

Asp Val Val Met Thr Gln Thr Pro Ala Leu Met Ser Ala Ser Pro Gly
1               5                   10                  15

Glu Lys Val Thr Met Thr Cys Ser Ala Ser Ser Val Ser Tyr Met
            20                  25                  30

Tyr Trp Tyr Gln Gln Lys Pro Arg Ser Ser Pro Lys Pro Trp Ile Tyr
        35                  40                  45

Leu Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Asn Ser Asn Pro Tyr Thr
                85                  90                  95

Phe Gly Gly Gly Thr Lys Leu Glu Ile Lys
            100                 105

<210> SEQ ID NO 137
<211> LENGTH: 5
<212> TYPE: PRT
<213> ORGANISM: Artificial Sequence
<220> FEATURE:
<223> OTHER INFORMATION: 5M1-A11 light chain CDR1

<400> SEQUENCE: 137

Ser Ser Val Ser Tyr
1               5

<210> SEQ ID NO 138
<211> LENGTH: 3
<212> TYPE: PRT
<213> ORGANISM: Artificial Sequence
<220> FEATURE:
<223> OTHER INFORMATION: 5M1-A11 light chain CDR2

<400> SEQUENCE: 138

Leu Thr Ser
1

<210> SEQ ID NO 139
<211> LENGTH: 9
<212> TYPE: PRT
<213> ORGANISM: Artificial Sequence
<220> FEATURE:
<223> OTHER INFORMATION: 5M1-A11 light chain CDR3

<400> SEQUENCE: 139

Gln Gln Trp Asn Ser Asn Pro Tyr Thr
1               5

<210> SEQ ID NO 140
<211> LENGTH: 26
<212> TYPE: PRT
<213> ORGANISM: Artificial Sequence
<220> FEATURE:
<223> OTHER INFORMATION: 5M1-A11 light chain FR1

<400> SEQUENCE: 140

-continued

Asp Val Val Met Thr Gln Thr Pro Ala Leu Met Ser Ala Ser Pro Gly
1               5                   10                  15

Glu Lys Val Thr Met Thr Cys Ser Ala Ser
            20                  25

<210> SEQ ID NO 141
<211> LENGTH: 17
<212> TYPE: PRT
<213> ORGANISM: Artificial Sequence
<220> FEATURE:
<223> OTHER INFORMATION: 5M1-A11 light chain FR2

<400> SEQUENCE: 141

Met Tyr Trp Tyr Gln Gln Lys Pro Arg Ser Ser Pro Lys Pro Trp Ile
1               5                   10                  15

Tyr

<210> SEQ ID NO 142
<211> LENGTH: 36
<212> TYPE: PRT
<213> ORGANISM: Artificial Sequence
<220> FEATURE:
<223> OTHER INFORMATION: 5M1-A11 light chain FR3

<400> SEQUENCE: 142

Asn Leu Ala Ser Gly Val Pro Ala Arg Phe Ser Gly Ser Gly Ser Gly
1               5                   10                  15

Thr Ser Tyr Ser Leu Thr Ile Ser Ser Met Glu Ala Glu Asp Ala Ala
            20                  25                  30

Thr Tyr Tyr Cys
            35

<210> SEQ ID NO 143
<211> LENGTH: 118
<212> TYPE: PRT
<213> ORGANISM: Artificial Sequence
<220> FEATURE:
<223> OTHER INFORMATION: 4M2-D5 heavy chain variable region

<400> SEQUENCE: 143

Gln Val Gln Leu Gln Gln Ser Gly Ala Glu Leu Ala Arg Pro Gly Ala
1               5                   10                  15

Ser Val Arg Met Ser Cys Lys Ala Ser Gly Tyr Thr Phe Thr Ser Tyr
            20                  25                  30

Thr Met Asn Trp Val Lys Gln Arg Pro Gly Gln Gly Leu Glu Trp Ile
        35                  40                  45

Gly Phe Ile Asn Pro Asp Ser Asp Tyr Thr Tyr Tyr Asp Gln Lys Phe
    50                  55                  60

Lys Asp Lys Ala Thr Leu Thr Ala Asp Ser Ser Ser Thr Ala Tyr
65                  70                  75                  80

Met Gln Leu Ser Ser Leu Thr Tyr Asp Asp Ser Ala Val Tyr Tyr Cys
                85                  90                  95

Thr Arg His Ser Tyr Gly Asn Tyr Gly Asp Tyr Trp Gly Gln Gly Thr
            100                 105                 110

Thr Leu Thr Val Ser Ser
            115

<210> SEQ ID NO 144
<211> LENGTH: 8
<212> TYPE: PRT
<213> ORGANISM: Artificial Sequence

```
<220> FEATURE:
<223> OTHER INFORMATION: 4M2-D5 heavy chain CDR1

<400> SEQUENCE: 144

Gly Tyr Thr Phe Thr Ser Tyr Thr
1               5

<210> SEQ ID NO 145
<211> LENGTH: 8
<212> TYPE: PRT
<213> ORGANISM: Artificial Sequence
<220> FEATURE:
<223> OTHER INFORMATION: 4M2-D5 heavy chain CDR2

<400> SEQUENCE: 145

Ile Asn Pro Asp Ser Asp Tyr Thr
1               5

<210> SEQ ID NO 146
<211> LENGTH: 11
<212> TYPE: PRT
<213> ORGANISM: Artificial Sequence
<220> FEATURE:
<223> OTHER INFORMATION: 4M2-D5 heavy chain CDR3

<400> SEQUENCE: 146

Thr Arg His Ser Tyr Gly Asn Tyr Gly Asp Tyr
1               5                   10

<210> SEQ ID NO 147
<211> LENGTH: 25
<212> TYPE: PRT
<213> ORGANISM: Artificial Sequence
<220> FEATURE:
<223> OTHER INFORMATION: 4M2-D5 heavy chain FR1

<400> SEQUENCE: 147

Gln Val Gln Leu Gln Gln Ser Gly Ala Glu Leu Ala Arg Pro Gly Ala
1               5                   10                  15

Ser Val Arg Met Ser Cys Lys Ala Ser
            20                  25

<210> SEQ ID NO 148
<211> LENGTH: 17
<212> TYPE: PRT
<213> ORGANISM: Artificial Sequence
<220> FEATURE:
<223> OTHER INFORMATION: 4M2-D5 heavy chain FR2

<400> SEQUENCE: 148

Met Asn Trp Val Lys Gln Arg Pro Gly Gln Gly Leu Glu Trp Ile Gly
1               5                   10                  15

Phe

<210> SEQ ID NO 149
<211> LENGTH: 38
<212> TYPE: PRT
<213> ORGANISM: Artificial Sequence
<220> FEATURE:
<223> OTHER INFORMATION: 4M2-D5 heavy chain FR3

<400> SEQUENCE: 149

Thr Tyr Asp Gln Lys Phe Lys Asp Lys Ala Thr Leu Thr Ala Asp Ser
1               5                   10                  15

Ser Ser Ser Thr Ala Tyr Met Gln Leu Ser Ser Leu Thr Tyr Asp Asp
```

Ser Ala Val Tyr Tyr Cys
        35

<210> SEQ ID NO 150
<211> LENGTH: 107
<212> TYPE: PRT
<213> ORGANISM: Artificial Sequence
<220> FEATURE:
<223> OTHER INFORMATION: 4M2-D5 light chain variable region

<400> SEQUENCE: 150

Asp Ile Val Leu Thr Gln Ser Pro Lys Phe Leu Leu Val Ser Ala Gly
1               5                   10                  15

Asp Arg Val Thr Ile Thr Cys Lys Ala Ser Gln Ser Val Thr Asn Asp
            20                  25                  30

Val Ala Trp Tyr Gln Gln Lys Pro Gly Gln Ser Pro Lys Leu Leu Ile
        35                  40                  45

Tyr Tyr Ala Ser Ser Arg Tyr Thr Gly Val Pro Asp Arg Phe Thr Gly
    50                  55                  60

Ser Gly Phe Gly Thr Asp Phe Thr Phe Thr Ile Asn Thr Val Gln Ala
65                  70                  75                  80

Glu Asp Leu Ala Val Tyr Phe Cys Gln Gln Asp Tyr Ser Ser Pro Tyr
                85                  90                  95

Thr Phe Gly Gly Gly Thr Lys Leu Glu Ile Lys
            100                 105

<210> SEQ ID NO 151
<211> LENGTH: 6
<212> TYPE: PRT
<213> ORGANISM: Artificial Sequence
<220> FEATURE:
<223> OTHER INFORMATION: 4M2-D5 light chain CDR1

<400> SEQUENCE: 151

Gln Ser Val Thr Asn Asp
1               5

<210> SEQ ID NO 152
<211> LENGTH: 3
<212> TYPE: PRT
<213> ORGANISM: Artificial Sequence
<220> FEATURE:
<223> OTHER INFORMATION: 4M2-D5, 4M2-A8 light chain CDR2

<400> SEQUENCE: 152

Tyr Ala Ser
1

<210> SEQ ID NO 153
<211> LENGTH: 9
<212> TYPE: PRT
<213> ORGANISM: Artificial Sequence
<220> FEATURE:
<223> OTHER INFORMATION: 4M2-D5, 4M2-A8 light chain CDR3

<400> SEQUENCE: 153

Gln Gln Asp Tyr Ser Ser Pro Tyr Thr
1               5

<210> SEQ ID NO 154
<211> LENGTH: 26
<212> TYPE: PRT

<213> ORGANISM: Artificial Sequence
<220> FEATURE:
<223> OTHER INFORMATION: 4M2-D5 light chain FR1

<400> SEQUENCE: 154

Asp Ile Val Leu Thr Gln Ser Pro Lys Phe Leu Leu Val Ser Ala Gly
1               5                   10                  15

Asp Arg Val Thr Ile Thr Cys Lys Ala Ser
            20                  25

<210> SEQ ID NO 155
<211> LENGTH: 17
<212> TYPE: PRT
<213> ORGANISM: Artificial Sequence
<220> FEATURE:
<223> OTHER INFORMATION: 4M2-D5, 4M2-A8 light chain FR2

<400> SEQUENCE: 155

Val Ala Trp Tyr Gln Gln Lys Pro Gly Gln Ser Pro Lys Leu Leu Ile
1               5                   10                  15

Tyr

<210> SEQ ID NO 156
<211> LENGTH: 36
<212> TYPE: PRT
<213> ORGANISM: Artificial Sequence
<220> FEATURE:
<223> OTHER INFORMATION: 4M2-D5 light chain FR3

<400> SEQUENCE: 156

Ser Arg Tyr Thr Gly Val Pro Asp Arg Phe Thr Gly Ser Gly Phe Gly
1               5                   10                  15

Thr Asp Phe Thr Phe Thr Ile Asn Thr Val Gln Ala Glu Asp Leu Ala
            20                  25                  30

Val Tyr Phe Cys
            35

<210> SEQ ID NO 157
<211> LENGTH: 118
<212> TYPE: PRT
<213> ORGANISM: Artificial Sequence
<220> FEATURE:
<223> OTHER INFORMATION: 4M2-A8 heavy chain variable region

<400> SEQUENCE: 157

Gln Val Gln Leu Gln Gln Ser Gly Ala Asp Leu Ala Arg Pro Gly Ala
1               5                   10                  15

Ser Val Lys Met Ser Cys Lys Ala Ser Gly Tyr Thr Phe Ile Asp Tyr
            20                  25                  30

Thr Val His Trp Val Lys Gln Arg Pro Gly Gln Gly Leu Glu Trp Ile
        35                  40                  45

Gly Phe Ile Asn Pro Ser Asn Asp Tyr Thr Ser Tyr Asn Gln Lys Phe
    50                  55                  60

Lys Asp Lys Ala Ser Leu Thr Ala Asp Thr Ser Ser Thr Thr Ala Tyr
65                  70                  75                  80

Met Gln Leu Ser Ser Leu Thr Ser Asp Asp Ser Ala Val Tyr Tyr Cys
                85                  90                  95

Ala Arg His Ser Tyr Gly Asn Tyr Gly Asp Tyr Trp Gly Gln Gly Thr
            100                 105                 110

Thr Leu Thr Val Ser Ser
            115

<210> SEQ ID NO 158
<211> LENGTH: 8
<212> TYPE: PRT
<213> ORGANISM: Artificial Sequence
<220> FEATURE:
<223> OTHER INFORMATION: 4M2-A8 heavy chain CDR1

<400> SEQUENCE: 158

Gly Tyr Thr Phe Ile Asp Tyr Thr
1               5

<210> SEQ ID NO 159
<211> LENGTH: 8
<212> TYPE: PRT
<213> ORGANISM: Artificial Sequence
<220> FEATURE:
<223> OTHER INFORMATION: 4M2-A8 heavy chain CDR2

<400> SEQUENCE: 159

Ile Asn Pro Ser Asn Asp Tyr Thr
1               5

<210> SEQ ID NO 160
<211> LENGTH: 11
<212> TYPE: PRT
<213> ORGANISM: Artificial Sequence
<220> FEATURE:
<223> OTHER INFORMATION: 4M2-A8 heavy chain CDR3

<400> SEQUENCE: 160

Ala Arg His Ser Tyr Gly Asn Tyr Gly Asp Tyr
1               5                   10

<210> SEQ ID NO 161
<211> LENGTH: 25
<212> TYPE: PRT
<213> ORGANISM: Artificial Sequence
<220> FEATURE:
<223> OTHER INFORMATION: 4M2-A8 heavy chain FR1

<400> SEQUENCE: 161

Gln Val Gln Leu Gln Gln Ser Gly Ala Asp Leu Ala Arg Pro Gly Ala
1               5                   10                  15
Ser Val Lys Met Ser Cys Lys Ala Ser
            20                  25

<210> SEQ ID NO 162
<211> LENGTH: 17
<212> TYPE: PRT
<213> ORGANISM: Artificial Sequence
<220> FEATURE:
<223> OTHER INFORMATION: 4M2-A8 heavy chain FR2

<400> SEQUENCE: 162

Val His Trp Val Lys Gln Arg Pro Gly Gln Gly Leu Glu Trp Ile Gly
1               5                   10                  15
Phe

<210> SEQ ID NO 163
<211> LENGTH: 38
<212> TYPE: PRT
<213> ORGANISM: Artificial Sequence
<220> FEATURE:
<223> OTHER INFORMATION: 4M2-A8 heavy chain FR3

```
<400> SEQUENCE: 163

Ser Tyr Asn Gln Lys Phe Lys Asp Lys Ala Ser Leu Thr Ala Asp Thr
1               5                   10                  15

Ser Ser Thr Thr Ala Tyr Met Gln Leu Ser Ser Leu Thr Ser Asp Asp
                20                  25                  30

Ser Ala Val Tyr Tyr Cys
            35

<210> SEQ ID NO 164
<211> LENGTH: 107
<212> TYPE: PRT
<213> ORGANISM: Artificial Sequence
<220> FEATURE:
<223> OTHER INFORMATION: 4M2-A8 light chain variable region

<400> SEQUENCE: 164

Asp Ile Val Met Thr Gln Ala Pro Lys Phe Leu Leu Val Ser Ala Gly
1               5                   10                  15

Asp Arg Val Thr Ile Thr Cys Lys Ala Ser Gln Ser Val Thr Asn Gly
                20                  25                  30

Val Ala Trp Tyr Gln Gln Lys Pro Gly Gln Ser Pro Lys Leu Leu Ile
            35                  40                  45

Tyr Tyr Ala Ser Asn Arg Tyr Thr Gly Val Pro Asp Arg Phe Thr Gly
    50                  55                  60

Ser Gly Phe Gly Thr Asp Phe Thr Phe Thr Ile Ser Thr Val Gln Ala
65                  70                  75                  80

Glu Asp Leu Ala Val Tyr Phe Cys Gln Gln Asp Tyr Ser Ser Pro Tyr
                85                  90                  95

Thr Phe Gly Gly Gly Thr Lys Leu Glu Ile Lys
            100                 105

<210> SEQ ID NO 165
<211> LENGTH: 6
<212> TYPE: PRT
<213> ORGANISM: Artificial Sequence
<220> FEATURE:
<223> OTHER INFORMATION: 4M2-A8 light chain CDR1

<400> SEQUENCE: 165

Gln Ser Val Thr Asn Gly
1               5

<210> SEQ ID NO 166
<211> LENGTH: 26
<212> TYPE: PRT
<213> ORGANISM: Artificial Sequence
<220> FEATURE:
<223> OTHER INFORMATION: 4M2-A8 light chain FR1

<400> SEQUENCE: 166

Asp Ile Val Met Thr Gln Ala Pro Lys Phe Leu Leu Val Ser Ala Gly
1               5                   10                  15

Asp Arg Val Thr Ile Thr Cys Lys Ala Ser
                20                  25

<210> SEQ ID NO 167
<211> LENGTH: 36
<212> TYPE: PRT
<213> ORGANISM: Artificial Sequence
<220> FEATURE:
<223> OTHER INFORMATION: 4M2-A8 light chain FR3
```

-continued

<400> SEQUENCE: 167

Asn Arg Tyr Thr Gly Val Pro Asp Arg Phe Thr Gly Ser Gly Phe Gly
1               5                   10                  15

Thr Asp Phe Thr Phe Thr Ile Ser Thr Val Gln Ala Glu Asp Leu Ala
            20                  25                  30

Val Tyr Phe Cys
        35

<210> SEQ ID NO 168
<211> LENGTH: 119
<212> TYPE: PRT
<213> ORGANISM: Artificial Sequence
<220> FEATURE:
<223> OTHER INFORMATION: 9M2-C12 heavy chain variable region

<400> SEQUENCE: 168

Gln Val Gln Leu Gln Gln Ser Gly Ala Glu Leu Val Lys Pro Gly Ala
1               5                   10                  15

Ser Val Arg Leu Ser Cys Lys Ala Ser Gly Tyr Thr Phe Thr Ser Tyr
            20                  25                  30

Trp Met His Trp Val Arg Gln Arg Pro Gly Leu Gly Leu Glu Trp Ile
        35                  40                  45

Gly Glu Ile Asp Pro Ser Asp Ser Tyr Thr Asn Cys Asn Gln Arg Phe
    50                  55                  60

Lys Gly Lys Ala Thr Leu Thr Val Asp Lys Ser Ser Thr Ala Tyr
65                  70                  75                  80

Thr Gln Leu Ser Ser Leu Thr Ser Glu Asp Ser Ala Val Tyr Tyr Cys
            85                  90                  95

Ala Arg Trp Ala Tyr Gly Pro Tyr Ala Met Asp Tyr Trp Gly Gln Gly
            100                 105                 110

Thr Ser Val Thr Val Ser Ser
        115

<210> SEQ ID NO 169
<211> LENGTH: 8
<212> TYPE: PRT
<213> ORGANISM: Artificial Sequence
<220> FEATURE:
<223> OTHER INFORMATION: 9M2-C12 heavy chain CDR1

<400> SEQUENCE: 169

Gly Tyr Thr Phe Thr Ser Tyr Trp
1               5

<210> SEQ ID NO 170
<211> LENGTH: 8
<212> TYPE: PRT
<213> ORGANISM: Artificial Sequence
<220> FEATURE:
<223> OTHER INFORMATION: 9M2-C12 heavy chain CDR2

<400> SEQUENCE: 170

Ile Asp Pro Ser Asp Ser Tyr Thr
1               5

<210> SEQ ID NO 171
<211> LENGTH: 12
<212> TYPE: PRT
<213> ORGANISM: Artificial Sequence
<220> FEATURE:
<223> OTHER INFORMATION: 9M2-C12 heavy chain CDR3

```
<400> SEQUENCE: 171

Ala Arg Trp Ala Tyr Gly Pro Tyr Ala Met Asp Tyr
1               5                   10

<210> SEQ ID NO 172
<211> LENGTH: 25
<212> TYPE: PRT
<213> ORGANISM: Artificial Sequence
<220> FEATURE:
<223> OTHER INFORMATION: 9M2-C12 heavy chain FR1

<400> SEQUENCE: 172

Gln Val Gln Leu Gln Gln Ser Gly Ala Glu Leu Val Lys Pro Gly Ala
1               5                   10                  15

Ser Val Arg Leu Ser Cys Lys Ala Ser
            20                  25

<210> SEQ ID NO 173
<211> LENGTH: 17
<212> TYPE: PRT
<213> ORGANISM: Artificial Sequence
<220> FEATURE:
<223> OTHER INFORMATION: 9M2-C12 heavy chain FR2

<400> SEQUENCE: 173

Met His Trp Val Arg Gln Arg Pro Gly Leu Gly Leu Glu Trp Ile Gly
1               5                   10                  15

Glu

<210> SEQ ID NO 174
<211> LENGTH: 38
<212> TYPE: PRT
<213> ORGANISM: Artificial Sequence
<220> FEATURE:
<223> OTHER INFORMATION: 9M2-C12 heavy chain FR3

<400> SEQUENCE: 174

Asn Cys Asn Gln Arg Phe Lys Gly Lys Ala Thr Leu Thr Val Asp Lys
1               5                   10                  15

Ser Ser Ser Thr Ala Tyr Thr Gln Leu Ser Ser Leu Thr Ser Glu Asp
            20                  25                  30

Ser Ala Val Tyr Tyr Cys
        35

<210> SEQ ID NO 175
<211> LENGTH: 11
<212> TYPE: PRT
<213> ORGANISM: Artificial Sequence
<220> FEATURE:
<223> OTHER INFORMATION: 9M2-C12 heavy chain FR4

<400> SEQUENCE: 175

Trp Gly Gln Gly Thr Ser Val Thr Val Ser Ser
1               5                   10

<210> SEQ ID NO 176
<211> LENGTH: 112
<212> TYPE: PRT
<213> ORGANISM: Artificial Sequence
<220> FEATURE:
<223> OTHER INFORMATION: 9M2-C12 light chain variable region

<400> SEQUENCE: 176

Asp Ile Val Met Thr Gln Thr Pro Leu Ser Leu Pro Val Ser Leu Gly
```

```
                1               5                  10                 15
            Asp Gln Ala Ser Ile Ser Cys Arg Ser Ser Gln Ser Leu Val His Ser
                            20                  25                  30

Asn Gly Asn Thr Tyr Leu His Trp Tyr Leu Gln Lys Pro Gly Gln Ser
                        35                  40                  45

Pro Lys Leu Leu Ile Tyr Lys Val Ser Asn Arg Phe Ser Gly Val Pro
                    50                  55                  60

Asp Arg Phe Ser Gly Ser Gly Ser Gly Thr Asp Phe Thr Leu Lys Ile
            65                  70                  75                  80

Ser Arg Val Glu Ala Glu Asp Leu Gly Val Tyr Phe Cys Ser Gln Ser
                            85                  90                  95

Thr His Val Pro Trp Thr Phe Gly Gly Thr Lys Leu Glu Ile Lys
                        100                 105                 110

<210> SEQ ID NO 177
<211> LENGTH: 11
<212> TYPE: PRT
<213> ORGANISM: Artificial Sequence
<220> FEATURE:
<223> OTHER INFORMATION: 9M2-C12 light chain CDR1

<400> SEQUENCE: 177

Gln Ser Leu Val His Ser Asn Gly Asn Thr Tyr
1               5                   10

<210> SEQ ID NO 178
<211> LENGTH: 3
<212> TYPE: PRT
<213> ORGANISM: Artificial Sequence
<220> FEATURE:
<223> OTHER INFORMATION: 9M2-C12, 13D5p, 13D5-1, 13D5-13 light chain
      CDR2

<400> SEQUENCE: 178

Lys Val Ser
1

<210> SEQ ID NO 179
<211> LENGTH: 9
<212> TYPE: PRT
<213> ORGANISM: Artificial Sequence
<220> FEATURE:
<223> OTHER INFORMATION: 9M2-C12 light chain CDR3

<400> SEQUENCE: 179

Ser Gln Ser Thr His Val Pro Trp Thr
1               5

<210> SEQ ID NO 180
<211> LENGTH: 26
<212> TYPE: PRT
<213> ORGANISM: Artificial Sequence
<220> FEATURE:
<223> OTHER INFORMATION: 9M2-C12 light chain FR1

<400> SEQUENCE: 180

Asp Ile Val Met Thr Gln Thr Pro Leu Ser Leu Pro Val Ser Leu Gly
1               5                   10                  15

Asp Gln Ala Ser Ile Ser Cys Arg Ser Ser
                20                  25

<210> SEQ ID NO 181
<211> LENGTH: 17
```

<212> TYPE: PRT
<213> ORGANISM: Artificial Sequence
<220> FEATURE:
<223> OTHER INFORMATION: 9M2-C12 light chain FR2

<400> SEQUENCE: 181

Leu His Trp Tyr Leu Gln Lys Pro Gly Gln Ser Pro Lys Leu Leu Ile
1               5                   10                  15

Tyr

<210> SEQ ID NO 182
<211> LENGTH: 36
<212> TYPE: PRT
<213> ORGANISM: Artificial Sequence
<220> FEATURE:
<223> OTHER INFORMATION: 9M2-C12 light chain FR3

<400> SEQUENCE: 182

Asn Arg Phe Ser Gly Val Pro Asp Arg Phe Ser Gly Ser Gly Ser Gly
1               5                   10                  15

Thr Asp Phe Thr Leu Lys Ile Ser Arg Val Glu Ala Glu Asp Leu Gly
                20                  25                  30

Val Tyr Phe Cys
            35

<210> SEQ ID NO 183
<211> LENGTH: 122
<212> TYPE: PRT
<213> ORGANISM: Artificial Sequence
<220> FEATURE:
<223> OTHER INFORMATION: 13D5p heavy chain variable region

<400> SEQUENCE: 183

Gln Val Gln Leu Gln Gln Ser Gly Ala Glu Leu Val Arg Pro Gly Thr
1               5                   10                  15

Ser Val Lys Ile Ser Cys Lys Ala Ser Gly Tyr Thr Phe Thr Asn Tyr
                20                  25                  30

Trp Leu Gly Trp Val Lys Gln Arg Pro Gly His Gly Leu Glu Trp Ile
            35                  40                  45

Gly Asp Ile Tyr Pro Gly Gly Gly Tyr Thr Asn Tyr Asn Glu Lys Phe
    50                  55                  60

Lys Gly Lys Ala Thr Leu Thr Ala Asp Thr Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Gly Gly Tyr Tyr Tyr Gly Ser Ser Trp Tyr Phe Asp Val Trp
                100                 105                 110

Gly Ala Gly Thr Thr Val Thr Val Ser Ser
            115                 120

<210> SEQ ID NO 184
<211> LENGTH: 8
<212> TYPE: PRT
<213> ORGANISM: Artificial Sequence
<220> FEATURE:
<223> OTHER INFORMATION: 13D5p, 13D5-1, 13D5-13 heavy chain CDR2

<400> SEQUENCE: 184

Ile Tyr Pro Gly Gly Gly Tyr Thr
1               5

```
<210> SEQ ID NO 185
<211> LENGTH: 15
<212> TYPE: PRT
<213> ORGANISM: Artificial Sequence
<220> FEATURE:
<223> OTHER INFORMATION: 13D5p heavy chain CDR3

<400> SEQUENCE: 185

Ala Arg Gly Gly Tyr Tyr Tyr Gly Ser Ser Trp Tyr Phe Asp Val
1               5                   10                  15

<210> SEQ ID NO 186
<211> LENGTH: 17
<212> TYPE: PRT
<213> ORGANISM: Artificial Sequence
<220> FEATURE:
<223> OTHER INFORMATION: 13D5p, 13D5-1, 13D5-13 heavy chain FR2

<400> SEQUENCE: 186

Leu Gly Trp Val Lys Gln Arg Pro Gly His Gly Leu Glu Trp Ile Gly
1               5                   10                  15

Asp

<210> SEQ ID NO 187
<211> LENGTH: 38
<212> TYPE: PRT
<213> ORGANISM: Artificial Sequence
<220> FEATURE:
<223> OTHER INFORMATION: 13D5p, 13D5-1 heavy chain FR3

<400> SEQUENCE: 187

Asn Tyr Asn Glu Lys Phe Lys Gly Lys Ala Thr Leu Thr Ala Asp Thr
1               5                   10                  15

Ser Ser Ser Thr Ala Tyr Met Gln Leu Ser Ser Leu Thr Ser Glu Asp
                20                  25                  30

Ser Ala Val Tyr Phe Cys
        35

<210> SEQ ID NO 188
<211> LENGTH: 112
<212> TYPE: PRT
<213> ORGANISM: Artificial Sequence
<220> FEATURE:
<223> OTHER INFORMATION: 13D5p light chain variable region

<400> SEQUENCE: 188

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
                20                  25                  30

Asn Gly Asn Thr Tyr Leu Glu Trp Tyr Leu Gln Lys Pro Gly Gln Ser
            35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Pro Thr Phe Gly Gly Gly Thr Lys Leu Glu Ile Lys
            100                 105                 110

<210> SEQ ID NO 189
```

```
<211> LENGTH: 11
<212> TYPE: PRT
<213> ORGANISM: Artificial Sequence
<220> FEATURE:
<223> OTHER INFORMATION: 13D5p light chain CDR1

<400> SEQUENCE: 189

Gln Ser Ile Val His Ser Asn Gly Asn Thr Tyr
1               5                   10

<210> SEQ ID NO 190
<211> LENGTH: 9
<212> TYPE: PRT
<213> ORGANISM: Artificial Sequence
<220> FEATURE:
<223> OTHER INFORMATION: 13D5p, 13D5-1, 13D5-13 light chain CDR3

<400> SEQUENCE: 190

Phe Gln Gly Ser His Val Pro Pro Thr
1               5

<210> SEQ ID NO 191
<211> LENGTH: 26
<212> TYPE: PRT
<213> ORGANISM: Artificial Sequence
<220> FEATURE:
<223> OTHER INFORMATION: 13D5p, 13D5-1, 13D5-13 light chain FR1

<400> SEQUENCE: 191

Asp Val Leu Met Thr Gln Thr Pro Leu Ser Leu Pro Val Ser Leu Gly
1               5                   10                  15

Asp Gln Ala Ser Ile Ser Cys Arg Ser Ser
            20                  25

<210> SEQ ID NO 192
<211> LENGTH: 17
<212> TYPE: PRT
<213> ORGANISM: Artificial Sequence
<220> FEATURE:
<223> OTHER INFORMATION: 13D5p, 13D5-13 light chain FR2

<400> SEQUENCE: 192

Leu Glu Trp Tyr Leu Gln Lys Pro Gly Gln Ser Pro Lys Leu Leu Ile
1               5                   10                  15

Tyr

<210> SEQ ID NO 193
<211> LENGTH: 36
<212> TYPE: PRT
<213> ORGANISM: Artificial Sequence
<220> FEATURE:
<223> OTHER INFORMATION: 13D5p, 13D5-1 light chain FR3

<400> SEQUENCE: 193

Asn Arg Phe Ser Gly Val Pro Asp Arg Phe Ser Gly Ser Gly Ser Gly
1               5                   10                  15

Thr Asp Phe Thr Leu Lys Ile Ser Arg Val Glu Ala Glu Asp Leu Gly
            20                  25                  30

Val Tyr Tyr Cys
        35

<210> SEQ ID NO 194
<211> LENGTH: 122
<212> TYPE: PRT
<213> ORGANISM: Artificial Sequence
```

<220> FEATURE:
<223> OTHER INFORMATION: 13D5-1 heavy chain variable region

<400> SEQUENCE: 194

Gln Val Gln Leu Gln Gln Ser Gly Ala Glu Leu Val Arg Pro Gly Thr
1               5                   10                  15

Ser Val Lys Ile Ser Cys Lys Ala Ser Gly Tyr Thr Phe Thr Asn Tyr
            20                  25                  30

Trp Leu Gly Trp Val Lys Gln Arg Pro Gly His Gly Leu Glu Trp Ile
        35                  40                  45

Gly Asp Ile Tyr Pro Gly Gly Tyr Thr Asn Tyr Asn Glu Lys Phe
    50                  55                  60

Lys Gly Lys Ala Thr Leu Thr Ala Asp Thr Ser Ser Thr Ala Tyr
65                  70                  75                  80

Met Gln Leu Ser Ser Leu Thr Ser Glu Asp Ser Ala Val Tyr Phe Cys
                85                  90                  95

Val Arg Ser Gly Tyr Tyr Tyr Gly Ser Ser Trp Tyr Phe Asp Val Trp
            100                 105                 110

Gly Ala Gly Thr Thr Val Thr Val Ser Ser
        115                 120

<210> SEQ ID NO 195
<211> LENGTH: 15
<212> TYPE: PRT
<213> ORGANISM: Artificial Sequence
<220> FEATURE:
<223> OTHER INFORMATION: 13D5-1 heavy chain CDR3

<400> SEQUENCE: 195

Val Arg Ser Gly Tyr Tyr Tyr Gly Ser Ser Trp Tyr Phe Asp Val
1               5                   10                  15

<210> SEQ ID NO 196
<211> LENGTH: 112
<212> TYPE: PRT
<213> ORGANISM: Artificial Sequence
<220> FEATURE:
<223> OTHER INFORMATION: 13D5-1 light chain variable region

<400> SEQUENCE: 196

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Ser Gly Asn Thr Tyr Leu Glu Trp Tyr Leu Gln Lys Pro Asp Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Pro Thr Phe Gly Gly Gly Thr Lys Leu Glu Ile Lys
            100                 105                 110

<210> SEQ ID NO 197
<211> LENGTH: 11
<212> TYPE: PRT
<213> ORGANISM: Artificial Sequence
<220> FEATURE:

<223> OTHER INFORMATION: 13D5-1 light chain CDR1

<400> SEQUENCE: 197

Gln Ser Ile Val His Ser Ser Gly Asn Thr Tyr
1               5                   10

<210> SEQ ID NO 198
<211> LENGTH: 17
<212> TYPE: PRT
<213> ORGANISM: Artificial Sequence
<220> FEATURE:
<223> OTHER INFORMATION: 13D5-1 light chain FR2

<400> SEQUENCE: 198

Leu Glu Trp Tyr Leu Gln Lys Pro Asp Gln Ser Pro Lys Leu Leu Ile
1               5                   10                  15

Tyr

<210> SEQ ID NO 199
<211> LENGTH: 122
<212> TYPE: PRT
<213> ORGANISM: Artificial Sequence
<220> FEATURE:
<223> OTHER INFORMATION: 13D5-13 heavy chain variable region

<400> SEQUENCE: 199

Gln Val Gln Leu Gln Gln Ser Gly Ala Glu Leu Val Arg Pro Gly Thr
1               5                   10                  15

Ser Val Lys Ile Ser Cys Lys Ala Ser Gly Tyr Thr Phe Thr Asn Tyr
                20                  25                  30

Trp Leu Gly Trp Val Lys Gln Arg Pro Gly His Gly Leu Glu Trp Ile
        35                  40                  45

Gly Asp Ile Tyr Pro Gly Gly Tyr Thr Asn Tyr Asn Glu Lys Phe
    50                  55                  60

Lys Gly Lys Ala Thr Leu Thr Ala Asp Ile Ser Ser Ser Thr Ala Tyr
65                  70                  75                  80

Met Gln Leu Ser Ser Leu Thr Ser Glu Asp Ser Ala Asp Tyr Phe Cys
                85                  90                  95

Val Arg Gly Gly Tyr Tyr Gly Ser Ser Trp Tyr Phe Asp Val Trp
                100                 105                 110

Gly Ala Gly Thr Thr Val Thr Val Ser Ser
        115                 120

<210> SEQ ID NO 200
<211> LENGTH: 15
<212> TYPE: PRT
<213> ORGANISM: Artificial Sequence
<220> FEATURE:
<223> OTHER INFORMATION: 13D5-13 heavy chain CDR3

<400> SEQUENCE: 200

Val Arg Gly Gly Tyr Tyr Tyr Gly Ser Ser Trp Tyr Phe Asp Val
1               5                   10                  15

<210> SEQ ID NO 201
<211> LENGTH: 38
<212> TYPE: PRT
<213> ORGANISM: Artificial Sequence
<220> FEATURE:
<223> OTHER INFORMATION: 13D5-13 heavy chain FR3

<400> SEQUENCE: 201

```
Asn Tyr Asn Glu Lys Phe Lys Gly Lys Ala Thr Leu Thr Ala Asp Ile
1               5                   10                  15

Ser Ser Ser Thr Ala Tyr Met Gln Leu Ser Ser Leu Thr Ser Glu Asp
                20                  25                  30

Ser Ala Asp Tyr Phe Cys
                35
```

<210> SEQ ID NO 202
<211> LENGTH: 112
<212> TYPE: PRT
<213> ORGANISM: Artificial Sequence
<220> FEATURE:
<223> OTHER INFORMATION: 13D5-13 light chain variable region

<400> SEQUENCE: 202

```
Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Thr Val His Ser
                20                  25                  30

Ile Gly Asn Thr Tyr Leu Glu Trp Tyr Leu Gln Lys Pro Gly Gln Ser
                35                  40                  45

Pro Lys Leu Leu Ile Tyr Lys Val Ser Asn Arg Phe Ser Gly Val Pro
    50                  55                  60

Asp Arg Phe Ser Gly Ser Glu Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Pro Thr Phe Gly Gly Gly Thr Lys Leu Glu Ile Lys
                100                 105                 110
```

<210> SEQ ID NO 203
<211> LENGTH: 11
<212> TYPE: PRT
<213> ORGANISM: Artificial Sequence
<220> FEATURE:
<223> OTHER INFORMATION: 13D5-13 light chain CDR1

<400> SEQUENCE: 203

```
Gln Ser Thr Val His Ser Ile Gly Asn Thr Tyr
1               5                   10
```

<210> SEQ ID NO 204
<211> LENGTH: 36
<212> TYPE: PRT
<213> ORGANISM: Artificial Sequence
<220> FEATURE:
<223> OTHER INFORMATION: 13D5-13 light chain FR3

<400> SEQUENCE: 204

```
Asn Arg Phe Ser Gly Val Pro Asp Arg Phe Ser Gly Ser Glu Ser Gly
1               5                   10                  15

Thr Asp Phe Thr Leu Lys Ile Ser Arg Val Glu Ala Glu Asp Leu Gly
                20                  25                  30

Val Tyr Tyr Cys
                35
```

<210> SEQ ID NO 205
<211> LENGTH: 330
<212> TYPE: PRT
<213> ORGANISM: Artificial Sequence
<220> FEATURE:
<223> OTHER INFORMATION: Human IgG1 constant region (IGHG1;

UniProt:P01857-1, v1)

<400> SEQUENCE: 205

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 206
<211> LENGTH: 98
<212> TYPE: PRT
<213> ORGANISM: Artificial Sequence
<220> FEATURE:
<223> OTHER INFORMATION: CH1 IgG1 (positions 1-98 of P01857-1, v1)

<400> SEQUENCE: 206

Ala Ser Thr Lys Gly Pro Ser Val Phe Pro Leu Ala Pro Ser Ser Lys
1               5                   10                  15

```
Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val
```

<210> SEQ ID NO 207
<211> LENGTH: 12
<212> TYPE: PRT
<213> ORGANISM: Artificial Sequence
<220> FEATURE:
<223> OTHER INFORMATION: Hinge IgG1 (positions 99-110 of P01857-1, v1)

<400> SEQUENCE: 207

```
Glu Pro Lys Ser Cys Asp Lys Thr His Thr Cys Pro
 1               5                  10
```

<210> SEQ ID NO 208
<211> LENGTH: 113
<212> TYPE: PRT
<213> ORGANISM: Artificial Sequence
<220> FEATURE:
<223> OTHER INFORMATION: CH2 IgG1 (positions 111-223 of P01857-1, v1)

<400> SEQUENCE: 208

```
Pro Cys Pro Ala Pro Glu Leu Leu Gly Gly Pro Ser Val Phe Leu Phe
 1               5                  10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
         35                  40                  45

Asn Trp Tyr Val Asp Gly Val Glu Val His Asn Ala Lys Thr Lys Pro
 50                  55                  60

Arg Glu Glu Gln Tyr Asn Ser Thr Tyr Arg Val Val Ser Val Leu Thr
 65                  70                  75                  80

Val Leu His Gln Asp Trp Leu Asn Gly Lys Glu Tyr Lys Cys Lys Val
                 85                  90                  95

Ser Asn Lys Ala Leu Pro Ala Pro Ile Glu Lys Thr Ile Ser Lys Ala
                100                 105                 110

Lys
```

<210> SEQ ID NO 209
<211> LENGTH: 107
<212> TYPE: PRT
<213> ORGANISM: Artificial Sequence
<220> FEATURE:
<223> OTHER INFORMATION: CH3 IgG1 (positions 224-330 of P01857-1, v1)

<400> SEQUENCE: 209

```
Gly Gln Pro Arg Glu Pro Gln Val Tyr Thr Leu Pro Pro Ser Arg Asp
 1               5                  10                  15

Glu Leu Thr Lys Asn Gln Val Ser Leu Thr Cys Leu Val Lys Gly Phe
            20                  25                  30
```

Tyr Pro Ser Asp Ile Ala Val Glu Trp Glu Ser Asn Gly Gln Pro Glu
            35                  40                  45

Asn Asn Tyr Lys Thr Thr Pro Pro Val Leu Asp Ser Asp Gly Ser Phe
 50                      55                  60

Phe Leu Tyr Ser Lys Leu Thr Val Asp Lys Ser Arg Trp Gln Gln Gly
 65                  70                  75                  80

Asn Val Phe Ser Cys Ser Val Met His Glu Ala Leu His Asn His Tyr
                 85                  90                  95

Thr Gln Lys Ser Leu Ser Leu Ser Pro Gly Lys
            100                 105

<210> SEQ ID NO 210
<211> LENGTH: 107
<212> TYPE: PRT
<213> ORGANISM: Artificial Sequence
<220> FEATURE:
<223> OTHER INFORMATION: CH3 (D356E, L358M; positions numbered according
      to EU numbering)

<400> SEQUENCE: 210

Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
            35                  40                  45

Asn Asn Tyr Lys Thr Thr Pro Pro Val Leu Asp Ser Asp Gly Ser Phe
 50                      55                  60

Phe Leu Tyr Ser Lys Leu Thr Val Asp Lys Ser Arg Trp Gln Gln Gly
 65                  70                  75                  80

Asn Val Phe Ser Cys Ser Val Met His Glu Ala Leu His Asn His Tyr
                 85                  90                  95

Thr Gln Lys Ser Leu Ser Leu Ser Pro Gly Lys
            100                 105

<210> SEQ ID NO 211
<211> LENGTH: 107
<212> TYPE: PRT
<213> ORGANISM: Artificial Sequence
<220> FEATURE:
<223> OTHER INFORMATION: Ckappa CL (IGCK; UniProt: P01834-1, v2)

<400> SEQUENCE: 211

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Ser
 50                      55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
            100                 105

```
<210> SEQ ID NO 212
<211> LENGTH: 449
<212> TYPE: PRT
<213> ORGANISM: Artificial Sequence
<220> FEATURE:
<223> OTHER INFORMATION: 4M2-C12 VH-CH1-CH2-CH3

<400> SEQUENCE: 212

Glu Val Lys Leu Val Glu Ser Gly Pro Gly Leu Val Lys Pro Ser Gln
1               5                   10                  15

Ser Leu Ser Leu Thr Cys Thr Val Thr Gly Tyr Ser Ile Thr Ser Asp
            20                  25                  30

Tyr Ala Trp Asn Trp Ile Arg Gln Phe Pro Gly Asn Lys Leu Glu Trp
        35                  40                  45

Met Gly Tyr Ile Thr Tyr Ser Gly Asn Ile Ser Tyr Asn Pro Ser Leu
    50                  55                  60

Arg Ser Arg Ile Ser Ile Thr Arg Asp Thr Ser Lys Asn Gln Phe Phe
65                  70                  75                  80

Leu Gln Leu Asn Ser Val Thr Pro Glu Asp Thr Ala Thr Tyr Ser Cys
                85                  90                  95

Ala Arg Ser Leu Tyr Tyr Pro Trp Tyr Phe Asp Val Trp Gly Ala Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365
```

-continued

Cys Leu Val Lys Gly Phe Tyr Pro Ser Asp Ile Ala Val Glu Trp Glu
 370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 213
<211> LENGTH: 214
<212> TYPE: PRT
<213> ORGANISM: Artificial Sequence
<220> FEATURE:
<223> OTHER INFORMATION: 4M2-C12 VL-Ckappa

<400> SEQUENCE: 213

Asp Ile Val Ile Thr Gln Thr Pro Ala Ile Leu Ser Thr Ser Pro Gly
1               5                   10                  15

Glu Lys Val Thr Met Thr Cys Arg Ala Ser Ser Ser Val Gly Tyr Ile
            20                  25                  30

His Trp Tyr Gln Gln Lys Pro Gly Ser Ser Pro Lys Pro Trp Ile Tyr
        35                  40                  45

Ala Thr Ser Asn Leu Ala Ser Gly Val Pro Ala Arg Phe Ser Gly Ser
    50                  55                  60

Gly Ser Gly Thr Ser Asn Ser Leu Thr Ile Thr Arg Val Glu Ala Glu
65                  70                  75                  80

Asp Ala Ala Thr Tyr Tyr Cys Gln Gln Trp Ser Ser Tyr Pro Pro Ile
                85                  90                  95

Thr Phe Gly Gly Gly Thr Lys Leu Glu Val Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 214
<211> LENGTH: 449
<212> TYPE: PRT
<213> ORGANISM: Artificial Sequence
<220> FEATURE:
<223> OTHER INFORMATION: 4M2-B4 VH-CH1-CH2-CH3

<400> SEQUENCE: 214

```
Glu Val Met Leu Val Glu Ser Gly Pro Gly Leu Val Lys Pro Ser Gln
1               5                   10                  15

Ser Leu Ser Leu Thr Cys Thr Val Thr Gly Tyr Ser Ile Thr Ser Asp
            20                  25                  30

Tyr Ala Trp Asn Trp Ile Arg Gln Phe Pro Gly Asn Lys Leu Glu Trp
        35                  40                  45

Met Gly Tyr Ile Thr Tyr Ser Gly Asn Ile Ser Tyr Asn Pro Ser Leu
    50                  55                  60

Arg Ser Arg Ile Ser Ile Thr Arg Asp Thr Ser Lys Asn Gln Phe Phe
65                  70                  75                  80

Leu Gln Leu Asn Ser Val Thr Pro Glu Asp Thr Ala Thr Tyr Ser Cys
                85                  90                  95

Ala Arg Ser Leu Tyr Tyr Pro Trp Tyr Phe Asp Val Trp Gly Ala Gly
            100                 105                 110

Thr Thr Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
    195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
    275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
```

```
                420             425             430
Ala Leu His Asn His Tyr Thr Gln Lys Ser Leu Ser Leu Ser Pro Gly
        435             440             445

Lys

<210> SEQ ID NO 215
<211> LENGTH: 214
<212> TYPE: PRT
<213> ORGANISM: Artificial Sequence
<220> FEATURE:
<223> OTHER INFORMATION: 4M2-B4 VL-Ckappa

<400> SEQUENCE: 215

Asp Ile Val Leu Thr Gln Thr Thr Ala Ile Leu Ser Thr Ser Pro Gly
1               5                   10                  15

Glu Lys Val Thr Met Thr Cys Arg Ala Ser Ser Ser Val Gly Tyr Ile
            20                  25                  30

His Trp Tyr Gln Gln Lys Pro Gly Ser Ser Pro Lys Pro Trp Ile Tyr
        35                  40                  45

Ala Thr Ser Asn Leu Ala Ser Gly Val Pro Ala Arg Phe Ser Gly Ser
    50                  55                  60

Gly Ser Gly Thr Ser Asn Ser Leu Thr Ile Thr Arg Val Glu Ala Glu
65                  70                  75                  80

Asp Ala Ala Thr Tyr Tyr Cys Gln Gln Trp Ser Ser Tyr Pro Pro Ile
                85                  90                  95

Thr Phe Gly Gly Gly Thr Lys Leu Glu Val Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 216
<211> LENGTH: 449
<212> TYPE: PRT
<213> ORGANISM: Artificial Sequence
<220> FEATURE:
<223> OTHER INFORMATION: V4H1 VH-CH1-CH2-CH3

<400> SEQUENCE: 216

Glu Val Gln Leu Leu Glu Ser Gly Gly Gly Leu Val Gln Pro Gly Gly
1               5                   10                  15

Ser Leu Arg Leu Ser Cys Ala Ala Ser Gly Tyr Thr Ile Thr Ser Asp
            20                  25                  30

Tyr Ala Met Ser Trp Val Arg Gln Ala Pro Gly Lys Gly Leu Glu Trp
        35                  40                  45

Val Ser Val Ile Thr Tyr Ser Gly Asn Ile Ser Tyr Ala Asp Ser Val
```

```
                50              55              60
Lys Gly Arg Phe Thr Ile Ser Arg Asp Asn Ser Lys Asn Thr Leu Tyr
 65                      70                  75                  80

Leu Gln Met Asn Ser Leu Arg Ala Glu Asp Thr Ala Val Tyr Tyr Cys
                    85                  90                  95

Ala Arg Ser Leu Tyr Tyr Pro Trp Tyr Phe Asp Val Trp Gly Ala Gly
                100                 105                 110

Thr Thr Val Thr Val Ser Ser Ala Ser Thr Lys Gly Pro Ser Val Phe
                115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
                195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
                290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
                355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445

Lys

<210> SEQ ID NO 217
<211> LENGTH: 214
```

<212> TYPE: PRT
<213> ORGANISM: Artificial Sequence
<220> FEATURE:
<223> OTHER INFORMATION: V4H1 VL-Ckappa

<400> SEQUENCE: 217

Glu Ile Val Ile Thr Gln Ser Pro Ala Thr Leu Ser Leu Ser Pro Gly
1               5                   10                  15

Glu Arg Ala Thr Leu Ser Cys Arg Ala Ser Ser Val Gly Tyr Leu
            20                  25                  30

Ala Trp Tyr Gln Gln Lys Pro Gly Gln Ala Pro Arg Pro Leu Ile Tyr
        35                  40                  45

Asp Thr Ser Asn Arg Ala Thr Gly Ile Pro Ala Arg Phe Ser Gly Ser
    50                  55                  60

Gly Ser Gly Thr Asp Asn Thr Leu Thr Ile Ser Ser Leu Glu Pro Glu
65                  70                  75                  80

Asp Phe Ala Val Tyr Tyr Cys Gln Gln Trp Ser Ser Tyr Pro Pro Ile
                85                  90                  95

Thr Phe Gly Gly Gly Thr Lys Leu Glu Val Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 218
<211> LENGTH: 449
<212> TYPE: PRT
<213> ORGANISM: Artificial Sequence
<220> FEATURE:
<223> OTHER INFORMATION: V4H2 VH-CH1-CH2-CH3

<400> SEQUENCE: 218

Gln Val Gln Leu Gln Glu Ser Gly Pro Gly Leu Val Lys Pro Ser Asp
1               5                   10                  15

Thr Leu Ser Leu Thr Cys Thr Val Ser Gly Tyr Ser Ile Thr Ser Asp
            20                  25                  30

Tyr Ala Trp Ser Trp Ile Arg Gln Pro Pro Gly Lys Gly Leu Glu Trp
        35                  40                  45

Ile Gly Tyr Ile Thr Tyr Ser Gly Asn Ile Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Asp Cys
                85                  90                  95

Ala Arg Ser Leu Tyr Tyr Pro Trp Tyr Phe Asp Val Trp Gly Ala Gly
            100                 105                 110

```
Thr Thr Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 219
<211> LENGTH: 214
<212> TYPE: PRT
<213> ORGANISM: Artificial Sequence
<220> FEATURE:
<223> OTHER INFORMATION: V4H2 VL-Ckappa

<400> SEQUENCE: 219

Asp Ile Gln Met Thr Gln Ser Pro Ser Ser Leu Ser Ala Ser Val Gly
1               5                   10                  15
```

Asp Arg Val Thr Ile Thr Cys Arg Ala Ser Ser Val Gly Tyr Leu
            20                  25                  30

Asn Trp Tyr Gln Gln Lys Pro Gly Lys Ala Pro Lys Pro Leu Ile Tyr
        35                  40                  45

Ala Ala Ser Ser Leu Gln Ser Gly Val Pro Ser Arg Phe Ser Gly Ser
    50                  55                  60

Gly Ser Gly Thr Asp Asn Thr Leu Thr Ile Ser Ser Leu Gln Pro Glu
65                  70                  75                  80

Asp Phe Ala Thr Tyr Tyr Cys Gln Gln Trp Ser Ser Tyr Pro Pro Ile
                85                  90                  95

Thr Phe Gly Gly Gly Thr Lys Leu Glu Val Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 220
<211> LENGTH: 451
<212> TYPE: PRT
<213> ORGANISM: Artificial Sequence
<220> FEATURE:
<223> OTHER INFORMATION: 2M1-B12 VH-CH1-CH2-CH3

<400> SEQUENCE: 220

Glu Val Gln Leu Gln Gln Ser Gly Ala Glu Leu Val Arg Pro Gly Thr
1               5                   10                  15

Ser Val Lys Thr Ser Cys Lys Ala Ser Gly Tyr Thr Phe Thr Asn Tyr
            20                  25                  30

Trp Leu Gly Trp Val Lys Glu Arg Ala Gly His Gly Leu Glu Trp Ile
        35                  40                  45

Gly Glu Ile Phe Pro Gly Gly Gly His Thr Asn Tyr Lys Glu Lys Phe
    50                  55                  60

Lys Gly Lys Ala Thr Leu Thr Ala Asp Thr Ser Ser Ser Thr Ala Tyr
65                  70                  75                  80

Met Lys Leu Ser Ser Leu Thr Ser Glu Asp Ser Ala Val Tyr Phe Cys
                85                  90                  95

Ala Gln Ile Pro Leu Tyr Tyr Gly His Tyr Arg Ser Ala Tyr Trp Gly
            100                 105                 110

Gln Gly Thr Leu Val Thr Val Ser Ala Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

```
Ser Trp Asn Ser Gly Ala Leu Thr Ser Gly Val His Thr Phe Pro Ala
            165                 170                 175
Val Leu Gln Ser Ser Gly Leu Tyr Ser Leu Ser Ser Val Val Thr Val
        180                 185                 190
Pro Ser Ser Ser Leu Gly Thr Gln Thr Tyr Ile Cys Asn Val Asn His
        195                 200                 205
Lys Pro Ser Asn Thr Lys Val Asp Lys Lys Val Glu Pro Lys Ser Cys
    210                 215                 220
Asp Lys Thr His Thr Cys Pro Pro Cys Pro Ala Pro Glu Leu Leu Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
            260                 265                 270
Glu Asp Pro Glu Val Lys Phe Asn Trp Tyr Val Asp Gly Val Glu Val
        275                 280                 285
His Asn Ala Lys Thr Lys Pro Arg Glu Glu Gln Tyr Asn Ser Thr Tyr
        290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
            340                 345                 350
Tyr Thr Leu Pro Pro Ser Arg Asp Glu Leu Thr Lys Asn Gln Val Ser
        355                 360                 365
Leu Thr Cys Leu Val Lys Gly Phe Tyr Pro Ser Asp Ile Ala Val Glu
    370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
            420                 425                 430
His Glu Ala Leu His Asn His Tyr Thr Gln Lys Ser Leu Ser Leu Ser
        435                 440                 445
Pro Gly Lys
    450

<210> SEQ ID NO 221
<211> LENGTH: 214
<212> TYPE: PRT
<213> ORGANISM: Artificial Sequence
<220> FEATURE:
<223> OTHER INFORMATION: 2M1-B12 VL-Ckappa

<400> SEQUENCE: 221

Asp Ile Gln Met Met Gln Ser Pro Ala Ser Leu Ser Ala Ser Val Gly
1               5                   10                  15
Glu Thr Val Ala Ile Thr Cys Gly Ala Ser Glu Asn Ile Tyr Gly Ala
            20                  25                  30
Leu Asn Trp Tyr Gln Arg Lys Gln Gly Lys Ser Pro Gln Leu Leu Ile
        35                  40                  45
Tyr Gly Ala Thr Asn Leu Ala Asp Gly Met Ser Ser Arg Phe Ser Gly
    50                  55                  60
```

```
Ser Gly Ser Gly Arg Gln Tyr Ser Leu Lys Ile Ser Ser Leu His Pro
 65                  70                  75                  80

Asp Asp Val Ala Thr Tyr Tyr Cys Gln Asn Val Leu Ser Thr Pro Tyr
                 85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
    210
```

<210> SEQ ID NO 222
<211> LENGTH: 453
<212> TYPE: PRT
<213> ORGANISM: Artificial Sequence
<220> FEATURE:
<223> OTHER INFORMATION: 4M2-C9 VH-CH1-CH2-CH3

<400> SEQUENCE: 222

```
Gln Val Thr Leu Lys Glu Cys Gly Pro Gly Ile Leu Gln Pro Ser Gln
 1               5                  10                  15

Thr Leu Ser Leu Thr Cys Ser Phe Ser Gly Phe Ser Leu Ser Thr Ser
            20                  25                  30

Gly Met Gly Val Ser Trp Ile Arg Gln Pro Ser Gly Lys Gly Leu Glu
        35                  40                  45

Trp Leu Ala His Ile Tyr Trp Asp Asp Asp Lys Arg Tyr Asn Pro Ser
 50                  55                  60

Leu Lys Ser Arg Leu Thr Ile Ser Lys Asp Ser Ser Ser Asn Gln Val
 65                  70                  75                  80

Phe Leu Lys Ile Thr Ser Val Asp Thr Ala Asp Thr Ala Thr Tyr Tyr
                 85                  90                  95

Cys Ala Arg Arg Leu Asp Gly Tyr Asn Asp Pro Tyr Tyr Phe Asp Tyr
            100                 105                 110

Trp Gly Gln Gly Thr Thr Leu Thr Val Ser Ser Ala Ser Thr Lys Gly
            115                 120                 125

Pro Ser Val Phe Pro Leu Ala Pro Ser Ser Lys Ser Thr Ser Gly Gly
            130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
                180                 185                 190

Thr Val Pro Ser Ser Ser Leu Gly Thr Gln Thr Tyr Ile Cys Asn Val
            195                 200                 205
```

```
Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 223
<211> LENGTH: 214
<212> TYPE: PRT
<213> ORGANISM: Artificial Sequence
<220> FEATURE:
<223> OTHER INFORMATION: 4M2-C9 VL-Ckappa

<400> SEQUENCE: 223

Asp Ile Val Met Thr Gln Ser Pro Ser Ser Leu Ser Ala Ser Leu Gly
1               5                   10                  15

Asp Thr Val Thr Ile Thr Cys His Ala Ser Gln Asn Val Asn Val Trp
            20                  25                  30

Leu Ser Trp Tyr Gln Gln Lys Pro Gly Asn Ile Pro Lys Leu Leu Ile
        35                  40                  45

Tyr Lys Ala Ser Asn Leu His Ala Gly Val Pro Ser Arg Phe Ser Gly
    50                  55                  60

Ser Gly Ser Gly Thr Gly Phe Thr Leu Thr Ile Ser Ser Leu Gln Pro
65                  70                  75                  80

Glu Asp Ile Ala Thr Tyr Tyr Cys Gln Gln Gly Gln Ser Tyr Pro Leu
                85                  90                  95

Thr Phe Gly Gly Gly Thr Lys Leu Glu Ile Lys Arg Thr Val Ala Ala
            100                 105                 110
```

```
Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
        210

<210> SEQ ID NO 224
<211> LENGTH: 451
<212> TYPE: PRT
<213> ORGANISM: Artificial Sequence
<220> FEATURE:
<223> OTHER INFORMATION: 2M1-D2 VH-CH1-CH2-CH3

<400> SEQUENCE: 224

Gln Val Gln Leu Gln Gln Ser Gly Ala Glu Leu Val Arg Pro Gly Thr
1               5                   10                  15

Ser Val Lys Ile Ser Cys Lys Ala Ser Gly Tyr Thr Phe Thr Asn Tyr
                20                  25                  30

Trp Leu Gly Trp Val Lys Glu Arg Ala Gly His Gly Leu Glu Trp Ile
            35                  40                  45

Gly Glu Ile Phe Pro Gly Gly His Thr Asn Tyr Lys Glu Lys Phe
        50                  55                  60

Lys Gly Lys Ala Thr Leu Thr Ala Asp Thr Ser Ser Ser Thr Ala Tyr
65                  70                  75                  80

Met Lys Leu Ser Ser Leu Thr Ser Glu Asp Ser Ala Val Tyr Phe Cys
                85                  90                  95

Ala Gln Ile Pro Leu Tyr Tyr Gly His Tyr Arg Ser Ala Tyr Trp Gly
                100                 105                 110

Gln Gly Thr Leu Val Thr Val Ser Ala Ala Ser Thr Lys Gly Pro Ser
        115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
                195                 200                 205

Lys Pro Ser Asn Thr Lys Val Asp Lys Val Glu Pro Lys Ser Cys
        210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255
```

```
Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
            290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
            370                 375                 380

Trp Glu Ser Asn Gly Gln Pro Glu Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450

<210> SEQ ID NO 225
<211> LENGTH: 214
<212> TYPE: PRT
<213> ORGANISM: Artificial Sequence
<220> FEATURE:
<223> OTHER INFORMATION: 2M1-D2 VL-Ckappa

<400> SEQUENCE: 225

Asp Ile Val Met Thr Gln Ser Pro Ala Ser Leu Ser Ala Ser Val Gly
1               5                   10                  15

Glu Thr Val Ala Ile Thr Cys Gly Ala Ser Glu Asn Ile Tyr Gly Ala
            20                  25                  30

Leu Asn Trp Tyr Gln Arg Lys Gln Gly Lys Ser Pro Gln Leu Leu Ile
            35                  40                  45

Tyr Gly Ala Thr Asn Leu Ala Asp Gly Met Ser Ser Arg Phe Ser Gly
    50                  55                  60

Ser Gly Ser Gly Arg Gln Tyr Ser Leu Lys Ile Ser Ser Leu His Pro
65                  70                  75                  80

Asp Asp Val Ala Thr Tyr Tyr Cys Gln Asn Val Leu Ser Thr Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160
```

```
Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 226
<211> LENGTH: 451
<212> TYPE: PRT
<213> ORGANISM: Artificial Sequence
<220> FEATURE:
<223> OTHER INFORMATION: 4M2-D9 VH-CH1-CH2-CH3

<400> SEQUENCE: 226

Glu Val Gln Leu Gln Glu Ser Gly Pro Gly Leu Val Lys Pro Ser Gln
1               5                   10                  15

Ser Leu Ser Leu Thr Cys Thr Val Thr Gly Tyr Ser Ile Thr Ser Asp
                20                  25                  30

Tyr Ala Trp Asn Trp Ile Arg Gln Phe Pro Gly Asn Arg Leu Glu Trp
            35                  40                  45

Met Gly Phe Ile Ser Tyr Ser Gly Phe Thr Thr Tyr Ser Pro Ser Leu
    50                  55                  60

Glu Ser Arg Ile Ser Ile Thr Arg Asp Thr Ser Lys Asn Gln Phe Phe
65                  70                  75                  80

Leu Gln Leu Ile Ser Val Thr Thr Glu Asp Thr Ala Thr Tyr Tyr Cys
                85                  90                  95

Ala Arg Asn His Tyr Gly Gly Ser Tyr Trp Tyr Phe Asp Val Trp Gly
            100                 105                 110

Ala Gly Thr Ser Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300
```

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
            325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450

<210> SEQ ID NO 227
<211> LENGTH: 218
<212> TYPE: PRT
<213> ORGANISM: Artificial Sequence
<220> FEATURE:
<223> OTHER INFORMATION: 4M2-D9 VL-Ckappa

<400> SEQUENCE: 227

Asp Ile Val Met Thr Gln Ser Pro Gly Ser Leu Ala Val Ser Leu Gly
1               5                   10                  15

Gln Arg Ala Thr Ile Ser Cys Arg Ala Ser Glu Ser Val Glu Tyr Tyr
            20                  25                  30

Gly Thr Ser Leu Met Gln Trp Tyr Leu Gln Lys Pro Gly Gln Pro Pro
        35                  40                  45

Lys Leu Leu Ile Tyr Ala Ala Ser Asn Val Glu Ser Gly Val Pro Asp
    50                  55                  60

Arg Phe Arg Gly Ser Gly Ser Gly Thr Asp Phe Ser Leu Asn Ile His
65                  70                  75                  80

Pro Val Glu Glu Asp Asp Ile Ala Met Tyr Phe Cys Gln Gln Ser Arg
                85                  90                  95

Lys Val Pro Trp Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
            195                 200                 205

```
Val Thr Lys Ser Phe Asn Arg Gly Glu Cys
    210                 215
```

<210> SEQ ID NO 228
<211> LENGTH: 449
<212> TYPE: PRT
<213> ORGANISM: Artificial Sequence
<220> FEATURE:
<223> OTHER INFORMATION: 1M2-D2 VH-CH1-CH2-CH3

<400> SEQUENCE: 228

```
Glu Val Lys Val Glu Glu Ser Gly Gly Gly Leu Val Gln Pro Gly Gly
1               5                   10                  15

Ser Met Lys Leu Ser Cys Ala Ala Ser Gly Phe Thr Phe Ser Asp Ala
            20                  25                  30

Trp Met Asp Trp Val His Gln Ser Pro Glu Lys Gly Leu Glu Trp Val
        35                  40                  45

Ala Glu Ile Arg Ser Lys Ala Asn Asn His Ala Thr Tyr Tyr Val Glu
    50                  55                  60

Ser Val Glu Gly Arg Phe Thr Ile Ser Arg Asp Asp Ser Lys Ser Ser
65                  70                  75                  80

Val Phe Leu Gln Val Asn Ser Leu Arg Pro Glu Asp Thr Gly Ile Tyr
            85                  90                  95

Tyr Cys Thr Arg Arg Asp Gly Tyr Tyr Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
        180                 185                 190

Ser Ser Leu Gly Thr Gln Thr Tyr Ile Cys Asn Val Asn His Lys Pro
    195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350
```

```
Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
            435                 440                 445

Lys

<210> SEQ ID NO 229
<211> LENGTH: 212
<212> TYPE: PRT
<213> ORGANISM: Artificial Sequence
<220> FEATURE:
<223> OTHER INFORMATION: 1M2-D2 VL-Ckappa

<400> SEQUENCE: 229

Asp Ile Val Leu Thr Gln Ser Pro Ala Ile Met Ser Ala Ser Leu Gly
1               5                   10                  15

Glu Glu Ile Thr Leu Thr Cys Ser Ala Ser Ser Ser Val Arg Asp Met
                20                  25                  30

His Trp Tyr Gln Gln Lys Ser Gly Thr Ser Pro Lys Val Leu Ile Tyr
            35                  40                  45

Asn Thr Phe Asn Leu Ala Ser Gly Val Pro Ser Arg Phe Ser Gly Ser
        50                  55                  60

Gly Ser Gly Thr Phe Tyr Ser Leu Thr Ile Ser Ser Val Glu Ala Gly
65                  70                  75                  80

Asp Ala Ala Thr Tyr Cys His Gln Trp Ser Tyr Pro Thr Phe
                85                  90                  95

Gly Gly Gly Thr Lys Leu Glu Ile Lys Arg Thr Val Ala Ala Pro Ser
                100                 105                 110

Val Phe Ile Phe Pro Pro Ser Asp Glu Gln Leu Lys Ser Gly Thr Ala
            115                 120                 125

Ser Val Val Cys Leu Leu Asn Asn Phe Tyr Pro Arg Glu Ala Lys Val
        130                 135                 140

Gln Trp Lys Val Asp Asn Ala Leu Gln Ser Gly Asn Ser Gln Glu Ser
145                 150                 155                 160

Val Thr Glu Gln Asp Ser Lys Asp Ser Thr Tyr Ser Leu Ser Ser Thr
                165                 170                 175

Leu Thr Leu Ser Lys Ala Asp Tyr Glu Lys His Lys Val Tyr Ala Cys
            180                 185                 190

Glu Val Thr His Gln Gly Leu Ser Ser Pro Val Thr Lys Ser Phe Asn
        195                 200                 205

Arg Gly Glu Cys
    210

<210> SEQ ID NO 230
<211> LENGTH: 453
<212> TYPE: PRT
<213> ORGANISM: Artificial Sequence
<220> FEATURE:
<223> OTHER INFORMATION: 5M1-A11 VH-CH1-CH2-CH3
```

<400> SEQUENCE: 230

```
Gln Val Thr Leu Lys Val Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Gly Met Gly Val Ser Trp Ile Arg Gln Pro Ser Gly Lys Gly Leu Glu
        35                  40                  45

Trp Leu Ala His Ile Tyr Trp Asp Asp Lys Arg Tyr Asn Pro Ser
    50                  55                  60

Leu Lys Ser Arg Leu Thr Ile Ser Lys Asp Ser Ser Asn Gln Val
65                  70                  75                  80

Phe Leu Lys Ile Thr Ser Val Asp Thr Ala Asp Thr Ala Thr Tyr Tyr
                85                  90                  95

Cys Ala Arg Arg Leu Asp Gly Tyr Asn Asp Pro Tyr Tyr Phe Asp Tyr
            100                 105                 110

Trp Gly Gln Gly Thr Thr Leu Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
```

```
                405                 410                 415
Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
            435                 440                 445

Leu Ser Pro Gly Lys
        450

<210> SEQ ID NO 231
<211> LENGTH: 213
<212> TYPE: PRT
<213> ORGANISM: Artificial Sequence
<220> FEATURE:
<223> OTHER INFORMATION: 5M1-A11 VL-Ckappa

<400> SEQUENCE: 231

Asp Val Val Met Thr Gln Thr Pro Ala Leu Met Ser Ala Ser Pro Gly
1               5                   10                  15

Glu Lys Val Thr Met Thr Cys Ser Ala Ser Ser Ser Val Ser Tyr Met
            20                  25                  30

Tyr Trp Tyr Gln Gln Lys Pro Arg Ser Ser Pro Lys Pro Trp Ile Tyr
        35                  40                  45

Leu Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Asn Ser Asn Pro Tyr Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 232
<211> LENGTH: 448
<212> TYPE: PRT
<213> ORGANISM: Artificial Sequence
<220> FEATURE:
<223> OTHER INFORMATION: 4M2-D5 VH-CH1-CH2-CH3

<400> SEQUENCE: 232

Gln Val Gln Leu Gln Gln Ser Gly Ala Glu Leu Ala Arg Pro Gly Ala
1               5                   10                  15

Ser Val Arg Met Ser Cys Lys Ala Ser Gly Tyr Thr Phe Thr Ser Tyr
            20                  25                  30
```

```
Thr Met Asn Trp Val Lys Gln Arg Pro Gly Gln Gly Leu Glu Trp Ile
    35                  40                  45
Gly Phe Ile Asn Pro Asp Ser Asp Tyr Thr Thr Tyr Asp Gln Lys Phe
50                  55                  60
Lys Asp Lys Ala Thr Leu Thr Ala Asp Ser Ser Ser Thr Ala Tyr
65                  70                  75                  80
Met Gln Leu Ser Ser Leu Thr Tyr Asp Asp Ser Ala Val Tyr Tyr Cys
            85                  90                  95
Thr Arg His Ser Tyr Gly Asn Tyr Gly Asp Tyr Trp Gly Gln Gly Thr
            100                 105                 110
Thr Leu Thr Val Ser Ser Ala Ser Thr Lys Gly Pro Ser Val Phe Pro
            115                 120                 125
Leu Ala Pro Ser Ser Lys Ser Thr Ser Gly Gly Thr Ala Ala Leu Gly
130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Ser Val Val Thr Val Pro Ser Ser
            180                 185                 190
Ser Leu Gly Thr Gln Thr Tyr Ile Cys Asn Val Asn His Lys Pro Ser
            195                 200                 205
Asn Thr Lys Val Asp Lys Lys Val Glu Pro Lys Ser Cys Asp Lys Thr
            210                 215                 220
His Thr Cys Pro Pro Cys Pro Ala Pro Glu Leu Leu Gly Gly Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Val Asp Val Ser His Glu Asp Pro
                260                 265                 270
Glu Val Lys Phe Asn Trp Tyr Val Asp Gly Val Glu Val His Asn Ala
            275                 280                 285
Lys Thr Lys Pro Arg Glu Glu Gln Tyr Asn Ser Thr Tyr Arg Val Val
            290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Pro Ala Pro Ile Glu Lys Thr
                325                 330                 335
Ile Ser Lys Ala Lys Gly Gln Pro Arg Glu Pro Gln Val Tyr Thr Leu
                340                 345                 350
Pro Pro Ser Arg Asp Glu Leu Thr Lys Asn Gln Val Ser Leu Thr Cys
            355                 360                 365
Leu Val Lys Gly Phe Tyr Pro Ser Asp Ile Ala Val Glu Trp Glu Ser
            370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Met His Glu Ala
                420                 425                 430
Leu His Asn His Tyr Thr Gln Lys Ser Leu Ser Leu Ser Pro Gly Lys
            435                 440                 445
```

```
<210> SEQ ID NO 233
<211> LENGTH: 214
<212> TYPE: PRT
<213> ORGANISM: Artificial Sequence
<220> FEATURE:
<223> OTHER INFORMATION: 4M2-D5 VL-Ckappa

<400> SEQUENCE: 233

Asp Ile Val Leu Thr Gln Ser Pro Lys Phe Leu Leu Val Ser Ala Gly
1               5                   10                  15

Asp Arg Val Thr Ile Thr Cys Lys Ala Ser Gln Ser Val Thr Asn Asp
            20                  25                  30

Val Ala Trp Tyr Gln Gln Lys Pro Gly Gln Ser Pro Lys Leu Leu Ile
        35                  40                  45

Tyr Tyr Ala Ser Ser Arg Tyr Thr Gly Val Pro Asp Arg Phe Thr Gly
    50                  55                  60

Ser Gly Phe Gly Thr Asp Phe Thr Phe Thr Ile Asn Thr Val Gln Ala
65                  70                  75                  80

Glu Asp Leu Ala Val Tyr Phe Cys Gln Gln Asp Tyr Ser Ser Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 234
<211> LENGTH: 448
<212> TYPE: PRT
<213> ORGANISM: Artificial Sequence
<220> FEATURE:
<223> OTHER INFORMATION: 4M2-A8 VH-CH1-CH2-CH3

<400> SEQUENCE: 234

Gln Val Gln Leu Gln Gln Ser Gly Ala Asp Leu Ala Arg Pro Gly Ala
1               5                   10                  15

Ser Val Lys Met Ser Cys Lys Ala Ser Gly Tyr Thr Phe Ile Asp Tyr
            20                  25                  30

Thr Val His Trp Val Lys Gln Arg Pro Gly Gln Gly Leu Glu Trp Ile
        35                  40                  45

Gly Phe Ile Asn Pro Ser Asn Asp Tyr Thr Ser Tyr Asn Gln Lys Phe
    50                  55                  60

Lys Asp Lys Ala Ser Leu Thr Ala Asp Thr Ser Ser Thr Thr Ala Tyr
65                  70                  75                  80

Met Gln Leu Ser Ser Leu Thr Ser Asp Asp Ser Ala Val Tyr Tyr Cys
                85                  90                  95
```

Ala Arg His Ser Tyr Gly Asn Tyr Gly Asp Tyr Trp Gly Gln Gly Thr
            100                 105                 110

Thr Leu Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 235
<211> LENGTH: 214
<212> TYPE: PRT
<213> ORGANISM: Artificial Sequence
<220> FEATURE:
<223> OTHER INFORMATION: 4M2-A8 VL-Ckappa

<400> SEQUENCE: 235

Asp Ile Val Met Thr Gln Ala Pro Lys Phe Leu Leu Val Ser Ala Gly
1               5                   10                  15

Asp Arg Val Thr Ile Thr Cys Lys Ala Ser Gln Ser Val Thr Asn Gly
            20                  25                  30

Val Ala Trp Tyr Gln Gln Lys Pro Gly Gln Ser Pro Lys Leu Leu Ile
            35                  40                  45

Tyr Tyr Ala Ser Asn Arg Tyr Thr Gly Val Pro Asp Arg Phe Thr Gly
50                      55                  60

Ser Gly Phe Gly Thr Asp Phe Thr Phe Thr Ile Ser Thr Val Gln Ala
65                  70                  75                  80

Glu Asp Leu Ala Val Tyr Phe Cys Gln Gln Asp Tyr Ser Ser Pro Tyr
                85                  90                  95

Thr Phe Gly Gly Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
            210

<210> SEQ ID NO 236
<211> LENGTH: 449
<212> TYPE: PRT
<213> ORGANISM: Artificial Sequence
<220> FEATURE:
<223> OTHER INFORMATION: 9M2-C12 VH-CH1-CH2-CH3

<400> SEQUENCE: 236

Gln Val Gln Leu Gln Gln Ser Gly Ala Glu Leu Val Lys Pro Gly Ala
1               5                   10                  15

Ser Val Arg Leu Ser Cys Lys Ala Ser Gly Tyr Thr Phe Thr Ser Tyr
            20                  25                  30

Trp Met His Trp Val Arg Gln Arg Pro Gly Leu Gly Leu Glu Trp Ile
            35                  40                  45

Gly Glu Ile Asp Pro Ser Asp Ser Tyr Thr Asn Cys Asn Gln Arg Phe
50                  55                  60

Lys Gly Lys Ala Thr Leu Thr Val Asp Lys Ser Ser Ser Thr Ala Tyr
65                  70                  75                  80

Thr Gln Leu Ser Ser Leu Thr Ser Glu Asp Ser Ala Val Tyr Tyr Cys
                85                  90                  95

Ala Arg Trp Ala Tyr Gly Pro Tyr Ala Met Asp Tyr Trp Gly Gln Gly
                100                 105                 110

Thr Ser Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

-continued

```
Asn Ser Gly Ala Leu Thr Ser Gly Val His Thr Phe Pro Ala Val Leu
            165                 170                 175
Gln Ser Ser Gly Leu Tyr Ser Leu Ser Ser Val Val Thr Val Pro Ser
        180                 185                 190
Ser Ser Leu Gly Thr Gln Thr Tyr Ile Cys Asn Val Asn His Lys Pro
    195                 200                 205
Ser Asn Thr Lys Val Asp Lys Lys Val Glu Pro Lys Ser Cys Asp Lys
210                 215                 220
Thr His Thr Cys Pro Pro Cys Pro Ala Pro Glu Leu Leu Gly Gly Pro
225                 230                 235                 240
Ser Val Phe Leu Phe Pro Pro Lys Pro Lys Asp Thr Leu Met Ile Ser
            245                 250                 255
Arg Thr Pro Glu Val Thr Cys Val Val Val Asp Val Ser His Glu Asp
        260                 265                 270
Pro Glu Val Lys Phe Asn Trp Tyr Val Asp Gly Val Glu Val His Asn
    275                 280                 285
Ala Lys Thr Lys Pro Arg Glu Glu Gln Tyr Asn Ser Thr Tyr Arg Val
290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
            325                 330                 335
Thr Ile Ser Lys Ala Lys Gly Gln Pro Arg Glu Pro Gln Val Tyr Thr
        340                 345                 350
Leu Pro Pro Ser Arg Asp Glu Leu Thr Lys Asn Gln Val Ser Leu Thr
    355                 360                 365
Cys Leu Val Lys Gly Phe Tyr Pro Ser Asp Ile Ala Val Glu Trp Glu
370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
            405                 410                 415
Ser Arg Trp Gln Gln Gly Asn Val Phe Ser Cys Ser Val Met His Glu
        420                 425                 430
Ala Leu His Asn His Tyr Thr Gln Lys Ser Leu Ser Leu Ser Pro Gly
    435                 440                 445
Lys

<210> SEQ ID NO 237
<211> LENGTH: 219
<212> TYPE: PRT
<213> ORGANISM: Artificial Sequence
<220> FEATURE:
<223> OTHER INFORMATION: 9M2-C12 VL-Ckappa

<400> SEQUENCE: 237

Asp Ile Val Met Thr Gln Thr Pro Leu Ser Leu Pro Val Ser Leu Gly
1               5                   10                  15
Asp Gln Ala Ser Ile Ser Cys Arg Ser Ser Gln Ser Leu Val His Ser
            20                  25                  30
Asn Gly Asn Thr Tyr Leu His Trp Tyr Leu Gln Lys Pro Gly Gln Ser
        35                  40                  45
Pro Lys Leu Leu Ile Tyr Lys Val Ser Asn Arg Phe Ser Gly Val Pro
    50                  55                  60
Asp Arg Phe Ser Gly Ser Gly Ser Gly Thr Asp Phe Thr Leu Lys Ile
```

```
                65                  70                  75                  80
Ser Arg Val Glu Ala Glu Asp Leu Gly Val Tyr Phe Cys Ser Gln Ser
                    85                  90                  95

Thr His Val Pro Trp Thr Phe Gly Gly Gly Thr Lys Leu Glu Ile Lys
                100                 105                 110

Arg Thr Val Ala Ala Pro Ser Val Phe Ile Phe Pro Pro Ser Asp Glu
                115                 120                 125

Gln Leu Lys Ser Gly Thr Ala Ser Val Val Cys Leu Leu Asn Asn Phe
            130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
                195                 200                 205

Pro Val Thr Lys Ser Phe Asn Arg Gly Glu Cys
                210                 215

<210> SEQ ID NO 238
<211> LENGTH: 452
<212> TYPE: PRT
<213> ORGANISM: Artificial Sequence
<220> FEATURE:
<223> OTHER INFORMATION: 13D5p VH-CH1-CH2-CH3

<400> SEQUENCE: 238

Gln Val Gln Leu Gln Gln Ser Gly Ala Glu Leu Val Arg Pro Gly Thr
1               5                   10                  15

Ser Val Lys Ile Ser Cys Lys Ala Ser Gly Tyr Thr Phe Thr Asn Tyr
                20                  25                  30

Trp Leu Gly Trp Val Lys Gln Arg Pro Gly His Gly Leu Glu Trp Ile
            35                  40                  45

Gly Asp Ile Tyr Pro Gly Gly Gly Tyr Thr Asn Tyr Asn Glu Lys Phe
        50                  55                  60

Lys Gly Lys Ala Thr Leu Thr Ala Asp Thr Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Gly Gly Tyr Tyr Tyr Gly Ser Ser Trp Tyr Phe Asp Val Trp
                100                 105                 110

Gly Ala Gly Thr Thr Val Thr Val Ser Ser Ala Ser Thr Lys Gly Pro
            115                 120                 125

Ser Val Phe Pro Leu Ala Pro Ser Ser Lys Ser Thr Ser Gly Gly Thr
        130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
                180                 185                 190

Val Pro Ser Ser Ser Leu Gly Thr Gln Thr Tyr Ile Cys Asn Val Asn
                195                 200                 205

His Lys Pro Ser Asn Thr Lys Val Asp Lys Lys Val Glu Pro Lys Ser
```

```
            210                 215                 220
Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
                260                 265                 270

His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser Thr
        290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
                340                 345                 350

Val Tyr Thr Leu Pro Pro Ser Arg Asp Glu Leu Thr Lys Asn Gln Val
            355                 360                 365

Ser Leu Thr Cys Leu Val Lys Gly Phe Tyr Pro Ser Asp Ile Ala Val
        370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
                420                 425                 430

Met His Glu Ala Leu His Asn His Tyr Thr Gln Lys Ser Leu Ser Leu
            435                 440                 445

Ser Pro Gly Lys
    450

<210> SEQ ID NO 239
<211> LENGTH: 219
<212> TYPE: PRT
<213> ORGANISM: Artificial Sequence
<220> FEATURE:
<223> OTHER INFORMATION: 13D5p VL-Ckappa

<400> SEQUENCE: 239

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Pro Thr Phe Gly Gly Gly Thr Lys Leu Glu Ile Lys
            100                 105                 110

Arg Thr Val Ala Ala Pro Ser Val Phe Ile Phe Pro Pro Ser Asp Glu
```

```
                    115                 120                 125
Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 240
<211> LENGTH: 452
<212> TYPE: PRT
<213> ORGANISM: Artificial Sequence
<220> FEATURE:
<223> OTHER INFORMATION: 13D5-1 VH-CH1-CH2-CH3

<400> SEQUENCE: 240

Gln Val Gln Leu Gln Gln Ser Gly Ala Glu Leu Val Arg Pro Gly Thr
1               5                   10                  15

Ser Val Lys Ile Ser Cys Lys Ala Ser Gly Tyr Thr Phe Thr Asn Tyr
                20                  25                  30

Trp Leu Gly Trp Val Lys Gln Arg Pro Gly His Gly Leu Glu Trp Ile
            35                  40                  45

Gly Asp Ile Tyr Pro Gly Gly Gly Tyr Thr Asn Tyr Asn Glu Lys Phe
        50                  55                  60

Lys Gly Lys Ala Thr Leu Thr Ala Asp Thr Ser Ser Ser Thr Ala Tyr
65                  70                  75                  80

Met Gln Leu Ser Ser Leu Thr Ser Glu Asp Ser Ala Val Tyr Phe Cys
                85                  90                  95

Val Arg Ser Gly Tyr Tyr Tyr Gly Ser Ser Trp Tyr Phe Asp Val Trp
                100                 105                 110

Gly Ala Gly Thr Thr Val Thr Val Ser Ser Ala Ser Thr Lys Gly Pro
            115                 120                 125

Ser Val Phe Pro Leu Ala Pro Ser Ser Lys Ser Thr Ser Gly Gly Thr
        130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
```

```
                260              265              270
His Glu Asp Pro Glu Val Lys Phe Asn Trp Tyr Val Asp Gly Val Glu
                275              280              285

Val His Asn Ala Lys Thr Lys Pro Arg Glu Glu Gln Tyr Asn Ser Thr
                290              295              300

Tyr Arg Val Val Ser Val Leu Thr Val Leu His Gln Asp Trp Leu Asn
305              310              315              320

Gly Lys Glu Tyr Lys Cys Lys Val Ser Asn Lys Ala Leu Pro Ala Pro
                325              330              335

Ile Glu Lys Thr Ile Ser Lys Ala Lys Gly Gln Pro Arg Glu Pro Gln
                340              345              350

Val Tyr Thr Leu Pro Pro Ser Arg Asp Glu Leu Thr Lys Asn Gln Val
                355              360              365

Ser Leu Thr Cys Leu Val Lys Gly Phe Tyr Pro Ser Asp Ile Ala Val
                370              375              380

Glu Trp Glu Ser Asn Gly Gln Pro Glu Asn Asn Tyr Lys Thr Thr Pro
385              390              395              400

Pro Val Leu Asp Ser Asp Gly Ser Phe Phe Leu Tyr Ser Lys Leu Thr
                405              410              415

Val Asp Lys Ser Arg Trp Gln Gln Gly Asn Val Phe Ser Cys Ser Val
                420              425              430

Met His Glu Ala Leu His Asn His Tyr Thr Gln Lys Ser Leu Ser Leu
                435              440              445

Ser Pro Gly Lys
    450

<210> SEQ ID NO 241
<211> LENGTH: 219
<212> TYPE: PRT
<213> ORGANISM: Artificial Sequence
<220> FEATURE:
<223> OTHER INFORMATION: 13D5-1 VL-Ckappa

<400> SEQUENCE: 241

Asp Val Leu Met Thr Gln Thr Pro Leu Ser Leu Pro Val Ser Leu Gly
1               5                10               15

Asp Gln Ala Ser Ile Ser Cys Arg Ser Ser Gln Ser Ile Val His Ser
                20               25               30

Ser Gly Asn Thr Tyr Leu Glu Trp Tyr Leu Gln Lys Pro Asp Gln Ser
                35               40               45

Pro Lys Leu Leu Ile Tyr Lys Val Ser Asn Arg Phe Ser Gly Val Pro
    50               55               60

Asp Arg Phe Ser Gly Ser Gly Ser Gly Thr Asp Phe Thr Leu Lys Ile
65               70               75               80

Ser Arg Val Glu Ala Glu Asp Leu Gly Val Tyr Tyr Cys Phe Gln Gly
                85               90               95

Ser His Val Pro Pro Thr Phe Gly Gly Gly Thr Lys Leu Glu Ile Lys
                100              105              110

Arg Thr Val Ala Ala Pro Ser Val Phe Ile Phe Pro Pro Ser Asp Glu
                115              120              125

Gln Leu Lys Ser Gly Thr Ala Ser Val Val Cys Leu Leu Asn Asn Phe
                130              135              140

Tyr Pro Arg Glu Ala Lys Val Gln Trp Lys Val Asp Asn Ala Leu Gln
145              150              155              160

Ser Gly Asn Ser Gln Glu Ser Val Thr Glu Gln Asp Ser Lys Asp Ser
```

165                 170                 175
Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
        210                 215

<210> SEQ ID NO 242
<211> LENGTH: 452
<212> TYPE: PRT
<213> ORGANISM: Artificial Sequence
<220> FEATURE:
<223> OTHER INFORMATION: 13D5-13 VH-CH1-CH2-CH3

<400> SEQUENCE: 242

Gln Val Gln Leu Gln Gln Ser Gly Ala Glu Leu Val Arg Pro Gly Thr
1               5                   10                  15

Ser Val Lys Ile Ser Cys Lys Ala Ser Gly Tyr Thr Phe Thr Asn Tyr
            20                  25                  30

Trp Leu Gly Trp Val Lys Gln Arg Pro Gly His Gly Leu Glu Trp Ile
        35                  40                  45

Gly Asp Ile Tyr Pro Gly Gly Gly Tyr Thr Asn Tyr Asn Glu Lys Phe
    50                  55                  60

Lys Gly Lys Ala Thr Leu Thr Ala Asp Ile Ser Ser Ser Thr Ala Tyr
65                  70                  75                  80

Met Gln Leu Ser Ser Leu Thr Ser Glu Asp Ser Ala Asp Tyr Phe Cys
                85                  90                  95

Val Arg Gly Gly Tyr Tyr Gly Ser Ser Trp Tyr Phe Asp Val Trp
            100                 105                 110

Gly Ala Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn

```
             305                 310                 315                 320
        Gly Lys Glu Tyr Lys Cys Lys Val Ser Asn Lys Ala Leu Pro Ala Pro
                         325                 330                 335

Ile Glu Lys Thr Ile Ser Lys Ala Lys Gly Gln Pro Arg Glu Pro Gln
                         340                 345                 350

Val Tyr Thr Leu Pro Pro Ser Arg Asp Glu Leu Thr Lys Asn Gln Val
                         355                 360                 365

Ser Leu Thr Cys Leu Val Lys Gly Phe Tyr Pro Ser Asp Ile Ala Val
                         370                 375                 380

Glu Trp Glu Ser Asn Gly Gln Pro Glu Asn Asn Tyr Lys Thr Thr Pro
        385                 390                 395                 400

Pro Val Leu Asp Ser Asp Gly Ser Phe Phe Leu Tyr Ser Lys Leu Thr
                         405                 410                 415

Val Asp Lys Ser Arg Trp Gln Gln Gly Asn Val Phe Ser Cys Ser Val
                         420                 425                 430

Met His Glu Ala Leu His Asn His Tyr Thr Gln Lys Ser Leu Ser Leu
                         435                 440                 445

Ser Pro Gly Lys
                    450

<210> SEQ ID NO 243
<211> LENGTH: 219
<212> TYPE: PRT
<213> ORGANISM: Artificial Sequence
<220> FEATURE:
<223> OTHER INFORMATION: 13D5-13 VL-Ckappa

<400> SEQUENCE: 243

Asp Val Leu Met Thr Gln Thr Pro Leu Ser Leu Pro Val Ser Leu Gly
        1               5                   10                  15

Asp Gln Ala Ser Ile Ser Cys Arg Ser Ser Gln Ser Thr Val His Ser
                         20                  25                  30

Ile Gly Asn Thr Tyr Leu Glu Trp Tyr Leu Gln Lys Pro Gly Gln Ser
                         35                  40                  45

Pro Lys Leu Leu Ile Tyr Lys Val Ser Asn Arg Phe Ser Gly Val Pro
                         50                  55                  60

Asp Arg Phe Ser Gly Ser Glu Ser Gly Thr Asp Phe Thr Leu Lys Ile
        65                  70                  75                  80

Ser Arg Val Glu Ala Glu Asp Leu Gly Val Tyr Tyr Cys Phe Gln Gly
                         85                  90                  95

Ser His Val Pro Pro Thr Phe Gly Gly Gly Thr Lys Leu Glu Ile Lys
                         100                 105                 110

Arg Thr Val Ala Ala Pro Ser Val Phe Ile Phe Pro Pro Ser Asp Glu
                         115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
        145                 150                 155                 160

Ser Gly Asn Ser Gln Glu Ser Val Thr Glu Gln Asp Ser Lys Asp Ser
                         165                 170                 175

Thr Tyr Ser Leu Ser Ser Thr Leu Thr Leu Ser Lys Ala Asp Tyr Glu
                         180                 185                 190

Lys His Lys Val Tyr Ala Cys Glu Val Thr His Gln Gly Leu Ser Ser
                         195                 200                 205

Pro Val Thr Lys Ser Phe Asn Arg Gly Glu Cys
```

<210> SEQ ID NO 244
<211> LENGTH: 9
<212> TYPE: PRT
<213> ORGANISM: Artificial Sequence
<220> FEATURE:
<223> OTHER INFORMATION: 4M2-C12 derived heavy chain CDR1 consensus
<220> FEATURE:
<221> NAME/KEY: MISC_FEATURE
<222> LOCATION: (3)..(3)
<223> OTHER INFORMATION: Xaa = S or T

<400> SEQUENCE: 244

Gly Tyr Xaa Ile Thr Ser Asp Tyr Ala
1               5

<210> SEQ ID NO 245
<211> LENGTH: 3
<212> TYPE: PRT
<213> ORGANISM: Artificial Sequence
<220> FEATURE:
<223> OTHER INFORMATION: 4M2-C12 derived light chain CDR2 consensus
<220> FEATURE:
<221> NAME/KEY: MISC_FEATURE
<222> LOCATION: (1)..(1)
<223> OTHER INFORMATION: Xaa = A or D
<220> FEATURE:
<221> NAME/KEY: MISC_FEATURE
<222> LOCATION: (2)..(2)
<223> OTHER INFORMATION: Xaa = T or A

<400> SEQUENCE: 245

Xaa Xaa Ser
1

<210> SEQ ID NO 246
<211> LENGTH: 15
<212> TYPE: PRT
<213> ORGANISM: Artificial Sequence
<220> FEATURE:
<223> OTHER INFORMATION: 13D5p derived heavy chain CDR3 consensus
<220> FEATURE:
<221> NAME/KEY: MISC_FEATURE
<222> LOCATION: (1)..(1)
<223> OTHER INFORMATION: Xaa = V or A
<220> FEATURE:
<221> NAME/KEY: MISC_FEATURE
<222> LOCATION: (3)..(3)
<223> OTHER INFORMATION: Xaa = G or S

<400> SEQUENCE: 246

Xaa Arg Xaa Gly Tyr Tyr Tyr Gly Ser Ser Trp Tyr Phe Asp Val
1               5                   10                  15

<210> SEQ ID NO 247
<211> LENGTH: 11
<212> TYPE: PRT
<213> ORGANISM: Artificial Sequence
<220> FEATURE:
<223> OTHER INFORMATION: 13D5p derived light chain CDR1 consensus
<220> FEATURE:
<221> NAME/KEY: MISC_FEATURE
<222> LOCATION: (3)..(3)
<223> OTHER INFORMATION: Xaa = I or T
<220> FEATURE:
<221> NAME/KEY: MISC_FEATURE
<222> LOCATION: (7)..(7)
<223> OTHER INFORMATION: Xaa = N, S or I

<400> SEQUENCE: 247

Gln Ser Xaa Val His Ser Xaa Gly Asn Thr Tyr
1               5                   10

<210> SEQ ID NO 248
<211> LENGTH: 449
<212> TYPE: PRT
<213> ORGANISM: Artificial Sequence
<220> FEATURE:
<223> OTHER INFORMATION: 4M2-C12 mIgG2a HC

<400> SEQUENCE: 248

Glu Val Lys Leu Val Glu Ser Gly Pro Gly Leu Val Lys Pro Ser Gln
1               5                   10                  15

Ser Leu Ser Leu Thr Cys Thr Val Thr Gly Tyr Ser Ile Thr Ser Asp
            20                  25                  30

Tyr Ala Trp Asn Trp Ile Arg Gln Phe Pro Gly Asn Lys Leu Glu Trp
        35                  40                  45

Met Gly Tyr Ile Thr Tyr Ser Gly Asn Ile Ser Tyr Asn Pro Ser Leu
    50                  55                  60

Arg Ser Arg Ile Ser Ile Thr Arg Asp Thr Ser Lys Asn Gln Phe Phe
65                  70                  75                  80

Leu Gln Leu Asn Ser Val Thr Pro Glu Asp Thr Ala Thr Tyr Ser Cys
                85                  90                  95

Ala Arg Ser Leu Tyr Tyr Pro Trp Tyr Phe Asp Val Trp Gly Ala Gly
            100                 105                 110

Thr Thr Val Thr Val Ser Ser Ala Lys Thr Thr Ala Pro Ser Val Tyr
        115                 120                 125

Pro Leu Ala Pro Val Cys Gly Asp Thr Thr Gly Ser Ser Val Thr Leu
    130                 135                 140

Gly Cys Leu Val Lys Gly Tyr Phe Pro Glu Pro Val Thr Leu Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Ser Val Thr Val Thr Ser Ser
            180                 185                 190

Thr Trp Pro Ser Gln Ser Ile Thr Cys Asn Val Ala His Pro Ala Ser
        195                 200                 205

Ser Thr Lys Val Asp Lys Lys Ile Glu Pro Arg Gly Pro Thr Ile Lys
    210                 215                 220

Pro Cys Pro Pro Cys Lys Cys Pro Ala Pro Asn Leu Leu Gly Gly Pro
225                 230                 235                 240

Ser Val Phe Ile Phe Pro Pro Lys Ile Lys Asp Val Leu Met Ile Ser
                245                 250                 255

Leu Ser Pro Ile Val Thr Cys Val Val Val Asp Val Ser Glu Asp Asp
            260                 265                 270

Pro Asp Val Gln Ile Ser Trp Phe Val Asn Asn Val Glu Val His Thr
        275                 280                 285

Ala Gln Thr Gln Thr His Arg Glu Asp Tyr Asn Ser Thr Leu Arg Val
    290                 295                 300

Val Ser Ala Leu Pro Ile Gln His Gln Asp Trp Met Ser Gly Lys Glu
305                 310                 315                 320

Phe Lys Cys Lys Val Asn Asn Lys Asp Leu Pro Ala Pro Ile Glu Arg
                325                 330                 335

Thr Ile Ser Lys Pro Lys Gly Ser Val Arg Ala Pro Gln Val Tyr Val
            340                 345                 350

Leu Pro Pro Pro Glu Glu Met Thr Lys Lys Gln Val Thr Leu Thr
           355                 360                 365

Cys Met Val Thr Asp Phe Met Pro Glu Asp Ile Tyr Val Glu Trp Thr
370                 375                 380

Asn Asn Gly Lys Thr Glu Leu Asn Tyr Lys Asn Thr Glu Pro Val Leu
385                 390                 395                 400

Asp Ser Asp Gly Ser Tyr Phe Met Tyr Ser Lys Leu Arg Val Glu Lys
                405                 410                 415

Lys Asn Trp Val Glu Arg Asn Ser Tyr Ser Cys Ser Val Val His Glu
            420                 425                 430

Gly Leu His Asn His His Thr Thr Lys Ser Phe Ser Arg Thr Pro Gly
        435                 440                 445

Lys

<210> SEQ ID NO 249
<211> LENGTH: 449
<212> TYPE: PRT
<213> ORGANISM: Artificial Sequence
<220> FEATURE:
<223> OTHER INFORMATION: 4M2-C12 mIgG2a LALA PG HC

<400> SEQUENCE: 249

Glu Val Lys Leu Val Glu Ser Gly Pro Gly Leu Val Lys Pro Ser Gln
1               5                   10                  15

Ser Leu Ser Leu Thr Cys Thr Val Thr Gly Tyr Ser Ile Thr Ser Asp
            20                  25                  30

Tyr Ala Trp Asn Trp Ile Arg Gln Phe Pro Gly Asn Lys Leu Glu Trp
        35                  40                  45

Met Gly Tyr Ile Thr Tyr Ser Gly Asn Ile Ser Tyr Asn Pro Ser Leu
    50                  55                  60

Arg Ser Arg Ile Ser Ile Thr Arg Asp Thr Ser Lys Asn Gln Phe Phe
65                  70                  75                  80

Leu Gln Leu Asn Ser Val Thr Pro Glu Asp Thr Ala Thr Tyr Ser Cys
                85                  90                  95

Ala Arg Ser Leu Tyr Tyr Pro Trp Tyr Phe Asp Val Trp Gly Ala Gly
            100                 105                 110

Thr Thr Val Thr Val Ser Ser Ala Lys Thr Thr Ala Pro Ser Val Tyr
        115                 120                 125

Pro Leu Ala Pro Val Cys Gly Asp Thr Thr Gly Ser Ser Val Thr Leu
    130                 135                 140

Gly Cys Leu Val Lys Gly Tyr Phe Pro Glu Pro Val Thr Leu Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Ser Val Thr Val Thr Ser Ser
            180                 185                 190

Thr Trp Pro Ser Gln Ser Ile Thr Cys Asn Val Ala His Pro Ala Ser
        195                 200                 205

Ser Thr Lys Val Asp Lys Lys Ile Glu Pro Arg Gly Pro Thr Ile Lys
    210                 215                 220

Pro Cys Pro Pro Cys Lys Cys Pro Ala Pro Asn Ala Ala Gly Gly Pro
225                 230                 235                 240

Ser Val Phe Ile Phe Pro Pro Lys Ile Lys Asp Val Leu Met Ile Ser
                245                 250                 255

Leu Ser Pro Ile Val Thr Cys Val Val Val Asp Val Ser Glu Asp Asp

```
                    260                 265                 270

Pro Asp Val Gln Ile Ser Trp Phe Val Asn Asn Val Glu Val His Thr
            275                 280                 285

Ala Gln Thr Gln Thr His Arg Glu Asp Tyr Asn Ser Thr Leu Arg Val
        290                 295                 300

Val Ser Ala Leu Pro Ile Gln His Gln Asp Trp Met Ser Gly Lys Glu
305                 310                 315                 320

Phe Lys Cys Lys Val Asn Asn Lys Asp Leu Gly Ala Pro Ile Glu Arg
                325                 330                 335

Thr Ile Ser Lys Pro Lys Gly Ser Val Arg Ala Pro Gln Val Tyr Val
            340                 345                 350

Leu Pro Pro Pro Glu Glu Met Thr Lys Lys Gln Val Thr Leu Thr
        355                 360                 365

Cys Met Val Thr Asp Phe Met Pro Glu Asp Ile Tyr Val Glu Trp Thr
    370                 375                 380

Asn Asn Gly Lys Thr Glu Leu Asn Tyr Lys Asn Thr Glu Pro Val Leu
385                 390                 395                 400

Asp Ser Asp Gly Ser Tyr Phe Met Tyr Ser Lys Leu Arg Val Glu Lys
                405                 410                 415

Lys Asn Trp Val Glu Arg Asn Ser Tyr Ser Cys Ser Val Val His Glu
            420                 425                 430

Gly Leu His Asn His His Thr Thr Lys Ser Phe Ser Arg Thr Pro Gly
        435                 440                 445

Lys

<210> SEQ ID NO 250
<211> LENGTH: 214
<212> TYPE: PRT
<213> ORGANISM: Artificial Sequence
<220> FEATURE:
<223> OTHER INFORMATION: 4M2-C12 LC

<400> SEQUENCE: 250

Asp Ile Val Ile Thr Gln Thr Pro Ala Ile Leu Ser Thr Ser Pro Gly
1               5                   10                  15

Glu Lys Val Thr Met Thr Cys Arg Ala Ser Ser Ser Val Gly Tyr Ile
            20                  25                  30

His Trp Tyr Gln Gln Lys Pro Gly Ser Ser Pro Lys Pro Trp Ile Tyr
        35                  40                  45

Ala Thr Ser Asn Leu Ala Ser Gly Val Pro Ala Arg Phe Ser Gly Ser
    50                  55                  60

Gly Ser Gly Thr Ser Asn Ser Leu Thr Ile Thr Arg Val Glu Ala Glu
65                  70                  75                  80

Asp Ala Ala Thr Tyr Tyr Cys Gln Gln Trp Ser Ser Tyr Pro Pro Ile
                85                  90                  95

Thr Phe Gly Gly Gly Thr Lys Leu Glu Val Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175
```

```
Ser Thr Leu Thr Leu Thr Lys Asp Glu Tyr Glu Arg His Asn Ser Tyr
            180                 185                 190

Thr Cys Glu Ala Thr His Lys Thr Ser Thr Pro Ile Val Lys Ser
        195                 200                 205

Phe Asn Arg Asn Glu Cys
    210

<210> SEQ ID NO 251
<211> LENGTH: 97
<212> TYPE: PRT
<213> ORGANISM: Artificial Sequence
<220> FEATURE:
<223> OTHER INFORMATION: mIgG2a CH1

<400> SEQUENCE: 251

Ala Lys Thr Thr Ala Pro Ser Val Tyr Pro Leu Ala Pro Val Cys Gly
1               5                   10                  15

Asp Thr Thr Gly Ser Ser Val Thr Leu Gly Cys Leu Val Lys Gly Tyr
            20                  25                  30

Phe Pro Glu Pro Val Thr Leu Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Thr Ser Ser Thr Trp Pro Ser Gln Ser Ile
65                  70                  75                  80

Thr Cys Asn Val Ala His Pro Ala Ser Ser Thr Lys Val Asp Lys Lys
                85                  90                  95

Ile

<210> SEQ ID NO 252
<211> LENGTH: 16
<212> TYPE: PRT
<213> ORGANISM: Artificial Sequence
<220> FEATURE:
<223> OTHER INFORMATION: mIgG2a Hinge

<400> SEQUENCE: 252

Glu Pro Arg Gly Pro Thr Ile Lys Pro Cys Pro Pro Cys Lys Cys Pro
1               5                   10                  15

<210> SEQ ID NO 253
<211> LENGTH: 110
<212> TYPE: PRT
<213> ORGANISM: Artificial Sequence
<220> FEATURE:
<223> OTHER INFORMATION: mIgG2a CH2

<400> SEQUENCE: 253

Ala Pro Asn Leu Leu Gly Gly Pro Ser Val Phe Ile Phe Pro Pro Lys
1               5                   10                  15

Ile Lys Asp Val Leu Met Ile Ser Leu Ser Pro Ile Val Thr Cys Val
            20                  25                  30

Val Val Asp Val Ser Glu Asp Asp Pro Asp Val Gln Ile Ser Trp Phe
        35                  40                  45

Val Asn Asn Val Glu Val His Thr Ala Gln Thr Gln Thr His Arg Glu
    50                  55                  60

Asp Tyr Asn Ser Thr Leu Arg Val Val Ser Ala Leu Pro Ile Gln His
65                  70                  75                  80

Gln Asp Trp Met Ser Gly Lys Glu Phe Lys Cys Lys Val Asn Asn Lys
```

```
                85                  90                  95

Asp Leu Pro Ala Pro Ile Glu Arg Thr Ile Ser Lys Pro Lys
            100                 105                 110

<210> SEQ ID NO 254
<211> LENGTH: 110
<212> TYPE: PRT
<213> ORGANISM: Artificial Sequence
<220> FEATURE:
<223> OTHER INFORMATION: mIgG2a CH2 LALA PG

<400> SEQUENCE: 254

Ala Pro Asn Ala Ala Gly Gly Pro Ser Val Phe Ile Phe Pro Pro Lys
1               5                   10                  15

Ile Lys Asp Val Leu Met Ile Ser Leu Ser Pro Ile Val Thr Cys Val
            20                  25                  30

Val Val Asp Val Ser Glu Asp Asp Pro Asp Val Gln Ile Ser Trp Phe
        35                  40                  45

Val Asn Asn Val Glu Val His Thr Ala Gln Thr Gln Thr His Arg Glu
    50                  55                  60

Asp Tyr Asn Ser Thr Leu Arg Val Val Ser Ala Leu Pro Ile Gln His
65                  70                  75                  80

Gln Asp Trp Met Ser Gly Lys Glu Phe Lys Cys Lys Val Asn Asn Lys
                85                  90                  95

Asp Leu Gly Ala Pro Ile Glu Arg Thr Ile Ser Lys Pro Lys
            100                 105                 110

<210> SEQ ID NO 255
<211> LENGTH: 107
<212> TYPE: PRT
<213> ORGANISM: Artificial Sequence
<220> FEATURE:
<223> OTHER INFORMATION: mIgG2a CH3

<400> SEQUENCE: 255

Gly Ser Val Arg Ala Pro Gln Val Tyr Val Leu Pro Pro Pro Glu Glu
1               5                   10                  15

Glu Met Thr Lys Lys Gln Val Thr Leu Thr Cys Met Val Thr Asp Phe
            20                  25                  30

Met Pro Glu Asp Ile Tyr Val Glu Trp Thr Asn Asn Gly Lys Thr Glu
        35                  40                  45

Leu Asn Tyr Lys Asn Thr Glu Pro Val Leu Asp Ser Asp Gly Ser Tyr
    50                  55                  60

Phe Met Tyr Ser Lys Leu Arg Val Glu Lys Lys Asn Trp Val Glu Arg
65                  70                  75                  80

Asn Ser Tyr Ser Cys Ser Val Val His Glu Gly Leu His Asn His His
                85                  90                  95

Thr Thr Lys Ser Phe Ser Arg Thr Pro Gly Lys
            100                 105

<210> SEQ ID NO 256
<211> LENGTH: 330
<212> TYPE: PRT
<213> ORGANISM: Artificial Sequence
<220> FEATURE:
<223> OTHER INFORMATION: Mouse Ig gamma-2A chain C region, A allele

<400> SEQUENCE: 256

Ala Lys Thr Thr Ala Pro Ser Val Tyr Pro Leu Ala Pro Val Cys Gly
1               5                   10                  15
```

```
Asp Thr Thr Gly Ser Ser Val Thr Leu Gly Cys Leu Val Lys Gly Tyr
             20                  25                  30

Phe Pro Glu Pro Val Thr Leu Thr Trp Asn Ser Gly Ser Leu Ser Ser
         35                  40                  45

Gly Val His Thr Phe Pro Ala Val Leu Gln Ser Asp Leu Tyr Thr Leu
     50                  55                  60

Ser Ser Ser Val Thr Val Thr Ser Ser Thr Trp Pro Ser Gln Ser Ile
65                  70                  75                  80

Thr Cys Asn Val Ala His Pro Ala Ser Ser Thr Lys Val Asp Lys Lys
                 85                  90                  95

Ile Glu Pro Arg Gly Pro Thr Ile Lys Pro Cys Pro Pro Cys Lys Cys
            100                 105                 110

Pro Ala Pro Asn Leu Leu Gly Gly Pro Ser Val Phe Ile Phe Pro Pro
         115                 120                 125

Lys Ile Lys Asp Val Leu Met Ile Ser Leu Ser Pro Ile Val Thr Cys
130                 135                 140

Val Val Val Asp Val Ser Glu Asp Asp Pro Asp Val Gln Ile Ser Trp
145                 150                 155                 160

Phe Val Asn Asn Val Glu Val His Thr Ala Gln Thr Gln Thr His Arg
                165                 170                 175

Glu Asp Tyr Asn Ser Thr Leu Arg Val Val Ser Ala Leu Pro Ile Gln
            180                 185                 190

His Gln Asp Trp Met Ser Gly Lys Glu Phe Lys Cys Lys Val Asn Asn
        195                 200                 205

Lys Asp Leu Pro Ala Pro Ile Glu Arg Thr Ile Ser Lys Pro Lys Gly
    210                 215                 220

Ser Val Arg Ala Pro Gln Val Tyr Val Leu Pro Pro Pro Glu Glu Glu
225                 230                 235                 240

Met Thr Lys Lys Gln Val Thr Leu Thr Cys Met Val Thr Asp Phe Met
                245                 250                 255

Pro Glu Asp Ile Tyr Val Glu Trp Thr Asn Asn Gly Lys Thr Glu Leu
            260                 265                 270

Asn Tyr Lys Asn Thr Glu Pro Val Leu Asp Ser Asp Gly Ser Tyr Phe
        275                 280                 285

Met Tyr Ser Lys Leu Arg Val Glu Lys Lys Asn Trp Val Glu Arg Asn
    290                 295                 300

Ser Tyr Ser Cys Ser Val Val His Glu Gly Leu His Asn His His Thr
305                 310                 315                 320

Thr Lys Ser Phe Ser Arg Thr Pro Gly Lys
                325                 330

<210> SEQ ID NO 257
<211> LENGTH: 217
<212> TYPE: PRT
<213> ORGANISM: Artificial Sequence
<220> FEATURE:
<223> OTHER INFORMATION: mIgG2a CH2, CH3 LALA PG

<400> SEQUENCE: 257

Ala Pro Asn Ala Ala Gly Gly Pro Ser Val Phe Ile Phe Pro Pro Lys
1               5                  10                  15

Ile Lys Asp Val Leu Met Ile Ser Leu Ser Pro Ile Val Thr Cys Val
            20                  25                  30

Val Val Asp Val Ser Glu Asp Asp Pro Asp Val Gln Ile Ser Trp Phe
        35                  40                  45
```

```
Val Asn Asn Val Glu Val His Thr Ala Gln Thr Gln Thr His Arg Glu
    50                  55                  60

Asp Tyr Asn Ser Thr Leu Arg Val Val Ser Ala Leu Pro Ile Gln His
65                  70                  75                  80

Gln Asp Trp Met Ser Gly Lys Glu Phe Lys Cys Lys Val Asn Asn Lys
                85                  90                  95

Asp Leu Gly Ala Pro Ile Glu Arg Thr Ile Ser Lys Pro Lys Gly Ser
            100                 105                 110

Val Arg Ala Pro Gln Val Tyr Val Leu Pro Pro Glu Glu Glu Met
        115                 120                 125

Thr Lys Lys Gln Val Thr Leu Thr Cys Met Val Thr Asp Phe Met Pro
    130                 135                 140

Glu Asp Ile Tyr Val Glu Trp Thr Asn Asn Gly Lys Thr Glu Leu Asn
145                 150                 155                 160

Tyr Lys Asn Thr Glu Pro Val Leu Asp Ser Asp Gly Ser Tyr Phe Met
                165                 170                 175

Tyr Ser Lys Leu Arg Val Glu Lys Lys Asn Trp Val Glu Arg Asn Ser
            180                 185                 190

Tyr Ser Cys Ser Val Val His Glu Gly Leu His Asn His His Thr Thr
        195                 200                 205

Lys Ser Phe Ser Arg Thr Pro Gly Lys
    210                 215

<210> SEQ ID NO 258
<211> LENGTH: 449
<212> TYPE: PRT
<213> ORGANISM: Artificial Sequence
<220> FEATURE:
<223> OTHER INFORMATION: 4M2-C12 mIgG2a NQ HC

<400> SEQUENCE: 258

Glu Val Lys Leu Val Glu Ser Gly Pro Gly Leu Val Lys Pro Ser Gln
1               5                   10                  15

Ser Leu Ser Leu Thr Cys Thr Val Thr Gly Tyr Ser Ile Thr Ser Asp
            20                  25                  30

Tyr Ala Trp Asn Trp Ile Arg Gln Phe Pro Gly Asn Lys Leu Glu Trp
        35                  40                  45

Met Gly Tyr Ile Thr Tyr Ser Gly Asn Ile Ser Tyr Asn Pro Ser Leu
    50                  55                  60

Arg Ser Arg Ile Ser Ile Thr Arg Asp Thr Ser Lys Asn Gln Phe Phe
65                  70                  75                  80

Leu Gln Leu Asn Ser Val Thr Pro Glu Asp Thr Ala Thr Tyr Ser Cys
                85                  90                  95

Ala Arg Ser Leu Tyr Tyr Pro Trp Tyr Phe Asp Val Trp Gly Ala Gly
            100                 105                 110

Thr Thr Val Thr Val Ser Ser Ala Lys Thr Thr Ala Pro Ser Val Tyr
        115                 120                 125

Pro Leu Ala Pro Val Cys Gly Asp Thr Thr Gly Ser Ser Val Thr Leu
    130                 135                 140

Gly Cys Leu Val Lys Gly Tyr Phe Pro Glu Pro Val Thr Leu Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Val Thr Val Thr Ser Ser
            180                 185                 190
```

-continued

```
Thr Trp Pro Ser Gln Ser Ile Thr Cys Asn Val Ala His Pro Ala Ser
        195                 200                 205

Ser Thr Lys Val Asp Lys Lys Ile Glu Pro Arg Gly Pro Thr Ile Lys
    210                 215                 220

Pro Cys Pro Pro Cys Lys Cys Pro Ala Pro Asn Leu Leu Gly Gly Pro
225                 230                 235                 240

Ser Val Phe Ile Phe Pro Pro Lys Ile Lys Asp Val Leu Met Ile Ser
                245                 250                 255

Leu Ser Pro Ile Val Thr Cys Val Val Asp Val Ser Glu Asp Asp
                260                 265                 270

Pro Asp Val Gln Ile Ser Trp Phe Val Asn Asn Val Glu Val His Thr
                275                 280                 285

Ala Gln Thr Gln Thr His Arg Glu Asp Tyr Gln Ser Thr Leu Arg Val
            290                 295                 300

Val Ser Ala Leu Pro Ile Gln His Gln Asp Trp Met Ser Gly Lys Glu
305                 310                 315                 320

Phe Lys Cys Lys Val Asn Asn Lys Asp Leu Pro Ala Pro Ile Glu Arg
                325                 330                 335

Thr Ile Ser Lys Pro Lys Gly Ser Val Arg Ala Pro Gln Val Tyr Val
                340                 345                 350

Leu Pro Pro Pro Glu Glu Glu Met Thr Lys Lys Gln Val Thr Leu Thr
            355                 360                 365

Cys Met Val Thr Asp Phe Met Pro Glu Asp Ile Tyr Val Glu Trp Thr
    370                 375                 380

Asn Asn Gly Lys Thr Glu Leu Asn Tyr Lys Asn Thr Glu Pro Val Leu
385                 390                 395                 400

Asp Ser Asp Gly Ser Tyr Phe Met Tyr Ser Lys Leu Arg Val Glu Lys
                405                 410                 415

Lys Asn Trp Val Glu Arg Asn Ser Tyr Ser Cys Ser Val Val His Glu
                420                 425                 430

Gly Leu His Asn His His Thr Thr Lys Ser Phe Ser Arg Thr Pro Gly
            435                 440                 445

Lys
```

<210> SEQ ID NO 259
<211> LENGTH: 110
<212> TYPE: PRT
<213> ORGANISM: Artificial Sequence
<220> FEATURE:
<223> OTHER INFORMATION: mIgG2a CH2 NQ

<400> SEQUENCE: 259

```
Ala Pro Asn Leu Leu Gly Gly Pro Ser Val Phe Ile Phe Pro Pro Lys
1               5                   10                  15

Ile Lys Asp Val Leu Met Ile Ser Leu Ser Pro Ile Val Thr Cys Val
            20                  25                  30

Val Val Asp Val Ser Glu Asp Asp Pro Asp Val Gln Ile Ser Trp Phe
        35                  40                  45

Val Asn Asn Val Glu Val His Thr Ala Gln Thr Gln Thr His Arg Glu
    50                  55                  60

Asp Tyr Gln Ser Thr Leu Arg Val Val Ser Ala Leu Pro Ile Gln His
65                  70                  75                  80

Gln Asp Trp Met Ser Gly Lys Glu Phe Lys Cys Lys Val Asn Asn Lys
                85                  90                  95
```

```
Asp Leu Pro Ala Pro Ile Glu Arg Thr Ile Ser Lys Pro Lys
            100                 105                 110
```

<210> SEQ ID NO 260
<211> LENGTH: 217
<212> TYPE: PRT
<213> ORGANISM: Artificial Sequence
<220> FEATURE:
<223> OTHER INFORMATION: mIgG2a CH2, CH3 NQ

<400> SEQUENCE: 260

```
Ala Pro Asn Leu Leu Gly Gly Pro Ser Val Phe Ile Phe Pro Pro Lys
1               5                   10                  15

Ile Lys Asp Val Leu Met Ile Ser Leu Ser Pro Ile Val Thr Cys Val
            20                  25                  30

Val Val Asp Val Ser Glu Asp Asp Pro Asp Val Gln Ile Ser Trp Phe
        35                  40                  45

Val Asn Asn Val Glu Val His Thr Ala Gln Thr Gln Thr His Arg Glu
50                  55                  60

Asp Tyr Gln Ser Thr Leu Arg Val Val Ser Ala Leu Pro Ile Gln His
65                  70                  75                  80

Gln Asp Trp Met Ser Gly Lys Glu Phe Lys Cys Lys Val Asn Asn Lys
                85                  90                  95

Asp Leu Pro Ala Pro Ile Glu Arg Thr Ile Ser Lys Pro Lys Gly Ser
            100                 105                 110

Val Arg Ala Pro Gln Val Tyr Val Leu Pro Pro Pro Glu Glu Glu Met
        115                 120                 125

Thr Lys Lys Gln Val Thr Leu Thr Cys Met Val Thr Asp Phe Met Pro
130                 135                 140

Glu Asp Ile Tyr Val Glu Trp Thr Asn Asn Gly Lys Thr Glu Leu Asn
145                 150                 155                 160

Tyr Lys Asn Thr Glu Pro Val Leu Asp Ser Asp Gly Ser Tyr Phe Met
                165                 170                 175

Tyr Ser Lys Leu Arg Val Glu Lys Lys Asn Trp Val Glu Arg Asn Ser
            180                 185                 190

Tyr Ser Cys Ser Val Val His Glu Gly Leu His Asn His His Thr Thr
        195                 200                 205

Lys Ser Phe Ser Arg Thr Pro Gly Lys
    210                 215
```

<210> SEQ ID NO 261
<211> LENGTH: 324
<212> TYPE: PRT
<213> ORGANISM: Artificial Sequence
<220> FEATURE:
<223> OTHER INFORMATION: Mouse IGHG1

<400> SEQUENCE: 261

```
Ala Lys Thr Thr Pro Pro Ser Val Tyr Pro Leu Ala Pro Gly Ser Ala
1               5                   10                  15

Ala Gln Thr Asn Ser Met Val Thr Leu Gly Cys Leu Val Lys Gly Tyr
            20                  25                  30

Phe Pro Glu Pro Val Thr Val Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Pro Ser Ser Thr Trp Pro Ser Glu Thr Val
65                  70                  75                  80
```

```
Thr Cys Asn Val Ala His Pro Ala Ser Ser Thr Lys Val Asp Lys Lys
                85                  90                  95

Ile Val Pro Arg Asp Cys Gly Cys Lys Pro Cys Ile Cys Thr Val Pro
            100                 105                 110

Glu Val Ser Ser Val Phe Ile Phe Pro Pro Lys Pro Lys Asp Val Leu
        115                 120                 125

Thr Ile Thr Leu Thr Pro Lys Val Thr Cys Val Val Val Asp Ile Ser
    130                 135                 140

Lys Asp Asp Pro Glu Val Gln Phe Ser Trp Phe Val Asp Asp Val Glu
145                 150                 155                 160

Val His Thr Ala Gln Thr Gln Pro Arg Glu Glu Gln Phe Asn Ser Thr
                165                 170                 175

Phe Arg Ser Val Ser Glu Leu Pro Ile Met His Gln Asp Trp Leu Asn
            180                 185                 190

Gly Lys Glu Phe Lys Cys Arg Val Asn Ser Ala Ala Phe Pro Ala Pro
        195                 200                 205

Ile Glu Lys Thr Ile Ser Lys Thr Lys Gly Arg Pro Lys Ala Pro Gln
    210                 215                 220

Val Tyr Thr Ile Pro Pro Pro Lys Glu Gln Met Ala Lys Asp Lys Val
225                 230                 235                 240

Ser Leu Thr Cys Met Ile Thr Asp Phe Phe Pro Glu Asp Ile Thr Val
                245                 250                 255

Glu Trp Gln Trp Asn Gly Gln Pro Ala Glu Asn Tyr Lys Asn Thr Gln
            260                 265                 270

Pro Ile Met Asn Thr Asn Gly Ser Tyr Phe Val Tyr Ser Lys Leu Asn
        275                 280                 285

Val Gln Lys Ser Asn Trp Glu Ala Gly Asn Thr Phe Thr Cys Ser Val
    290                 295                 300

Leu His Glu Gly Leu His Asn His His Thr Glu Lys Ser Leu Ser His
305                 310                 315                 320

Ser Pro Gly Lys

<210> SEQ ID NO 262
<211> LENGTH: 97
<212> TYPE: PRT
<213> ORGANISM: Artificial Sequence
<220> FEATURE:
<223> OTHER INFORMATION: mIgG1 CH1

<400> SEQUENCE: 262

Ala Lys Thr Thr Pro Pro Ser Val Tyr Pro Leu Ala Pro Gly Ser Ala
1               5                   10                  15

Ala Gln Thr Asn Ser Met Val Thr Leu Gly Cys Leu Val Lys Gly Tyr
            20                  25                  30

Phe Pro Glu Pro Val Thr Val Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Pro Ser Ser Thr Trp Pro Ser Glu Thr Val
65                  70                  75                  80

Thr Cys Asn Val Ala His Pro Ala Ser Ser Thr Lys Val Asp Lys Lys
                85                  90                  95

Ile
```

```
<210> SEQ ID NO 263
<211> LENGTH: 13
<212> TYPE: PRT
<213> ORGANISM: Artificial Sequence
<220> FEATURE:
<223> OTHER INFORMATION: mIgG1 Hinge

<400> SEQUENCE: 263

Val Pro Arg Asp Cys Gly Cys Lys Pro Cys Ile Cys Thr
1               5                   10

<210> SEQ ID NO 264
<211> LENGTH: 107
<212> TYPE: PRT
<213> ORGANISM: Artificial Sequence
<220> FEATURE:
<223> OTHER INFORMATION: mIgG1 CH2

<400> SEQUENCE: 264

Val Pro Glu Val Ser Ser Val Phe Ile Phe Pro Pro Lys Pro Lys Asp
1               5                   10                  15

Val Leu Thr Ile Thr Leu Thr Pro Lys Val Thr Cys Val Val Val Asp
            20                  25                  30

Ile Ser Lys Asp Asp Pro Glu Val Gln Phe Ser Trp Phe Val Asp Asp
        35                  40                  45

Val Glu Val His Thr Ala Gln Thr Gln Pro Arg Glu Glu Gln Phe Asn
    50                  55                  60

Ser Thr Phe Arg Ser Val Ser Glu Leu Pro Ile Met His Gln Asp Trp
65                  70                  75                  80

Leu Asn Gly Lys Glu Phe Lys Cys Arg Val Asn Ser Ala Ala Phe Pro
                85                  90                  95

Ala Pro Ile Glu Lys Thr Ile Ser Lys Thr Lys
            100                 105

<210> SEQ ID NO 265
<211> LENGTH: 107
<212> TYPE: PRT
<213> ORGANISM: Artificial Sequence
<220> FEATURE:
<223> OTHER INFORMATION: mIgG1 CH3

<400> SEQUENCE: 265

Gly Arg Pro Lys Ala Pro Gln Val Tyr Thr Ile Pro Pro Lys Glu
1               5                   10                  15

Gln Met Ala Lys Asp Lys Val Ser Leu Thr Cys Met Ile Thr Asp Phe
            20                  25                  30

Phe Pro Glu Asp Ile Thr Val Glu Trp Gln Trp Asn Gly Gln Pro Ala
        35                  40                  45

Glu Asn Tyr Lys Asn Thr Gln Pro Ile Met Asn Thr Asn Gly Ser Tyr
    50                  55                  60

Phe Val Tyr Ser Lys Leu Asn Val Gln Lys Ser Asn Trp Glu Ala Gly
65                  70                  75                  80

Asn Thr Phe Thr Cys Ser Val Leu His Glu Gly Leu His Asn His His
                85                  90                  95

Thr Glu Lys Ser Leu Ser His Ser Pro Gly Lys
            100                 105

<210> SEQ ID NO 266
<211> LENGTH: 443
<212> TYPE: PRT
<213> ORGANISM: Artificial Sequence
```

<220> FEATURE:
<223> OTHER INFORMATION: 4M2-C12 mIgG1 HC

<400> SEQUENCE: 266

```
Glu Val Lys Leu Val Glu Ser Gly Pro Gly Leu Val Lys Pro Ser Gln
1               5                   10                  15

Ser Leu Ser Leu Thr Cys Thr Val Thr Gly Tyr Ser Ile Thr Ser Asp
            20                  25                  30

Tyr Ala Trp Asn Trp Ile Arg Gln Phe Pro Gly Asn Lys Leu Glu Trp
        35                  40                  45

Met Gly Tyr Ile Thr Tyr Ser Gly Asn Ile Ser Tyr Asn Pro Ser Leu
    50                  55                  60

Arg Ser Arg Ile Ser Ile Thr Arg Asp Thr Ser Lys Asn Gln Phe Phe
65                  70                  75                  80

Leu Gln Leu Asn Ser Val Thr Pro Glu Asp Thr Ala Thr Tyr Ser Cys
                85                  90                  95

Ala Arg Ser Leu Tyr Tyr Pro Trp Tyr Phe Asp Val Trp Gly Ala Gly
            100                 105                 110

Thr Thr Val Thr Val Ser Ser Ala Lys Thr Thr Pro Pro Ser Val Tyr
        115                 120                 125

Pro Leu Ala Pro Gly Ser Ala Ala Gln Thr Asn Ser Met Val Thr Leu
    130                 135                 140

Gly Cys Leu Val Lys Gly Tyr Phe Pro Glu Pro Val Thr Val Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Ser Val Thr Val Pro Ser Ser
            180                 185                 190

Thr Trp Pro Ser Glu Thr Val Thr Cys Asn Val Ala His Pro Ala Ser
        195                 200                 205

Ser Thr Lys Val Asp Lys Lys Ile Val Pro Arg Asp Cys Gly Cys Lys
    210                 215                 220

Pro Cys Ile Cys Thr Val Pro Glu Val Ser Ser Val Phe Ile Phe Pro
225                 230                 235                 240

Pro Lys Pro Lys Asp Val Leu Thr Ile Thr Leu Thr Pro Lys Val Thr
                245                 250                 255

Cys Val Val Asp Ile Ser Lys Asp Asp Pro Glu Val Gln Phe Ser
            260                 265                 270

Trp Phe Val Asp Asp Val Glu Val His Thr Ala Gln Thr Gln Pro Arg
        275                 280                 285

Glu Glu Gln Phe Asn Ser Thr Phe Arg Ser Val Ser Glu Leu Pro Ile
    290                 295                 300

Met His Gln Asp Trp Leu Asn Gly Lys Glu Phe Lys Cys Arg Val Asn
305                 310                 315                 320

Ser Ala Ala Phe Pro Ala Pro Ile Glu Lys Thr Ile Ser Lys Thr Lys
                325                 330                 335

Gly Arg Pro Lys Ala Pro Gln Val Tyr Thr Ile Pro Pro Lys Glu
            340                 345                 350

Gln Met Ala Lys Asp Lys Val Ser Leu Thr Cys Met Ile Thr Asp Phe
        355                 360                 365

Phe Pro Glu Asp Ile Thr Val Glu Trp Gln Trp Asn Gly Gln Pro Ala
    370                 375                 380

Glu Asn Tyr Lys Asn Thr Gln Pro Ile Met Asn Thr Asn Gly Ser Tyr
385                 390                 395                 400
```

```
Phe Val Tyr Ser Lys Leu Asn Val Gln Lys Ser Asn Trp Glu Ala Gly
                405                 410                 415

Asn Thr Phe Thr Cys Ser Val Leu His Glu Gly Leu His Asn His His
            420                 425                 430

Thr Glu Lys Ser Leu Ser His Ser Pro Gly Lys
        435                 440

<210> SEQ ID NO 267
<211> LENGTH: 449
<212> TYPE: PRT
<213> ORGANISM: Artificial Sequence
<220> FEATURE:
<223> OTHER INFORMATION: IGN175A HC

<400> SEQUENCE: 267

Gln Val Gln Leu Gln Gln Ser Gly Ala Glu Leu Met Lys Pro Gly Ala
1               5                   10                  15

Ser Val Lys Ile Ser Cys Lys Ala Thr Gly Tyr Thr Phe Ser Thr His
            20                  25                  30

Trp Ile Glu Trp Val Lys Gln Arg Pro Gly His Gly Leu Glu Trp Ile
        35                  40                  45

Gly Glu Ile Leu Pro Gly Ser Gly Ser Thr Ser Tyr Asn Glu Lys Phe
    50                  55                  60

Lys Gly Lys Ala Thr Phe Thr Ala Asp Thr Ser Ser Asn Thr Ala Tyr
65                  70                  75                  80

Met Gln Leu Ser Ser Leu Thr Ser Glu Asp Ser Ala Val Tyr Tyr Cys
                85                  90                  95

Ala Arg Trp Leu Leu Tyr Tyr Tyr Ala Met Asp Tyr Trp Gly Gln Gly
            100                 105                 110

Thr Ser Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320
```

```
Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 268
<211> LENGTH: 219
<212> TYPE: PRT
<213> ORGANISM: Artificial Sequence
<220> FEATURE:
<223> OTHER INFORMATION: IGN175A LC

<400> SEQUENCE: 268

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Leu Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Phe Pro Tyr Thr Phe Gly Gly Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

```
<210> SEQ ID NO 269
<211> LENGTH: 450
<212> TYPE: PRT
<213> ORGANISM: Artificial Sequence
<220> FEATURE:
<223> OTHER INFORMATION: VSTB112 HC

<400> SEQUENCE: 269

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Leu Leu Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ser Tyr Gly Trp Ser Tyr Glu Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365
```

```
Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly Lys
    450

<210> SEQ ID NO 270
<211> LENGTH: 214
<212> TYPE: PRT
<213> ORGANISM: Artificial Sequence
<220> FEATURE:
<223> OTHER INFORMATION: VSTB112 LC

<400> SEQUENCE: 270

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asp Thr Arg
                20                  25                  30

Leu Asn Trp Tyr Gln Gln Lys Pro Gly Lys Ala Pro Lys Leu Leu Ile
                35                  40                  45

Tyr Ser Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Ala Tyr Asn Pro Ile
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
    210

<210> SEQ ID NO 271
<211> LENGTH: 10
<212> TYPE: PRT
<213> ORGANISM: Artificial Sequence
<220> FEATURE:
<223> OTHER INFORMATION: VSTB112 major epitope 1

<400> SEQUENCE: 271
```

```
Pro Val Asp Lys Gly His Asp Val Thr Phe
1               5                   10

<210> SEQ ID NO 272
<211> LENGTH: 12
<212> TYPE: PRT
<213> ORGANISM: Artificial Sequence
<220> FEATURE:
<223> OTHER INFORMATION: VSTB112 major epitope 2

<400> SEQUENCE: 272

Arg Arg Pro Ile Arg Asn Leu Thr Phe Gln Asp Leu
1               5                   10

<210> SEQ ID NO 273
<211> LENGTH: 14
<212> TYPE: PRT
<213> ORGANISM: Artificial Sequence
<220> FEATURE:
<223> OTHER INFORMATION: VSTB112 minor epitope 1

<400> SEQUENCE: 273

Thr Trp Tyr Arg Ser Ser Arg Gly Glu Val Gln Thr Cys Ser
1               5                   10

<210> SEQ ID NO 274
<211> LENGTH: 17
<212> TYPE: PRT
<213> ORGANISM: Artificial Sequence
<220> FEATURE:
<223> OTHER INFORMATION: VSTB112 minor epitope 2

<400> SEQUENCE: 274

Glu Ile Arg His His His Ser Glu His Arg Val His Gly Ala Met Glu
1               5                   10                  15

Leu

<210> SEQ ID NO 275
<211> LENGTH: 32
<212> TYPE: PRT
<213> ORGANISM: Artificial Sequence
<220> FEATURE:
<223> OTHER INFORMATION: IGN175A epitope

<400> SEQUENCE: 275

Phe Lys Val Ala Thr Pro Tyr Ser Leu Tyr Val Cys Pro Glu Gly Gln
1               5                   10                  15

Asn Val Thr Leu Thr Cys Arg Leu Leu Gly Pro Val Asp Lys Gly His
            20                  25                  30

<210> SEQ ID NO 276
<211> LENGTH: 119
<212> TYPE: PRT
<213> ORGANISM: Artificial Sequence
<220> FEATURE:
<223> OTHER INFORMATION: V4-C1 heavy chain variable region

<400> SEQUENCE: 276

Gln Val Gln Leu Gln Glu Ser Gly Pro Gly Leu Val Lys Pro Ser Asp
1               5                   10                  15

Thr Leu Ser Leu Thr Cys Thr Val Ser Gly Tyr Ser Ile Thr Ser Asp
            20                  25                  30

Tyr Ala Trp Asn Trp Ile Arg Gln Thr Pro Gly Lys Gly Leu Glu Trp
        35                  40                  45
```

```
Ile Gly Tyr Ile Thr Tyr Ser Gly Tyr Ile Ser Tyr Asn Pro Ser Leu
        50                  55                  60
Arg Ser Arg Val Thr Ile Ser Arg Asp Thr Ser Lys Asn Gln Phe Ser
 65                  70                  75                  80
Leu Lys Leu Ser Ser Val Thr Ala Ala Asp Thr Ala Val Tyr Ser Cys
                 85                  90                  95
Ala Arg Ala Leu Tyr Tyr Pro Trp Tyr Phe Asp Val Trp Gly Thr Gly
             100                 105                 110
Thr Thr Val Thr Val Ser Ser
            115
```

<210> SEQ ID NO 277
<211> LENGTH: 7
<212> TYPE: PRT
<213> ORGANISM: Artificial Sequence
<220> FEATURE:
<223> OTHER INFORMATION: V4-C1 heavy chain CDR2

<400> SEQUENCE: 277

```
Ile Thr Tyr Ser Gly Tyr Ile
 1               5
```

<210> SEQ ID NO 278
<211> LENGTH: 12
<212> TYPE: PRT
<213> ORGANISM: Artificial Sequence
<220> FEATURE:
<223> OTHER INFORMATION: V4-C1, V4-C9, V4-C24, V4-C26, V4-C27, V4-C28,
      V4-C30, V4-C31 heavy chain CDR3

<400> SEQUENCE: 278

```
Ala Arg Ala Leu Tyr Tyr Pro Trp Tyr Phe Asp Val
 1               5                  10
```

<210> SEQ ID NO 279
<211> LENGTH: 17
<212> TYPE: PRT
<213> ORGANISM: Artificial Sequence
<220> FEATURE:
<223> OTHER INFORMATION: V4-C1, V4-C9 heavy chain FR2

<400> SEQUENCE: 279

```
Trp Asn Trp Ile Arg Gln Thr Pro Gly Lys Gly Leu Glu Trp Ile Gly
 1               5                  10                  15
Tyr
```

<210> SEQ ID NO 280
<211> LENGTH: 38
<212> TYPE: PRT
<213> ORGANISM: Artificial Sequence
<220> FEATURE:
<223> OTHER INFORMATION: V4-C1, V4-C9 heavy chain FR3

<400> SEQUENCE: 280

```
Ser Tyr Asn Pro Ser Leu Arg Ser Arg Val Thr Ile Ser Arg Asp Thr
 1               5                  10                  15
Ser Lys Asn Gln Phe Ser Leu Lys Leu Ser Ser Val Thr Ala Ala Asp
                20                  25                  30
Thr Ala Val Tyr Ser Cys
            35
```

<210> SEQ ID NO 281

```
<211> LENGTH: 11
<212> TYPE: PRT
<213> ORGANISM: Artificial Sequence
<220> FEATURE:
<223> OTHER INFORMATION: V4-C1, V4-C9, V4-C24, V4-C26, V4-C27, V4-C28,
      V4-C30, V4-C31 heavy chain FR4

<400> SEQUENCE: 281

Trp Gly Thr Gly Thr Thr Val Thr Val Ser Ser
1               5                   10

<210> SEQ ID NO 282
<211> LENGTH: 107
<212> TYPE: PRT
<213> ORGANISM: Artificial Sequence
<220> FEATURE:
<223> OTHER INFORMATION: V4-C1 light chain variable region

<400> SEQUENCE: 282

Glu Ile Val Ile Thr Gln Ser Pro Ala Thr Leu Ser Leu Ser Pro Gly
1               5                   10                  15

Glu Arg Ala Thr Leu Ser Cys Arg Ala Ser Ser Ser Val Gly Tyr Ile
            20                  25                  30

His Trp Tyr Gln Gln Lys Pro Gly Gln Ala Pro Arg Pro Leu Ile Tyr
        35                  40                  45

Ala Thr Ser Asn Arg Ala Thr Gly Ile Pro Ala Arg Phe Ser Gly Ser
    50                  55                  60

Gly Ser Gly Thr Asp Asn Thr Leu Thr Ile Ser Ser Leu Glu Pro Glu
65                  70                  75                  80

Asp Ser Ala Val Tyr Tyr Cys Gln Gln Trp Ser Ser Tyr Pro Pro Ile
                85                  90                  95

Thr Phe Gly Gly Gly Thr Lys Leu Glu Val Lys
            100                 105

<210> SEQ ID NO 283
<211> LENGTH: 17
<212> TYPE: PRT
<213> ORGANISM: Artificial Sequence
<220> FEATURE:
<223> OTHER INFORMATION: V4-C1, V4-C9, V4-C24, V4-C27, V4-C28, V4-C30,
      V4-C31 light chain FR2

<400> SEQUENCE: 283

Ile His Trp Tyr Gln Gln Lys Pro Gly Gln Ala Pro Arg Pro Leu Ile
1               5                   10                  15

Tyr

<210> SEQ ID NO 284
<211> LENGTH: 36
<212> TYPE: PRT
<213> ORGANISM: Artificial Sequence
<220> FEATURE:
<223> OTHER INFORMATION: V4-C1, V4-C9, V4-C26, V4-C27 light chain FR3

<400> SEQUENCE: 284

Asn Arg Ala Thr Gly Ile Pro Ala Arg Phe Ser Gly Ser Gly Ser Gly
1               5                   10                  15

Thr Asp Asn Thr Leu Thr Ile Ser Ser Leu Glu Pro Glu Asp Ser Ala
            20                  25                  30

Val Tyr Tyr Cys
        35
```

```
<210> SEQ ID NO 285
<211> LENGTH: 119
<212> TYPE: PRT
<213> ORGANISM: Artificial Sequence
<220> FEATURE:
<223> OTHER INFORMATION: V4-C9 heavy chain variable region

<400> SEQUENCE: 285

Gln Val Gln Leu Gln Glu Ser Gly Pro Gly Leu Val Lys Pro Ser Asp
1               5                   10                  15

Thr Leu Ser Leu Thr Cys Thr Val Ser Gly Tyr Ser Ile Thr Ser Asp
            20                  25                  30

Tyr Ala Trp Asn Trp Ile Arg Gln Thr Pro Gly Lys Gly Leu Glu Trp
        35                  40                  45

Ile Gly Tyr Ile Thr Tyr Ser Gly Tyr Val Ser Tyr Asn Pro Ser Leu
    50                  55                  60

Arg Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Ser Cys
                85                  90                  95

Ala Arg Ala Leu Tyr Tyr Pro Trp Tyr Phe Asp Val Trp Gly Thr Gly
            100                 105                 110

Thr Thr Val Thr Val Ser Ser
        115

<210> SEQ ID NO 286
<211> LENGTH: 7
<212> TYPE: PRT
<213> ORGANISM: Artificial Sequence
<220> FEATURE:
<223> OTHER INFORMATION: V4-C9 heavy chain CDR2

<400> SEQUENCE: 286

Ile Thr Tyr Ser Gly Tyr Val
1               5

<210> SEQ ID NO 287
<211> LENGTH: 107
<212> TYPE: PRT
<213> ORGANISM: Artificial Sequence
<220> FEATURE:
<223> OTHER INFORMATION: V4-C9 light chain variable region

<400> SEQUENCE: 287

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Val Gly Tyr Ile
            20                  25                  30

His Trp Tyr Gln Gln Lys Pro Gly Gln Ala Pro Arg Pro Leu Ile Tyr
        35                  40                  45

Ala Thr Ser Asn Arg Ala Thr Gly Ile Pro Ala Arg Phe Ser Gly Ser
    50                  55                  60

Gly Ser Gly Thr Asp Asn Thr Leu Thr Ile Ser Ser Leu Glu Pro Glu
65                  70                  75                  80

Asp Ser Ala Val Tyr Tyr Cys Gln Gln Trp Ser Ser Tyr Pro Pro Ile
                85                  90                  95

Thr Phe Gly Gly Gly Thr Lys Leu Glu Val Lys
            100                 105

<210> SEQ ID NO 288
```

```
<211> LENGTH: 26
<212> TYPE: PRT
<213> ORGANISM: Artificial Sequence
<220> FEATURE:
<223> OTHER INFORMATION: V4-C9, V4-C24, V4-C26, V4-C27, V4-C28, V4-C30,
      V4-C31 light chain FR1

<400> SEQUENCE: 288

Glu Ile Val Leu Thr Gln Ser Pro Ala Thr Leu Ser Leu Ser Pro Gly
1               5                   10                  15

Glu Arg Ala Thr Leu Ser Cys Arg Ala Ser
            20                  25

<210> SEQ ID NO 289
<211> LENGTH: 119
<212> TYPE: PRT
<213> ORGANISM: Artificial Sequence
<220> FEATURE:
<223> OTHER INFORMATION: V4-C24, V4-C26, V4-C27, V4-C28, V4-C30, V4-C31
      heavy chain variable region

<400> SEQUENCE: 289

Gln Val Gln Leu Gln Glu Ser Gly Pro Gly Leu Val Lys Pro Ser Asp
1               5                   10                  15

Thr Leu Ser Leu Thr Cys Thr Val Ser Gly Tyr Ser Ile Thr Ser Asp
            20                  25                  30

Tyr Thr Trp Asn Trp Ile Arg Gln Thr Pro Gly Lys Gly Leu Glu Trp
        35                  40                  45

Ile Gly His Ile Thr Tyr Ser Gly Ser Val Ser Tyr Asn Pro Ser Leu
    50                  55                  60

Arg Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Thr Tyr Ser Cys
                85                  90                  95

Ala Arg Ala Leu Tyr Tyr Pro Trp Tyr Phe Asp Val Trp Gly Thr Gly
            100                 105                 110

Thr Thr Val Thr Val Ser Ser
        115

<210> SEQ ID NO 290
<211> LENGTH: 9
<212> TYPE: PRT
<213> ORGANISM: Artificial Sequence
<220> FEATURE:
<223> OTHER INFORMATION: V4-C24, V4-C26, V4-C27, V4-C28, V4-C30, V4-C31
      heavy chain CDR1

<400> SEQUENCE: 290

Gly Tyr Ser Ile Thr Ser Asp Tyr Thr
1               5

<210> SEQ ID NO 291
<211> LENGTH: 7
<212> TYPE: PRT
<213> ORGANISM: Artificial Sequence
<220> FEATURE:
<223> OTHER INFORMATION: V4-C24, V4-C26, V4-C27, V4-C28, V4-C30, V4-C31
      heavy chain CDR2

<400> SEQUENCE: 291

Ile Thr Tyr Ser Gly Ser Val
1               5
```

<210> SEQ ID NO 292
<211> LENGTH: 17
<212> TYPE: PRT
<213> ORGANISM: Artificial Sequence
<220> FEATURE:
<223> OTHER INFORMATION: V4-C24, V4-C26, V4-C27, V4-C28, V4-C30, V4-C31
      heavy chain FR2

<400> SEQUENCE: 292

Trp Asn Trp Ile Arg Gln Thr Pro Gly Lys Gly Leu Glu Trp Ile Gly
1               5                   10                  15

His

<210> SEQ ID NO 293
<211> LENGTH: 38
<212> TYPE: PRT
<213> ORGANISM: Artificial Sequence
<220> FEATURE:
<223> OTHER INFORMATION: V4-C24, V4-C26, V4-C27, V4-C28, V4-C30, V4-C31
      heavy chain FR3

<400> SEQUENCE: 293

Ser Tyr Asn Pro Ser Leu Arg Ser Arg Val Thr Ile Ser Arg Asp Thr
1               5                   10                  15

Ser Lys Asn Gln Phe Ser Leu Lys Leu Ser Ser Val Thr Ala Ala Asp
            20                  25                  30

Thr Ala Thr Tyr Ser Cys
        35

<210> SEQ ID NO 294
<211> LENGTH: 107
<212> TYPE: PRT
<213> ORGANISM: Artificial Sequence
<220> FEATURE:
<223> OTHER INFORMATION: V4-C24 light chain variable region

<400> SEQUENCE: 294

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Val Gly Tyr Ile
            20                  25                  30

His Trp Tyr Gln Gln Lys Pro Gly Gln Ala Pro Arg Pro Leu Ile Tyr
        35                  40                  45

Thr Thr Ser Tyr Arg Ala Thr Gly Ile Pro Ala Arg Phe Ser Gly Ser
    50                  55                  60

Gly Ser Gly Thr Asp Asn Thr Leu Thr Ile Ser Ser Leu Glu Pro Glu
65                  70                  75                  80

Asp Ser Ala Val Tyr Tyr Cys Gln Gln Trp Ser Ser Tyr Pro Pro Ile
                85                  90                  95

Thr Phe Gly Gly Gly Thr Lys Leu Glu Val Lys
            100                 105

<210> SEQ ID NO 295
<211> LENGTH: 3
<212> TYPE: PRT
<213> ORGANISM: Artificial Sequence
<220> FEATURE:
<223> OTHER INFORMATION: V4-C24, V4-C26 light chain CDR2

<400> SEQUENCE: 295

Thr Thr Ser
1

<210> SEQ ID NO 296
<211> LENGTH: 36
<212> TYPE: PRT
<213> ORGANISM: Artificial Sequence
<220> FEATURE:
<223> OTHER INFORMATION: V4-C24, V4-C28, V4-C30 light chain FR3

<400> SEQUENCE: 296

Tyr Arg Ala Thr Gly Ile Pro Ala Arg Phe Ser Gly Ser Gly
1               5                   10                  15

Thr Asp Asn Thr Leu Thr Ile Ser Ser Leu Glu Pro Glu Asp Ser Ala
                20                  25                  30

Val Tyr Tyr Cys
            35

<210> SEQ ID NO 297
<211> LENGTH: 107
<212> TYPE: PRT
<213> ORGANISM: Artificial Sequence
<220> FEATURE:
<223> OTHER INFORMATION: V4-C26 light chain variable region

<400> SEQUENCE: 297

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Val Gly Tyr Ile
                20                  25                  30

His Trp Tyr Gln Gln Lys Pro Gly Gln Ala Pro Arg Pro Ile Ile Tyr
            35                  40                  45

Thr Thr Ser Asn Arg Ala Thr Gly Ile Pro Ala Arg Phe Ser Gly Ser
        50                  55                  60

Gly Ser Gly Thr Asp Asn Thr Leu Thr Ile Ser Ser Leu Glu Pro Glu
65                  70                  75                  80

Asp Ser Ala Val Tyr Tyr Cys Gln Gln Trp Ser Ser Tyr Pro Pro Ile
                85                  90                  95

Thr Phe Gly Gly Gly Thr Lys Leu Glu Val Lys
            100                 105

<210> SEQ ID NO 298
<211> LENGTH: 17
<212> TYPE: PRT
<213> ORGANISM: Artificial Sequence
<220> FEATURE:
<223> OTHER INFORMATION: V4-C26 light chain FR2

<400> SEQUENCE: 298

Ile His Trp Tyr Gln Gln Lys Pro Gly Gln Ala Pro Arg Pro Ile Ile
1               5                   10                  15

Tyr

<210> SEQ ID NO 299
<211> LENGTH: 107
<212> TYPE: PRT
<213> ORGANISM: Artificial Sequence
<220> FEATURE:
<223> OTHER INFORMATION: V4-C27 light chain variable region

<400> SEQUENCE: 299

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Val Gly Tyr Ile

-continued

```
                20                  25                  30

His Trp Tyr Gln Gln Lys Pro Gly Gln Ala Pro Arg Pro Leu Ile Tyr
            35                  40                  45

Ala Thr Tyr Asn Arg Ala Thr Gly Ile Pro Ala Arg Phe Ser Gly Ser
        50                  55                  60

Gly Ser Gly Thr Asp Asn Thr Leu Thr Ile Ser Ser Leu Glu Pro Glu
 65                  70                  75                  80

Asp Ser Ala Val Tyr Tyr Cys Gln Gln Trp Ser Ser Tyr Pro Pro Ile
                85                  90                  95

Thr Phe Gly Gly Gly Thr Lys Leu Glu Val Lys
            100                 105

<210> SEQ ID NO 300
<211> LENGTH: 3
<212> TYPE: PRT
<213> ORGANISM: Artificial Sequence
<220> FEATURE:
<223> OTHER INFORMATION: V4-C27, V4-C30, V4-C31 light chain CDR2

<400> SEQUENCE: 300

Ala Thr Tyr
1

<210> SEQ ID NO 301
<211> LENGTH: 107
<212> TYPE: PRT
<213> ORGANISM: Artificial Sequence
<220> FEATURE:
<223> OTHER INFORMATION: V4-C28 light chain variable region

<400> SEQUENCE: 301

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Ser Ser Val Gly Tyr Ile
                20                  25                  30

His Trp Tyr Gln Gln Lys Pro Gly Gln Ala Pro Arg Pro Leu Ile Tyr
            35                  40                  45

Ala Thr Ser Tyr Arg Ala Thr Gly Ile Pro Ala Arg Phe Ser Gly Ser
        50                  55                  60

Gly Ser Gly Thr Asp Asn Thr Leu Thr Ile Ser Ser Leu Glu Pro Glu
 65                  70                  75                  80

Asp Ser Ala Val Tyr Tyr Cys Gln Gln Trp Ser Ser Tyr Pro Pro Ile
                85                  90                  95

Thr Phe Gly Gly Gly Thr Lys Leu Glu Val Lys
            100                 105

<210> SEQ ID NO 302
<211> LENGTH: 107
<212> TYPE: PRT
<213> ORGANISM: Artificial Sequence
<220> FEATURE:
<223> OTHER INFORMATION: V4-C30 light chain variable region

<400> SEQUENCE: 302

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Ser Ser Val Gly Tyr Ile
                20                  25                  30

His Trp Tyr Gln Gln Lys Pro Gly Gln Ala Pro Arg Pro Leu Ile Tyr
            35                  40                  45
```

```
Ala Thr Tyr Tyr Arg Ala Thr Gly Ile Pro Ala Arg Phe Ser Gly Ser
        50                  55                  60

Gly Ser Gly Thr Asp Asn Thr Leu Thr Ile Ser Ser Leu Glu Pro Glu
 65                  70                  75                  80

Asp Ser Ala Val Tyr Tyr Cys Gln Gln Trp Ser Ser Tyr Pro Pro Ile
                85                  90                  95

Thr Phe Gly Gly Gly Thr Lys Leu Glu Val Lys
            100                 105

<210> SEQ ID NO 303
<211> LENGTH: 107
<212> TYPE: PRT
<213> ORGANISM: Artificial Sequence
<220> FEATURE:
<223> OTHER INFORMATION: V4-C31 light chain variable region

<400> SEQUENCE: 303

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Ser Ser Val Gly Tyr Ile
                20                  25                  30

His Trp Tyr Gln Gln Lys Pro Gly Gln Ala Pro Arg Pro Leu Ile Tyr
            35                  40                  45

Ala Thr Tyr Tyr Arg Thr Thr Gly Ile Pro Ala Arg Phe Ser Gly Ser
        50                  55                  60

Gly Ser Gly Thr Asp Asn Thr Leu Thr Ile Ser Ser Leu Glu Pro Glu
 65                  70                  75                  80

Asp Ser Ala Val Tyr Tyr Cys Gln Gln Trp Ser Ser Tyr Pro Pro Ile
                85                  90                  95

Thr Phe Gly Gly Gly Thr Lys Leu Glu Val Lys
            100                 105

<210> SEQ ID NO 304
<211> LENGTH: 36
<212> TYPE: PRT
<213> ORGANISM: Artificial Sequence
<220> FEATURE:
<223> OTHER INFORMATION: V4-C31 light chain FR3

<400> SEQUENCE: 304

Tyr Arg Thr Thr Gly Ile Pro Ala Arg Phe Ser Gly Ser Gly Ser Gly
 1               5                  10                  15

Thr Asp Asn Thr Leu Thr Ile Ser Ser Leu Glu Pro Glu Asp Ser Ala
                20                  25                  30

Val Tyr Tyr Cys
        35

<210> SEQ ID NO 305
<211> LENGTH: 9
<212> TYPE: PRT
<213> ORGANISM: Artificial Sequence
<220> FEATURE:
<223> OTHER INFORMATION: 4M2-C12 derived heavy chain CDR1 consensus
<220> FEATURE:
<221> NAME/KEY: MISC_FEATURE
<222> LOCATION: (3)..(3)
<223> OTHER INFORMATION: X = S or T
<220> FEATURE:
<221> NAME/KEY: MISC_FEATURE
<222> LOCATION: (9)..(9)
<223> OTHER INFORMATION: X = T or A
```

```
<400> SEQUENCE: 305

Gly Tyr Xaa Ile Thr Ser Asp Tyr Xaa
1               5

<210> SEQ ID NO 306
<211> LENGTH: 7
<212> TYPE: PRT
<213> ORGANISM: Artificial Sequence
<220> FEATURE:
<223> OTHER INFORMATION: 4M2-C12 derived heavy chain CDR2 consensus
<220> FEATURE:
<221> NAME/KEY: MISC_FEATURE
<222> LOCATION: (6)..(6)
<223> OTHER INFORMATION: X = S, N or Y
<220> FEATURE:
<221> NAME/KEY: MISC_FEATURE
<222> LOCATION: (7)..(7)
<223> OTHER INFORMATION: X = V or I

<400> SEQUENCE: 306

Ile Thr Tyr Ser Gly Xaa Xaa
1               5

<210> SEQ ID NO 307
<211> LENGTH: 12
<212> TYPE: PRT
<213> ORGANISM: Artificial Sequence
<220> FEATURE:
<223> OTHER INFORMATION: 4M2-C12 derived heavy chain CDR3 consensus
<220> FEATURE:
<221> NAME/KEY: MISC_FEATURE
<222> LOCATION: (3)..(3)
<223> OTHER INFORMATION: X = A or S

<400> SEQUENCE: 307

Ala Arg Xaa Leu Tyr Tyr Pro Trp Tyr Phe Asp Val
1               5                   10

<210> SEQ ID NO 308
<211> LENGTH: 3
<212> TYPE: PRT
<213> ORGANISM: Artificial Sequence
<220> FEATURE:
<223> OTHER INFORMATION: 4M2-C12 derived light chain CDR2 consensus
<220> FEATURE:
<221> NAME/KEY: MISC_FEATURE
<222> LOCATION: (1)..(1)
<223> OTHER INFORMATION: X = A, T or D
<220> FEATURE:
<221> NAME/KEY: MISC_FEATURE
<222> LOCATION: (2)..(2)
<223> OTHER INFORMATION: X = T or A
<220> FEATURE:
<221> NAME/KEY: MISC_FEATURE
<222> LOCATION: (3)..(3)
<223> OTHER INFORMATION: X = S or Y

<400> SEQUENCE: 308

Xaa Xaa Xaa
1

<210> SEQ ID NO 309
<211> LENGTH: 3
<212> TYPE: PRT
<213> ORGANISM: Artificial Sequence
<220> FEATURE:
<223> OTHER INFORMATION: C24/C26/C27 light chain CDR2 consensus
<220> FEATURE:
<221> NAME/KEY: MISC_FEATURE
<222> LOCATION: (1)..(1)
<223> OTHER INFORMATION: X = T or A
```

```
<220> FEATURE:
<221> NAME/KEY: MISC_FEATURE
<222> LOCATION: (3)..(3)
<223> OTHER INFORMATION: X = S or Y

<400> SEQUENCE: 309

Xaa Thr Xaa
1

<210> SEQ ID NO 310
<211> LENGTH: 109
<212> TYPE: PRT
<213> ORGANISM: Artificial Sequence
<220> FEATURE:
<223> OTHER INFORMATION: C24/C26/C27 light chain variable region
      consensus
<220> FEATURE:
<221> NAME/KEY: MISC_FEATURE
<222> LOCATION: (46)..(46)
<223> OTHER INFORMATION: X = L or I
<220> FEATURE:
<221> NAME/KEY: MISC_FEATURE
<222> LOCATION: (49)..(49)
<223> OTHER INFORMATION: X = T or A
<220> FEATURE:
<221> NAME/KEY: MISC_FEATURE
<222> LOCATION: (51)..(51)
<223> OTHER INFORMATION: X = S or Y
<220> FEATURE:
<221> NAME/KEY: MISC_FEATURE
<222> LOCATION: (52)..(52)
<223> OTHER INFORMATION: X = N or Y

<400> SEQUENCE: 310

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Val Gly Tyr Ile
            20                  25                  30

His Trp Tyr Gln Gln Lys Pro Gly Gln Ala Pro Arg Pro Xaa Ile Tyr
        35                  40                  45

Xaa Thr Xaa Xaa Tyr Asn Arg Ala Thr Gly Ile Pro Ala Arg Phe Ser
    50                  55                  60

Gly Ser Gly Ser Gly Thr Asp Asn Thr Leu Thr Ile Ser Ser Leu Glu
65                  70                  75                  80

Pro Glu Asp Ser Ala Val Tyr Tyr Cys Gln Gln Trp Ser Ser Tyr Pro
                85                  90                  95

Pro Ile Thr Phe Gly Gly Gly Thr Lys Leu Glu Val Lys
            100                 105

<210> SEQ ID NO 311
<211> LENGTH: 449
<212> TYPE: PRT
<213> ORGANISM: Artificial Sequence
<220> FEATURE:
<223> OTHER INFORMATION: V4-C1 VH-CH1-CH2-CH3

<400> SEQUENCE: 311

Gln Val Gln Leu Gln Glu Ser Gly Pro Gly Leu Val Lys Pro Ser Asp
1               5                   10                  15

Thr Leu Ser Leu Thr Cys Thr Val Ser Gly Tyr Ser Ile Thr Ser Asp
            20                  25                  30

Tyr Ala Trp Asn Trp Ile Arg Gln Thr Pro Gly Lys Gly Leu Glu Trp
        35                  40                  45

Ile Gly Tyr Ile Thr Tyr Ser Gly Tyr Ile Ser Tyr Asn Pro Ser Leu
    50                  55                  60
```

```
Arg Ser Arg Val Thr Ile Ser Arg Asp Thr Ser Lys Asn Gln Phe Ser
 65                  70                  75                  80

Leu Lys Leu Ser Ser Val Thr Ala Ala Asp Thr Ala Val Tyr Ser Cys
             85                  90                  95

Ala Arg Ala Leu Tyr Tyr Pro Trp Tyr Phe Asp Val Trp Gly Thr Gly
        100                 105                 110

Thr Thr Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 312
<211> LENGTH: 214
<212> TYPE: PRT
```

-continued

<213> ORGANISM: Artificial Sequence
<220> FEATURE:
<223> OTHER INFORMATION: V4-C1 VL-Ckappa

<400> SEQUENCE: 312

Glu Ile Val Ile Thr Gln Ser Pro Ala Thr Leu Ser Leu Ser Pro Gly
1               5                   10                  15

Glu Arg Ala Thr Leu Ser Cys Arg Ala Ser Ser Ser Val Gly Tyr Ile
            20                  25                  30

His Trp Tyr Gln Gln Lys Pro Gly Gln Ala Pro Arg Pro Leu Ile Tyr
        35                  40                  45

Ala Thr Ser Asn Arg Ala Thr Gly Ile Pro Ala Arg Phe Ser Gly Ser
    50                  55                  60

Gly Ser Gly Thr Asp Asn Thr Leu Thr Ile Ser Ser Leu Glu Pro Glu
65                  70                  75                  80

Asp Ser Ala Val Tyr Tyr Cys Gln Gln Trp Ser Ser Tyr Pro Pro Ile
                85                  90                  95

Thr Phe Gly Gly Gly Thr Lys Leu Glu Val Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 313
<211> LENGTH: 449
<212> TYPE: PRT
<213> ORGANISM: Artificial Sequence
<220> FEATURE:
<223> OTHER INFORMATION: V4-C9 VH-CH1-CH2-CH3

<400> SEQUENCE: 313

Gln Val Gln Leu Gln Glu Ser Gly Pro Gly Leu Val Lys Pro Ser Asp
1               5                   10                  15

Thr Leu Ser Leu Thr Cys Thr Val Ser Gly Tyr Ser Ile Thr Ser Asp
            20                  25                  30

Tyr Ala Trp Asn Trp Ile Arg Gln Thr Pro Gly Lys Gly Leu Glu Trp
        35                  40                  45

Ile Gly Tyr Ile Thr Tyr Ser Gly Tyr Val Ser Tyr Asn Pro Ser Leu
    50                  55                  60

Arg Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Ser Cys
                85                  90                  95

Ala Arg Ala Leu Tyr Tyr Pro Trp Tyr Phe Asp Val Trp Gly Thr Gly
            100                 105                 110

```
Thr Thr Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 314
<211> LENGTH: 214
<212> TYPE: PRT
<213> ORGANISM: Artificial Sequence
<220> FEATURE:
<223> OTHER INFORMATION: V4-C9 VL-Ckappa

<400> SEQUENCE: 314

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Val Gly Tyr Ile
```

```
                20                  25                  30
His Trp Tyr Gln Gln Lys Pro Gly Gln Ala Pro Arg Pro Leu Ile Tyr
            35                  40                  45

Ala Thr Ser Asn Arg Ala Thr Gly Ile Pro Ala Arg Phe Ser Gly Ser
        50                  55                  60

Gly Ser Gly Thr Asp Asn Thr Leu Thr Ile Ser Ser Leu Glu Pro Glu
65                  70                  75                  80

Asp Ser Ala Val Tyr Tyr Cys Gln Gln Trp Ser Ser Tyr Pro Pro Ile
                85                  90                  95

Thr Phe Gly Gly Gly Thr Lys Leu Glu Val Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 315
<211> LENGTH: 449
<212> TYPE: PRT
<213> ORGANISM: Artificial Sequence
<220> FEATURE:
<223> OTHER INFORMATION: V4-C24/C26/C27/C28/C30/C31 VH-CH1-CH2-CH3

<400> SEQUENCE: 315

Gln Val Gln Leu Gln Glu Ser Gly Pro Gly Leu Val Lys Pro Ser Asp
1               5                   10                  15

Thr Leu Ser Leu Thr Cys Thr Val Ser Gly Tyr Ser Ile Thr Ser Asp
            20                  25                  30

Tyr Thr Trp Asn Trp Ile Arg Gln Thr Pro Gly Lys Gly Leu Glu Trp
        35                  40                  45

Ile Gly His Ile Thr Tyr Ser Gly Ser Val Ser Tyr Asn Pro Ser Leu
    50                  55                  60

Arg Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Thr Tyr Ser Cys
                85                  90                  95

Ala Arg Ala Leu Tyr Tyr Pro Trp Tyr Phe Asp Val Trp Gly Thr Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
```

165                 170                 175
Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
            210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 316
<211> LENGTH: 214
<212> TYPE: PRT
<213> ORGANISM: Artificial Sequence
<220> FEATURE:
<223> OTHER INFORMATION: V4-C24 VL-Ckappa

<400> SEQUENCE: 316

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Val Gly Tyr Ile
            20                  25                  30

His Trp Tyr Gln Gln Lys Pro Gly Gln Ala Pro Arg Pro Leu Ile Tyr
            35                  40                  45

Thr Thr Ser Tyr Arg Ala Thr Gly Ile Pro Ala Arg Phe Ser Gly Ser
            50                  55                  60

Gly Ser Gly Thr Asp Asn Thr Leu Thr Ile Ser Ser Leu Glu Pro Glu
65                  70                  75                  80

```
Asp Ser Ala Val Tyr Tyr Cys Gln Gln Trp Ser Ser Tyr Pro Pro Ile
                85                  90                  95

Thr Phe Gly Gly Gly Thr Lys Leu Glu Val Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 317
<211> LENGTH: 214
<212> TYPE: PRT
<213> ORGANISM: Artificial Sequence
<220> FEATURE:
<223> OTHER INFORMATION: V4-C26 VL-Ckappa

<400> SEQUENCE: 317

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Val Gly Tyr Ile
            20                  25                  30

His Trp Tyr Gln Gln Lys Pro Gly Gln Ala Pro Arg Pro Ile Ile Tyr
        35                  40                  45

Thr Thr Ser Asn Arg Ala Thr Gly Ile Pro Ala Arg Phe Ser Gly Ser
    50                  55                  60

Gly Ser Gly Thr Asp Asn Thr Leu Thr Ile Ser Ser Leu Glu Pro Glu
65                  70                  75                  80

Asp Ser Ala Val Tyr Tyr Cys Gln Gln Trp Ser Ser Tyr Pro Pro Ile
                85                  90                  95

Thr Phe Gly Gly Gly Thr Lys Leu Glu Val Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 318
<211> LENGTH: 214
<212> TYPE: PRT
<213> ORGANISM: Artificial Sequence
<220> FEATURE:
<223> OTHER INFORMATION: V4-C27 VL-Ckappa

<400> SEQUENCE: 318

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Val Gly Tyr Ile
            20                  25                  30

His Trp Tyr Gln Gln Lys Pro Gly Gln Ala Pro Arg Pro Leu Ile Tyr
        35                  40                  45

Ala Thr Tyr Asn Arg Ala Thr Gly Ile Pro Ala Arg Phe Ser Gly Ser
    50                  55                  60

Gly Ser Gly Thr Asp Asn Thr Leu Thr Ile Ser Ser Leu Glu Pro Glu
65                  70                  75                  80

Asp Ser Ala Val Tyr Tyr Cys Gln Gln Trp Ser Ser Tyr Pro Pro Ile
                85                  90                  95

Thr Phe Gly Gly Gly Thr Lys Leu Glu Val Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 319
<211> LENGTH: 214
<212> TYPE: PRT
<213> ORGANISM: Artificial Sequence
<220> FEATURE:
<223> OTHER INFORMATION: V4-C28 VL-Ckappa

<400> SEQUENCE: 319

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Val Gly Tyr Ile
            20                  25                  30

His Trp Tyr Gln Gln Lys Pro Gly Gln Ala Pro Arg Pro Leu Ile Tyr
        35                  40                  45

Ala Thr Ser Tyr Arg Ala Thr Gly Ile Pro Ala Arg Phe Ser Gly Ser
    50                  55                  60

Gly Ser Gly Thr Asp Asn Thr Leu Thr Ile Ser Ser Leu Glu Pro Glu
65                  70                  75                  80

Asp Ser Ala Val Tyr Tyr Cys Gln Gln Trp Ser Ser Tyr Pro Pro Ile
```

```
                     85                  90                  95
Thr Phe Gly Gly Gly Thr Lys Leu Glu Val Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 320
<211> LENGTH: 214
<212> TYPE: PRT
<213> ORGANISM: Artificial Sequence
<220> FEATURE:
<223> OTHER INFORMATION: V4-C30 VL-Ckappa

<400> SEQUENCE: 320

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Val Gly Tyr Ile
                20                  25                  30

His Trp Tyr Gln Gln Lys Pro Gly Gln Ala Pro Arg Pro Leu Ile Tyr
            35                  40                  45

Ala Thr Tyr Tyr Arg Ala Thr Gly Ile Pro Ala Arg Phe Ser Gly Ser
        50                  55                  60

Gly Ser Gly Thr Asp Asn Thr Leu Thr Ile Ser Ser Leu Glu Pro Glu
65                  70                  75                  80

Asp Ser Ala Val Tyr Tyr Cys Gln Gln Trp Ser Ser Tyr Pro Pro Ile
                85                  90                  95

Thr Phe Gly Gly Gly Thr Lys Leu Glu Val Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

```
<210> SEQ ID NO 321
<211> LENGTH: 214
<212> TYPE: PRT
<213> ORGANISM: Artificial Sequence
<220> FEATURE:
<223> OTHER INFORMATION: V4-C31 VL-Ckappa

<400> SEQUENCE: 321

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Val Gly Tyr Ile
            20                  25                  30

His Trp Tyr Gln Gln Lys Pro Gly Gln Ala Pro Arg Pro Leu Ile Tyr
        35                  40                  45

Ala Thr Tyr Tyr Arg Thr Thr Gly Ile Pro Ala Arg Phe Ser Gly Ser
    50                  55                  60

Gly Ser Gly Thr Asp Asn Thr Leu Thr Ile Ser Ser Leu Glu Pro Glu
65                  70                  75                  80

Asp Ser Ala Val Tyr Tyr Cys Gln Gln Trp Ser Ser Tyr Pro Pro Ile
                85                  90                  95

Thr Phe Gly Gly Gly Thr Lys Leu Glu Val Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 322
<211> LENGTH: 6
<212> TYPE: PRT
<213> ORGANISM: Artificial Sequence
<220> FEATURE:
<223> OTHER INFORMATION: VISTA sequence to which 4M2-C12 and derivatives
      bind

<400> SEQUENCE: 322

Ser Arg Gly Glu Val Gln
1               5

<210> SEQ ID NO 323
<211> LENGTH: 412
<212> TYPE: PRT
<213> ORGANISM: Homo sapiens
<220> FEATURE:
<221> NAME/KEY: misc_feature
<222> LOCATION: (1)..(412)
<223> OTHER INFORMATION: PSGL-1 isoform 1 (UniProt: Q14242-1, v1)

<400> SEQUENCE: 323

Met Pro Leu Gln Leu Leu Leu Leu Leu Ile Leu Leu Gly Pro Gly Asn
1               5                   10                  15
```

```
Ser Leu Gln Leu Trp Asp Thr Trp Ala Asp Glu Ala Glu Lys Ala Leu
         20                  25                  30
Gly Pro Leu Ala Arg Asp Arg Gln Ala Thr Glu Tyr Glu Tyr
         35                  40                  45
Leu Asp Tyr Asp Phe Leu Pro Glu Thr Glu Pro Glu Met Leu Arg
 50                  55                  60
Asn Ser Thr Asp Thr Thr Pro Leu Thr Gly Pro Gly Thr Pro Glu Ser
 65                  70                  75                  80
Thr Thr Val Glu Pro Ala Ala Arg Arg Ser Thr Gly Leu Asp Ala Gly
                 85                  90                  95
Gly Ala Val Thr Glu Leu Thr Thr Glu Leu Ala Asn Met Gly Asn Leu
                100                 105                 110
Ser Thr Asp Ser Ala Ala Met Glu Ile Gln Thr Thr Gln Pro Ala Ala
                115                 120                 125
Thr Glu Ala Gln Thr Thr Gln Pro Val Pro Thr Glu Ala Gln Thr Thr
                130                 135                 140
Pro Leu Ala Ala Thr Glu Ala Gln Thr Thr Arg Leu Thr Ala Thr Glu
145                 150                 155                 160
Ala Gln Thr Thr Pro Leu Ala Ala Thr Glu Ala Gln Thr Thr Pro Pro
                165                 170                 175
Ala Ala Thr Glu Ala Gln Thr Thr Gln Pro Thr Gly Leu Glu Ala Gln
                180                 185                 190
Thr Thr Ala Pro Ala Ala Met Glu Ala Gln Thr Thr Ala Pro Ala Ala
                195                 200                 205
Met Glu Ala Gln Thr Thr Pro Pro Ala Ala Met Glu Ala Gln Thr Thr
                210                 215                 220
Gln Thr Thr Ala Met Glu Ala Gln Thr Thr Ala Pro Glu Ala Thr Glu
225                 230                 235                 240
Ala Gln Thr Thr Gln Pro Thr Ala Thr Glu Ala Gln Thr Thr Pro Leu
                245                 250                 255
Ala Ala Met Glu Ala Leu Ser Thr Glu Pro Ser Ala Thr Glu Ala Leu
                260                 265                 270
Ser Met Glu Pro Thr Thr Lys Arg Gly Leu Phe Ile Pro Phe Ser Val
                275                 280                 285
Ser Ser Val Thr His Lys Gly Ile Pro Met Ala Ala Ser Asn Leu Ser
                290                 295                 300
Val Asn Tyr Pro Val Gly Ala Pro Asp His Ile Ser Val Lys Gln Cys
305                 310                 315                 320
Leu Leu Ala Ile Leu Ile Leu Ala Leu Val Ala Thr Ile Phe Phe Val
                325                 330                 335
Cys Thr Val Val Leu Ala Val Arg Leu Ser Arg Lys Gly His Met Tyr
                340                 345                 350
Pro Val Arg Asn Tyr Ser Pro Thr Glu Met Val Cys Ile Ser Ser Leu
                355                 360                 365
Leu Pro Asp Gly Gly Glu Gly Pro Ser Ala Thr Ala Asn Gly Gly Leu
                370                 375                 380
Ser Lys Ala Lys Ser Pro Gly Leu Thr Pro Glu Pro Arg Glu Asp Arg
385                 390                 395                 400
Glu Gly Asp Asp Leu Thr Leu His Ser Phe Leu Pro
                405                 410

<210> SEQ ID NO 324
<211> LENGTH: 428
```

```
<212> TYPE: PRT
<213> ORGANISM: Homo sapiens
<220> FEATURE:
<221> NAME/KEY: misc_feature
<222> LOCATION: (1)..(428)
<223> OTHER INFORMATION: PSGL-1 isoform 2 (UniProt: Q14242-2)

<400> SEQUENCE: 324
```

| | | | | | | | | | | | | | | |
|---|---|---|---|---|---|---|---|---|---|---|---|---|---|---|
| Met | Ala | Val | Gly | Ala | Ser | Gly | Leu | Glu | Gly | Asp | Lys | Met | Ala | Gly |
| 1 | | | | 5 | | | | | 10 | | | | | 15 |
| Met | Pro | Leu | Gln | Leu | Leu | Leu | Leu | Ile | Leu | Leu | Gly | Pro | Gly | Asn |
| | | | 20 | | | | | 25 | | | | | 30 | |
| Ser | Leu | Gln | Leu | Trp | Asp | Thr | Trp | Ala | Asp | Glu | Ala | Glu | Lys | Ala | Leu |
| | | 35 | | | | | 40 | | | | | 45 | | |
| Gly | Pro | Leu | Leu | Ala | Arg | Asp | Arg | Arg | Gln | Ala | Thr | Glu | Tyr | Glu | Tyr |
| | 50 | | | | | 55 | | | | | 60 | | | |
| Leu | Asp | Tyr | Asp | Phe | Leu | Pro | Glu | Thr | Glu | Pro | Pro | Glu | Met | Leu | Arg |
| 65 | | | | | 70 | | | | | 75 | | | | | 80 |
| Asn | Ser | Thr | Asp | Thr | Thr | Pro | Leu | Thr | Gly | Pro | Gly | Thr | Pro | Glu | Ser |
| | | | | 85 | | | | | 90 | | | | | 95 | |
| Thr | Thr | Val | Glu | Pro | Ala | Ala | Arg | Arg | Ser | Thr | Gly | Leu | Asp | Ala | Gly |
| | | | 100 | | | | | 105 | | | | | 110 | | |
| Gly | Ala | Val | Thr | Glu | Leu | Thr | Thr | Glu | Leu | Ala | Asn | Met | Gly | Asn | Leu |
| | | 115 | | | | | 120 | | | | | 125 | | | |
| Ser | Thr | Asp | Ser | Ala | Ala | Met | Glu | Ile | Gln | Thr | Thr | Gln | Pro | Ala | Ala |
| | 130 | | | | | 135 | | | | | 140 | | | | |
| Thr | Glu | Ala | Gln | Thr | Thr | Gln | Pro | Val | Pro | Thr | Glu | Ala | Gln | Thr | Thr |
| 145 | | | | | 150 | | | | | 155 | | | | | 160 |
| Pro | Leu | Ala | Ala | Thr | Glu | Ala | Gln | Thr | Thr | Arg | Leu | Thr | Ala | Thr | Glu |
| | | | | 165 | | | | | 170 | | | | | 175 | |
| Ala | Gln | Thr | Thr | Pro | Leu | Ala | Ala | Thr | Glu | Ala | Gln | Thr | Thr | Pro | Pro |
| | | | 180 | | | | | 185 | | | | | 190 | | |
| Ala | Ala | Thr | Glu | Ala | Gln | Thr | Thr | Gln | Pro | Thr | Gly | Leu | Glu | Ala | Gln |
| | | 195 | | | | | 200 | | | | | 205 | | | |
| Thr | Thr | Ala | Pro | Ala | Ala | Met | Glu | Ala | Gln | Thr | Thr | Ala | Pro | Ala | Ala |
| | 210 | | | | | 215 | | | | | 220 | | | | |
| Met | Glu | Ala | Gln | Thr | Thr | Pro | Pro | Ala | Ala | Met | Glu | Ala | Gln | Thr | Thr |
| 225 | | | | | 230 | | | | | 235 | | | | | 240 |
| Gln | Thr | Thr | Ala | Met | Glu | Ala | Gln | Thr | Thr | Ala | Pro | Glu | Ala | Thr | Glu |
| | | | | 245 | | | | | 250 | | | | | 255 | |
| Ala | Gln | Thr | Thr | Gln | Pro | Thr | Ala | Thr | Glu | Ala | Gln | Thr | Thr | Pro | Leu |
| | | | 260 | | | | | 265 | | | | | 270 | | |
| Ala | Ala | Met | Glu | Ala | Leu | Ser | Thr | Glu | Pro | Ser | Ala | Thr | Glu | Ala | Leu |
| | | 275 | | | | | 280 | | | | | 285 | | | |
| Ser | Met | Glu | Pro | Thr | Thr | Lys | Arg | Gly | Leu | Phe | Ile | Pro | Phe | Ser | Val |
| | 290 | | | | | 295 | | | | | 300 | | | | |
| Ser | Ser | Val | Thr | His | Lys | Gly | Ile | Pro | Met | Ala | Ala | Ser | Asn | Leu | Ser |
| 305 | | | | | 310 | | | | | 315 | | | | | 320 |
| Val | Asn | Tyr | Pro | Val | Gly | Ala | Pro | Asp | His | Ile | Ser | Val | Lys | Gln | Cys |
| | | | | 325 | | | | | 330 | | | | | 335 | |
| Leu | Leu | Ala | Ile | Leu | Ile | Leu | Ala | Leu | Val | Ala | Thr | Ile | Phe | Phe | Val |
| | | | 340 | | | | | 345 | | | | | 350 | | |
| Cys | Thr | Val | Val | Leu | Ala | Val | Arg | Leu | Ser | Arg | Lys | Gly | His | Met | Tyr |
| | | 355 | | | | | 360 | | | | | 365 | | | |
| Pro | Val | Arg | Asn | Tyr | Ser | Pro | Thr | Glu | Met | Val | Cys | Ile | Ser | Ser | Leu |

```
                    370                 375                 380
Leu Pro Asp Gly Gly Glu Gly Pro Ser Ala Thr Ala Asn Gly Leu
385                 390                 395                 400

Ser Lys Ala Lys Ser Pro Gly Leu Thr Pro Glu Pro Arg Glu Asp Arg
                405                 410                 415

Glu Gly Asp Asp Leu Thr Leu His Ser Phe Leu Pro
                420                 425

<210> SEQ ID NO 325
<211> LENGTH: 395
<212> TYPE: PRT
<213> ORGANISM: Homo sapiens
<220> FEATURE:
<221> NAME/KEY: misc_feature
<222> LOCATION: (1)..(395)
<223> OTHER INFORMATION: Mature human PSGL-1 isoform 1 (Q14242-1, v1
      positions 18 to 412)

<400> SEQUENCE: 325

Leu Gln Leu Trp Asp Thr Trp Ala Asp Glu Ala Glu Lys Ala Leu Gly
1               5                   10                  15

Pro Leu Leu Ala Arg Asp Arg Arg Gln Ala Thr Glu Tyr Glu Tyr Leu
                20                  25                  30

Asp Tyr Asp Phe Leu Pro Glu Thr Glu Pro Pro Glu Met Leu Arg Asn
            35                  40                  45

Ser Thr Asp Thr Thr Pro Leu Thr Gly Pro Gly Thr Pro Glu Ser Thr
        50                  55                  60

Thr Val Glu Pro Ala Ala Arg Arg Ser Thr Gly Leu Asp Ala Gly Gly
65                  70                  75                  80

Ala Val Thr Glu Leu Thr Thr Glu Leu Ala Asn Met Gly Asn Leu Ser
                85                  90                  95

Thr Asp Ser Ala Ala Met Glu Ile Gln Thr Thr Gln Pro Ala Ala Thr
            100                 105                 110

Glu Ala Gln Thr Thr Gln Pro Val Pro Thr Glu Ala Gln Thr Thr Pro
        115                 120                 125

Leu Ala Ala Thr Glu Ala Gln Thr Thr Arg Leu Thr Ala Thr Glu Ala
    130                 135                 140

Gln Thr Thr Pro Leu Ala Ala Thr Glu Ala Gln Thr Thr Pro Pro Ala
145                 150                 155                 160

Ala Thr Glu Ala Gln Thr Thr Gln Pro Thr Gly Leu Glu Ala Gln Thr
                165                 170                 175

Thr Ala Pro Ala Ala Met Glu Ala Gln Thr Thr Ala Pro Ala Ala Met
            180                 185                 190

Glu Ala Gln Thr Thr Pro Pro Ala Ala Met Glu Ala Gln Thr Thr Gln
        195                 200                 205

Thr Thr Ala Met Glu Ala Gln Thr Thr Ala Pro Glu Ala Thr Glu Ala
    210                 215                 220

Gln Thr Thr Gln Pro Thr Ala Thr Glu Ala Gln Thr Thr Pro Leu Ala
225                 230                 235                 240

Ala Met Glu Ala Leu Ser Thr Glu Pro Ser Ala Thr Glu Ala Leu Ser
                245                 250                 255

Met Glu Pro Thr Thr Lys Arg Gly Leu Phe Ile Pro Phe Ser Val Ser
            260                 265                 270

Ser Val Thr His Lys Gly Ile Pro Met Ala Ala Ser Asn Leu Ser Val
        275                 280                 285

Asn Tyr Pro Val Gly Ala Pro Asp His Ile Ser Val Lys Gln Cys Leu
```

```
                    290                 295                 300

Leu Ala Ile Leu Ile Leu Ala Leu Val Ala Thr Ile Phe Phe Val Cys
305                 310                 315                 320

Thr Val Val Leu Ala Val Arg Leu Ser Arg Lys Gly His Met Tyr Pro
                    325                 330                 335

Val Arg Asn Tyr Ser Pro Thr Glu Met Val Cys Ile Ser Ser Leu Leu
                340                 345                 350

Pro Asp Gly Gly Glu Gly Pro Ser Ala Thr Ala Asn Gly Gly Leu Ser
                355                 360                 365

Lys Ala Lys Ser Pro Gly Leu Thr Pro Glu Pro Arg Glu Asp Arg Glu
        370                 375                 380

Gly Asp Asp Leu Thr Leu His Ser Phe Leu Pro
385                 390                 395

<210> SEQ ID NO 326
<211> LENGTH: 303
<212> TYPE: PRT
<213> ORGANISM: Artificial Sequence
<220> FEATURE:
<223> OTHER INFORMATION: PSGL-1 extracellular domain (Q14242-1, v1
      positions 18 to 320)

<400> SEQUENCE: 326

Leu Gln Leu Trp Asp Thr Trp Ala Asp Glu Ala Glu Lys Ala Leu Gly
1               5                   10                  15

Pro Leu Leu Ala Arg Asp Arg Arg Gln Ala Thr Glu Tyr Glu Tyr Leu
                20                  25                  30

Asp Tyr Asp Phe Leu Pro Glu Thr Glu Pro Pro Glu Met Leu Arg Asn
            35                  40                  45

Ser Thr Asp Thr Thr Pro Leu Thr Gly Pro Gly Thr Pro Glu Ser Thr
        50                  55                  60

Thr Val Glu Pro Ala Ala Arg Arg Ser Thr Gly Leu Asp Ala Gly Gly
65                  70                  75                  80

Ala Val Thr Glu Leu Thr Thr Glu Leu Ala Asn Met Gly Asn Leu Ser
                85                  90                  95

Thr Asp Ser Ala Ala Met Glu Ile Gln Thr Thr Gln Pro Ala Ala Thr
            100                 105                 110

Glu Ala Gln Thr Thr Gln Pro Val Pro Thr Glu Ala Gln Thr Thr Pro
        115                 120                 125

Leu Ala Ala Thr Glu Ala Gln Thr Thr Arg Leu Thr Ala Thr Glu Ala
130                 135                 140

Gln Thr Thr Pro Leu Ala Ala Thr Glu Ala Gln Thr Thr Pro Pro Ala
145                 150                 155                 160

Ala Thr Glu Ala Gln Thr Thr Gln Pro Thr Gly Leu Glu Ala Gln Thr
                165                 170                 175

Thr Ala Pro Ala Ala Met Glu Ala Gln Thr Thr Ala Pro Ala Ala Met
            180                 185                 190

Glu Ala Gln Thr Thr Pro Pro Ala Ala Met Glu Ala Gln Thr Thr Gln
        195                 200                 205

Thr Thr Ala Met Glu Ala Gln Thr Thr Ala Pro Glu Ala Thr Glu Ala
    210                 215                 220

Gln Thr Thr Gln Pro Thr Ala Thr Glu Ala Gln Thr Thr Pro Leu Ala
225                 230                 235                 240

Ala Met Glu Ala Leu Ser Thr Glu Pro Ser Ala Thr Glu Ala Leu Ser
                245                 250                 255
```

```
Met Glu Pro Thr Thr Lys Arg Gly Leu Phe Ile Pro Phe Ser Val Ser
            260                 265                 270

Ser Val Thr His Lys Gly Ile Pro Met Ala Ala Ser Asn Leu Ser Val
        275                 280                 285

Asn Tyr Pro Val Gly Ala Pro Asp His Ile Ser Val Lys Gln Cys
    290                 295                 300

<210> SEQ ID NO 327
<211> LENGTH: 21
<212> TYPE: PRT
<213> ORGANISM: Artificial Sequence
<220> FEATURE:
<223> OTHER INFORMATION: PSGL-1 transmembrane domain (Q14242-1, v1
      positions 321 to 341)

<400> SEQUENCE: 327

Leu Leu Ala Ile Leu Ile Leu Ala Leu Val Ala Thr Ile Phe Phe Val
1               5                   10                  15

Cys Thr Val Val Leu
            20

<210> SEQ ID NO 328
<211> LENGTH: 71
<212> TYPE: PRT
<213> ORGANISM: Artificial Sequence
<220> FEATURE:
<223> OTHER INFORMATION: PSGL-1 cytoplasmic domain (Q14242-1, v1
positions 342 to 412)

<400> SEQUENCE: 328

Ala Val Arg Leu Ser Arg Lys Gly His Met Tyr Pro Val Arg Asn Tyr
1               5                   10                  15

Ser Pro Thr Glu Met Val Cys Ile Ser Ser Leu Leu Pro Asp Gly Gly
            20                  25                  30

Glu Gly Pro Ser Ala Thr Ala Asn Gly Gly Leu Ser Lys Ala Lys Ser
        35                  40                  45

Pro Gly Leu Thr Pro Glu Pro Arg Glu Asp Arg Glu Gly Asp Asp Leu
    50                  55                  60

Thr Leu His Ser Phe Leu Pro
65                  70

<210> SEQ ID NO 329
<211> LENGTH: 140
<212> TYPE: PRT
<213> ORGANISM: Artificial Sequence
<220> FEATURE:
<223> OTHER INFORMATION: PSGL-1 extracellular domain repeat region
      (Q14242-1, v1 positions 122 to 261)

<400> SEQUENCE: 329

Gln Thr Thr Gln Pro Ala Ala Thr Glu Ala Gln Thr Thr Gln Pro Val
1               5                   10                  15

Pro Thr Glu Ala Gln Thr Thr Pro Leu Ala Ala Thr Glu Ala Gln Thr
            20                  25                  30

Thr Arg Leu Thr Ala Thr Glu Ala Gln Thr Thr Pro Leu Ala Ala Thr
        35                  40                  45

Glu Ala Gln Thr Thr Pro Pro Ala Ala Thr Glu Ala Gln Thr Thr Gln
    50                  55                  60

Pro Thr Gly Leu Glu Ala Gln Thr Thr Ala Pro Ala Ala Met Glu Ala
65                  70                  75                  80

Gln Thr Thr Ala Pro Ala Ala Met Glu Ala Gln Thr Thr Pro Pro Ala
```

```
                   85                  90                  95
Ala Met Glu Ala Gln Thr Thr Gln Thr Thr Ala Met Glu Ala Gln Thr
               100                 105                 110

Thr Ala Pro Glu Ala Thr Glu Ala Gln Thr Thr Gln Pro Thr Ala Thr
           115                 120                 125

Glu Ala Gln Thr Thr Pro Leu Ala Ala Met Glu Ala
       130                 135                 140

<210> SEQ ID NO 330
<211> LENGTH: 446
<212> TYPE: PRT
<213> ORGANISM: Artificial Sequence
<220> FEATURE:
<223> OTHER INFORMATION: 4M2-C12 VH-CH1-CH2-CH3 IgG4

<400> SEQUENCE: 330

Glu Val Lys Leu Val Glu Ser Gly Pro Gly Leu Val Lys Pro Ser Gln
1               5                   10                  15

Ser Leu Ser Leu Thr Cys Thr Val Thr Gly Tyr Ser Ile Thr Ser Asp
            20                  25                  30

Tyr Ala Trp Asn Trp Ile Arg Gln Phe Pro Gly Asn Lys Leu Glu Trp
        35                  40                  45

Met Gly Tyr Ile Thr Tyr Ser Gly Asn Ile Ser Tyr Asn Pro Ser Leu
    50                  55                  60

Arg Ser Arg Ile Ser Ile Thr Arg Asp Thr Ser Lys Asn Gln Phe Phe
65                  70                  75                  80

Leu Gln Leu Asn Ser Val Thr Pro Glu Asp Thr Ala Thr Tyr Ser Cys
                85                  90                  95

Ala Arg Ser Leu Tyr Tyr Pro Trp Tyr Phe Asp Val Trp Gly Ala Gly
            100                 105                 110

Thr Thr Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Ser Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
```

-continued

```
305                 310                 315                 320
Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Gln Glu Glu Met Thr Lys Asn Gln Val Ser Leu Thr Cys Leu Val
                355                 360                 365

Lys Gly Phe Tyr Pro Ser Asp Ile Ala Val Glu Trp Glu Ser Asn Gly
                370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
                420                 425                 430

Asn His Tyr Thr Gln Lys Ser Leu Ser Leu Ser Leu Gly Lys
                435                 440                 445
```